(12) United States Patent
Leimbach et al.

(10) Patent No.: US 12,611,213 B1
(45) Date of Patent: Apr. 28, 2026

(54) CONTROL SYSTEMS FOR SURGICAL INSTRUMENTS

(71) Applicant: Cilag GmbH International, Zug (CH)

(72) Inventors: Richard L. Leimbach, Cincinnati, OH (US); Mark D. Overmyer, Cincinnati, OH (US); Shane R. Adams, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 19/004,978

(22) Filed: Dec. 30, 2024

Related U.S. Application Data

(63) Continuation of application No. 18/421,044, filed on Jan. 24, 2024, now Pat. No. 12,193,671, which is a continuation of application No. 17/550,310, filed on Dec. 14, 2021, now Pat. No. 11,992,214, which is a continuation of application No. 16/682,240, filed on Nov. 13, 2019, now Pat. No. 11,266,406, which is a continuation of application No. 15/480,882, filed on Apr. 6, 2017, now Pat. No. 10,617,416, which is a continuation of application No. 14/200,111, filed on Mar. 7, 2014, now Pat. No. 9,629,629.

(60) Provisional application No. 61/782,866, filed on Mar. 14, 2013.

(51) Int. Cl.
| | |
|---|---|
| *A61B 17/072* | (2006.01) |
| *A61B 17/00* | (2006.01) |
| *A61B 17/29* | (2006.01) |
| *A61B 90/00* | (2016.01) |

(52) U.S. Cl.
CPC ................... *A61B 17/07207* (2013.01); *A61B 2017/00017* (2013.01); *A61B 2017/00398* (2013.01); *A61B 2017/0046* (2013.01); *A61B 2017/00734* (2013.01); *A61B 2017/2927* (2013.01); *A61B 2090/0808* (2016.02)

(58) Field of Classification Search
CPC ................................................ A61B 17/07207
See application file for complete search history.

(56) References Cited

U.S. PATENT DOCUMENTS

| | | | |
|---|---|---|---|
| 4,470,414 | A | 9/1984 | Imagawa et al. |
| 9,629,629 | B2 | 4/2017 | Leimbach et al. |
| 10,617,416 | B2 | 4/2020 | Leimbach et al. |
| 11,266,406 | B2 | 3/2022 | Leimbach et al. |

(Continued)

*Primary Examiner* — Nathaniel C Chukwurah
(74) *Attorney, Agent, or Firm* — FBT Gibbons LLP

(57) ABSTRACT

Surgical instruments and control systems therefor are disclosed. A surgical instrument can comprise: a power circuit comprising a power source and a switch, a microcontroller coupled to the power circuit, a handle comprising an attachment portion, and a control circuit in signal communication with the microcontroller. The attachment portion can comprise a first electrical contact in signal communication with the microcontroller. The control circuit can comprise a sensor configured to detect an attachment state of the attachment portion. The control circuit can communicate the detected attachment state to the microcontroller, and the microcontroller can ignore signals from the first electrical contact when the control circuit communicates a detached state. The attachment portion can comprise a second electrical contact coupled to a second power circuit, and the second power circuit can decouple the second electrical contact and the second power source when the sensor detects the detached state.

20 Claims, 173 Drawing Sheets

(56)                    References Cited

U.S. PATENT DOCUMENTS

| | | | |
|---|---|---|---|
| 11,992,214 | B2 | 5/2024 | Leimbach et al. |
| 12,193,671 | B2 | 1/2025 | Leimbach et al. |
| 2011/0125138 | A1* | 5/2011 | Malinouskas .......... A61B 90/90 |
| | | | 606/1 |
| 2011/0174099 | A1* | 7/2011 | Ross ...................... A61B 17/00 |
| | | | 74/89.32 |
| 2012/0265196 | A1 | 10/2012 | Turner et al. |

* cited by examiner

10456

10449

10448

10438

10454

10437

10449

10447

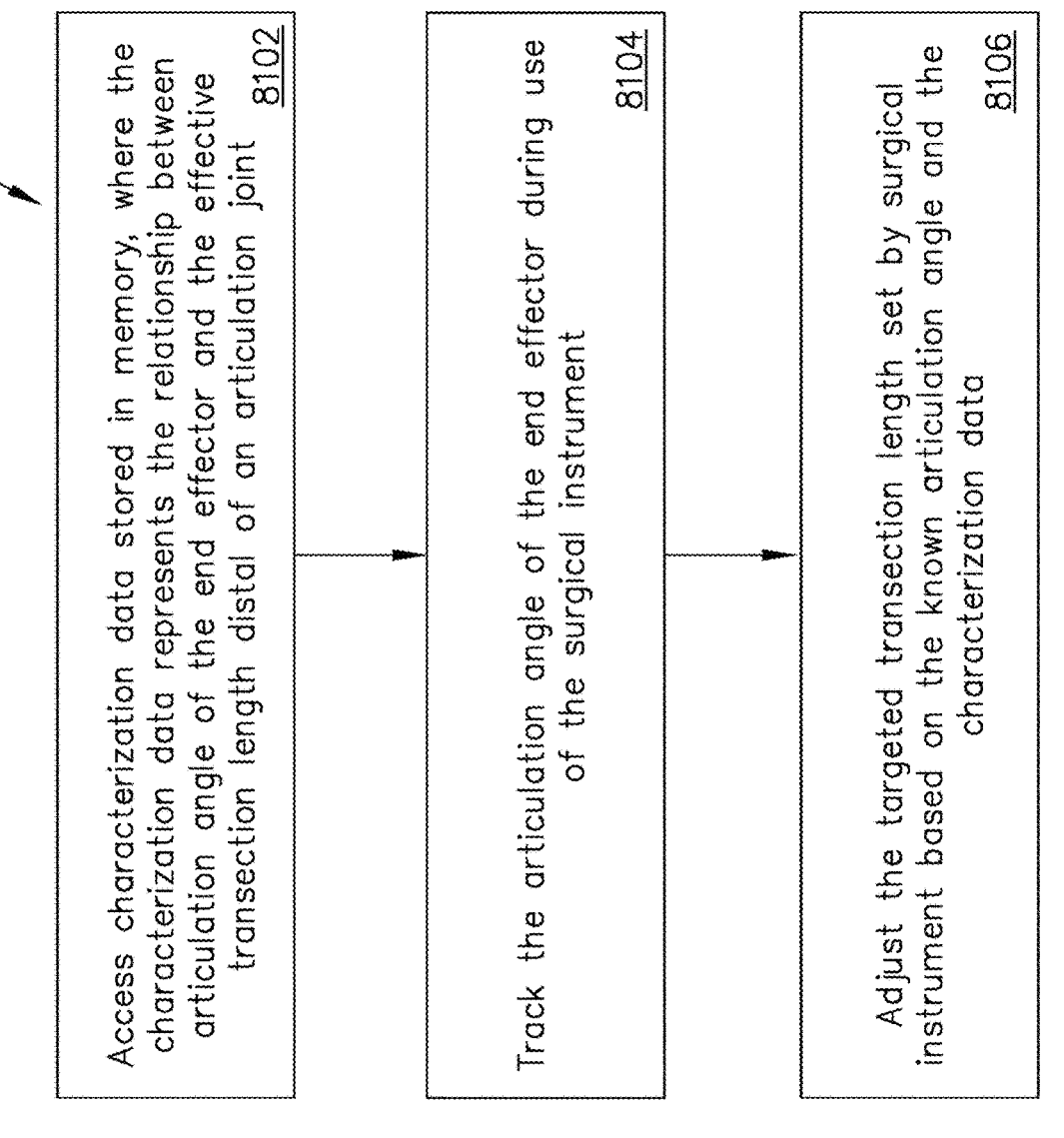

Access characterization data stored in memory, where the characterization data represents the relationship between articulation angle of the end effector and the effective transection length distal of an articulation joint  8102

Track the articulation angle of the end effector during use of the surgical instrument  8104

Adjust the targeted transection length set by surgical instrument based on the known articulation angle and the characterization data  8106

FIG. 196

Key

| | SET PORT B TO | | | | | READ PORT B AS | | |
|---|---|---|---|---|---|---|---|---|
| | RB3 | RB2 | RB1 | RB0 | \| | RB3 | RB2 | RB1 |
| RB0 | | | | | | | | |
| SW1 | HiZ | HiZ | HiZ | 0 | \| | 0 | 0 | 1 | X |
| SW2 | HiZ | HiZ | HiZ | 0 | \| | 0 | 1 | 0 | X |
| SW3 | HiZ | HiZ | HiZ | 0 | \| | 0 | 1 | 1 | X |
| SW4 | HiZ | HiZ | HiZ | 0 | \| | 1 | 0 | 0 | X |
| SW5 | HiZ | HiZ | 0 | HiZ | \| | 0 | 0 | X | 1 |
| SW6 | HiZ | HiZ | 0 | HiZ | \| | 0 | 1 | X | 1 |
| SW7 | HiZ | HiZ | 0 | HiZ | \| | 0 | 1 | X | 0 |
| SW8 | HiZ | HiZ | 0 | HiZ | \| | 1 | 0 | X | 1 |
| SW9 | HiZ | 0 | HiZ | HiZ | \| | 0 | X | 1 | 1 |
| SW10 | HiZ | 0 | HiZ | HiZ | \| | 0 | X | 0 | 1 |
| SW11 | HiZ | 0 | HiZ | HiZ | \| | 0 | X | 1 | 0 |
| SW12 | HiZ | 0 | HiZ | HiZ | \| | 1 | X | 0 | 1 |
| SW13 | 0 | HiZ | HiZ | HiZ | \| | X | 0 | 1 | 1 |
| SW14 | 0 | HiZ | HiZ | HiZ | \| | X | 1 | 0 | 1 |
| SW15 | 0 | HiZ | HiZ | HiZ | \| | X | 1 | 1 | 0 |
| SW16 | 0 | HiZ | HiZ | HiZ | \| | X | 0 | 0 | 1 |

| voltage | 3.3 |  | divider resistor | 10000 |
|---|---|---|---|---|
| SW1 | 11000 | 0.000157 | 1.728571 |  |
| SW2 | 12000 | 0.00015 | 1.8 |  |
| SW3 | 14000 | 0.000138 | 1.925 |  |
| SW4 | 18000 | 0.000118 | 2.121429 |  |
| SW5 | 21000 | 0.000106 | 2.235484 |  |
| SW6 | 22000 | 0.000103 | 2.26875 |  |
| SW7 | 24000 | 9.17E−05 | 2.329412 |  |
| SW8 | 28000 | 8.68E−05 | 2.431579 |  |
| SW9 | 31000 | 8.05E−05 | 2.495122 |  |
| SW10 | 32000 | 7.86E−05 | 2.514286 |  |
| SW11 | 34000 | 0.000075 | 2.55 |  |
| SW12 | 38000 | 6.88E−05 | 2.6125 |  |
| SW13 | 41000 | 6.47E−05 | 2.652941 |  |
| SW14 | 42000 | 6.35E−05 | 2.665385 |  |
| SW15 | 44000 | 6.11E−05 | 2.688889 |  |
| SW16 | 48000 | 5.69E−05 | 2.731034 |  |

CONTROL SYSTEMS FOR SURGICAL INSTRUMENTS

PRIORITY

This application is a continuation of U.S. patent application Ser. No. 18/421,044, entitled "Control Systems For Surgical Instruments" filed Jan. 24, 2024, issued as U.S. Pat. No. 12,193,671 on Jan. 14, 2025, which is a continuation of U.S. patent application Ser. No. 17/550,310, entitled "Control Systems For Surgical Instruments," filed Dec. 14, 2021, issued as U.S. Pat. No. 11,992,214 on May 28, 2024, which is a continuation of U.S. patent application Ser. No. 16/682, 240, entitled "Control Systems For Surgical Instruments," filed Nov. 13, 2019, issued as U.S. Pat. No. 11,266,406 on Mar. 8, 2022, which is a continuation of U.S. patent application Ser. No. 15/480,882, entitled "Control Systems For Surgical Instruments," filed Apr. 6, 2017, issued as U.S. Pat. No. 10,617,416 on Apr. 14, 2020, which is a continuation of U.S. patent application Ser. No. 14/200,111, entitled "Control Systems For Surgical Instruments," filed Mar. 7, 2014, issued as U.S. Pat. No. 9,629,629 on Apr. 25, 2017, which claims priority to U.S. Prov. App. No. 61/782,866, entitled "Control Systems For Surgical Instruments," filed Mar. 14, 2013, the disclosures of which are incorporated by reference herein in their entireties.

BACKGROUND

The present invention relates to surgical instruments and, in various embodiments, to surgical cutting and stapling instruments and staple cartridges therefor that are designed to cut and staple tissue.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 102 is a schematic illustrating, one, a clutch assembly for operably connecting an articulation drive to a firing drive of a surgical instrument and, two, an articulation lock configured to releasably hold the articulation drive, and an end effector of the surgical instrument, in position, wherein FIG. 102 illustrates the clutch assembly in an engaged position and the articulation lock in a locked condition;

FIG. 116 is an exploded view of the articulation lock of FIG. 114;

FIG. 117 is a perspective view of another alternative embodiment of an articulation lock illustrated in a locked condition;

FIG. 118 is an exploded view of the articulation lock of FIG. 117;

FIG. 119 is an elevational view of the articulation lock of FIG. 117 illustrating the articulation lock illustrated in a locked condition;

FIG. 120 is an elevational view of the articulation lock of FIG. 117 illustrating the articulation lock in a first unlocked condition to articulate an end effector in a first direction;

FIG. 121 is an elevational view of the articulation lock of FIG. 117 illustrating the articulation lock in a second unlocked condition to articulate an end effector in a second direction;

FIG. 122 is another exploded view of the articulation lock of FIG. 117;

FIG. 123 is a perspective view of a first lock cam of the articulation lock of FIG. 117;

FIG. 124 is a perspective view of a second lock cam of the articulation lock of FIG. 117;

FIG. 125 is a perspective view of another alternative embodiment of an articulation lock illustrated in a locked condition;

FIG. 126 is an exploded view of the articulation lock of FIG. 125;

FIG. 127 is a cross-sectional elevational view of the articulation lock of FIG. 125 illustrating the articulation lock in a first unlocked condition for articulating an end effector in a first direction;

Figure 34:
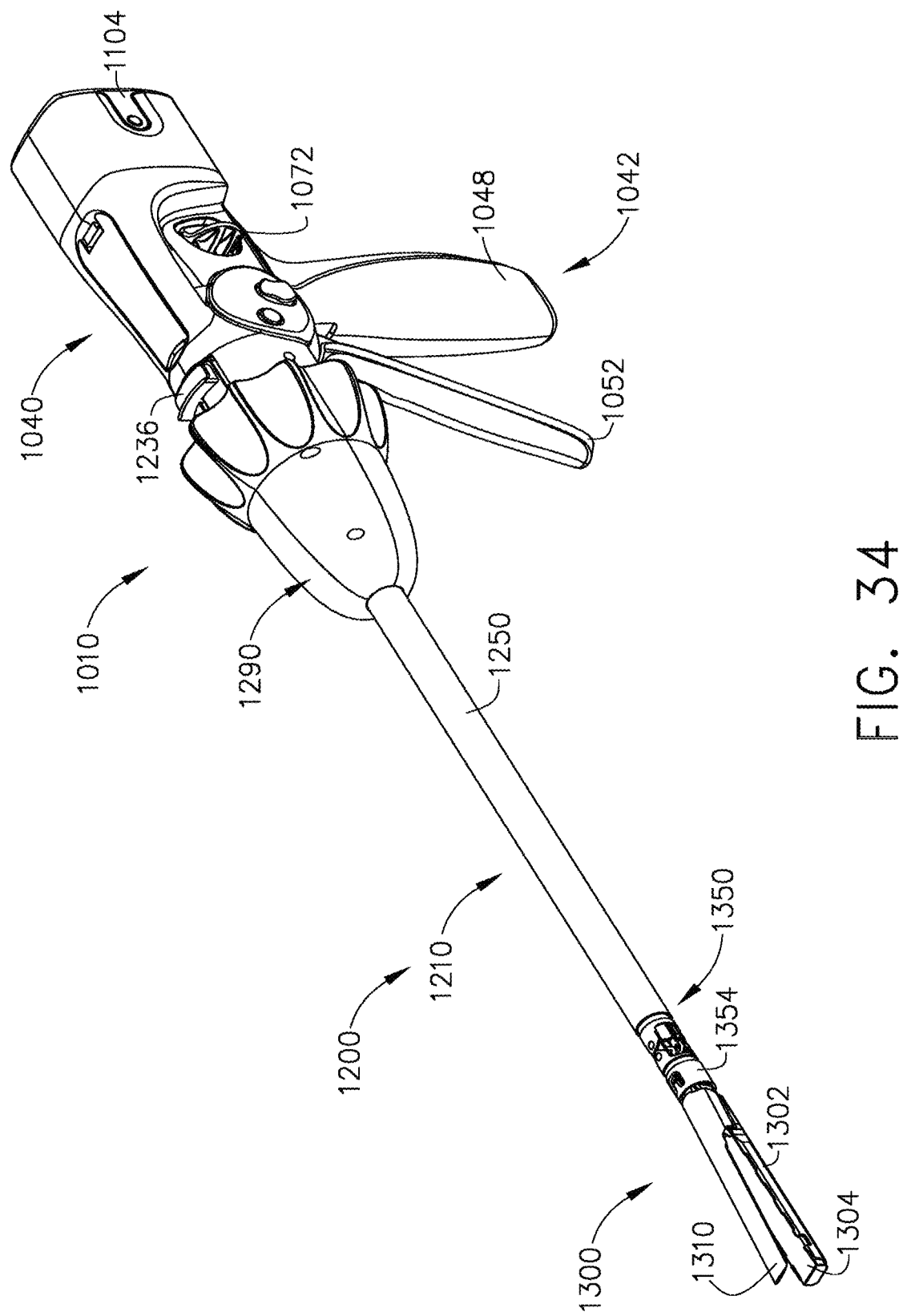
FIG. 34 is a perspective view of a surgical instrument handle coupled to an interchangeable shaft assembly.
Figures 125, 126:
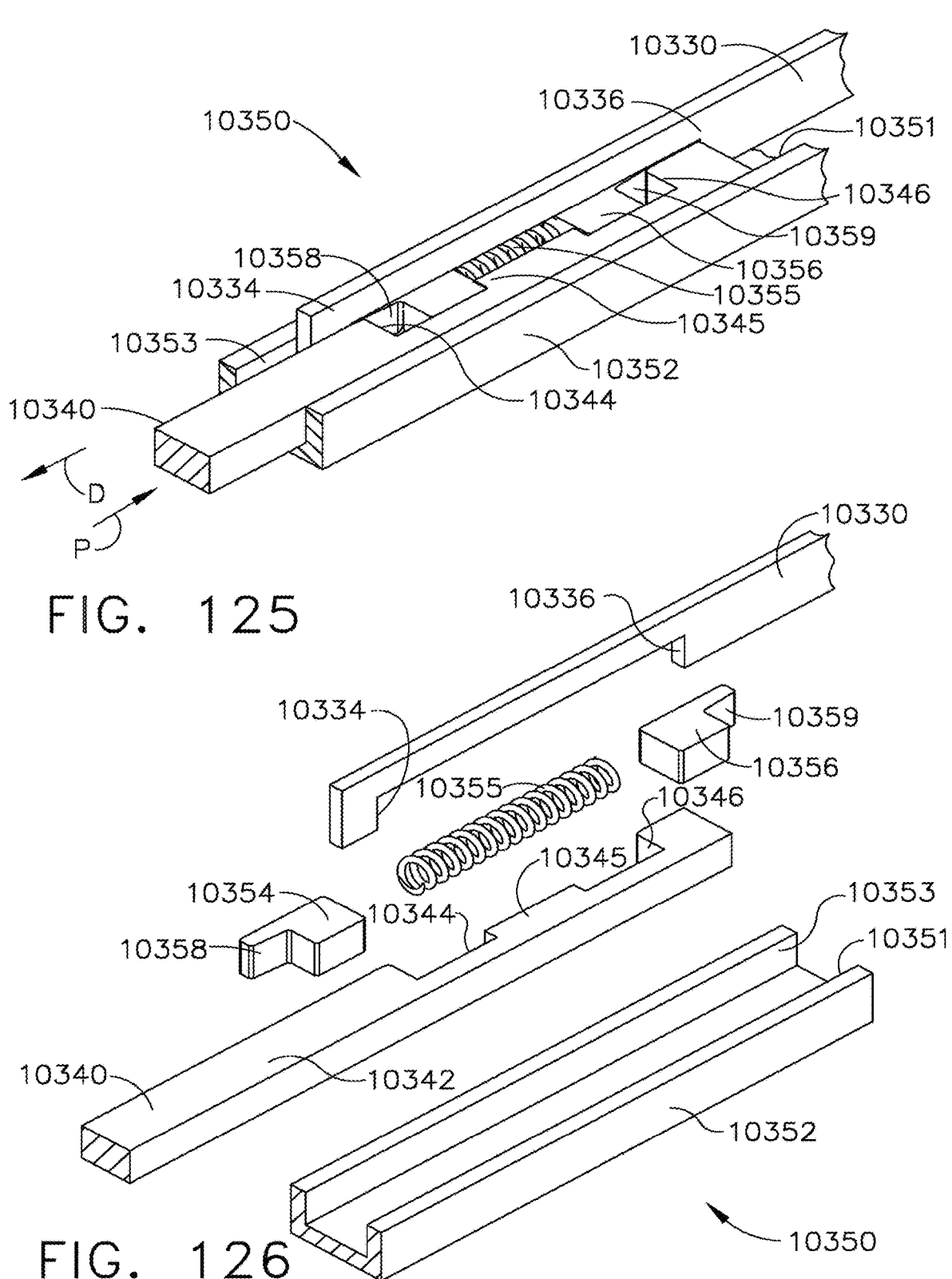
Figures 127, 128:
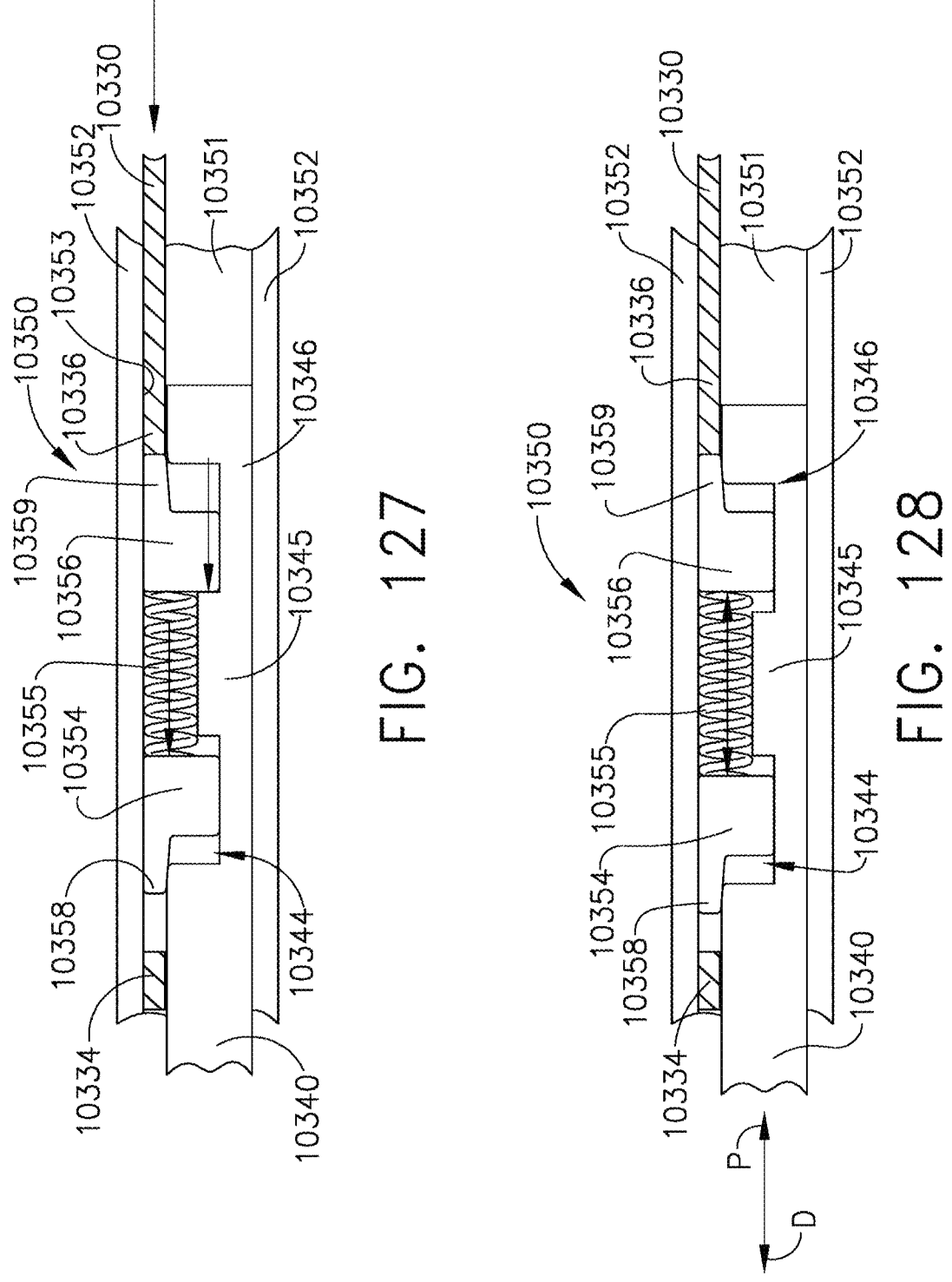
Figure 129:
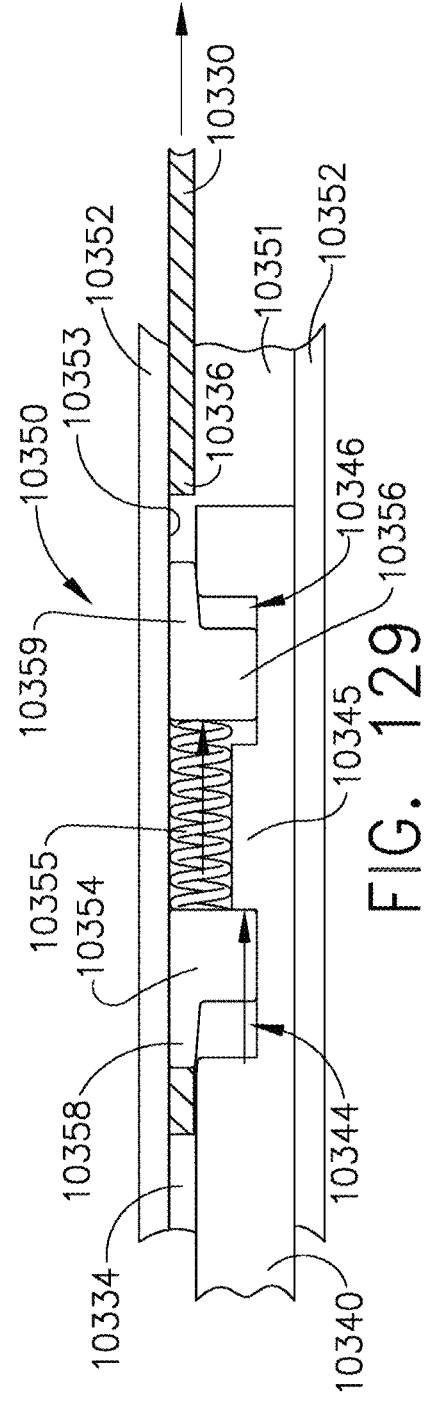
Figure 130:
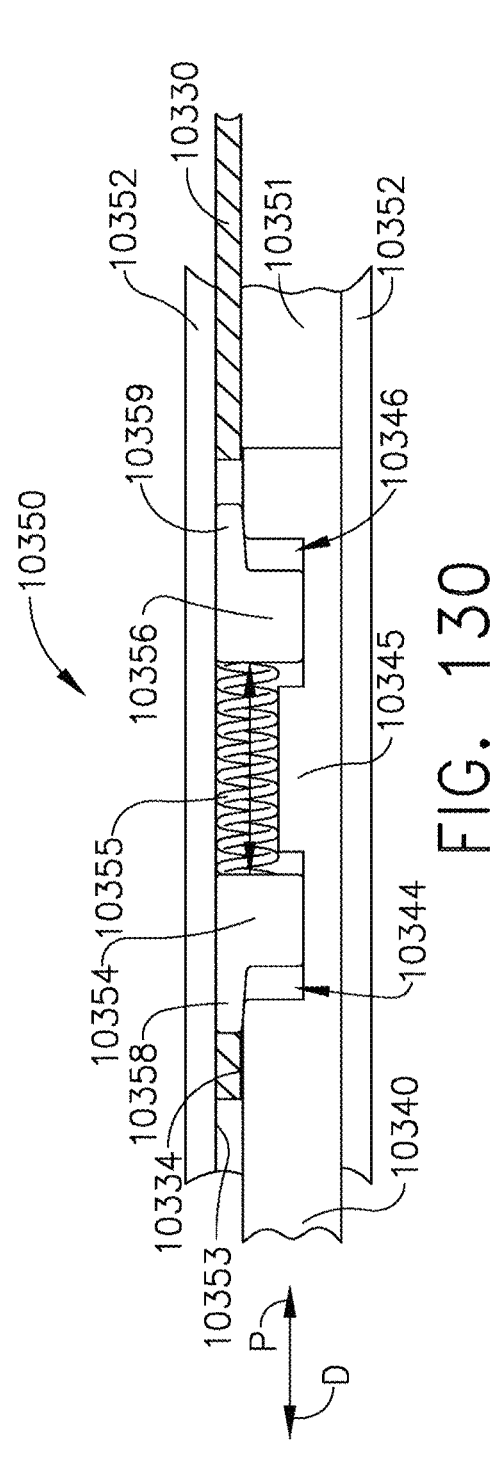
Figure 131:
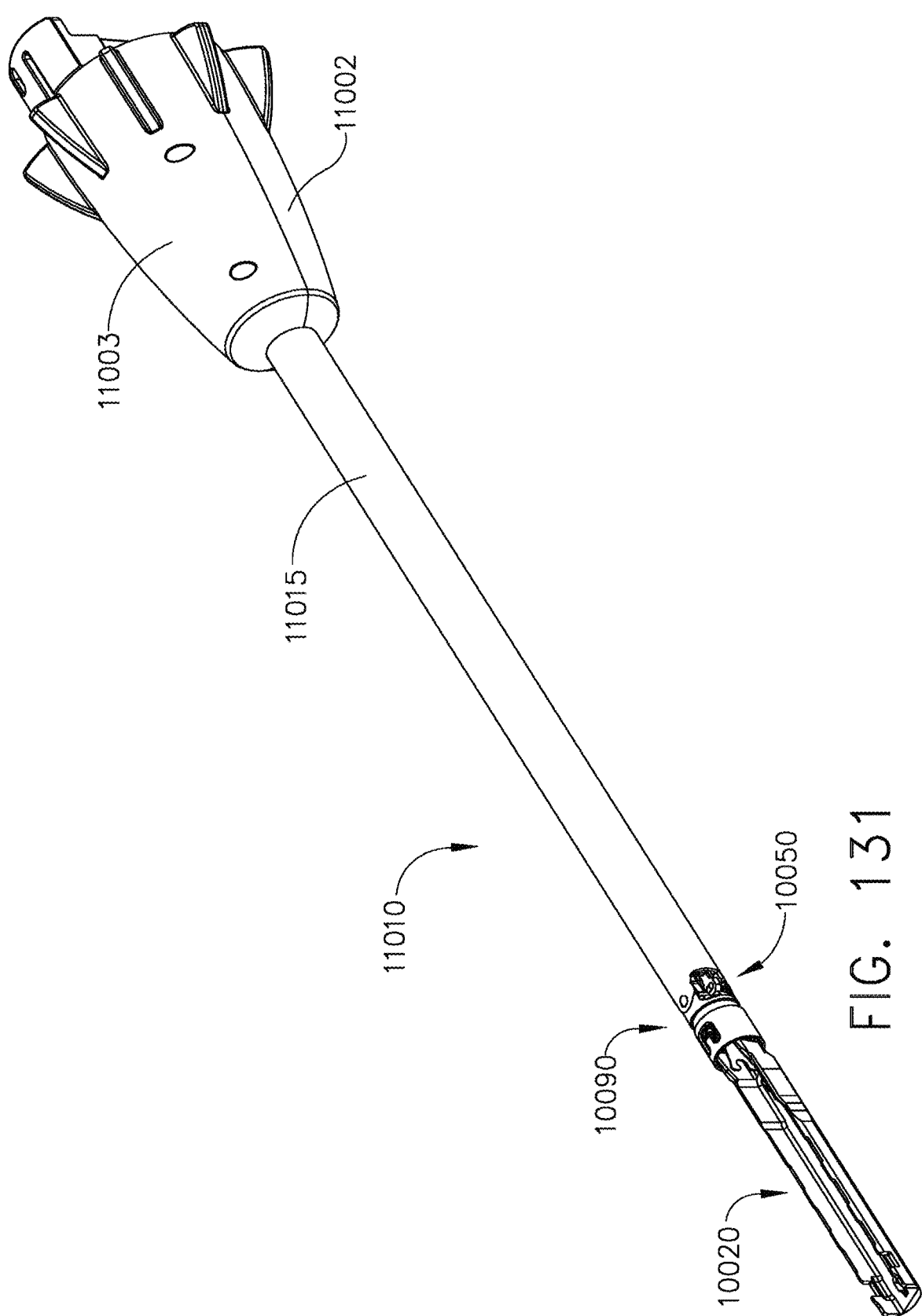
Figure 132:
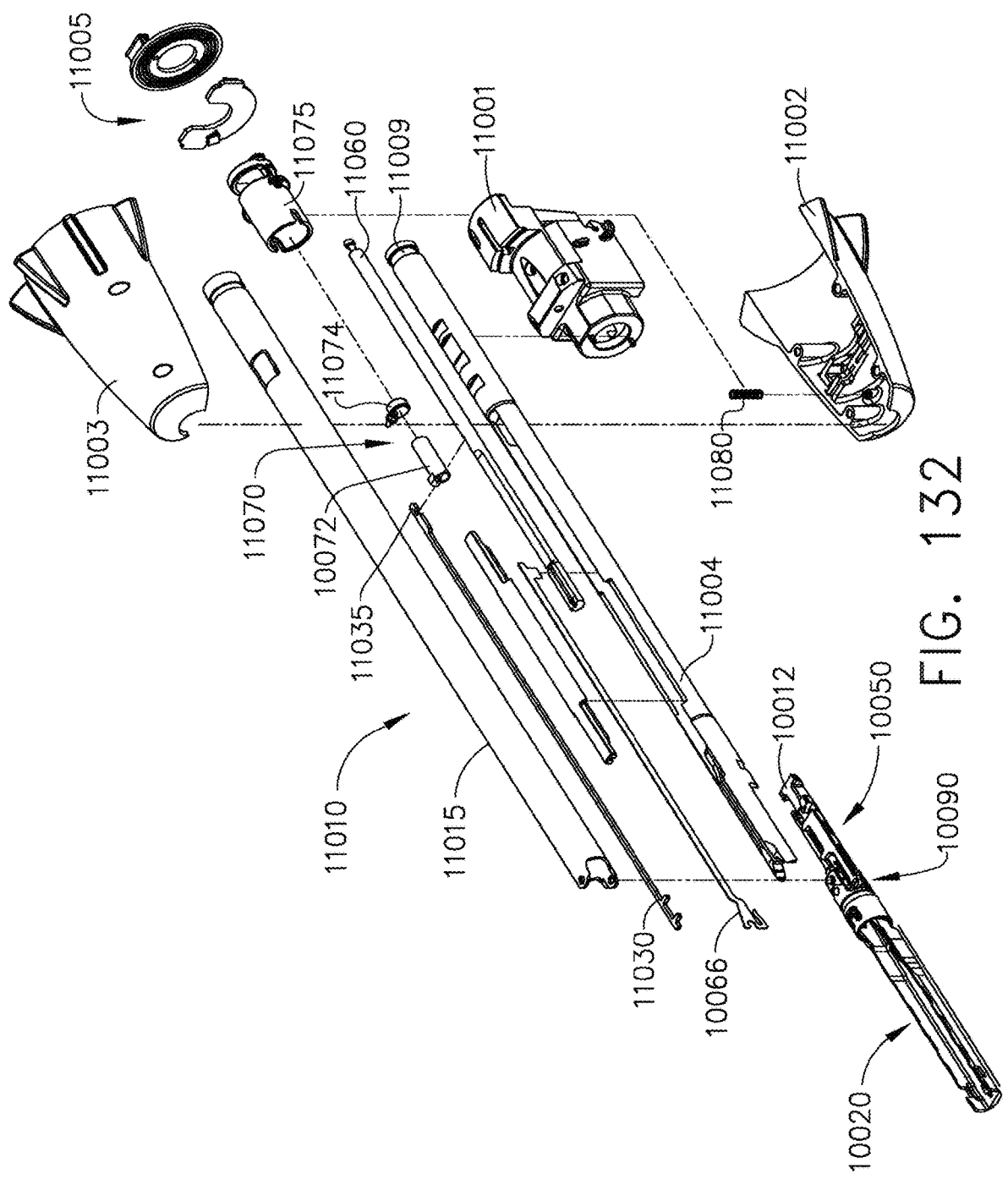
Figure 133:
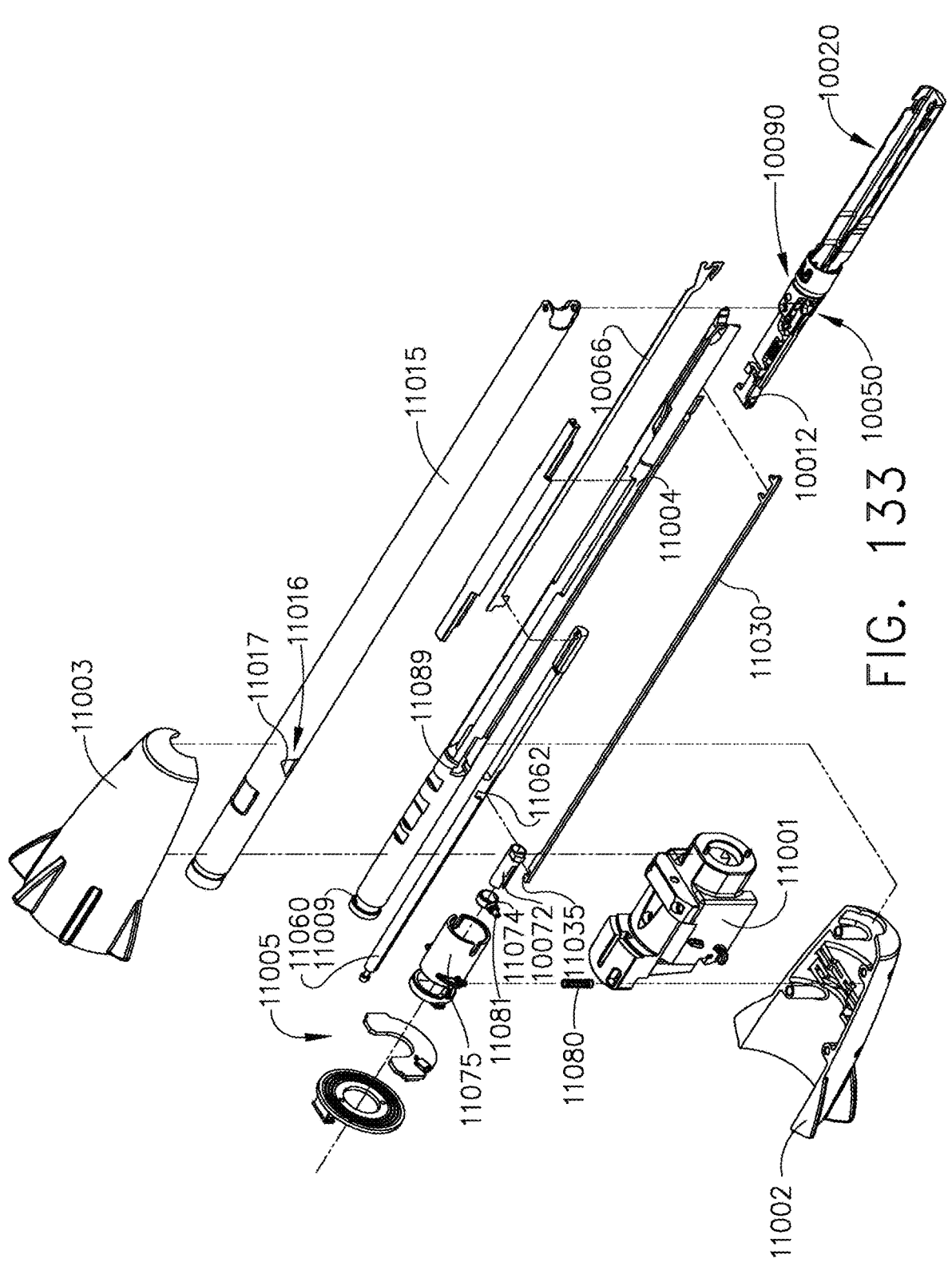
Figure 134:
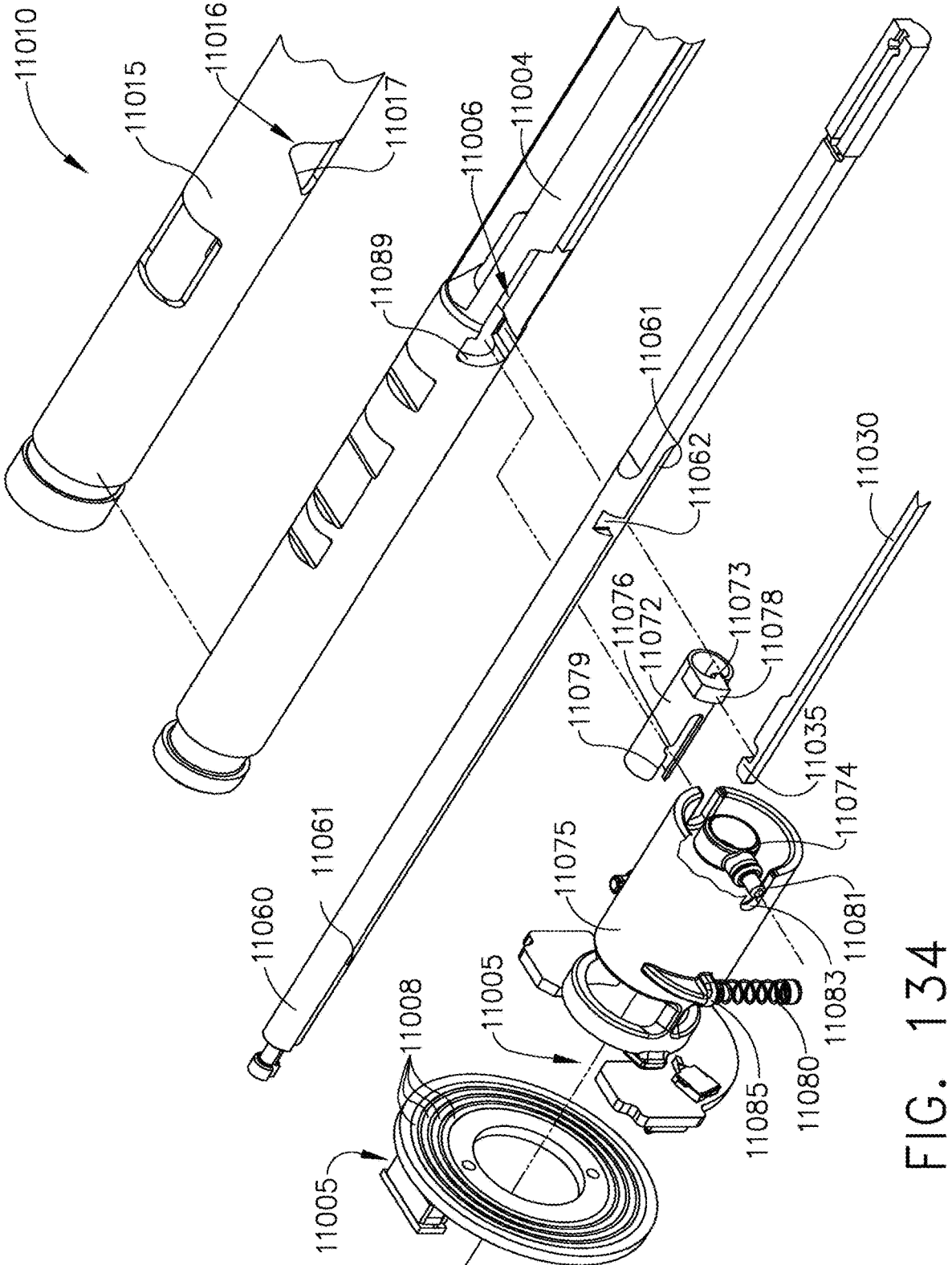
Figure 135:
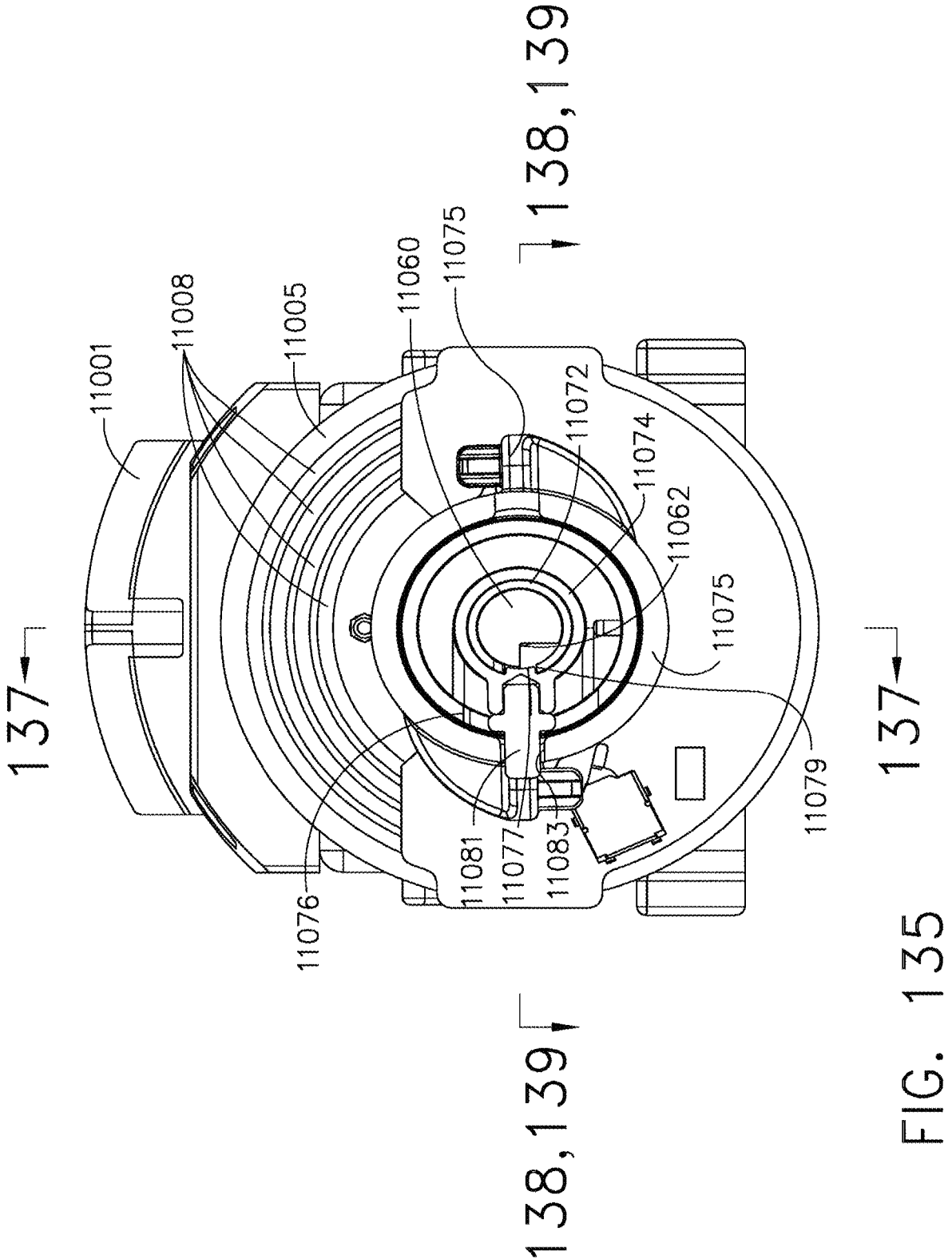
Figure 136:
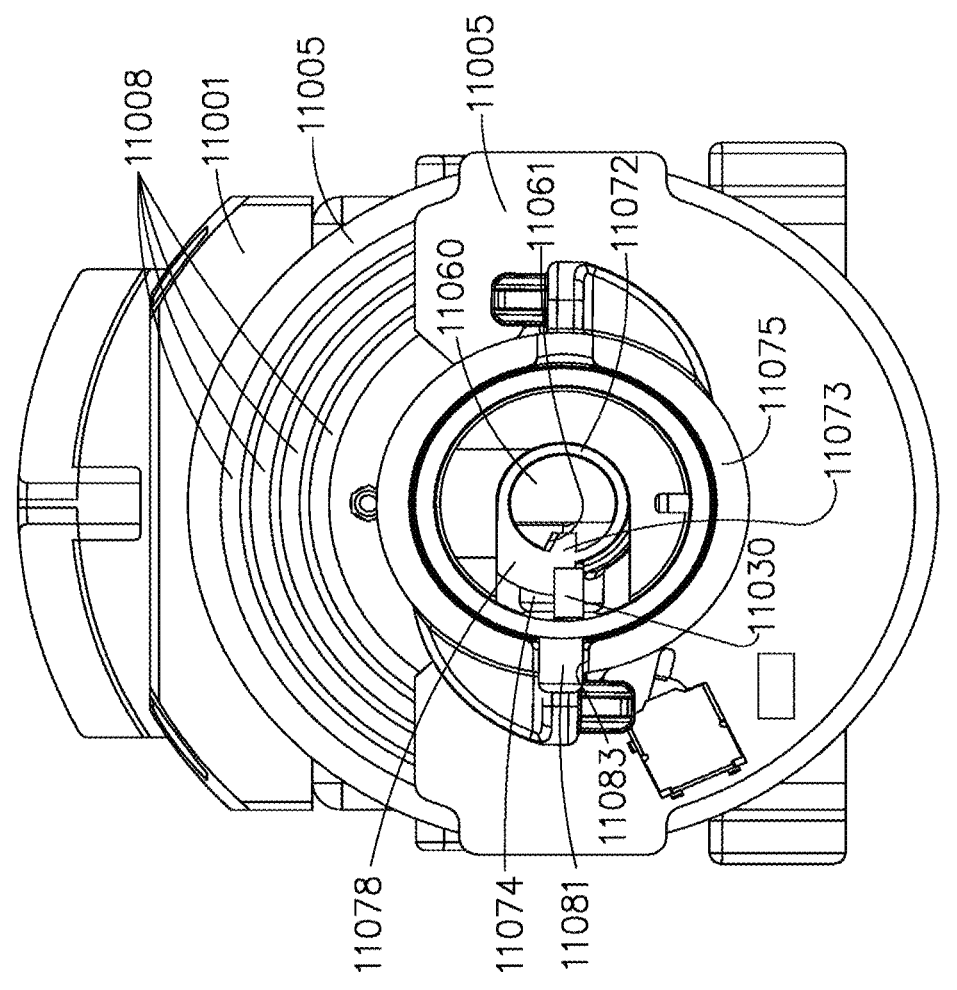
Figure 137:
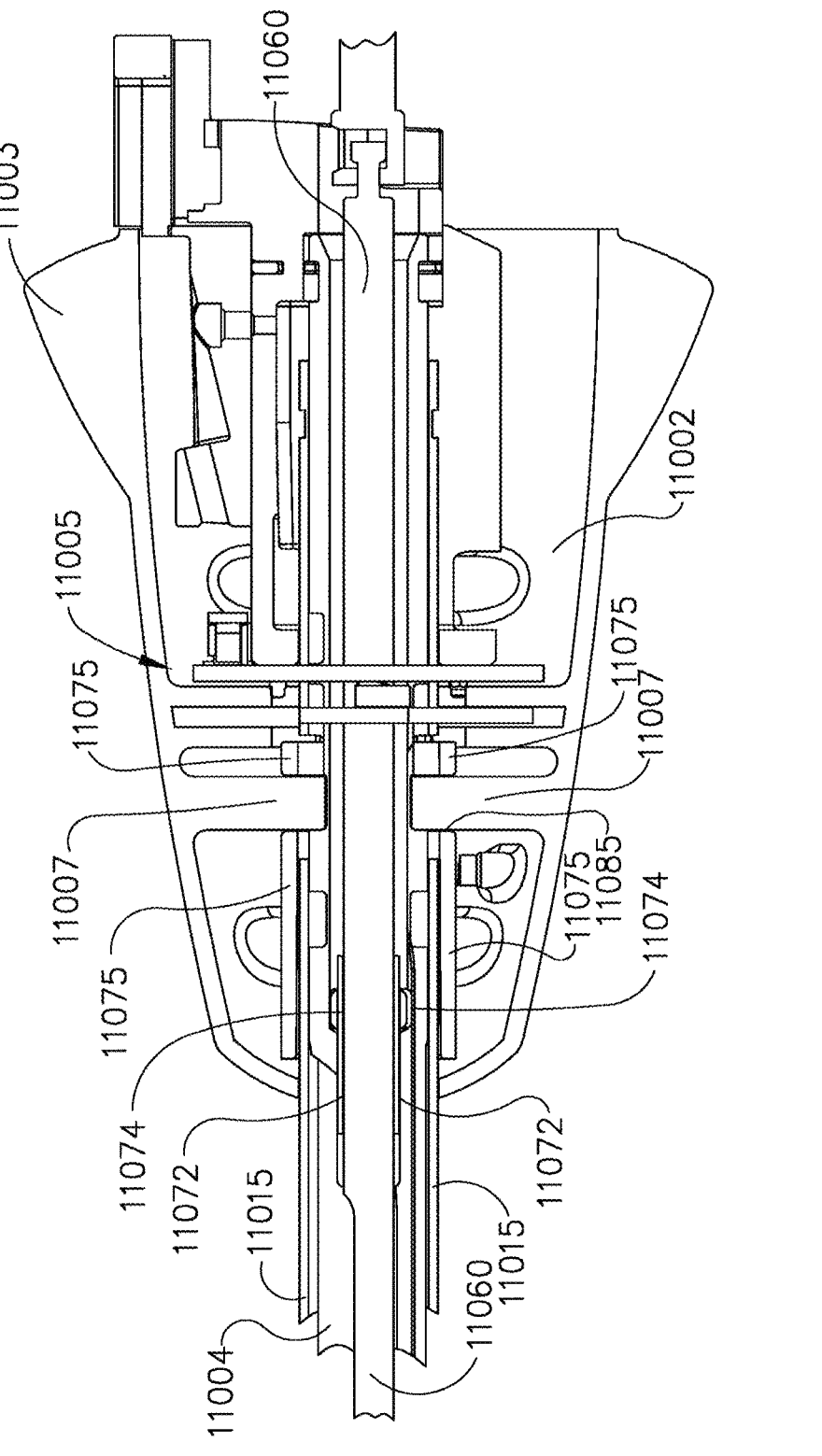
Figure 138:
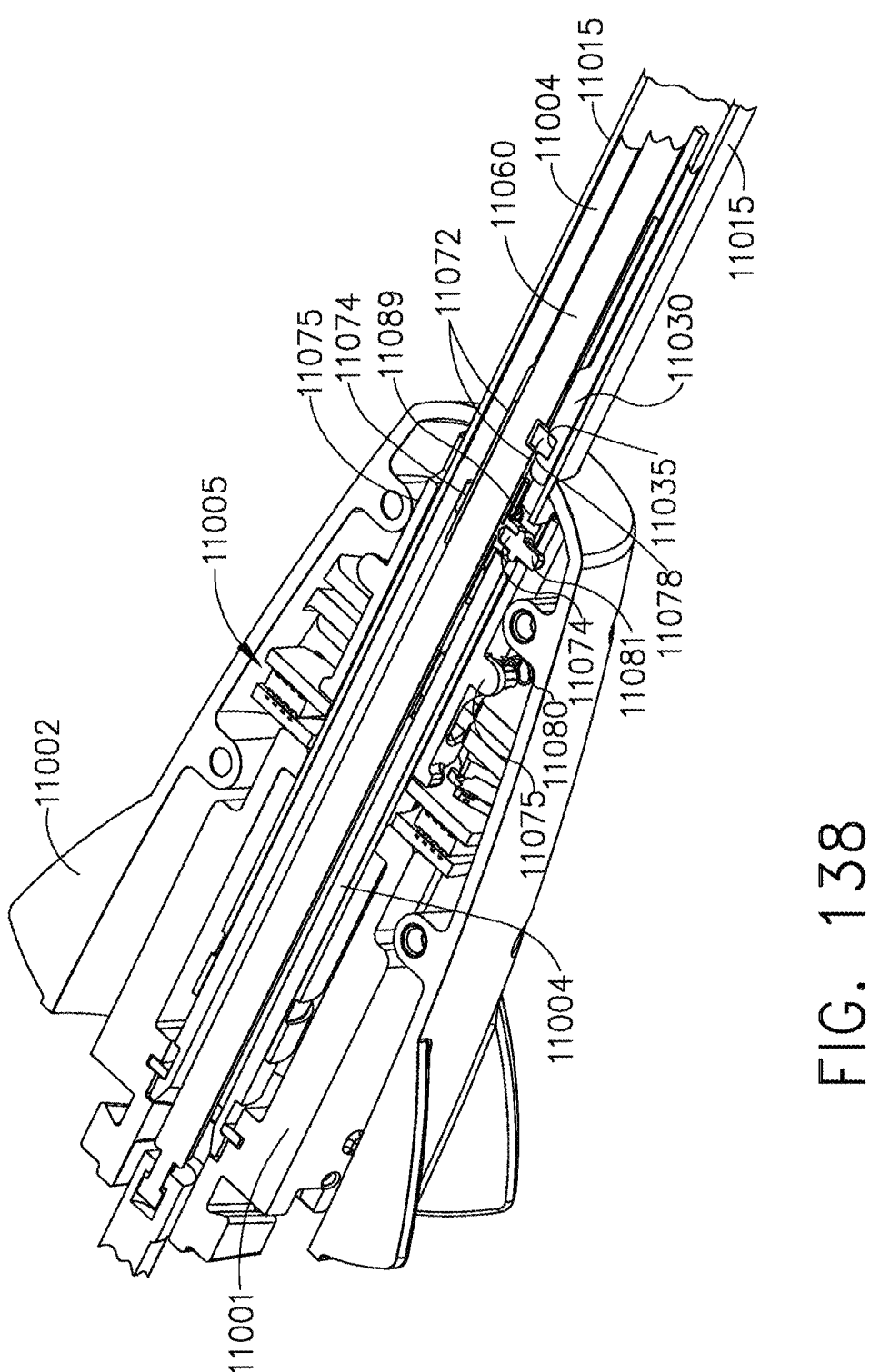
Figure 139:
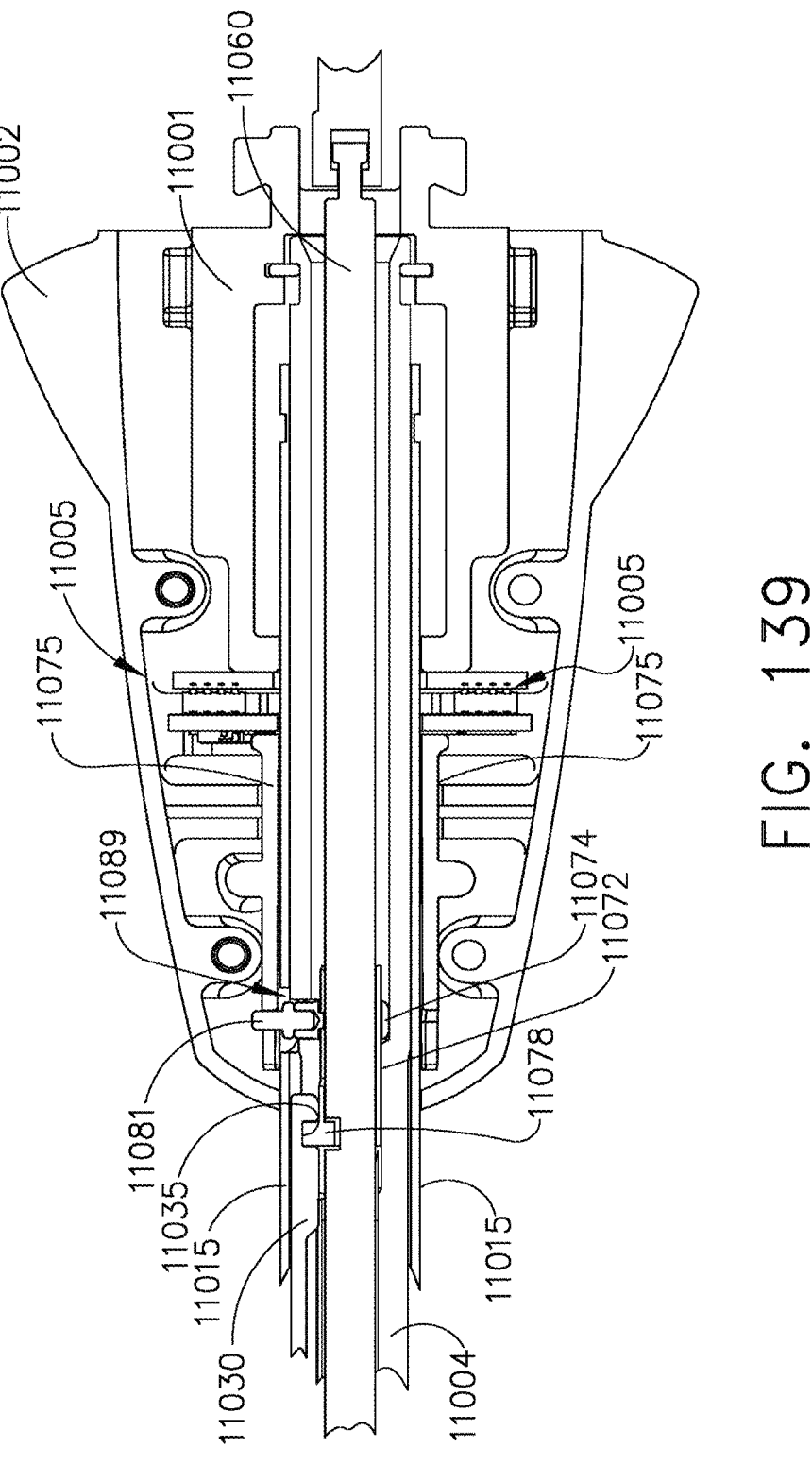
Figure 140:
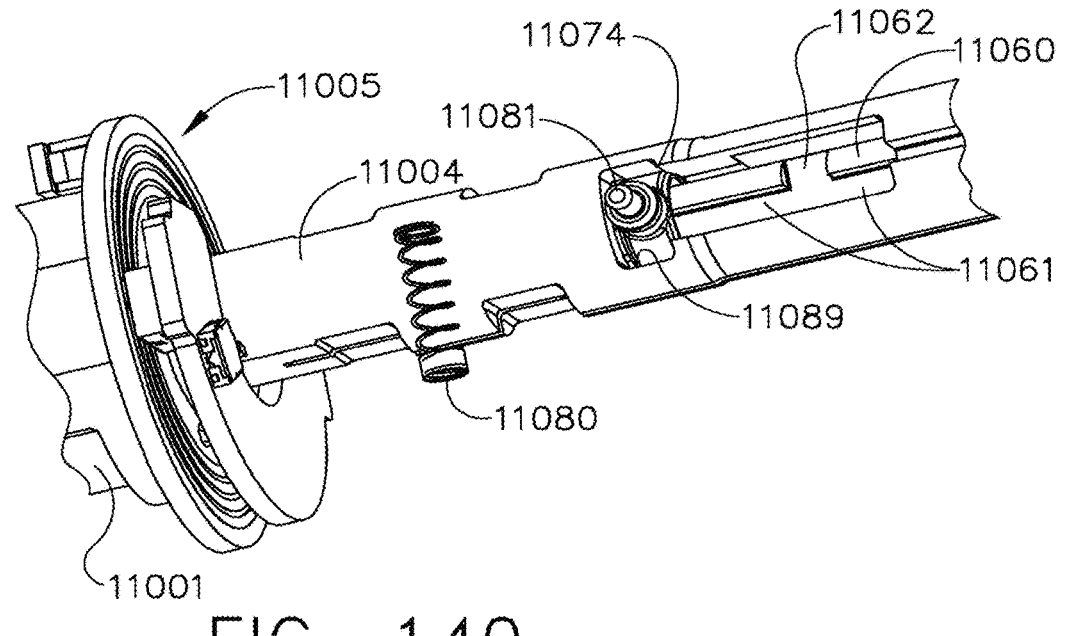
Figure 141:
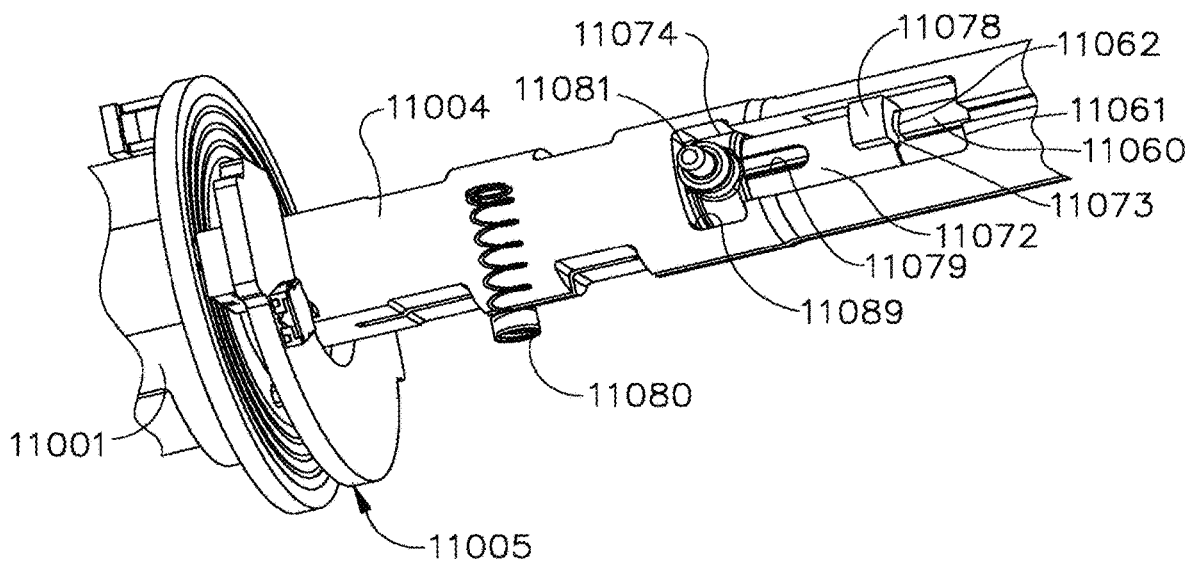
Figure 142:
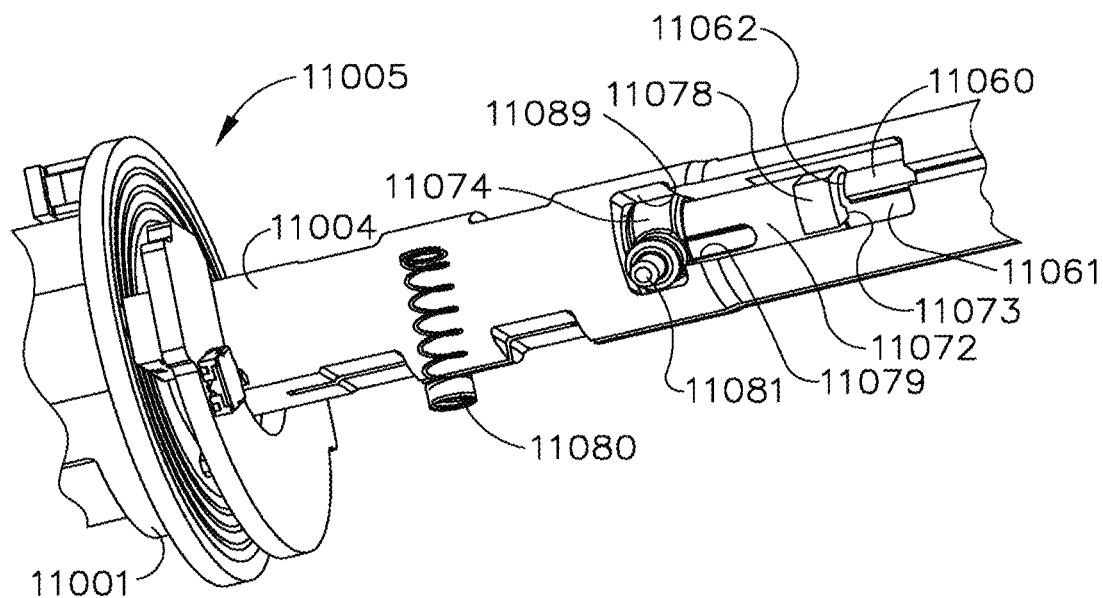
Figure 143:
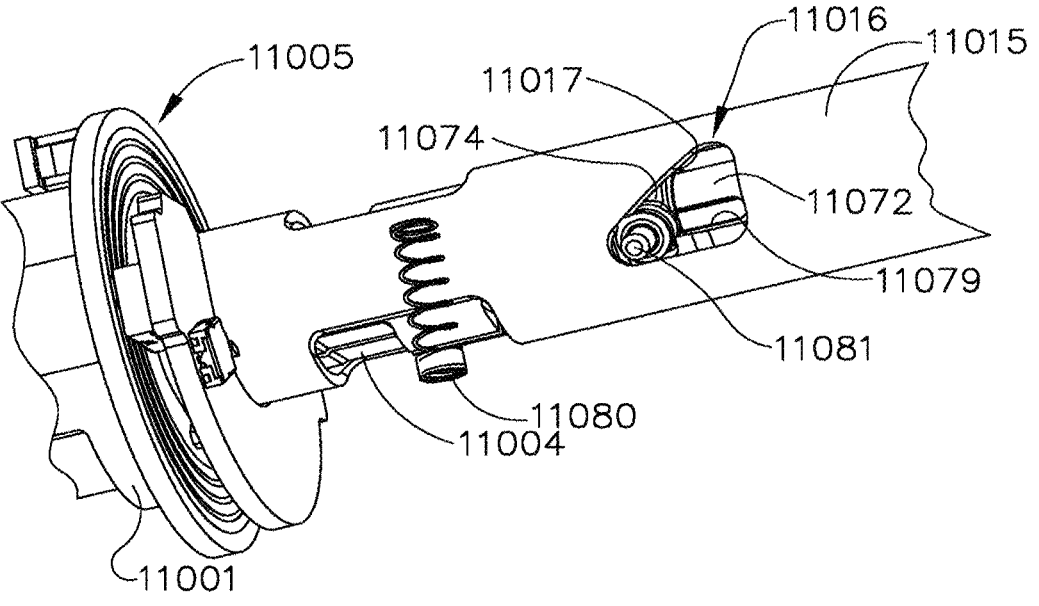
Figure 144:
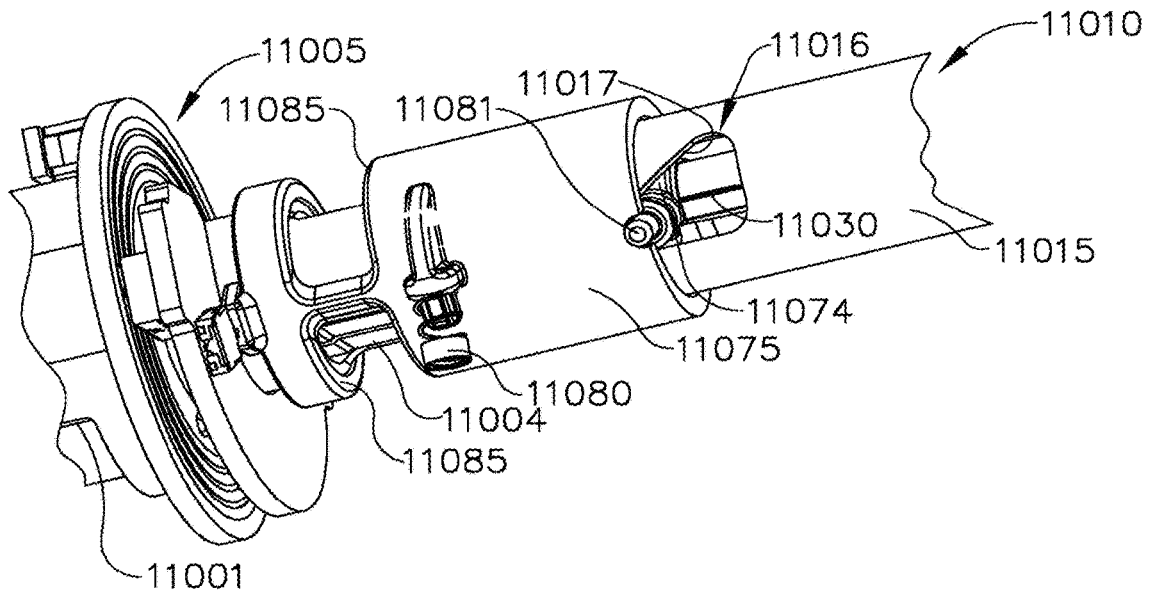
Figure 145:
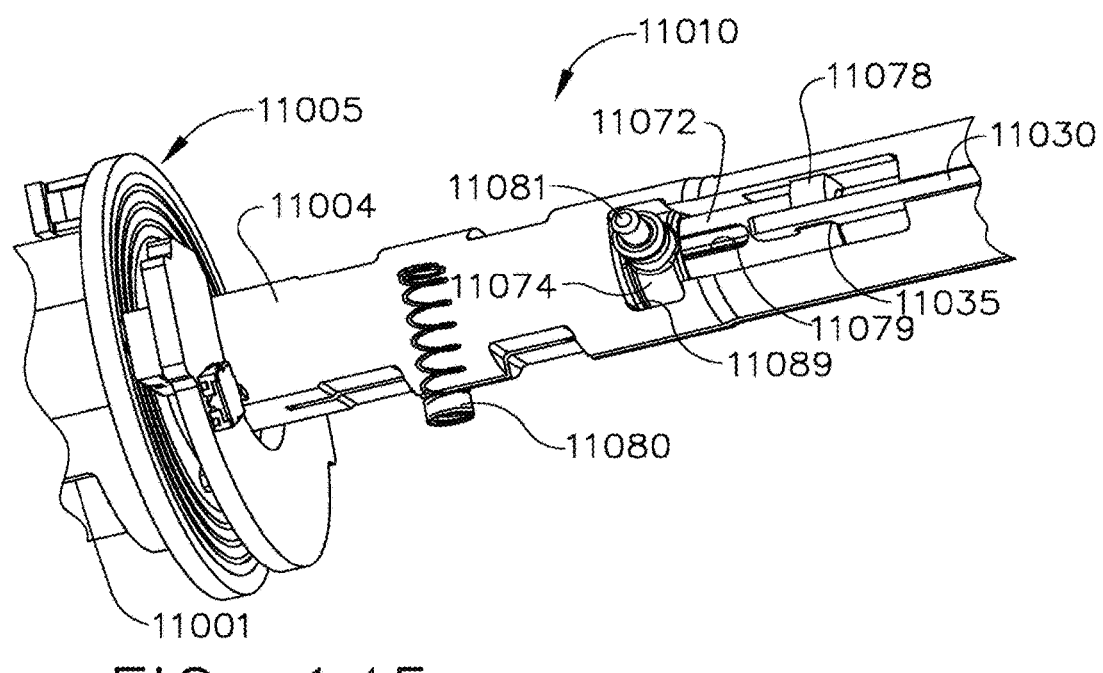
Figure 146:
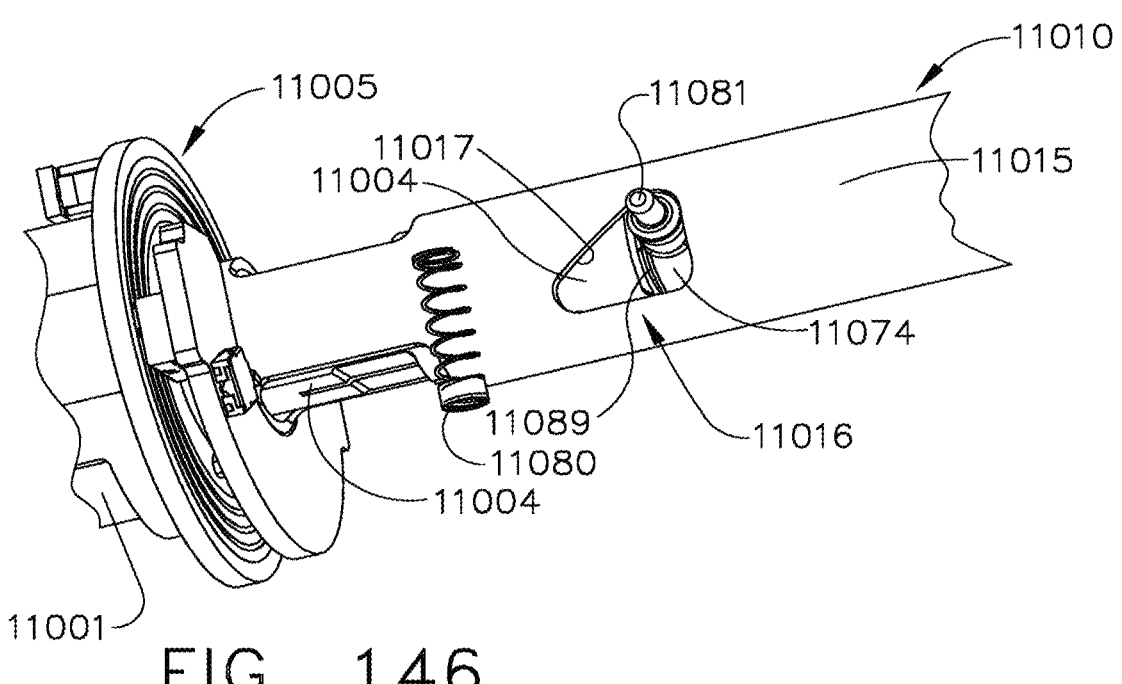
Figure 147:
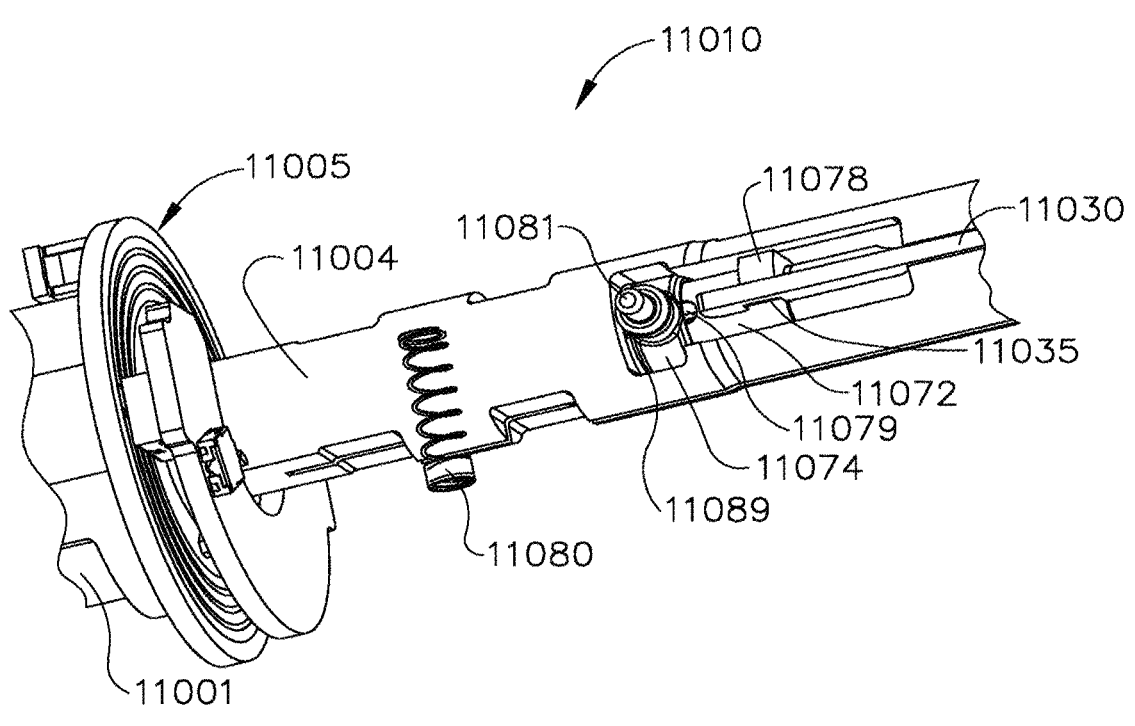
Figure 148:
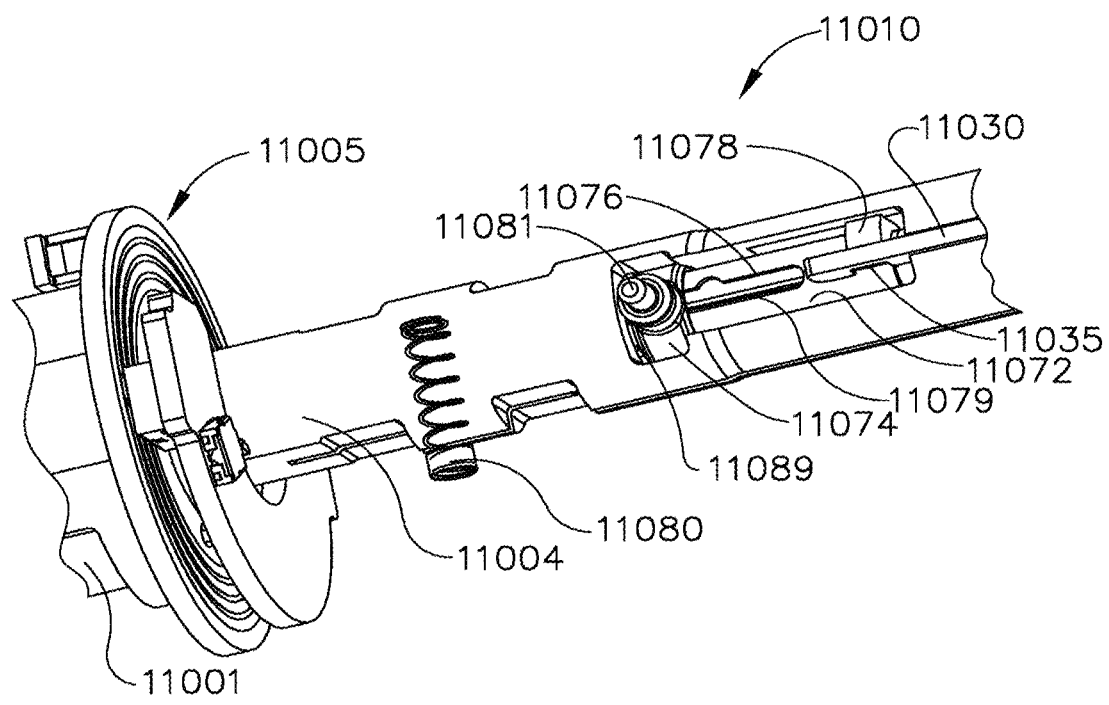
Figure 149:
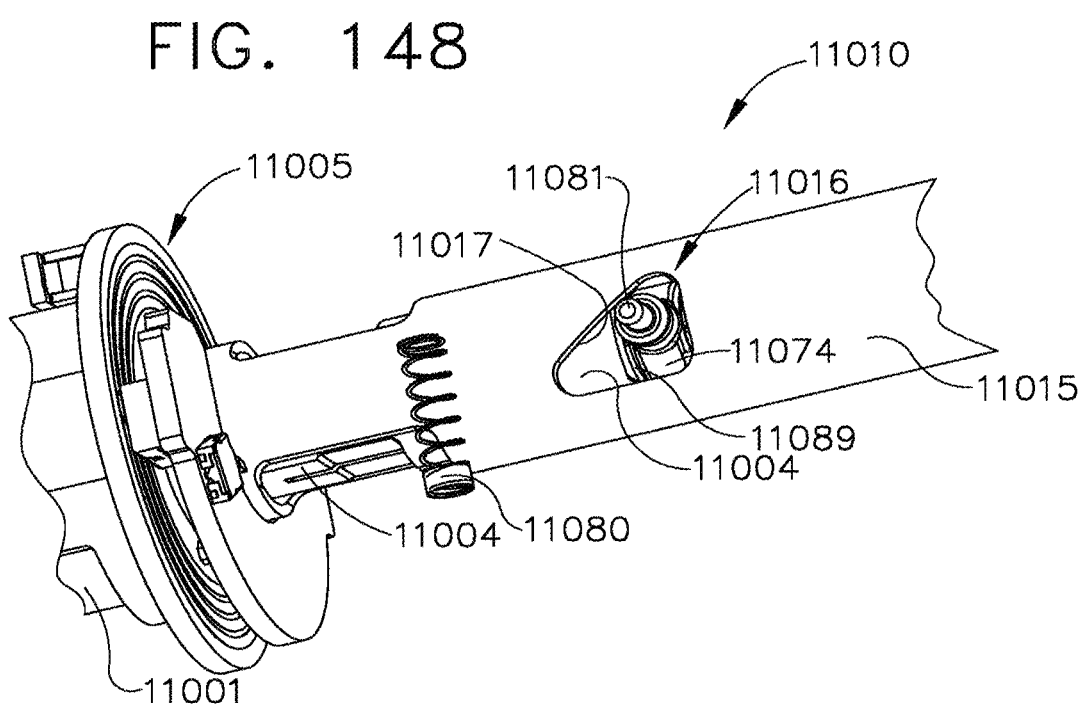
Figure 150:
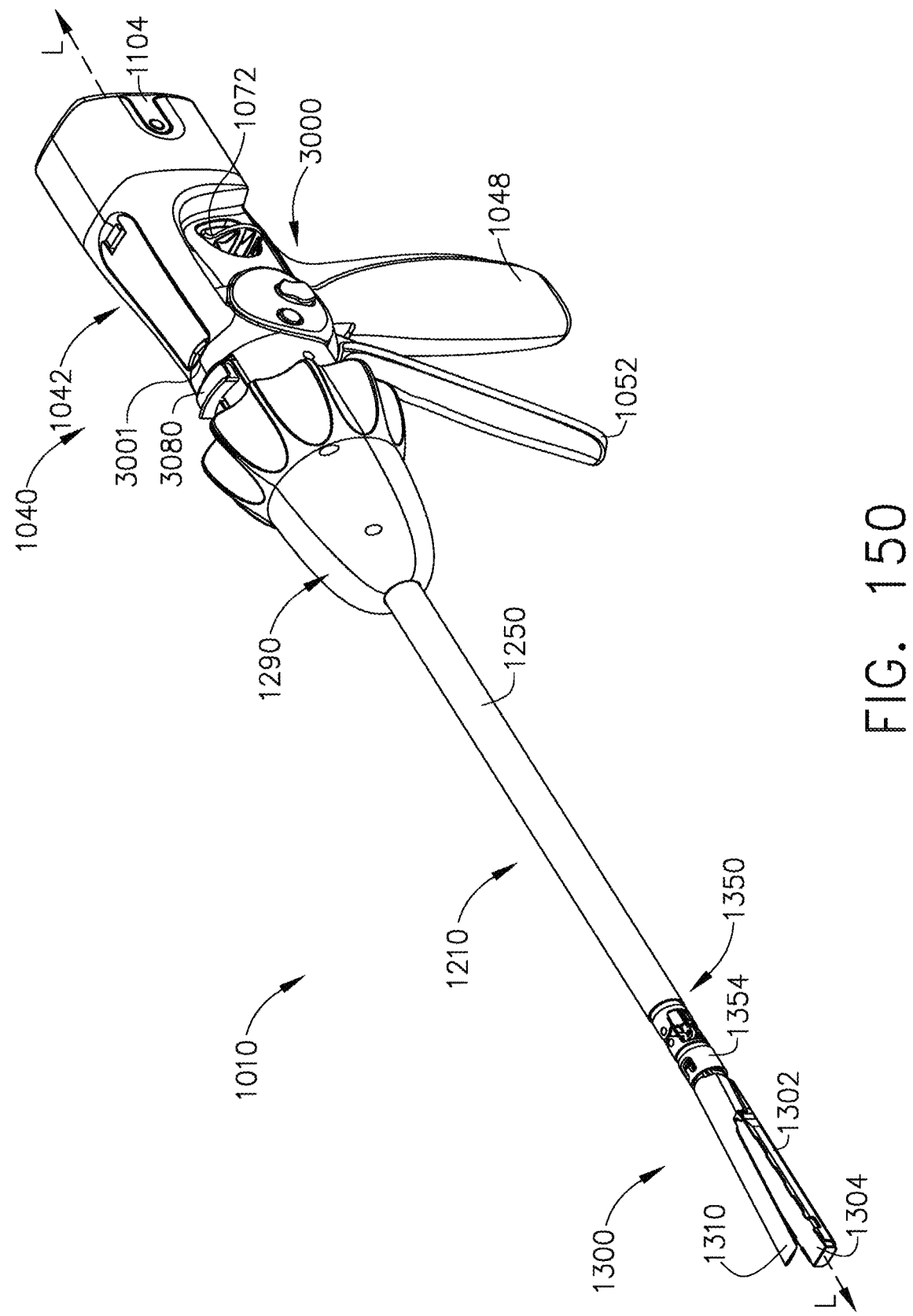
Figure 151:
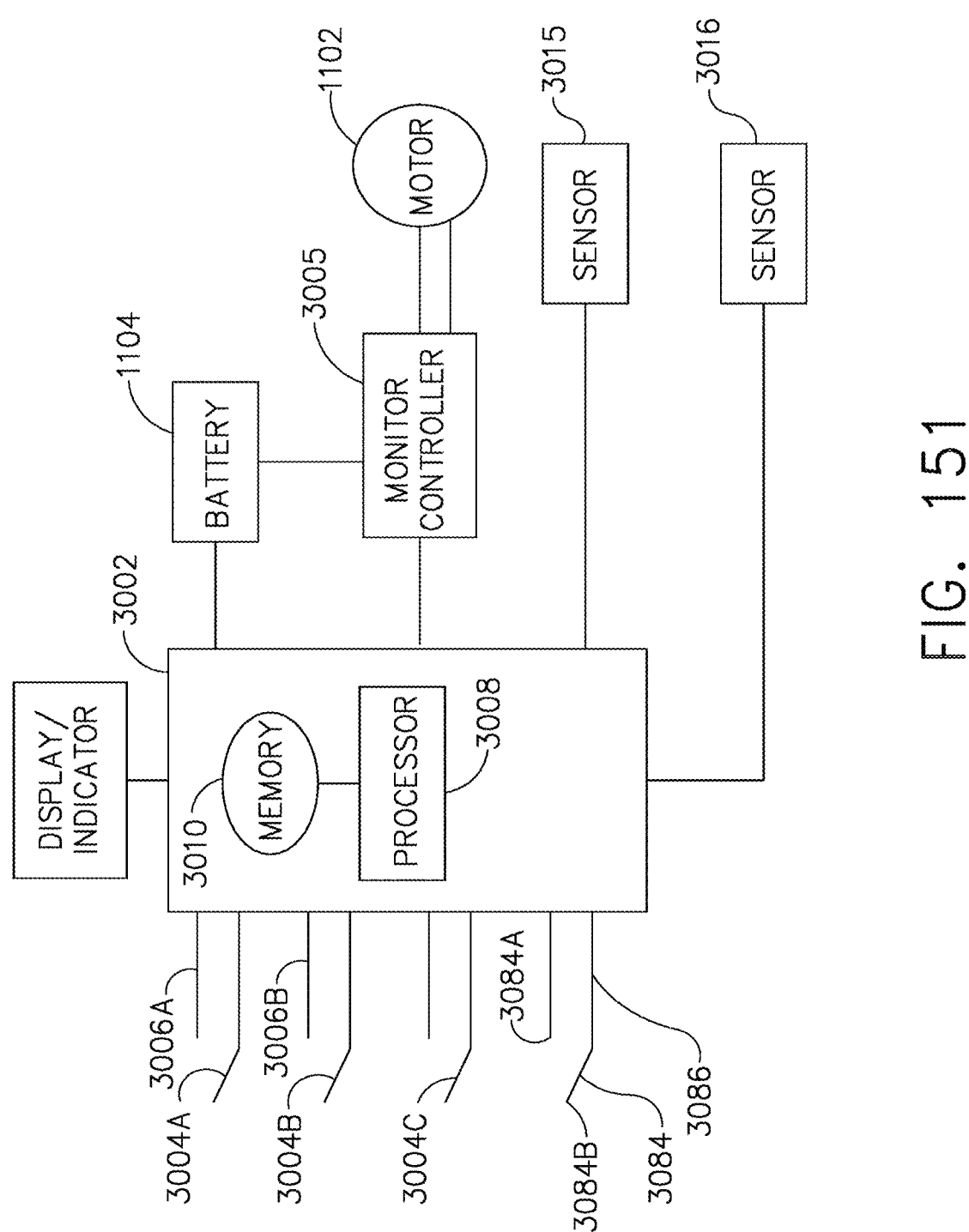
Figure 152:
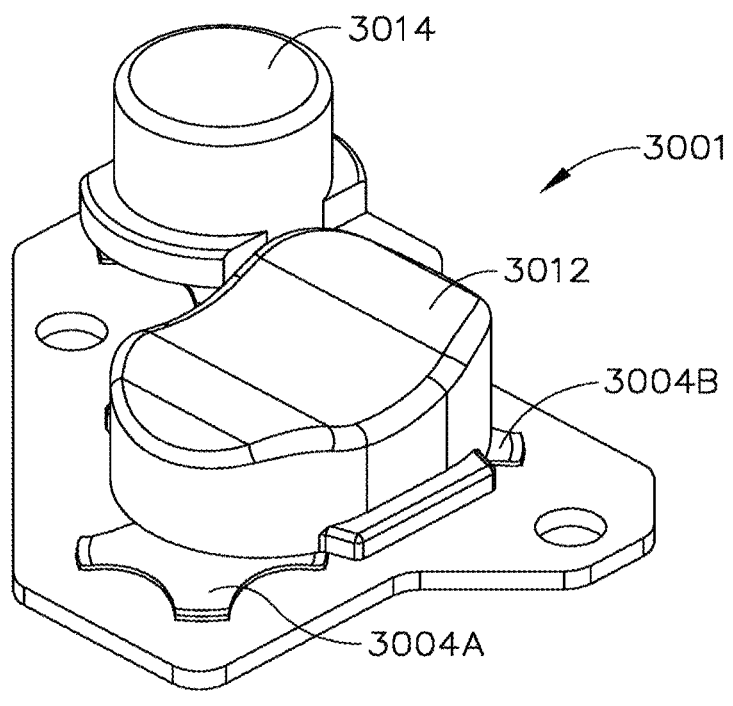
Figure 153:
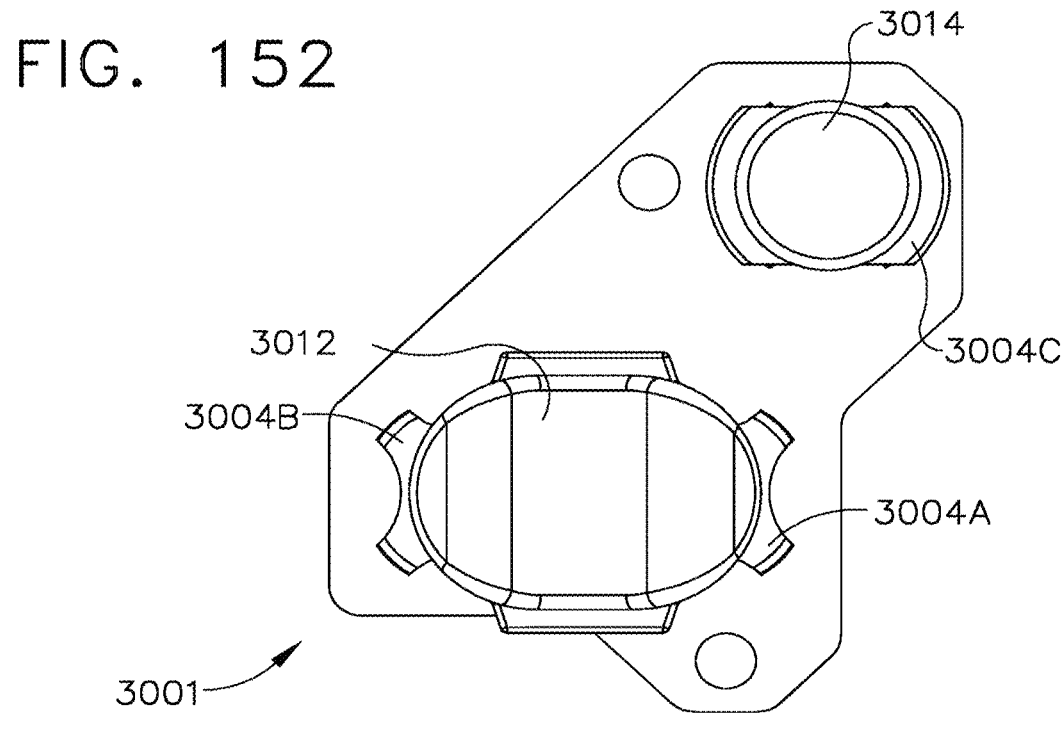
Figure 154:
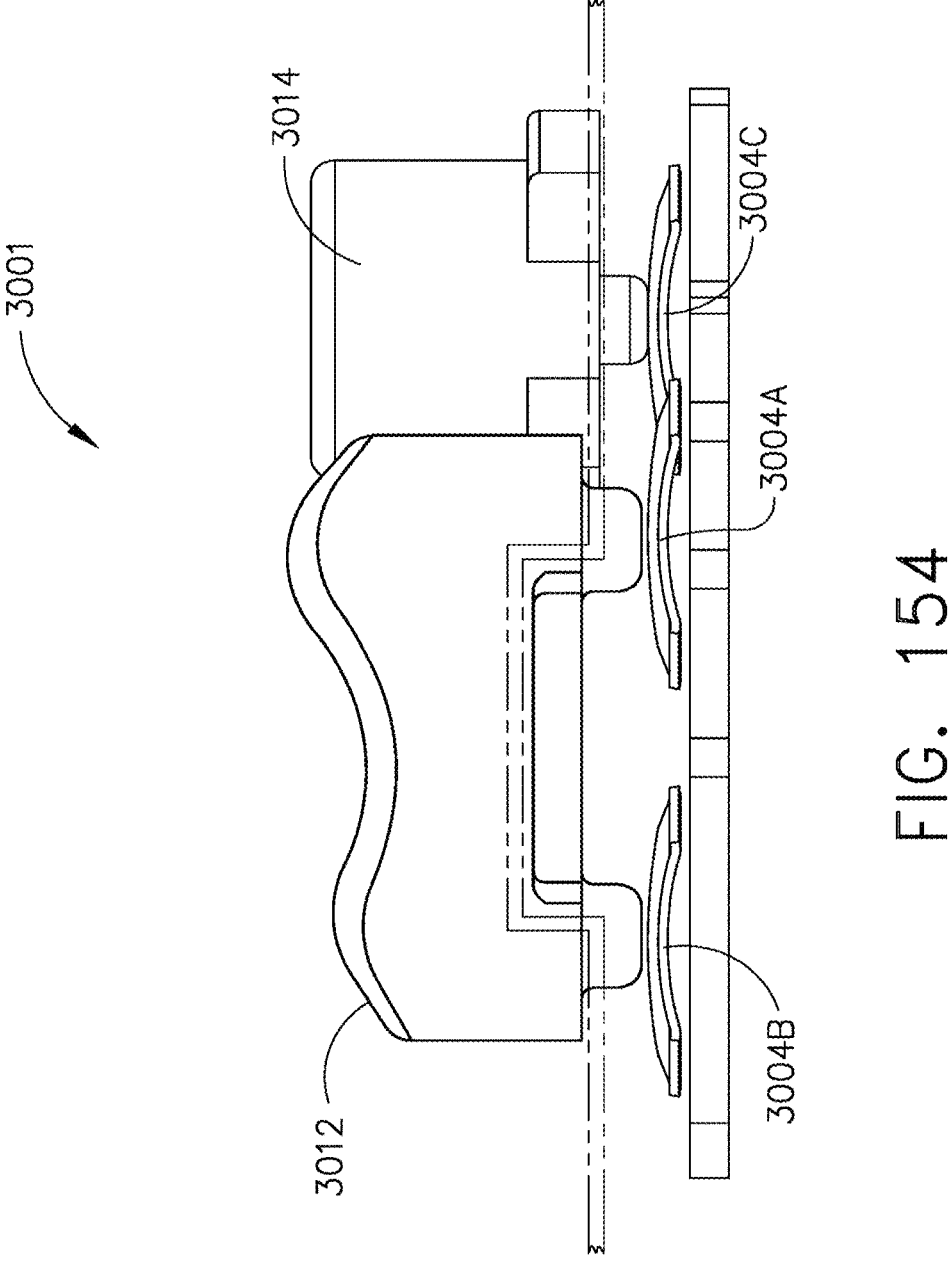
Figure 155:
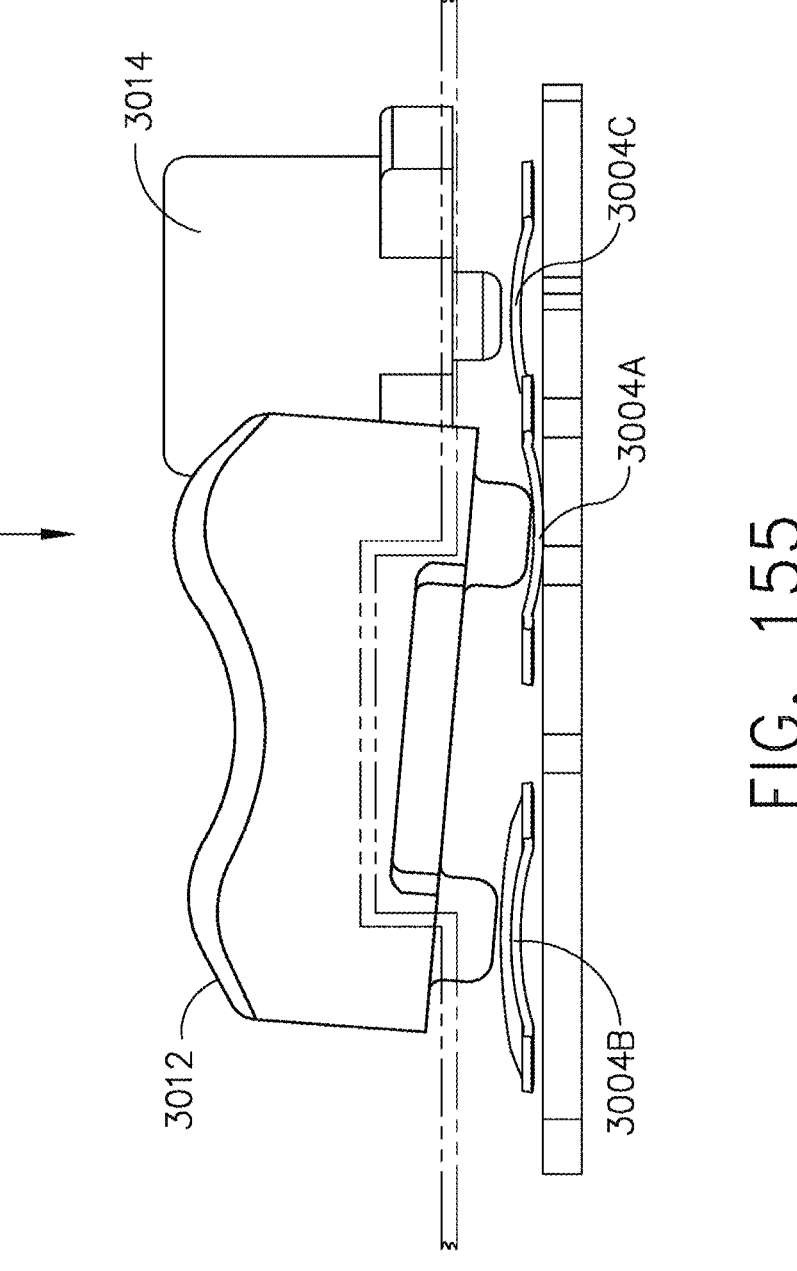
Figure 156:
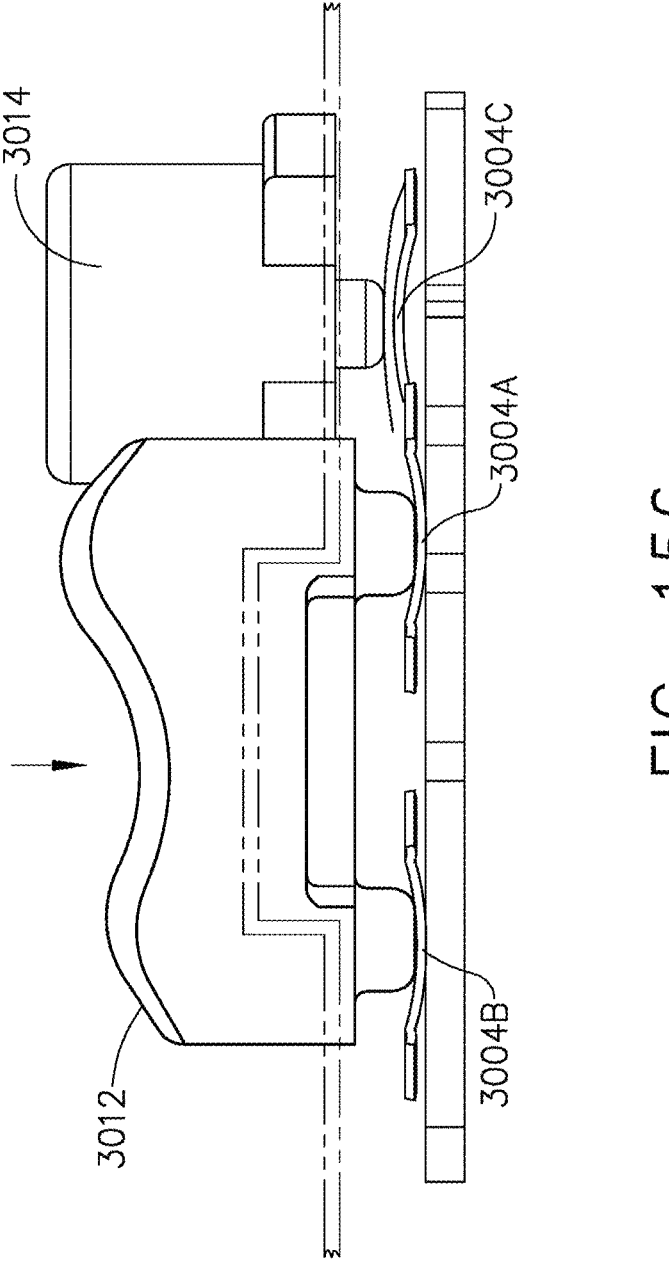
Figures 157, 158, 159:
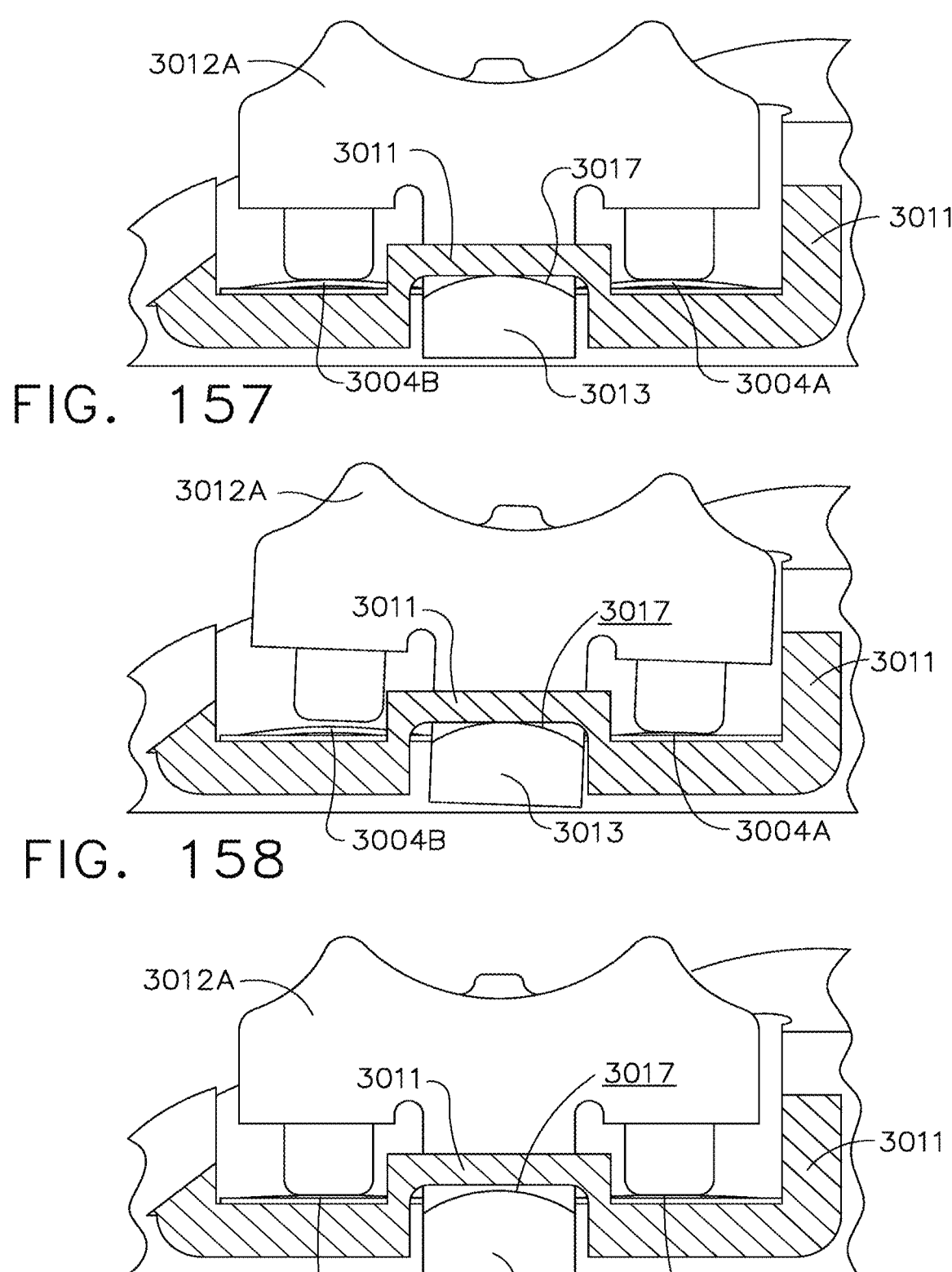
Figure 160:
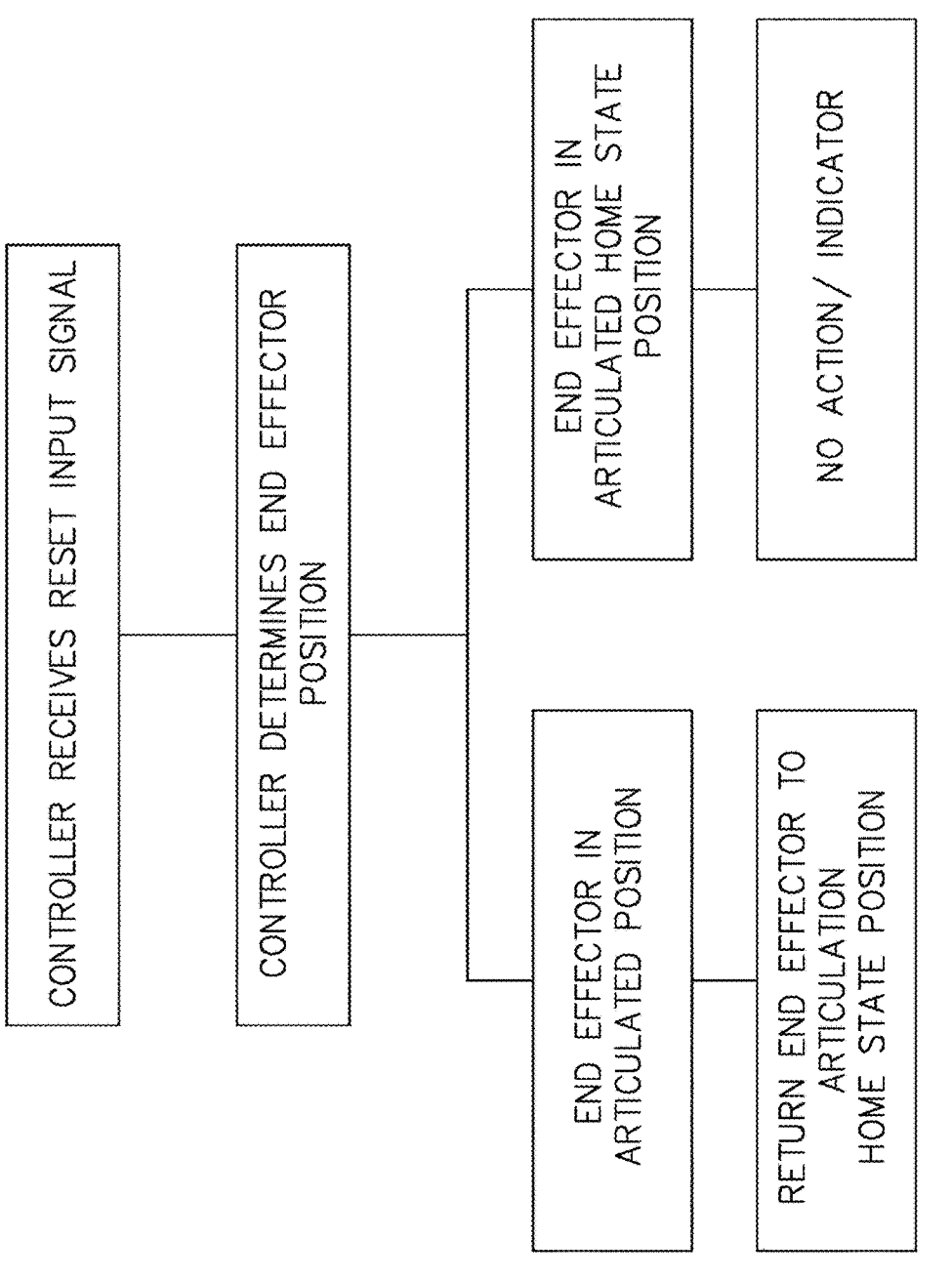
Figure 161:
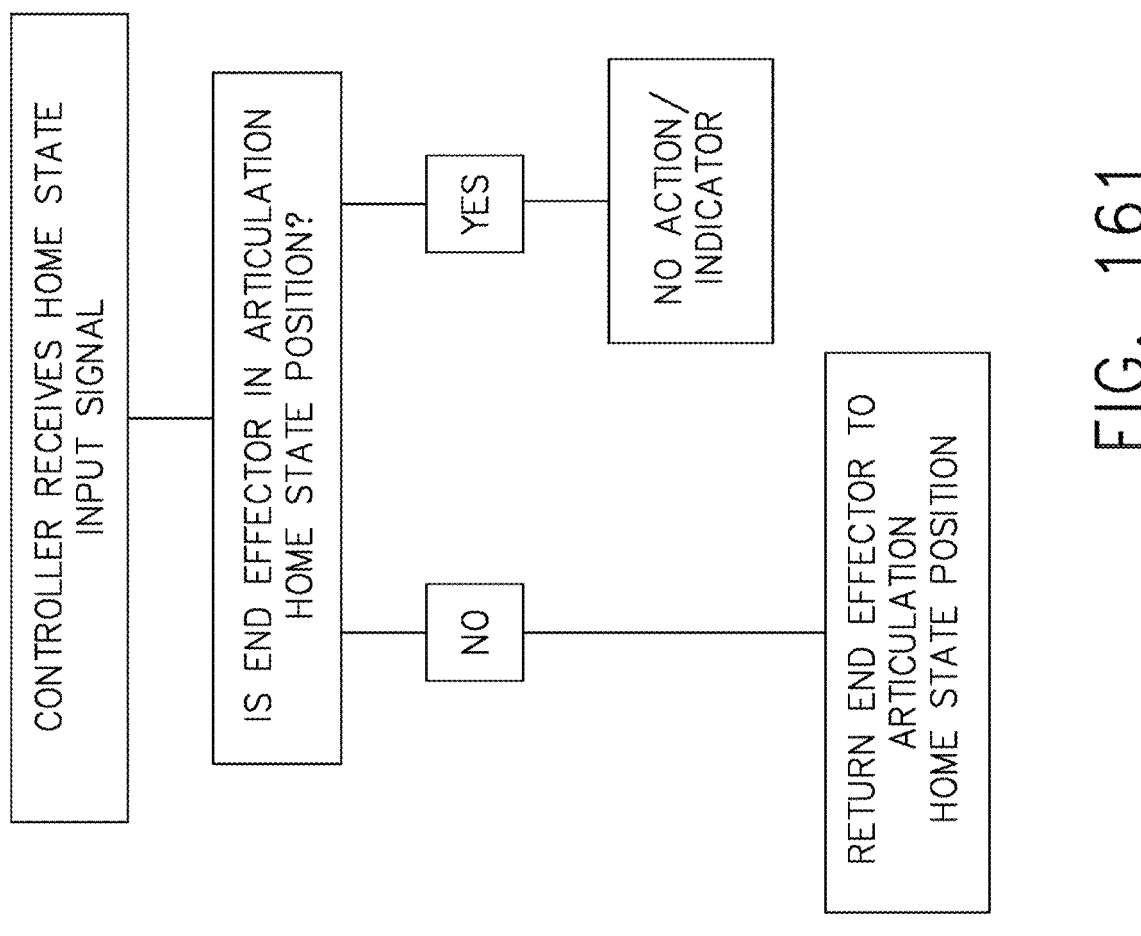
Figure 162:
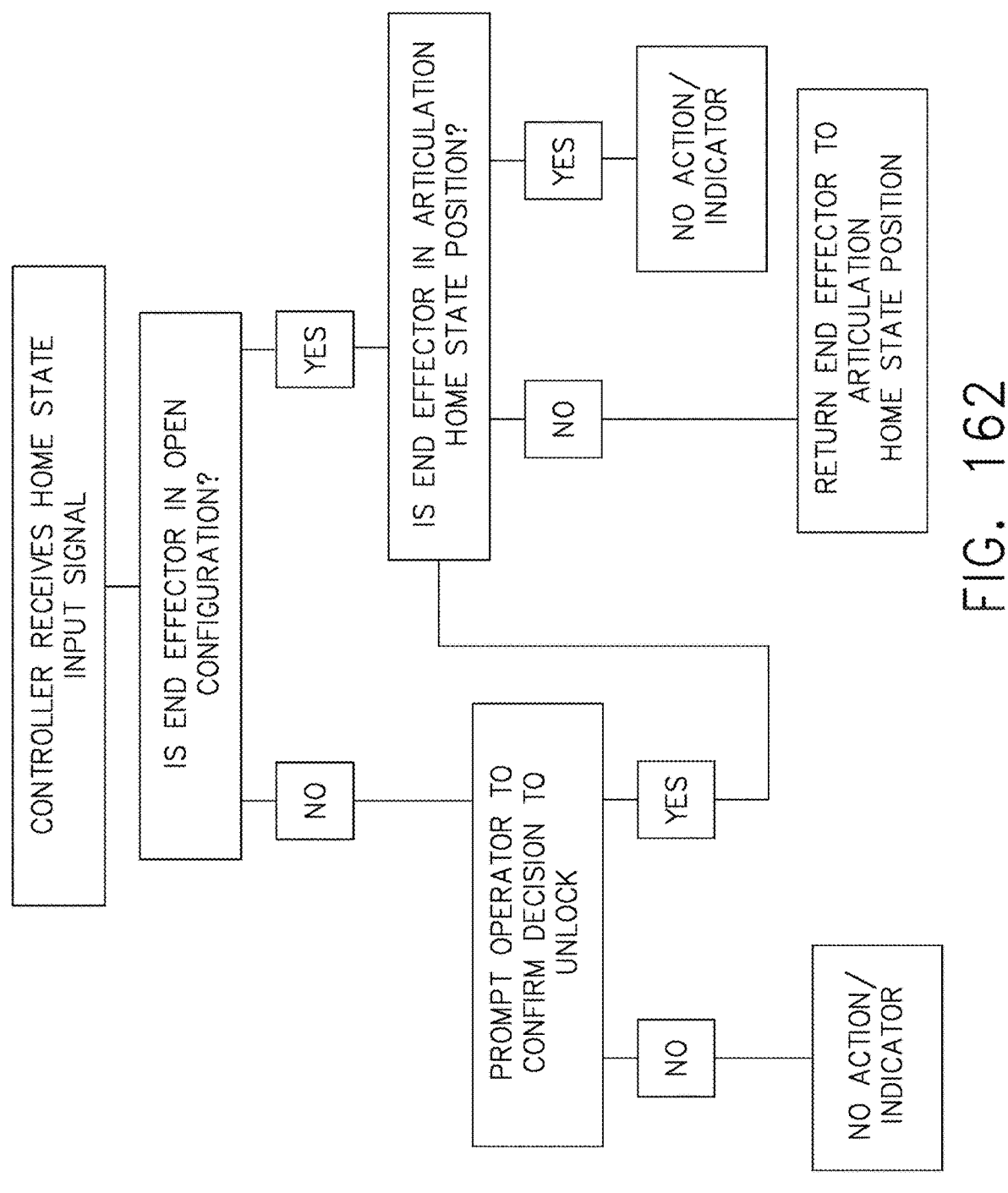
Figure 163:
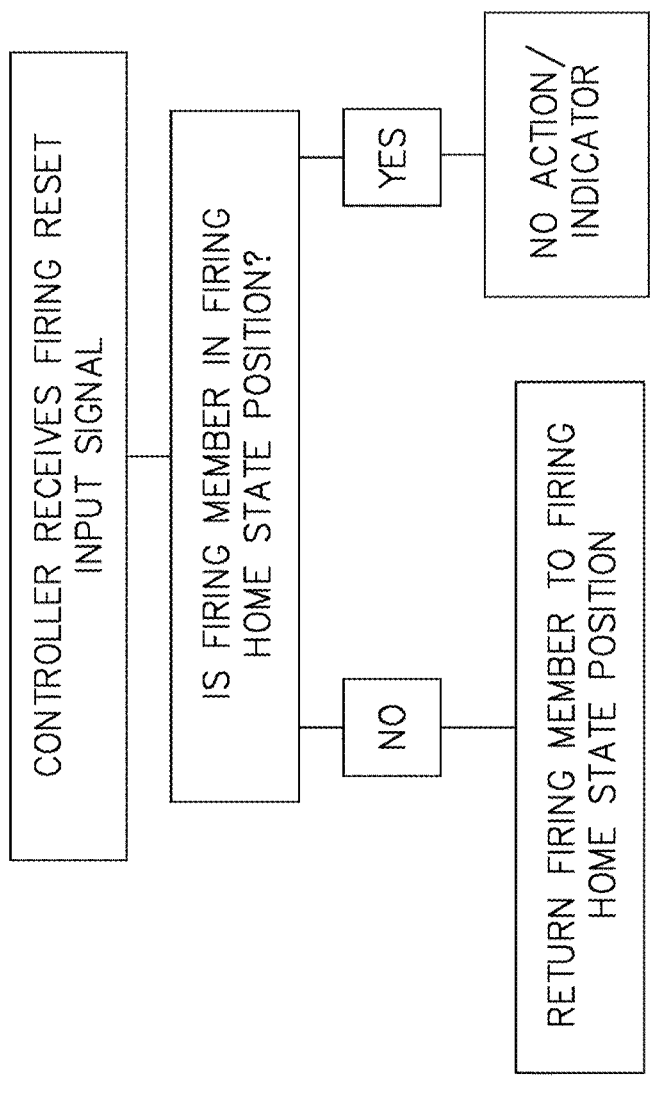
Figure 164:
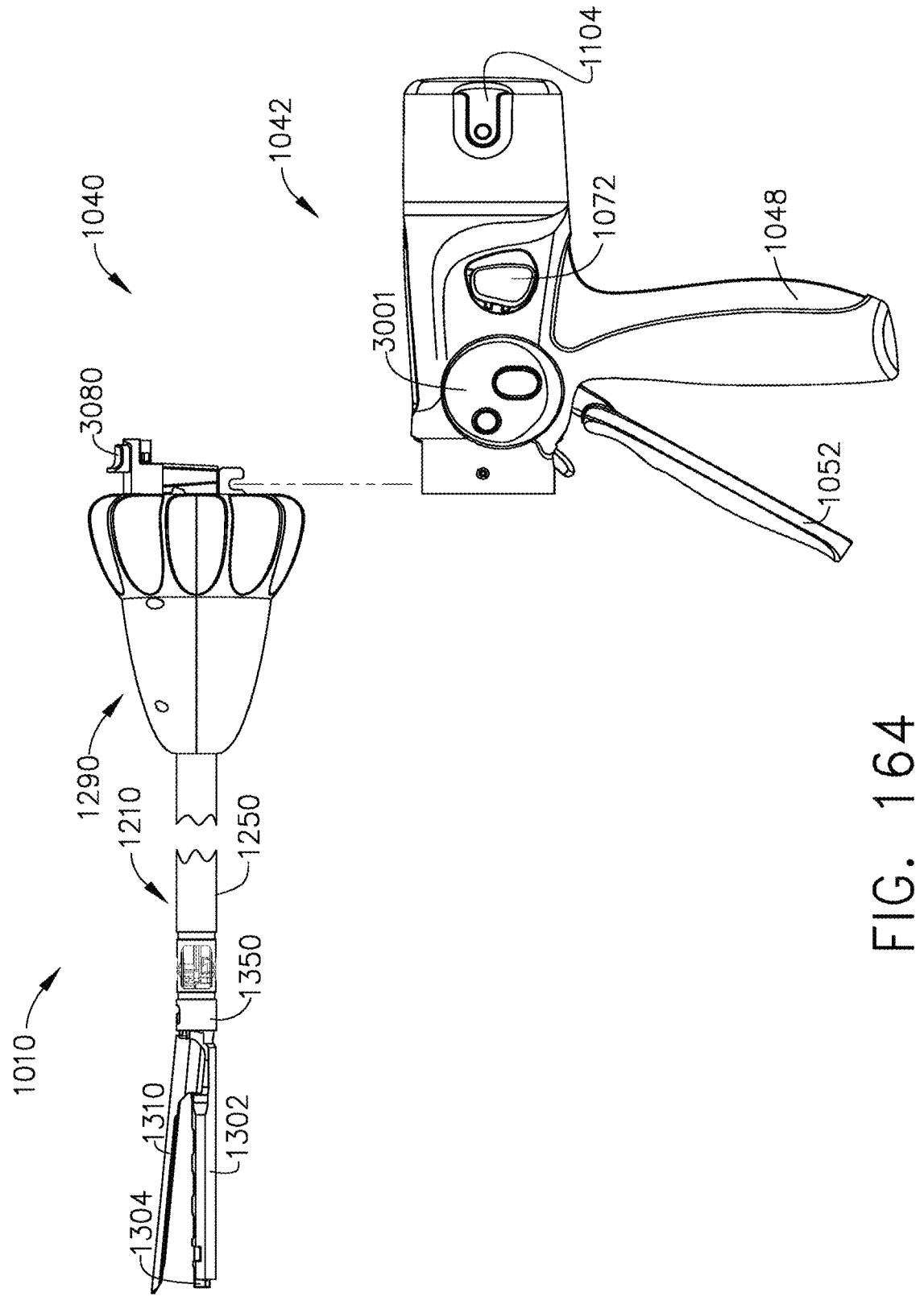
Figure 165:
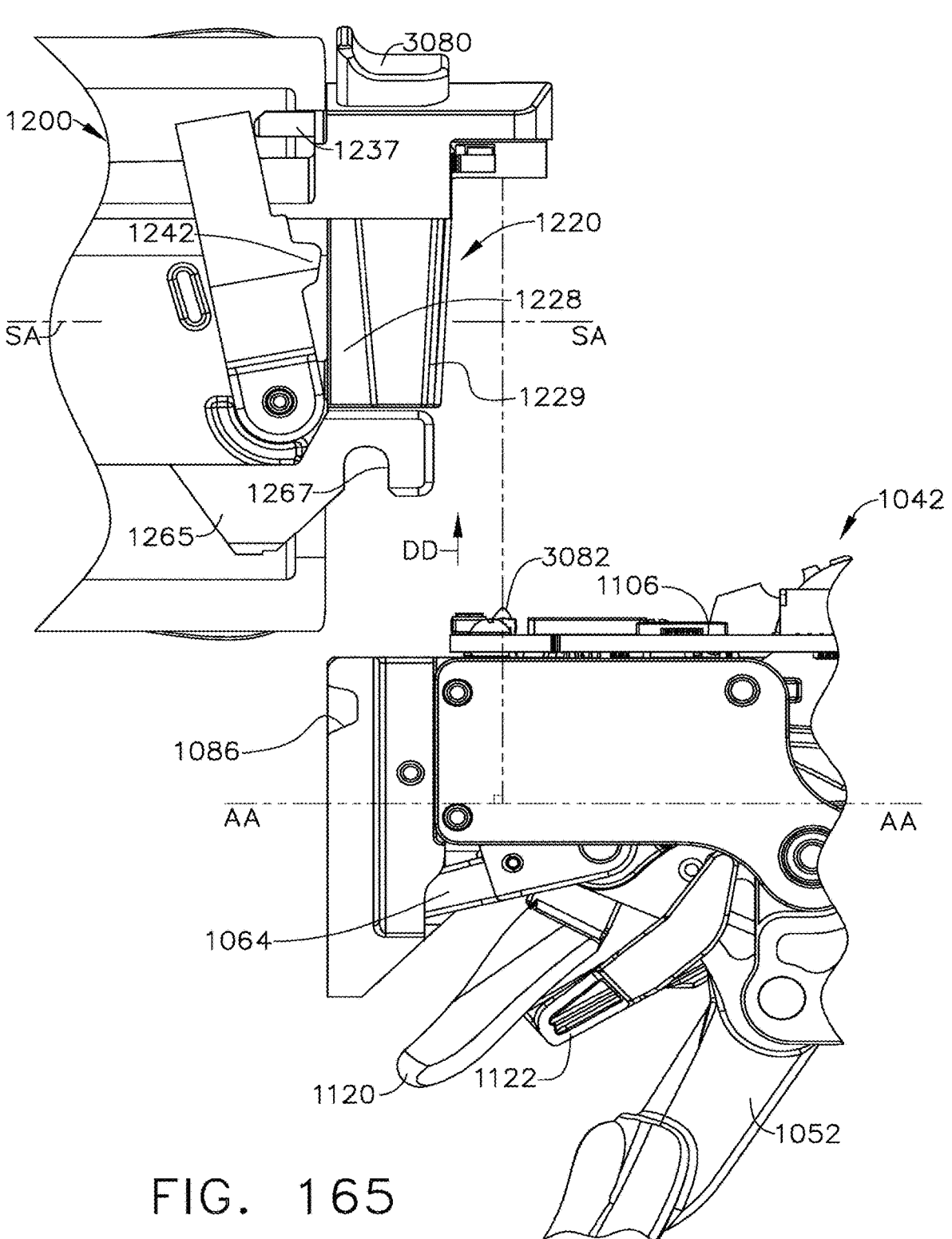
Figure 166:
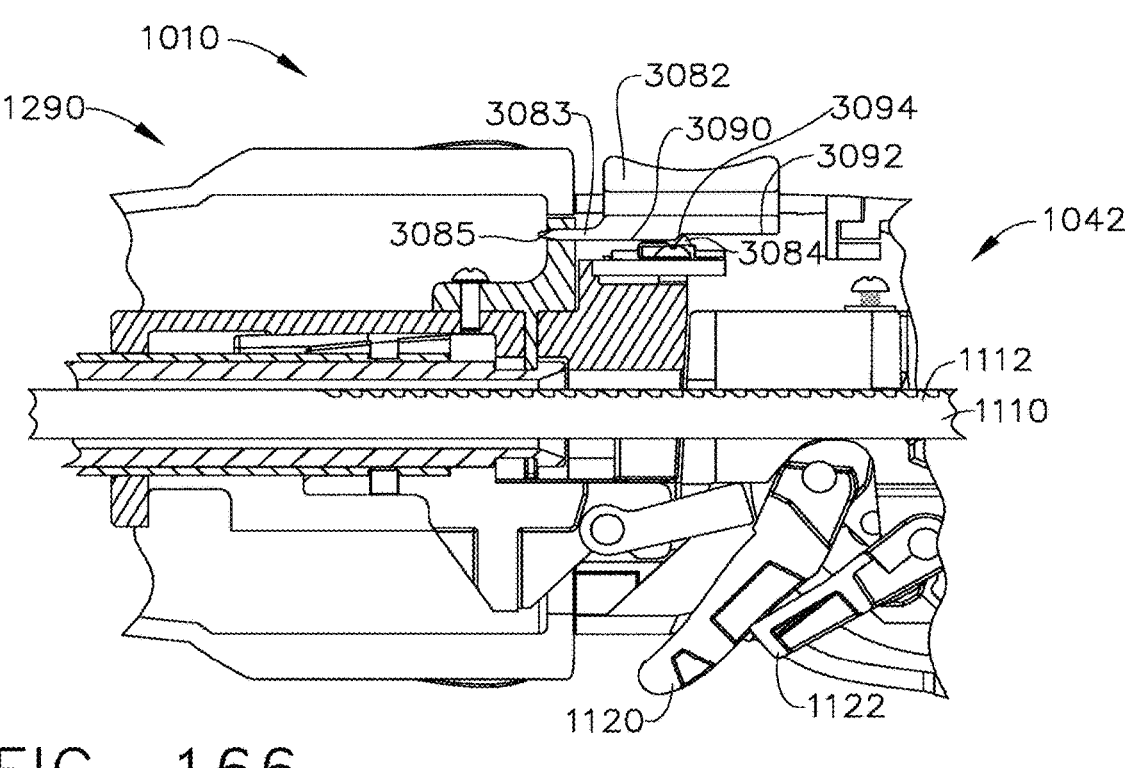
Figure 167:
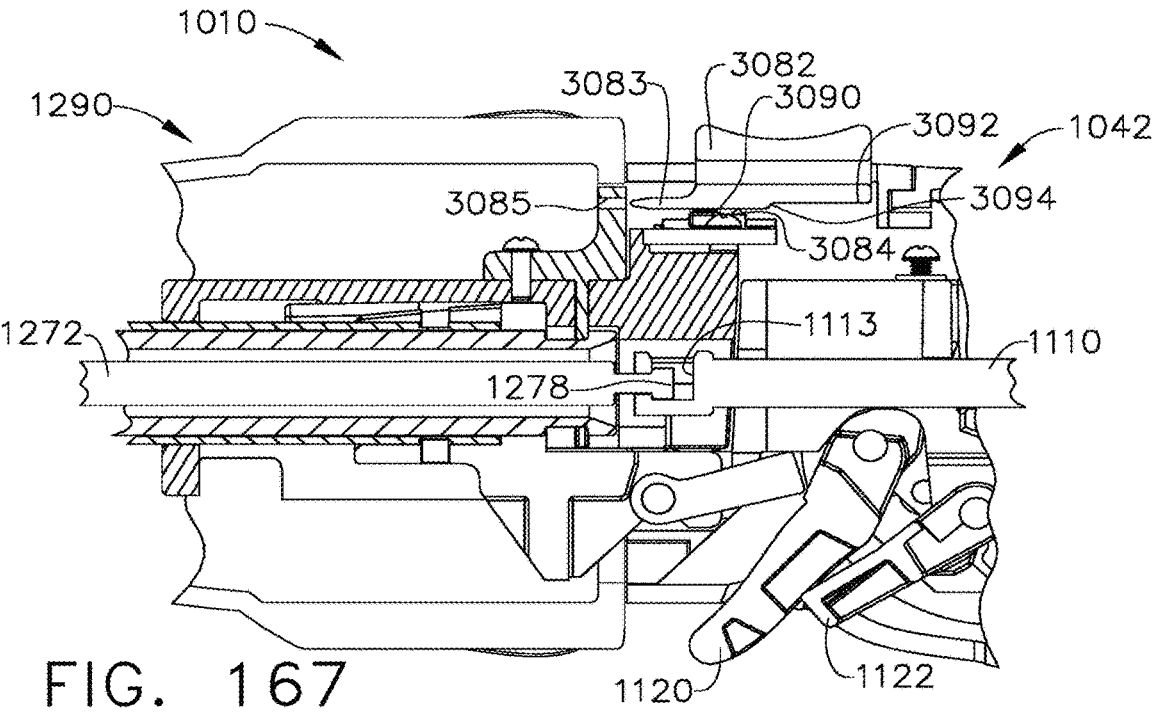
Figures 167A, 167B:
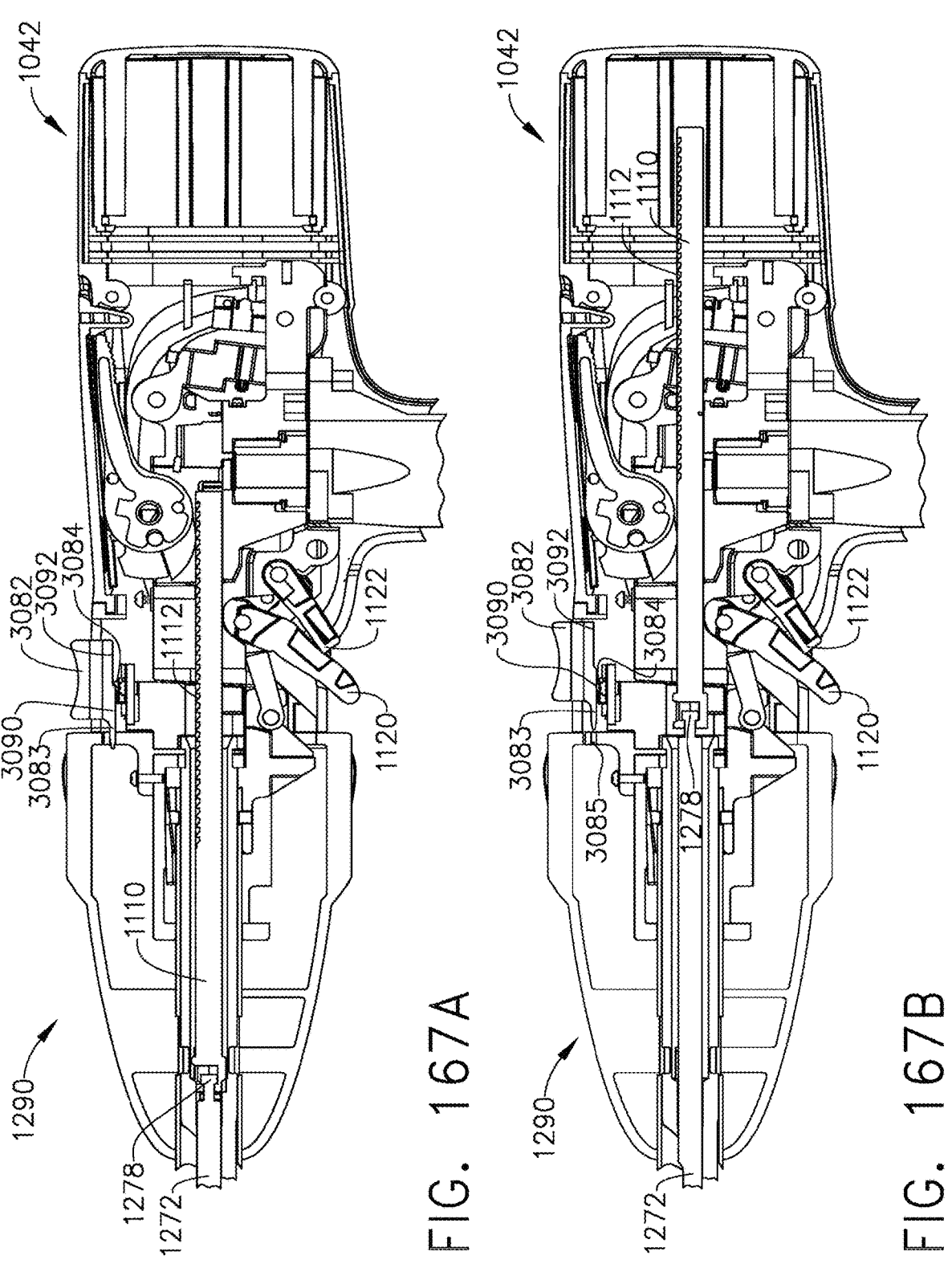
Figure 168:
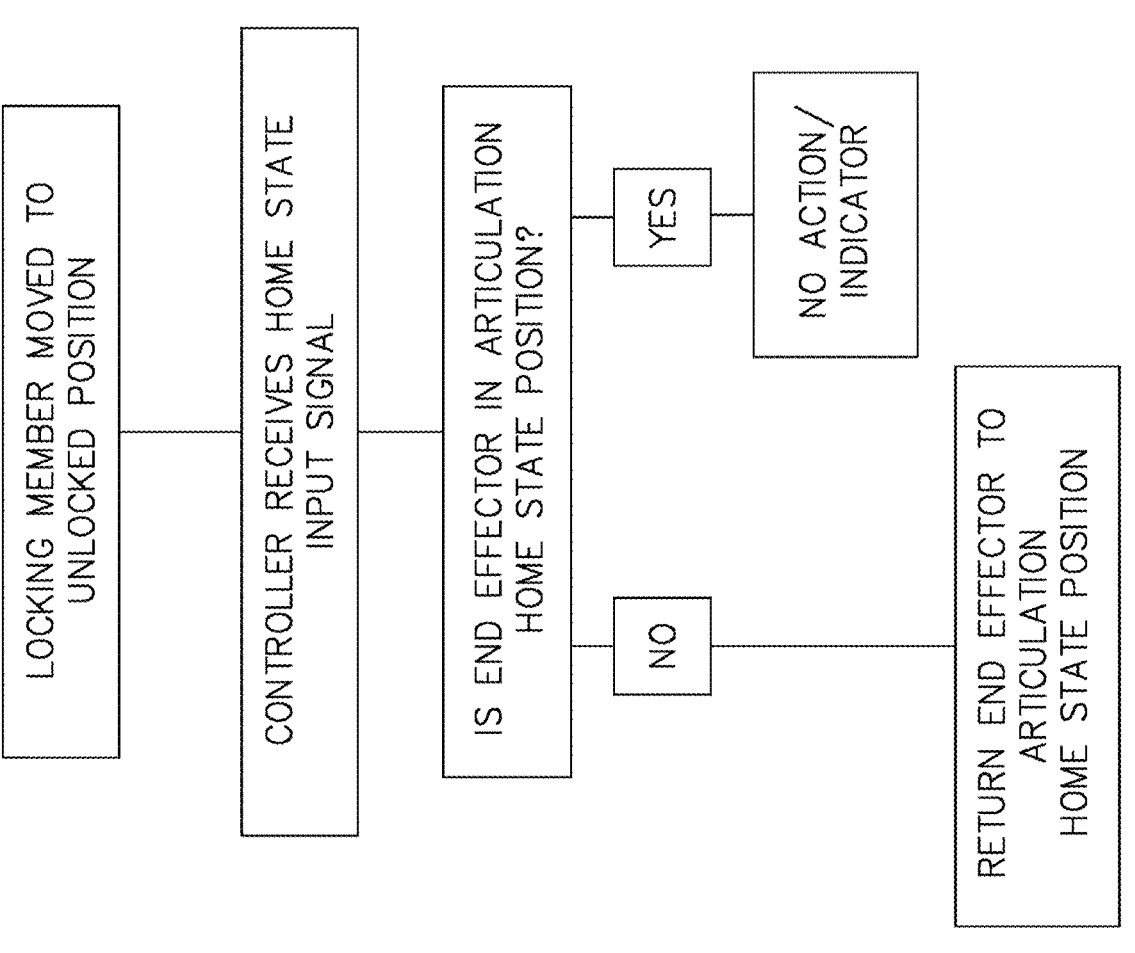
Figure 169:
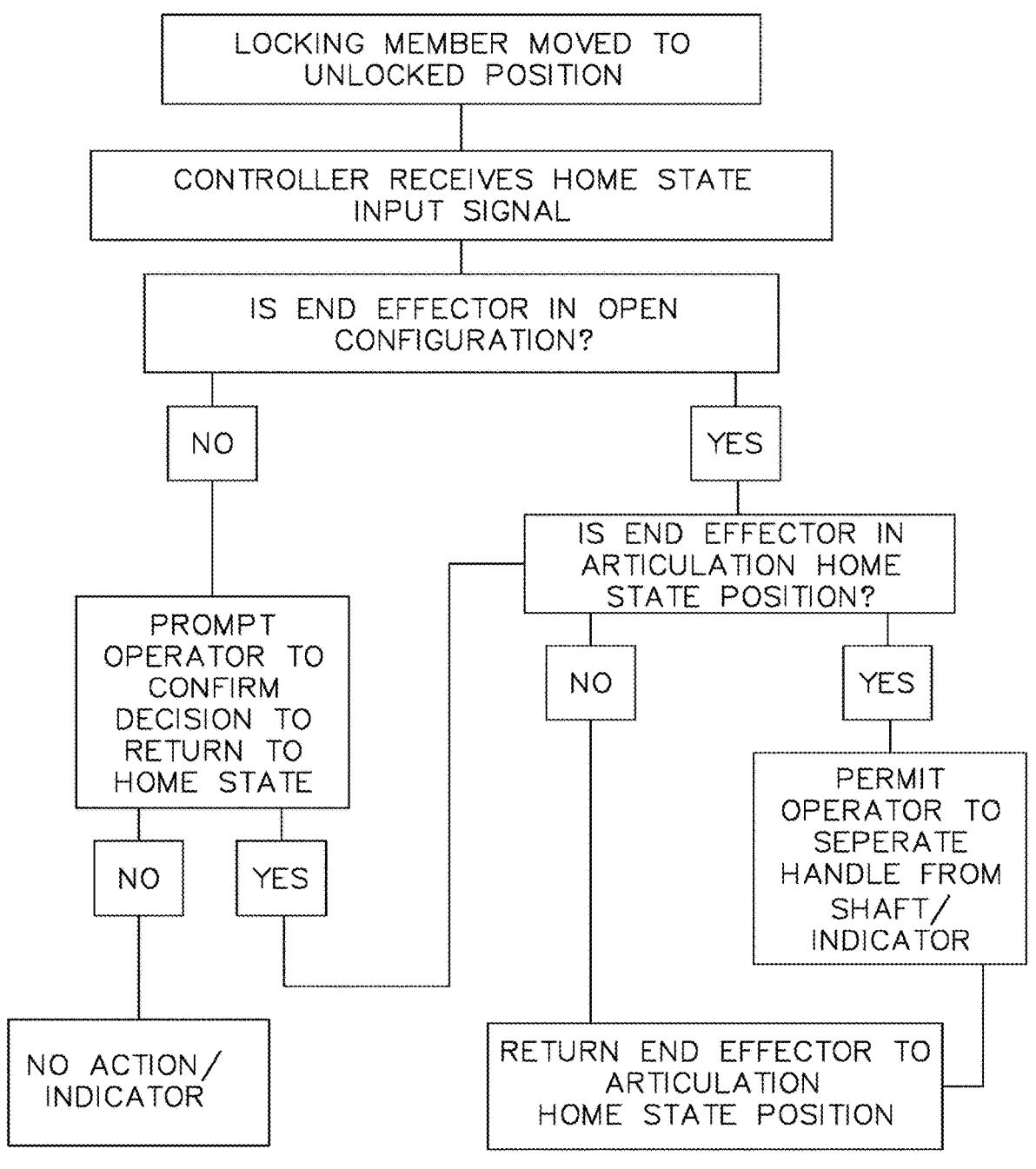
Figure 170:
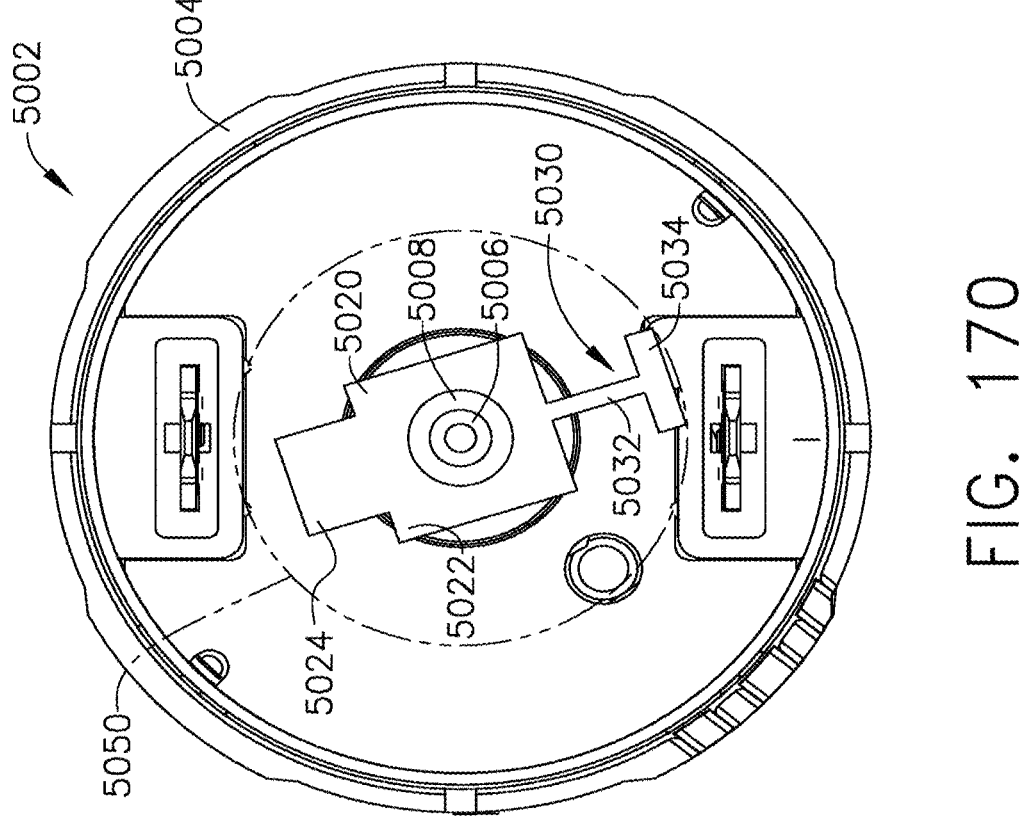
Figures 171, 172:
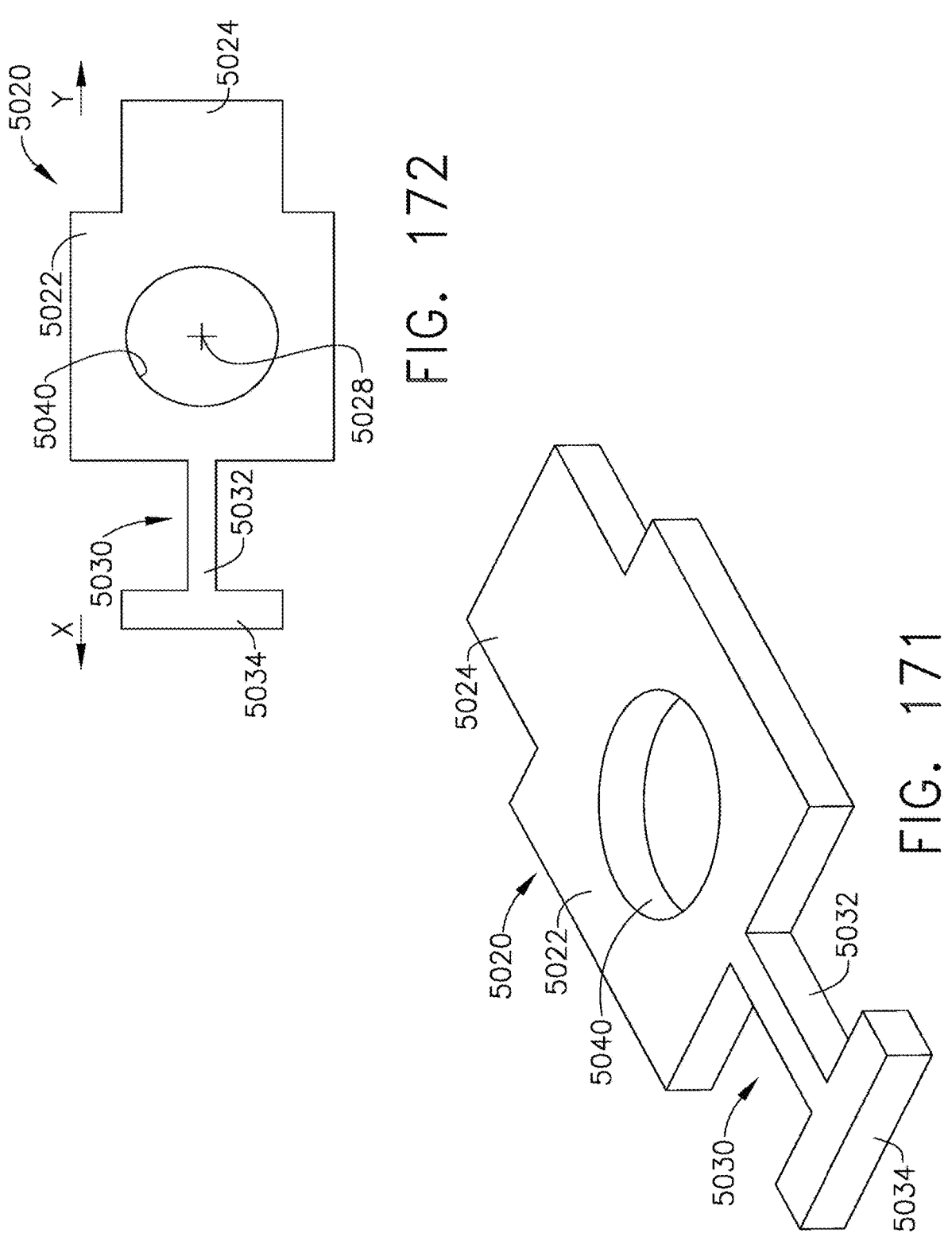
Figures 173, 174:
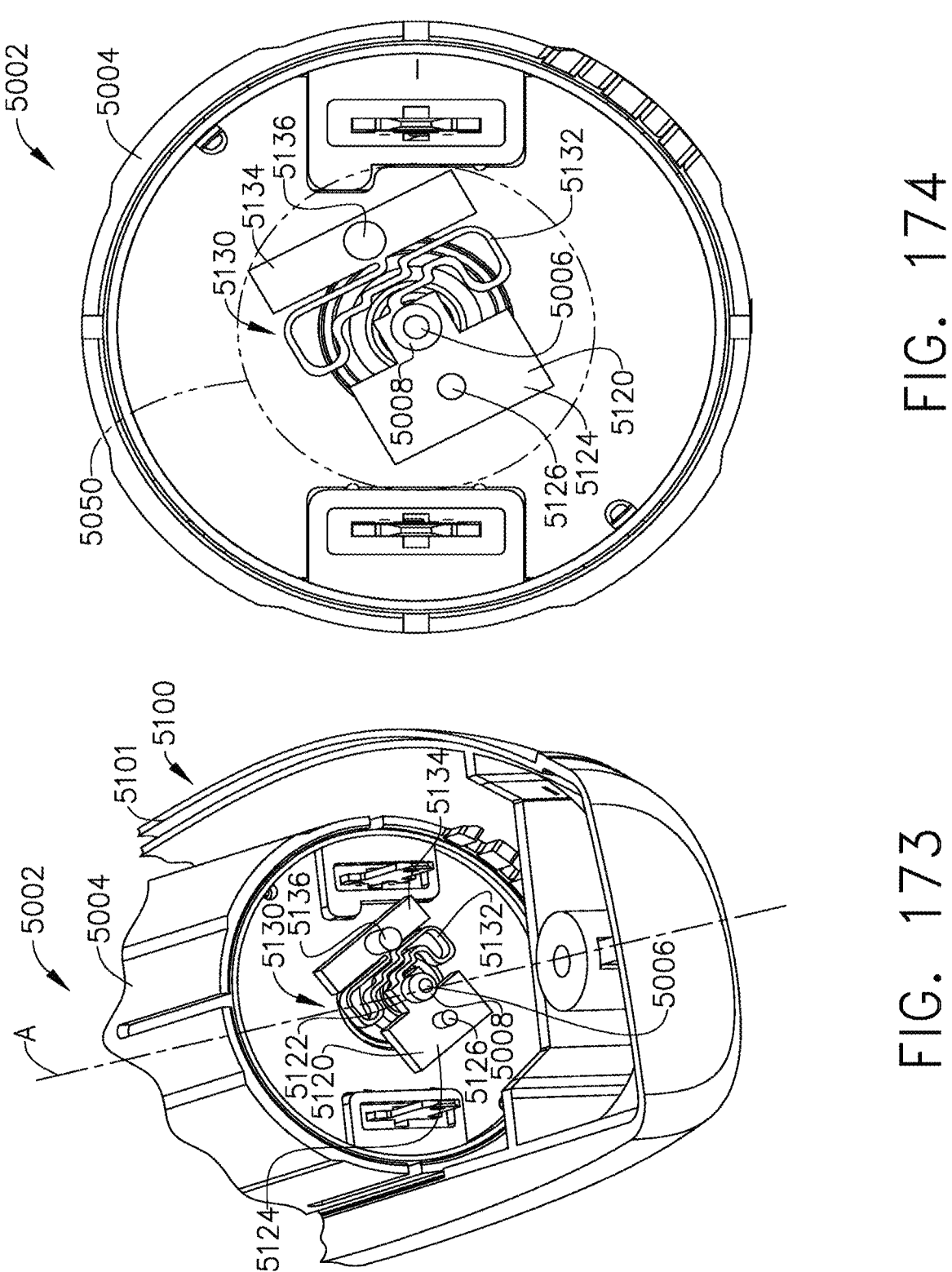
Figures 175, 176:
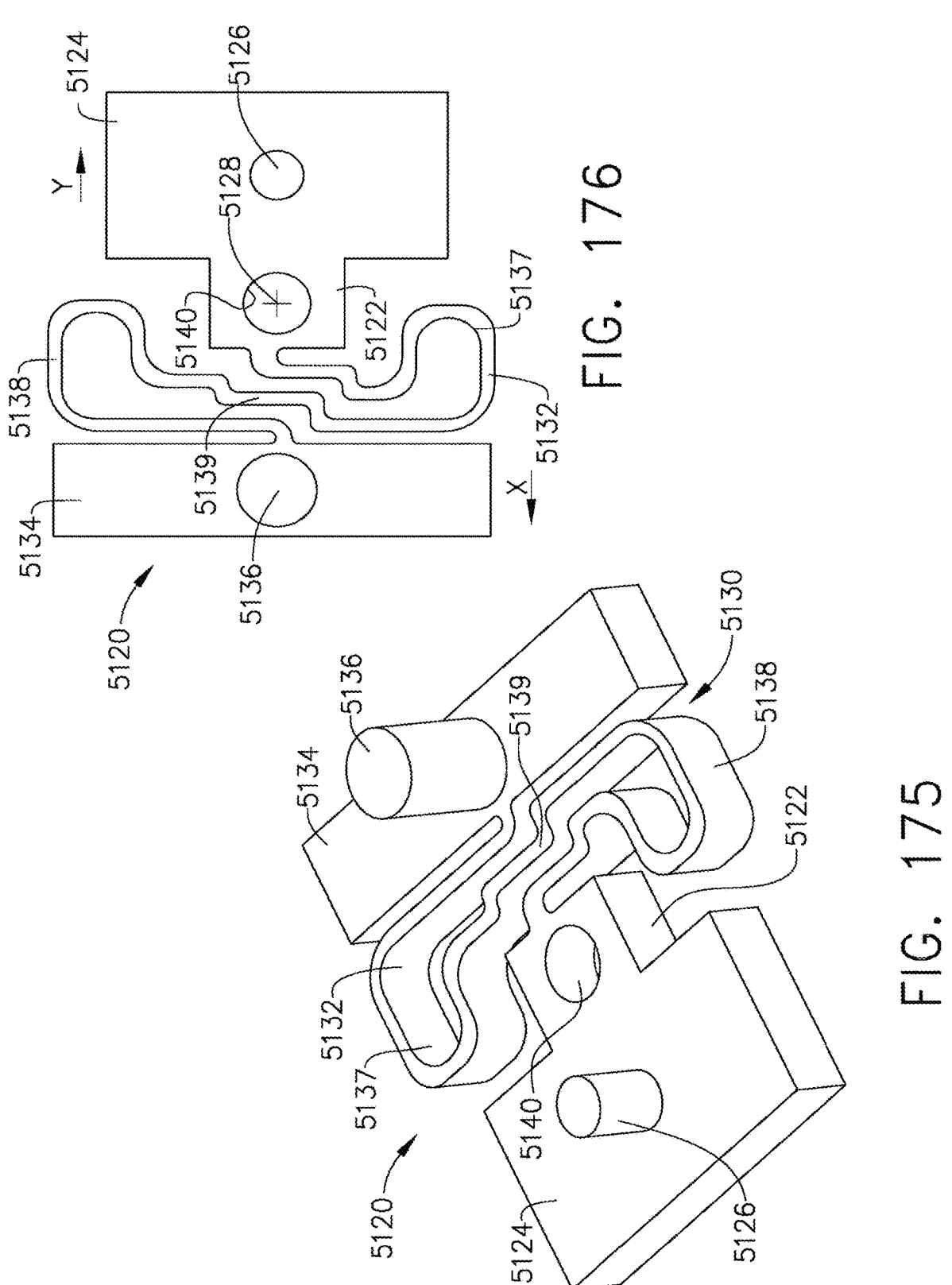
Figures 177, 178:
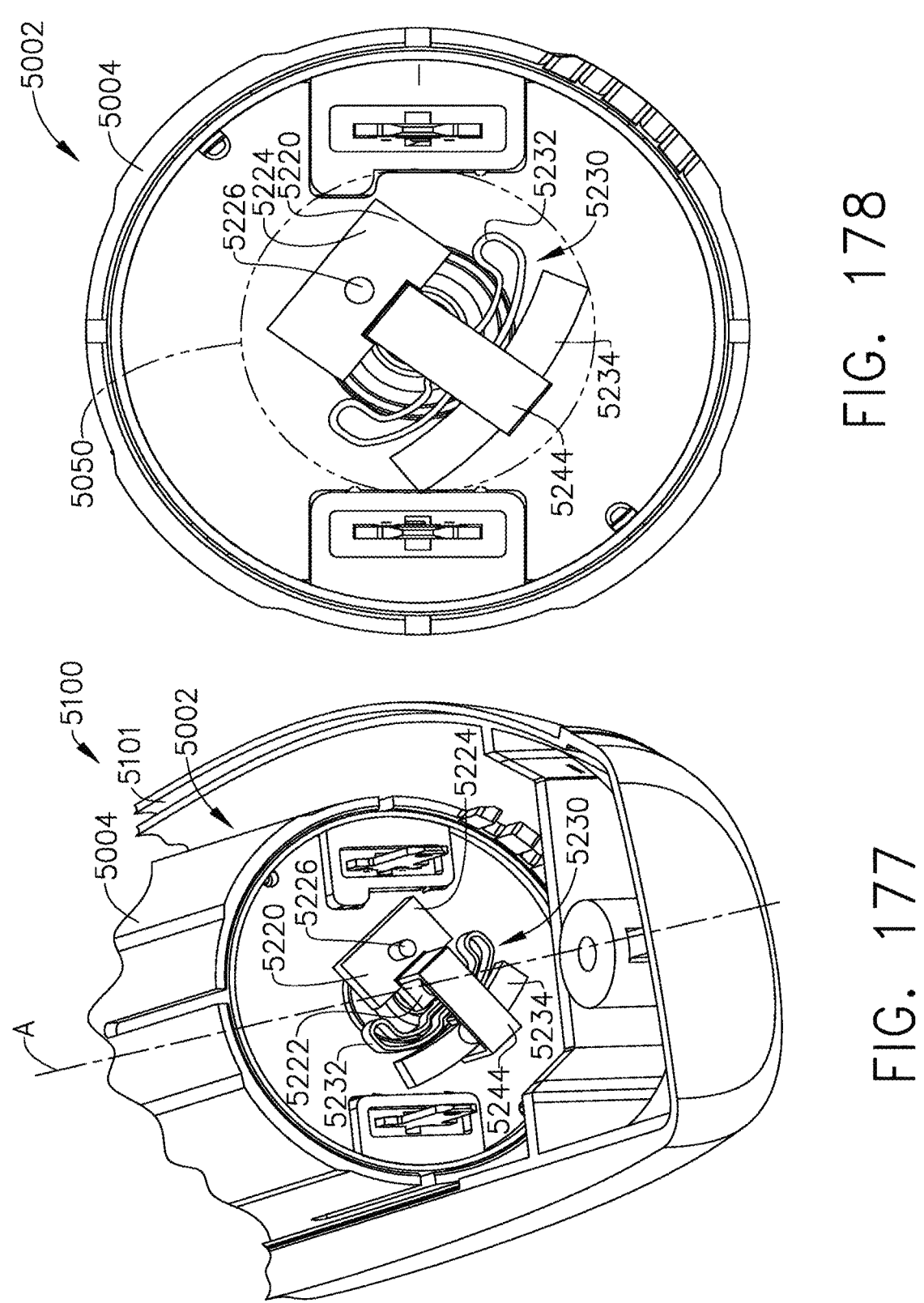
Figure 179:
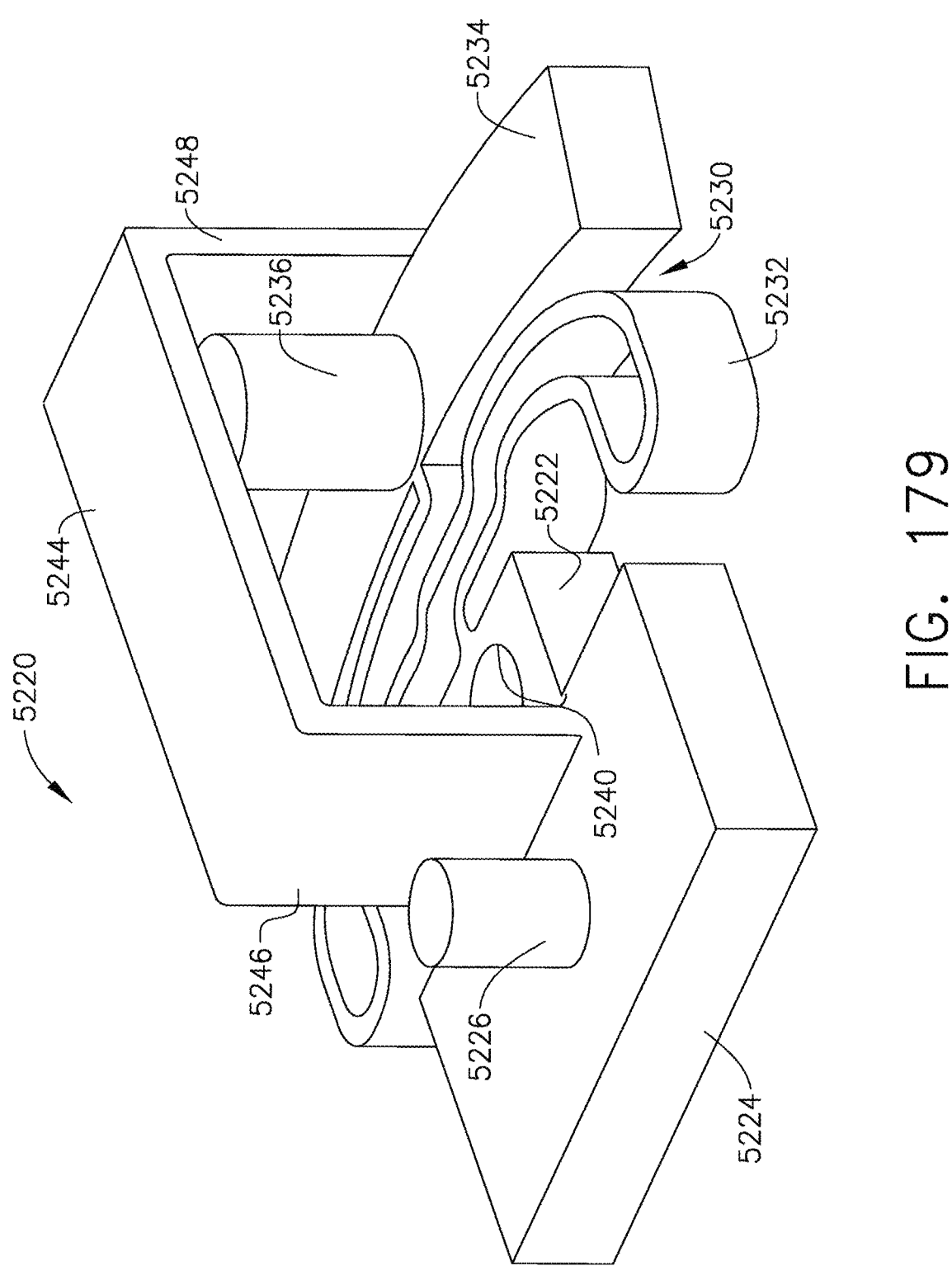
Figure 180:
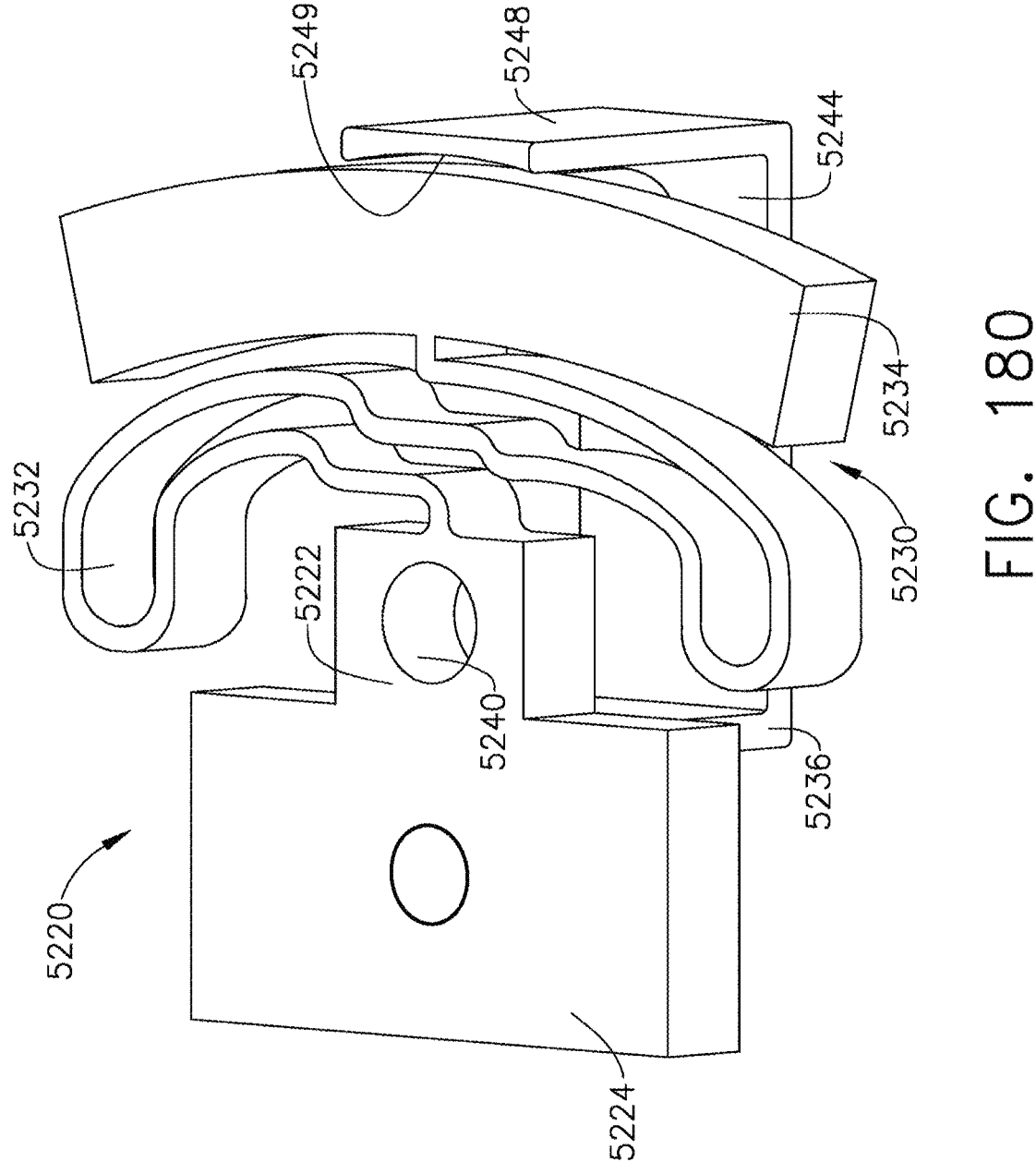
Figure 181:
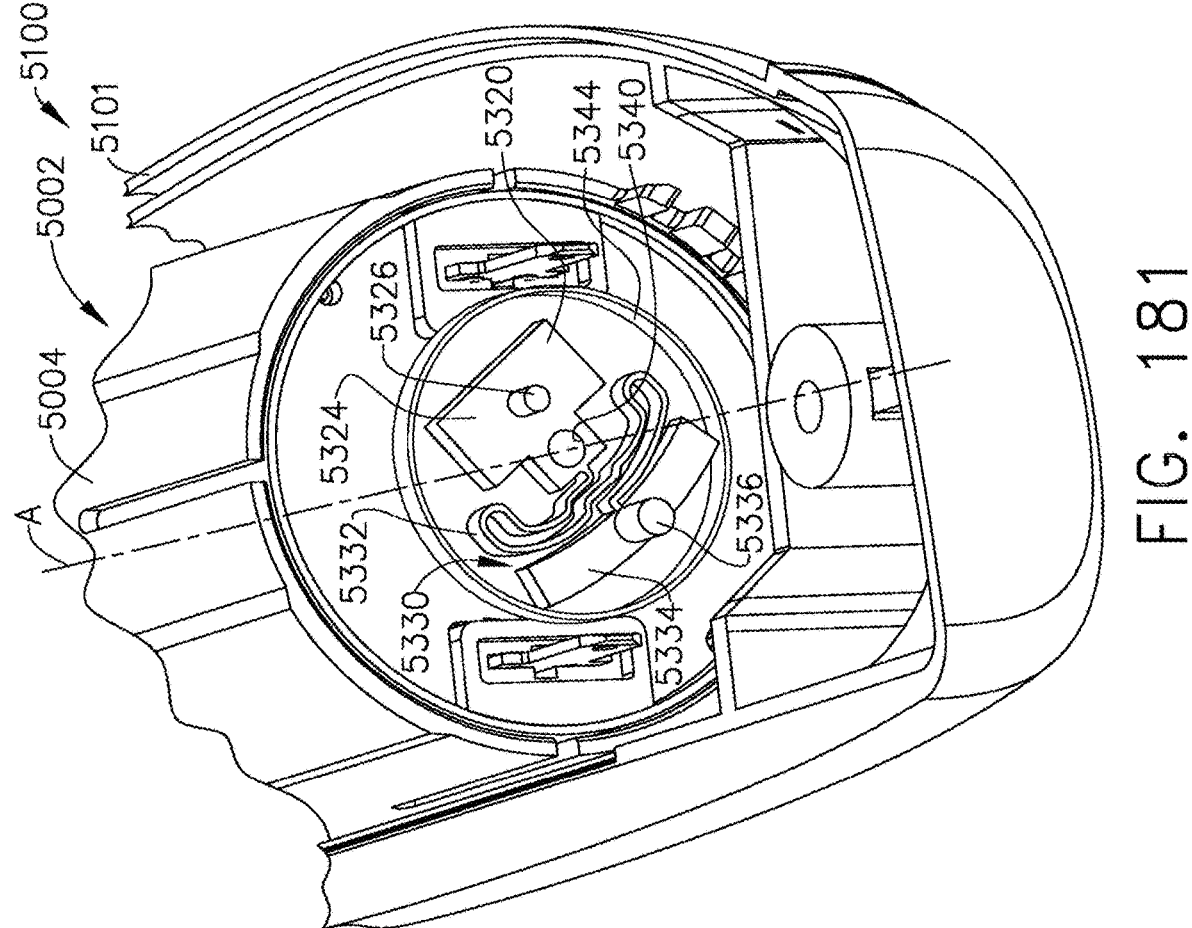
Figure 182:
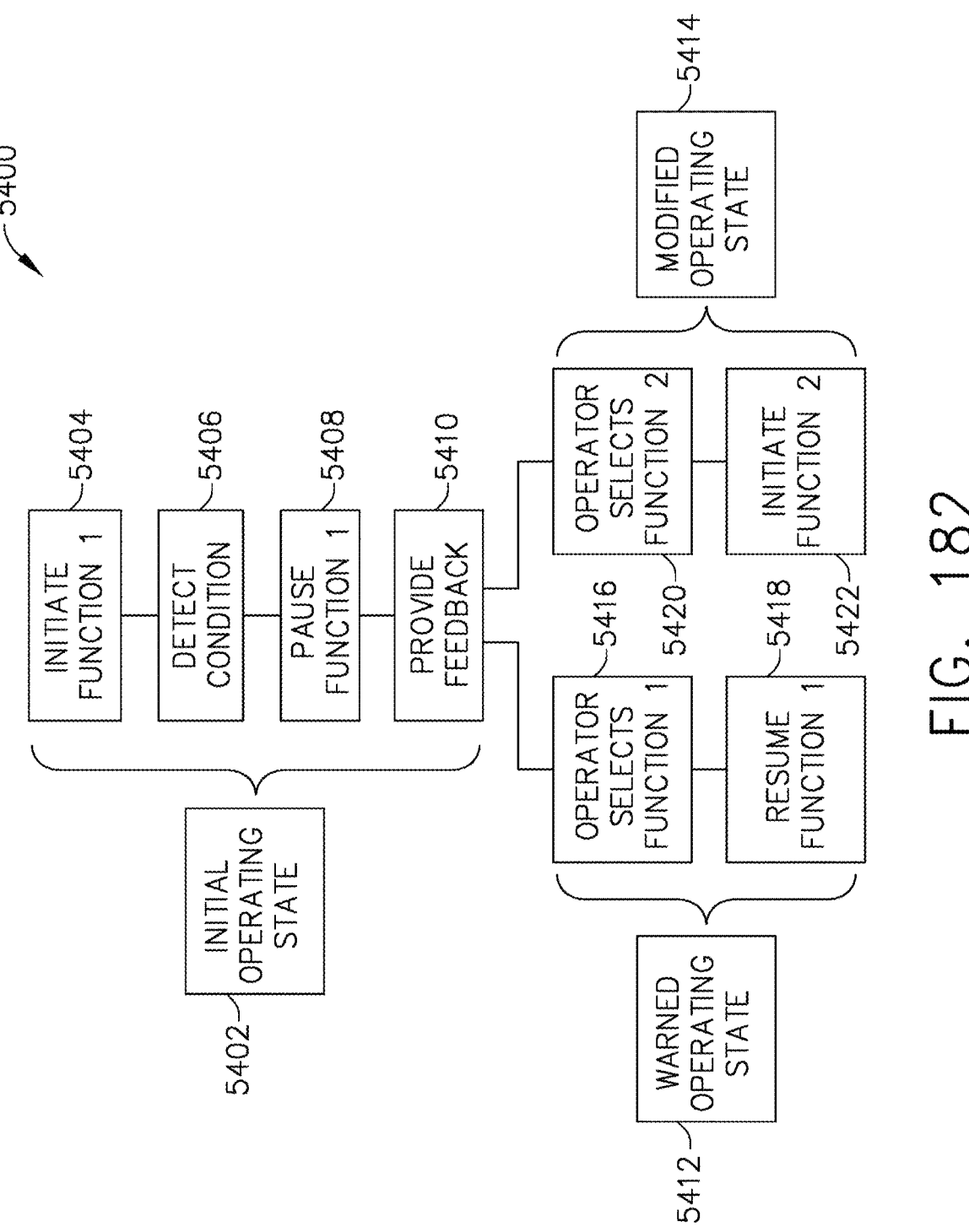
Figure 183:
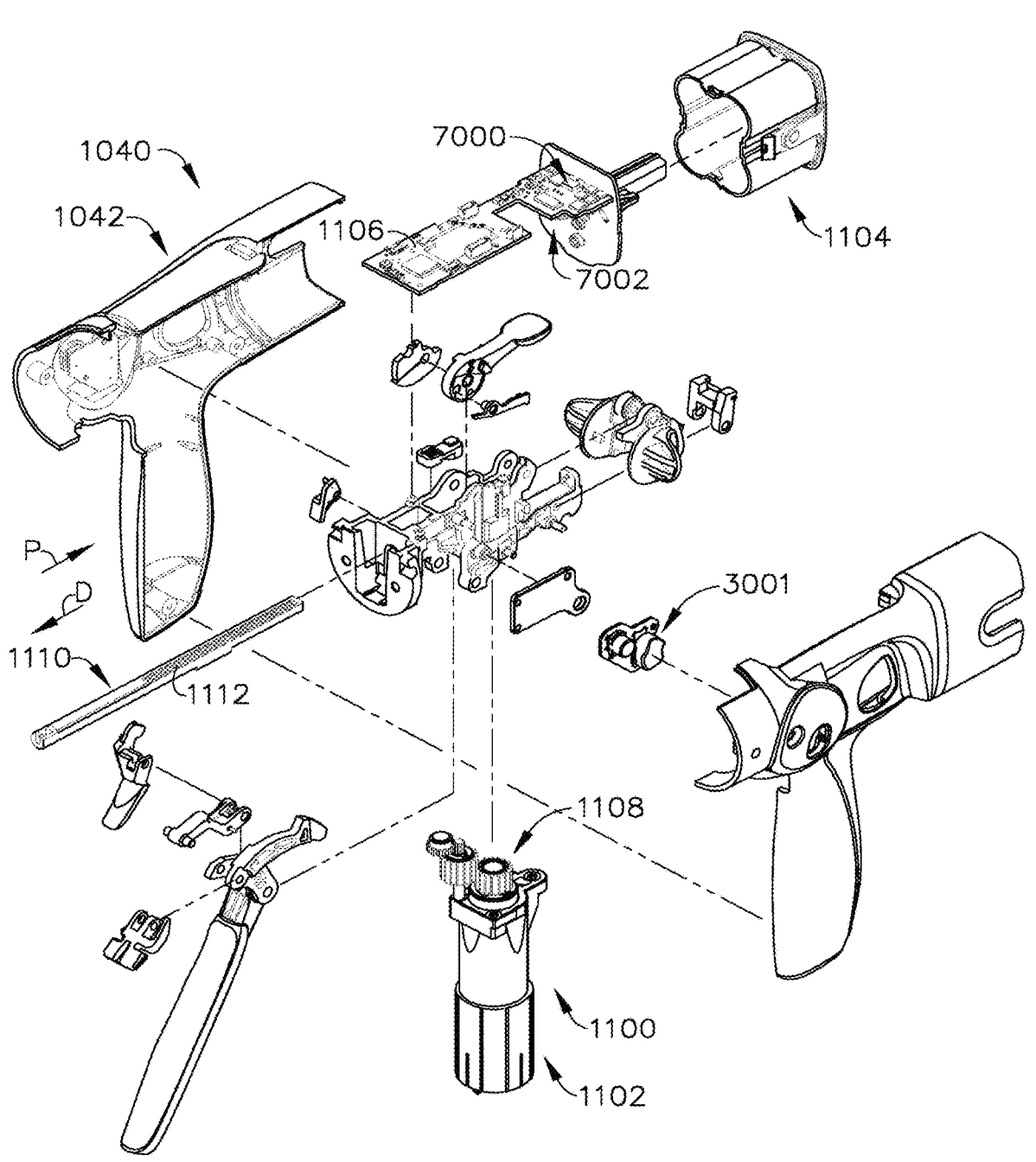
Figure 184:
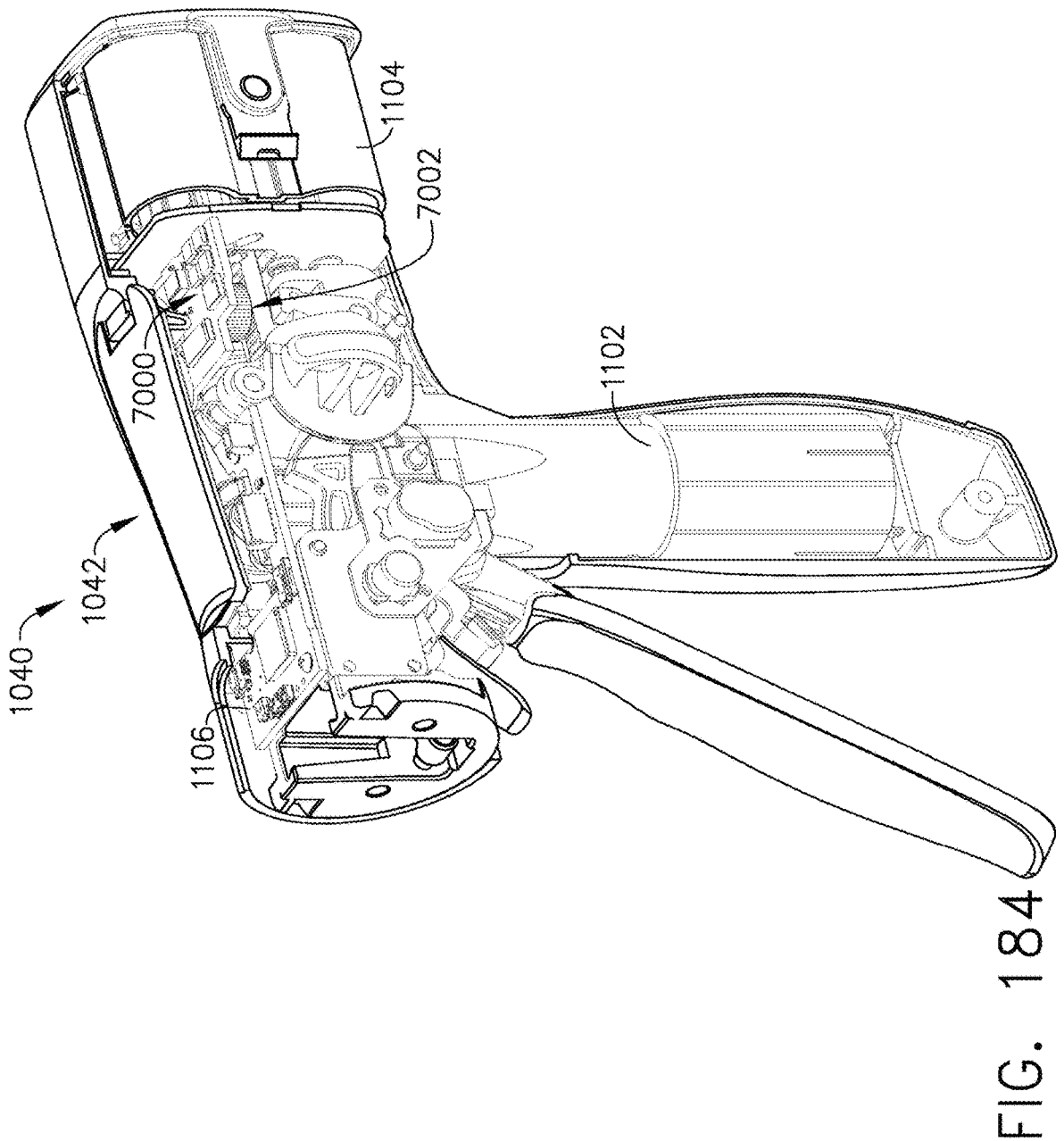
Figure 185:
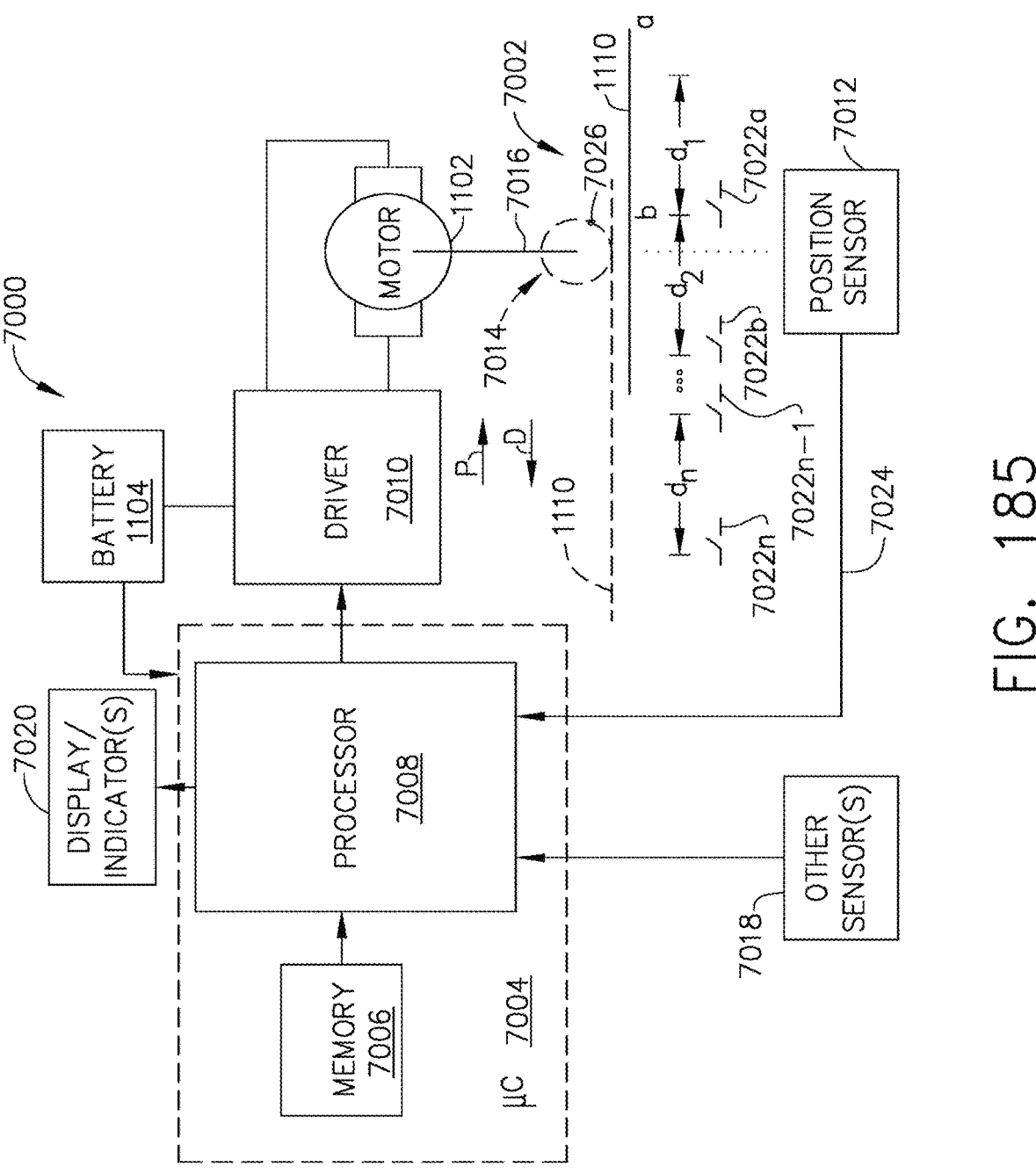
Figure 186:
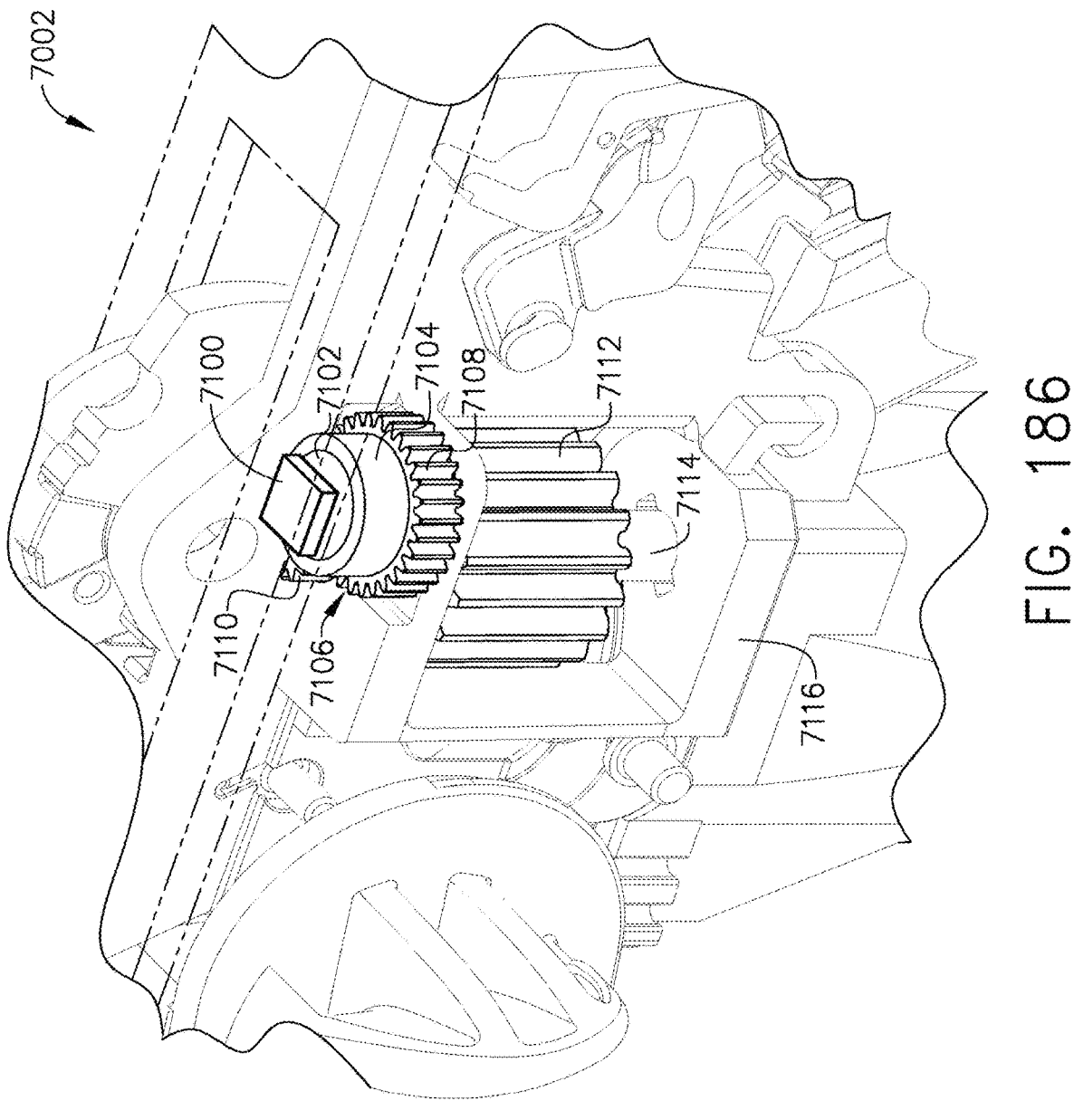
Figure 187:
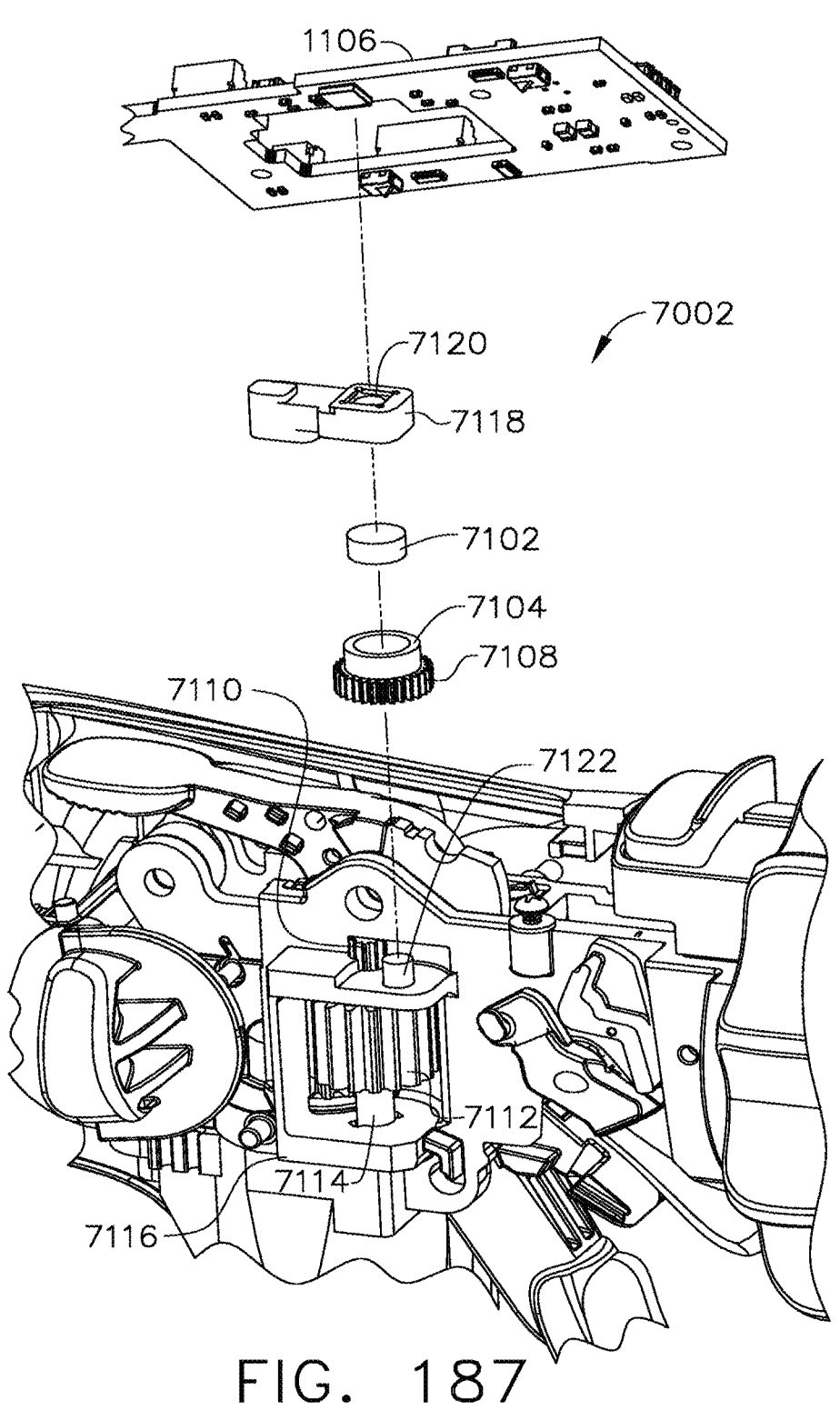
Figure 188:
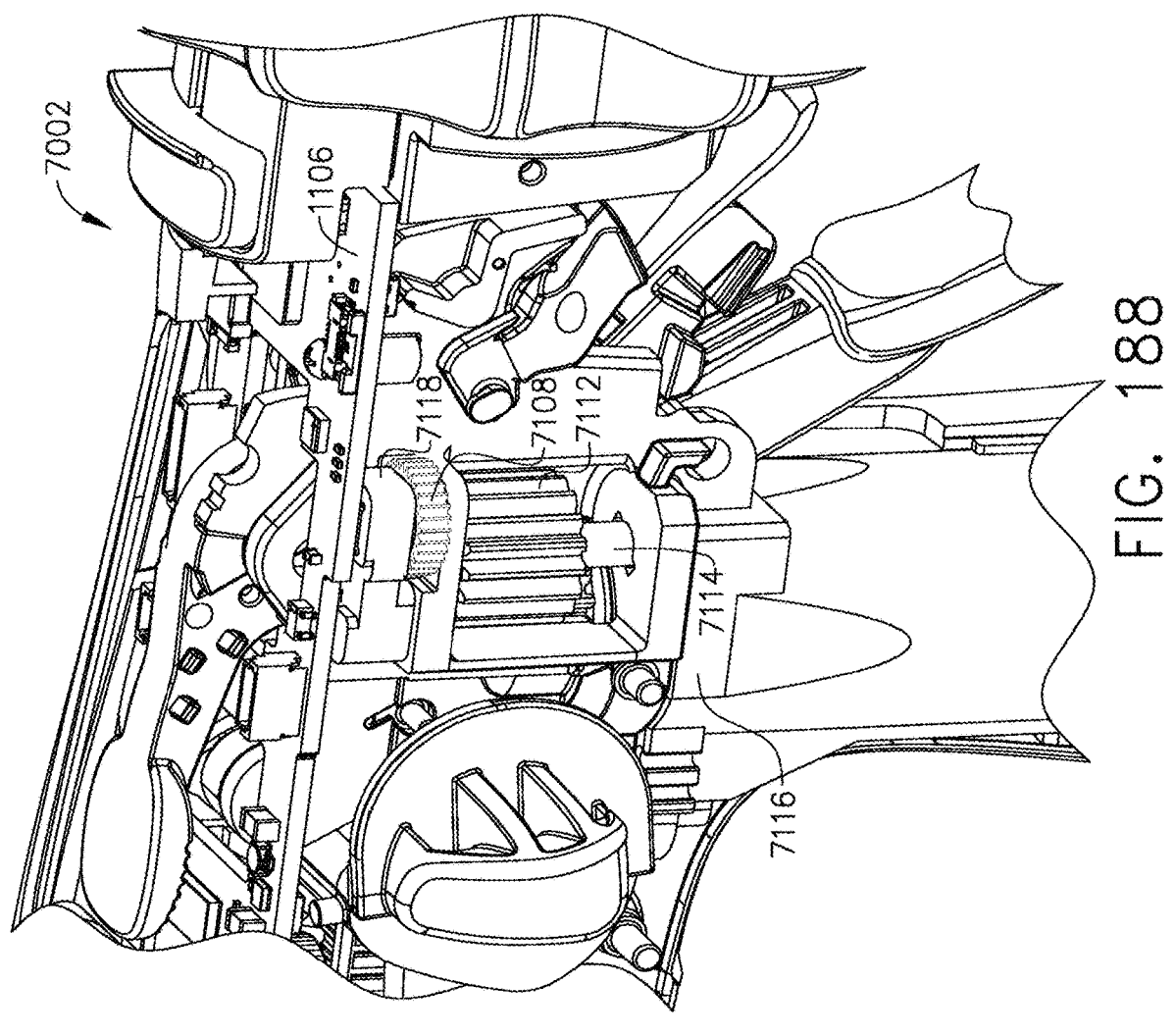
Figure 189:
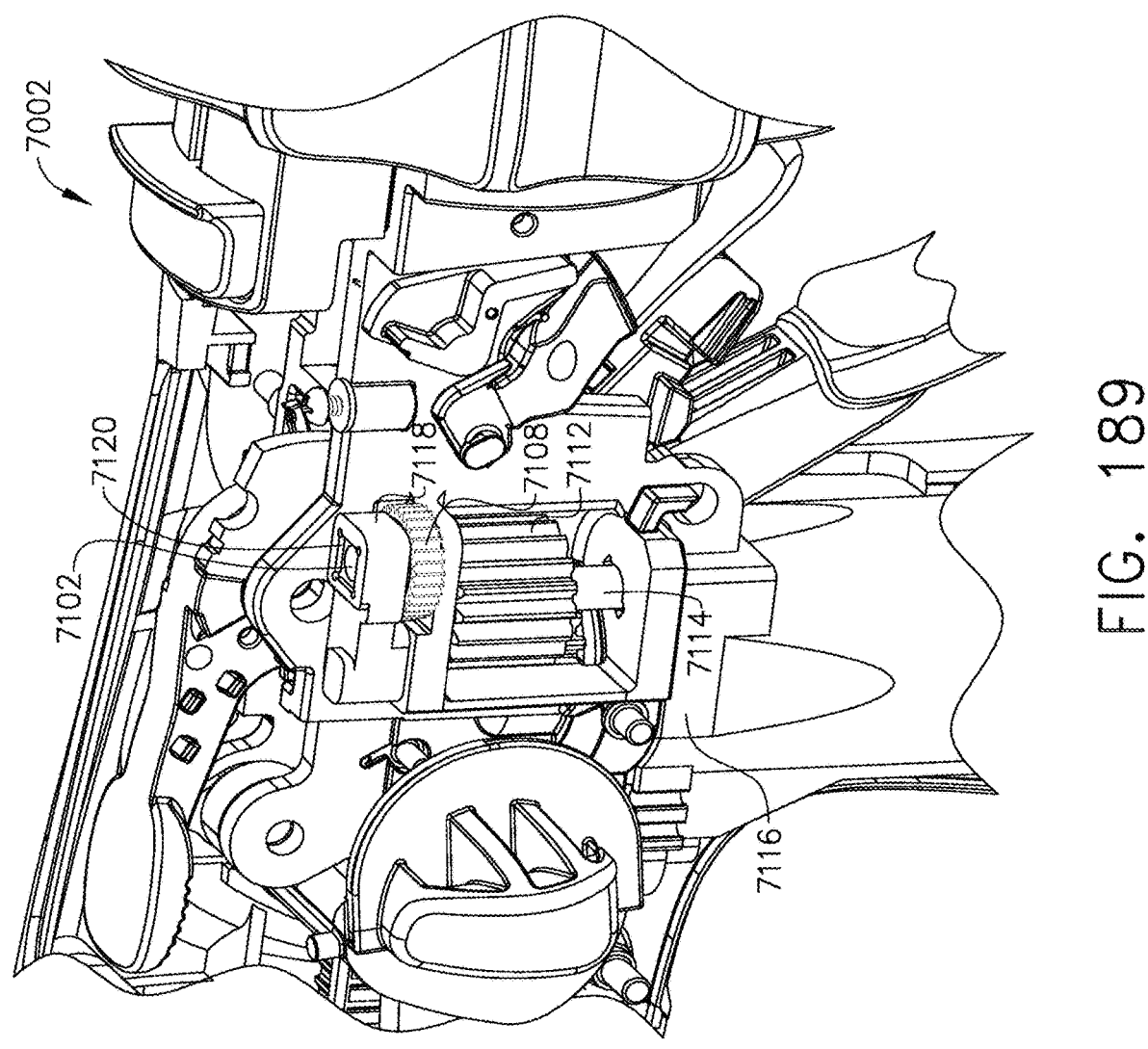
Figure 190:
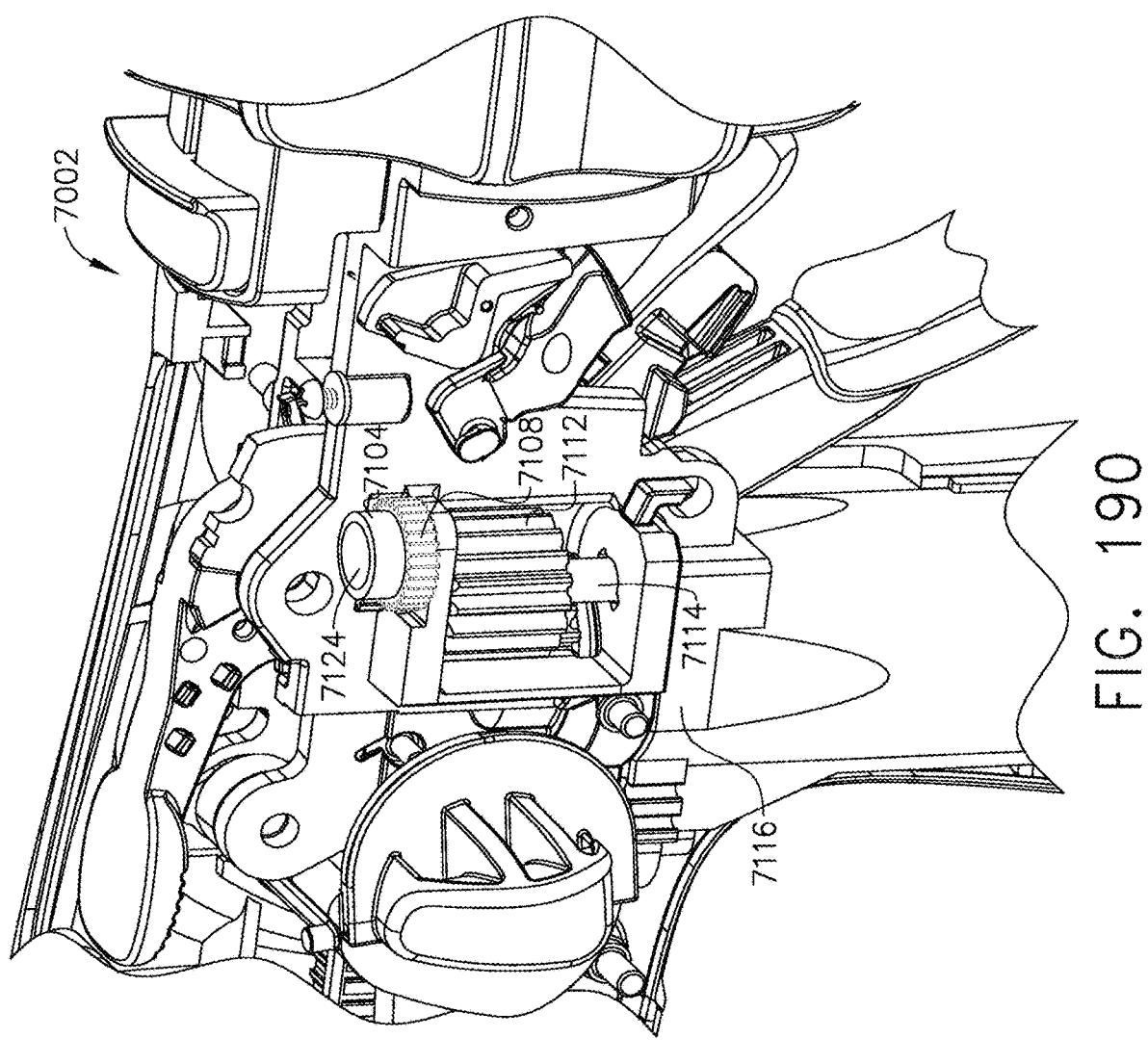
Figure 191:
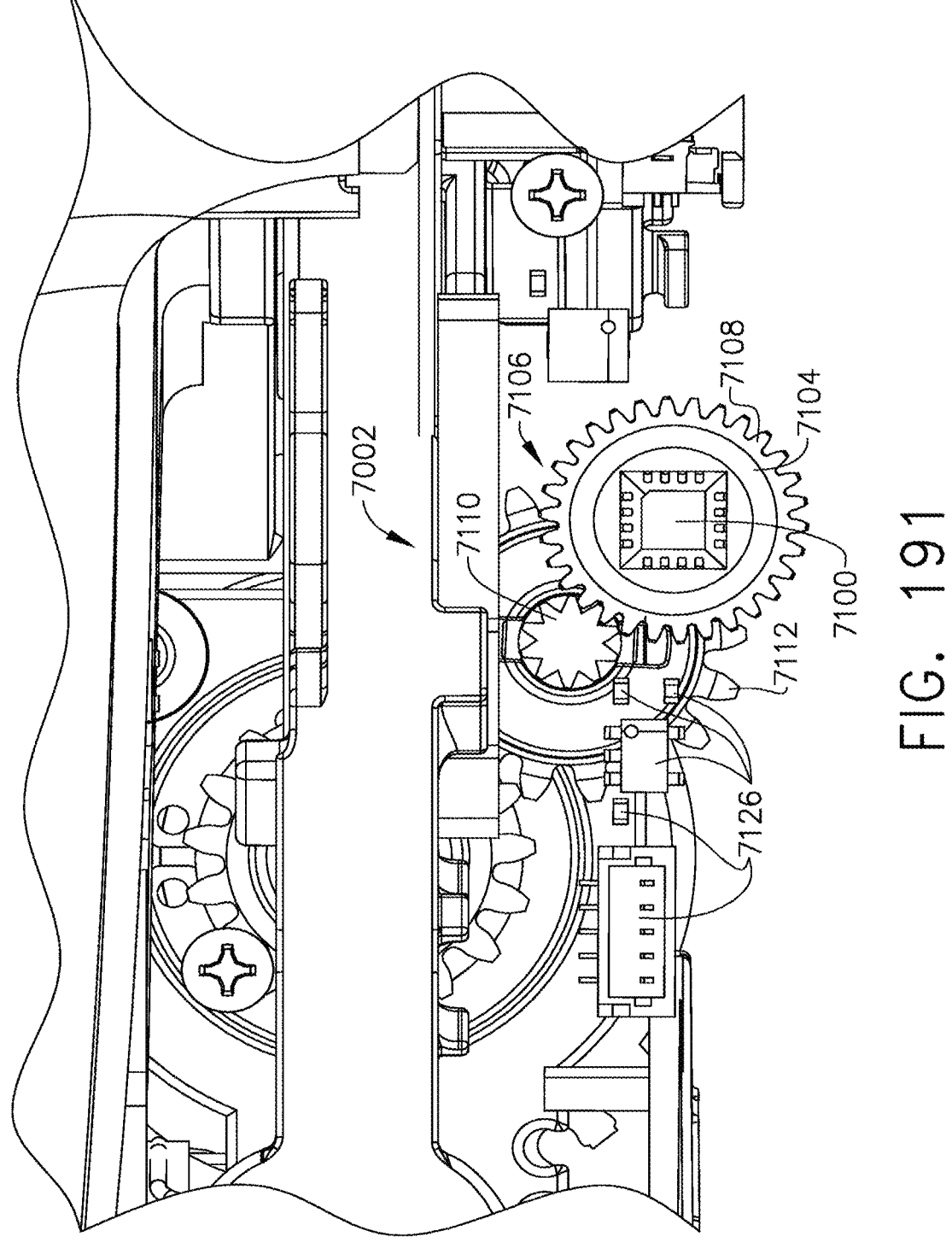
Figure 192:
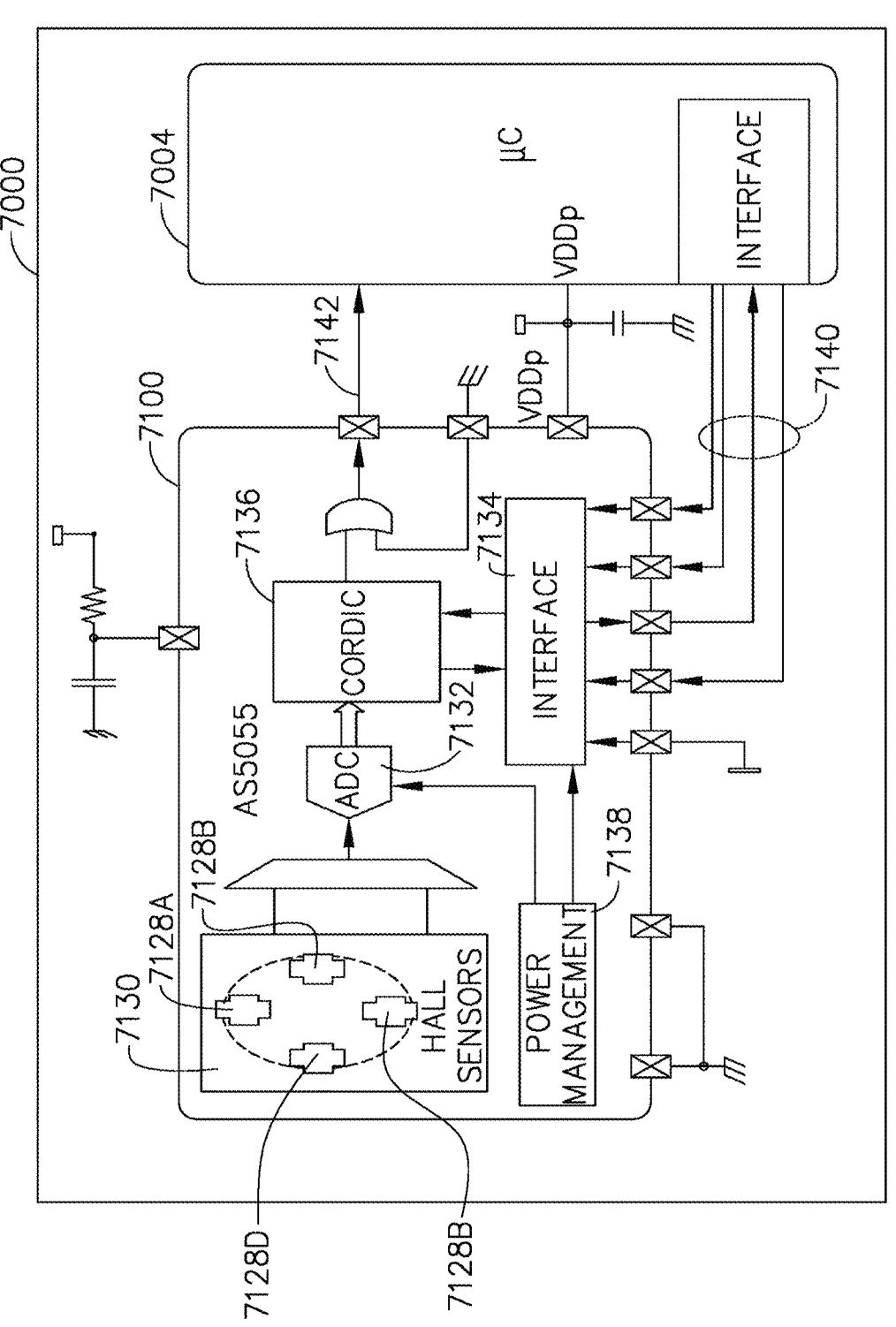
Figure 193:
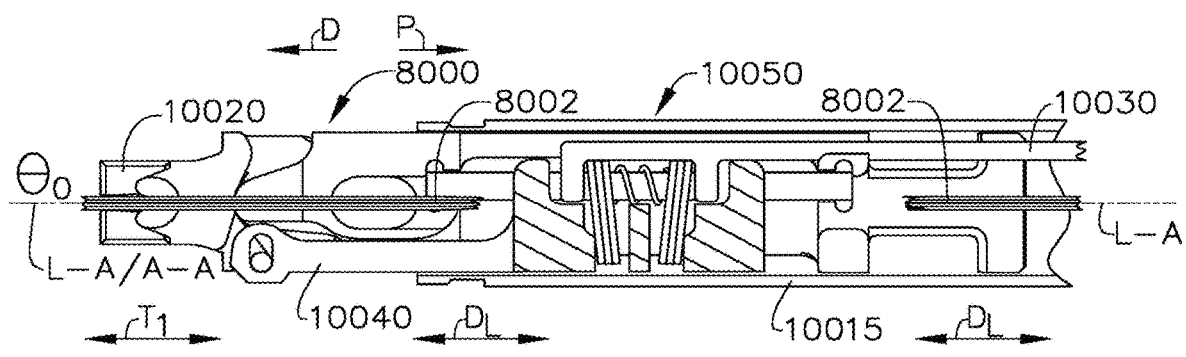
Figure 194:
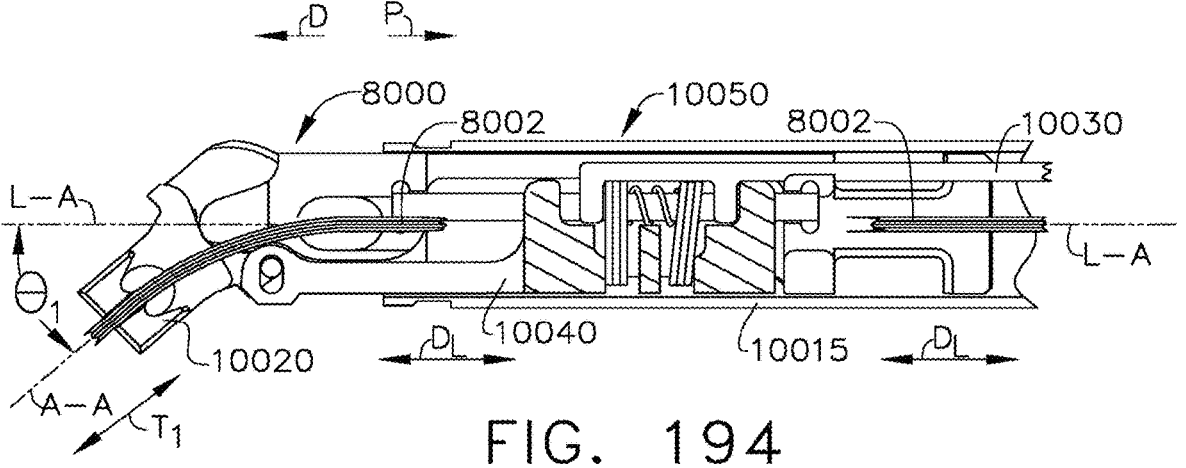
Figure 195:
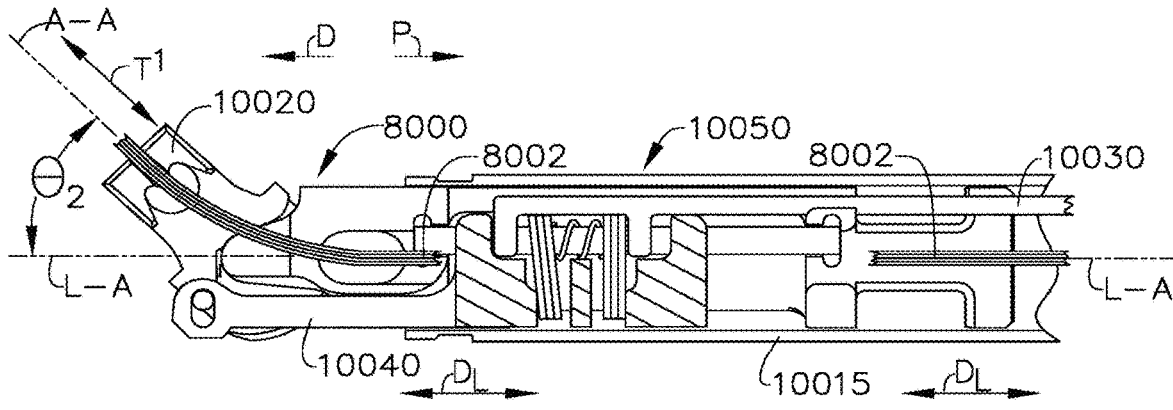
Figure 197:
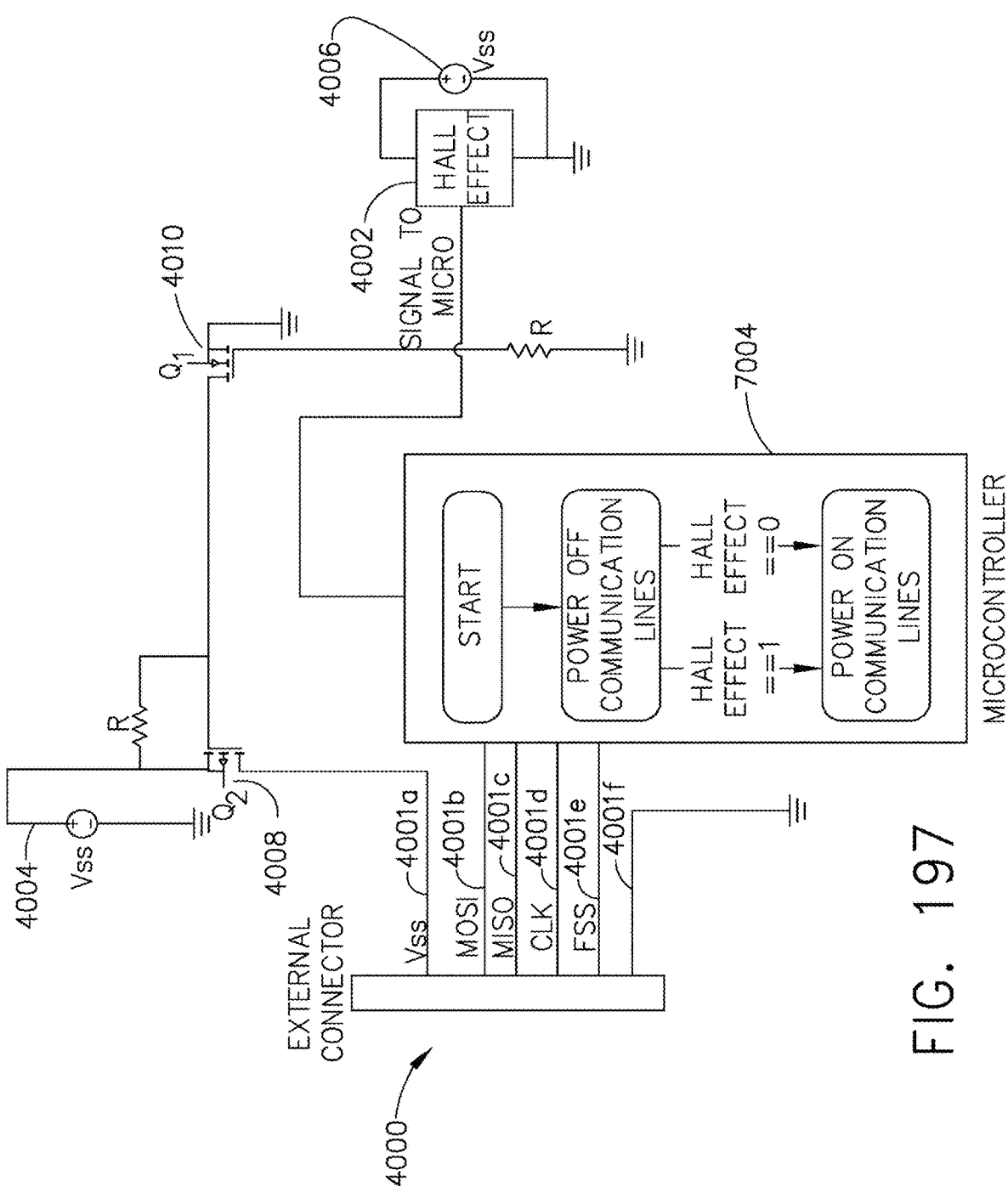
Figures 198, 199:
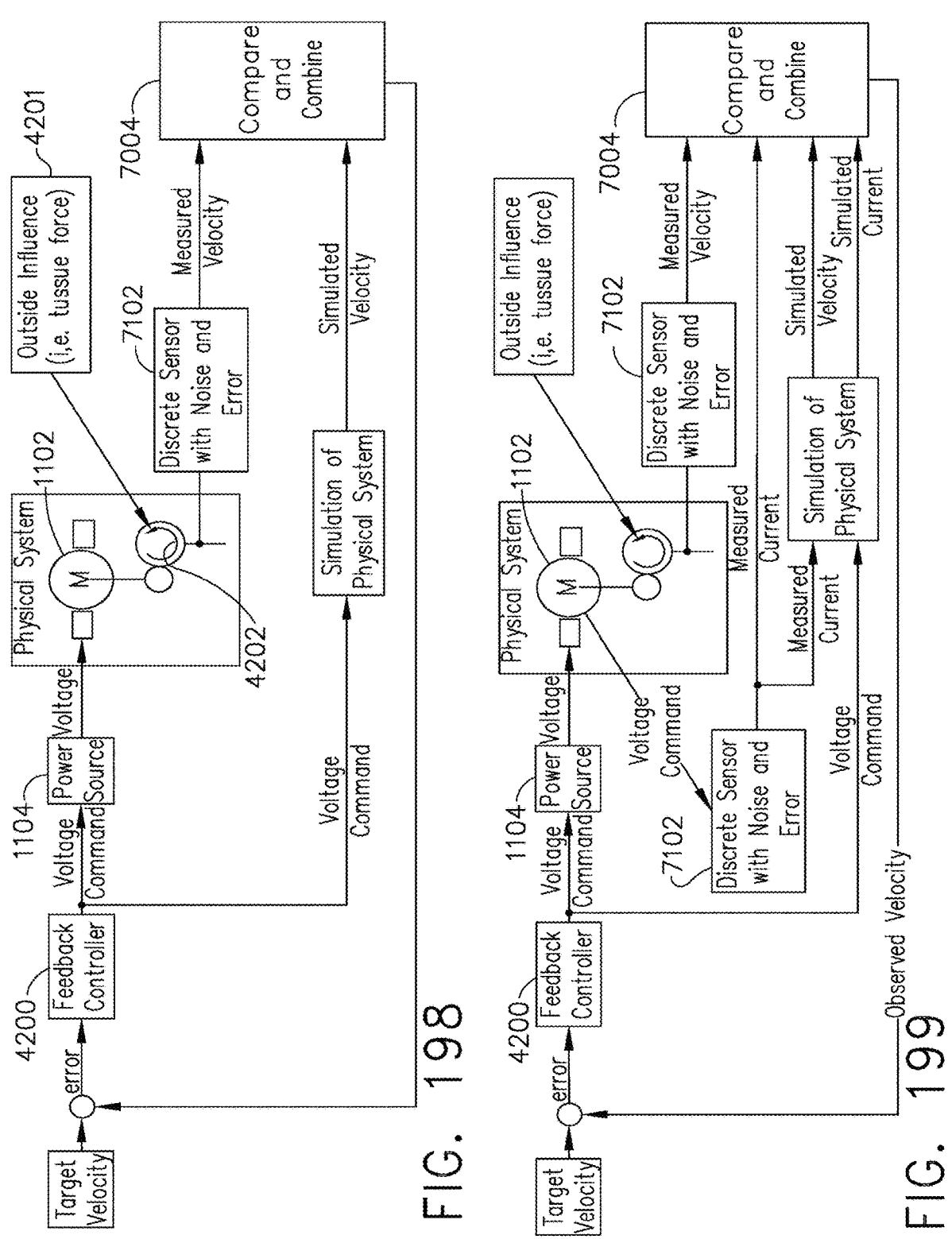
Figure 200:
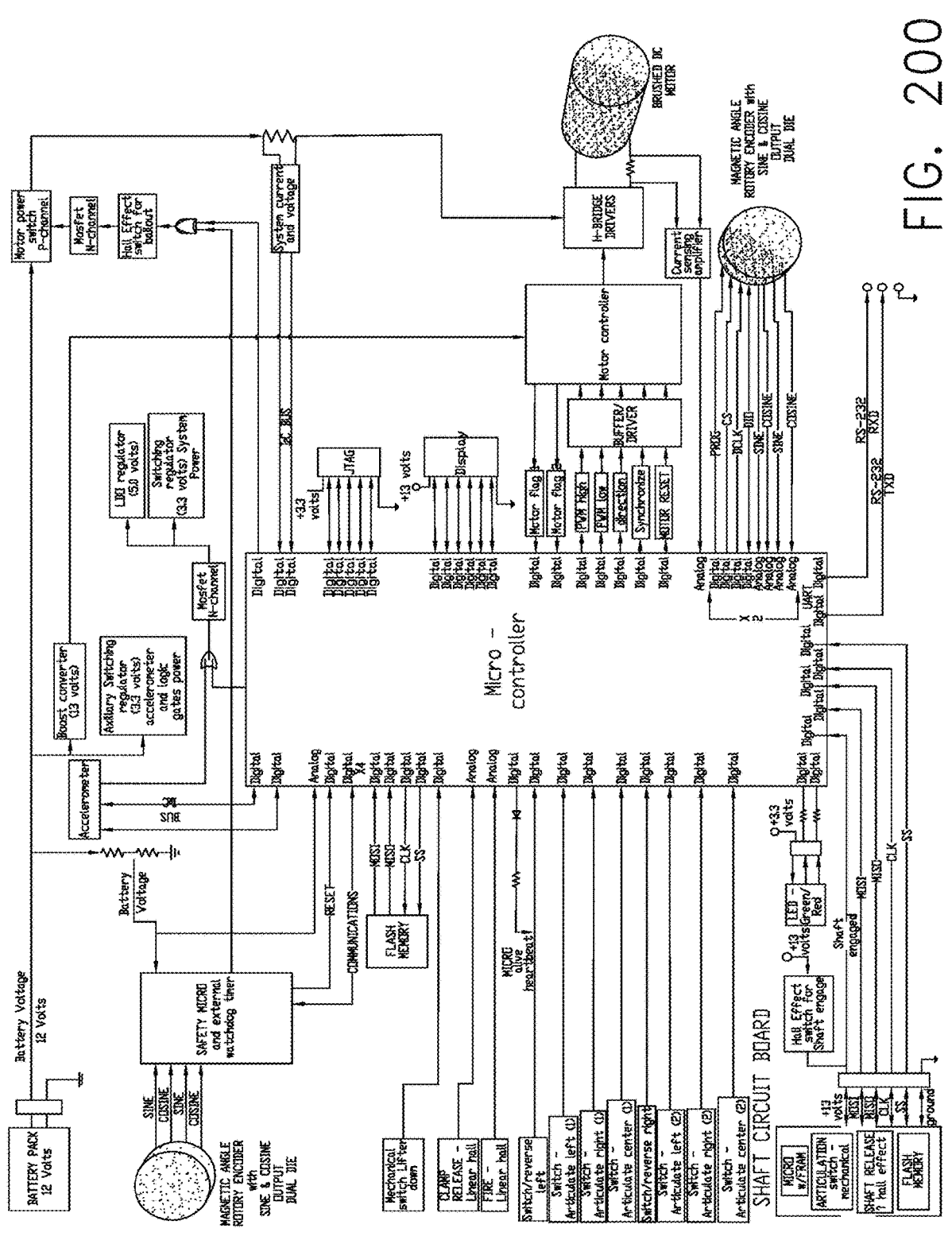
Figure 200A:
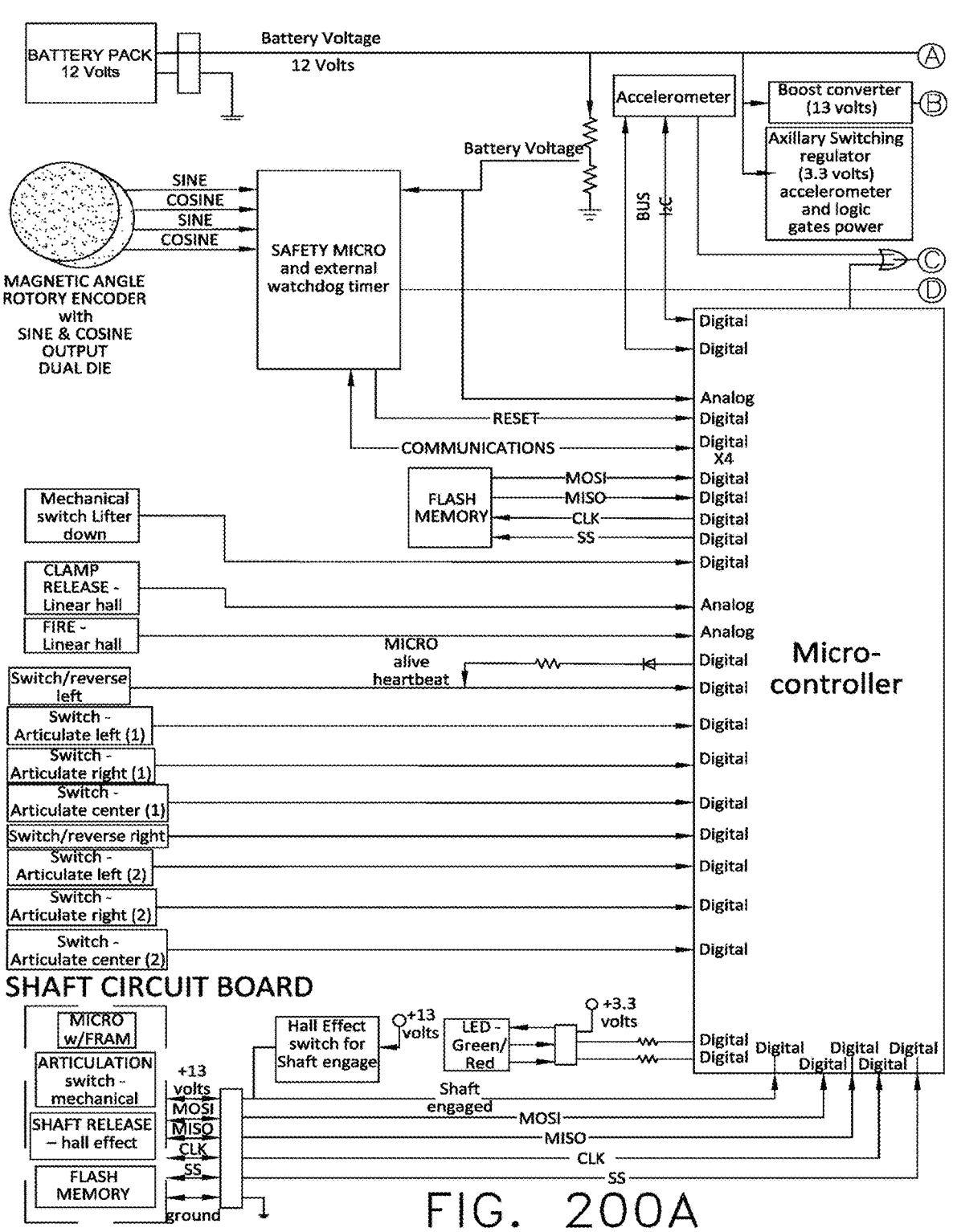
Figure 200B:
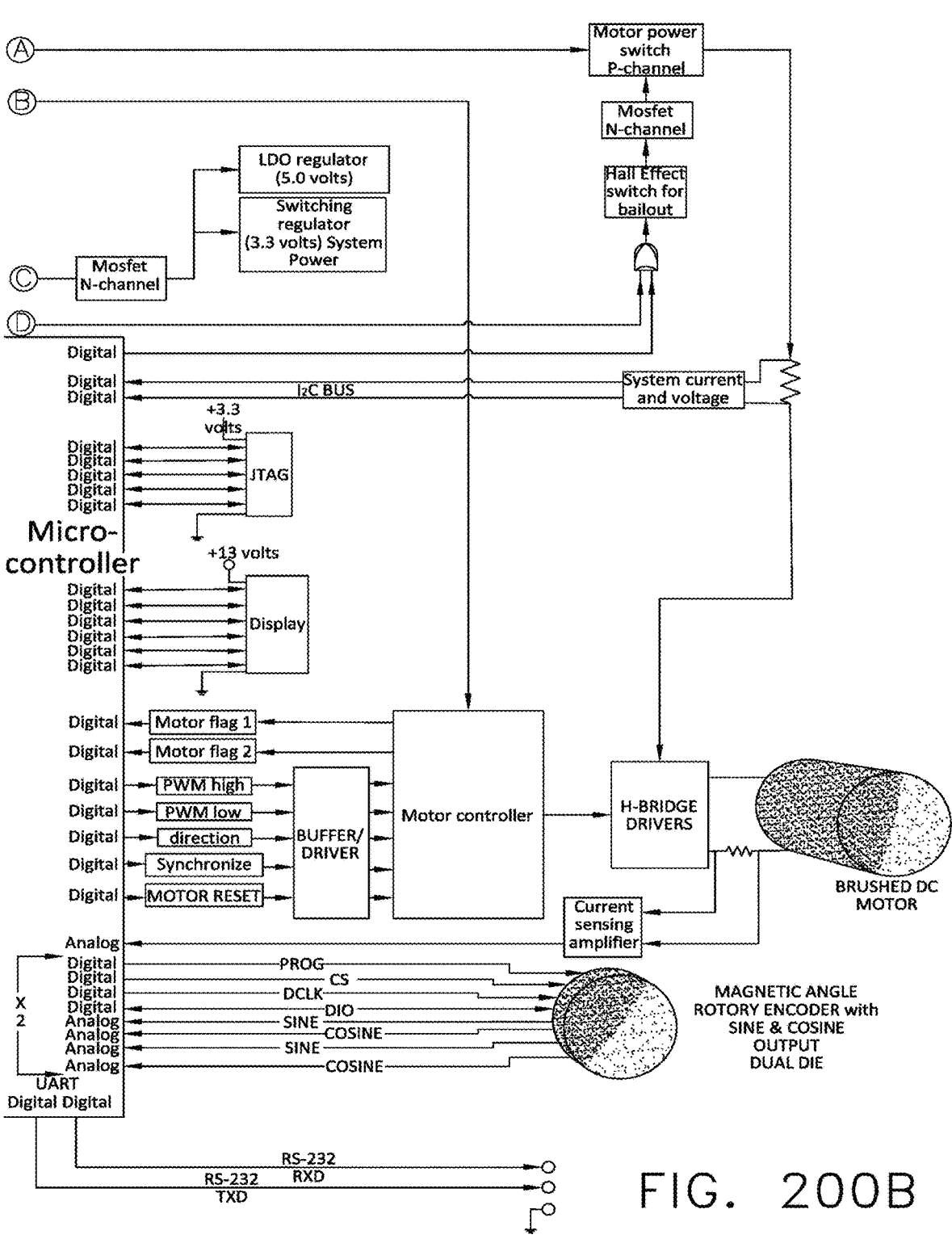
Figure 201:
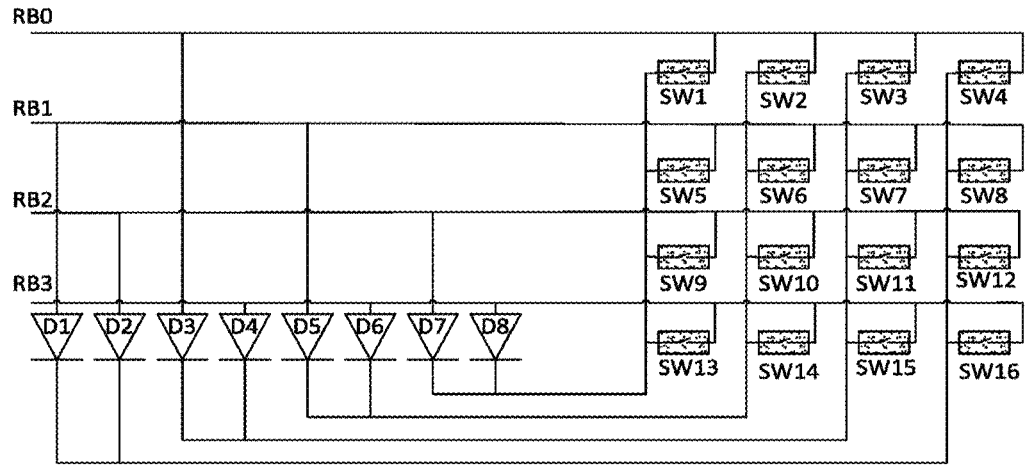
Figure 202:
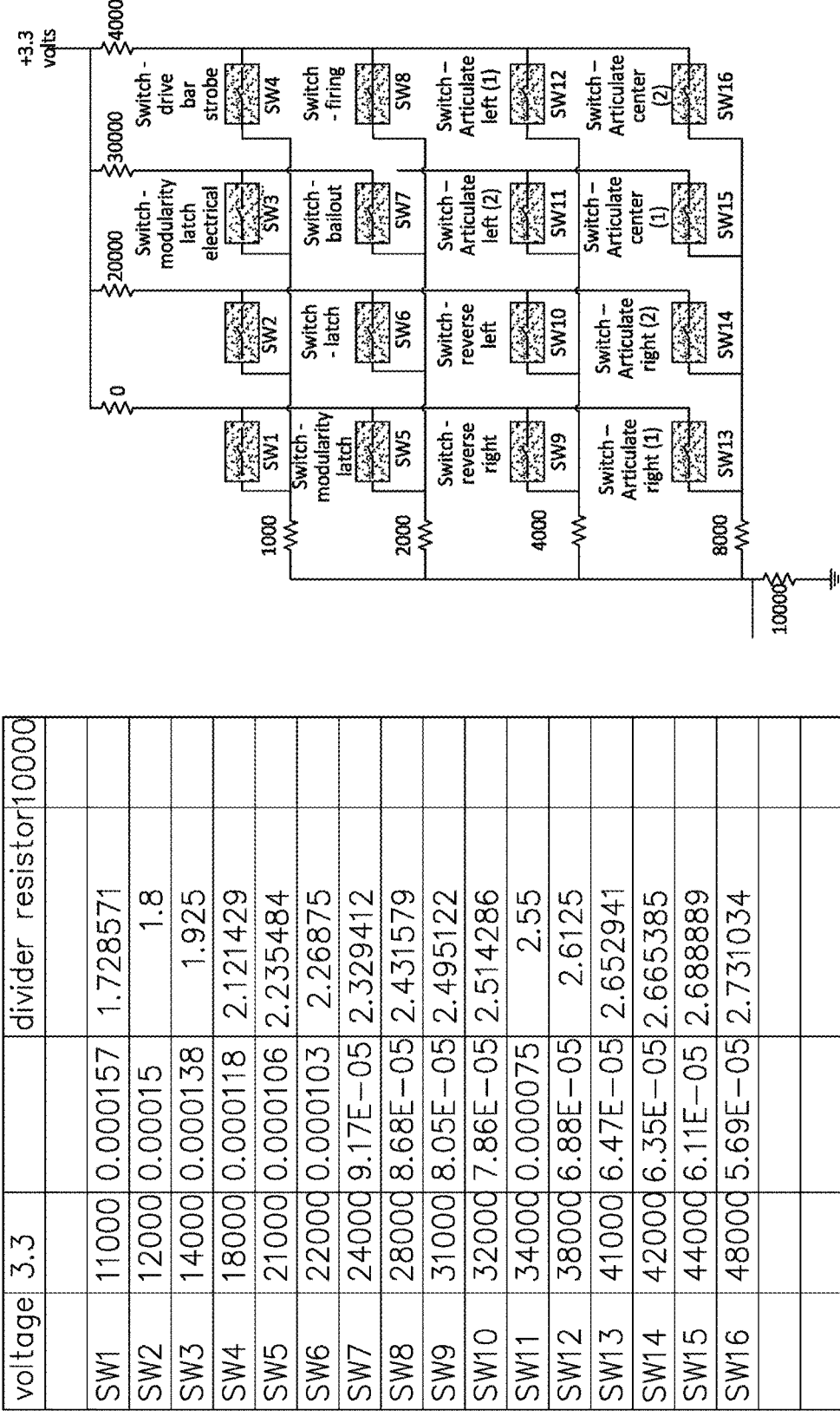
Figure 203:
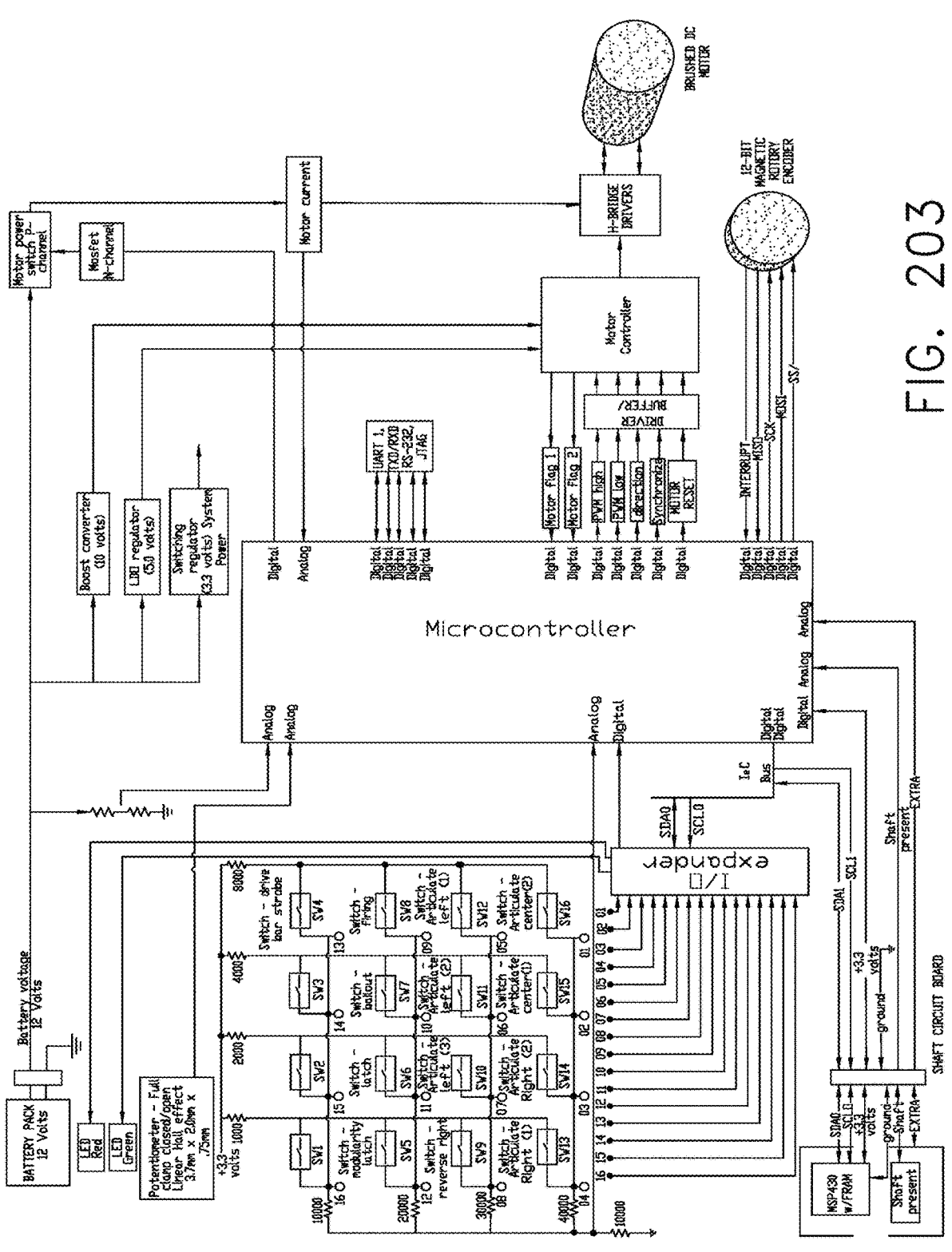
Figure 203A:
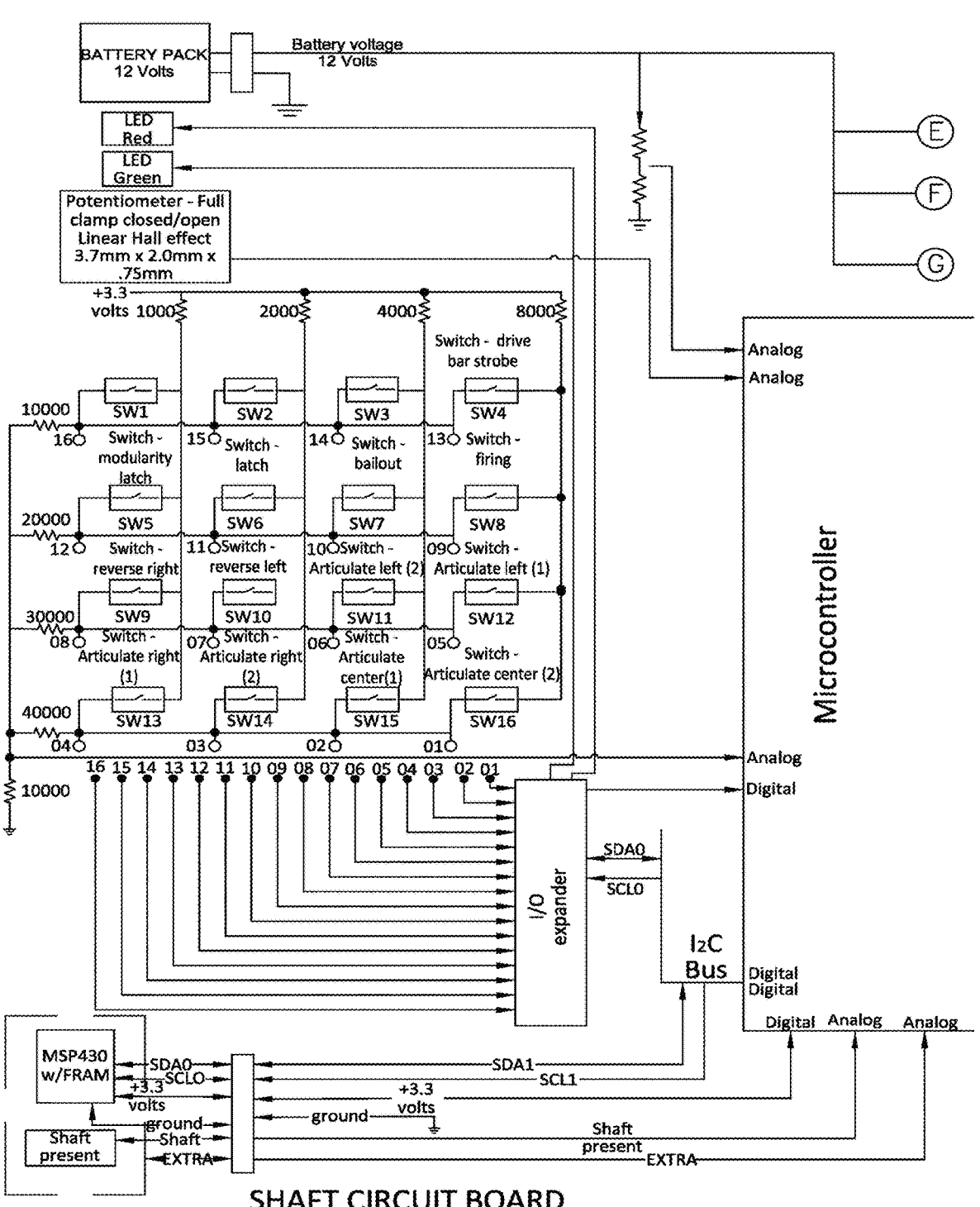
Figure 203B:
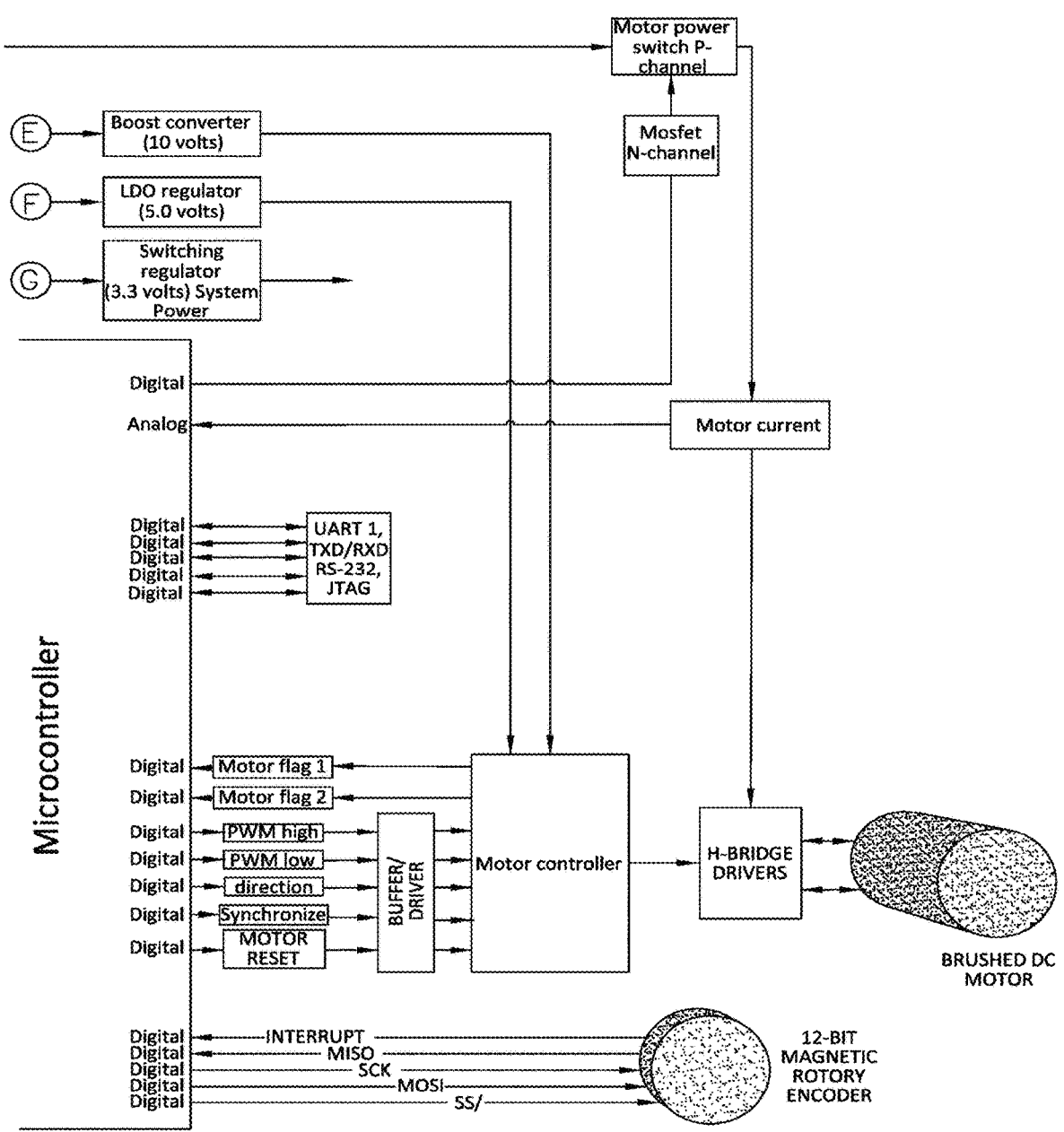
Figure 204:
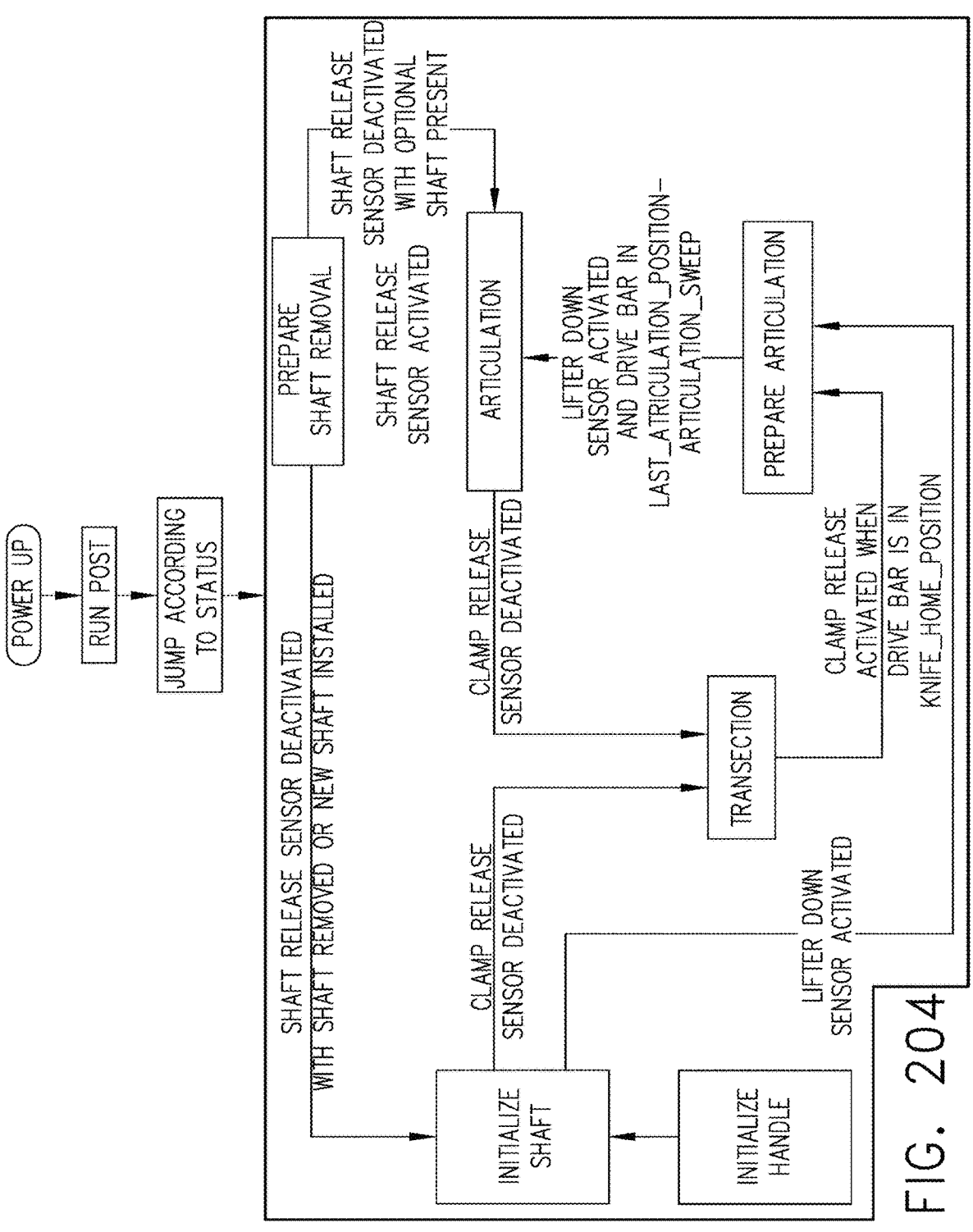
Figure 205:
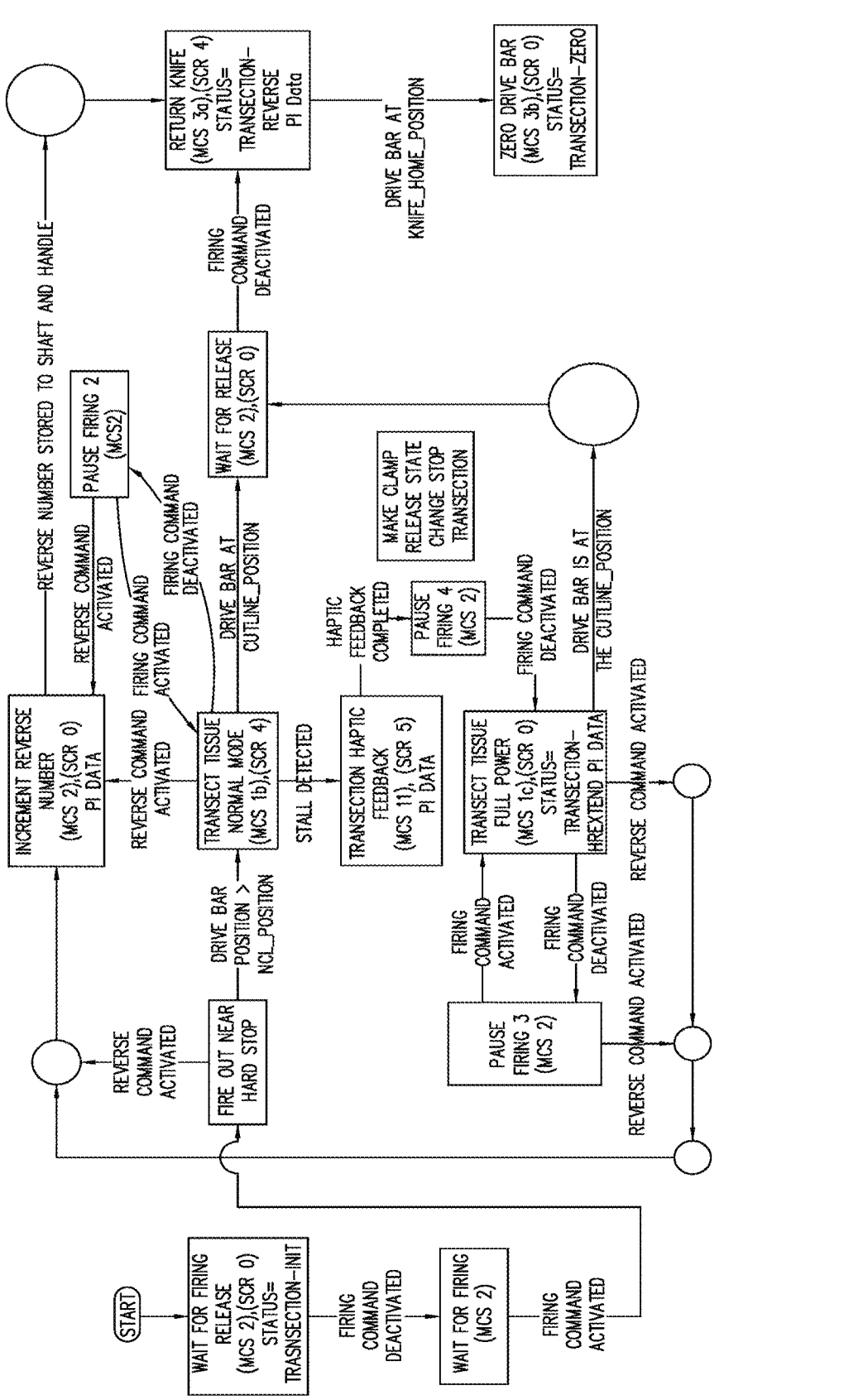
Figure 206:
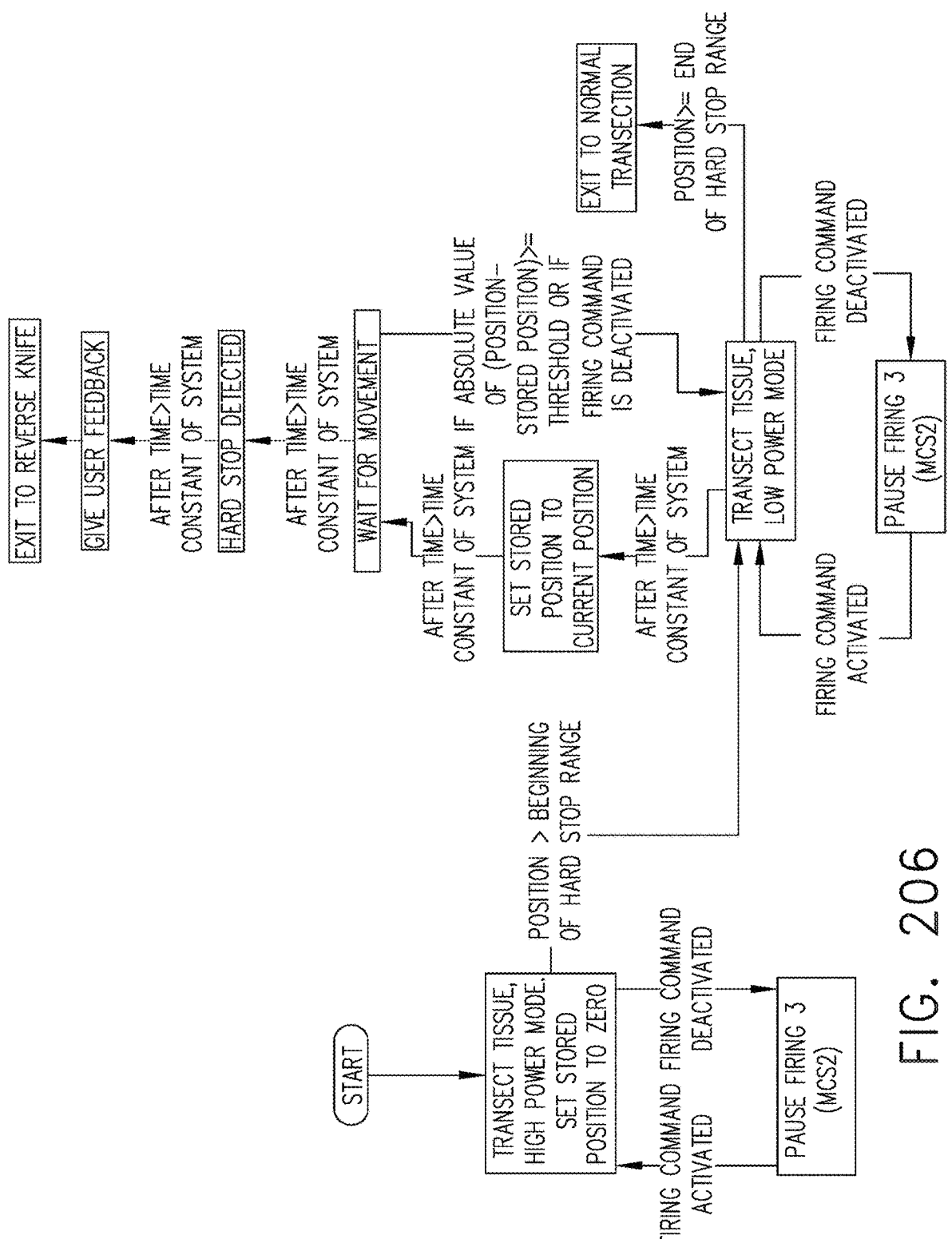

FIG. 128 is a cross-sectional elevational view of the articulation lock of FIG. 125 illustrating the articulation lock in a locked condition;

FIG. 129 is a cross-sectional elevational view of the articulation lock of FIG. 125 illustrating the articulation lock in a second unlocked condition for articulating an end effector in a second direction;

FIG. 130 is a cross-sectional elevational view of the articulation lock of FIG. 125 illustrating the articulation lock in a locked condition;

FIG. 131 is a perspective view of a shaft assembly;

FIG. 132 is an exploded view of the shaft assembly of FIG. 131 illustrating an alternative embodiment of a clutch assembly for operably connecting an articulation drive with a firing drive of the shaft assembly;

FIG. 133 is another exploded view of the shaft assembly of FIG. 131;

FIG. 134 is a partial exploded view of the shaft assembly of FIG. 131 illustrated with portions removed for the purposes of illustration;

FIG. 135 is an end view of the shaft assembly of FIG. 131 illustrated with portions removed for the purposes of illustration;

FIG. 136 is another end view of the shaft assembly of FIG. 131 illustrated with portions removed for the purposes of illustration;

FIG. 137 is a partial cross-sectional elevational view of the shaft assembly of FIG. 131;

FIG. 138 is a partial cross-sectional perspective view of the shaft assembly of FIG. 131;

FIG. 139 is another partial cross-sectional view of the shaft assembly of FIG. 131;

FIG. 140 is a perspective view of the shaft assembly of FIG. 131 illustrating the clutch assembly in an engaged position and illustrated with portions removed for the purposes of clarity; specifically, a clutch actuator is illustrated while a clutch sleeve, a switch drum, a proximal articulation driver, and a closure tube are not illustrated;

FIG. 141 is a perspective view of the shaft assembly of FIG. 131 illustrating the clutch assembly in an engaged position and illustrated with portions removed for the purposes of clarity; specifically, the clutch actuator and the clutch sleeve are illustrated while the switch drum, the proximal articulation driver, and the closure tube are not illustrated;

FIG. 142 is a perspective view of the shaft assembly of FIG. 131 illustrating the clutch assembly in a disengaged position and illustrated with portions removed for the purposes of clarity; specifically, the clutch actuator and the clutch sleeve are illustrated while the switch drum, the proximal articulation driver, and the closure tube are not illustrated;

FIG. 143 is a perspective view of the shaft assembly of FIG. 131 illustrating the clutch assembly in a disengaged position and illustrated with portions removed for the purposes of clarity; specifically, the clutch actuator, the clutch sleeve, and the closure tube are illustrated while the switch drum and the proximal articulation driver are not illustrated;

FIG. 144 is a perspective view of the shaft assembly of FIG. 131 illustrating the clutch assembly in a disengaged position; the clutch actuator, the clutch sleeve, the closure tube, the switch drum, and the proximal articulation driver are illustrated;

FIG. 145 is a perspective view of the shaft assembly of FIG. 131 illustrating the clutch assembly in an engaged position and illustrated with portions removed for the purposes of clarity; specifically, the clutch actuator, the clutch sleeve, and the proximal articulation driver are illustrated while the switch drum and the closure tube are not illustrated;

FIG. 146 is a perspective view of the shaft assembly of FIG. 131 illustrating the clutch assembly in an engaged position and illustrated with portions removed for the purposes of clarity; specifically, the clutch actuator, the clutch sleeve, the proximal articulation driver, and closure tube are illustrated while the switch drum is not illustrated; moreover, the articulation drive system of the shaft assembly is illustrated in a centered, or unarticulated, condition;

FIG. 147 is a perspective view of the shaft assembly of FIG. 131 illustrating the clutch assembly in an engaged position and illustrated with portions removed for the purposes of clarity; specifically, the clutch actuator, the clutch sleeve, and the proximal articulation driver are illustrated while the switch drum and the closure tube are not illustrated; moreover, the articulation drive system of the shaft assembly is illustrated in a condition in which an end effector of the shaft assembly would be articulated to the left of a longitudinal axis of the shaft assembly;

FIG. 148 is a perspective view of the shaft assembly of FIG. 131 illustrating the clutch assembly in an engaged position and illustrated with portions removed for the purposes of clarity; specifically, the clutch actuator, the clutch sleeve, and the proximal articulation driver are illustrated while the switch drum and the closure tube are not illustrated; moreover, the articulation drive system of the shaft assembly is illustrated in a condition in which the end effector of the shaft assembly would be articulated to the right of the longitudinal axis of the shaft assembly;

FIG. 149 is a perspective view of the shaft assembly of FIG. 131 illustrating the clutch assembly in an engaged position and illustrated with portions removed for the purposes of clarity; specifically, the clutch actuator, the clutch sleeve, the closure tube, and the proximal articulation driver are illustrated while the switch drum is not illustrated;

FIG. 150 is a perspective view of a surgical instrument in accordance with certain embodiments described herein;

FIG. 151 is a schematic block diagram of a control system of a surgical instrument in accordance with certain embodiments described herein;

FIG. 152 is a perspective view of an interface of a surgical instrument in accordance with certain embodiments described herein;

FIG. 153 is a top view of the interface of FIG. 152;

FIG. 154 is a cross-sectional view of the interface of FIG. 152 in an inactive or neutral configuration in accordance with certain embodiments described herein;

FIG. 155 is a cross-sectional view of the interface of FIG. 152 activated to articulate an end effector in accordance with certain embodiments described herein;

FIG. 156 is a cross-sectional view of the interface of FIG. 152 activated to return an end effector to an articulation home state position in accordance with certain embodiments described herein;

FIG. 157 is a cross-sectional view of an interface similar to the interface of FIG. 152 in an inactive or neutral configuration in accordance with certain embodiments described herein;

FIG. 158 is a cross-sectional view of the interface of FIG. 152 activated to articulate an end effector in accordance with certain embodiments described herein;

FIG. 159 is a cross-sectional view of the interface of FIG. 152 activated to return the end effector to an articulation home state position in accordance with certain embodiments described herein;

FIG. 160 is a schematic block diagram outlining a response of a controller of the surgical instrument of FIG. 150 to a reset input signal in accordance with certain embodiments described herein;

FIG. 161 is a schematic block diagram outlining a response of a controller of the surgical instrument of FIG. 150 to a home state input signal in accordance with certain embodiments described herein;

FIG. 162 is a schematic block diagram outlining a response of a controller of the surgical instrument of FIG. 150 to a home state input signal in accordance with certain embodiments described herein;

FIG. 163 is a schematic block diagram outlining a response of a controller of the surgical instrument of FIG. 150 to a firing home state input signal in accordance with certain embodiments described herein;

FIG. 164 is side elevational view of a surgical instrument including a handle separated from a shaft according to various embodiments described herein;

FIG. 165 is a side elevational view of a handle portion including an interlock switch and a shaft portion including a locking member according to various embodiments described herein;

FIG. 166 is a partial cross-sectional view of the surgical instrument in FIG. 150 illustrating a locking member in the locked configuration and an open switch according to various embodiments described herein;

FIG. 167 is a partial cross-sectional view of the surgical instrument in FIG. 150 illustrating a locking member in the unlocked configuration and a s closed switch depressed by the locking member according to various embodiments described herein;

FIG. 167A is a partial cross-sectional view of the surgical instrument in FIG. 150 illustrating an advanced firing drive according to various embodiments described herein;

FIG. 167B is a partial cross-sectional view of the surgical instrument in FIG. 150 illustrating a firing drive in a retracted or default position according to various embodiments described herein;

FIG. 168 is a schematic block diagram outlining a response of a controller of the surgical instrument of FIG. 150 to an input signal in accordance with certain embodiments described herein;

FIG. 169 is a schematic block diagram outlining a response of a controller of the surgical instrument of FIG. 150 to an input signal in accordance with certain embodiments described herein;

FIG. 170 is a bottom view of an electric motor and a resonator according to various embodiments of the present disclosure;

FIG. 171 is a perspective view of the resonator of FIG. 170;

FIG. 172 is a bottom view of the resonator of FIG. 170;

FIG. 173 is a partial perspective view of a handle of a surgical instrument depicting the electric motor of FIG. 170 and a resonator positioned within the handle according to various embodiments of the present disclosure;

FIG. 174 is a bottom view of the electric motor and the resonator of FIG. 173;

FIG. 175 is a perspective view of the resonator of FIG. 173;

FIG. 176 is a bottom view of the resonator of FIG. 173;

FIG. 177 is a partial perspective view of the handle of FIG. 173 depicting the electric motor of FIG. 170 and a resonator positioned within the handle according to various embodiments of the present disclosure;

FIG. 178 is a bottom view of the electric motor and the resonator of FIG. 177;

FIG. 179 is a first perspective view of the resonator of FIG. 177;

FIG. 180 is a second perspective view of the resonator of FIG. 177;

FIG. 181 is a perspective view of the handle of FIG. 173, depicting the electric motor of FIG. 170, a resonator, and a retaining ring positioned within the handle according to various embodiments of the present disclosure;

FIG. 182 is a flowchart of the operation of a surgical instrument during a surgical procedure according to various embodiments of the present disclosure;

FIG. 183 is an exploded perspective view of the surgical instrument handle of FIG. 34 showing a portion of a sensor arrangement for an absolute positioning system, according to one embodiment;

FIG. 184 is a side elevational view of the handle of FIGS. 34 and 183 with a portion of the handle housing removed showing a portion of a sensor arrangement for an absolute positioning system, according to one embodiment;

FIG. 185 is a schematic diagram of an absolute positioning system comprising a microcontroller controlled motor drive circuit arrangement comprising a sensor arrangement, according to one embodiment;

FIG. 186 is a detail perspective view of a sensor arrangement for an absolute positioning system, according to one embodiment;

FIG. 187 is an exploded perspective view of the sensor arrangement for an absolute positioning system showing a control circuit board assembly and the relative alignment of the elements of the sensor arrangement, according to one embodiment;

FIG. 188 is a side perspective view of the sensor arrangement for an absolute positioning system showing a control circuit board assembly, according to one embodiment;

FIG. 189 is a side perspective view of the sensor arrangement for an absolute positioning system with the control circuit board assembly removed to show a sensor element holder assembly, according to one embodiment;

FIG. 190 is a side perspective view of the sensor arrangement for an absolute positioning system with the control circuit board and the sensor element holder assemblies removed to show the sensor element, according to one embodiment;

FIG. 191 is a top view of the sensor arrangement for an absolute positioning system shown in with the control circuit board removed but the electronic components still visible to show the relative position between the position sensor and the circuit components, according to one embodiment;

FIG. 192 is a schematic diagram of one embodiment of a position sensor for an absolute positioning system comprising a magnetic rotary absolute positioning system, according to one embodiment;

FIG. 193 illustrates an articulation joint in a straight position, i.e., at a zero angle relative to the longitudinal direction, according to one embodiment;

FIG. 194 illustrates the articulation joint of FIG. 193 articulated in one direction at a first angle defined between a longitudinal axis L-A and an articulation axis A-A, according to one embodiment;

FIG. 195 illustrates the articulation joint of FIG. 193 articulated in another at a second angle defined between the longitudinal axis L-A and the articulation axis A'-A, according to one embodiment;

FIG. 196 illustrates one embodiment of a logic diagram for a method of compensating for the effect of splay in flexible knife bands on transection length;

FIG. 197 is a schematic of a system for powering down an electrical connector of a surgical instrument handle when a shaft assembly is not coupled thereto;

FIG. 198 is a schematic illustrating a system for controlling the speed of a motor and/or the speed of a driveable member of a surgical instrument disclosed herein;

FIG. 199 is a schematic illustrating another system for controlling the speed of a motor and/or the speed of a driveable member of a surgical instrument disclosed herein;

FIG. 200 is a schematic illustrating a control system for controlling various operations of the various surgical instruments described herein according to various embodiments of the present disclosure;

FIG. 200A is a partial view of the schematic of FIG. 200;

FIG. 200B is a partial view of the schematic of FIG. 200;

FIG. 201 is a schematic illustrating a switching circuit for a control system according to various embodiments of the present disclosure;

FIG. 202 is a schematic illustrating a switching circuit for a control system according to various embodiments of the present disclosure;

FIG. 203 is a schematic illustrating a control system for controlling various operations of the various surgical instruments described herein according to various embodiments of the present disclosure;

FIG. 203A is a partial view of the schematic of FIG. 203;

FIG. 203B is a partial view of the schematic of FIG. 203;

FIG. 204 is a schematic illustrating a control system for controlling various operations of the various surgical instruments described herein according to various embodiments of the present disclosure;

FIG. 205 is a schematic illustrating various sub-operations of the Transection Operation of FIG. 204 according to various embodiments of the present disclosure; and FIG. 206 is a schematic illustrating various sub-operations of the Fire Out Near Hard Stop Operation of FIG. 205 according to various embodiments of the present disclosure.

Corresponding reference characters indicate corresponding parts throughout the several views. The exemplifications set out herein illustrate certain embodiments of the invention, in one form, and such exemplifications are not to be construed as limiting the scope of the invention in any manner.

DETAILED DESCRIPTION

Certain illustrative embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting illustrative embodiments and that the scope of the various embodiments of the present invention is defined solely by the claims. The features illustrated or described in connection with one illustrative embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various illustrative devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Figure 1:
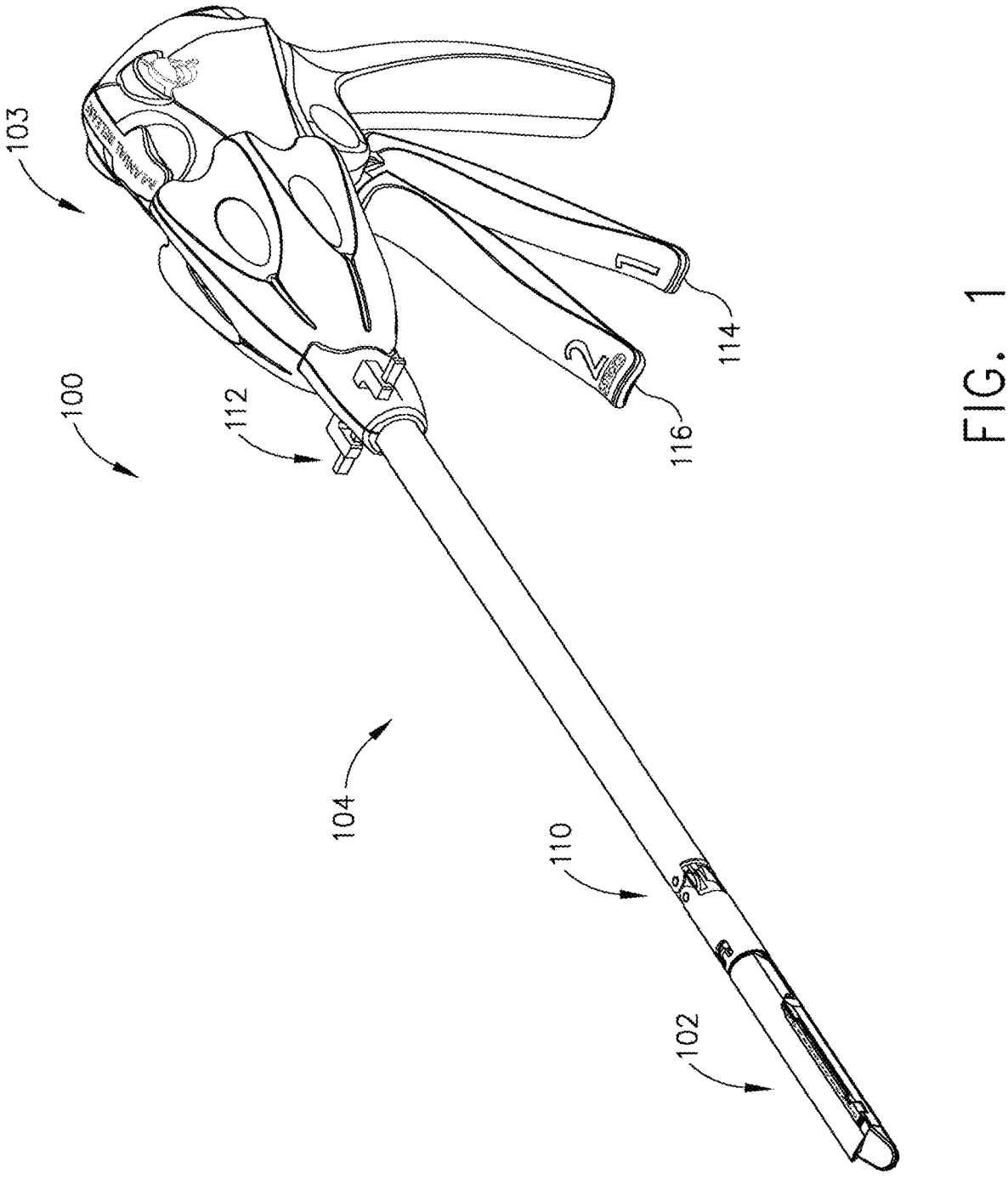
FIG. 1 is a perspective view of a surgical instrument comprising a handle, a shaft, and an articulatable end effector.
Figures 2, 3:
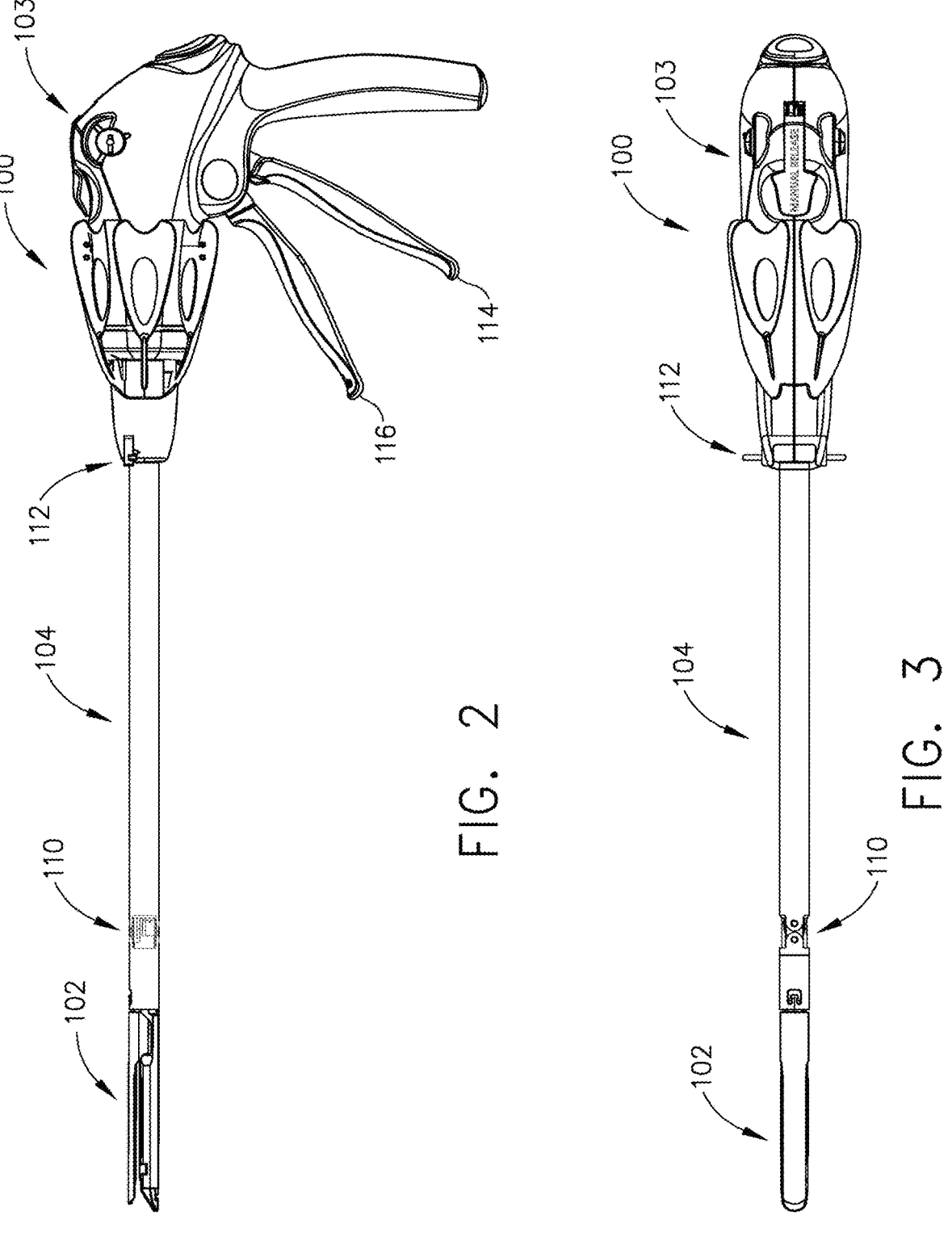
FIG. 2 is an elevational view of the surgical instrument of FIG. 1.
FIG. 3 is a plan view of the surgical instrument of FIG. 1.

FIGS. 1-3 illustrate an illustrative surgical instrument 100 which can include a handle 103, a shaft 104 and an articulating end effector 102 pivotally connected to the shaft 104 at articulation joint 110. An articulation control 112 is provided to effect rotation of the end effector 102 about articulation joint 110. The end effector 102 is shown configured to act as an endocutter for clamping, severing and stapling tissue, however, it will be appreciated that various embodiments may include end effectors configured to act as other surgical devices including, for example, graspers, cutters, staplers, clip appliers, access devices, drug/gene therapy delivery devices, ultrasound, RF, and/or laser energy devices, etc. The handle 103 of the instrument 100 may include closure trigger 114 and firing trigger 116 for actuating the end effector 102. It will be appreciated that instruments having end effectors directed to different surgical tasks may have different numbers or types of triggers or other suitable controls for operating an end effector. The end effector 102 is connected to the handle 103 by shaft 104. A clinician may articulate the end effector 102 relative to the shaft 104 by utilizing the articulation control 112, as described in greater detail further below.

It should be appreciated that spatial terms such as vertical, horizontal, right, left etc., are given herein with reference to the figures assuming that the longitudinal axis of the surgical instrument 100 is co-axial to the central axis of the shaft 104, with the triggers 114, 116 extending downwardly at an acute angle from the bottom of the handle 103. In actual practice, however, the surgical instrument 100 may be oriented at various angles and as such these spatial terms are used relative to the surgical instrument 100 itself. Further, proximal is used to denote a perspective of a clinician who is behind the handle 103 who places the end effector 102 distal, or away from him or herself. As used herein, the phrase, "substantially transverse to the longitudinal axis" where the "longitudinal axis" is the axis of the shaft, refers to a direction that is nearly perpendicular to the longitudinal axis. It will be appreciated, however, that directions that deviate some from perpendicular to the longitudinal axis are also substantially transverse to the longitudinal axis.

Figure 4:
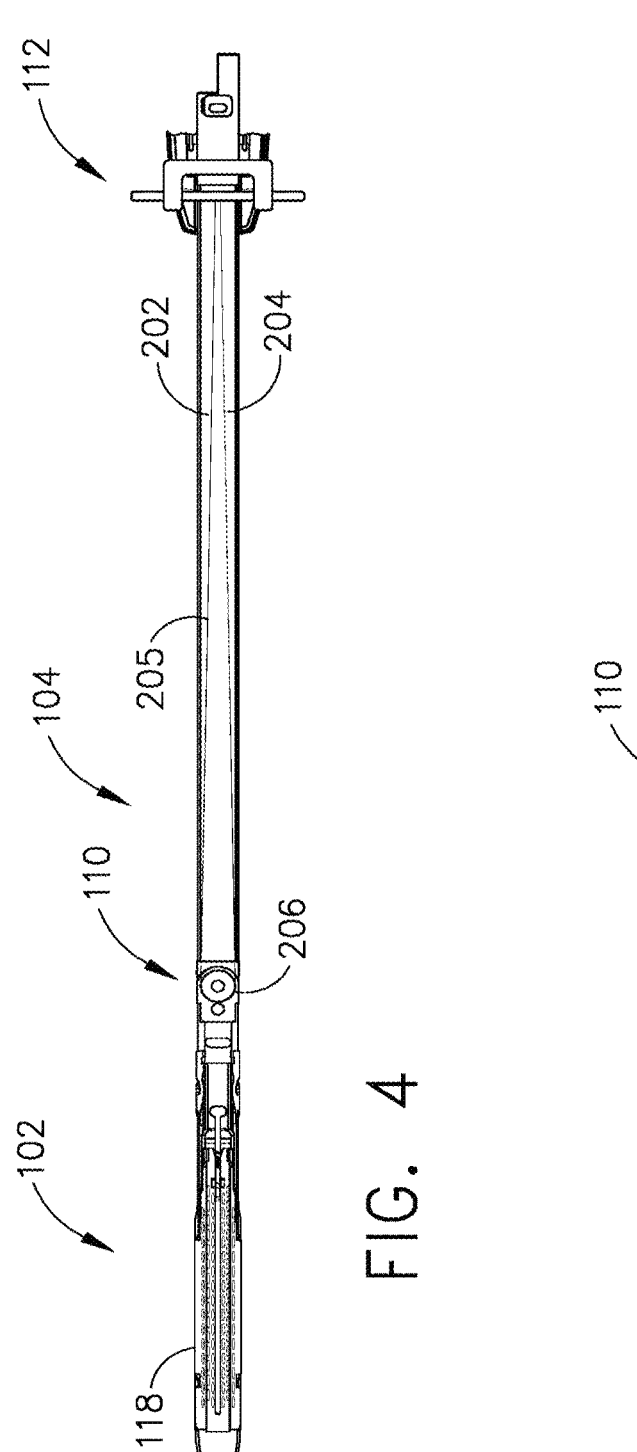
FIG. 4 is a cross-sectional view of the end effector and the shaft of the surgical instrument of FIG. 1.
Figure 5:
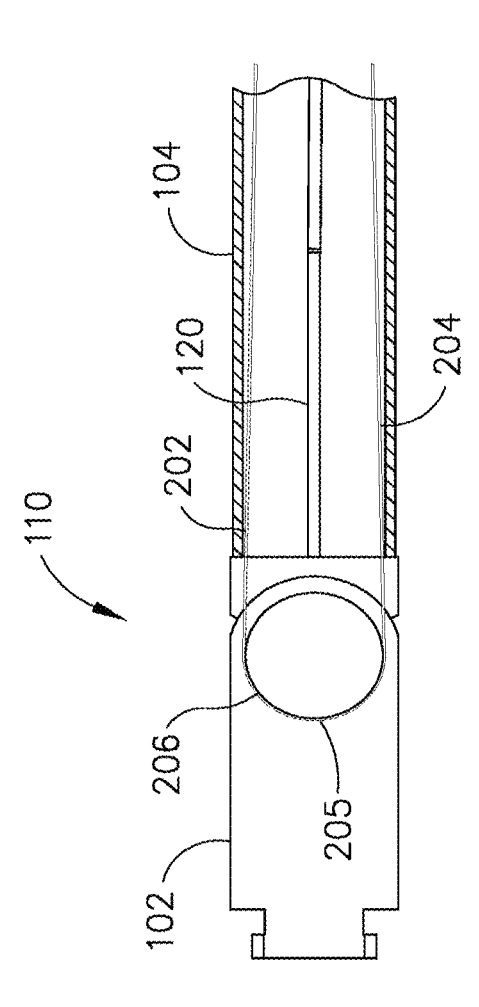
FIG. 5 is a detail view of an articulation joint which rotatable connects the shaft and the end effector of FIG. 1 which illustrates the end effector in a neutral, or centered, position.

Various embodiments disclosed herein are directed to instruments having an articulation joint driven by bending cables or bands. FIGS. 4 and 5 show a cross-sectional top view of the elongate shaft 104 and the end effector 102 including a band 205 that is mechanically coupled to a boss 206 extending from the end effector 102. The band 205 may include band portions 202 and 204 extending proximally from the boss 206 along the elongate shaft 104 and through the articulation control 112. The band 205 and band portions 202, 204 can have a fixed length. The band 205 may be mechanically coupled to the boss 206 as shown using any suitable fastening method including, for example, glue, welding, etc. In various embodiments, each band portion 202, 204 may be provided as a separate band, with each separate band having one end mechanically coupled to the boss 206 and another end extending through the shaft 104 and articulation controller 112. The separate bands may be mechanically coupled to the boss 206 as described above.

Figures 6, 8:
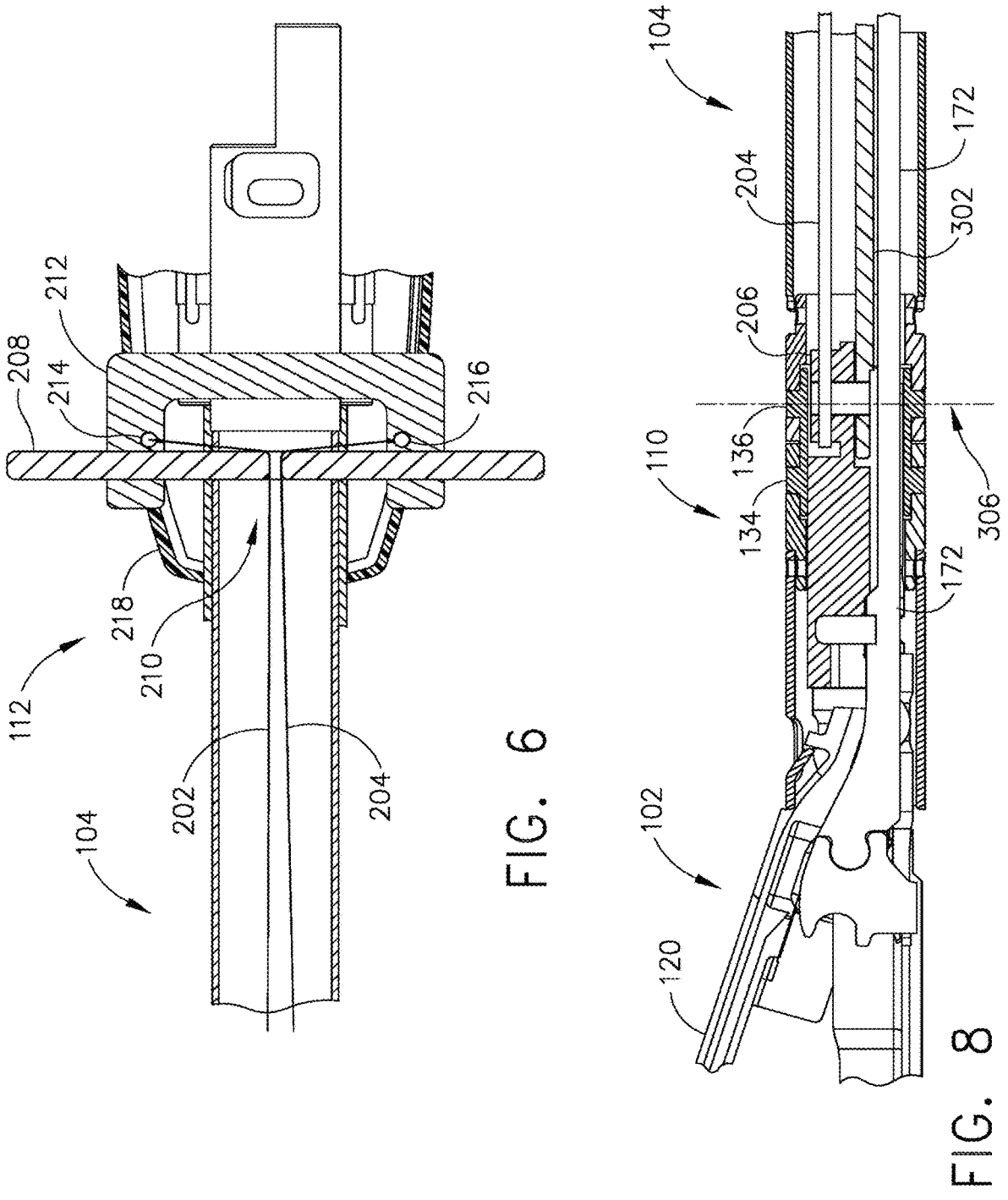
FIG. 6 is a cross-sectional view of an articulation control of the surgical instrument of FIG. 1 in a neutral, or centered, position.
FIG. 8 is a cross-sectional view of the end effector, elongate shaft, and articulation joint of the surgical instrument of FIG. 1.

Further to the above, band portions 202, 204 may extend from the boss 206, through the articulation joint 110 and along the shaft 104 to the articulation control 112, shown in FIG. 6. The articulation control 112 can include an articulation slide 208, a frame 212 and an enclosure 218. Band portions 202, 204 may pass through the articulation slide 208 by way of slot 210 or other aperture, although it will be appreciated that the band portions 202, 204 may be coupled to the slide 208 by any suitable means. The articulation slide 208 may be one piece, as shown in FIG. 6, or may include two pieces with an interface between the two pieces defining the slot 210. In one non-limiting embodiment, the articulation slide 208 may include multiple slots, for example, with each slot configured to receive one of the band portions 202, 204. Enclosure 218 may cover the various components of the articulation control 112 to prevent debris from entering the articulation control 112.

Referring again to FIG. 6, the band portions 202, 204 may be anchored to the frame 212 at connection points 214, 216, respectively, which are proximally located from the slot 210. It will be appreciated that band portions 202, 204 may be anchored anywhere in the instrument 10 located proximally from the slot 210, including the handle 103. The non-limiting embodiment of FIG. 6 shows that the band portions 202, 204 can comprise a bent configuration between the connection points 214, 216 and the slot 210 located near the longitudinal axis of the shaft 104. Other embodiments are envisioned in which the band portions 202, 204 are straight.

Figure 7:
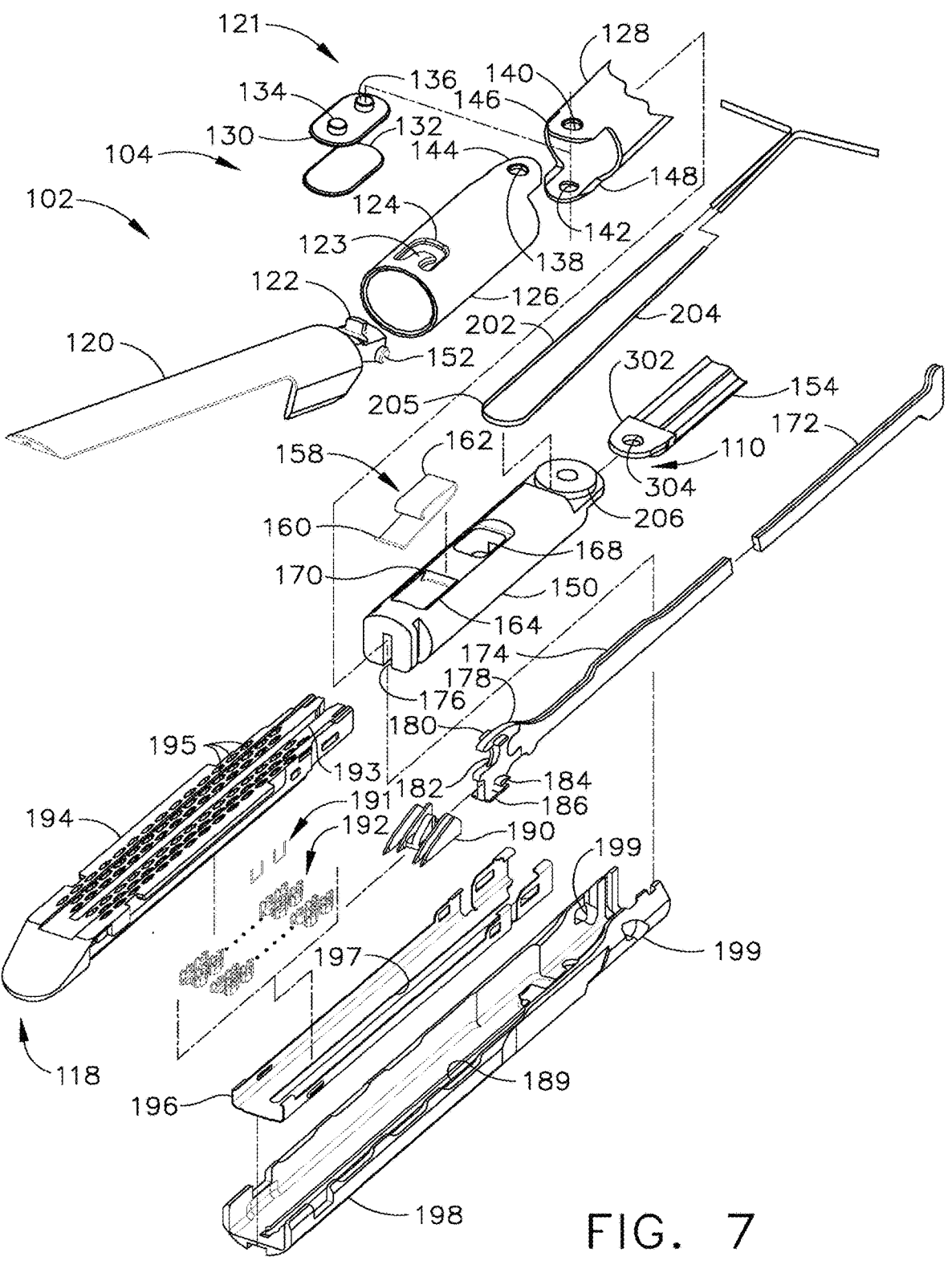
FIG. 7 is an exploded view of the end effector, elongate shaft, and articulation joint of the surgical instrument of FIG. 1.
Figure 9:
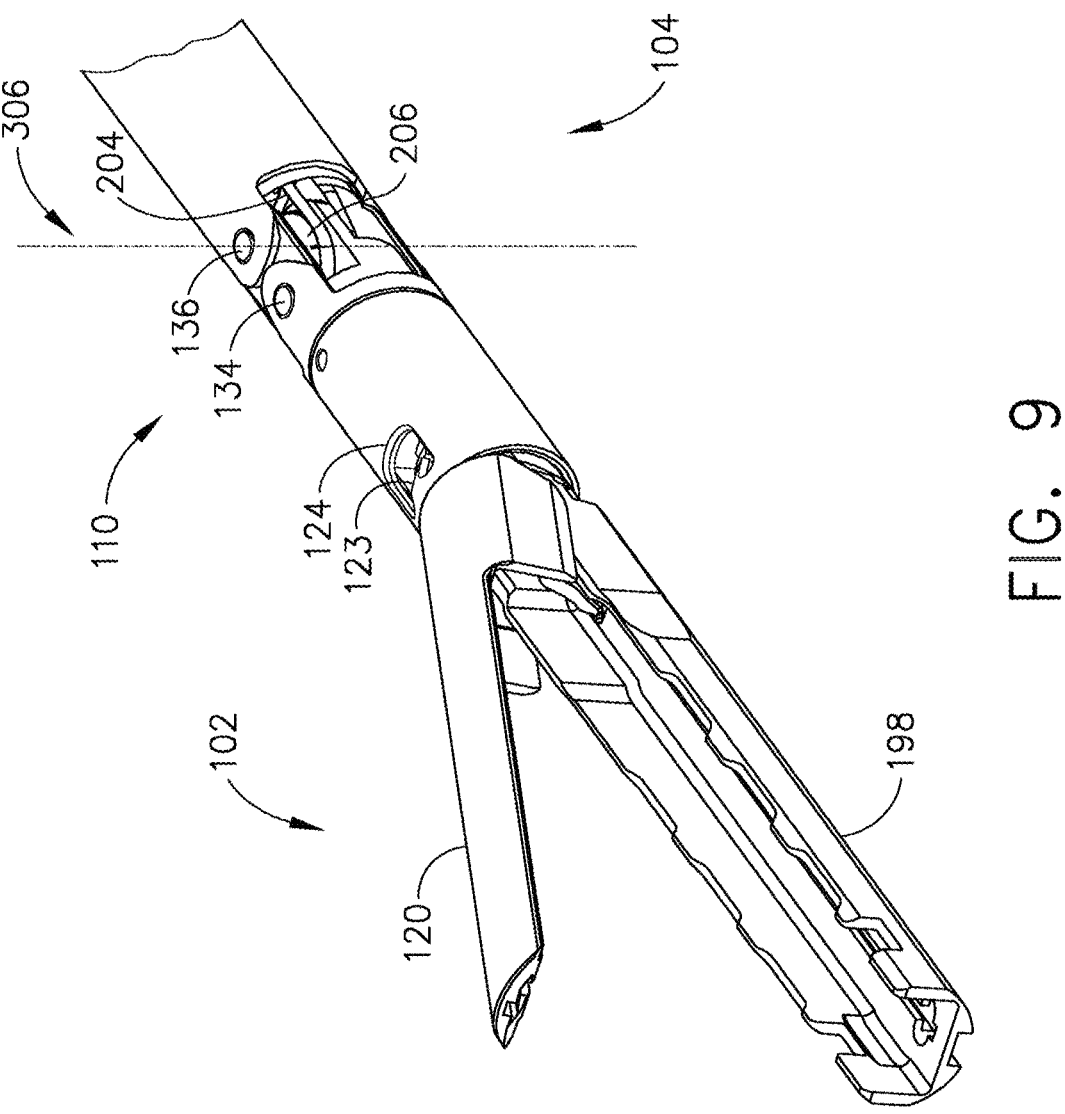
FIG. 9 is a perspective view of the end effector, elongate shaft, and articulation joint of the surgical instrument of FIG. 1.
Figures 10, 11:
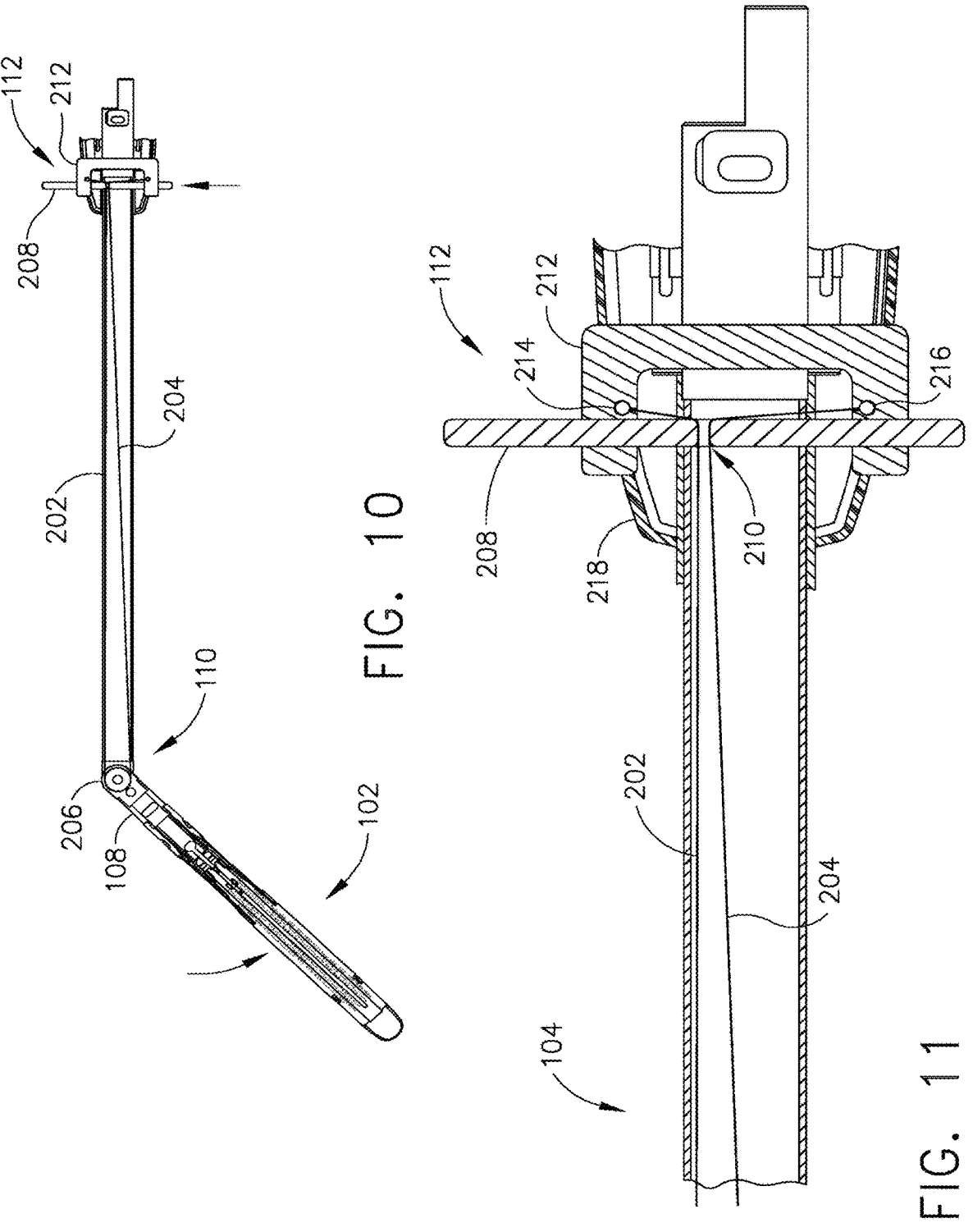
FIG. 10 depicts the end effector of the surgical instrument of FIG. 1 articulated about the articulation joint.
FIG. 11 is a cross-sectional view of the articulation control of FIG. 6 actuated to move the end effector as shown in FIG. 12.

FIGS. 7-9 show views of the end effector 102 and elongate shaft 104 of the instrument 100 including the articulation joint 110 shown in FIG. 5. FIG. 7 shows an exploded view of the end effector 102 and elongate shaft 104 including various internal components. In at least one embodiment, an end effector frame 150 and shaft frame 154 are configured to be joined at articulation joint 110. Boss 206 may be integral to the end effector frame 150 with band 205 interfacing the boss 206 as shown. The shaft frame 154 may include a distally directed tang 302 defining an aperture 304. The aperture 304 may be positioned to interface an articulation pin (not shown) included in end effector frame 150 allowing the end effector frame 150 to pivot relative to the shaft frame 154, and accordingly, the end effector 102 to pivot relative to the shaft 104. When assembled, the various components may pivot about articulation joint 110 at an articulation axis 306 shown in FIGS. 9 and 10.

FIG. 7 also shows an anvil 120. In this non-limiting embodiment, the anvil 120 is coupled to an elongate channel 198. For example, apertures 199 can be defined in the elongate channel 198 which can receive pins 152 extending from the anvil 120 and allow the anvil 120 to pivot from an open position to a closed position relative to the elongate channel 198 and staple cartridge 118. In addition, FIG. 7 shows a firing bar 172, configured to longitudinally translate through the shaft frame 154, through the flexible closure and pivoting frame articulation joint 110, and through a firing slot 176 in the distal frame 150 into the end effector 102. The firing bar 172 may be constructed from one solid section, or in various embodiments, may include a laminate material comprising, for example, a stack of steel plates. It will be appreciated that a firing bar 172 made from a laminate material may lower the force required to articulate the end effector 102. In various embodiments, a spring clip 158 can be mounted in the end effector frame 150 to bias the firing bar 172 downwardly. Distal and proximal square apertures 164, 168 formed on top of the end effector frame 150 may define a clip bar 170 therebetween that receives a top arm 162 of a clip spring 158 whose lower, distally extended arm 160 asserts a downward force on a raised portion 174 of the firing bar 172, as discussed below.

A distally projecting end of the firing bar 172 can be attached to an E-beam 178 that can, among other things, assist in spacing the anvil 120 from a staple cartridge 118 positioned in the elongate channel 198 when the anvil 120 is in a closed position. The E-beam 178 can also include a sharpened cutting edge 182 which can be used to sever tissue as the E-beam 178 is advanced distally by the firing bar 172. In operation, the E-beam 178 can also actuate, or fire, the staple cartridge 118. The staple cartridge 118 can include a molded cartridge body 194 that holds a plurality of staples 191 resting upon staple drivers 192 within respective upwardly open staple cavities 195. A wedge sled 190 is driven distally by the E-beam 178, sliding upon a cartridge tray 196 that holds together the various components of the replaceable staple cartridge 118. The wedge sled 190 upwardly cams the staple drivers 192 to force out the staples 191 into deforming contact with the anvil 120 while a cutting surface 182 of the E-beam 178 severs clamped tissue.

Further to the above, the E-beam 178 can include upper pins 180 which engage the anvil 120 during firing. The E-beam 178 can further include middle pins 184 and a bottom foot 186 which can engage various portions of the cartridge body 194, cartridge tray 196 and elongate channel 198. When a staple cartridge 118 is positioned within the elongate channel 198, a slot 193 defined in the cartridge body 194 can be aligned with a slot 197 defined in the cartridge tray 196 and a slot 189 defined in the elongate channel 198. In use, the E-beam 178 can slide through the aligned slots 193, 197, and 189 wherein, as indicated in FIG. 7, the bottom foot 186 of the E-beam 178 can engage a groove running along the bottom surface of channel 198 along the length of slot 189, the middle pins 184 can engage the top surfaces of cartridge tray 196 along the length of longitudinal slot 197, and the upper pins 180 can engage the anvil 120. In such circumstances, the E-beam 178 can space, or limit the relative movement between, the anvil 120 and the staple cartridge 118 as the firing bar 172 is moved distally to fire the staples from the staple cartridge 118 and/or incise the tissue captured between the anvil 120 and the staple cartridge 118. Thereafter, the firing bar 172 and the E-beam 178 can be retracted proximally allowing the anvil 120 to be opened to release the two stapled and severed tissue portions (not shown).

FIGS. 7-9 also show a double pivot closure sleeve assembly 121 according to various embodiments. With particular reference to FIG. 7, the double pivot closure sleeve assembly 121 includes a shaft closure tube section 128 having upper and lower distally projecting tangs 146, 148. An end effector closure tube section 126 includes a horseshoe aperture 124 and a tab 123 for engaging the opening tab 122 on the anvil 120. The horseshoe aperture 124 and tab 123 engage tab 122 when the anvil 120 is opened. The closure tube section 126 is shown having upper 144 and lower (not visible) proximally projecting tangs. An upper double pivot link 130 includes upwardly projecting distal and proximal pivot pins 134, 136 that engage respectively an upper distal pin hole 138 in the upper proximally projecting tang 144 and an upper proximal pin hole 140 in the upper distally projecting tang 146. A lower double pivot link 132 includes downwardly projecting distal and proximal pivot pins (not shown in FIG. 7, but see FIG. 8) that engage respectively a lower distal pin hole in the lower proximally projecting tang and a lower proximal pin hole 142 in the lower distally projecting tang 148.

In use, the closure sleeve assembly 121 is translated distally to close the anvil 120, for example, in response to the actuation of the closure trigger 114. The anvil 120 is closed by distally translating the closure tube section 126, and thus the sleeve assembly 121, causing it to strike a proximal surface on the anvil 120 located in FIG. 9A to the left of the tab 122. As shown more clearly in FIGS. 8 and 9, the anvil 120 is opened by proximally translating the tube section 126, and sleeve assembly 121, causing tab 123 and the horseshoe aperture 124 to contact and push against the tab 122 to lift the anvil 120. In the anvil-open position, the double pivot closure sleeve assembly 121 is moved to its proximal position.

Figure 12:
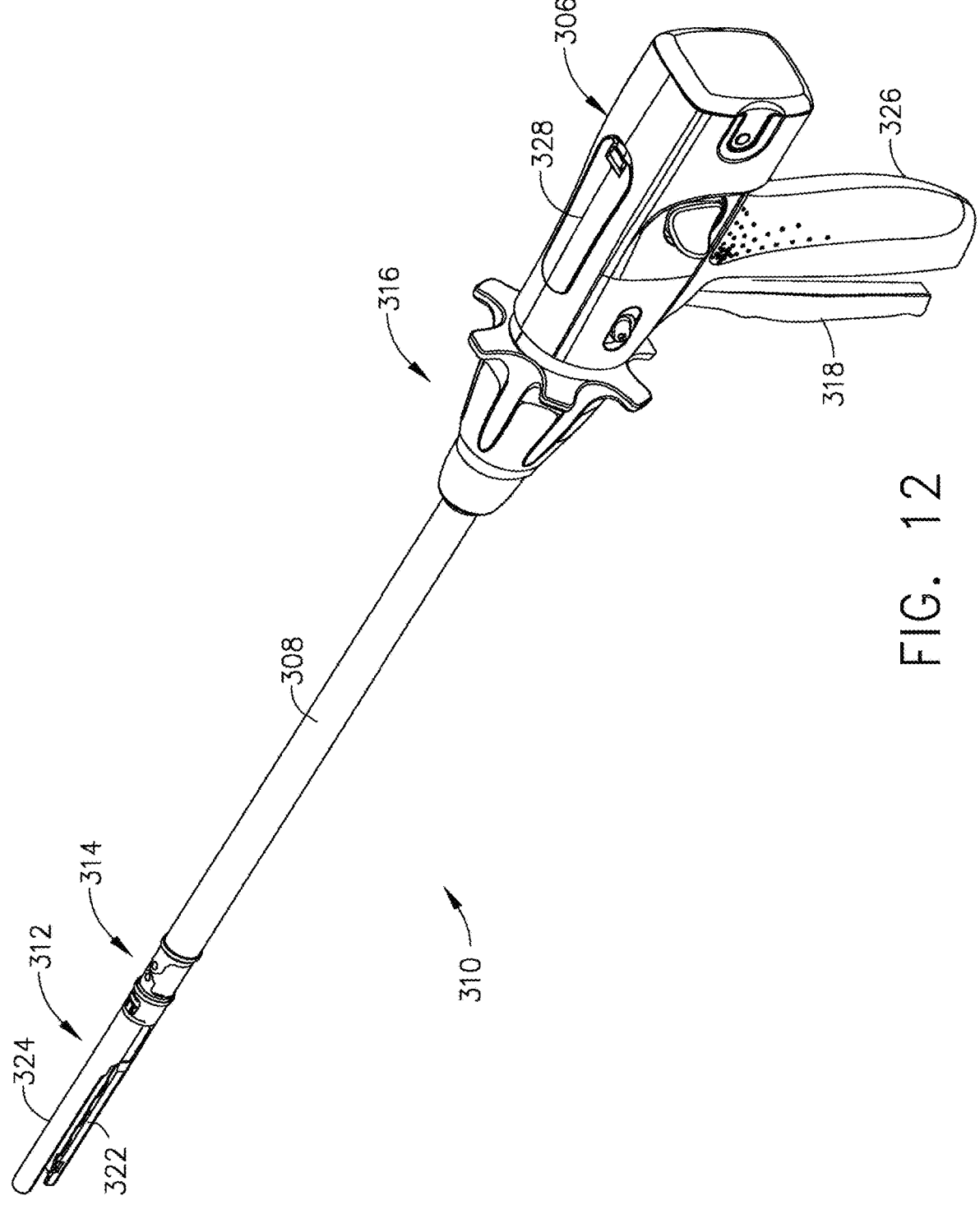
FIG. 12 is a perspective view of a surgical instrument comprising a handle, a shaft, and an articulatable end effector.

In operation, the clinician may articulate the end effector 102 of the instrument 100 relative to the shaft 104 about pivot 110 by pushing the control 112 laterally. From the neutral position, the clinician may articulate the end effector 102 to the left relative to the shaft 104 by providing a lateral force to the left side of the control 112. In response to force, the articulation slide 208 may be pushed at least partially into the frame 212. As the slide 208 is pushed into the frame 212, the slot 210 as well as band portion 204 may be translated across the elongate shaft 104 in a transverse direction, for example, a direction substantially transverse, or perpendicular, to the longitudinal axis of the shaft 104. Accordingly, a force is applied to band portion 204, causing it to resiliently bend and/or displace from its initial pre-bent position toward the opposite side of the shaft 104. Concurrently, band portion 202 is relaxed from its initial pre-bent position. Such movement of the band portion 204, coupled with the straightening of band portion 202, can apply a counter-clockwise rotational force at boss 206 which in turn causes the boss 206 and end effector 102 to pivot to the left about the articulation pivot 110 to a desired angle relative to the axis of the shaft 104 as shown in FIG. 12. The relaxation of the band portion 202 decreases the tension on that band portion, allowing the band portion 204 to articulate the end effector 102 without substantial interference from the band portion 202. It will be appreciated that the clinician may also articulate the end effector 102 to the right relative to the shaft 104 by providing a lateral force to the right side of the control 112. This bends cable portion 202, causing a clockwise rotational force at boss 206 which, in turn, causes the boss 206 and end effector to pivot to the right about articulation pivot 110. Similar to the above, band portion 204 can be concurrently relaxed to permit such movement.

Figure 13:
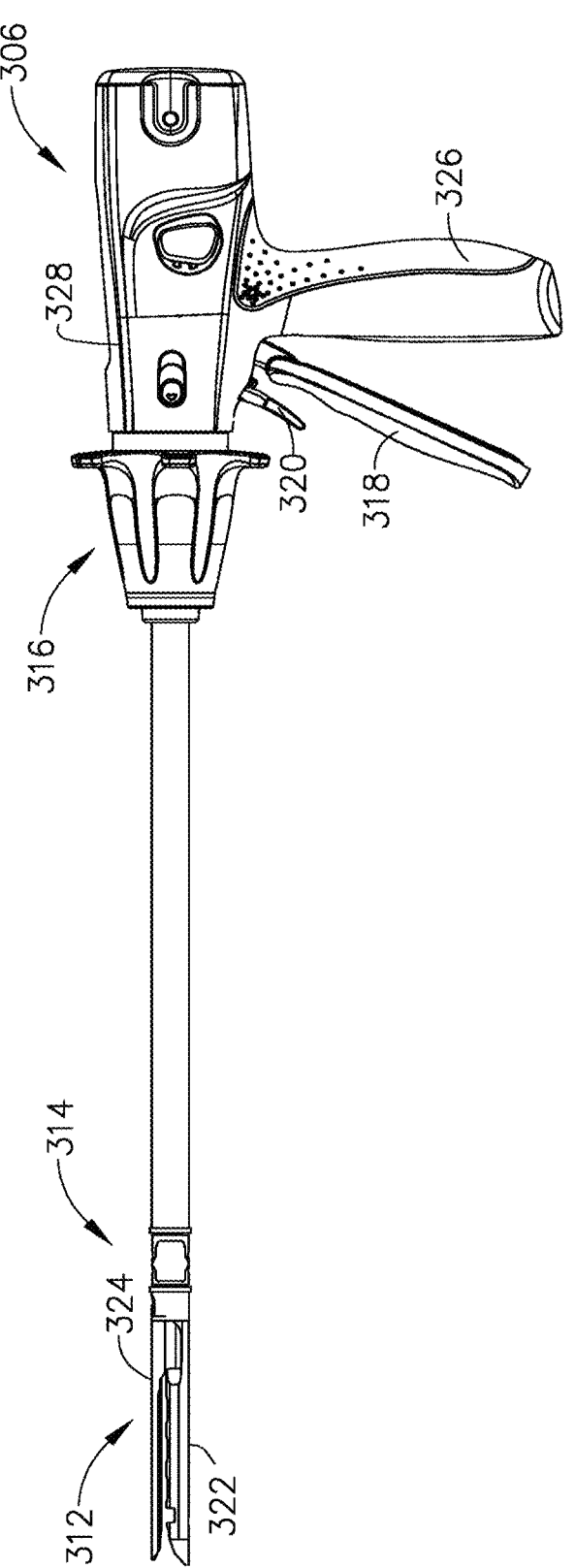
FIG. 13 is a side view of the surgical instrument of FIG. 12.

FIGS. 12 and 13 depict a motor-driven surgical cutting and fastening instrument 310. This illustrated embodiment depicts an endoscopic instrument and, in general, the instrument 310 is described herein as an endoscopic surgical cutting and fastening instrument; however, it should be noted that the invention is not so limited and that, according to other embodiments, any instrument disclosed herein may comprise a non-endoscopic surgical cutting and fastening instrument. The surgical instrument 310 depicted in FIGS. 12 and 13 comprises a handle 306, a shaft 308, and an end effector 312 connected to the shaft 308. In various embodiments, the end effector 312 can be articulated relative to the shaft 308 about an articulation joint 314. Various means for articulating the end effector 312 and/or means for permitting the end effector 312 to articulate relative to the shaft 308 are disclosed in U.S. Pat. No. 7,753,245, entitled SURGICAL STAPLING INSTRUMENTS, which issued on Jul. 13, 2010, and U.S. Pat. No. 7,670,334, entitled SURGICAL INSTRUMENT HAVING AN ARTICULATING END EFFECTOR, which issued on Mar. 2, 2010, the entire disclosures of which are incorporated by reference herein. Various other means for articulating the end effector 312 are discussed in greater detail below. Similar to the above, the end effector 312 is configured to act as an endocutter for clamping, severing, and/or stapling tissue, although, in other embodiments, different types of end effectors may be used, such as end effectors for other types of surgical devices, graspers, cutters, staplers, clip appliers, access devices, drug/gene therapy devices, ultrasound, RF and/or laser devices, etc. Several RF devices may be found in U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL CUTTING AND FASTENING INSTRUMENT HAVING RF ELECTRODES, filed Feb. 14, 2008, the entire disclosures of which are incorporated by reference in their entirety.

It will be appreciated that the terms "proximal" and "distal" are used herein with reference to a clinician gripping the handle 306 of the instrument 310. Thus, the end effector 312 is distal with respect to the more proximal handle 306. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The end effector 312 can include, among other things, a staple channel 322 and a pivotally translatable clamping member, such as an anvil 324, for example. The handle 306 of the instrument 310 may include a closure trigger 318 and a firing trigger 320 for actuating the end effector 312. It will be appreciated that instruments having end effectors directed to different surgical tasks may have different numbers or types of triggers or other suitable controls for operating the end effector 312. The handle 306 can include a downwardly extending pistol grip 326 toward which the closure trigger 318 is pivotally drawn by the clinician to cause clamping or closing of the anvil 324 toward the staple channel 322 of the end effector 312 to thereby clamp tissue positioned between the anvil 324 and channel 322. In other embodiments, different types of clamping members in addition to or lieu of the anvil 324 could be used. The handle 306 can further include a lock which can be configured to releasably hold the closure trigger 318 in its closed position. More details regarding embodiments of an illustrative closure system for closing (or clamping) the anvil 324 of the end effector 312 by retracting the closure trigger 318 are provided in U.S. Pat. No. 7,000,818, entitled SURGICAL STAPLING INSTRUMENT HAVING SEPARATE DISTINCT CLOSING AND FIRING SYSTEMS, which issued on Feb. 21, 2006, U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008, and U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008, the entire disclosures of which are incorporated by reference herein.

Once the clinician is satisfied with the positioning of the end effector 312, the clinician may draw back the closure trigger 318 to its fully closed, locked position proximate to the pistol grip 326. The firing trigger 320 may then be actuated, or fired. In at least one such embodiment, the firing trigger 320 can be farther outboard of the closure trigger 318 wherein the closure of the closure trigger 318 can move, or rotate, the firing trigger 320 toward the pistol grip 326 so that the firing trigger 320 can be reached by the operator using one hand, in various circumstances. Thereafter, the operator may pivotally draw the firing trigger 320 toward the pistol grip 312 to cause the stapling and severing of clamped tissue in the end effector 312. Thereafter, the firing trigger 320 can be returned to its unactuated, or unfired, position (shown in FIGS. 1 and 2) after the clinician relaxes or releases the force being applied to the firing trigger 320. A release button on the handle 306, when depressed, may release the locked closure trigger 318. The release button may be implemented in various forms such as, for example, those disclosed in U.S. Patent Application Publication No. 2007/0175955, entitled SURGICAL CUTTING AND FASTENING INSTRUMENT WITH CLOSURE TRIGGER LOCKING MECHANISM, which was filed on Jan. 31, 2006, the entire disclosure of which is incorporated herein by reference in its entirety.

Further to the above, the end effector 312 may include a cutting instrument, such as knife, for example, for cutting tissue clamped in the end effector 312 when the firing trigger 320 is retracted by a user. Also further to the above, the end effector 312 may also comprise means for fastening the tissue severed by the cutting instrument, such as staples, RF electrodes, and/or adhesives, for example. A longitudinally movable drive shaft located within the shaft 308 of the instrument 310 may drive/actuate the cutting instrument and the fastening means in the end effector 312. An electric motor, located in the handle 306 of the instrument 310 may be used to drive the drive shaft, as described further herein. In various embodiments, the motor may be a DC brushed driving motor having a maximum rotation of, approximately, 25,000 RPM, for example. In other embodiments, the motor may include a brushless motor, a cordless motor, a synchronous motor, a stepper motor, or any other suitable electric motor. A battery (or "power source" or "power pack"), such as a Li ion battery, for example, may be provided in the pistol grip portion 26 of the handle 6 adjacent to the motor wherein the battery can supply electric power to the motor via a motor control circuit. According to various embodiments, a number of battery cells connected in series may be used as the power source to power the motor. In addition, the power source may be replaceable and/or rechargeable.

Figure 14:
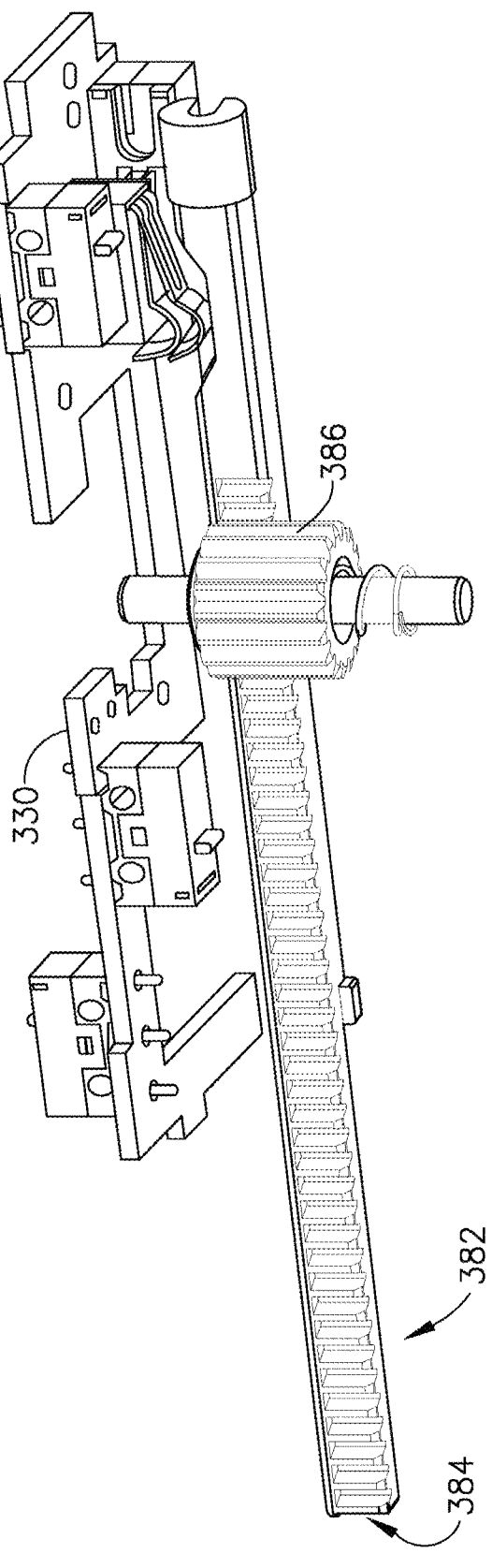
FIG. 14 is a perspective view of a firing member and a pinion gear positioned within the handle of FIG. 12.
Figure 15:
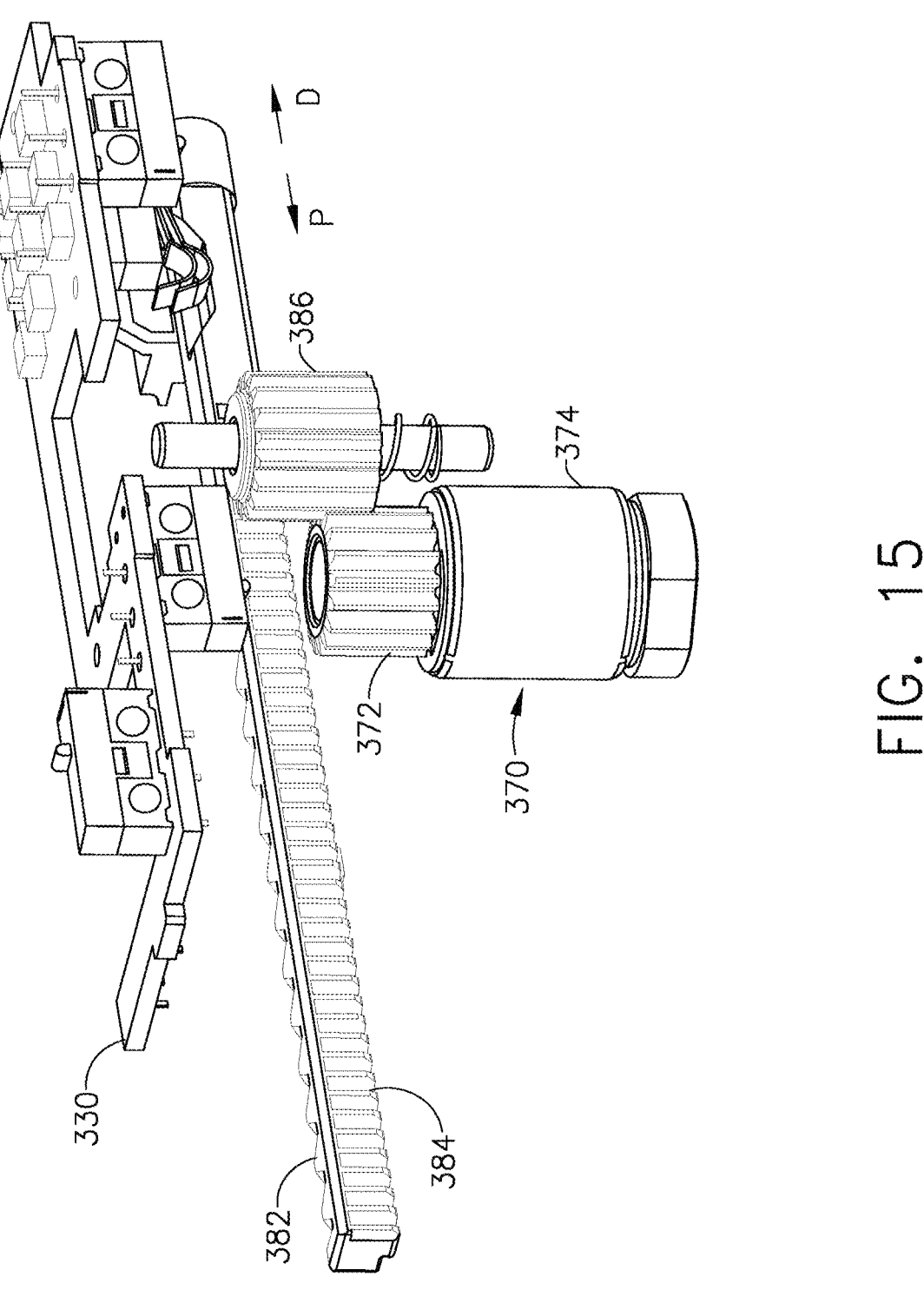
FIG. 15 is a perspective view of the firing member and the pinion gear of FIG. 14 and a gear reducer assembly operably engaged with the pinion gear.
Figure 16:
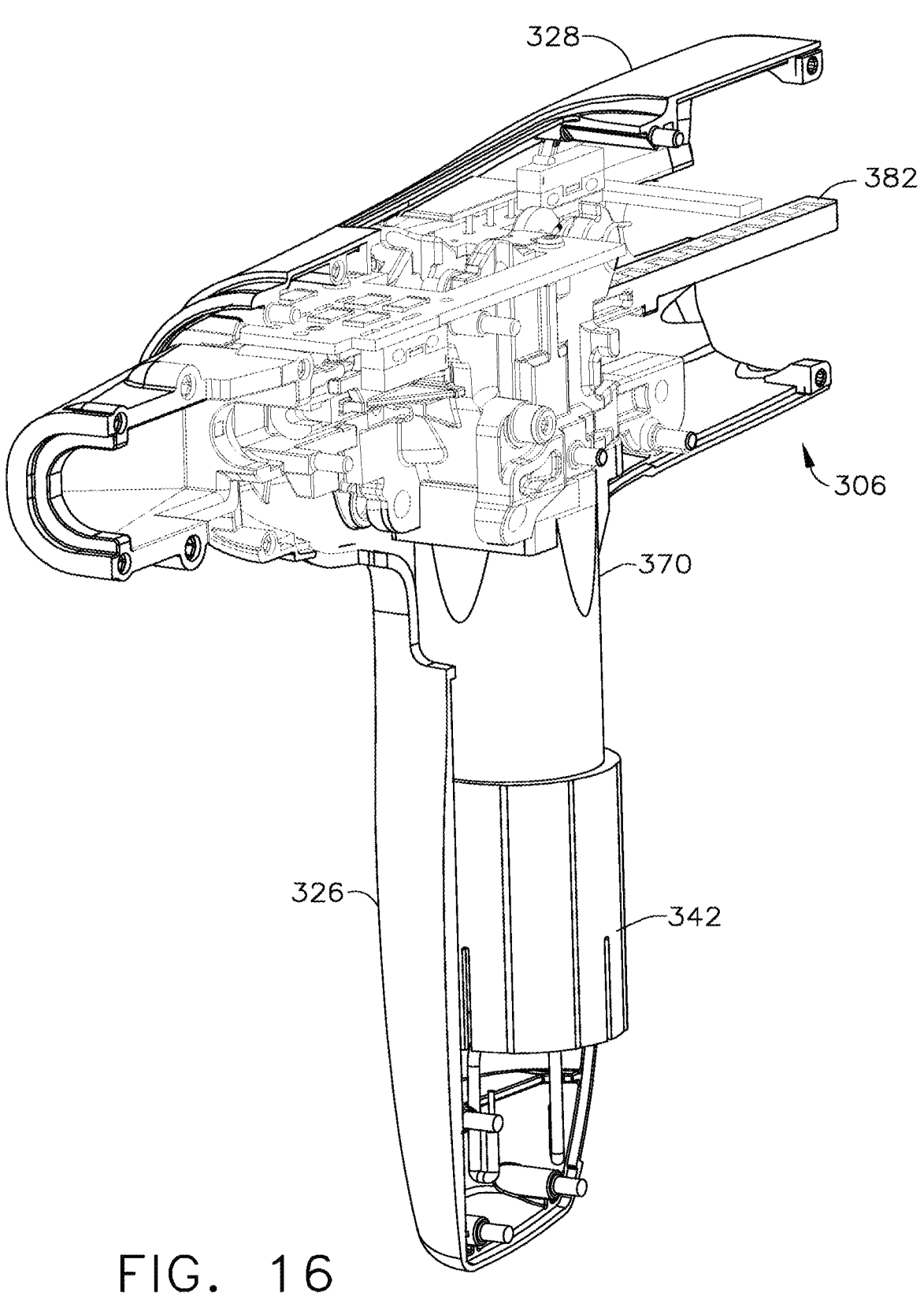
FIG. 16 is a perspective view of the handle of FIG. 12 with portions thereof removed to illustrate the firing member and the pinion gear of FIG. 14, the gear reducer assembly of FIG. 15, and an electric motor configured to drive the firing member distally and/or proximally depending on the direction in which the electric motor is turned.

As outlined above, the electric motor in the handle 306 of the instrument 310 can be operably engaged with the longitudinally-movable drive member positioned within the shaft 308. Referring now to FIGS. 14-16, an electric motor 342 can be mounted to and positioned within the pistol grip portion 326 of the handle 306. The electric motor 342 can include a rotatable shaft operably coupled with a gear reducer assembly 370 wherein the gear reducer assembly 370 can include, among other things, a housing 374 and an output pinion gear 372. In certain embodiments, the output pinion gear 372 can be directly operably engaged with a longitudinally-movable drive member 382 or, alternatively, operably engaged with the drive member 382 via one or more intermediate gears 386. The intermediate gear 386, in at least one such embodiment, can be meshingly engaged with a set, or rack, of drive teeth 384 defined in the drive member 382. In use, the electric motor 342 can be drive the drive member distally, indicated by an arrow D (FIG. 15), and/or proximally, indicated by an arrow D (FIG. 16), depending on the direction in which the electric motor 342 rotates the intermediate gear 386. In use, a voltage polarity provided by the battery can operate the electric motor 342 in a clockwise direction wherein the voltage polarity applied to the electric motor by the battery can be reversed in order to operate the electric motor 342 in a counter-clockwise direction. The handle 306 can include a switch which can be configured to reverse the polarity applied to the electric motor 342 by the battery. The handle 306 can also include a sensor 330 configured to detect the position of the drive member 382 and/or the direction in which the drive member 382 is being moved.

As indicated above, the surgical instrument 310 can include an articulation joint 314 about which the end effector 312 can be articulated. The instrument 310 can further include an articulation lock which can be configured and operated to selectively lock the end effector 312 in position. In at least one such embodiment, the articulation lock can extend from the proximal end of the shaft 308 to the distal end of the shaft 308 wherein a distal end of the articulation lock can engage the end effector 312 to lock the end effector 312 in position. Referring again to FIGS. 12 and 13, the instrument 310 can further include an articulation control 316 which can be engaged with a proximal end of the articulation lock and can be configured to operate the articulation lock between a locked state and an unlocked state. In use, the articulation control 316 can be pulled proximally to unlock the end effector 312 and permit the end effector 312 to rotate about the articulation joint 314. After the end effector 312 has been suitably articulated, the articulation control 316 can be moved distally to re-lock the end effector 312 in position. In at least one such embodiment, the handle 306 can further include a spring and/or other suitable biasing elements configured to bias the articulation control 316 distally and to bias the articulation lock into a locked configuration with the end effector 312. If the clinician desires, the clinician can once again pull the articulation control 316 back, or proximally, to unlock the end effector 312, articulate the end effector 312, and then move the articulation control 316 back into its locked state. In such a locked state, the end effector 312 may not articulate relative to the shaft 308.

As outlined above, the surgical instrument 310 can include an articulation lock configured to hold the end effector 312 in position relative to the shaft 308. As also outlined above, the end effector 312 can be rotated, or articulated, relative to the shaft 308 when the articulation lock is in its unlocked state. In such an unlocked state, the end effector 312 can be positioned and pushed against soft tissue and/or bone, for example, surrounding the surgical site within the patient in order to cause the end effector 312 to articulate relative to the shaft 308. In certain embodiments, the articulation control 316 can comprise an articulation switch or can be configured to operate an articulation switch which can selectively permit and/or prevent the firing trigger 320 from operating the electric motor 342. For instance, such an articulation switch can be placed in series with the electric motor 342 and a firing switch operably associated with the firing trigger 320 wherein the articulation switch can be in a closed state when the articulation control 316 is in a locked state. When the articulation control 316 is moved into an unlocked state, the articulation control 316 can open the articulation switch thereby electrically decoupling the operation of the firing trigger 320 and the operation of the electric motor 342. In such circumstances, the firing drive of the instrument 310 cannot be fired while the end effector 312 is in an unlocked state and is articulatable relative to the shaft 308. When the articulation control 316 is returned to its locked state, the articulation control 316 can re-close the articulation switch which can then electrically couple the operation of the firing trigger 320 with the electric motor 342. Various details of one or more surgical stapling instruments are disclosed in U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, which was filed on Dec. 24, 2009, now U.S. Pat. No. 8,220,688, the entire disclosure of which are incorporated by reference herein.

Turning now to FIGS. 17-29, a surgical instrument 400 can comprise a handle 403, a shaft 404 extending from the handle 403, and an end effector 402 extending from the shaft 404. As the reader will note, portions of the handle 403 have been removed for the purposes of illustration; however, the handle 403 can include a closure trigger and a firing trigger similar to the closure trigger 114 and the firing trigger 116 depicted in FIG. 1, for example. As will be described in greater detail below, the firing trigger 116 can be operably coupled with a firing drive including a firing member 470 extending through the shaft 404 wherein the operation of the firing trigger 116 can advance the firing member 470 distally toward the end effector 402. As will also be described in greater detail below, the surgical instrument 400 can further include an articulation drive which can be selectively coupled with the firing member 470 such that, when the firing member 470 is motivated by the firing trigger 116 and/or by a separate articulation trigger and/or button, for example, the articulation drive can be driven by the firing member 470 and the articulation drive can, in turn, articulate the end effector 402 about an articulation joint 410.

Figure 17:
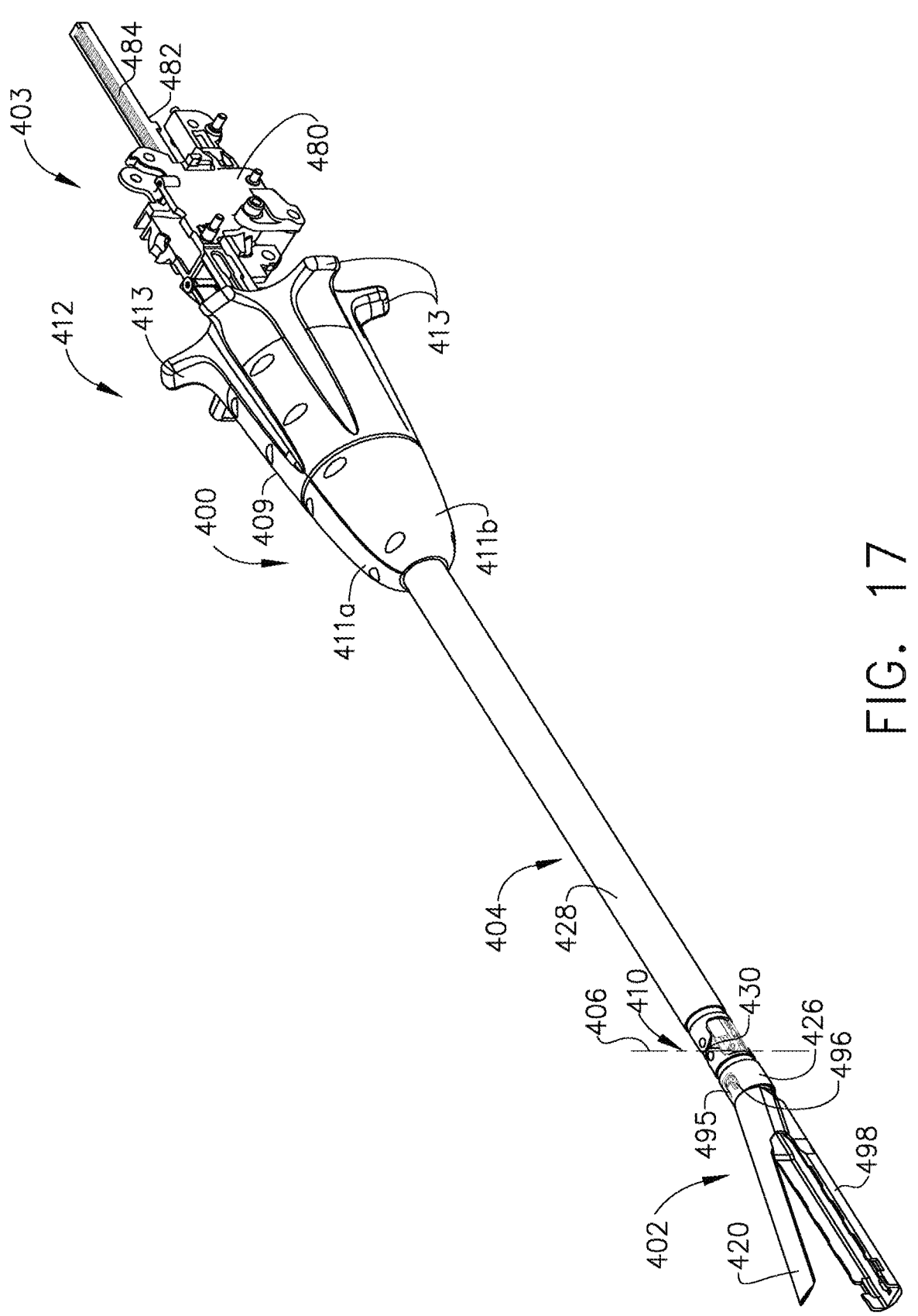
FIG. 17 is a perspective view of a surgical instrument comprising a handle, a shaft, an end effector, and an articulation joint connecting the end effector to the shaft illustrated with portions of the handle removed for the purposes of illustration.
Figure 19:
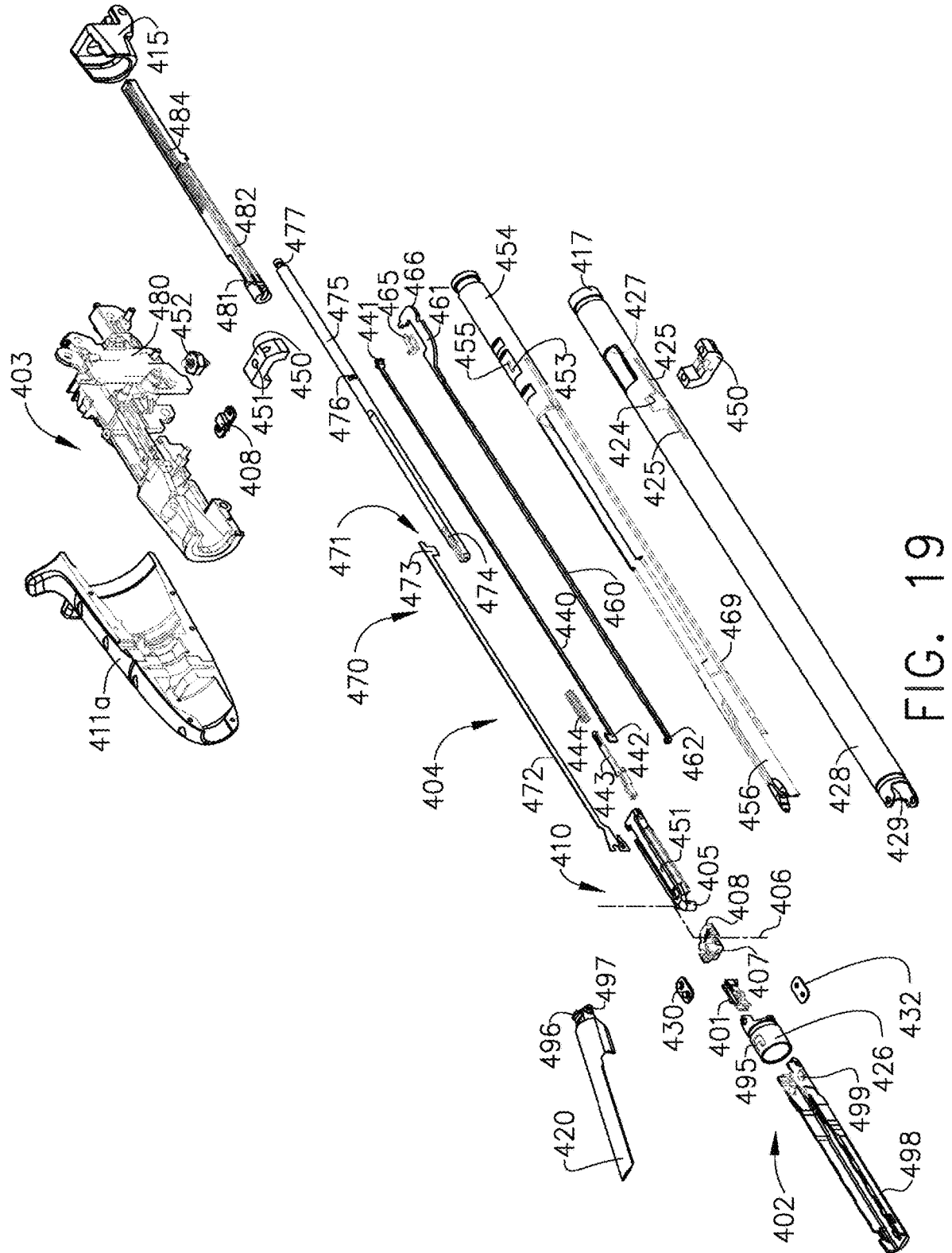
FIG. 19 is an exploded view of the surgical instrument of FIG. 17.
Figure 20:
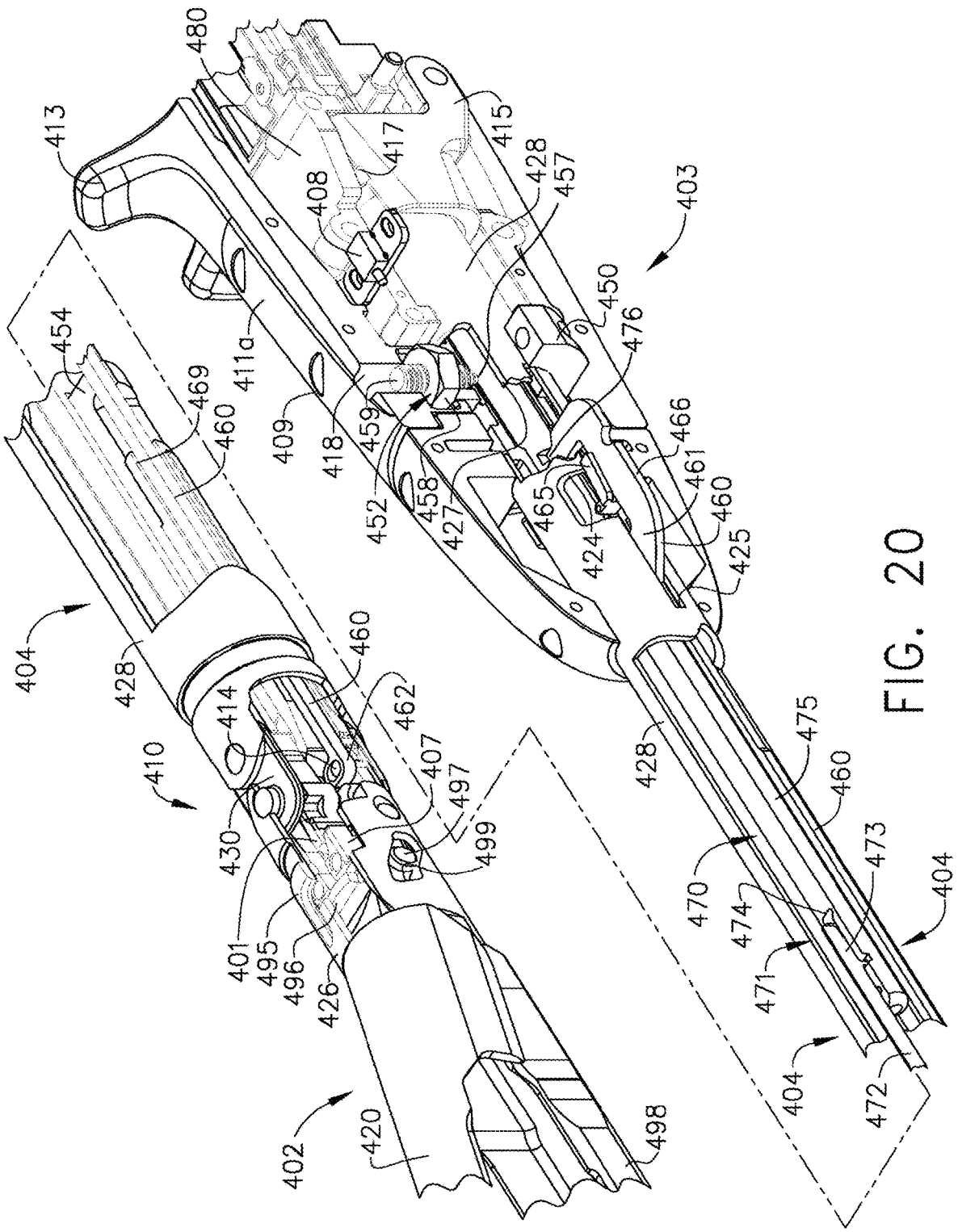
FIG. 20 is a cross-sectional detail view of the surgical instrument of FIG. 17 illustrated with the end effector in an open configuration, the articulation joint in an unlocked configuration, and an articulation lock actuator of the surgical instrument handle illustrated in an unlocked configuration.
Figure 23:
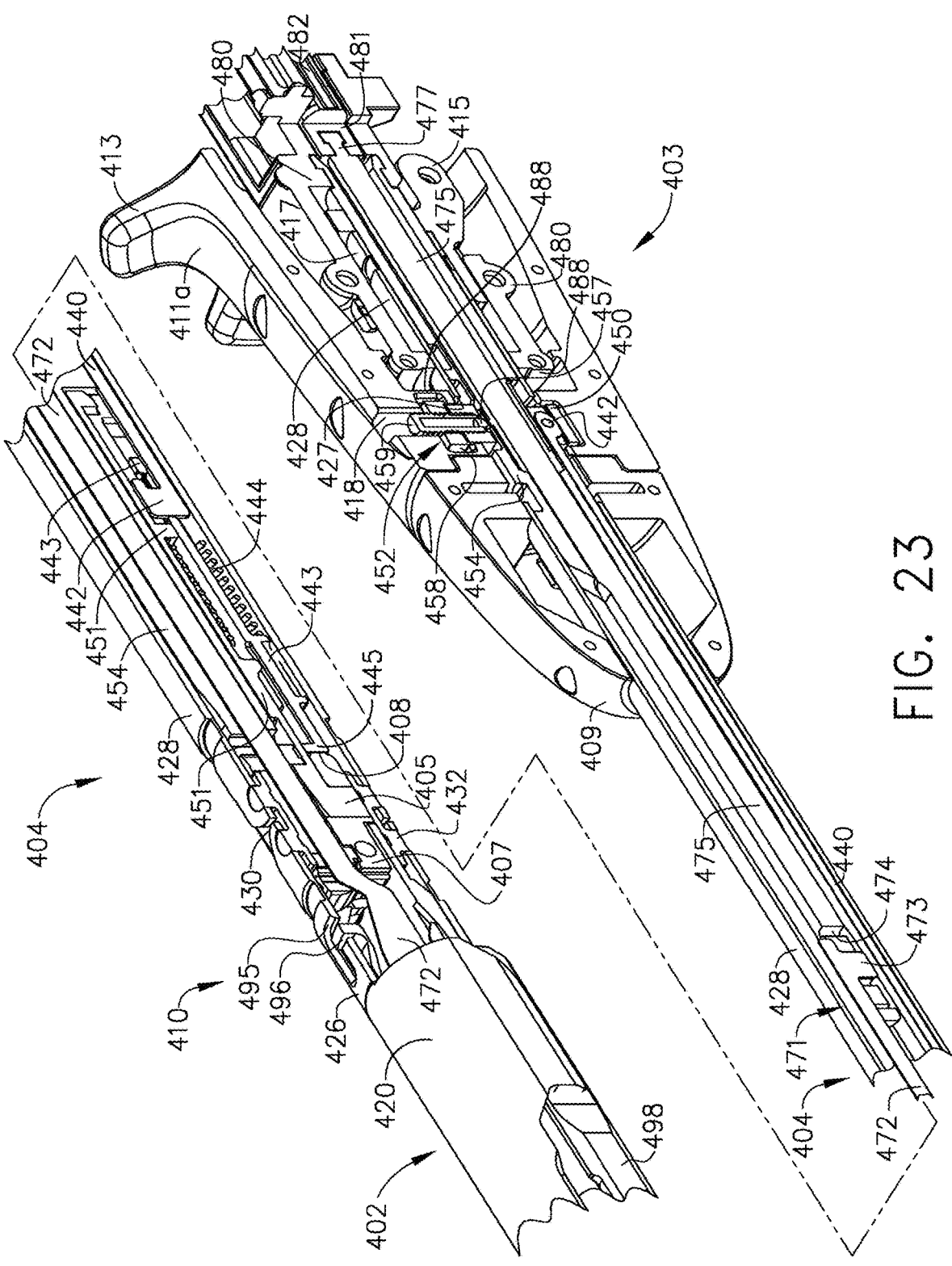
FIG. 23 is a cross-sectional detail view of the surgical instrument of FIG. 17 illustrating the end effector in a closed configuration and the articulation joint in a locked configuration, wherein the actuated closing drive prevents the articulation lock actuator from being moved into its unlocked configuration illustrated in FIGS. 20-22.
Figures 24A, 24B:
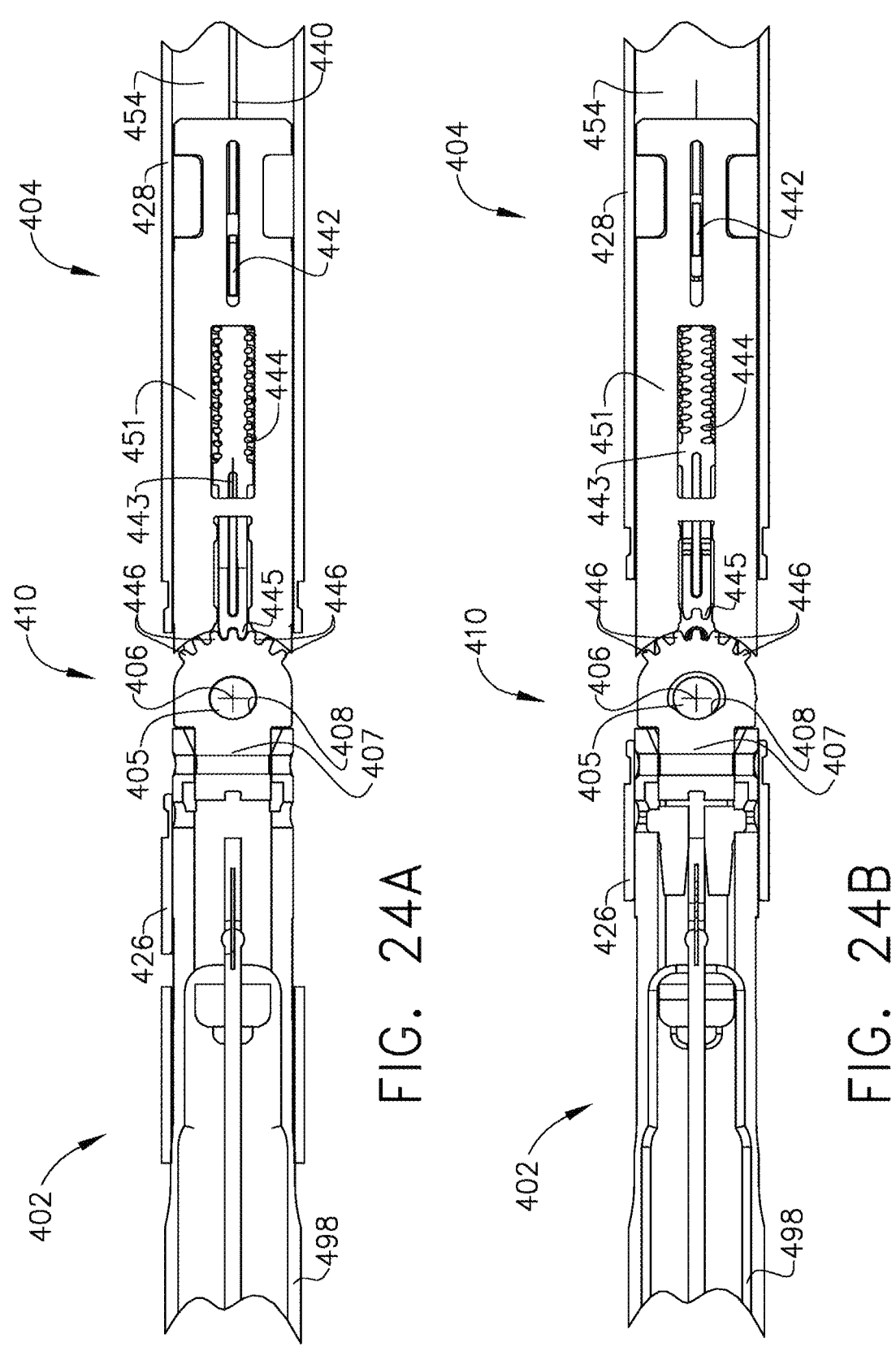
FIG. 24A is a plan view of the articulation joint of the surgical instrument of FIG. 17 illustrated in a locked configuration.
FIG. 24B is a plan view of the articulation joint of the surgical instrument of FIG. 17 illustrated in an unlocked configuration.

Turning now to FIG. 17, the reader will note that the end effector 402 of the surgical instrument 400 is illustrated in an open configuration. More particularly, a first jaw of the end effector 402 comprising an anvil 420 is illustrated in an open position relative to a channel 498 of a second jaw of the end effector 402. Similar to the above, the channel 498 can be configured to receive and secure a staple cartridge therein. Turning now to FIG. 20 which also illustrates the end effector 420 in an open configuration, the handle 403 of the surgical instrument 400 can include an articulation lock actuator 409 which can be moved between a distal, or locked, position in which the end effector 402 is locked in position relative to the shaft 404 and a proximal, or unlocked, position in which the end effector 402 can be articulated relative to the shaft 404 about the articulation joint 410. Although the end effector 402 and the shaft 404 are illustrated in FIG. 20 as being aligned in a straight configuration, the articulation lock actuator 409 is illustrated in its retracted, unlocked position and, as a result, the end effector 402 can be articulated relative to the shaft 404. Referring to FIGS. 19, 24A and 24B, the articulation lock actuator 409 (FIG. 21) can be operably coupled with an articulation lock 443 wherein the articulation lock actuator 409 can move the articulation lock 443 between a distal position (FIG. 24A) in which the articulation lock 443 is engaged with a proximal lock member 407 of the end effector 402 and a proximal position (FIG. 24B) in which the articulation lock 443 is disengaged from the end effector 402. As the reader will appreciate, the distal, locked, position of the articulation lock actuator 409 corresponds with the distal position of the articulation lock 443 and the proximal, unlocked, position of the articulation lock actuator 409 corresponds with the proximal position of the articulation lock 443. Turning now to FIG. 19, the articulation lock 443 is coupled to the articulation lock actuator 409 by an articulation lock bar 440 which comprises a distal end 442 engaged with the articulation lock 443, as better seen in FIG. 24A, and a proximal end 441 engaged with the articulation lock actuator 409, as better seen in FIG. 22. As illustrated in FIGS. 24A and 24B, the articulation lock 443 can comprise one or more teeth 445 which can be configured to meshingly engage one or more teeth 446 defined around the perimeter of the proximal lock member 407, for example. Referring primarily to FIG. 19, the shaft 404 can further comprise a biasing member, such as a spring 444, for example, which can be configured to bias the teeth 445 of the articulation lock 443 into engagement with the teeth 446 of the proximal lock member 407 of the end effector 402. Similarly, the handle 403 can further comprise a biasing member positioned within the cavity 488 (FIG. 23) defined between the articulation lock actuator 409 and the frame 480 such that the biasing member can push the articulation lock actuator 409 towards its distal, locked, position.

As illustrated in FIG. 17, the articulation lock actuator 409 can be comprised of two nozzle halves, or portions, 411a and 411b wherein, as the reader will note, the nozzle portion 411b has been removed from FIGS. 18-27 for the purposes of illustration. As also illustrated in FIG. 17, the articulation lock actuator 409 can comprise a plurality of finger hooks 413 which can be grasped by the surgeon, or other clinician, in order to retract the articulation lock actuator 409 into its proximal, unlocked, configuration. The articulation lock actuator 409, referring again to FIG. 20, can further include a detent assembly 452 which can be configured to bias a detent member 457 against the frame of the shaft 404 or the frame of the handle 403. More particularly, the shaft 404 can comprise a shaft frame 454 extending from a handle frame 480 wherein the detent assembly 452 can be configured to bias the detent member 457 against the shaft frame 454. Referring to FIG. 19, the shaft frame 454 can include a detent channel 453 defined therein which can be aligned with the detent member 457 such that, as the articulation lock actuator 409 is slid between its locked and unlocked positions described above, the detent member 457 can slide within the detent channel 453. The detent assembly 452, referring again to FIG. 20, can include a stationary frame portion 458 which can define a threaded aperture configured to receive an adjustable threaded member 459. The adjustable threaded member 459 can include an internal aperture wherein at least a portion of the detent member 457 can be positioned within the internal aperture and wherein the detent member 457 can be biased to the end of the internal aperture by a spring, for example, positioned intermediate the detent member 457 and a closed end of the internal aperture, for example. As illustrated in FIG. 19, the proximal end of the detent channel 453 can comprise a detent seat 455 which can be configured to removably receive the detent member 457 when the articulation lock actuator 409 has reached its proximal, unlocked, position. In various circumstances, the detent member 457, the detent seat 455, and the biasing spring positioned in the adjustable threaded member 459 can be sized and configured such that the detent assembly 452 can releasably hold the articulation lock actuator 409 in its proximal, unlocked, position. As described in greater detail below, the articulation lock actuator 409 can be held in its proximal, unlocked, position until the end effector 402 has been suitably articulated. At such point, the articulation lock actuator 409 can be pushed forward to disengage the detent member 457 from the detent seat 455. As the reader will appreciate, referring primarily to FIG. 20, the adjustable threaded member 459 can be rotated downwardly toward the shaft frame 454 in order to increase the force needed to unseat the detent member 457 from the detent seat 455 while the adjustable threaded member 459 can be rotated upwardly away from the shaft frame 454 in order to decrease the force needed to unseat the detent member 457 from the detent seat 455. As also illustrated in FIG. 20, the articulation lock actuator 409 can comprise an access port 418 which can be utilized to access and rotate the threaded member 459.

Figure 18:
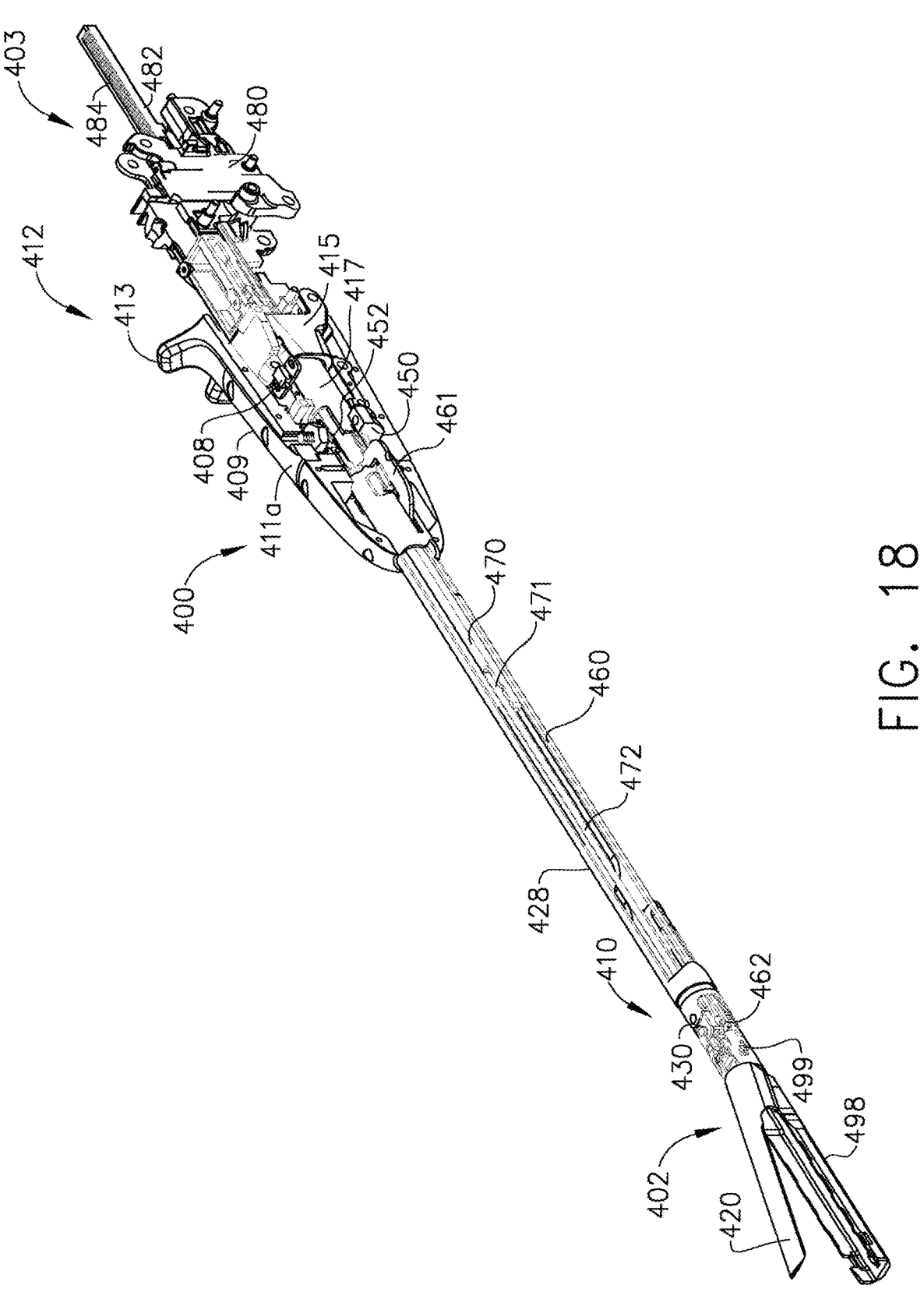
FIG. 18 is a cross-sectional view of the surgical instrument of FIG. 17.
Figure 21:
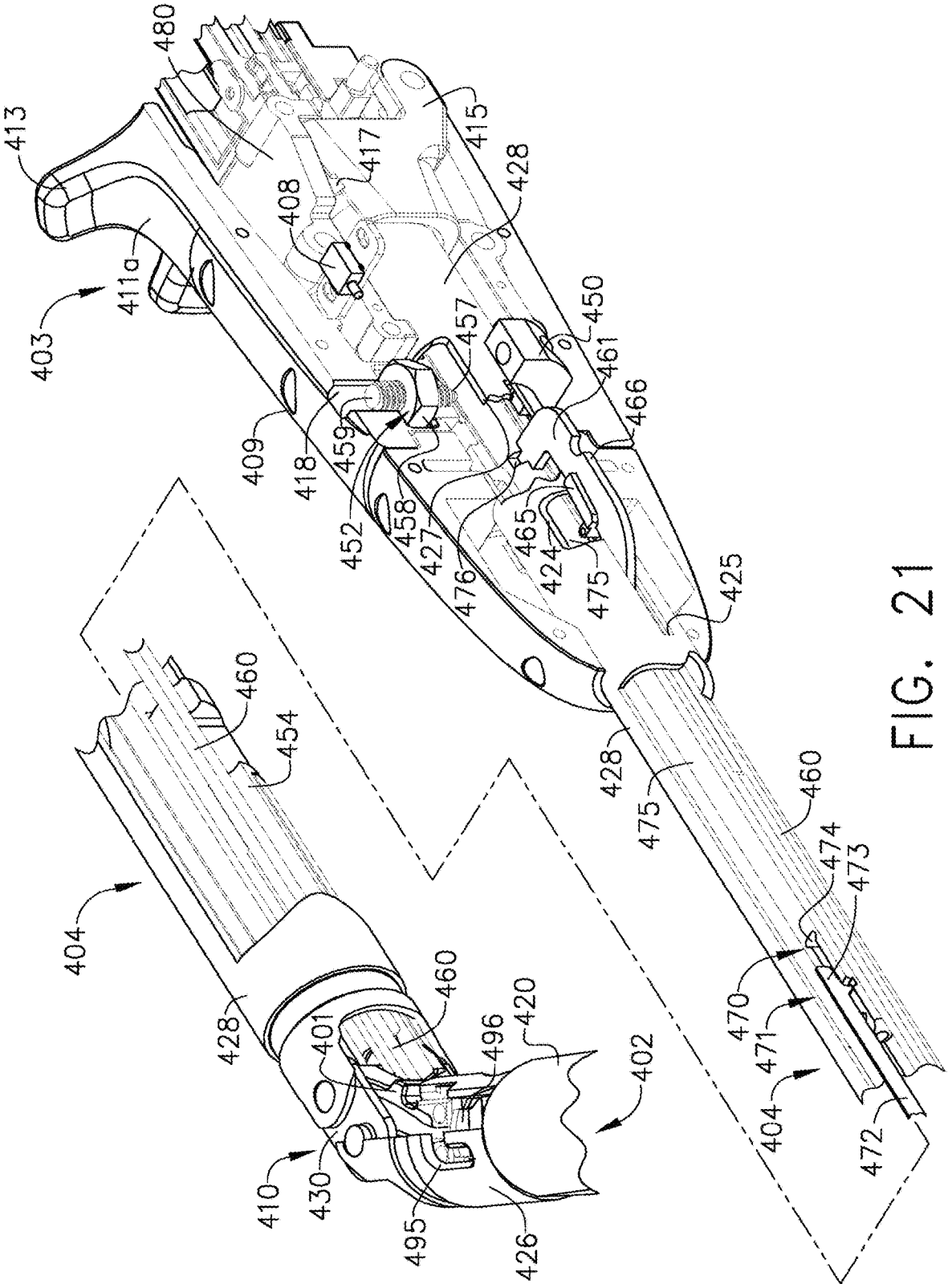
FIG. 21 is a cross-sectional detail view of the surgical instrument of FIG. 17 illustrating the end effector in an articulated, open configuration, the articulation joint in an unlocked configuration, and an articulation driver engaged with a firing member of the surgical instrument of FIG. 17, wherein the movement of the firing member can motivate the articulation driver and articulate the end effector.

As discussed above, the articulation lock actuator 409 is in a retracted, unlocked, position in FIG. 20 and the end effector 402 is in an unlocked configuration, as illustrated in FIG. 24B. Referring now to FIGS. 19 and 20, the surgical instrument 400 further comprises an articulation driver 460 which can be pushed distally to rotate the end effector 402 about the articulation joint 410 in a first direction and pulled proximally to rotate the end effector 402 about the articulation joint in a second, or opposite, direction, as illustrated in FIG. 21. Upon comparing FIGS. 20 and 21, the reader will note that the articulation driver 460 has been pulled proximally by the firing member 470. More specifically, an intermediate portion 475 of the firing member 470 can comprise a notch, or slot, 476 defined therein which can be configured to receive a proximal end 461 of the articulation driver 460 such that, when the firing member 470 is pulled proximally, the firing member 470 can pull the articulation driver 460 proximally as well. Similarly, when the firing member 470 is pushed distally, the firing member 470 can push the articulation driver 460 distally. As also illustrated in FIGS. 20 and 21, the articulation driver 460 can comprise a distal end 462 engaged with a projection 414 extending from the proximal lock member 407, for example, which can be configured to transmit the proximal and distal articulation motions of the articulation driver 460 to the end effector 102. Referring primarily to FIGS. 18-20, the handle 404 can further comprise a proximal firing member portion 482 of the firing member 470 including a distal end 481 engaged with a proximal end 477 of the intermediate portion 475 of the firing member 470. Similar to the above, the handle 403 can include an electric motor comprising an output shaft and a gear operably engaged with the output shaft wherein the gear can be operably engaged with a longitudinal set of teeth 484 defined in a surface of the firing member portion 482. In use, further to the above, the electric motor can be operated in a first direction to advance the firing member 470 distally and a second, or opposite, direction to retract the firing member 470 proximally. Although not illustrated, the handle 403 can further comprise a switch which can be positioned in a first condition to operate the electric motor in its first direction, a second condition to operate the electric motor in its second direction, and/or a neutral condition in which the electric motor is not operated in either direction. In at least one such embodiment, the switch can include at least one biasing member, such as a spring, for example, which can be configured to bias the switch into its neutral condition, for example. Also, in at least one such embodiment, the first condition of the articulation switch can comprise a first position of a switch toggle on a first side of a neutral position and the second condition of the articulation switch can comprise a second position of the switch toggle on a second, or opposite, side of the neutral position, for example.

In various circumstances, further to the above, the articulation switch can be used to make small adjustments in the position of the end effector 402. For instance, the surgeon can move the articulation switch in a first direction to rotate the end effector 402 about the articulation joint in a first direction and then reverse the movement of the end effector 402 by moving the articulation switch in the second direction, and/or any other suitable combinations of movements in the first and second directions, until the end effector 402 is positioned in a desired position. Referring primarily to FIGS. 19, 24A, and 24B, the articulation joint 410 can include a pivot pin 405 extending from a shaft frame member 451 and, in addition, an aperture 408 defined in the proximal lock member 407 which is configured to closely receive the pivot pin 405 therein such that the rotation of the end effector 402 is constrained to rotation about an articulation axis 406, for example. Referring primarily to FIG. 19, the distal end of the shaft frame 454 can include a recess 456 configured to receive the shaft frame member 451 therein. As will be described in greater detail below, the shaft 404 can include an outer sleeve which can be slid relative to the shaft frame 454 in order to close the anvil 420. Referring primarily to FIGS. 19-21, the outer sleeve of the shaft 410 can comprise a proximal portion 428 and a distal portion 426 which can be connected to one another by articulation links 430 and 432. When the outer sleeve is slid relative to the articulation joint 410, the articulation links 430 can accommodate the angled relative movement between the distal portion 426 and the proximal portion 428 of the outer sleeve when the end effector 402 has been articulated, as illustrated in FIG. 21. In various circumstances, the articulation links 430 and 432 can provide two or more degrees of freedom at the articulation joint 410 in order to accommodate the articulation of the end effector 402. The reader will also note that the articulation joint 410 can further include a guide 401 which can be configured to receive a distal cutting portion 472 of the firing member 470 therein and guide the distal cutting portion 472 as it is advanced distally and/or retracted proximally within and/or relative to the articulation joint 410.

As outlined above, the firing member 470 can be advanced distally in order to advance the articulation driver 460 distally and, as a result, rotate the end effector 402 in a first direction and, similarly, the firing member 470 can be retracted proximally in order to retract the articulation driver 460 proximally and, as a result, rotate the end effector 402 in an opposite direction. In some circumstances, however, it may be undesirable to move, or at least substantially move, the distal cutting portion 472 of the firing member 470 when the firing member 470 is being utilized to articulate the end effector 402. Turning now to FIGS. 19-21, the intermediate portion 475 of the firing member 470 can comprise a longitudinal slot 474 defined in the distal end thereof which can be configured to receive the proximal end 473 of the distal cutting portion 472. The longitudinal slot 474 and the proximal end 473 can be sized and configured to permit relative movement therebetween and can comprise a slip joint 471. The slip joint 471 can permit the intermediate portion 475 of the firing drive 470 to be moved to articulate the end effector 402 without moving, or at least substantially moving, the distal cutting portion 472. Once the end effector 402 has been suitably oriented, the intermediate portion 475 can be advanced distally until a proximal sidewall of the longitudinal slot 474 comes into contact with the proximal end 473 in order to advance the distal cutting portion 472 and fire the staple cartridge positioned within the channel 498, as described in greater detail further below. Referring primarily to FIG. 19, the shaft frame 454 can comprise a longitudinal slot 469 defined therein which can be configured to slidably receive the articulation driver 460 and, similarly, the proximal portion 428 of the outer shaft sleeve can comprise a longitudinal opening 425 configured to accommodate the relative movement between the articulation driver 460 and the outer sleeve of the shaft 404 described above.

Further to the above, the articulation lock actuator 409 can be configured to bias the proximal portion 461 of the articulation driver 460 toward the drive member 470 when the articulation lock actuator 409 is in its proximal, unlocked, position. More particularly, in at least one such embodiment, the inner surface of the articulation lock actuator 409 can comprise a cam which can engage a lateral side 466 of the proximal portion 461 and bias the proximal portion 461 into engagement with the slot 476 defined in the intermediate portion 475 of the drive member 470. When the articulation lock actuator 409 is moved back into its distal, locked, position, the articulation lock actuator 409 may no longer bias the proximal portion 461 inwardly toward the drive member 470. In at least one such embodiment, the handle 403 and/or the shaft 404 can comprise a resilient member, such as a spring, for example, which can be configured to bias the proximal portion 461 outwardly away from the firing member 470 such that the proximal portion 461 is not operably engaged with the slot 476 unless the biasing force of the resilient member is overcome by the articulation lock actuator 409 when the articulation lock actuator 409 is moved proximally into its unlocked position, as described above. In various circumstances, the proximal portion 461 and the slot 476 can comprise a force-limiting clutch.

Figure 22:
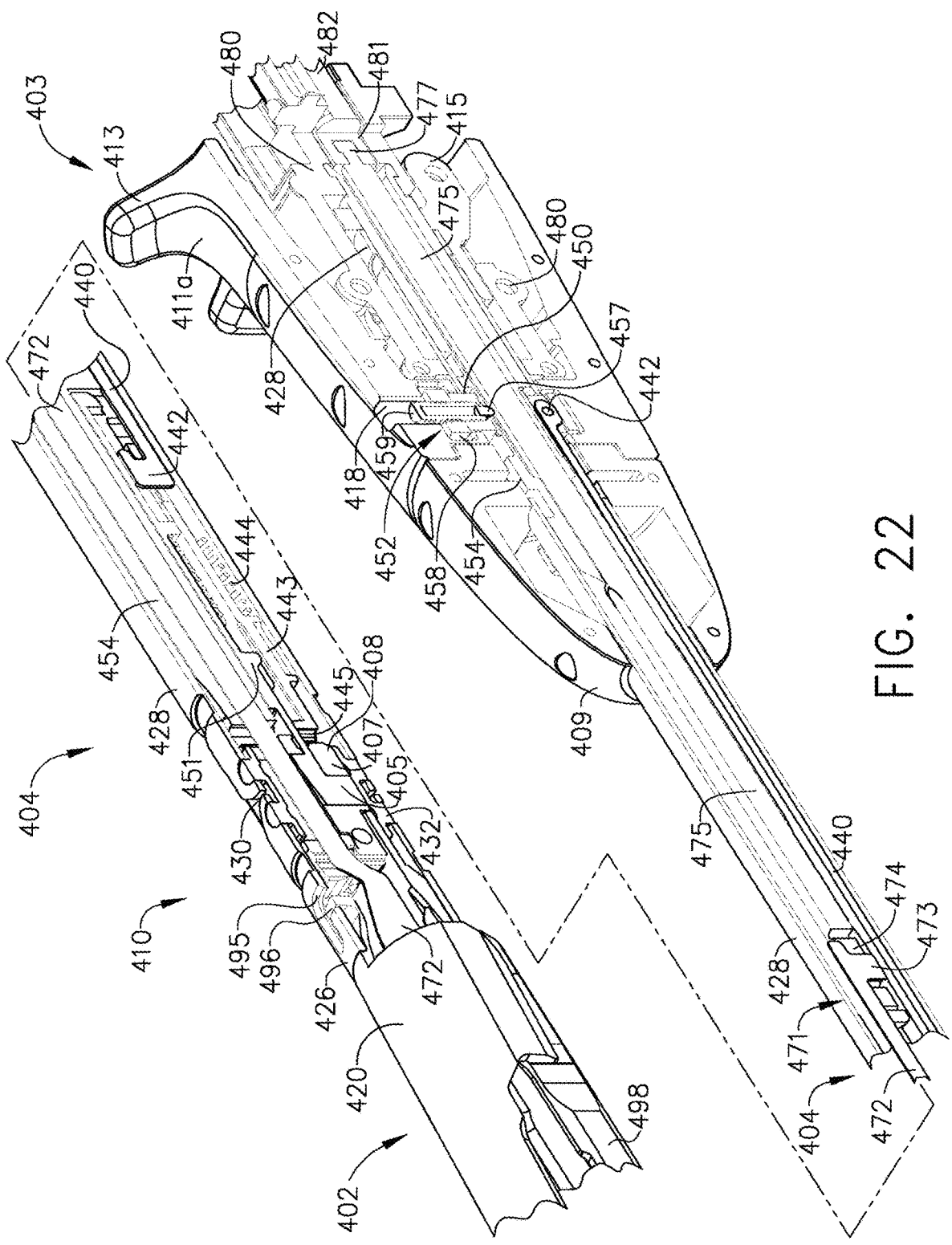
FIG. 22 is a cross-sectional detail view of the surgical instrument of FIG. 17 illustrating the end effector in a closed configuration, the articulation joint in an unlocked configuration, and an end effector closing drive being actuated to close the end effector and move the articulation lock actuator into a locked configuration.
Figure 22A:
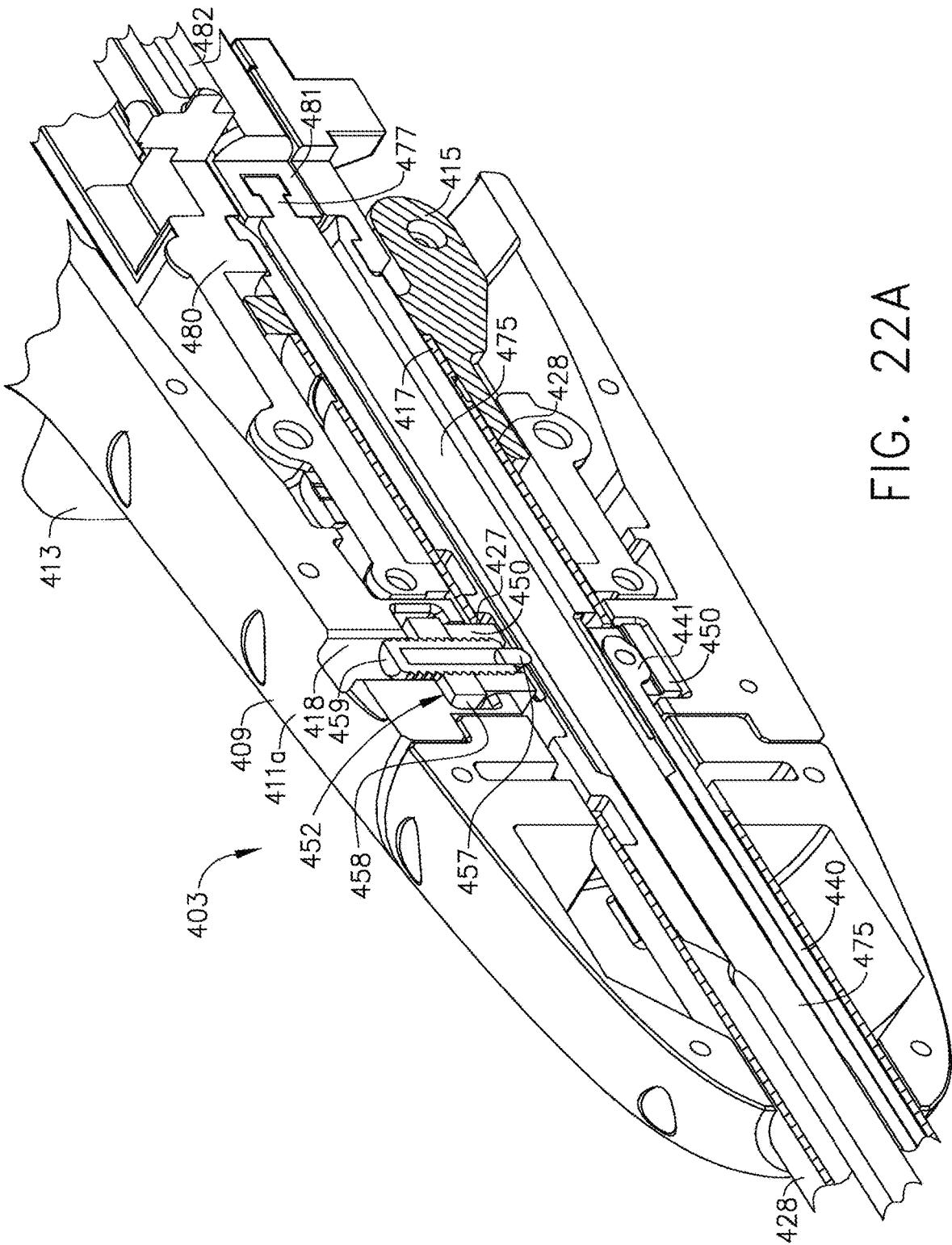
FIG. 22A is a cross-sectional detail view of the handle of the surgical instrument of FIG. 17 illustrated in the configuration described with regard to FIG. 22.

Once the end effector 402 has been articulated into the desired orientation, further to the above, the closure trigger 114 can be actuated to move the anvil 420 toward its closed position, as illustrated in FIG. 22. More particularly, the closure trigger 114 can advance the outer sleeve of the shaft 410 distally such that the distal portion 426 of the outer sleeve can push the anvil 420 distally and downwardly, for example. The anvil 420 can comprise projections 497 extending from opposite sides of the anvil 420 which can each be configured to slide and rotate within elongate slots 499 defined in the cartridge channel 498. The anvil 420 can further comprise a projection 496 extending upwardly therefrom which can be positioned within an aperture 495 defined in the distal portion 426 of the outer sleeve wherein a sidewall of the aperture 495 can contact the projection 496 as the distal portion 426 is advanced distally to move the anvil 420 toward the cartridge channel 498. The actuation of the closure drive, further to the above, can also move the articulation lock actuator 409 from its proximal, unlocked, position (FIGS. 20-22) into its distal, locked, position (FIG. 23). More specifically, the closure drive can be configured to advance a closure drive carriage 415 distally which can contact a collar 450 mounted within the articulation actuator 409, as illustrated in FIG. 22. As illustrated in FIGS. 19 and 22, the collar 450 can comprise opposing portions, or halves, which can be assembled together such that the opposing portions of the collar 450 can surround the shaft 404. The collar 450 can also support the detent assembly 452, which is discussed above, and can include a mounting portion engaged with the proximal end 441 of the articulation lock bar 440, which is also discussed above. In any event, the closure drive carriage 415 can contact the collar 450 and slide the articulation lock actuator 409 distally and, further to the above, displace the detent member 457 from the detent seat 455, referring to FIG. 19, into the detent channel 453 such that the articulation lock actuator 409 can be pushed into its locked position and the articulation lock 443 can be moved into engagement with the proximal lock portion 407 to lock the end effector 402 in position, as illustrated in FIG. 23. At such point, the closure drive carriage 415 can prevent the end effector 402 from being unlocked and articulated until the closure drive and the anvil 420 is reopened and the closure drive carriage 415 is moved proximally, as described in greater detail further below.

Figure 25:
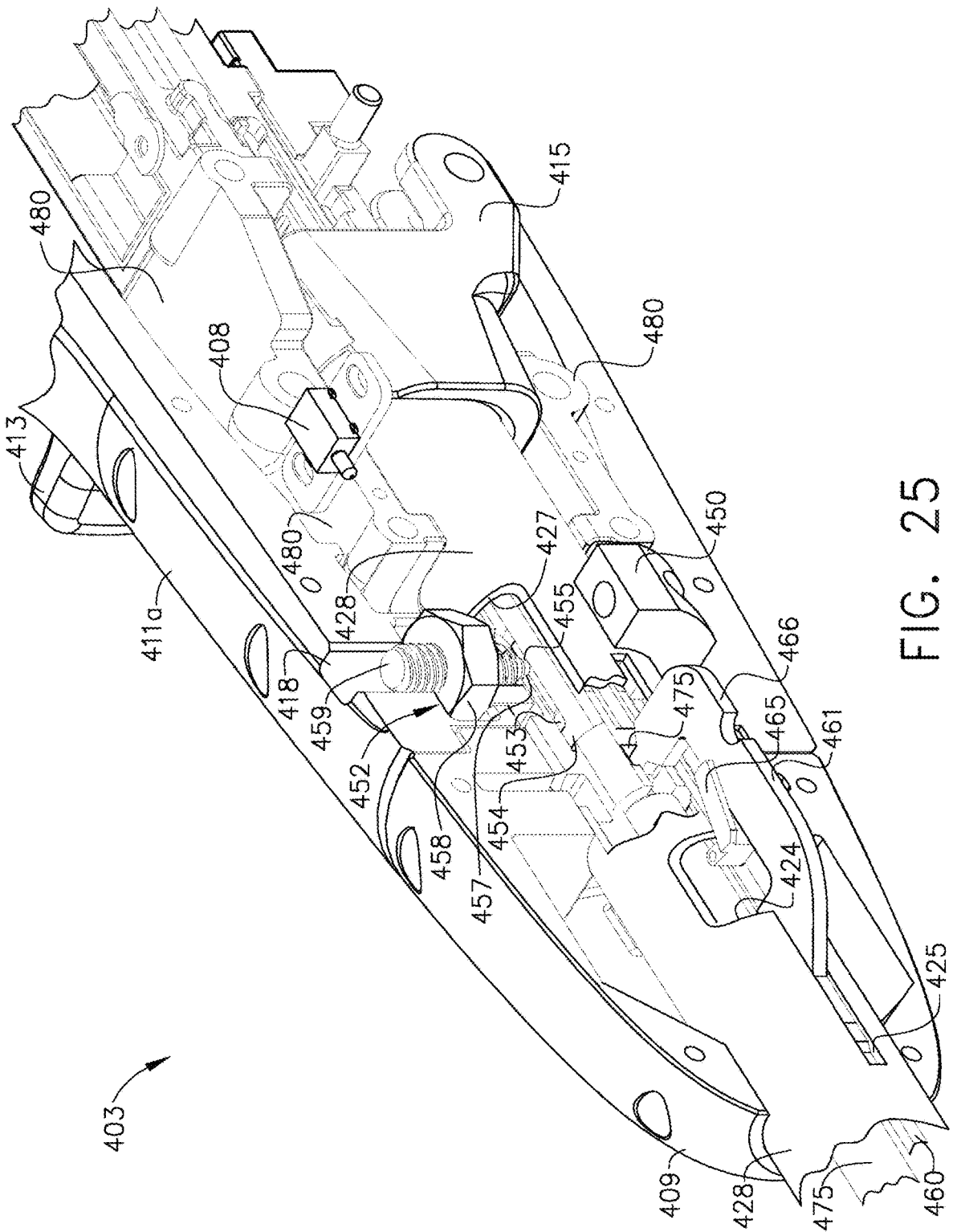
FIG. 25 is a cross-sectional detail view of the handle of the surgical instrument of FIG. 17 illustrating the articulation driver disconnected from the firing member by closure drive.

Referring now to FIG. 25, the actuation of the closure drive by the closure drive actuator 114 and the distal advancement of the outer sleeve 428 of the shaft 410 can also operably disengage the articulation driver 460 from the firing drive 470. Upon reviewing FIGS. 20 and 21 once again, the reader will note that the outer sleeve 428 includes a window 424 defined therein within which a rotatable cam member 465 can be positioned. The cam member 465 can comprise a first end rotatably pinned or coupled to the shaft frame 454 and a second end configured to rotate relative to the pinned end of the cam member 465 while, in other embodiments, the cam member 465 can comprise any suitable shape. When the outer sleeve 428 is in its proximal position and the anvil 420 is in its open configuration, the cam member 465 can be in a first position which permits the proximal end 461 of the articulation driver 460 to be engaged with the slot 476 defined in the firing member 470; however, when the outer sleeve 428 is advanced distally, a sidewall of the window 424 can engage the cam member 465 and lift the second end of the cam member 465 away from the shaft frame 454 into a second position. In this second position, the cam member 465 can move the proximal end 461 of the articulation driver 460 away from the firing drive 470 such that the proximal end 461 is no longer positioned within the slot 476 defined in the firing drive 470. Thus, when the closure drive has been actuated to close the anvil 420, the closure drive can push the articulation lock actuator 409 into its distal, locked, configuration, the articulation lock actuator 409 can push the articulation lock 445 into a locked configuration with the end effector 402, and, in addition, the closure drive can operably disconnect the articulation driver 460 from the firing drive 470. At such point in the operation of the surgical instrument 400, the actuation of the firing drive 470 will not articulate the end effector 402 and the firing drive 470 can move independently of the articulation driver 460.

Figure 26:
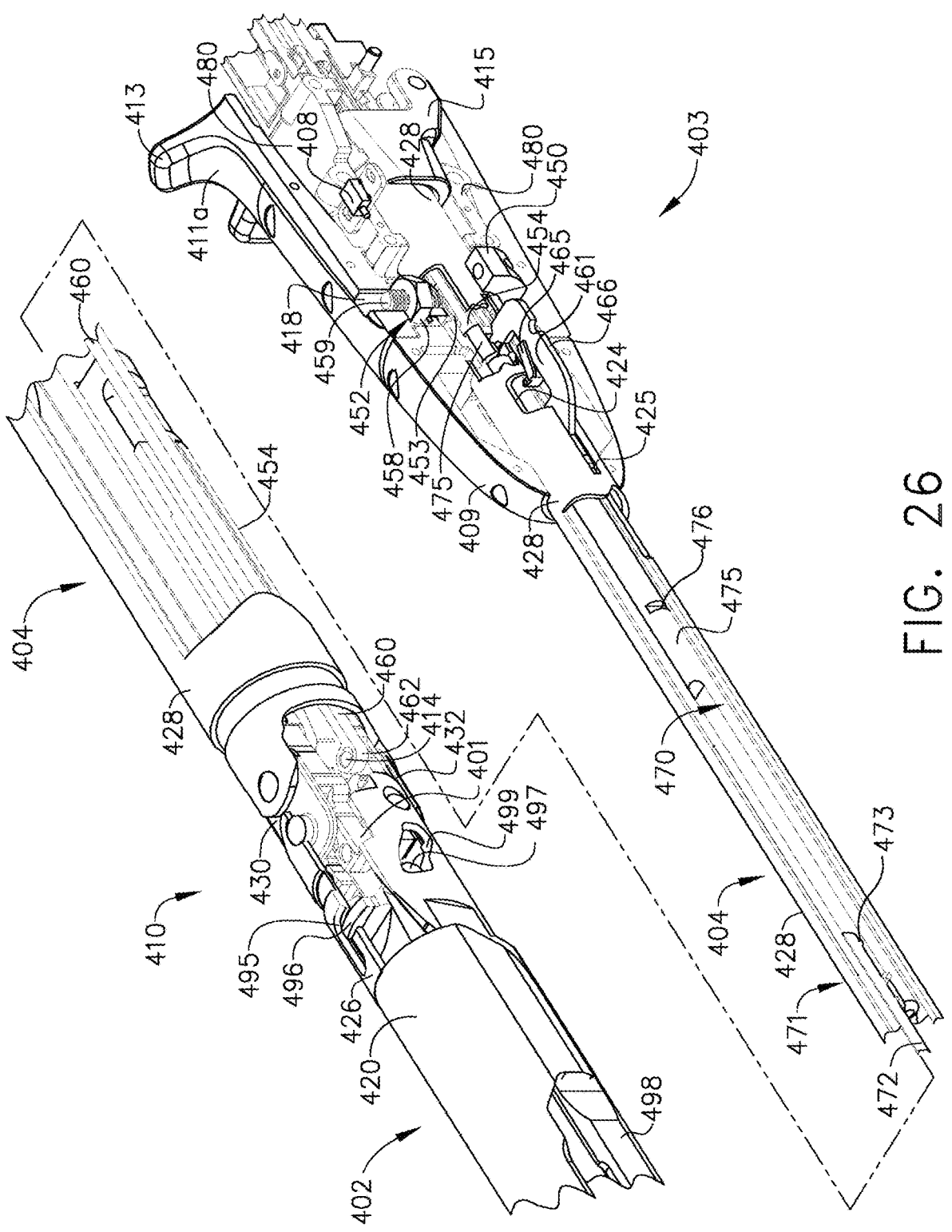
FIG. 26 is a cross-sectional detail view of the surgical instrument of FIG. 17 illustrating the firing member in an at least partially fired position and the articulation driver disconnected from the firing member by the closure drive.

Turning now to FIG. 26, as mentioned above, the firing drive 470 can be advanced distally to eject staples from a staple cartridge positioned within the channel 498 of the end effector 402 and to deform the staples against the anvil 420.

Figure 27:
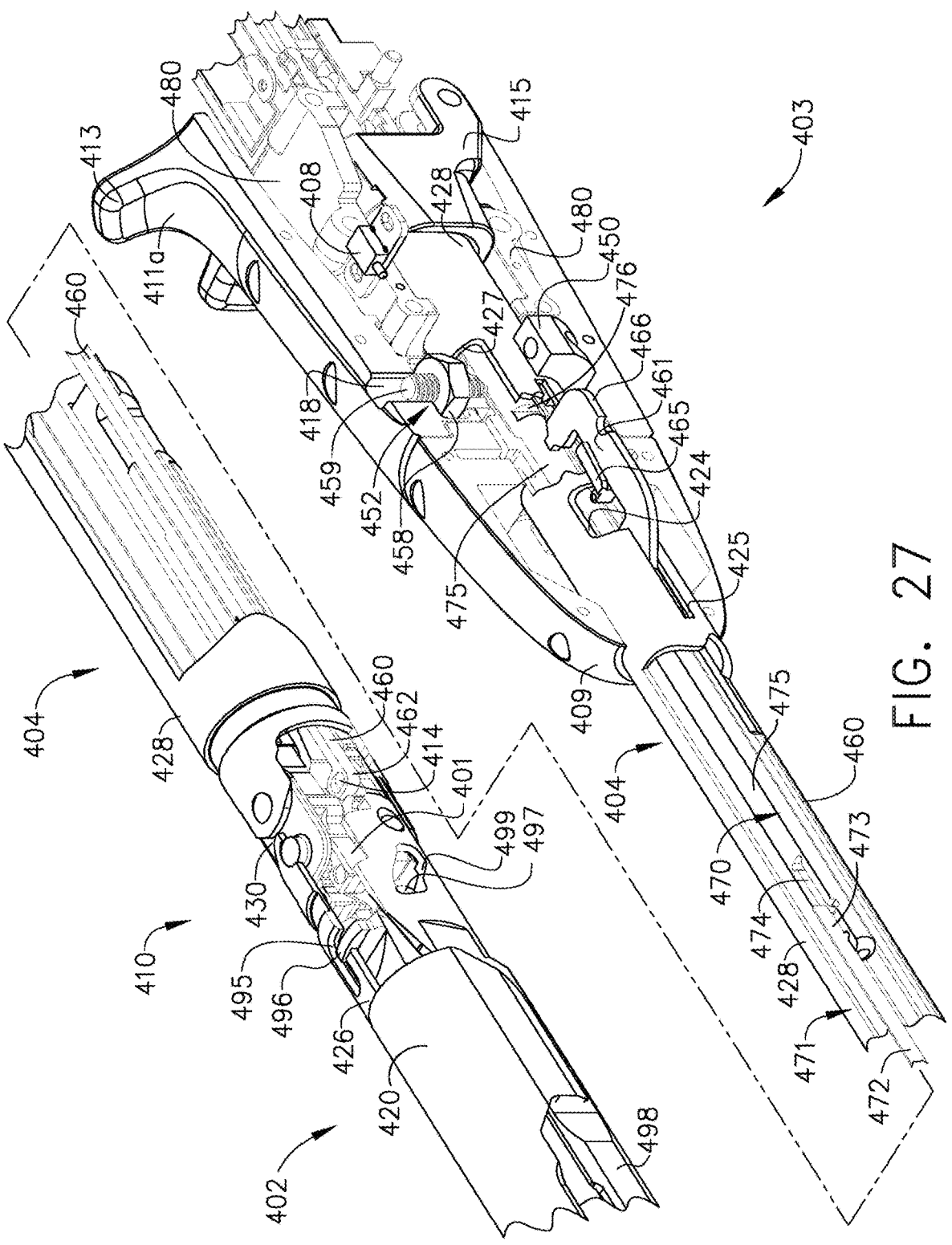
FIG. 27 is a cross-sectional detail view of the surgical instrument of FIG. 17 illustrating end effector in a closed configuration, the articulation joint and the articulation joint actuator in a locked configuration, and the firing member in a retracted position.
Figure 28:
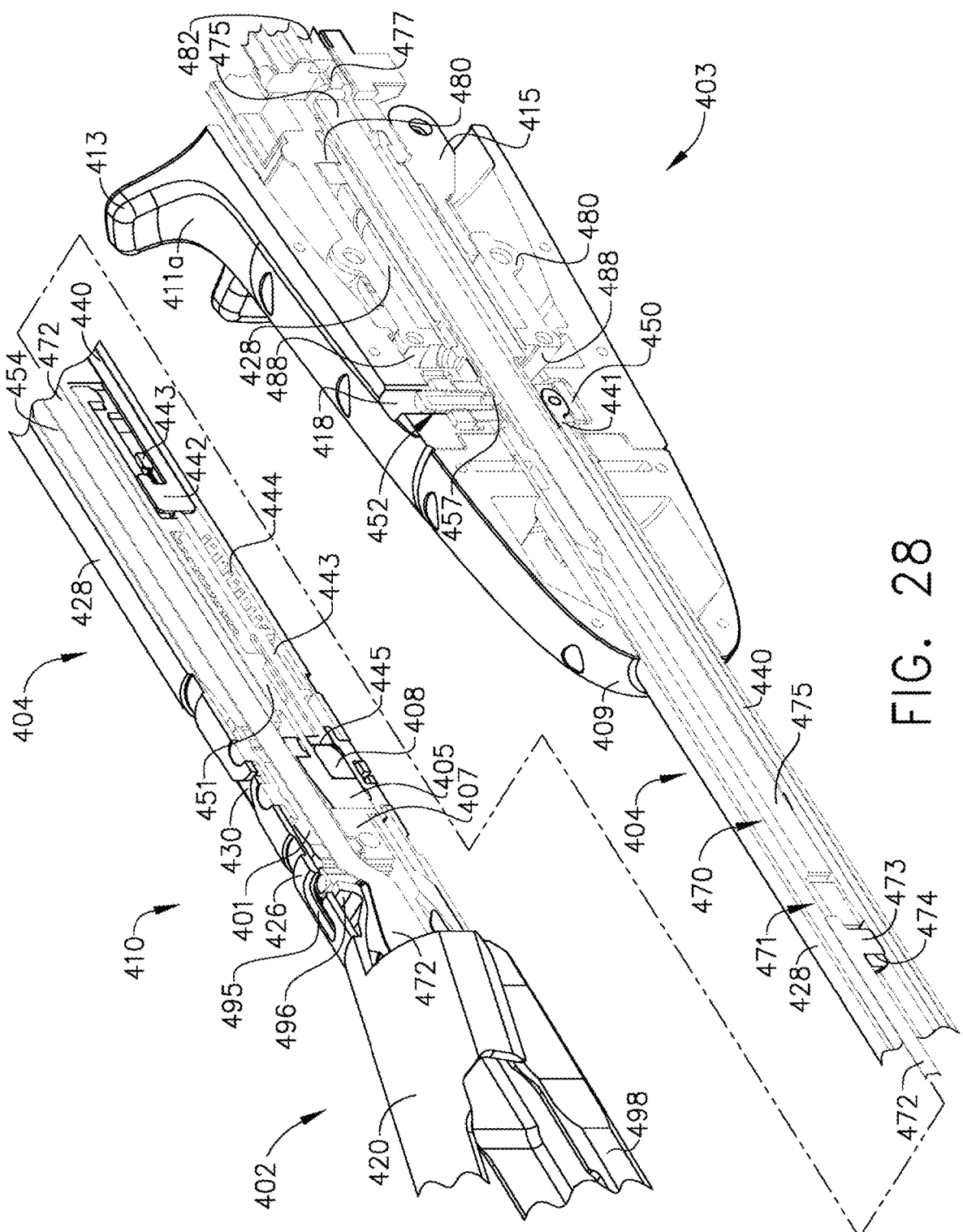
FIG. 28 is a cross-sectional detail view of the surgical instrument of FIG. 17 illustrating the end effector in an open configuration, the end effector closing drive in a retracted position, and the articulation joint in a locked configuration.

As outlined above, the firing drive 470 can further comprise a cutting member which can be configured to transect the tissue captured within the end effector 402. As also mentioned above, the electric motor within the handle 403 can be operated by the firing actuator 116 in order to advance the firing member 470 distally wherein, in various circumstances, the electric motor can be operated until the distal cutting portion 472 of the firing member 470 reaches the distal end of the staple cartridge and/or any other suitable position within the staple cartridge. In any event, the rotation of the electric motor can be reversed to retract the firing member 470 proximally, as illustrated in FIG. 27. In various circumstances, the electric motor can retract the proximal drive portion 482 and the intermediate portion 475 until the distal sidewall of the longitudinal slot 474 defined in the intermediate portion 475 comes into contact with the proximal end 473 of the distal cutting member 472. At such point, the further retraction of the proximal drive portion 482 and the intermediate portion 475 will retract the distal cutting member 472 proximally. In various circumstances, the electric motor can be operated until the slot 476 defined in the intermediate portion 475 of the firing member 470 is realigned with the proximal portion 461 of the articulation driver 460; however, as the closure sleeve 428 is still in a distally advanced position, the cam member 465 may still be biasing the articulation driver 460 out of engagement with the firing member 470. In order to permit the articulation driver 460 to be re-engaged with the firing member 470, in such circumstances, the closure drive would have to be re-opened to bring the window 424 defined in the outer sleeve portion 428 into alignment with the cam member 465 such that the cam member 465 can be pivoted inwardly toward the shaft frame 454 into its first position. In various circumstances, the articulation driver 460 can be resiliently flexed out of engagement with the firing member 470 such that, when the cam member 465 is permitted to move back into its first position, the articulation driver 460 can resiliently flex inwardly toward the shaft frame 454 to re-engage the proximal portion 461 of the articulation driver 460 with the slot 476 defined in the intermediate portion 475 of the drive member 470. In various embodiments, the surgical instrument 400 can further comprise a biasing member which can be configured to bias the proximal portion 461 back into engagement with the intermediate portion 475.

The reader will note that the intermediate portion 475 of the firing member 470 has been retracted proximally in FIG. 27 such that the slot 476 defined in the intermediate portion 475 is positioned proximally with respect to the proximal portion 461 of the articulation driver 460. In such circumstances, as a result, the proximal portion 461 may not be operably re-connected to the firing member 470 until the intermediate portion 475 is advanced distally to align the slot 476 with the proximal portion 461. Such circumstances may arise as a result of the relative slip between the intermediation portion 475 and the cutting member portion 472 of the firing member 470 created by the slip joint 471 which can be addressed by momentarily re-actuating the electric motor in the first direction, for example.

Figure 29:
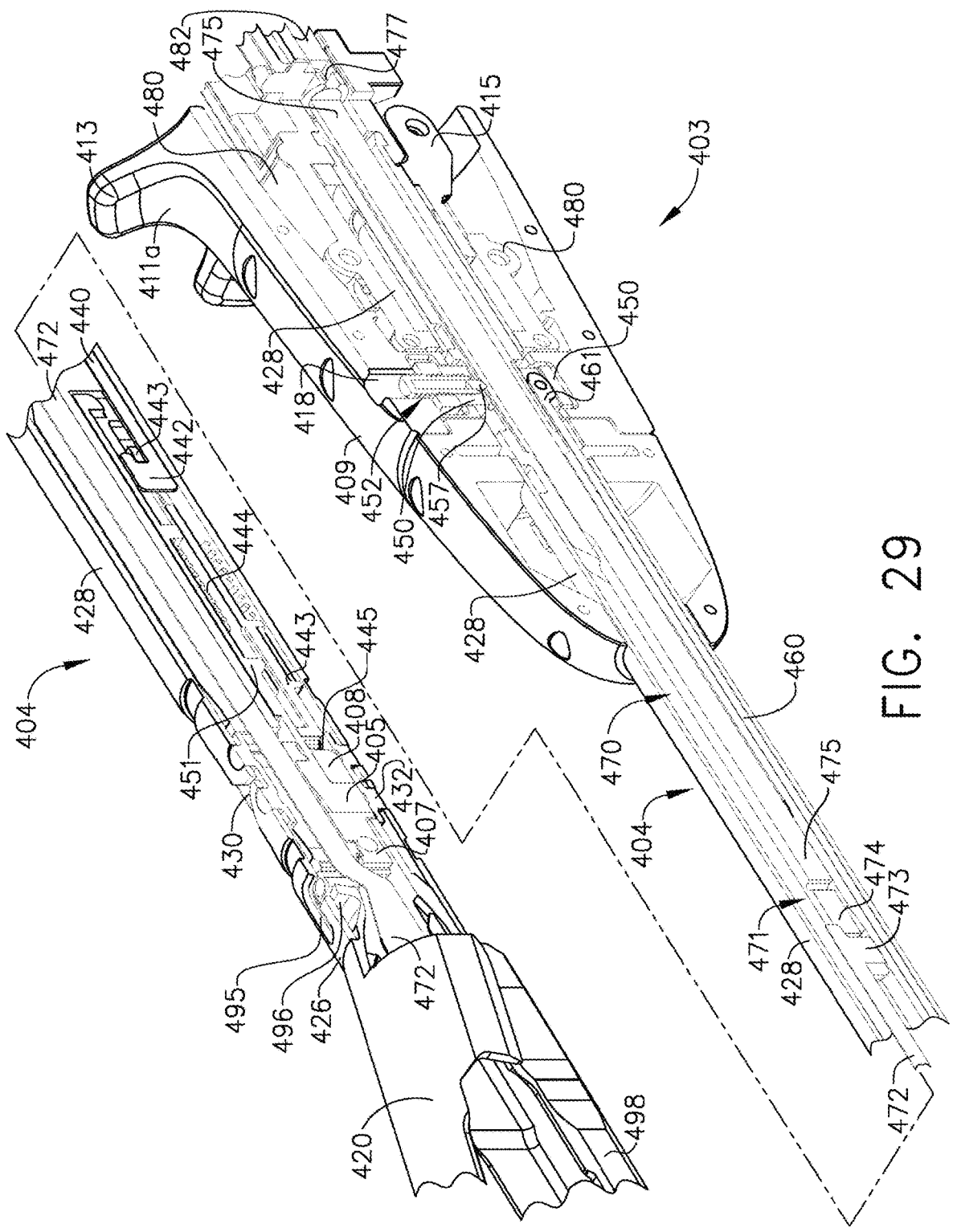
FIG. 29 is a cross-sectional detail view of the surgical instrument of FIG. 17 illustrating the end effector in an open configuration and the articulation joint and the articulation joint actuator in an unlocked configuration wherein the articulation driver can be reconnected to the firing drive and utilized to articulate the end effector once again.

Referring again to FIG. 27, the firing member 470 may be in a retracted or reset position, however, the closure drive is still in an actuated, or closed, configuration which can prevent the anvil 420 from being re-opened and the end effector 402 from being re-articulated. When the closure drive is released, referring now to FIG. 28, the closure drive carriage 415 can be retracted into a proximal position in which the closure sleeve including portions 426 and 428 are pulled proximally as well. Referring again to FIG. 19, the proximal sleeve portion 428 can include a proximal end 417 which can be engaged with the closure drive carriage 415 such that the proximal sleeve portion 428 and the closure drive carriage 415 move together in the distal direction and/or the proximal direction. In any event, further to the above, the proximal movement of the distal sleeve portion 426 can cause the distal sidewall of the aperture 495 to engage the projection 496 extending from the anvil 420 in order to pivot the anvil 420 into its open position, as illustrated in FIG. 29. Furthermore, the proximal movement of the closure drive carriage 415 can unlock the articulation lock actuator 409 such that the articulation lock actuator 409 can be moved into is proximal, unlocked, position which can, as a result, pull the articulation lock 443 proximally to compress the spring 444 and unlock the end effector 402. As described above, the end effector 402 can be then articulated about the articulation joint 410 and the operation of the surgical instrument 400 described above can be repeated. Referring primarily to FIGS. 18-20, the handle 404 can further comprise a switch 408 mounted to the handle frame 480 which can be configured to detect whether the articulation lock actuator 409 is in its proximal, unlocked, position. In some embodiments, the switch 408 can be operably coupled with an indicator in the handle 404, such as light, for example, which can indicate to the operator of the surgical instrument 400 that the end effector 402 is in an unlocked condition and that the operator may utilize the articulation switch to articulate the end effector 402, for example.

Figure 30:
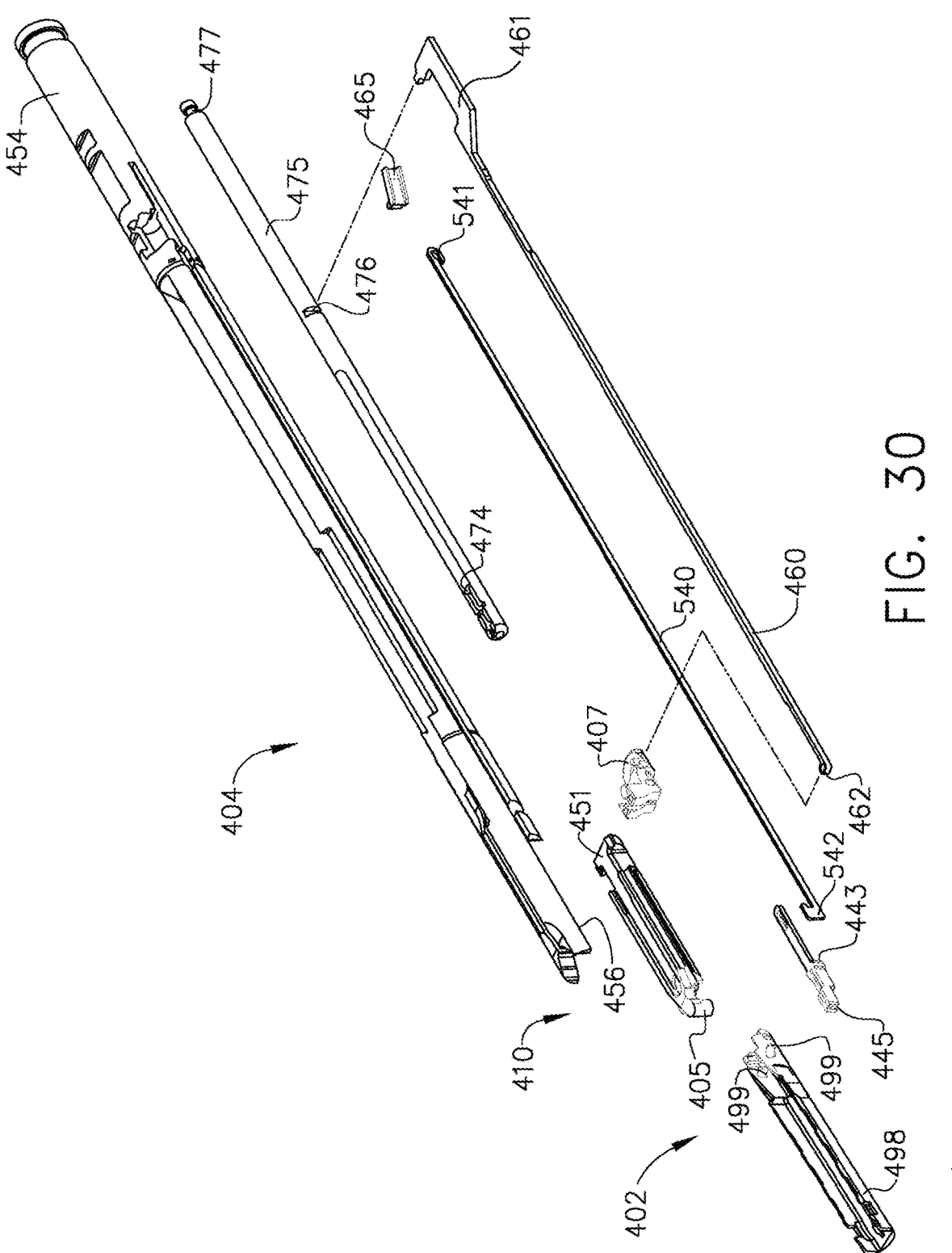
FIG. 30 is an exploded view of a shaft and an end effector of a surgical instrument including an alternative articulation lock arrangement.
Figure 31:
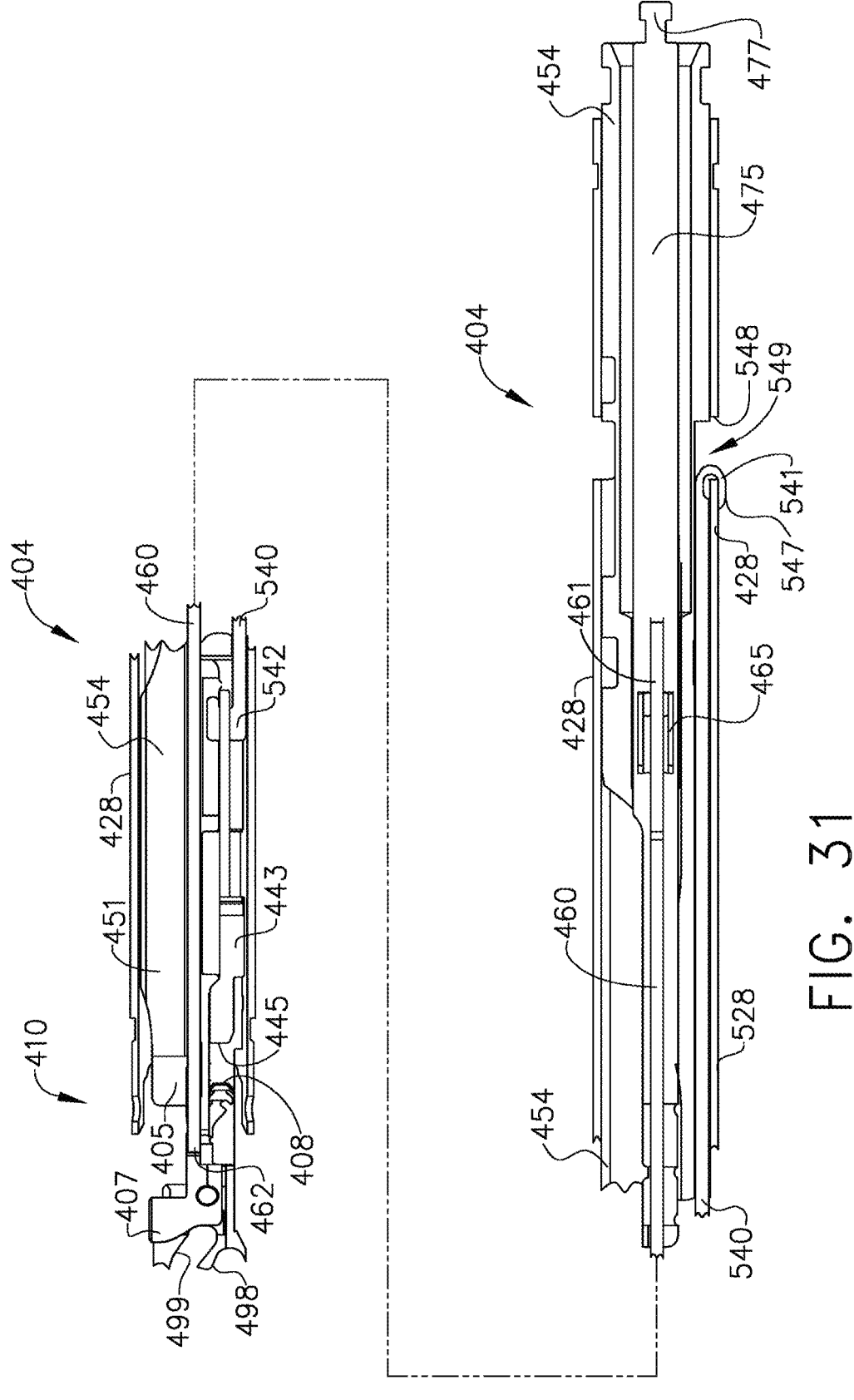
FIG. 31 is a cross-sectional elevational view of the end effector and the shaft of the surgical instrument of FIG. 30 illustrating the end effector in an unlocked configuration.
Figure 32:
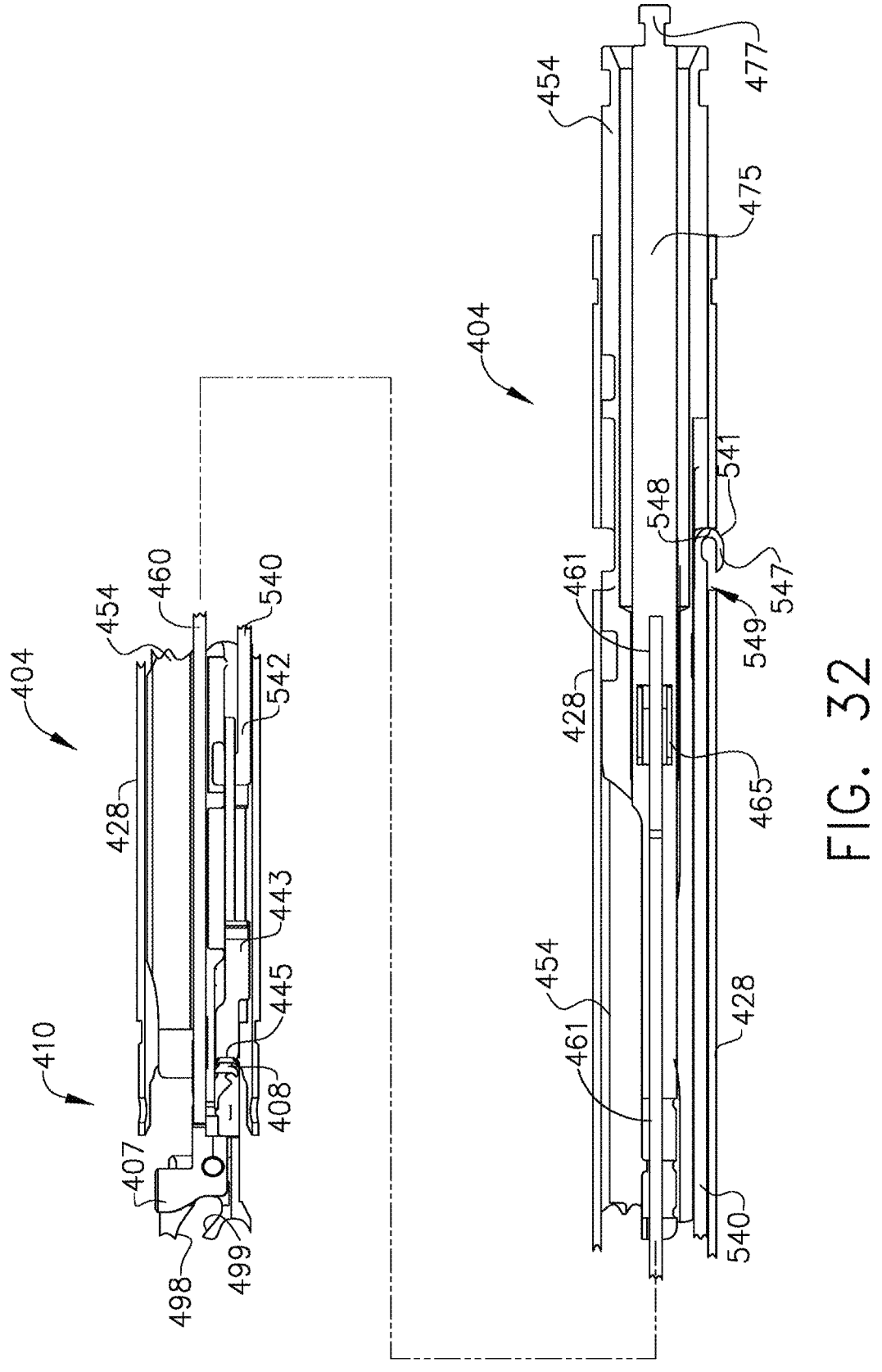
FIG. 32 is a cross-sectional elevational view of the end effector and the shaft of the surgical instrument of FIG. 30 illustrating the end effector in a locked configuration.

As described above in connection with the embodiment of FIG. 17, the surgical instrument 400 can comprise an articulation lock system configured to lock and unlock the end effector 402 and a closure drive configured to open and close the anvil 420 of the end effector 402. Although these two systems of the surgical instrument 400 interact in several respects, which are described above, the systems can be actuated independently of one another in other respects. For instance, the articulation lock actuator 409 and the end effector lock 443 can be actuated without closing the anvil 420. In this embodiment of the surgical instrument 400, the closure drive is operated independently to close the anvil 420. Turning now to FIGS. 30-32, the surgical instrument 400 can include an alternate arrangement in which the closure drive is actuated to, one, close the anvil 420 and, two, lock the end effector 402 in position. Referring primarily to FIGS. 31 and 32, the shaft 404 can comprise an articulation lock bar 540 which can be moved between a proximal, unlocked, position (FIG. 31) in which the end effector 402 can be articulated about the articulation joint 410 and a distal, locked, position (FIG. 32) in which the end effector 402 can be locked in position. Similar to the articulation lock bar 440, the articulation lock bar 540 can include a distal end 542 which is operably engaged with the articulation lock 443 such that, when the articulation lock bar 540 is pulled proximally, the articulation lock 443 can be pulled proximally. Similarly, when the articulation lock bar 540 is pushed distally, the articulation lock 443 can be pushed distally as well. In contrast to the articulation lock bar 440 which is pushed distally and pulled proximally by the articulation lock actuator 409, as described above, the articulation lock bar 540 can be pushed distally and pulled proximally by the closure sleeve 428. More particularly, the proximal end 541 of the articulation lock bar 540 can comprise a hook 547 which, when the closure sleeve 428 is pulled proximally, can catch a portion of the closure sleeve 428 and be pulled proximally with the closure sleeve 428. In such circumstances, the sleeve 428 can pull the articulation lock bar 540 into an unlocked condition. As the reader will note, the closure sleeve 428 can include a window 549 within which the proximal end 541 of the articulation lock bar 540 can be positioned. When the closure sleeve 428 is pushed distally, further to the above, a proximal sidewall 548 of the window 549 can contact the proximal end 541 and push the articulation lock bar 540 and the articulation lock 443 distally in order to lock the end effector 402 in position.

Figure 33:
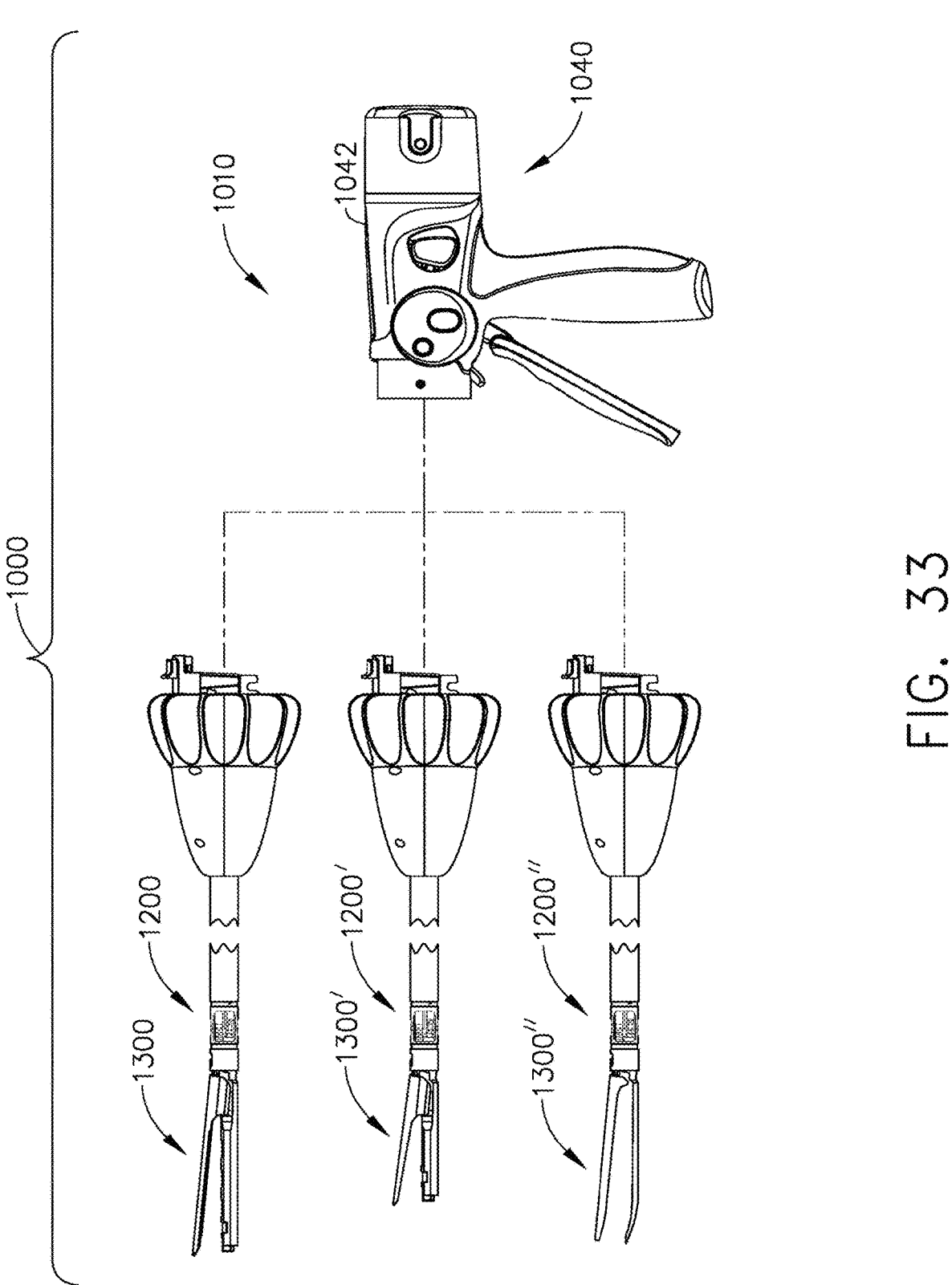
FIG. 33 is an assembly view of one form of surgical system including a surgical instrument and a plurality of interchangeable shaft assemblies.

As described herein, it may be desirable to employ surgical systems and devices that may include reusable portions that are configured to be used with interchangeable surgical components. Referring to FIG. 33, for example, there is shown a surgical system, generally designated as 1000, that, in at least one form, comprises a surgical instrument 1010 that may or may not be reused. The surgical instrument 1010 can be employed with a plurality of interchangeable shaft assemblies 1200, 1200', 1200". The interchangeable shaft assemblies 1200, 1200', 1200" may have a surgical end effector 1300, 1300', 1300" operably coupled thereto that is configured to perform one or more surgical tasks or procedures. For example, each of the surgical end effectors 1300, 1300', 1300" may comprise a surgical cutting and fastening device that is configured to operably support a surgical staple cartridge therein. Each of the shaft assemblies may employ end effectors that are adapted to support different sizes and types of staple cartridges, have different shaft lengths, sizes, and types, etc. While the present Figures illustrate end effectors that are configured to cut and staple tissue, various aspects of the surgical system 1000 may also be effectively employed with surgical instruments that are configured to apply other motions and forms of energy such as, for example, radio frequency (RF) energy, ultrasonic energy and/or motion, to interchangeable shaft-mounted end effector arrangements that are used in various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly. In various circumstances, a shaft assembly can be selected to be attached to a handle of a surgical instrument and a fastener cartridge can be selected to be attached to the shaft assembly.

The surgical instrument 1010 depicted in the FIG. 33 comprises a housing 1040 that consists of a handle 1042 that is configured to be grasped, manipulated and actuated by the clinician. As the present Detailed Description proceeds, however, it will be understood that the various unique and novel arrangements of the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. Patent Application Publication No. 2012/0298719, now U.S. Pat. No. 9,072,535. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, is incorporated by reference herein in its entirety.

FIG. 34 illustrates the surgical instrument 1010 with an interchangeable shaft assembly 1200 operably coupled thereto. In the illustrated form, the surgical instrument includes a handle 1042. In at least one form, the handle 1042 may comprise a pair of interconnectable housing segments 1044, 1046 that may be interconnected by screws, snap features, adhesive, etc. See FIG. 35. In the illustrated arrangement, the handle housing segments 1044, 1046 cooperate to form a pistol grip portion 1048 that can be gripped and manipulated by the clinician. As will be discussed in further detail below, the handle 1042 operably supports a plurality of drive systems therein that are configured to generate and apply various control motions to corresponding portions of the interchangeable shaft assembly that is operably attached thereto.

Figure 35:
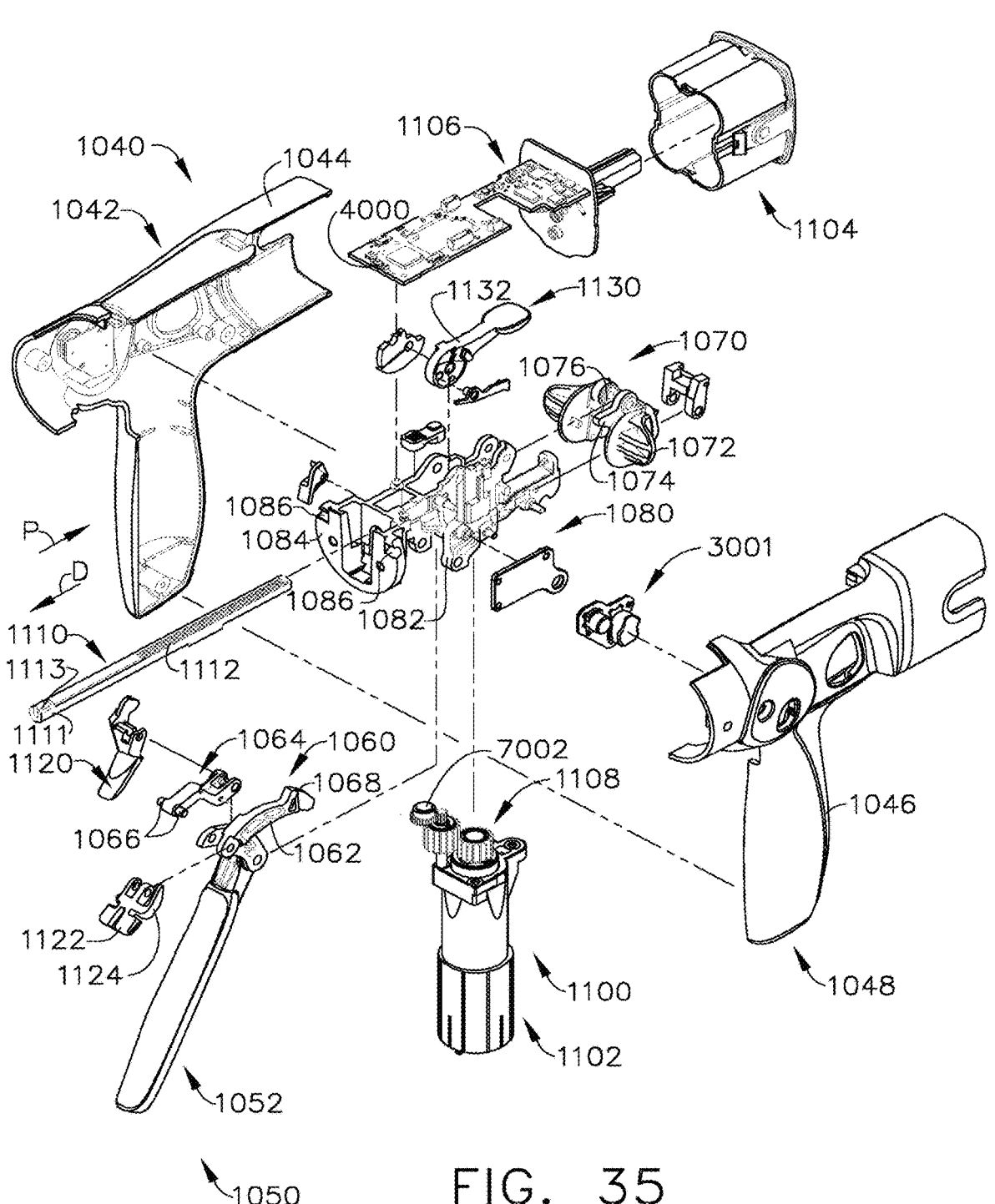
FIG. 35 is an exploded perspective view of the surgical instrument handle of FIG. 34.

The handle 1042 may further include a frame 1080 that operably supports a plurality of drive systems. For example, the frame 1080 can operably support a first or closure drive system, generally designated as 1050, which may be employed to apply a closing and opening motions to interchangeable shaft assembly 1200 that is operably attached or coupled thereto. In at least one form, the closure drive system 1050 may include an actuator in the form of a closure trigger 1052 that is pivotally supported by the frame 1080. More specifically, as illustrated in FIG. 35, the closure trigger 1052 may be pivotally supported by frame 1080 such that when the clinician grips the pistol grip portion 1048 of the handle 1042, the closure trigger 1052 may be easily pivoted from a starting or unactuated position to an actuated position and more particularly to a fully compressed or fully actuated position. The closure trigger 1052 may be biased into the unactuated position by spring or other biasing arrangement (not shown). In various forms, the closure drive system 1050 further includes a closure linkage assembly 1060 that is pivotally coupled to the closure trigger 1052. As can be seen in FIG. 35, the closure linkage assembly 1060 may include a closure trigger 1052 that is pivotally coupled to a closure link 1064 that has a pair of laterally extending attachment lugs or portions 1066 protruding therefrom. The closure link 1064 may also be referred to herein as an "attachment member".

Still referring to FIG. 35, it can be observed that the closure trigger 1052 may have a locking wall 1068 thereon that is configured to cooperate with a closure release assembly 1070 that is pivotally coupled to the frame 1080. In at least one form, the closure release assembly 1070 may comprise a release button assembly 1072 that has a distally protruding cam follower arm 1074 formed thereon. The release button assembly 1072 may be pivoted in a counterclockwise direction by a release spring 1076. As the clinician depresses the closure trigger 1052 from its unactuated position towards the pistol grip portion 1048 of the handle 1042, the closure link 1062 pivots upward to a point wherein the cam follower arm 1072 drops into retaining engagement with the locking wall 1068 on the closure link 1062 thereby preventing the closure trigger 1052 from returning to the unactuated position. Thus, the closure release assembly 1070 serves to lock the closure trigger 1052 in the fully actuated position. When the clinician desires to unlock the closure trigger 1052 to permit it to be biased to the unactuated position, the clinician simply pivots the closure release button assembly 1072 such that the cam follower arm 1074 is moved out of engagement with the locking wall

1068 on the closure trigger 1052. When the cam follower arm 1074 has been moved out of engagement with the closure trigger 1052, the closure trigger 1052 may pivot back to the unactuated position. Other closure trigger locking and release arrangements may also be employed.

In at least one form, the handle 1042 and the frame 1080 may operably support another drive system referred to herein as firing drive system 1100 that is configured to apply firing motions to corresponding portions of the interchangeable shaft assembly attached thereto. The firing drive system may also be referred to herein as a "second drive system". The firing drive system 1100 may employ an electric motor 1102, located in the pistol grip portion 1048 of the handle 1042. In various forms, the motor 1102 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. A battery 1104 (or "power source" or "power pack"), such as a Li ion battery, for example, may be coupled to the handle 1042 to supply power to a control circuit board assembly 1106 and ultimately to the motor 1102. FIG. 34 illustrates a battery pack housing 1104 that is configured to be releasably mounted to the handle 1042 for supplying control power to the surgical instrument 1010. A number of battery cells connected in series may be used as the power source to power the motor. In addition, the power source may be replaceable and/or rechargeable.

As outlined above with respect to other various forms, the electric motor 1102 can include a rotatable shaft (not shown) that operably interfaces with a gear reducer assembly 1108 that is mounted in meshing engagement with a with a set, or rack, of drive teeth 1112 on a longitudinally-movable drive member 1110. In use, a voltage polarity provided by the battery can operate the electric motor 1102 in a clockwise direction wherein the voltage polarity applied to the electric motor by the battery can be reversed in order to operate the electric motor 1102 in a counter-clockwise direction. When the electric motor 1102 is rotated in one direction, the drive member 1110 will be axially driven in the distal direction "D". When the motor 1102 is driven in the opposite rotary direction, the drive member 1110 will be axially driven in a proximal direction "P". See, for example, FIG. 35. The handle 1042 can include a switch which can be configured to reverse the polarity applied to the electric motor 1102 by the battery. As with the other forms described herein, the handle 1042 can also include a sensor that is configured to detect the position of the drive member 1110 and/or the direction in which the drive member 1110 is being moved.

Figure 36:
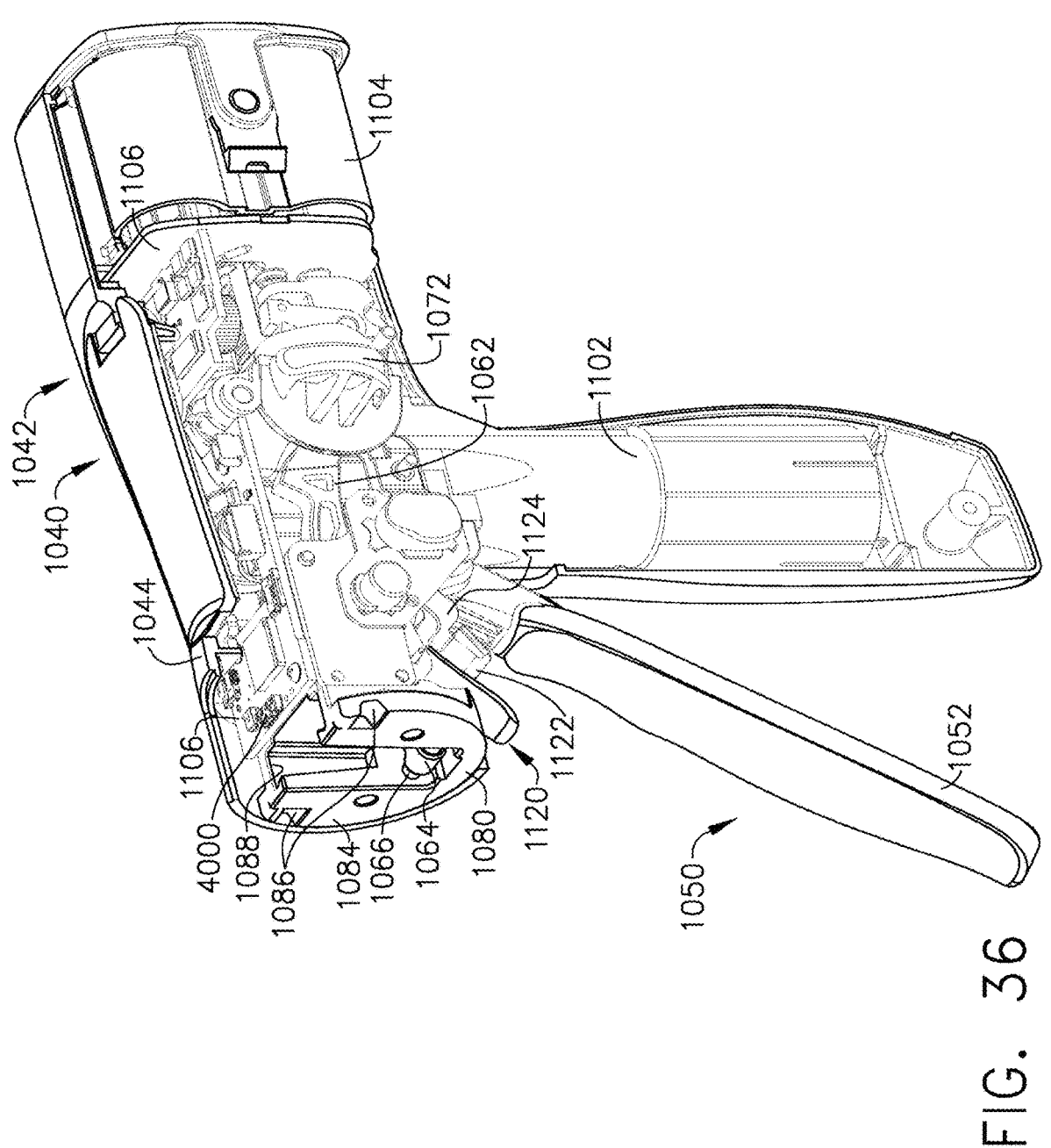
FIG. 36 is a side elevational view of the handle of FIG. 35 with a portion of the handle housing removed.
Figure 38:
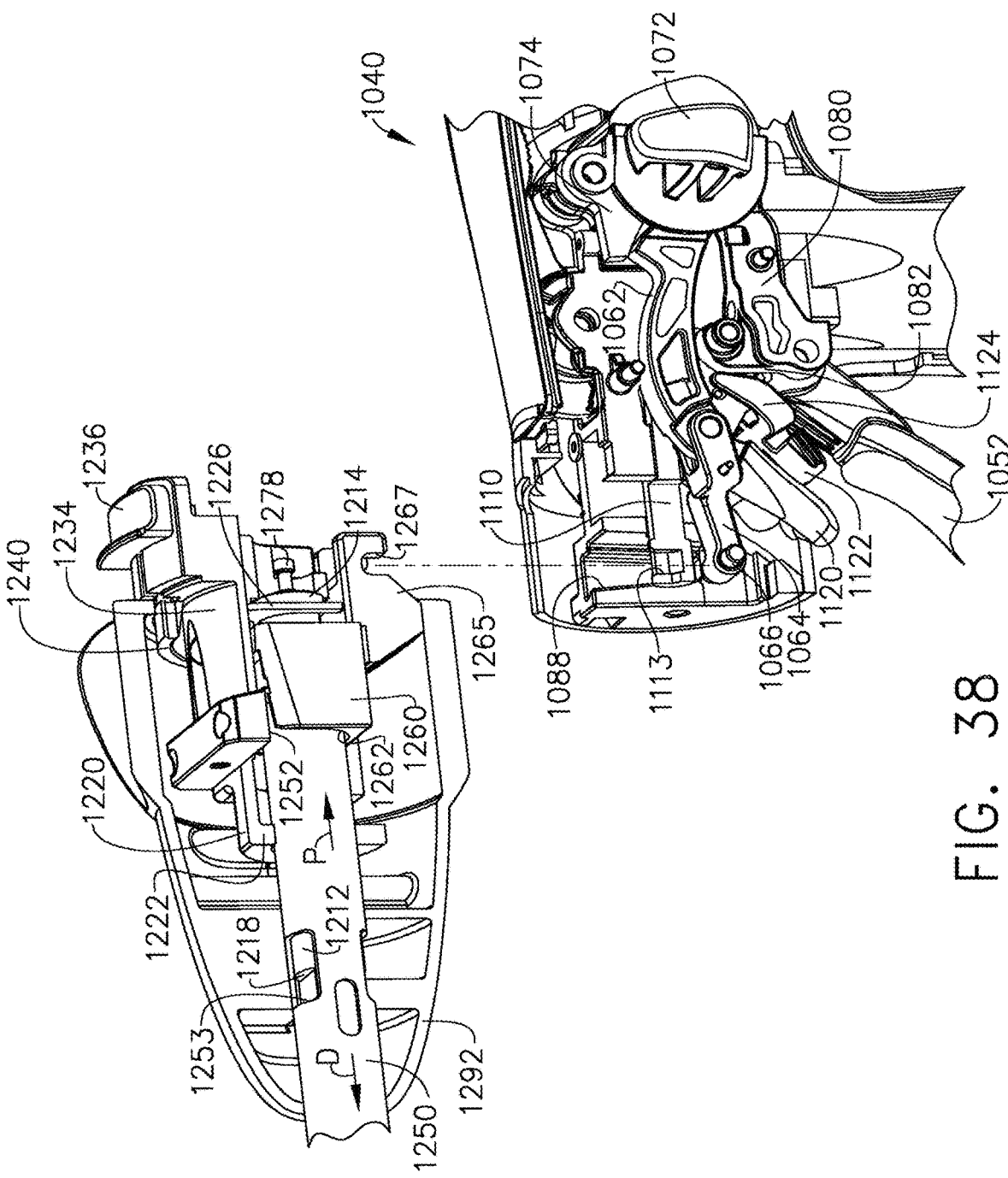
FIG. 38 is a side elevational assembly view of a portion of the handle and interchangeable shaft assembly of FIG. 34 illustrating the alignment of those components prior to being coupled together and with portions thereof omitted for clarity.

Actuation of the motor 1102 can be controlled by a firing trigger 1120 that is pivotally supported on the handle 1042. The firing trigger 1120 may be pivoted between an unactuated position and an actuated position. The firing trigger 1120 may be biased into the unactuated position by a spring (not shown) or other biasing arrangement such that when the clinician releases the firing trigger 1120, it may be pivoted or otherwise returned to the unactuated position by the spring or biasing arrangement. In at least one form, the firing trigger 1120 can be positioned "outboard" of the closure trigger 1052 as was discussed above. In at least one form, a firing trigger safety button 1122 may be pivotally mounted to the closure trigger 1052. As can be seen in FIGS. 35 and 36, for example, the safety button 1122 may be positioned between the firing trigger 1120 and the closure trigger 1052 and have a pivot arm 1124 protruding therefrom. As shown in FIG. 38, when the closure trigger 1052 is in the unactuated position, the safety button 1122 is contained in the handle housing where the clinician cannot readily access it and move it between a safety position preventing actuation of the firing trigger 1120 and a firing position wherein the firing trigger 1120 may be fired. As the clinician depresses the closure trigger 1052, the safety button 1122 and the firing trigger 1120 pivot down wherein they can then be manipulated by the clinician.

As indicated above, in at least one form, the longitudinally movable drive member 1110 has a rack of teeth 1112 formed thereon for meshing engagement with a corresponding drive gear 1114 of the gear reducer assembly 1108. At least one form may also include a manually-actuatable "bailout" assembly 1130 that is configured to enable the clinician to manually retract the longitudinally movable drive member 1110 should the motor become disabled. The bailout assembly 1130 may include a lever or bailout handle assembly 1132 that is configured to be manually pivoted into ratcheting engagement with the teeth 1112 in the drive member 1110. Thus, the clinician can manually retract the drive member 1110 by using the bailout handle assembly 1132 to ratchet the drive member in the proximal direction "P". U.S. Patent Application Publication No. 2010/0089970, now U.S. Pat. No. 8,608,045, discloses bailout arrangements and other components, arrangements and systems that may also be employed with the various instruments disclosed herein. U.S. patent application Ser. No. 12/249,117, entitled POWERED SURGICAL CUTTING G AND STAPLING APPARATUS WITH MANUALLY RETRACTABLE FIRING SYSTEM, now U.S. Pat. No. 8,608,045, is incorporated by reference in its entirety.

Figure 37:
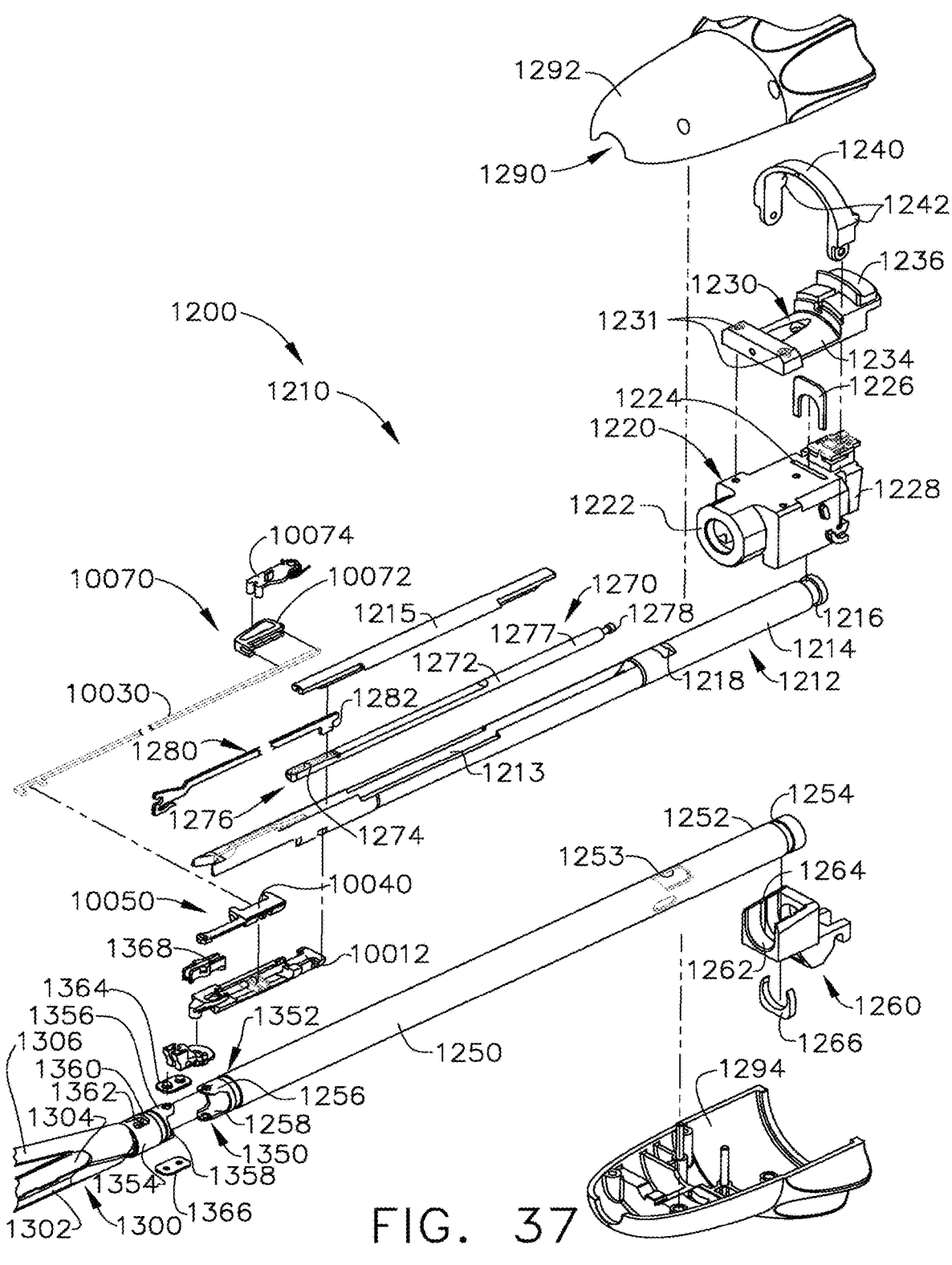
FIG. 37 is an exploded perspective view of an interchangeable shaft assembly.

FIGS. 34 and 37 illustrate one form of interchangeable shaft assembly 1200 that has, for example, a surgical end effector 1300 operably attached thereto. The end effector 1300 as illustrated in those Figures may be configured to cut and staple tissue in the various manners disclosed herein. For example, the end effector 1300 may include a channel 1302 that is configured to support a surgical staple cartridge 1304. The staple cartridge 1304 may comprise a removable staple cartridge 1304 such that it may be replaced when spent. However, the staple cartridge in other arrangements may be configured such that once installed within the channel 1302, it is not intended to be removed therefrom. The channel 1032 and staple cartridge 1304 may be collectively referred to as a "first jaw portion" of the end effector 1300. In various forms, the end effector 1300 may have a "second jaw portion", in the form of an anvil 1310, that is movably or pivotally supported on the channel 1302 in the various manners discussed herein.

The interchangeable shaft assembly 1200 may further include a shaft 1210 that includes a shaft frame 1212 that is coupled to a shaft attachment module or shaft attachment portion 1220. In at least one form, a proximal end 1214 of the shaft frame 1212 may extend through a hollow collar portion 1222 formed on the shaft attachment module 1220 and be rotatably attached thereto. For example, an annular groove 1216 may be provided in the proximal end 1214 of the shaft frame 1212 for engagement with a U-shaped retainer 1226 that extends through a slot 1224 in the shaft attachment module 1220. Such arrangement enables the shaft frame 1212 to be rotated relative to the shaft attachment module 1220.

The shaft assembly 1200 may further comprise a hollow outer sleeve or closure tube 1250 through which the shaft frame 1212 extends. The outer sleeve 1250 may also be referred to herein as a "first shaft" and/or a "first shaft assembly". The outer sleeve 1250 has a proximal end 1252 that is adapted to be rotatably coupled to a closure tube attachment yoke 1260. As can be seen in FIG. 37, the proximal end 1252 of the outer sleeve 1250 is configured to be received within a cradle 1262 in the closure tube attachment yoke 1260. A U-shaped connector 1266 extends through a slot 1264 in the closure tube attachment yoke 1260 to be received in an annular groove 1254 in the proximal end 1252 of the outer sleeve 1250. Such arrangement serves to rotatably couple the outer sleeve 1250 to the closure tube attachment yoke 1260 such that the outer sleeve 1250 may rotate relative thereto.

Figure 39:
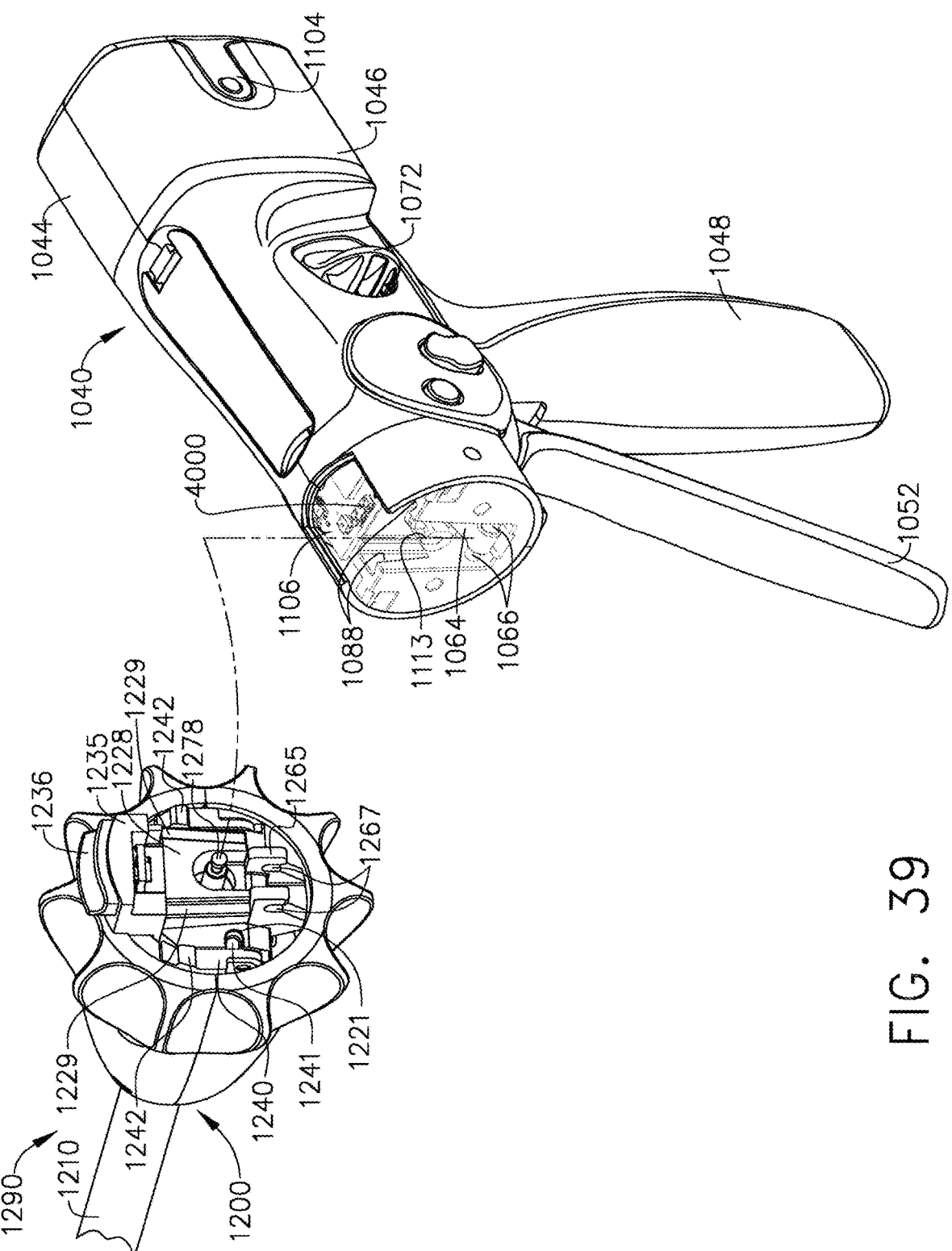
FIG. 39 is a perspective view of a portion of an interchangeable shaft assembly prior to attachment to a handle of a surgical instrument.

As can be seen in FIGS. 38 and 39, the proximal end 1214 of the shaft frame 1214 protrudes proximally out of the proximal end 1252 of the outer sleeve 1250 and is rotatably coupled to the shaft attachment module 1220 by the U-shaped retainer 1226 (shown in FIG. 38). The closure tube attachment yoke 1260 is configured to be slidably received within a passage 1268 in the shaft attachment module 1220. Such arrangement permits the outer sleeve 1250 to be axially moved in the proximal direction "P" and the distal direction "D" on the shaft frame 1212 relative to the shaft attachment module 1220 as will be discussed in further detail below.

In at least one form, the interchangeable shaft assembly 1200 may further include an articulation joint 1350. Other interchangeable shaft assemblies, however, may not be capable of articulation. As can be seen in FIG. 37, for example, the articulation joint 1350 includes a double pivot closure sleeve assembly 1352. According to various forms, the double pivot closure sleeve assembly 1352 includes a shaft closure sleeve assembly 1354 having upper and lower distally projecting tangs 1356, 1358. An end effector closure sleeve assembly 1354 includes a horseshoe aperture 1360 and a tab 1362 for engaging an opening tab on the anvil 1310 in the manner described above. As described above, the horseshoe aperture 1360 and tab 1362 engage the anvil tab when the anvil 1310 is opened. An upper double pivot link 1364 includes upwardly projecting distal and proximal pivot pins that engage respectively an upper distal pin hole in the upper proximally projecting tang 1356 and an upper proximal pin hole in an upper distally projecting tang 1256 on the outer sleeve 1250. A lower double pivot link 1366 includes downwardly projecting distal and proximal pivot pins that engage respectively a lower distal pin hole in the lower proximally projecting tang 1358 and a lower proximal pin hole in the lower distally projecting tang 1258.

In use, the closure sleeve assembly 1354 is translated distally (direction "D") to close the anvil 1310, for example, in response to the actuation of the closure trigger 1052. The anvil 1310 is closed by distally translating the outer sleeve 1250, and thus the shaft closure sleeve assembly 1354, causing it to strike a proximal surface on the anvil 1310 in the manner described above. As was also described above, the anvil 1310 is opened by proximally translating the outer sleeve 1250 and the shaft closure sleeve assembly 1354, causing tab 1362 and the horseshoe aperture 1360 to contact and push against the anvil tab to lift the anvil 1310. In the anvil-open position, the shaft closure sleeve assembly 1352 is moved to its proximal position.

In at least one form, the interchangeable shaft assembly 1200 further includes a firing member 1270 that is supported for axial travel within the shaft frame 1212. The firing member 1270 includes an intermediate firing shaft portion 1272 that is configured for attachment to a distal cutting portion 1280. The firing member 1270 may also be referred to herein as a "second shaft" and/or a "second shaft assembly". As can be seen in FIG. 37, the intermediate firing shaft portion 1272 may include a longitudinal slot 1274 in the distal end thereof which can be configured to receive the proximal end 1282 of the distal cutting portion 1280. The longitudinal slot 1274 and the proximal end 1282 can be sized and configured to permit relative movement therebetween and can comprise a slip joint 1276. The slip joint 1276 can permit the intermediate firing shaft portion 1272 of the firing drive 1270 to be moved to articulate the end effector 1300 without moving, or at least substantially moving, the distal cutting portion 1280. Once the end effector 1300 has been suitably oriented, the intermediate firing shaft portion 1272 can be advanced distally until a proximal sidewall of the longitudinal slot 1272 comes into contact with the proximal end 1282 in order to advance the distal cutting portion 1280 and fire the staple cartridge positioned within the channel 1302, as described herein. As can be further seen in FIG. 37, the shaft frame 1212 has an elongate opening or window 1213 therein to facilitate assembly and insertion of the intermediate firing shaft portion 1272 into the shaft frame 1212. Once the intermediate firing shaft portion 1272 has been inserted therein, a top frame segment 1215 may be engaged with the shaft frame 1212 to enclose the intermediate firing shaft portion 1272 and distal cutting portion 1280 therein. The reader will also note that the articulation joint 1350 can further include a guide 1368 which can be configured to receive the distal cutting portion 1280 of the firing member 1270 therein and guide the distal cutting portion 1280 as it is advanced distally and/or retracted proximally within and/or relative to the articulation joint 1350.

As can be seen in FIG. 37, the shaft attachment module 1220 may further include a latch actuator assembly 1230 that may be removably attached to the shaft attachment module by cap screws (not shown) or other suitable fasteners. The latch actuator assembly 1230 is configured to cooperate with a lock yoke 1240 that is pivotally coupled to the shaft attachment module 1220 for selective pivotal travel relative thereto. See FIG. 41. Referring to FIG. 39, the lock yoke 1240 may include two proximally protruding lock lugs 1242 (FIG. 37) that are configured for releasable engagement with corresponding lock detents or grooves 1086 formed in a frame attachment module portion 1084 of the frame 1080 as will be discussed in further detail below. The lock yoke 1240 is substantially U-shaped and is installed over the latch actuator assembly 1230 after the latch actuator assembly 1230 has been coupled to the shaft attachment module 1220. The latch actuator assembly 1230 may have an arcuate body portion 1234 that provides sufficient clearance for the lock yoke 1240 to pivot relative thereto between latched and unlatched positions.

In various forms, the lock yoke 1240 is biased in the proximal direction by spring or biasing member (not shown). Stated another way, the lock yoke 1240 is biased into the latched position (FIG. 40) and can be pivoted to an unlatched position (FIG. 41) by a latch button 1236 that is movably supported on the latch actuator assembly 1230. In at least one arrangement, for example, the latch button 1236 is slidably retained within a latch housing portion 1235 and is biased in the proximal direction "P" by a latch spring or biasing member (not shown). As will be discussed in further detail below, the latch button 1236 has a distally protruding release lug 1237 that is designed to engage the lock yoke 1240 and pivot it from the latched position to the unlatched position shown in FIG. 41 upon actuation of the latch button 1236.

The interchangeable shaft assembly 1200 may further include a nozzle assembly 1290 that is rotatably supported on the shaft attachment module 1220. In at least one form, for example, the nozzle assembly 1290 can be comprised of two nozzle halves, or portions, 1292, 1294 that may be interconnected by screws, snap features, adhesive, etc. When mounted on the shaft attachment module 1220, the nozzle assembly 1290 may interface with the outer sleeve 1250 and shaft frame 1212 to enable the clinician to selectively rotate the shaft 1210 relative to the shaft attachment module 1220 about a shaft axis SA-SA which may be defined for example, the axis of the firing member assembly 1270. In particular, a portion of the nozzle assembly 1290 may extend through a window 1253 in the outer sleeve to engage a notch 1218 in the shaft frame 1212. See FIG. 37. Thus, rotation of the nozzle assembly 1290 will result in rotation of the shaft frame 1212 and outer sleeve 1250 about axis A-A relative to the shaft attachment module 1220.

Figures 42, 43:
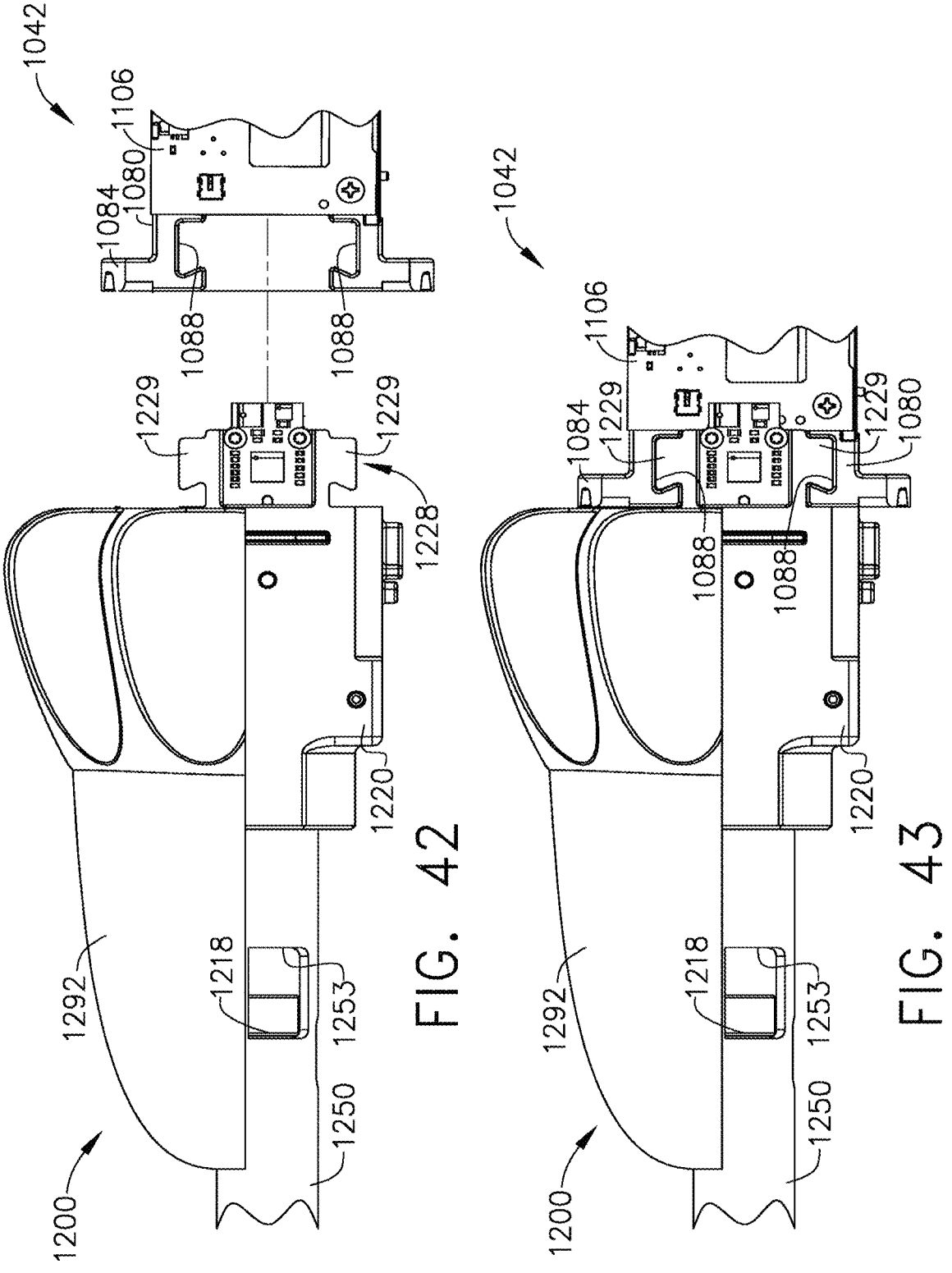
FIG. 42 is a top view of a portion of an interchangeable shaft assembly and handle prior to being coupled together.
FIG. 43 is another top view of the interchangeable shaft assembly and handle of FIG. 42 coupled together.
Figure 44:
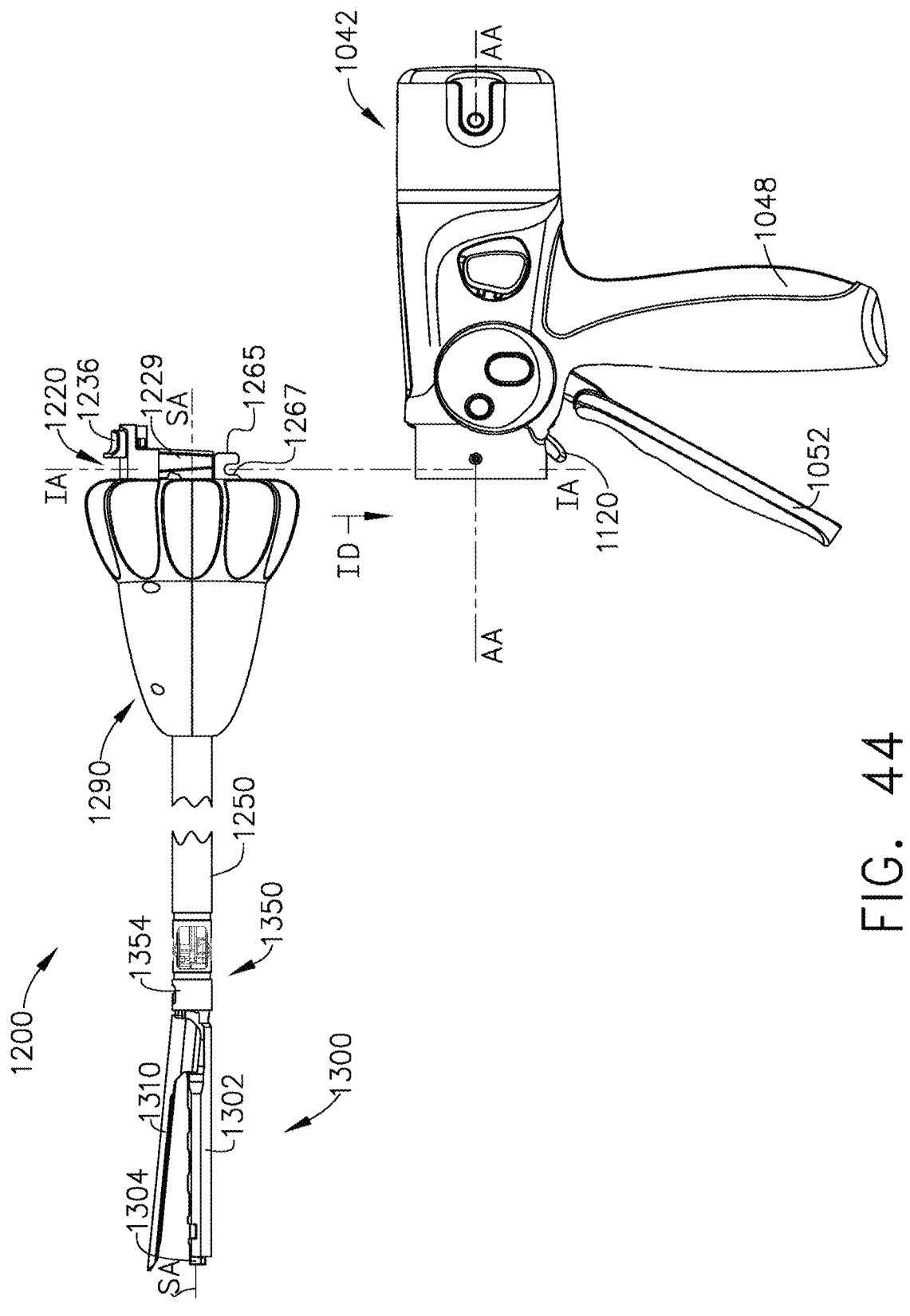
FIG. 44 is a side elevational view of an interchangeable shaft assembly aligned with a surgical instrument handle prior to being coupled together.

Referring now to FIGS. 42 and 43, the reader will observe that the frame attachment module portion 1084 of the frame 1080 is formed with two inwardly facing dovetail receiving slots 1088. Each dovetail receiving slot 1088 may be tapered or, stated another way, be somewhat V-shaped. See, for example, FIGS. 36 and 38 (only one of the slots 1088 is shown). The dovetail receiving slots 1088 are configured to releasably receive corresponding tapered attachment or lug portions 1229 of a proximally-extending connector portion 1228 of the shaft attachment module 1220. As can be further seen in FIGS. 37-39, a shaft attachment lug 1278 is formed on the proximal end 1277 of the intermediate firing shaft 1272. As will be discussed in further detail below, when the interchangeable shaft assembly 1200 is coupled to the handle 1042, the shaft attachment lug 1278 is received in a firing shaft attachment cradle 1113 formed in the distal end 1111 of the longitudinal drive member 1110. Also, the closure tube attachment yoke 1260 includes a proximally-extending yoke portion 1265 that includes two capture slots 1267 that open downwardly to capture the attachment lugs 1066 on the closure attachment bar 1064.

Figure 47:
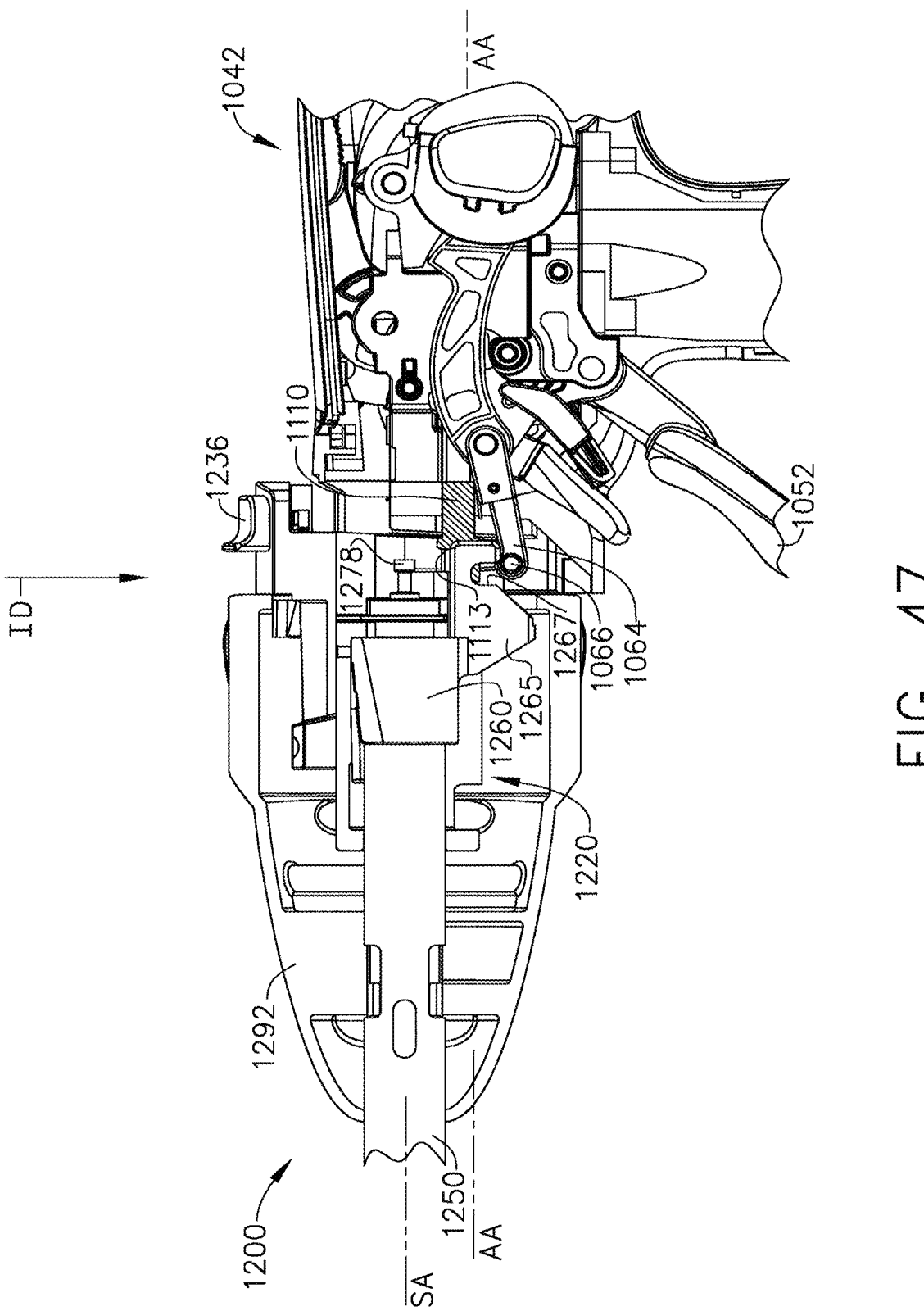
FIG. 47 is another side elevational view of the interchangeable shaft assembly and handle of FIG. 46 wherein the shaft assembly is in partial coupling engagement with the handle.
Figure 48:
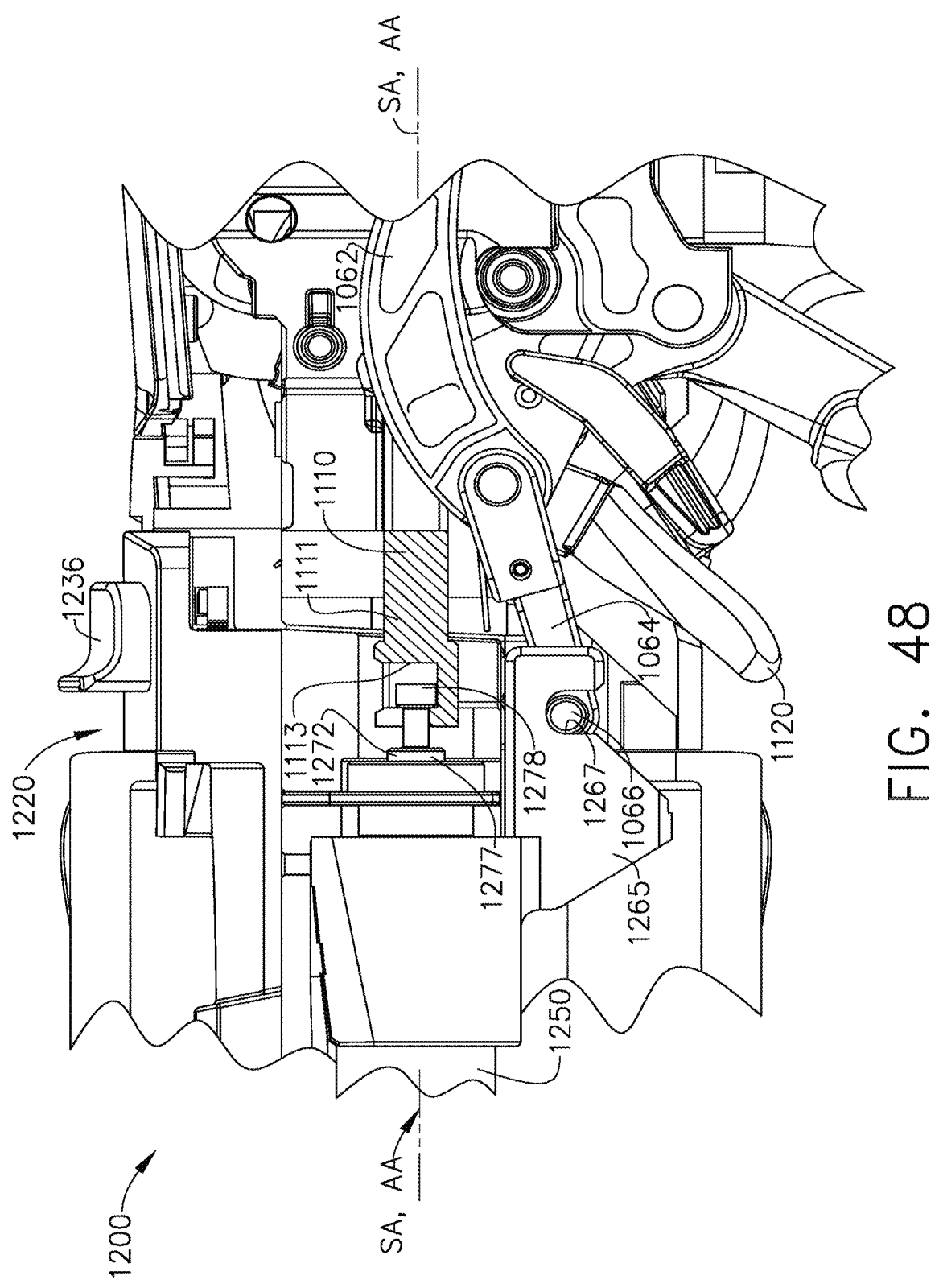
FIG. 48 is another side elevational view of the interchangeable shaft assembly and handle of FIGS. 46 and 47 after being coupled together.

Attachment of the interchangeable shaft assembly 1220 to the handle 1042 will now be described with reference to FIGS. 44-48. In various forms, the frame 1080 or at least one of the drive systems define an actuation axis AA-AA. For example, the actuation axis AA-AA may be defined by the axis of the longitudinally-movable drive member 1110. As such, when the intermediate firing shaft 1272 is operably coupled to the longitudinally movable drive member 1110, the actuation axis AA-AA is coaxial with the shaft axis SA-SA as shown in FIG. 48.

Figure 45:
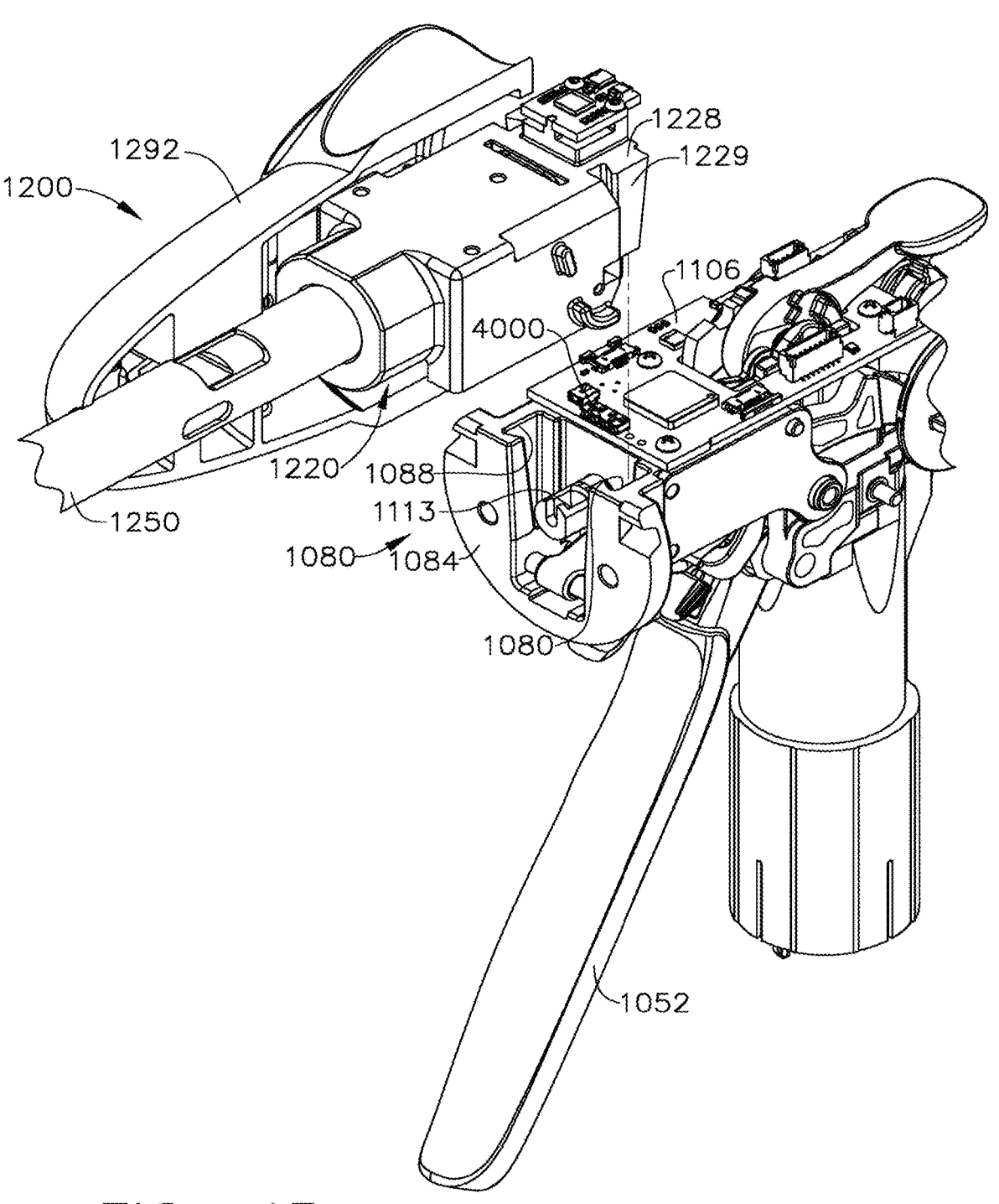
FIG. 45 is a front perspective view of the interchangeable shaft assembly and surgical instrument handle of FIG. 44 with portions thereof removed for clarity.
Figure 46:
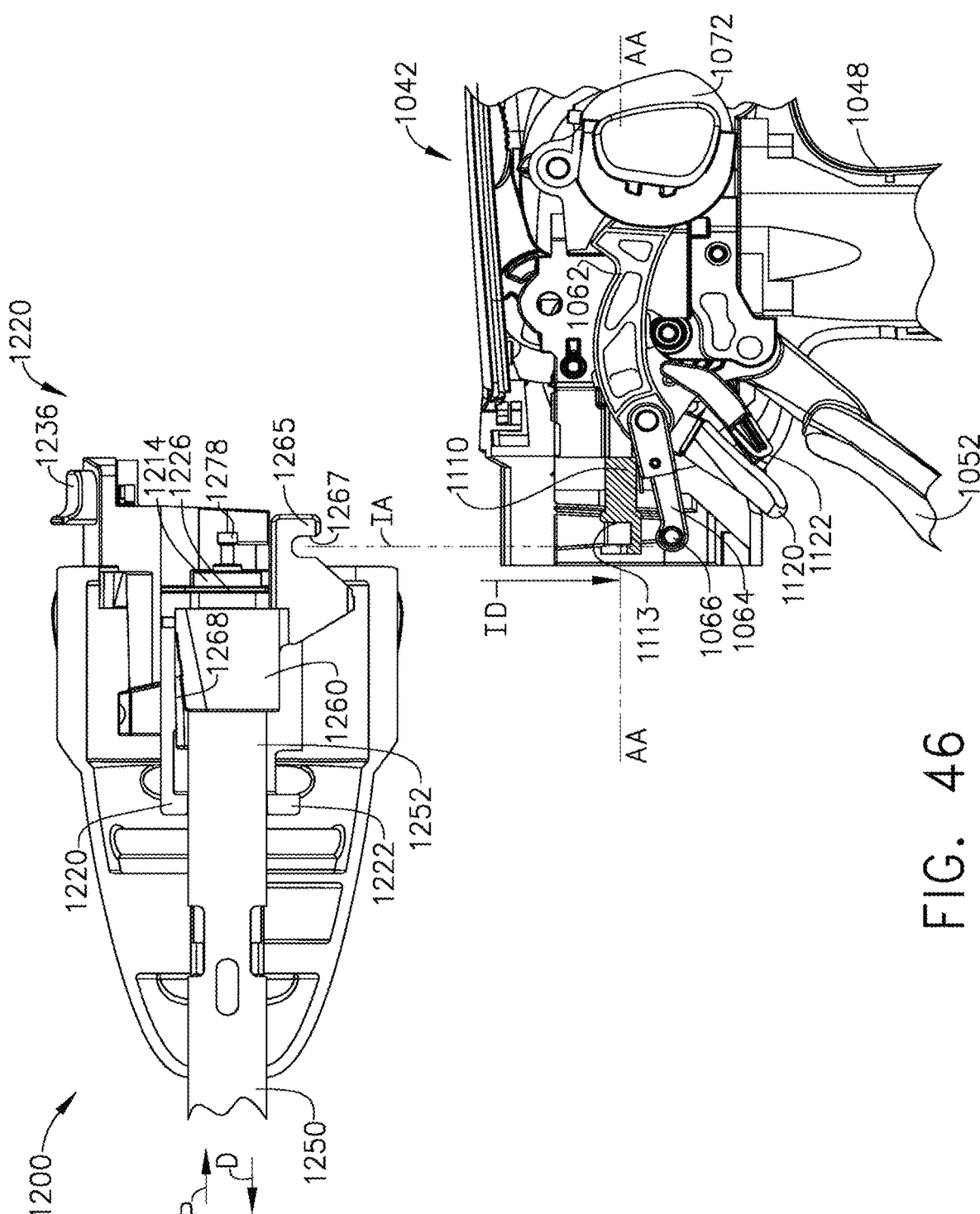
FIG. 46 is a side view of a portion of an interchangeable shaft assembly aligned with a portion of a surgical instrument handle prior to being coupled together and with portions thereof omitted for clarity.

To commence the coupling process, the clinician may position the shaft attachment module 1220 of the interchangeable shaft assembly 1200 above or adjacent to the frame attachment module portion 1084 of the frame 1080 such that the attachment lugs 1229 formed on the connector portion 1228 of the shaft attachment module 1220 are aligned with the dovetail slots 1088 in the attachment module portion 1084 as shown in FIG. 45. The clinician may then move the shaft attachment module 1220 along an installation axis IA-IA that is substantially transverse to the actuation axis AA-AA. Stated another way, the shaft attachment module 1220 is moved in an installation direction "ID" that is substantially transverse to the actuation axis AA-AA until the attachment lugs 1229 of the connector portion 1228 are seated in "operable engagement" with the corresponding dovetail receiving slots 1088. Sec FIGS. 44 and 46. FIG. 47 illustrates the position of the shaft attachment module 1220 prior to the shaft attachment lug 1278 on the intermediate firing shaft 1272 entering the cradle 1113 in the longitudinally movable drive member 1110 and the attachment lugs 1066 on the closure attachment bar 1064 entering the corresponding slots 1267 in the yoke portion 1265 of the closure tube attachment yoke 1260. FIG. 48 illustrates the position of the shaft attachment module 1220 after the attachment process has been completed. As can be seen in that Figure, the lugs 1066 (only one is shown) are seated in operable engagement in their respective slots 1267 in the yoke portion 1265 of the closure tube attachment yoke 1260. As used herein, the term "operable engagement" in the context of two components means that the two components are sufficiently engaged with each other so that upon application of an actuation motion thereto, the components may carry out their intended action, function and/or procedure.

As discussed above, referring again to FIGS. 44-49, at least five systems of the interchangeable shaft assembly 1200 can be operably coupled with at least five corresponding systems of the handle 1042. A first system can comprise a frame system which couples and/or aligns the frame of the shaft assembly 1200 with the frame of the handle 1042. As outlined above, the connector portion 1228 of the shaft assembly 1200 can be engaged with the attachment module portion 1084 of the handle frame 1080. A second system can comprise a closure drive system which can operably connect the closure trigger 1052 of the handle 1042 and the closure tube 1250 and the anvil 1310 of the shaft assembly 1200. As outlined above, the closure tube attachment yoke 1260 of the shaft assembly 1200 can be engaged with the attachment lugs 1066 of the handle 1042. A third system can comprise a firing drive system which can operably connect the firing trigger 1120 of the handle 1042 with the intermediate firing shaft 1272 of the shaft assembly 1200. As outlined above, the shaft attachment lug 1278 can be operably connected with the cradle 1113 of the longitudinal drive member 1110. A fourth system can comprise an electrical system which can, one, signal to a controller in the handle 1042, such as microcontroller 7004, for example, that a shaft assembly, such as shaft assembly 1200, for example, has been operably engaged with the handle 1042 and/or, two, conduct power and/or communication signals between the shaft assembly 1200 and the handle 1042. For instance, the shaft assembly 1200 can include six electrical contacts and the electrical connector 4000 can also include six electrical contacts wherein each electrical contact on the shaft assembly 1200 can be paired and mated with an electrical contact on the electrical connector 4000 when the shaft assembly 1200 is assembled to the handle 1042. The shaft assembly 1200 can also include a latch 1236 which can be part of a fifth system, such as a lock system, which can releasably lock the shaft assembly 1200 to the handle 1042. In various circumstances, the latch 1236 can close a circuit in the handle 1042, for example, when the latch 1236 is engaged with the handle 1042.

Further to the above, the frame system, the closure drive system, the firing drive system, and the electrical system of the shaft assembly 1200 can be assembled to the corresponding systems of the handle 1042 in a transverse direction, i.e., along axis IA-IA, for example. In various circumstances, the frame system, the closure drive system, and the firing drive system of the shaft assembly 1200 can be simultaneously coupled to the corresponding systems of the handle 1042. In certain circumstances, two of the frame system, the closure drive system, and the firing drive system of the shaft assembly 1200 can be simultaneously coupled to the corresponding systems of the handle 1042. In at least one circumstance, the frame system can be at least initially coupled before the closure drive system and the firing drive system are coupled. In such circumstances, the frame system can be configured to align the corresponding components of the closure drive system and the firing drive system before they are coupled as outlined above. In various circumstances, the electrical system portions of the housing assembly 1200 and the handle 1042 can be configured to be coupled at the same time that the frame system, the closure drive system, and/or the firing drive system are finally, or fully, seated. In certain circumstances, the electrical system portions of the housing assembly 1200 and the handle 1042 can be configured to be coupled before the frame system, the closure drive system, and/or the firing drive system are finally, or fully, seated. In some circumstances, the electrical system portions of the housing assembly 1200 and the handle 1042 can be configured to be coupled after the frame system has been at least partially coupled, but before the closure drive system and/or the firing drive system are have been coupled. In various circumstances, the locking system can be configured such that it is the last system to be engaged, i.e., after the frame system, the closure drive system, the firing drive system, and the electrical system have all been engaged.

As outlined above, referring again to FIGS. 44-49, the electrical connector 4000 of the handle 1042 can comprise a plurality of electrical contacts. Turning now to FIG. 197, the electrical connector 4000 can comprise a first contact 4001a, a second contact 4001b, a third contact 4001c, a fourth contact 4001d, a fifth contact 4001e, and a sixth contact 4001f, for example. While the illustrated embodiment utilizes six contacts, other embodiments are envisioned which may utilize more than six contacts or less than six contacts. As illustrated in FIG. 197, the first contact 4001a can be in electrical communication with a transistor 4008, contacts 4001b-4001e can be in electrical communication with a microcontroller 7004, and the sixth contact 4001f can be in electrical communication with a ground. Microcontroller 7004 is discussed in greater detail further below. In certain circumstances, one or more of the electrical contacts 4001b-4001e may be in electrical communication with one or more output channels of the microcontroller 7004 and can be energized, or have a voltage potential applied thereto, when the handle 1042 is in a powered state. In some circumstances, one or more of the electrical contacts 4001b-4001e may be in electrical communication with one or more input channels of the microcontroller 7004 and, when the handle 1042 is in a powered state, the microcontroller 7004 can be configured to detect when a voltage potential is applied to such electrical contacts. When a shaft assembly, such as shaft assembly 1200, for example, is assembled to the handle 1042, the electrical contacts 4001a-4001f may not communicate with each other. When a shaft assembly is not assembled to the handle 1042, however, the electrical contacts 4001a-4001f of the electrical connector 4000 may be exposed and, in some circumstances, one or more of the contacts 4001a-4001f may be accidentally placed in electrical communication with each other. Such circumstances can arise when one or more of the contacts 4001a-4001f come into contact with an electrically conductive material, for example. When this occurs, the microcontroller 7004 can receive an erroneous input and/or the shaft assembly 1200 can receive an erroneous output, for example. To address this issue, in various circumstances, the handle 1042 may be unpowered when a shaft assembly, such as shaft assembly 1200, for example, is not attached to the handle 1042. In other circumstances, the handle 1042 can be powered when a shaft assembly, such as shaft assembly 1200, for example, is not attached thereto. In such circumstances, the microcontroller 7004 can be configured to ignore inputs, or voltage potentials, applied to the contacts in electrical communication with the microcontroller 7004, i.e., contacts 4001*b*-4001*e*, for example, until a shaft assembly is attached to the handle 1042. Eventhough the microcontroller 7004 may be supplied with power to operate other functionalities of the handle 1042 in such circumstances, the handle 1042 may be in a powered-down state. In a way, the electrical connector 4000 may be in a powered-down state as voltage potentials applied to the electrical contacts 4001*b*-4001*e* may not affect the operation of the handle 1042. The reader will appreciate that, eventhough contacts 4001*b*-4001*e* may be in a powered-down state, the electrical contacts 4001*a* and 4001*f*, which are not in electrical communication with the microcontroller 7004, may or may not be in a powered-down state. For instance, sixth contact 4001*f* may remain in electrical communication with a ground regardless of whether the handle 1042 is in a powered-up or a powered-down state. Furthermore, the transistor 4008, and/or any other suitable arrangement of transistors, such as transistor 4010, for example, and/or switches may be configured to control the supply of power from a power source 4004, such as a battery 1104 within the handle 1042, for example, to the first electrical contact 4001*a* regardless of whether the handle 1042 is in a powered-up or a powered-down state as outlined above. In various circumstances, the latch 1236 of the shaft assembly 1200, for example, can be configured to change the state of the transistor 4008 when the latch 1236 is engaged with the handle 1042. In various circumstances, as described elsewhere herein, the latch 1236 can be configured to close a circuit when it engages the handle 1042 and, as a result, affect the state of the transistor 4008. In certain circumstances, further to the below, a Hall effect sensor 4002 can be configured to switch the state of transistor 4010 which, as a result, can switch the state of transistor 4008 and ultimately supply power from power source 4004 to first contact 4001*a*. In this way, further to the above, both the power circuits and the signal circuits to the connector 4000 can be powered down when a shaft assembly is not installed to the handle 1042 and powered up when a shaft assembly is installed to the handle 1042.

In various circumstances, referring again to FIG. 197, the handle 1042 can include the Hall effect sensor 4002, for example, which can be configured to detect a detectable element, such as a magnetic element, for example, on a shaft assembly, such as shaft assembly 1200, for example, when the shaft assembly is coupled to the handle 1042. The Hall effect sensor 4002 can be powered by a power source 4006, such as a battery, for example, which can, in effect, amplify the detection signal of the Hall effect sensor 4002 and communicate with an input channel of the microcontroller 7004 via the circuit illustrated in FIG. 197. Once the microcontroller 7004 has a received an input indicating that a shaft assembly has been at least partially coupled to the handle 1042, and that, as a result, the electrical contacts 4001*a*-4001*f* are no longer exposed, the microcontroller 7004 can enter into its normal, or powered-up, operating state. In such an operating state, the microcontroller 7004 will evaluate the signals transmitted to one or more of the contacts 4001*b*-4001*e* from the shaft assembly and/or transmit signals to the shaft assembly through one or more of the contacts 4001*b*-4001*e* in normal use thereof. In various circumstances, the shaft assembly 1200 may have to be fully seated before the Hall effect sensor 4002 can detect the magnetic element. While a Hall effect sensor 4002 can be utilized to detect the presence of the shaft assembly 1200, any suitable system of sensors and/or switches can be utilized to detect whether a shaft assembly has been assembled to the handle 1042, for example. In this way, further to the above, both the power circuits and the signal circuits to the connector 4000 can be powered down when a shaft assembly is not installed to the handle 1042 and powered up when a shaft assembly is installed to the handle 1042.

In various embodiments, any number of magnetic sensing elements may be employed to detect whether a shaft assembly has been assembled to the handle 1042, for example. For example, the technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

Figure 40:
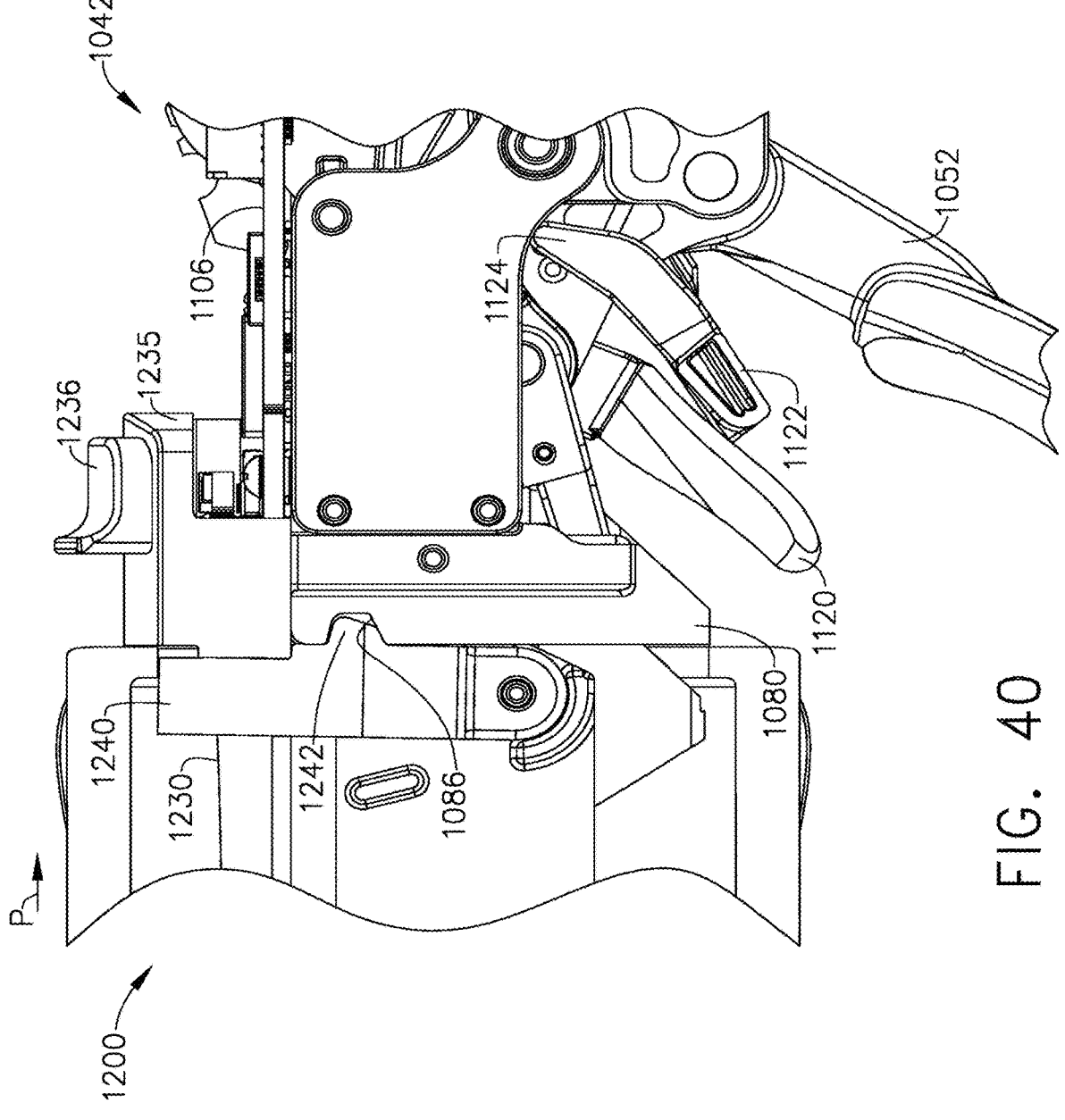
FIG. 40 is a side view of a portion of an interchangeable shaft assembly coupled to a handle with the lock yoke in a locked or engaged position with a portion of the frame attachment module of the handle.

After the interchangeable shaft assembly 1200 has been operably coupled to the handle 1042, actuation of the closure trigger 1052 will result in the distal axial advancement of the outer sleeve 1250 and the shaft closure sleeve assembly 1354 coupled thereto to actuate the anvil 1310 in the various manners disclosed herein. As can also be seen in FIG. 48, the firing member 1270 in the interchangeable shaft assembly 1200 is coupled to the longitudinally movable drive member 1110 in the handle 1042. More specifically, the shaft attachment lug 1278 formed on the proximal end 1277 of the intermediate firing shaft 1272 is receive within the firing shaft attachment cradle 1113 formed in the distal end 1111 of the longitudinally movable drive member 1110. Thus, actuation of the firing trigger 1120 which results in powering of the motor 1102 to axially advance the longitudinally movable drive member 1110 will also cause the firing member 1270 to axially move within the shaft frame 1212. Such action will cause the advancement of the distal cutting portion 1280 through the tissue clamped in the end effector 1300 in the various manners disclosed herein. Although not observable in FIG. 48, those of ordinary skill in the art will also understand that when in the coupled position depicted in that Figure, the attachment lug portions 1229 of the shaft attachment module 1220 are seated within their respective dovetail receiving slots 1088 in the attachment module portion 1084 of the frame 1080. Thus, the shaft attachment module 1220 is coupled to the frame 1080. In addition, although not shown in FIG. 48 (but which can be seen in FIG. 40), when the shaft attachment module 1220 has been coupled to the frame 1080, the lock lugs 1242 on the lock yoke 1240 are seated within their respective lock grooves 1086 (only one is shown in FIG. 40) in the attachment module portion 1084 of the frame 1080 to releasably retain the shaft attachment module 1220 in coupled operable engagement with the frame 1080.

Figure 41:
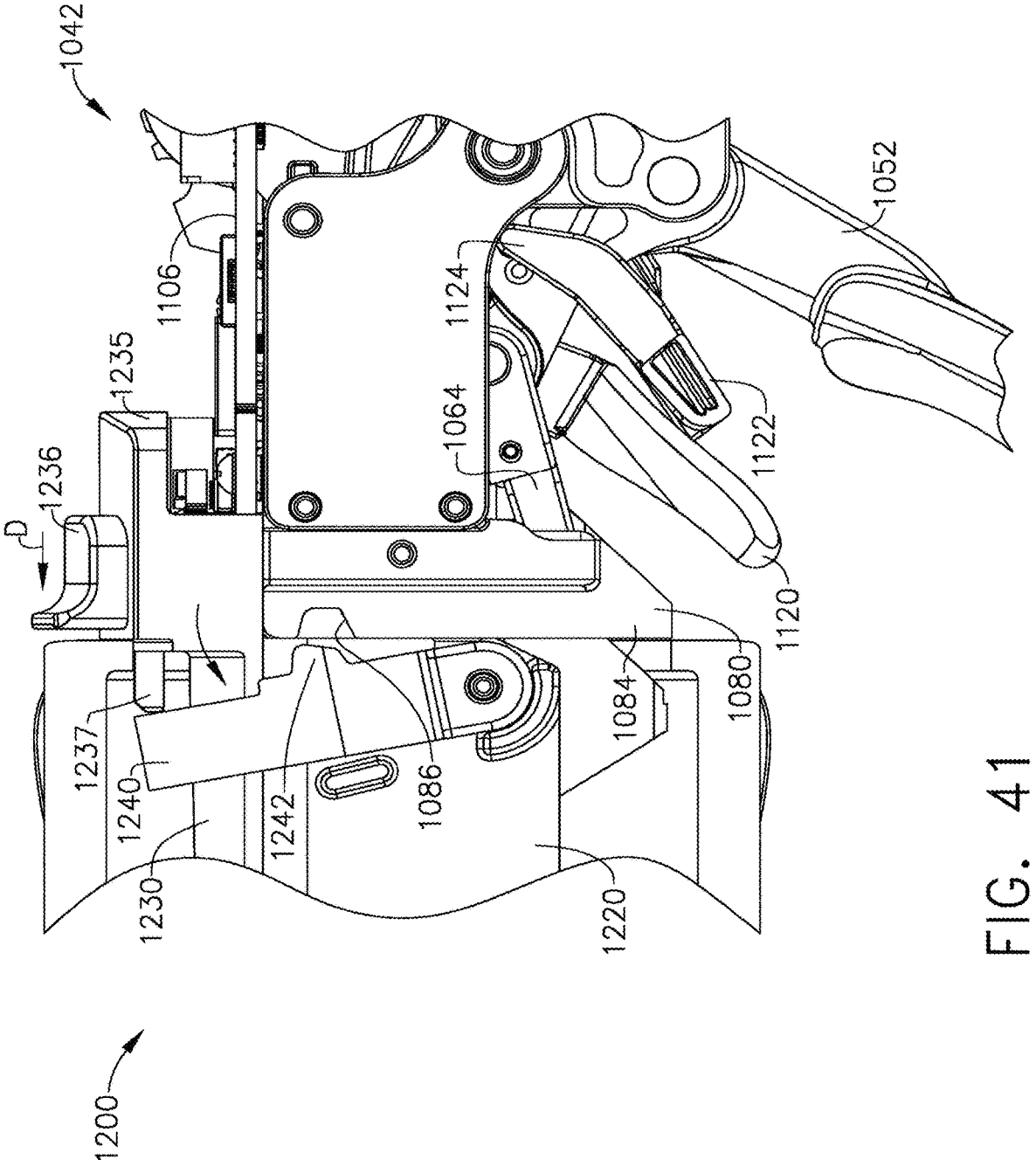
FIG. 41 is another side view of the interchangeable shaft assembly and handle of FIG. 40 with the lock yoke in the disengaged or unlocked position.
Figure 49:
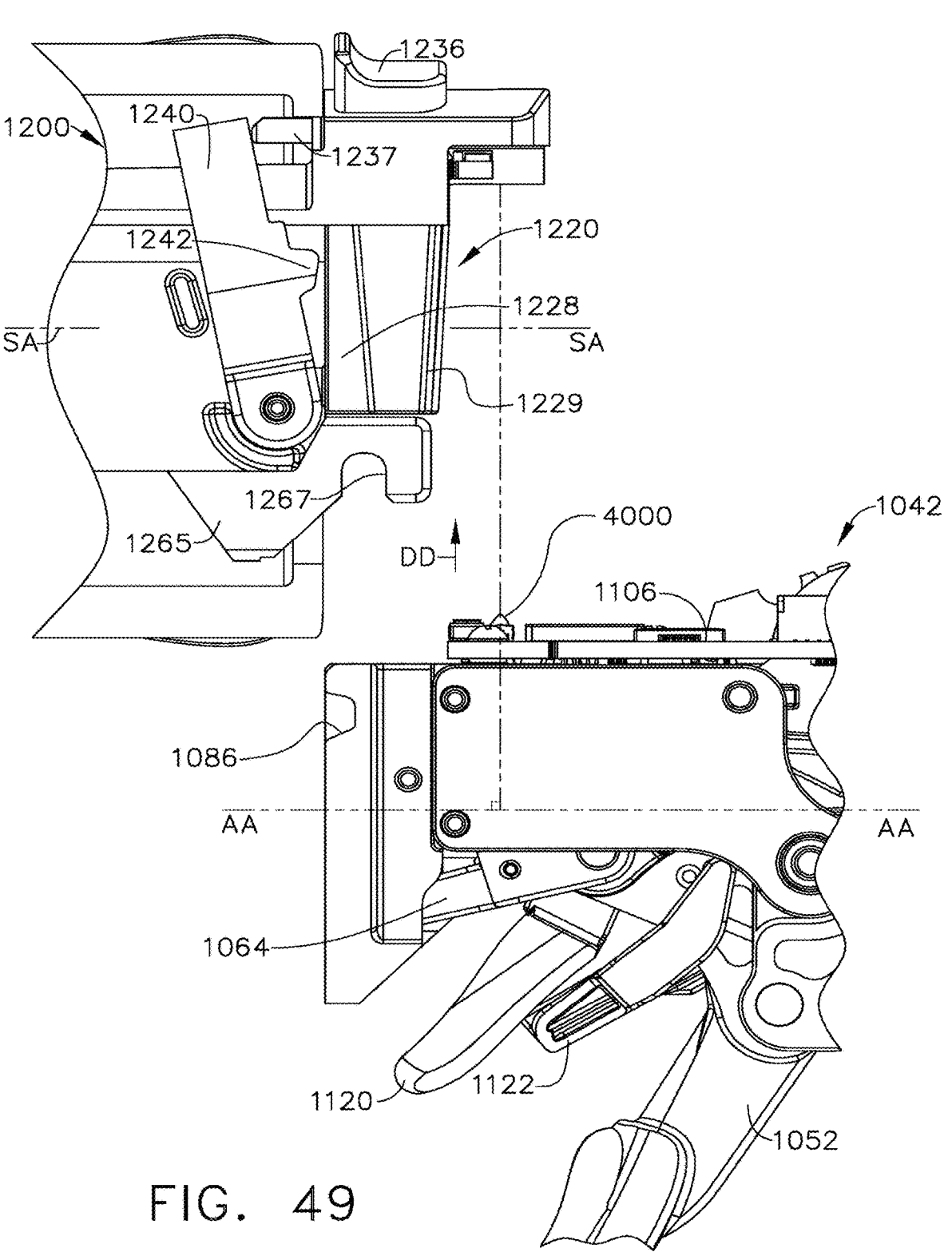
FIG. 49 is another side elevational view of a portion of an interchangeable shaft assembly aligned with a portion of handle prior to commencing the coupling process.
Figures 50, 51:
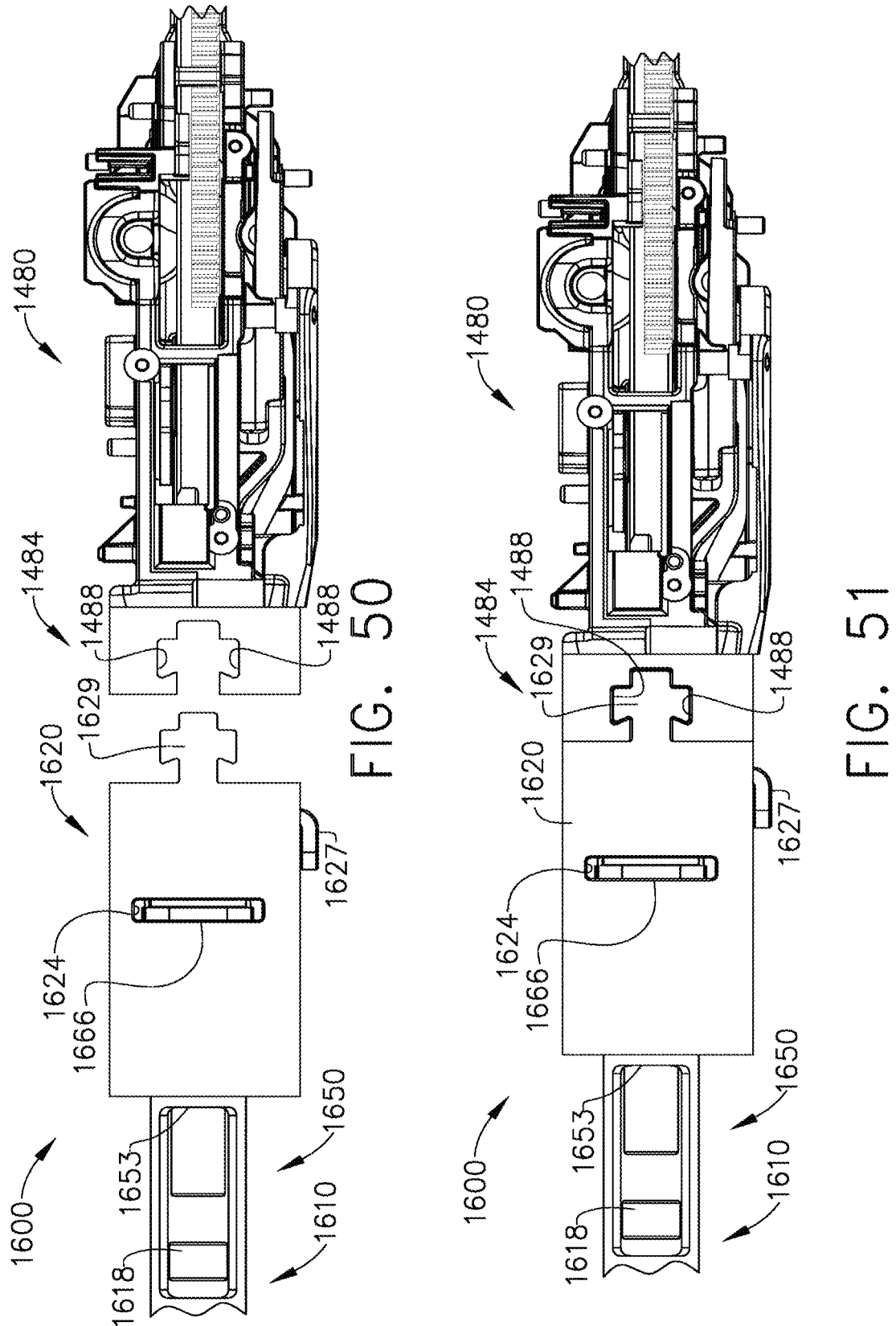
FIG. 50 is a top view of a portion of another interchangeable shaft assembly and a portion of another surgical instrument frame arrangement.
FIG. 51 is another top view of the interchangeable shaft assembly and frame portion of FIG. 50 after being coupled together.

To detach the interchangeable shaft assembly 1220 from the frame 1080, the clinician pushes the latch button 1236 in the distal direction "D" to cause the lock yoke 1240 to pivot as shown in FIG. 41. Such pivotal movement of the lock yoke 1240 causes the lock lugs 1242 thereon to move out of retaining engagement with the lock grooves 1086. The clinician may then move the shaft attachment module 1220 away from the handle in a disconnecting direction "DD" as shown in FIG. 49.

Those of ordinary skill in the art will understand that the shaft attachment module 1220 may also be held stationary and the handle 1042 moved along the installation axis IA-IA that is substantially transverse to the shaft axis SA-SA to bring the lugs 1229 on the connector portion 1228 into seating engagement with the dovetail slots 1088. It will be further understood that the shaft attachment module 1220 and the handle 1042 may be simultaneously moved toward each other along the installation axis IA-IA that is substantially transverse to the shaft axis SA-SA and the actuation axis AA-AA.

As used herein, the phrase, "substantially transverse to the actuation axis and/or to the shaft axis" refers to a direction that is nearly perpendicular to the actuation axis and/or shaft axis. It will be appreciated, however, that directions that deviate some from perpendicular to the actuation axis and/or the shaft axis are also substantially transverse to those axes.

FIGS. 50-57 illustrate another arrangement for coupling an interchangeable shaft assembly 1600 to a frame 1480 of a handle (not shown) that otherwise functions like the handle 1042 discussed in detail herein. Thus, only those details necessary to understand the unique and novel coupling features of the shaft assembly 1600 will be discussed in further detail. Those of ordinary skill in the art will understand, however, that the frame may be supported within a housing of a robotic system that otherwise operably supports or houses a plurality of drive systems. In other arrangements, the frame may comprise portion of a robotic system for operably affixing interchangeable shaft assemblies thereto.

Figure 57:
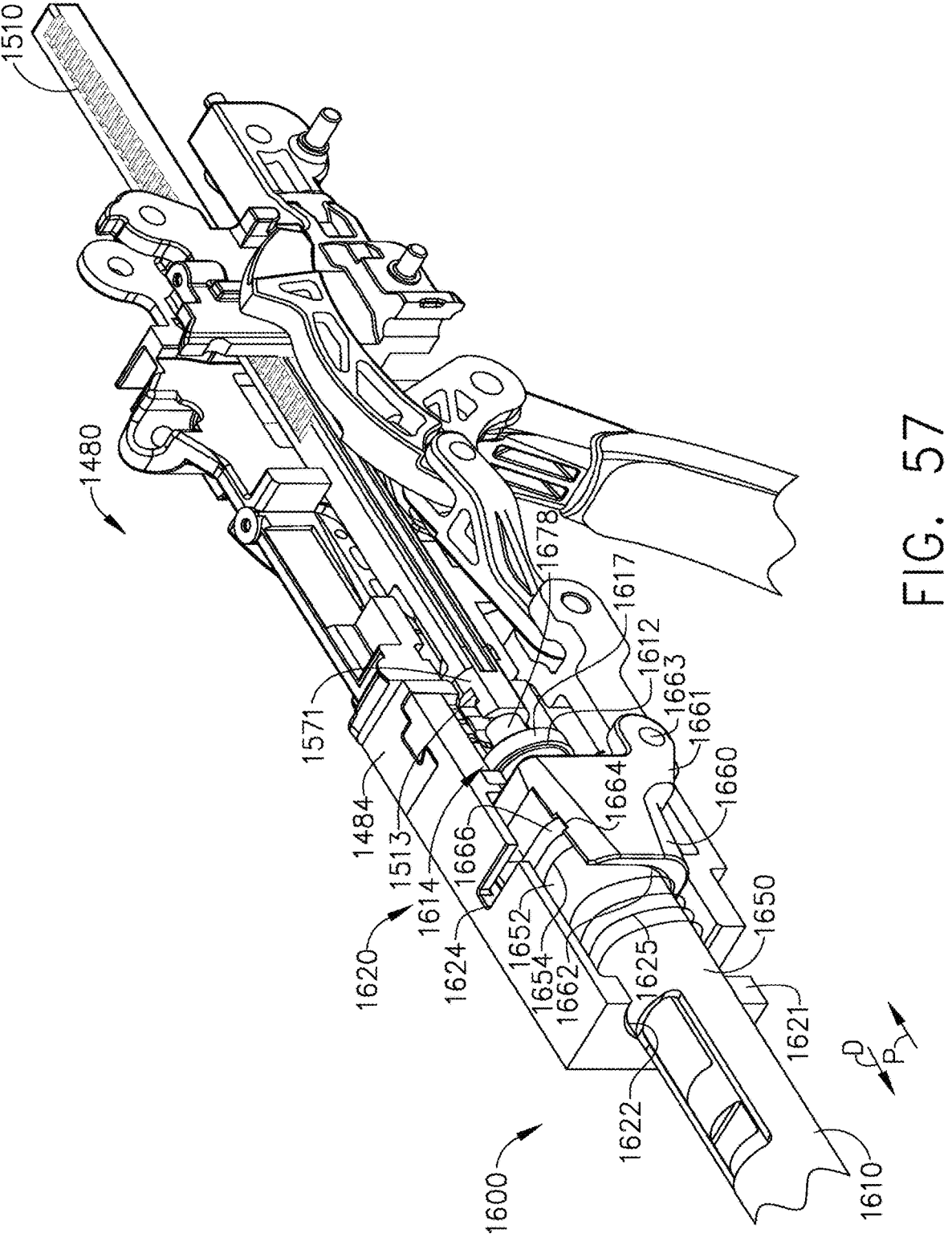
FIG. 57 is another perspective view of the interchangeable shaft assembly and frame portion of FIGS. 55 and 56 with portions thereof omitted for clarity.
Figures 58, 59:
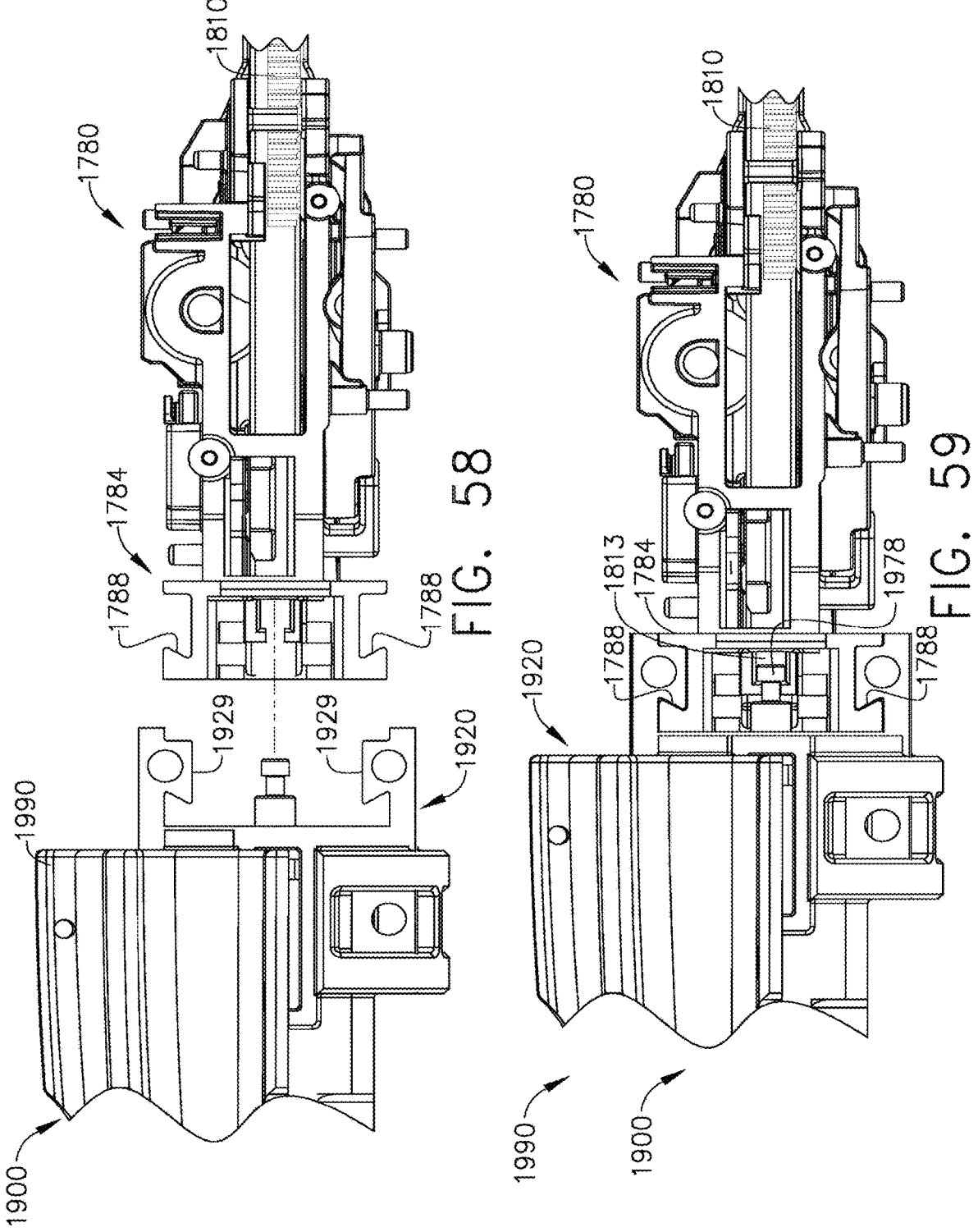
FIG. 58 is a top view of a portion of another interchangeable shaft assembly and frame portion of a surgical instrument prior to being coupled together.
FIG. 59 is another top view of the interchangeable shaft assembly and frame portion of FIG. 58 after being coupled together.

In at least one form, the shaft assembly 1600 includes a shaft 1610 that may include all of the other components of shaft 1210 described above and may have an end effector (not shown) of the type described above operably attached thereto. Turning to FIG. 57, in the illustrated arrangement, the shaft assembly 1600 includes a closure tube attachment yoke 1660 that may be rotatably coupled to an outer sleeve 1650 in the manner in which the closure tube yoke assembly 1260 was rotatably coupled to the outer sleeve 1250.

In various forms, the shaft assembly 1600 includes a shaft attachment module or shaft attachment portion 1620 that has an open bottom 1621. The shaft 1610 is coupled to the shaft attachment module 1620 by inserting the proximal end of the shaft 1610 through an opening 1622 in the shaft attachment module 1620. The closure tube attachment yoke 1660 may be inserted into the shaft attachment module 1620 through the open bottom portion 1621 such that the proximal end 1652 of the outer sleeve 1650 is received within the cradle 1662 in the closure tube attachment yoke 1660. In the manner discussed above, a U-shaped connector 1666 is passed through a slot 1624 in the shaft attachment module 1620 to engage an annular groove 1654 in the proximal end 1652 of the outer sleeve 1250 and slots 1664 in the closure tube attachment yoke 1660 to affix the outer sleeve 1650 to the closure tube attachment yoke 1660. As was discussed above, such arrangement enables the outer sleeve 1650 to rotate relative to the shaft attachment module 1620.

In at least one form, the closure tube attachment yoke 1660 is configured to be supported within the shaft attachment module 1620 such that the closure tube yoke attachment yoke 1660 may move axially therein in the distal and proximal directions. In at least one form, a closure spring 1625 is provided within the shaft attachment module to bias the closure tube yoke assembly 1660 in the proximal direction "P". See FIG. 57. As with the above described shaft assembly 1210, the proximal end 1614 of the shaft frame 1612 protrudes proximally out of the proximal end 1652 of the outer sleeve 1650. As can be seen in FIG. 57 a retaining collar 1617 may be formed on the proximal end 1614 of the shaft frame 1612. A U-shaped retainer member 1627 is inserted through a lateral slot 1633 in the shaft attachment module 1620 to retain the proximal end 1652 of the outer sleeve in that axial position while enabling the outer sleeve 1650 to rotate relative to the shaft attachment module 1620.

Such arrangement permits the clinician to rotate the shaft 1610 about the shaft axis SA-SA relative to the shaft attachment module 1620. Those of ordinary skill in the art will appreciate that the shaft 1610 may be rotated by the same or similar nozzle arrangement that was described above. For example, the nozzle portions (not shown) may be assembled around the outer sleeve 1650 and engage the notch 1618 in the shaft frame 1612 through the window 1653 in the outer sleeve 1650. See FIG. 53.

Figure 52:
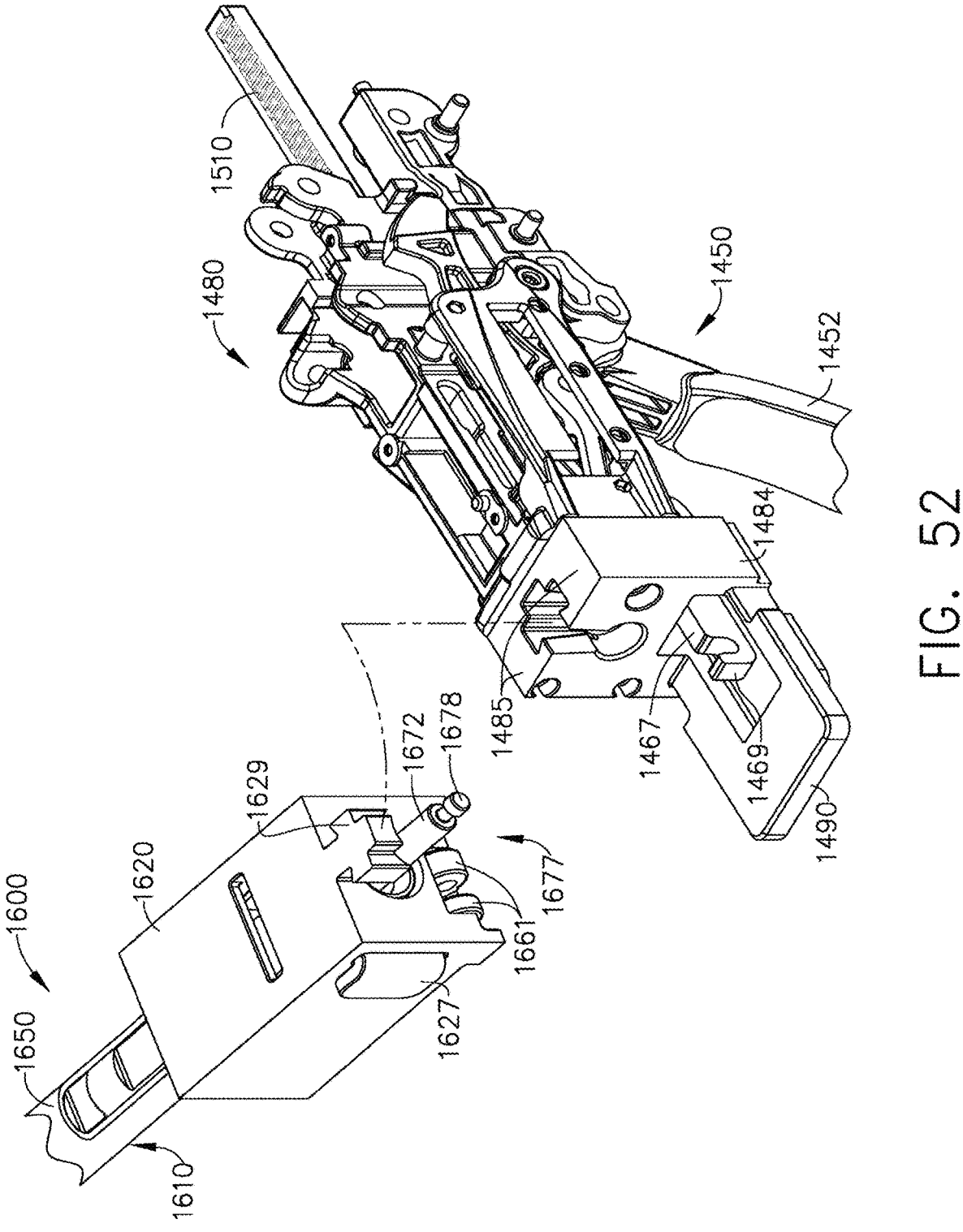
FIG. 52 is an exploded perspective view of the interchangeable shaft assembly and frame portion of FIG. 50.

In at least one form, the frame 1480 has a frame attachment module or frame attachment portion 1484 formed thereon or attached thereto. The frame attachment module 1484 may be formed with opposed dovetail receiving slots 1488. Each dovetail receiving slot 1488 may be tapered or, stated another way, be somewhat V-shaped. The slots 1488 are configured to releasably receive corresponding portion of a dovetail connector 1629 protruding from a proximal end of the shaft attachment module 1620. As can be seen in FIG. 52, the proximal end 1677 of the intermediate firing shaft 1672 protrudes proximally out of the shaft attachment module 1620 and has a shaft attachment lug 1678 formed thereon. The proximal end 1677 of the intermediate firing shaft 1672 may extend through the space between the end walls 1485 of the frame attachment module 1484 to enable the shaft attachment lug 1678 formed thereon to be received in a firing shaft attachment cradle 1513 formed in the distal end 1511 of the longitudinally moveable drive member 1510. See FIG. 57. When the interchangeable shaft assembly 1600 is coupled to the handle or housing or frame of the surgical instrument, device, robotic system, etc., the shaft attachment lug 1678 is received in a firing shaft attachment cradle 1513 formed in the distal end 1511 of the longitudinally movable drive member 1510.

As can also be seen in FIGS. 52-55, the frame attachment module 1484 may have a distally protruding bottom member 1490 that is adapted to enclose at least a portion of the open bottom 1621 of the shaft attachment module 1620 when the shaft attachment module 1620 is operably coupled to the frame attachment module 1484. In one form, the closure tube attachment yoke 1660 has a pair of proximally extending, spaced yoke arms 1661 protruding therefrom. A transverse yoke attachment pin 1663 may extend therebetween. See FIG. 57. When the shaft attachment module 1620 is brought into operable engagement with the frame attachment module 1484, the yoke attachment pin 1663 is configured to be hookingly engaged by a hook 1469 formed on a closure link 1467 of the closure drive system 1450. The closure drive system 1450 may be similar to the closure drive system 1050 described above and include a closure trigger 1452 and a closure linkage assembly 1460. The closure linkage assembly 1460 may include a closure link 1462 that is pivotally coupled to the closure attachment bar 1464. The closure attachment bar 1464 is pivotally coupled to the closure link 1467. See FIG. 54.

Figure 53:
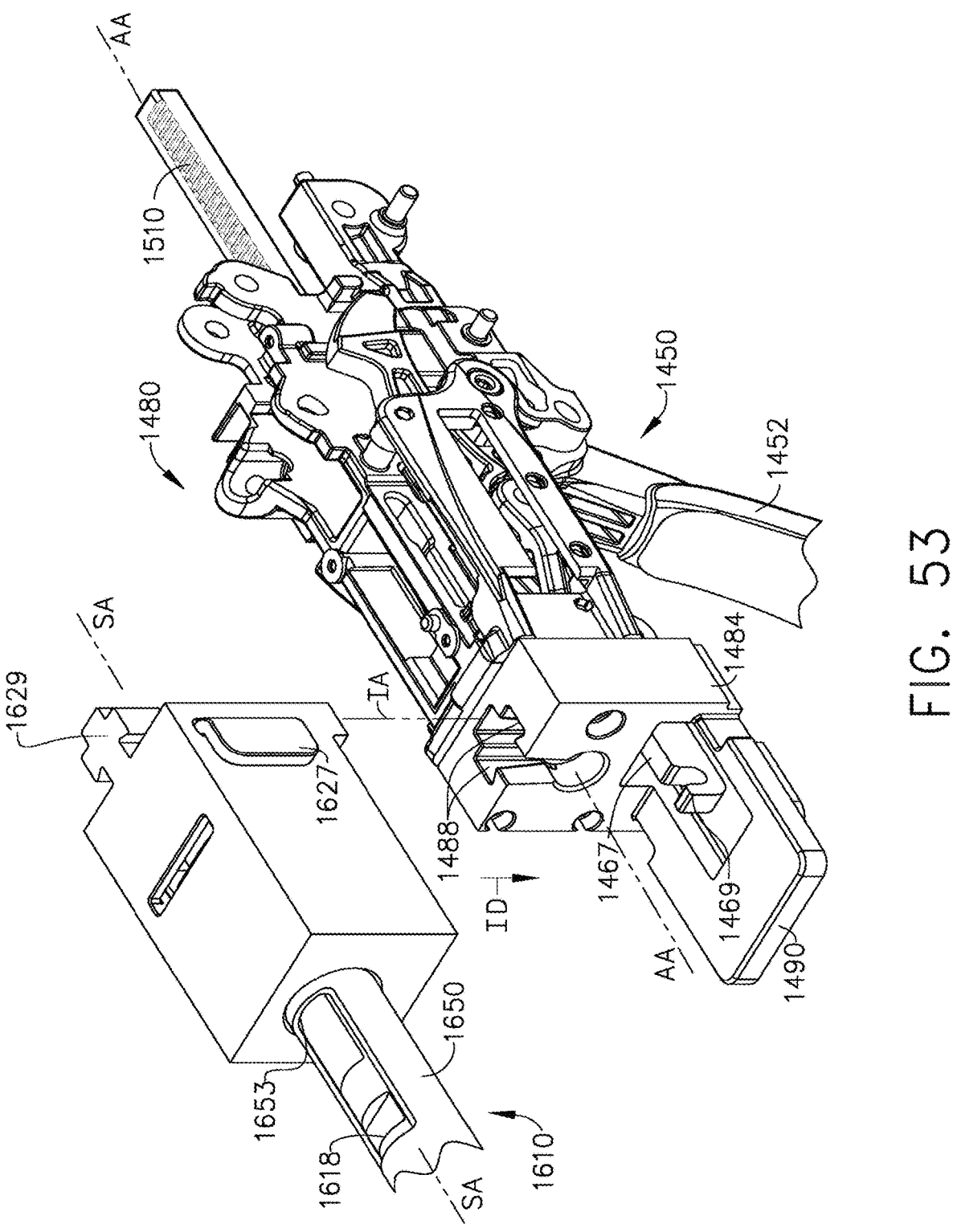
FIG. 53 is another exploded perspective view of the interchangeable shaft assembly and frame portion of FIG. 52 with the shaft attachment module of the shaft assembly in alignment with the frame attachment module of the frame portion prior to coupling.
Figure 54:
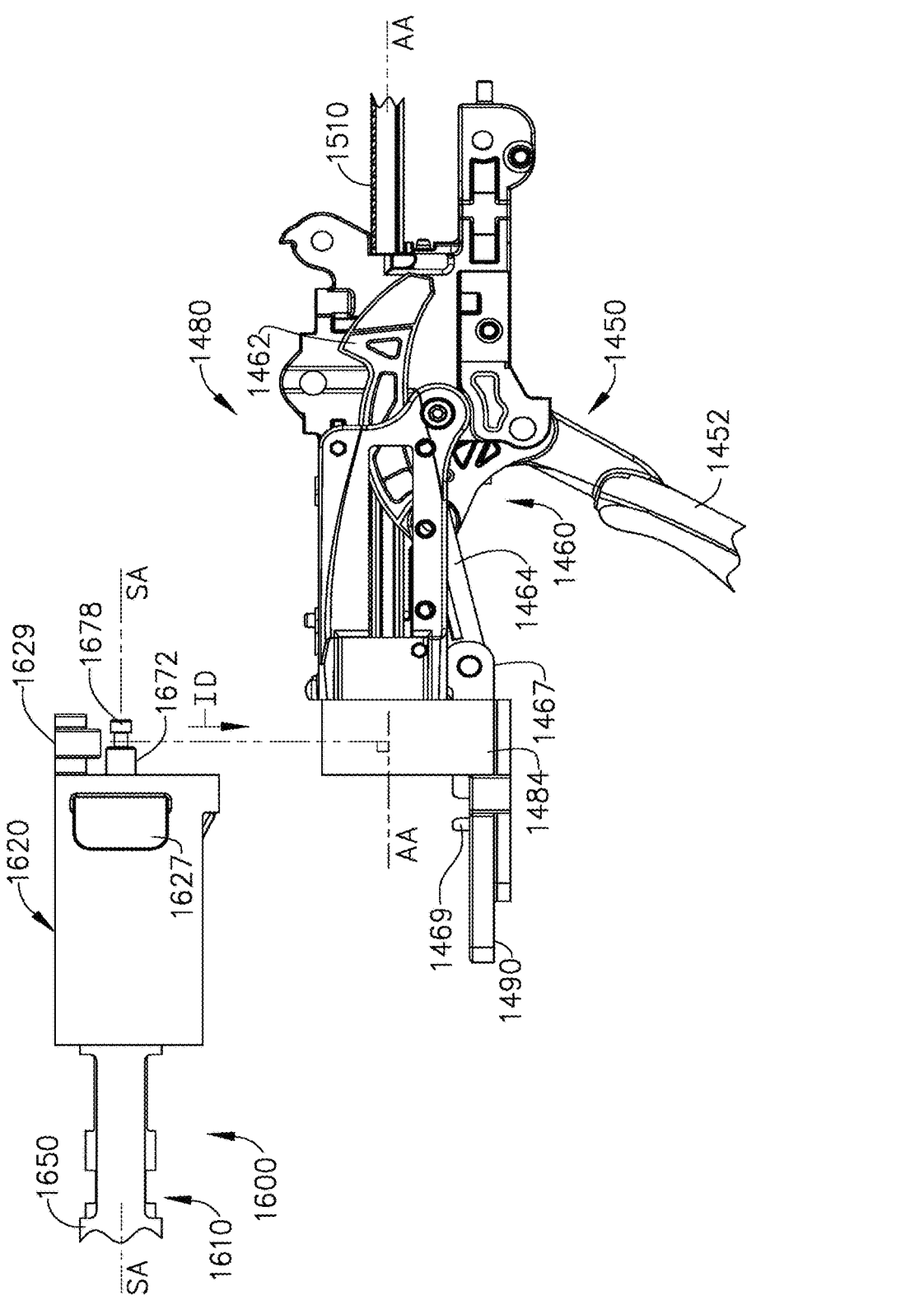
FIG. 54 is a side elevational view of the interchangeable shaft assembly and frame portion of FIG. 52.
Figure 55:
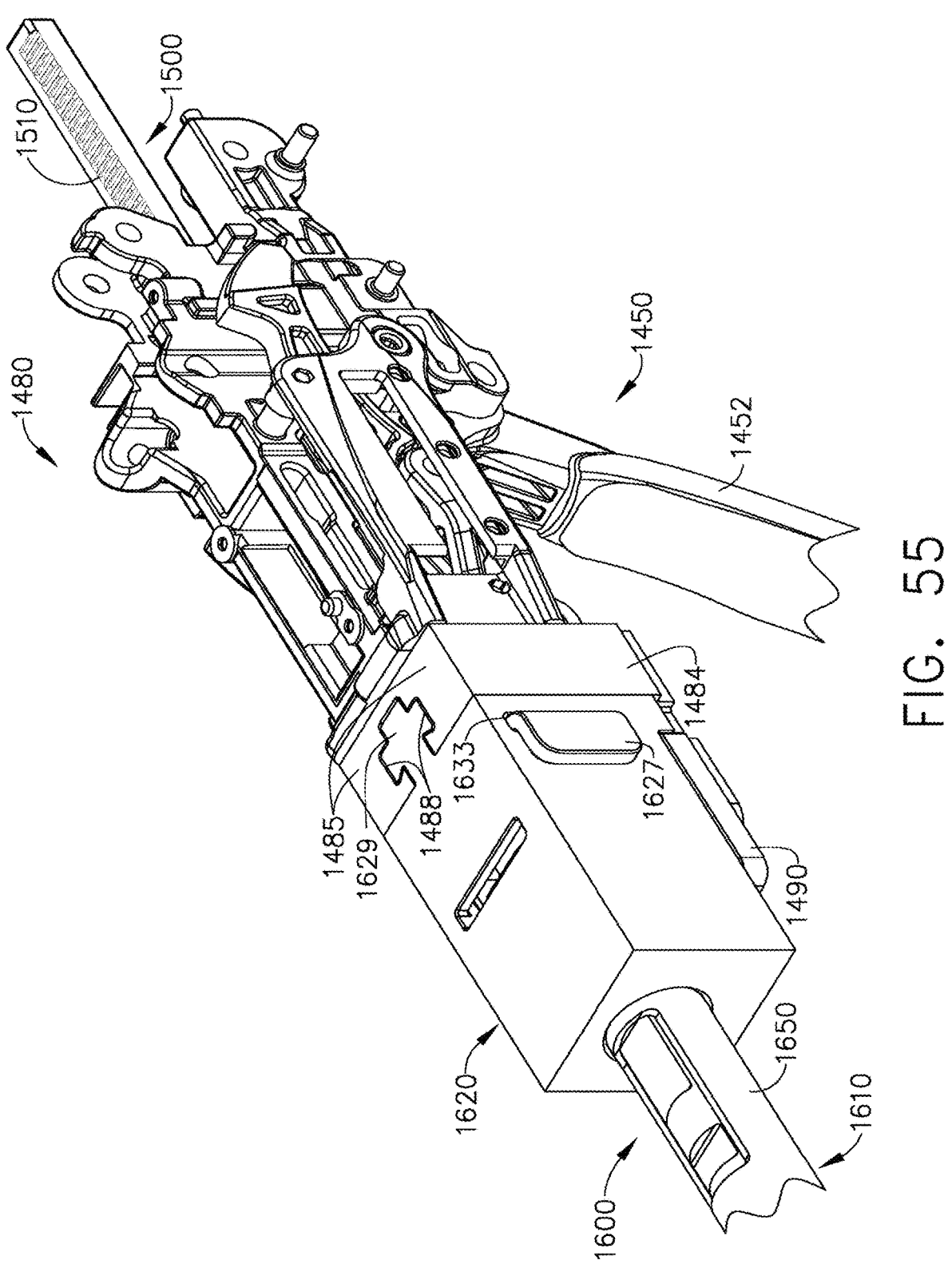
FIG. 55 is a perspective view of the interchangeable shaft assembly and frame portion of FIGS. 53 and 54 after being coupled together.
Figure 56:
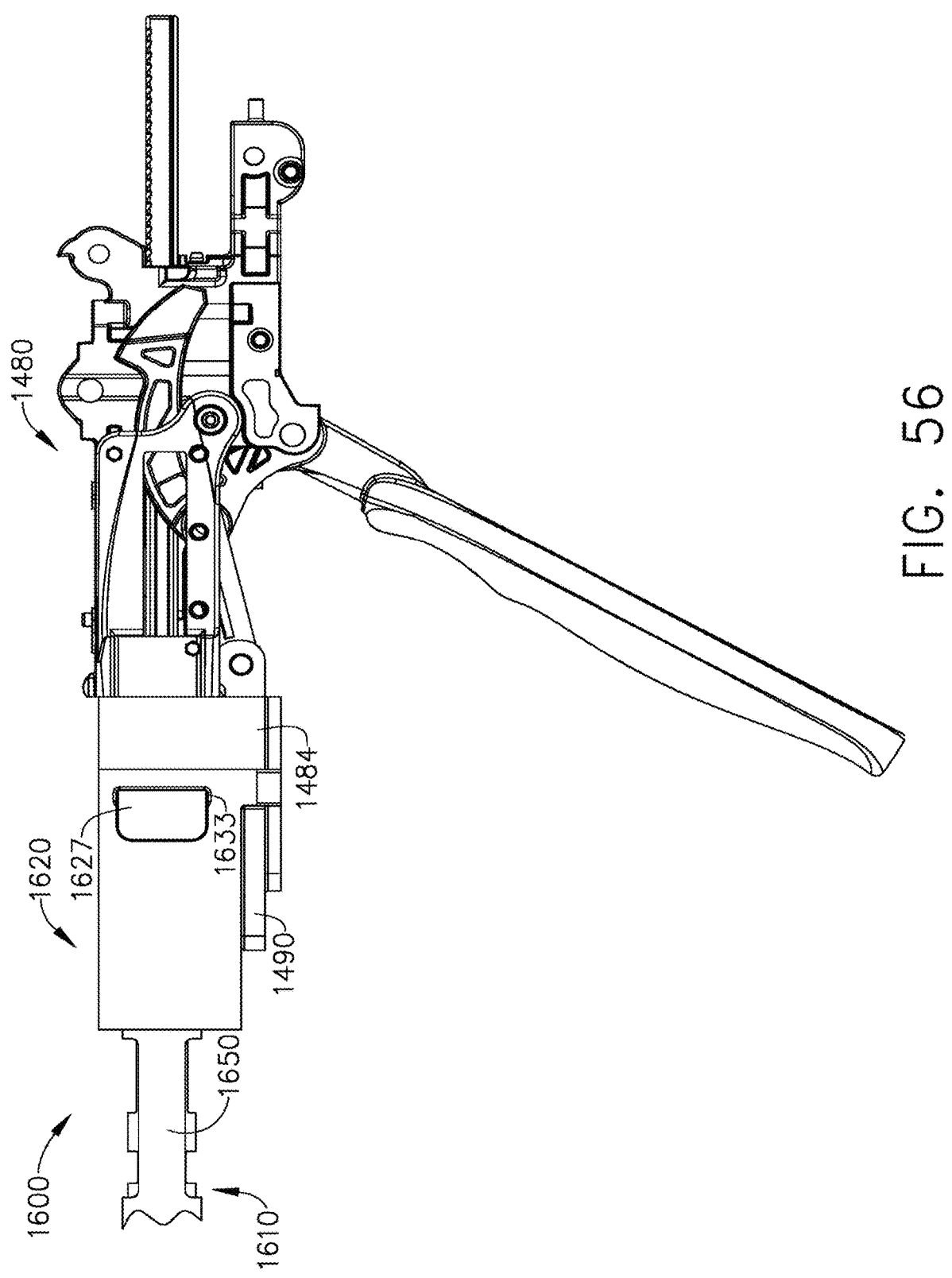
FIG. 56 is a side elevational view of the interchangeable shaft assembly and frame portion of FIG. 55.

A method for coupling the shaft assembly 1600 to the frame 1480 may be understood from reference to FIGS. 53 and 54. As with other arrangements disclosed herein, the shaft assembly 1600 may define a shaft axis SA-SA and the frame 1480 may define an actuation axis AA-AA. For example, the shaft axis SA-SA may be defined by the firing member 1670 and the actuation axis AA-AA may be defined by the longitudinally movable drive member 1510. To commence the coupling process, the clinician may position the shaft attachment module 1620 of the interchangeable shaft assembly 1600 above or adjacent to the frame attachment module 1484 of the frame 1480 such that the dovetail connector 1629 of the shaft attachment module 1620 is aligned with the dovetail slots 1488 in the frame attachment module 1484 as shown in FIG. 53. The clinician may then move the shaft attachment module 1620 along an installation axis IA-IA that is substantially transverse to the actuation axis AA-AA. Stated another way, the shaft attachment module 1620 is moved in an installation direction "ID" that is substantially transverse to the actuation axis AA-AA until the dovetail connector 1629 is seated in the dovetail slots 1488 in the frame module 1484. See FIGS. 55-57. When the shaft attachment module 1620 has been operably engaged with the frame attachment module 1484, the closure tube attachment yoke 1665 will be operably engaged with the closure drive system 1450 and actuation of the closure trigger 1452 will result in the distal axial advancement of the outer sleeve 1650 and the shaft closure tube assembly coupled thereto to actuate the anvil in the various manners disclosed herein. Likewise, the firing member 1270 will be operably engaged with the longitudinally movable drive member 1510. See FIG. 57. Thus, actuation of the motor (not shown) of the firing drive system 1500 will result in the axial advancement of the longitudinally movable drive member 1510 as well as the firing member 1670. Such action will cause the advancement of the distal cutting portion of the firing member (not shown) through the tissue clamped in the end effector in the various manners disclosed herein.

FIGS. 58-62 illustrate another arrangement for coupling an interchangeable shaft assembly 1900 to a frame 1780 of a handle (not shown) that otherwise functions like the handle 1042 discussed in detail herein. Thus, only those details necessary to understand the unique and novel coupling features of the shaft assembly 1900 will be discussed in further detail. Those of ordinary skill in the art will understand, however, that the frame may be supported within a housing or other portion of a robotic system that otherwise operably supports or houses a plurality of drive systems. In other arrangements, the frame may comprise portion of a robotic system for operably affixing interchangeable shaft assemblies thereto.

Figure 62:
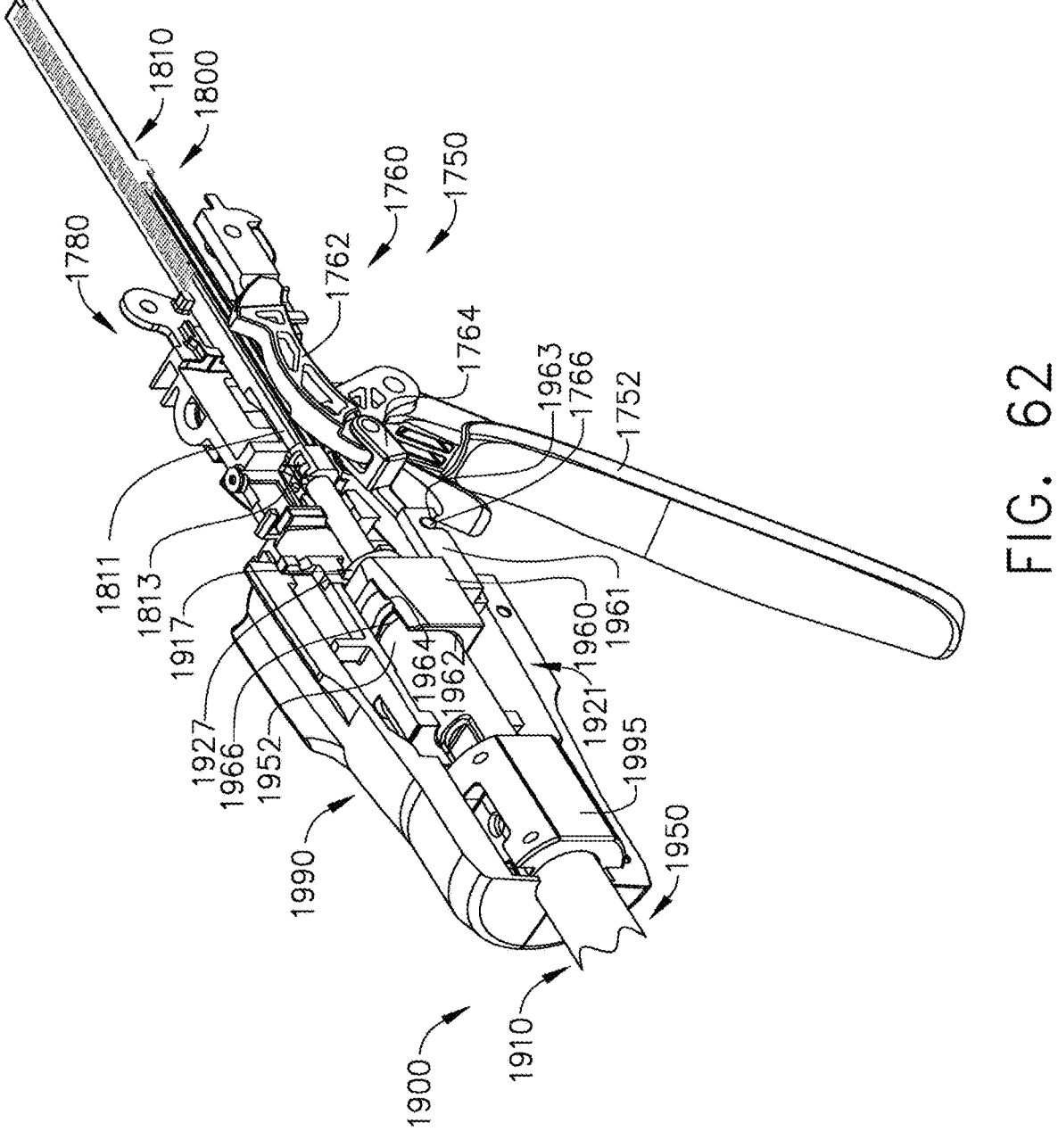
FIG. 62 is another perspective view of the interchangeable shaft assembly and frame portion of FIGS. 58-60 after being coupled together, with portions of the shaft assembly shown in cross-section.

In at least one form, the shaft assembly 1900 includes a shaft 1910 that may include all of the other components of shaft 1210 described above and may have an end effector of the type described above, for example, (not shown) operably attached thereto. Turning to FIG. 62, in the illustrated arrangement, the shaft assembly 1900 includes a closure tube attachment yoke 1960 that may be rotatably coupled to an outer sleeve 1950 in the manner in which the closure tube yoke assembly 1260 was rotatably coupled to the outer sleeve 1250.

In various forms, the shaft assembly 1900 may include a shaft attachment module or shaft attachment portion 1920 that has an open bottom 1921. The shaft 1910 is coupled to the shaft attachment module 1920 by inserting the proximal end of the shaft 1910 through an opening 1922 in the shaft attachment module 1920. The closure tube attachment yoke 1960 may be inserted into the shaft attachment module 1920 through the open bottom portion 1921 such that the proximal end 1952 of the outer sleeve 1950 is received within the cradle 1962 in the closure tube attachment yoke 1660. In the manner discussed above, a U-shaped connector 1966 engages an annular groove (not shown) in the proximal end 1952 of the outer sleeve 1950 and slots 1964 in the closure tube attachment yoke 1960 to affix the outer sleeve 1950 to the closure tube attachment yoke 1960. As was discussed above, such arrangement enables the outer sleeve 1950 to rotate relative to the shaft attachment module 1920.

In at least one form, the closure tube attachment yoke 1960 is configured to be supported within the shaft attachment module 1920 such that the closure tube yoke assembly 1960 may move axially therein in the distal ("D") and proximal ("P") directions. As with the above described shaft assembly 1210, the proximal end of the shaft frame protrudes proximally out of the proximal end 1952 of the outer sleeve 1950. As can be seen in FIG. 62, a retaining collar 1917 may be formed on the proximal end of the shaft frame. A U-shaped retainer member 1927 may be employed to retain the proximal end of the shaft frame in that axial position while enabling the shaft frame to rotate relative to the shaft attachment module 1920. Such arrangement permits the clinician to rotate the shaft 1910 about the shaft axis SA-SA relative to the shaft attachment module 1920. A nozzle assembly 1990 may be employed in the various manners discussed herein to facilitate rotation of the shaft 1910 relative to the shaft attachment module 1920.

The interchangeable shaft assembly 1900 may further include a nozzle assembly 1990 that is rotatably supported on the shaft attachment module 1920. In at least one form, for example, the nozzle assembly 1990 can be comprised of two nozzle halves, or portions that may be interconnected by screws, snap features, adhesive, etc. When mounted on the shaft attachment module 1920, the nozzle assembly 1990 may interface with a shaft rotation adapter 1995 that is configured to engage the outer sleeve 1950 and shaft frame 1912 to enable the clinician to selectively rotate the shaft 1910 relative to the shaft attachment module 1920 about a shaft axis SA-SA which may be defined for example, the axis of the firing member assembly. Thus, rotation of the nozzle assembly 1990 will result in rotation of the shaft frame and outer sleeve 1950 about axis A-A relative to the shaft attachment module 1920.

Figure 60:
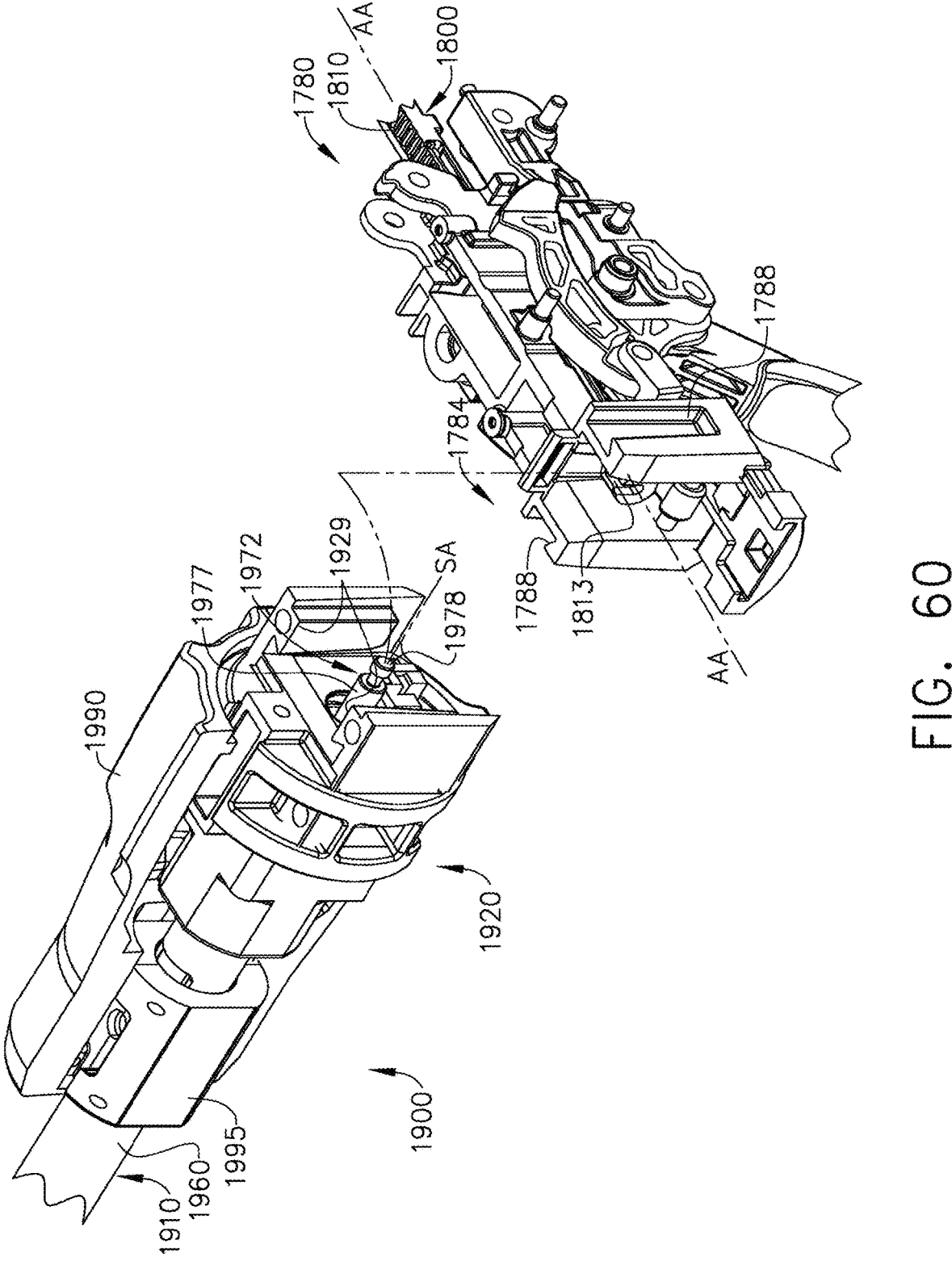
FIG. 60 is a perspective view of the interchangeable shaft assembly and frame of FIGS. 58 and 59 prior to being coupled together.
Figure 61:
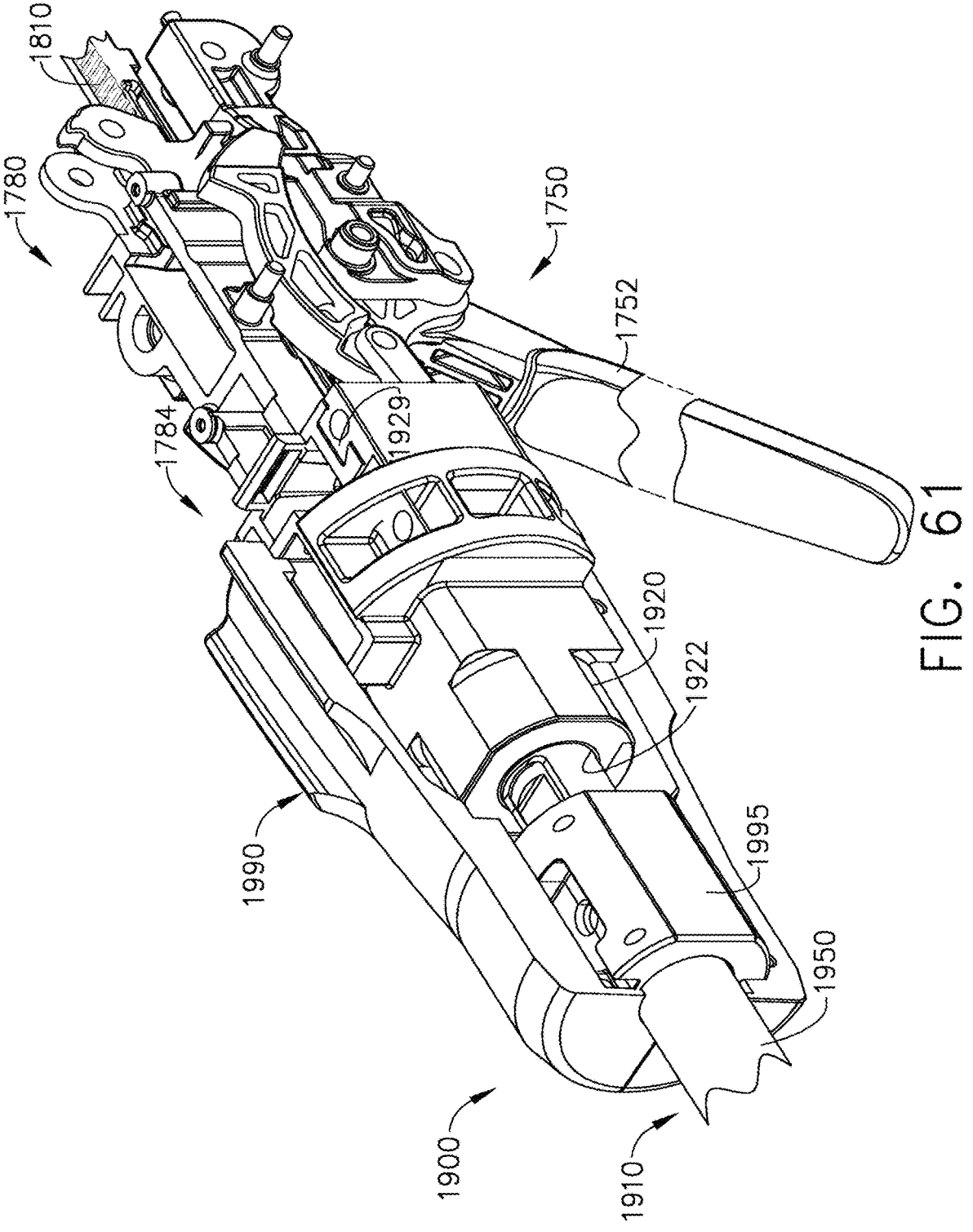
FIG. 61 is another perspective view of the interchangeable shaft assembly and frame portion of FIGS. 58-60 after being coupled together.

In at least one form, the frame 1780 has a frame attachment module or frame attachment portion 1784 formed thereon or attached thereto. The frame attachment module 1784 may be formed with outwardly facing dovetail receiving slots 1788. Each dovetail receiving slot 1788 may be tapered or, stated another way, be somewhat V-shaped. See FIG. 60. The slots 1788 are configured to releasably operably engage corresponding inwardly-facing dovetail connector portions 1929 formed on the shaft attachment module 1920. As can be seen in FIG. 60, the proximal end 1977 of the intermediate firing shaft 1972 protrudes proximally out of the shaft attachment module 1920 and has a shaft attachment lug 1978 formed thereon. The shaft attachment lug 1978 is configured to be received in a firing shaft attachment cradle 1813 formed in the distal end 1811 of the longitudinally moveable drive member 1810. See FIG. 62. When the interchangeable shaft assembly 1900 is in operable engagement with the frame or housing of the surgical instrument, device, robotic system, etc., the shaft attachment lug 1978 is received in operable engagement in a firing shaft attachment cradle 1813 formed in the distal end 1811 of the longitudinal drive member 1810.

In at least one form, the closure tube attachment yoke 1960 has a proximally extending yoke arm 1961 protruding therefrom that has a downwardly open hook 1963 formed thereon to engage an attachment lug 1766 formed on the closure attachment bar 1764 of the closure drive system 1750. See FIG. 62. When the shaft attachment module 1920 is brought into coupling engagement with the frame attachment module 1784, the attachment lug 1766 is hookingly engaged by a hook 1963 formed on the closure tube yoke arm 1961. The closure drive system 1750 may be similar to the closure drive system 1050 described above and include a closure trigger 1752 and a closure linkage assembly 1760. The closure linkage assembly 1760 may include a closure link 1762 that is pivotally coupled to the closure attachment bar 1764. See FIG. 62. Actuation of the closure trigger 1752 will result in the axial movement of the closure attachment bar 1764 in the distal direction "D".

As with other arrangements disclosed herein, the shaft assembly 1900 may define a shaft axis SA-SA and the frame 1780 may define an actuation axis AA-AA. For example, the shaft axis SA-SA may be defined by the firing member 1970 and the actuation axis AA-AA may be defined by the longitudinally movable drive member 1810 operably supported by the frame 1780. To commence the coupling process, the clinician may position the shaft attachment module 1920 of the interchangeable shaft assembly 1900 above or adjacent to the frame attachment module 1784 of the frame 1780 such that the dovetail connector portions 1929 of the shaft attachment module 1920 are each aligned with their corresponding dovetail slot 1788 in the frame attachment module 1784. The clinician may then move the shaft attachment module 1920 along an installation axis that is substantially transverse to the actuation axis AA-AA. Stated another way, the shaft attachment module 1920 is moved in an installation direction that is substantially transverse to the actuation axis AA-AA until the dovetail connectors 1929 are seated in operable engagement in their corresponding dovetail slot 1788 in the frame module 1784. When the shaft attachment module 1920 has been attached to the frame attachment module 1784, the closure tube attachment yoke 1960 will be operably coupled to the closure drive system 1750 and actuation of the closure trigger 1752 will result in the distal axial advancement of the outer sleeve 1950 and the shaft closure tube assembly coupled thereto to actuate the anvil in the various manners disclosed herein. Likewise, the firing member will be coupled in operable engagement with the longitudinally movable drive member 1810. See FIG. 62. Thus, actuation of the motor (not shown) of the firing drive system 1800 will result in the axial advancement of the longitudinally movable drive member 1810 as well as the firing member 1970. Such action will cause the advancement of the distal cutting portion of the firing member (not shown) through the tissue clamped in the end effector in the various manners disclosed herein.

FIGS. 63-66 illustrate another arrangement for coupling an interchangeable shaft assembly 2200 to a frame 2080 of a handle (not shown) that may function like the handle 1042 discussed in detail herein. Thus, only those details necessary to understand the unique and novel coupling features of the shaft assembly 2200 will be discussed in further detail. Those of ordinary skill in the art will understand, however, that the frame may be supported within a housing or other portion of a robotic system that otherwise operably supports or houses a plurality of drive systems. In other arrangements, the frame may comprise portion of a robotic system for operably affixing interchangeable shaft assemblies thereto.

In at least one form, the shaft assembly 2200 includes a shaft 2210 that may include all of the other components of shaft 1210 described above and may have an end effector (not shown) of the type described above operably attached thereto. The various constructions and operations of those features are described above. In the illustrated arrangement, the shaft assembly 2200 includes a closure tube attachment yoke 2260 that may be rotatably coupled to an outer sleeve 2250 in the manner in which the closure tube yoke attachment yoke 1260 was rotatably coupled to the outer sleeve

1250. The shaft assembly 2200, however, does not include a shaft attachment module as was described above.

Figure 63:
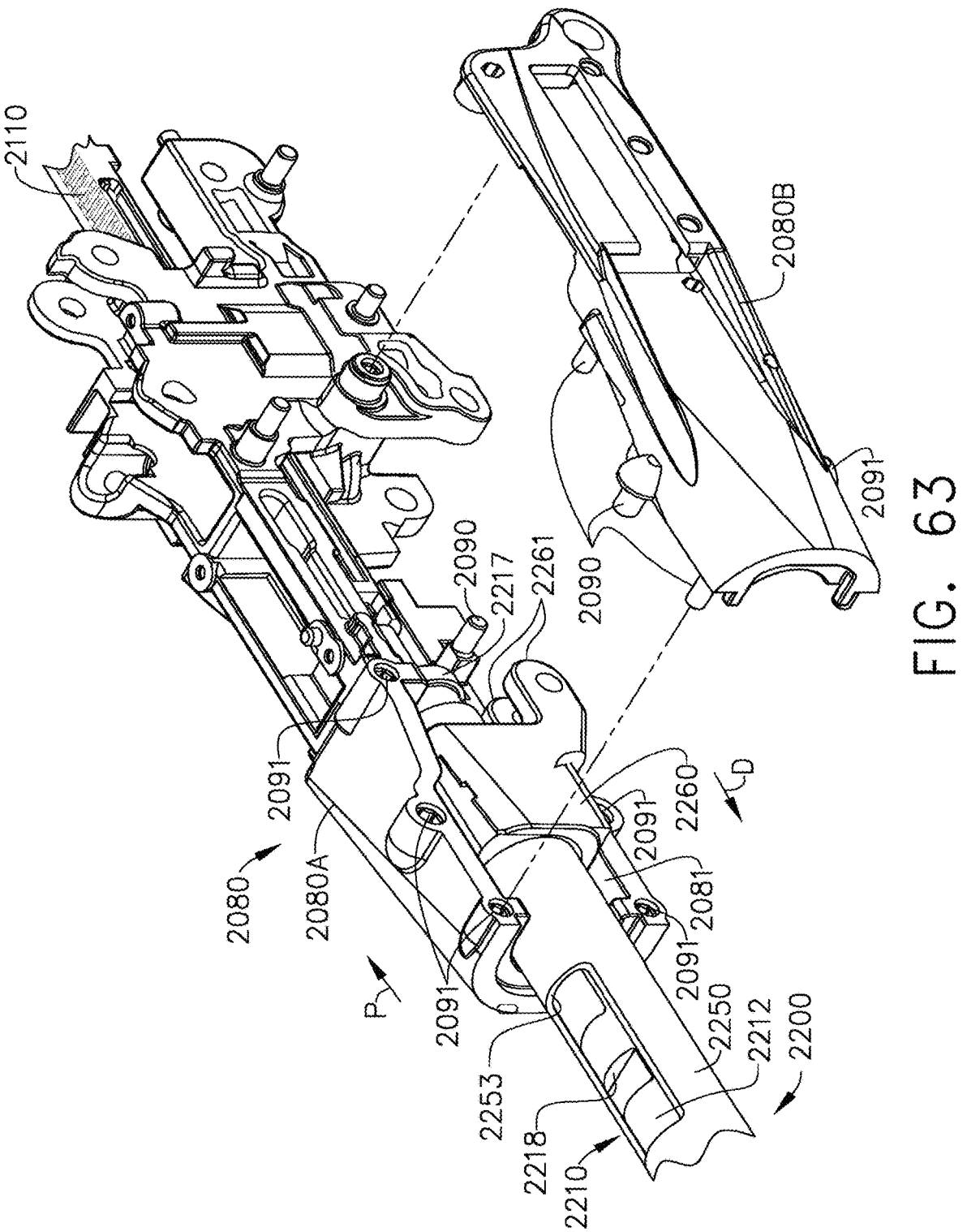
FIG. 63 is an exploded perspective assembly view of another end effector shaft assembly and frame portion of a surgical instrument.
Figure 64:
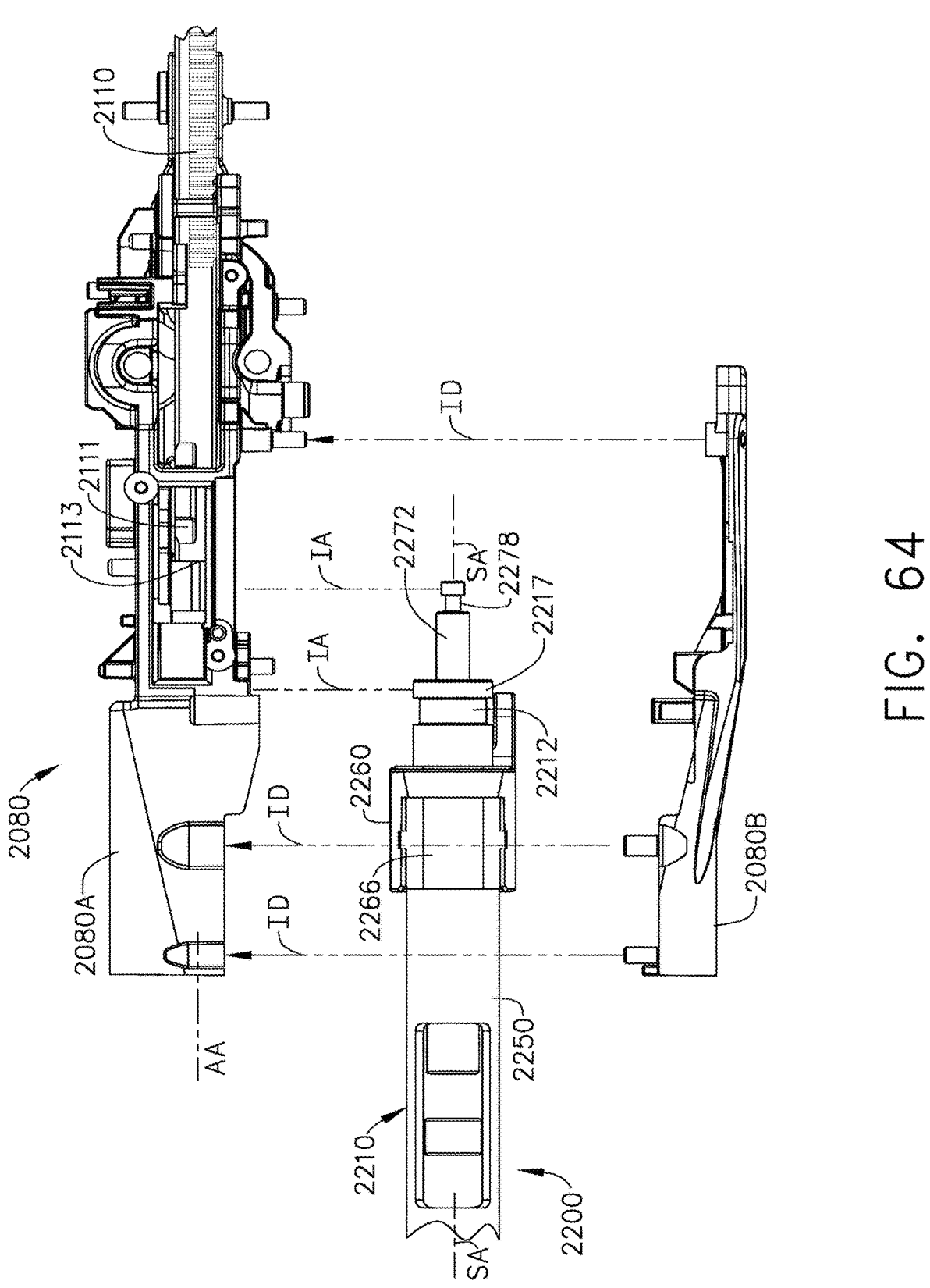
FIG. 64 is a top exploded assembly view of the end effector shaft assembly and frame portion of FIG. 63.
Figure 65:
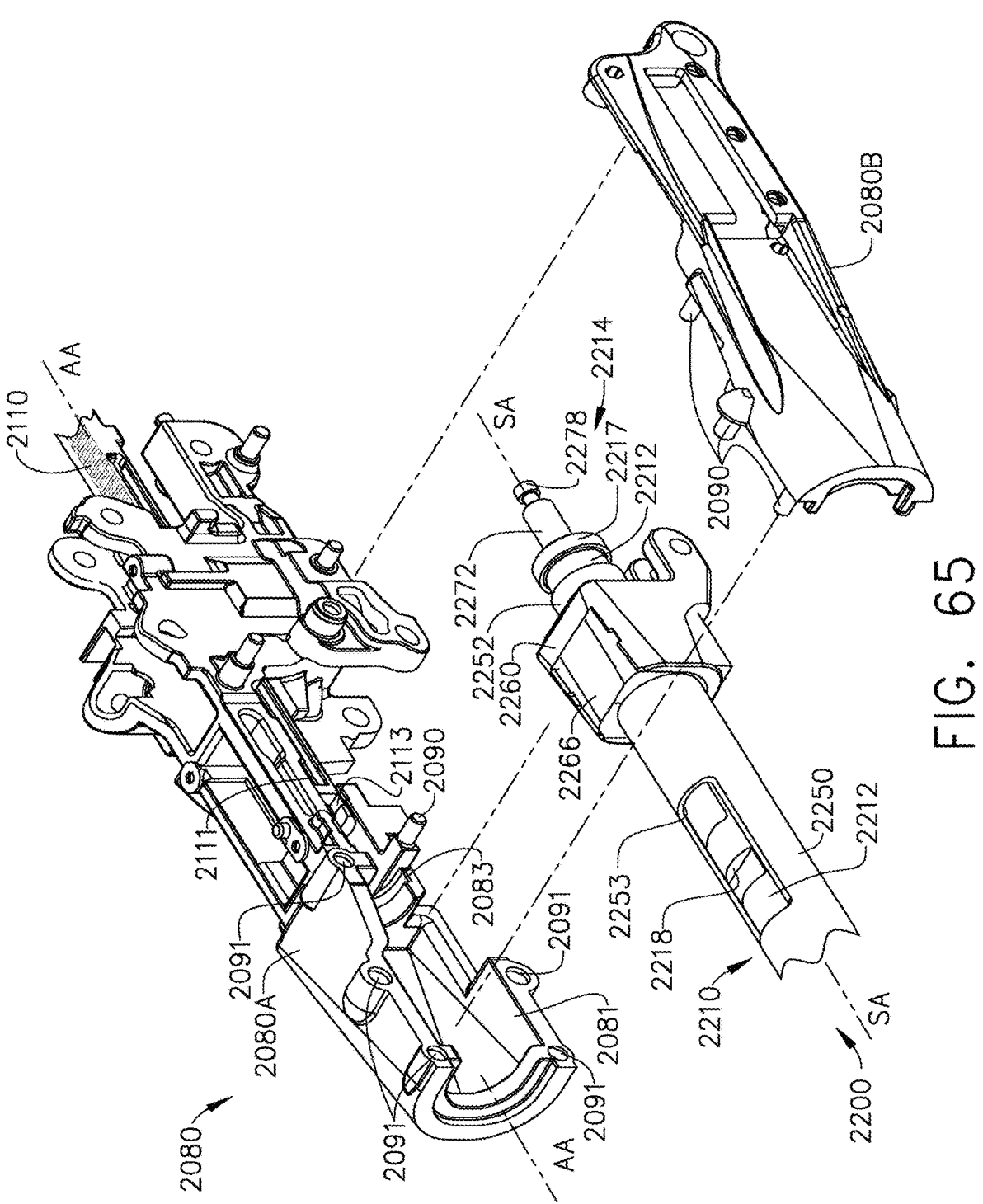
FIG. 65 is another exploded perspective assembly view of the end effector shaft assembly and frame portion of FIGS. 63 and 64.

As can be seen in FIGS. 63-65, the frame 2080 may be formed in first frame part 2080A and a second frame part 2080B. In those applications wherein the frame 2080 is employed with a handle, the first and second frame parts 2080A and 2080B may each be associated with a handle housing portion. Thus, when the clinician desires to attach a different shaft assembly 2200, the clinician may have to detach the handle housing portions from each other. In such arrangements for example, the housing portions may be connected together by removable fasteners or other arrangements that facilitate easy detachment of the housing portions. In other embodiments, the shaft assembly 2200 may be configured for a single use. In the illustrated arrangement, the first frame part 2080A may operably support the various drive systems therein and the second frame part 2080B may comprise a frame portion that retains the various components of the shaft assembly 2200 in operable engagement with their corresponding drive system components supported by the first frame part 2080A.

In at least one form, the closure tube attachment yoke 2260 is configured to be supported within a passage 2081 in the frame 2080 such that the closure tube attachment yoke 2260 may move axially therein in the distal and proximal directions. As with the above described shaft assembly 1210, the proximal end 2214 of the shaft frame 2212 protrudes proximally out of the proximal end of the 2252 of the outer sleeve 2250. As can be seen in FIG. 63, a retaining collar 2217 may be formed on the proximal end 2214 of the shaft frame 2212. The retaining collar 2217 may be adapted to be rotatably received within an annular groove 2083 formed in the frame 2080. Such arrangement serves to operable couple the shaft frame 2212 to the frame 2080 to prevent any relative axial movement between those components while enabling the shaft frame 2212 to rotate relative to the frame 2080. This arrangement further permits the clinician to rotate the shaft 2210 about the shaft axis SA-SA relative to the frame. Those of ordinary skill in the art will appreciate that a nozzle arrangement that was described above may be employed to rotate the shaft 2210 about the shaft axis SA-SA relative to the frame 2080. For example, the nozzle portions (not shown) may be assembled around the outer sleeve 2250 and engage the notch 2218 in the shaft frame 2212 through the window 2253 in the outer sleeve 2250. See FIG. 64.

As can be further seen in FIG. 64, the proximal end 2277 of the intermediate firing shaft 2272 protrudes proximally out of the proximal end 2214 of the shaft frame 2212 and has a shaft attachment lug 2278 formed thereon. The firing shaft attachment cradle 2113 formed in the distal end 2111 of the longitudinally moveable drive member 2110 is formed to enable the firing shaft attachment lug 2278 to be loaded from the side. In an effort to aid the clinician in aligning the components of the shaft assembly 2220 and the first and second frame portions 2080A and 2080B during assembly, the second frame portion 2080B may be provided with lugs 2090 that are configured to be received in corresponding holes or pockets 2091 formed in the first frame portion 2080A and visa versa. In those single use applications wherein it is not desirable to be able to detach the shaft assembly 2200 from the frame 2080, the pockets 2090 may be configured to permanently grip or engage the lugs 2090 inserted therein.

The first frame portion 2080A and/or the longitudinally movable drive member 2110 which is movably supported by the first frame portion 2080A may define an actuation axis A-A and the shaft assembly 2200 defines a shaft axis SA-SA. As can be seen in FIG. 64, to commence the coupling process, the shaft assembly 2200 and the first frame portion 2080A may be oriented relative to each other such that the shaft axis SA-SA is substantially parallel to the actuation axis AA-AA and such that the collar 2217 is laterally-aligned along an installation axis IA that is substantially transverse to the actuation axis with the annular groove 2083 and the shaft attachment lug 2278 is laterally aligned along another installation axis IA-IA that is also substantially transverse to the actuation axis AA-AA. The shaft assembly 2200 is then moved in an installation direction "ID" that is substantially transverse to the actuation axis AA-AA until the closure tube attachment yoke 2260 is seated with the portion of the passage 2081 formed in the first frame portion 2080A, the collar 2217 is seated within the portion of the annular groove 2083 formed in the first frame portion 2080A and the shaft attachment lug 2278 is seated in the shaft attachment cradle 2113 formed in the longitudinally movable drive member 2110. In another arrangement, the shaft assembly 2200 and the first frame portion 2080A may be brought together in a similar manner by holding the shaft assembly 2200 stationary and moving the first frame portion 2080A toward the handle assembly 2200 until the above-mentioned component portions are operably seated together or the handle assembly 2200 and the first frame portion 2080A may each be moved toward each other until they are seated together. Once the handle assembly 2200 has been operably seated within first frame portion 2080A as shown in FIG. 63, the second frame portion 2080B may be joined with the first frame portion 2080A by aligning the posts 2090 with their corresponding holes or pockets 2091 and joining the components together. The first and second frame portions 2080A and 2080B may be retained together by fasteners (e.g., screws, bolts, etc.), adhesive and/or snap features. In still other arrangements, the first frame portion 2080A and the second frame portion 2080B may be retained together in coupled engagement when their respective housing segments are joined together.

Figure 66:
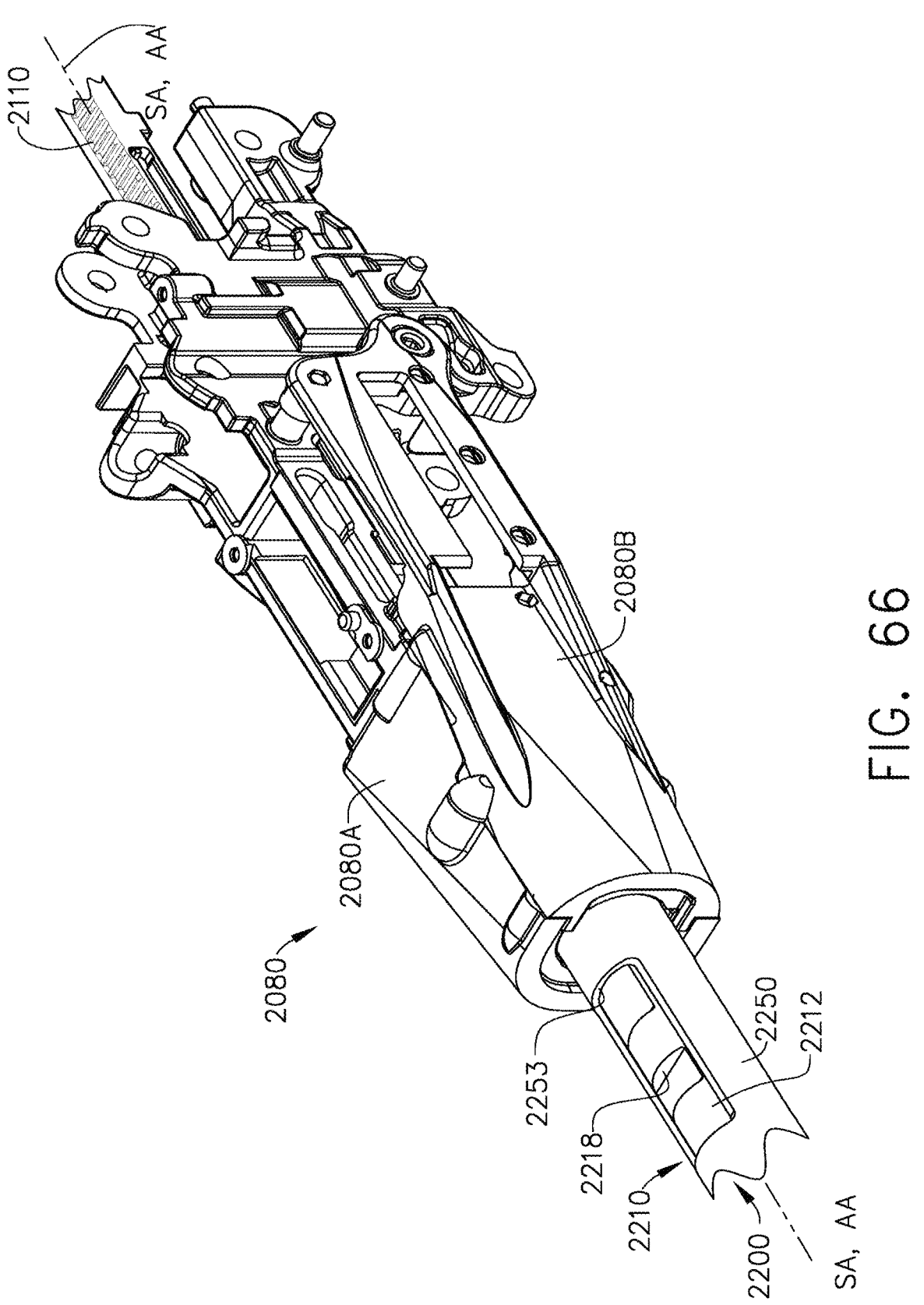
FIG. 66 is a perspective view of the end effector shaft assembly and frame portion of FIGS. 63-65 after being coupled together.
Figure 67:
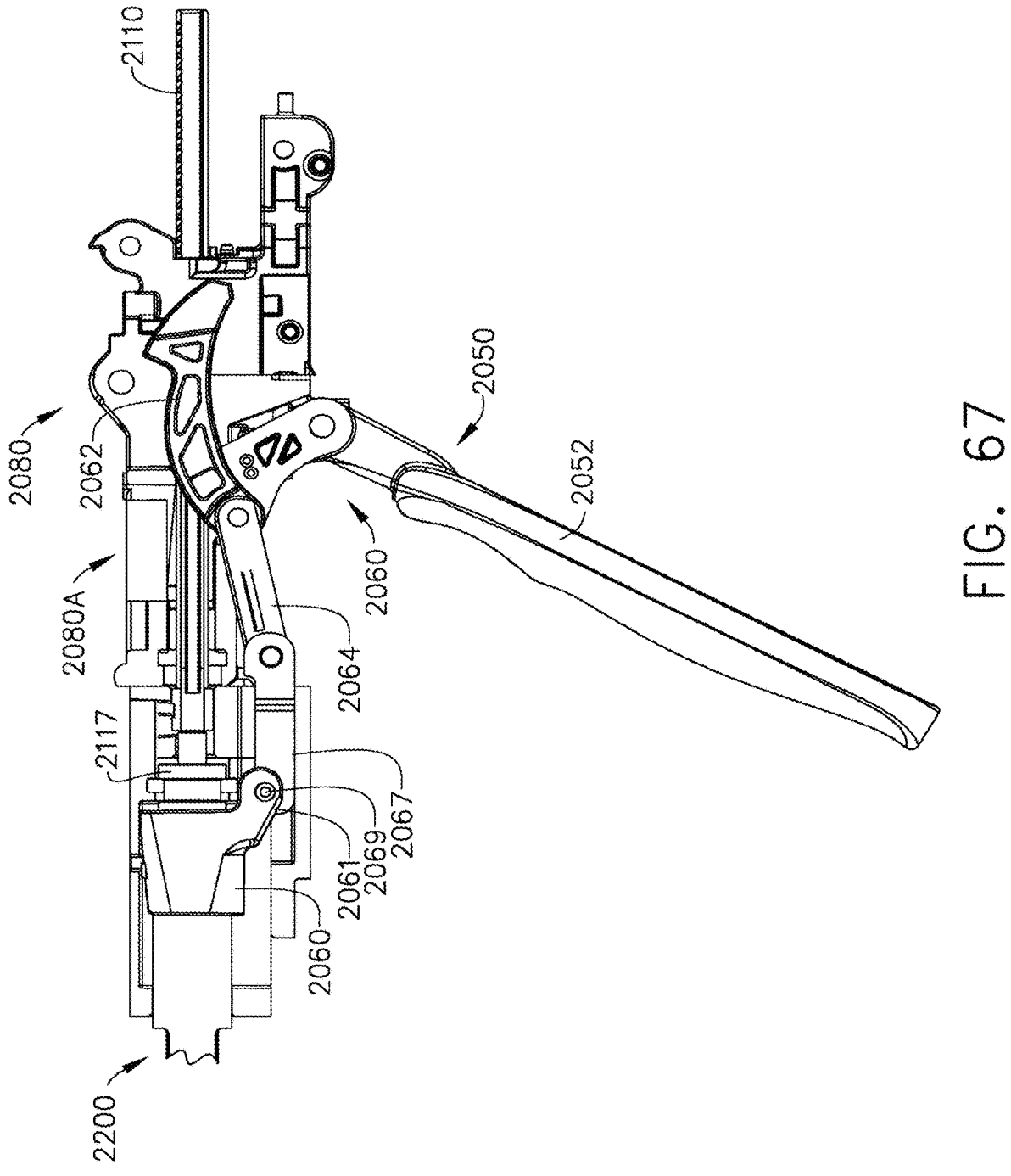
FIG. 67 is a side elevational view of the end effector shaft assembly and frame portion of FIG. 66 with portions thereof omitted for clarity.

Once the first and second frame portions 2080A, 2080b have been joined together as shown in FIGS. 65 and 66, the clinician may then couple the closure drive system 2050 to the closure tube attachment yoke 2260. The closure drive system 2050 may be similar to the closure drive system 1050 described above and include a closure trigger 2052 and a closure linkage assembly 2060. The closure linkage assembly may include a closure link 2062 that is pivotally coupled to the closure attachment bar 2064. In addition, another closure link 2067 is pivotally coupled to the closure attachment bar 2064. The closure link 2067 may be configured for pivotal attachment to the arms 2261 of the closure tube attachment yoke 2260 by a pin 2269. Sec FIG. 66.

FIGS. 68-74 illustrate another arrangement for coupling an interchangeable shaft assembly 2500 to a frame 2380. The frame 2380 may be employed with handle as described herein or may be employed in connection with a robotic system. In at least one form, the shaft assembly 2500 includes a shaft 2510 that may include all of the other components of shaft 1210 described above and may have an end effector (not shown) of the type described above operably attached thereto. The various constructions and operations of those features are described above. As can be seen in FIGS. 68-74, the shaft assembly 2500 includes a shaft attachment module or shaft attachment portion 2520 that is configured to pivotally engage a frame attachment module portion 2384 of the frame 2380 as will be discussed in further detail below. The shaft attachment module 2520, for example, may have a collar portion 2522 through which the proximal end of the shaft 2510 extends. The shaft attachment module 2520 cooperates with a frame attachment module portion 2384 of the frame 2380 to form a passage 2581 therein for movably supporting a closure tube attachment yoke 2560 therein. The closure tube yoke assembly 2560 may be supported on a portion of the shaft attachment module 2520 and is configured to be supported within the passage 2581 such that the closure tube yoke assembly 2560 may move axially therein in the distal and proximal directions. As with the above described shaft assemblies, the proximal end of the shaft frame 2512 is rotatably coupled to the shaft attachment module 2520 such that it may rotate relative thereto. The proximal end of the outer sleeve 2550 is rotatably coupled to the closure tube attachment yoke 2560 in the above described manners such that it may rotate relative thereto. In various forms, a nozzle 2590 may be employed in the above-described manners to rotate the shaft 2510 about the shaft axis SA-SA relative to the frame shaft attachment module 2520.

Figures 68, 69:
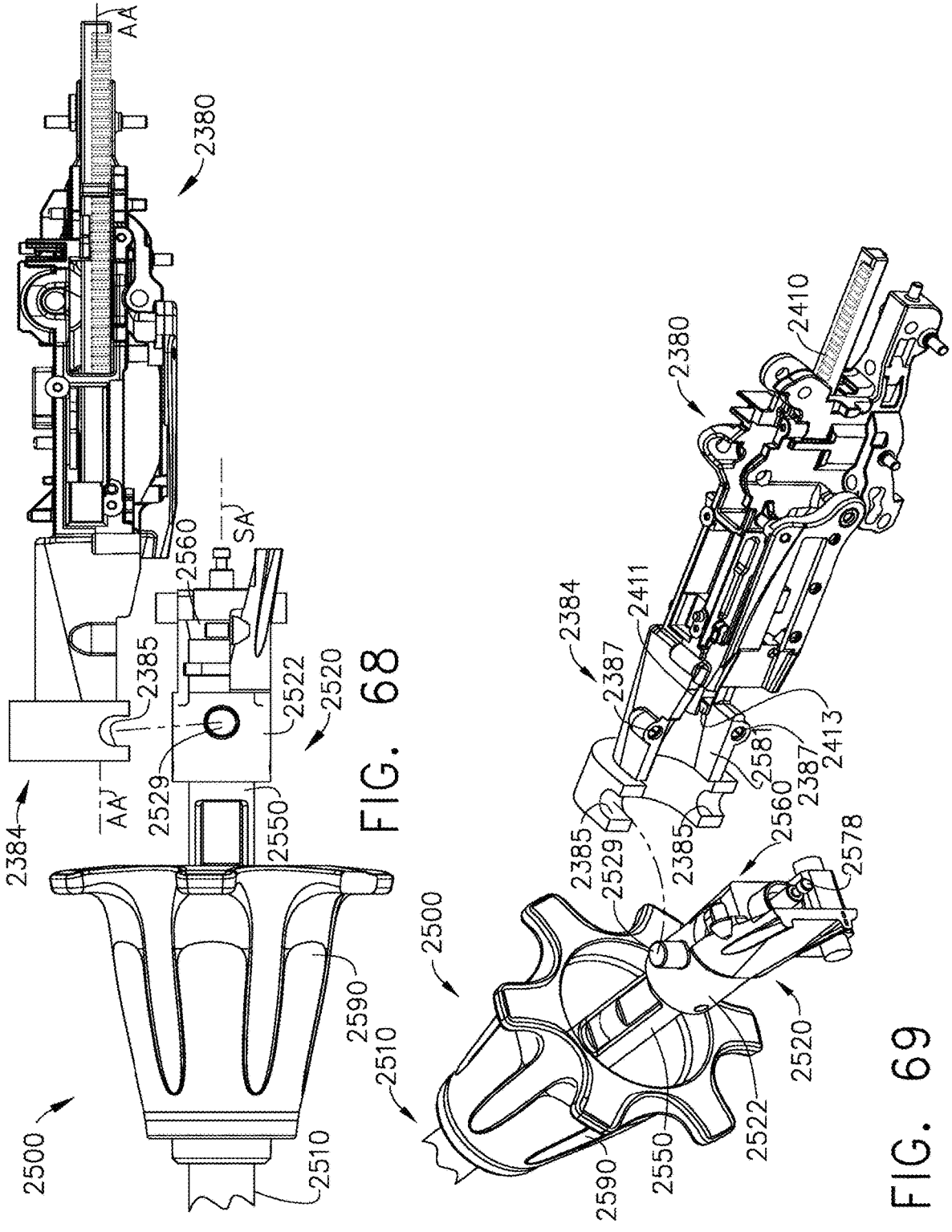
FIG. 68 is a top exploded assembly view of another end effector shaft assembly and frame portion of another surgical instrument.
FIG. 69 is a perspective exploded assembly view of the end effector shaft assembly and frame portion of FIG. 68.
Figure 70:
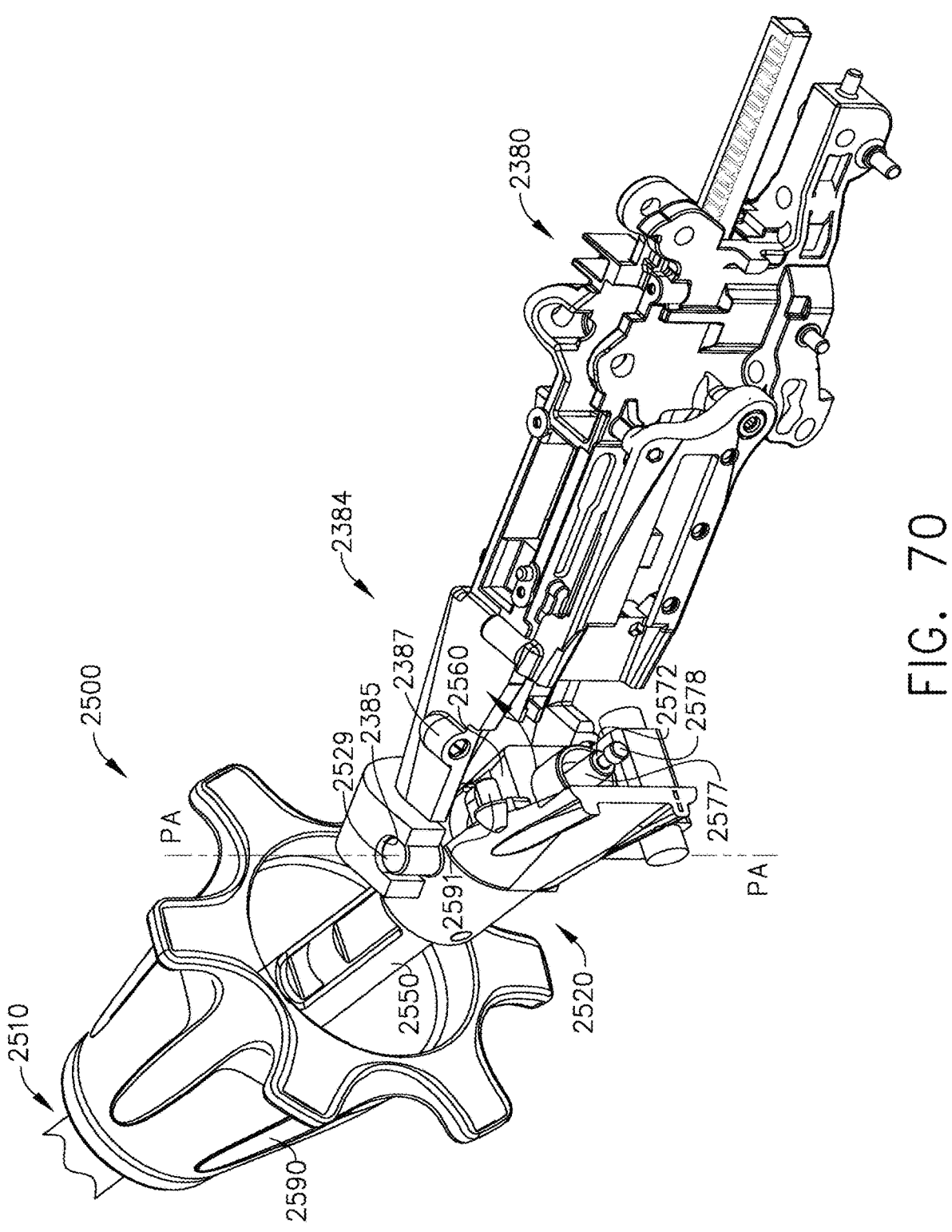
FIG. 70 is another perspective assembly view of the end effector shaft assembly and frame portion of FIGS. 68 and 69 with the end effector shaft assembly prior to being latched in coupled engagement with the frame portion.
Figure 71:
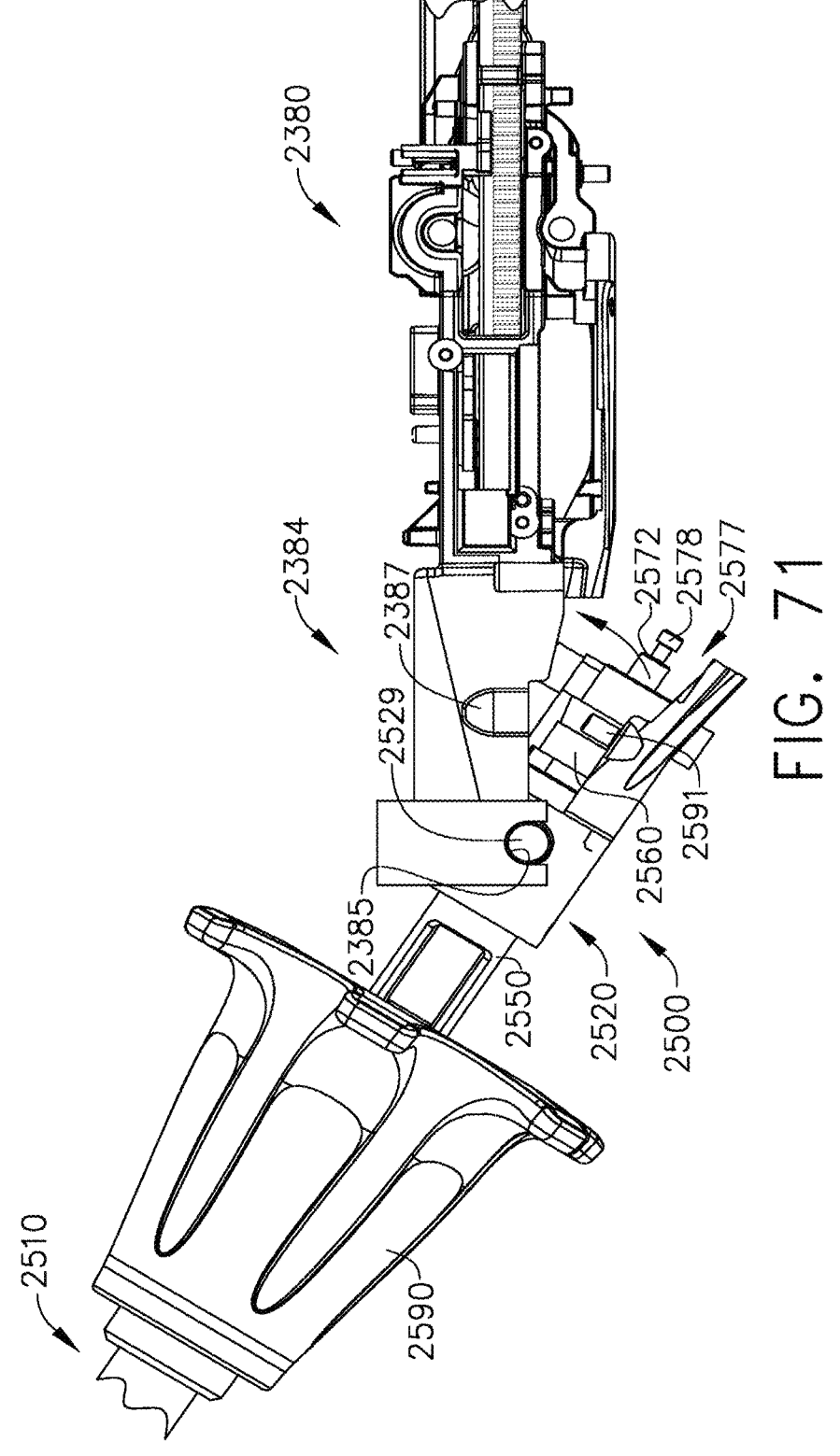
FIG. 71 is a top view of the end effector shaft assembly and frame portion of FIG. 70.

As can be further seen in FIG. 68-70, the proximal end 2577 of the intermediate firing shaft 2572 protrudes proximally out of the closure tube attachment yoke 2560 and has a shaft attachment lug 2578 formed thereon. The firing shaft attachment cradle 2413 formed in the distal end 2411 of the longitudinally moveable drive member 2410 is formed to enable the firing shaft attachment lug 2578 to be pivotally be loaded from the side.

As can be seen in FIG. 69, the frame attachment module portion 2384 has a pair of pivot cradles 2385 formed therein that are adapted to receive corresponding pivot lugs 2529 formed on the shaft attachment module 2520. When the lugs 2529 are supported within the pivot cradles 2385, the shaft attachment module 2520 may be pivoted into operable engagement with the frame attachment module 2384 as illustrated in FIG. 70. In particular, the lugs 2529 may define a pivot axis PA-PA that may be substantially transverse to the actuation axis AA-AA. See FIG. 73. The shaft attachment module 2520 may have laterally protruding latch pins 2591 that are configured to latchingly engage corresponding latch pockets 2387 in the frame attachment module 2384. To initiate the coupling process, the intermediate firing shaft 2572 is brought into operable engagement with the longitudinally movable drive member in a direction that is substantially transverse to the actuation axis AA-AA.

Figures 72, 73:
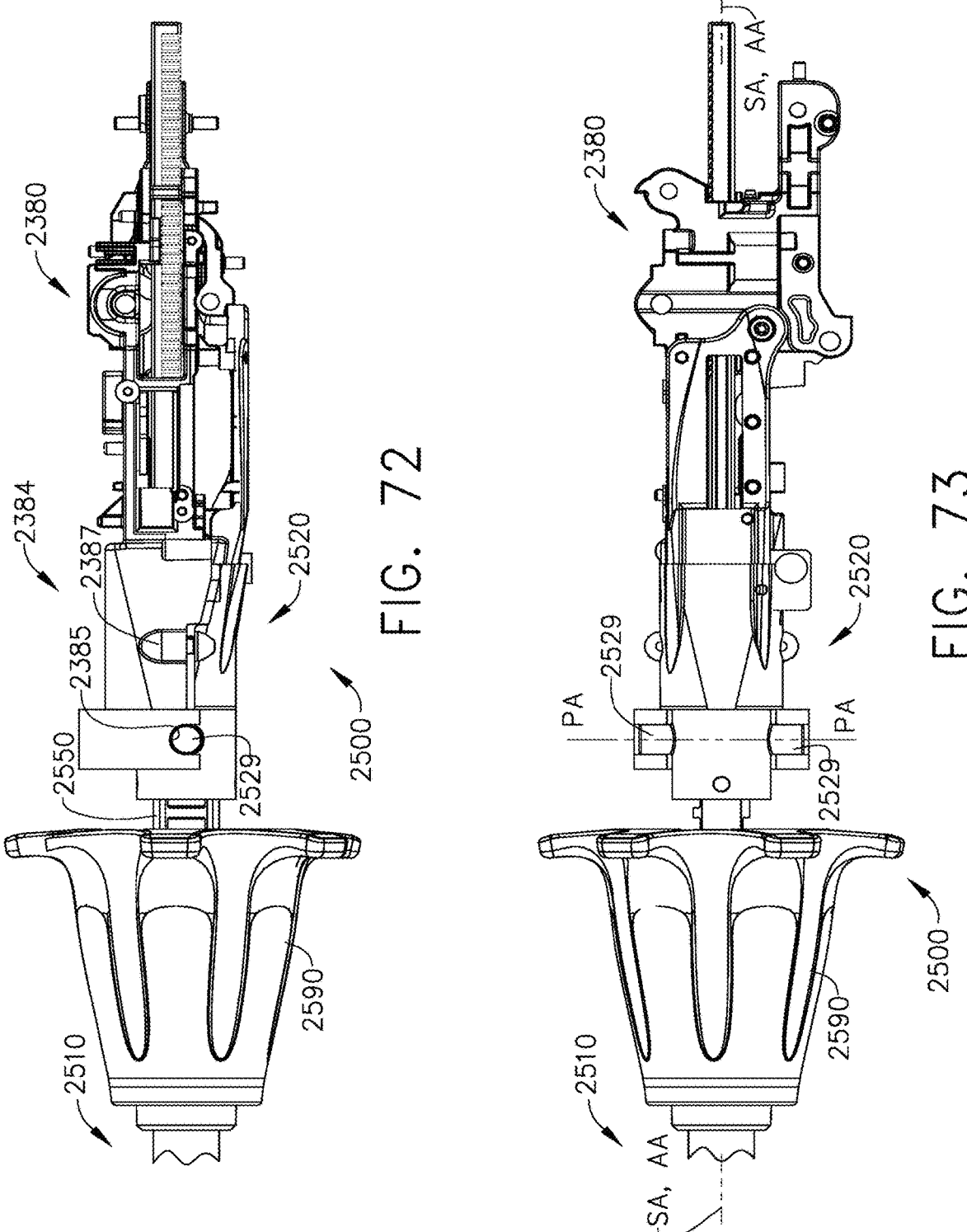
FIG. 72 is a top view of the end effector shaft assembly and frame portion of FIGS. 68-71 after being coupled together.
FIG. 73 is a side elevational view of the end effector shaft assembly and frame portion of FIG. 72.
Figure 74:
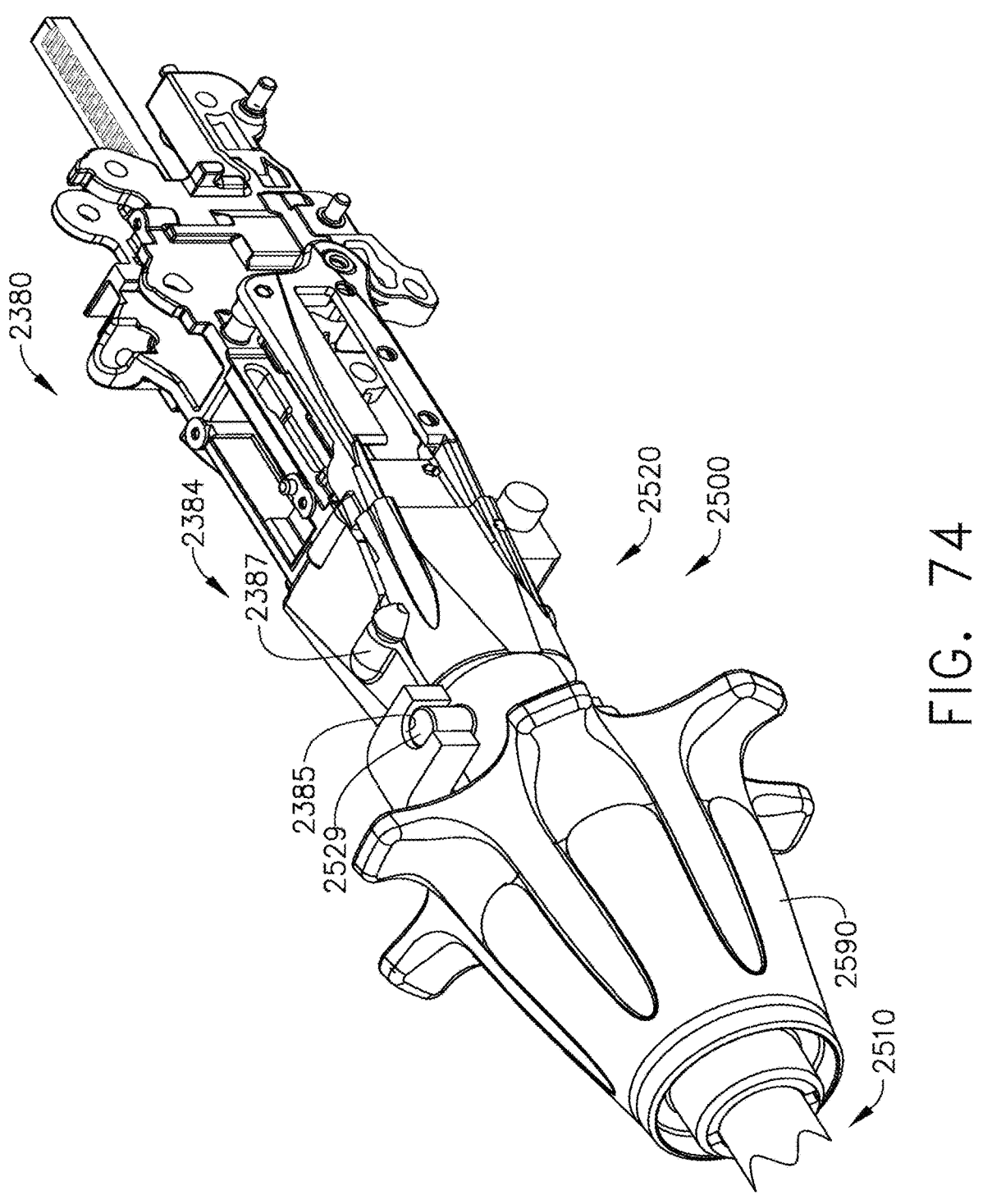
FIG. 74 is a perspective view of the end effector shaft assembly and frame portion of FIGS. 72 and 73.

Once the shaft attachment module 2520 has been latched to the frame attachment module 2384 as shown in FIGS. 72 and 73, the clinician may then couple the closure drive system (which may be similar to the closure drive systems described herein) to the closure tube attachment yoke 2560.

The various interchangeable shaft arrangements disclosed herein represent vast improvements over prior surgical instrument arrangements that employ dedicated shafts. For example, one shaft arrangement may be used on multiple handle arrangements and/or with robotically controlled surgical systems. The methods of coupling the shaft arrangements also differ from prior shaft arrangements that employ bayonet connections and other structures that require the application of a rotary motion to the shaft and/or the handle or housing during the coupling process. The various illustrative descriptions of the coupling processes employed by the shaft assemblies disclosed herein include bringing a portion of the interchangeable shaft assembly into coupling engagement with a corresponding portion of a housing, a handle, and/or a frame in a direction or orientation that is substantially transverse to an actuation axis. These coupling processes are intended to encompass movement of either one or both of the shaft assembly and housing, handle and/or frame during the coupling process. For example, one method may encompass retaining the handle, housing and/or frame stationary while moving the shaft assembly into coupling engagement with it. Another method may encompass retaining the shaft assembly stationary while moving the handle, housing and/or frame into coupling engagement with it. Still another method may involve simultaneously moving the shaft assembly and the handle, housing and/or frame together into coupling engagement. It will be understood that the coupling procedures employed for coupling the various shaft assembly arrangements disclosed herein may encompass one or more (including all) of such variations.

Figure 75:
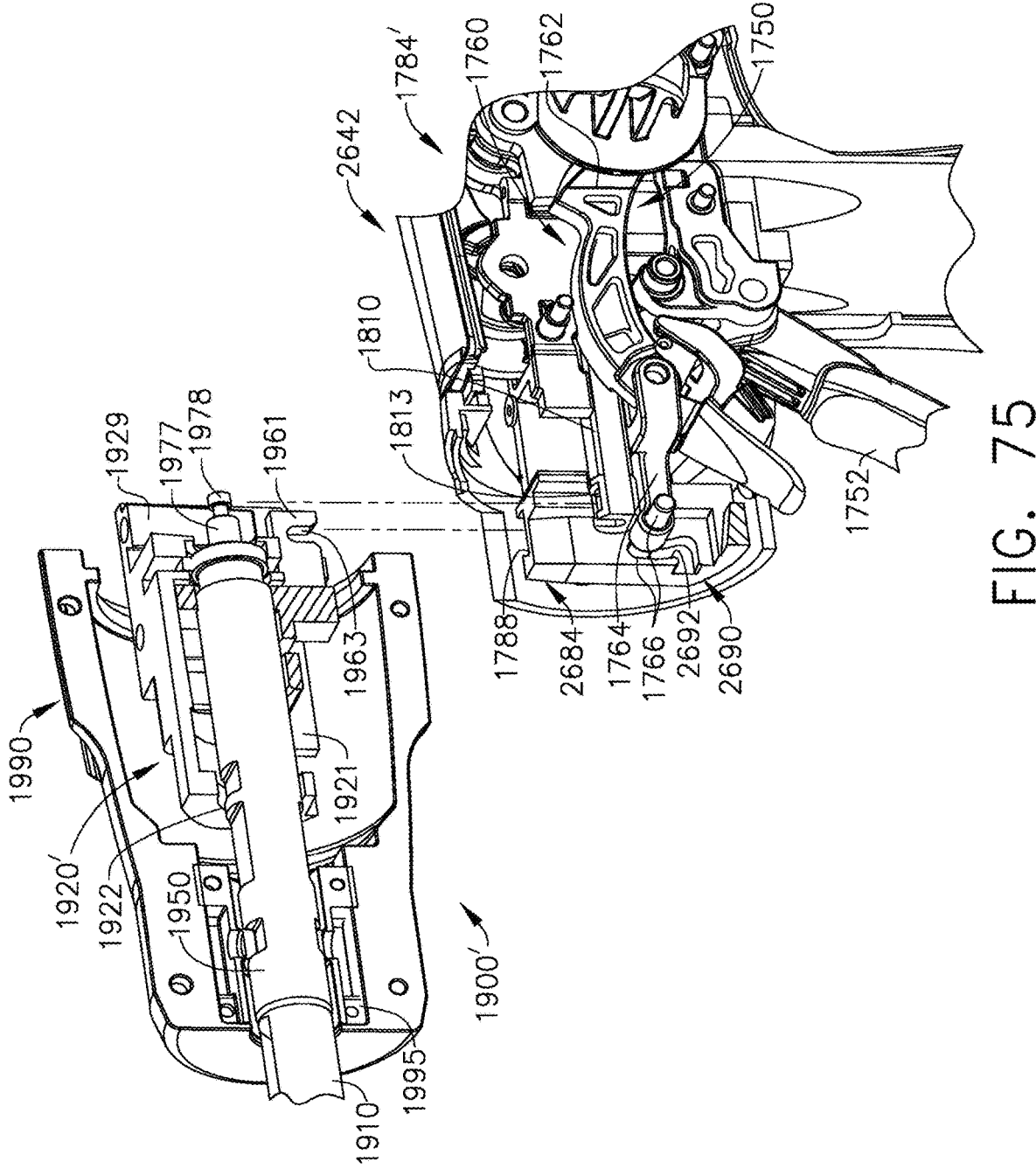
FIG. 75 is an exploded assembly view of an interchangeable shaft assembly and corresponding handle with some components thereof shown in cross-section.
Figure 76:
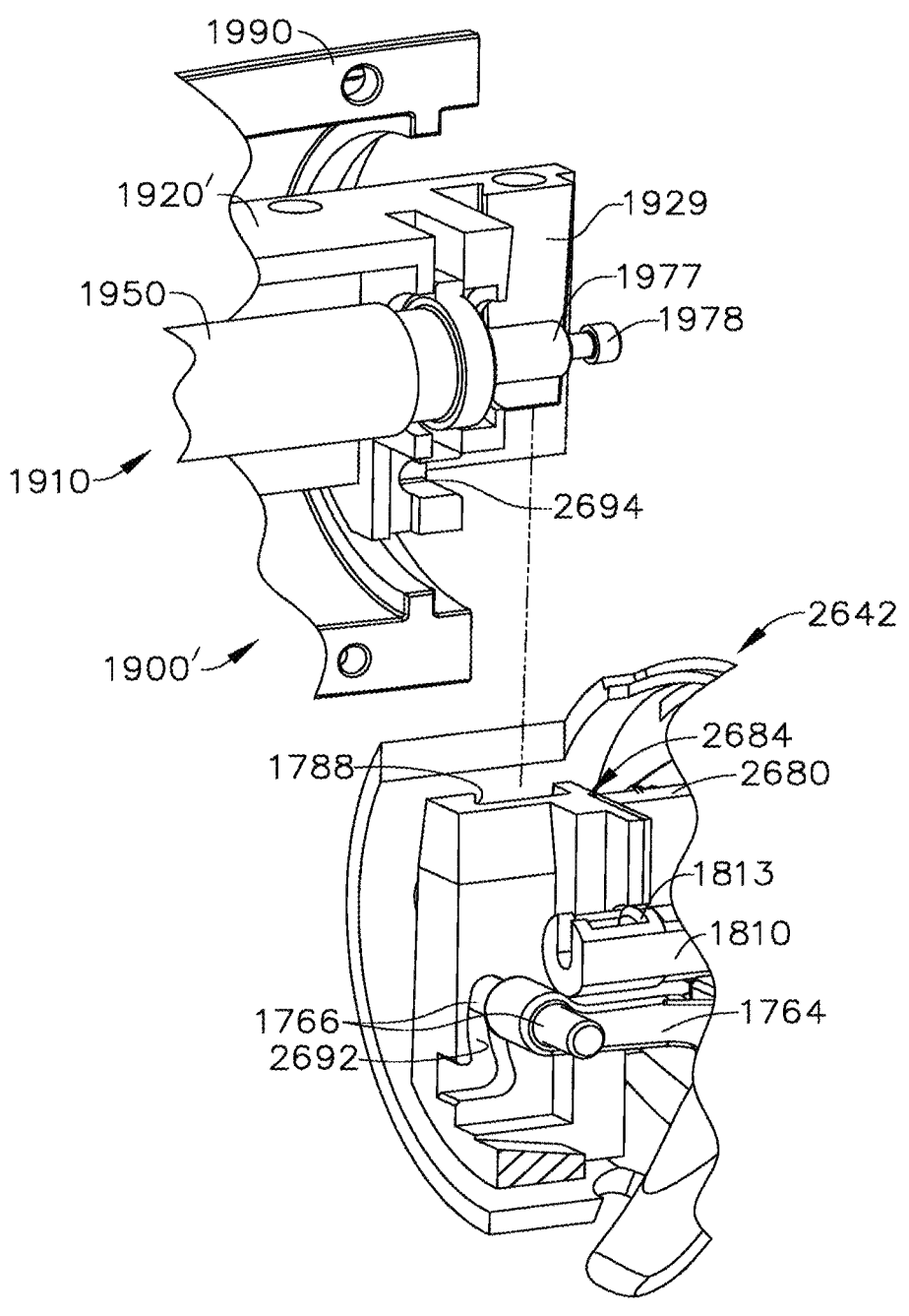
FIG. 76 is a partial cross-sectional perspective view of portions of the end effector shaft assembly and the handle of FIG. 75.

Referring to FIGS. 75-80, there is shown a handle 2642 that may be substantially identical to the handle 1042 described above, except that the frame attachment module or frame attachment portion 2684 of the frame 2680 includes a lockout assembly 2690 for preventing the inadvertent actuation of the closure drive system 1750. As can be seen in FIGS. 75 and 76, for example, a proximal lockout slot segment 2692 is formed in the frame attachment module 2684 such that, prior to attachment of the interchangeable shaft assembly 1900' thereto, the corresponding attachment lug 1066 on the closure attachment bar 1764 is slidably received therein. Thus, when the closure attachment bar 1764 is in that position, the clinician is unable to actuate the closure drive system. Stated another way, when the actuation lug 1766 is received in the proximal lockout slot segment 2692, the clinician is unable to actuate the closure trigger 1752. In various forms, only one proximal lockout slot segment 2692 may be employed. In other forms, two proximal lockout slot segments 2692 are provided such that each attachment lug 1766 may be received in a corresponding proximal lockout slot segment 2692. In various forms, a lockout spring 2695 may be employed to bias the linkage assembly 1760, such that when the closure trigger 1752 is in the unactuated position, the closure attachment bar 1764 is biased to a position wherein at least one of the attachment lugs 1766 is received in the proximal lockout slot segment 2692.

Figures 77, 78:
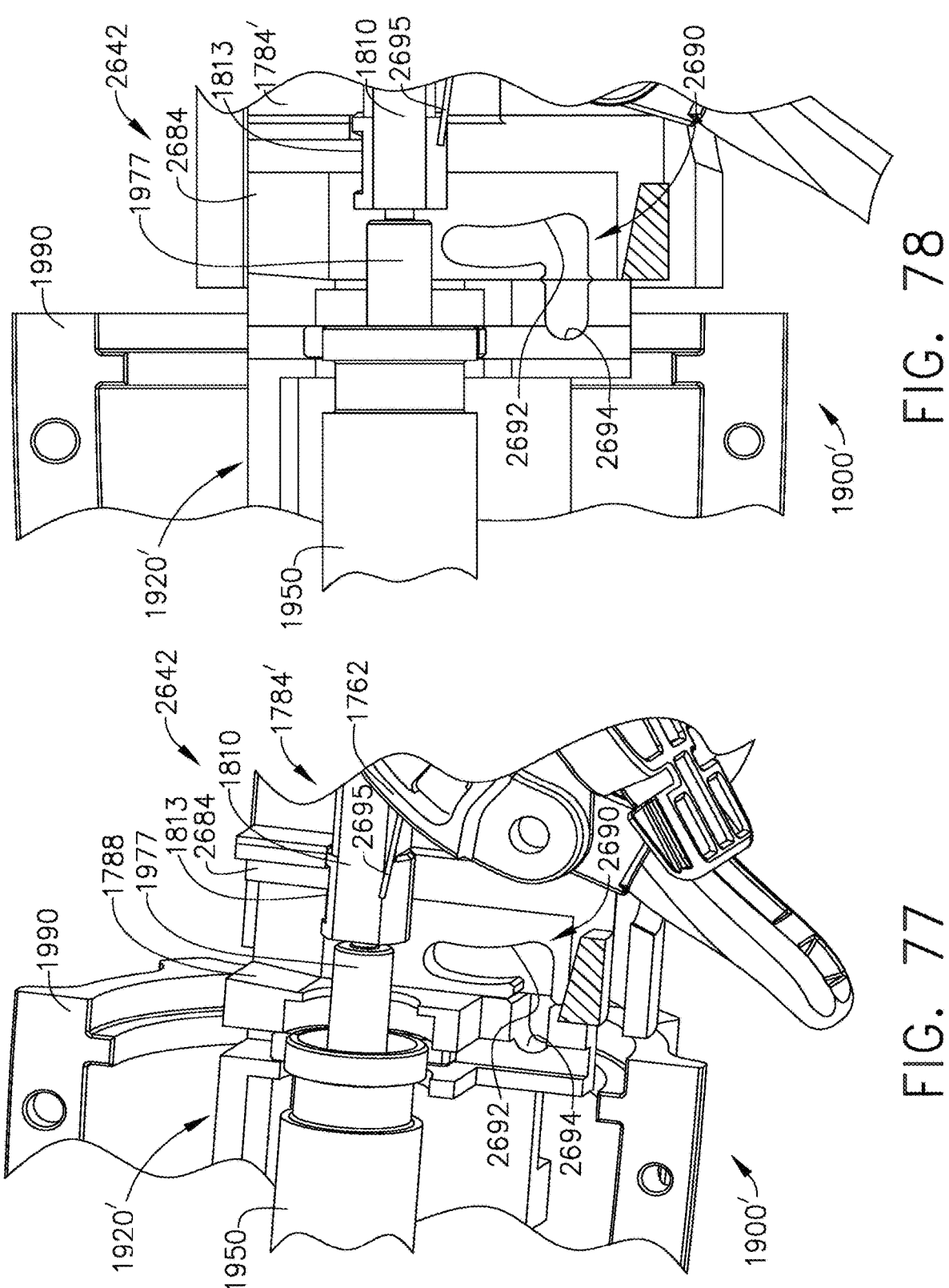
FIG. 77 is a partial perspective view of the end effector shaft assembly and handle of FIGS. 75 and 76 coupled together with various components omitted for clarity.
FIG. 78 is a side elevational view of the end effector shaft assembly and handle of FIG. 77.

As can be seen in FIGS. 77 and 78, the lockout assembly 2690 may further include a distal lug slot 2694 that is formed in the shaft attachment module 1920' and located such that, when the shaft attachment module 1920' has been completely attached to the frame 2680, the distal lug slot 2694 opens into the proximal lockout slot segment 2692 as shown in FIGS. 77 and 78.

Figure 79:
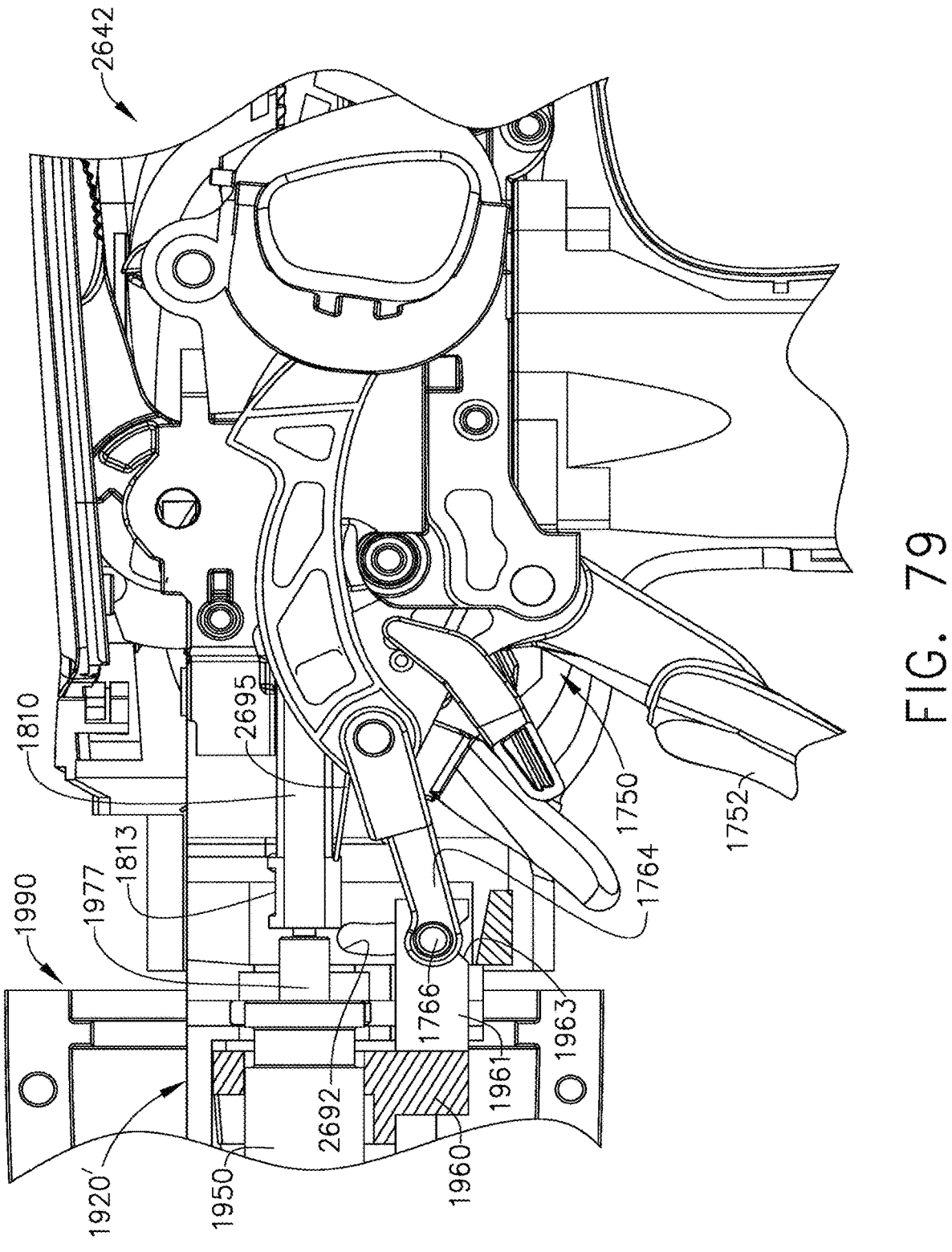
FIG. 79 is a side elevational view of the end effector shaft assembly and handle of FIGS. 75-78 coupled together with the closure drive in an unactuated position and with some components shown in cross-section.
Figure 80:
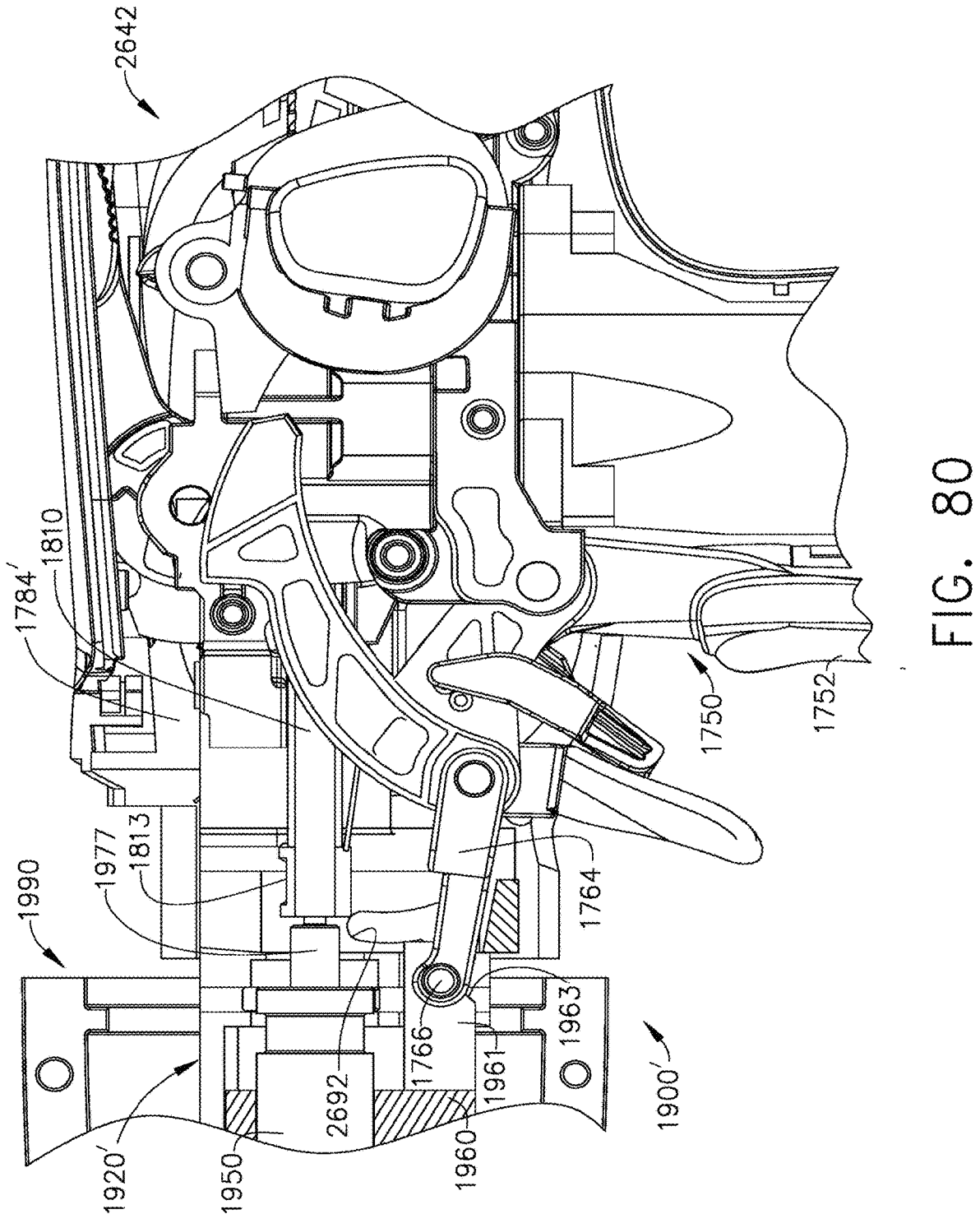
FIG. 80 is another side elevational view of the end effector shaft assembly and handle of FIG. 79 with the closure drive in a fully actuated position.
Figure 81:
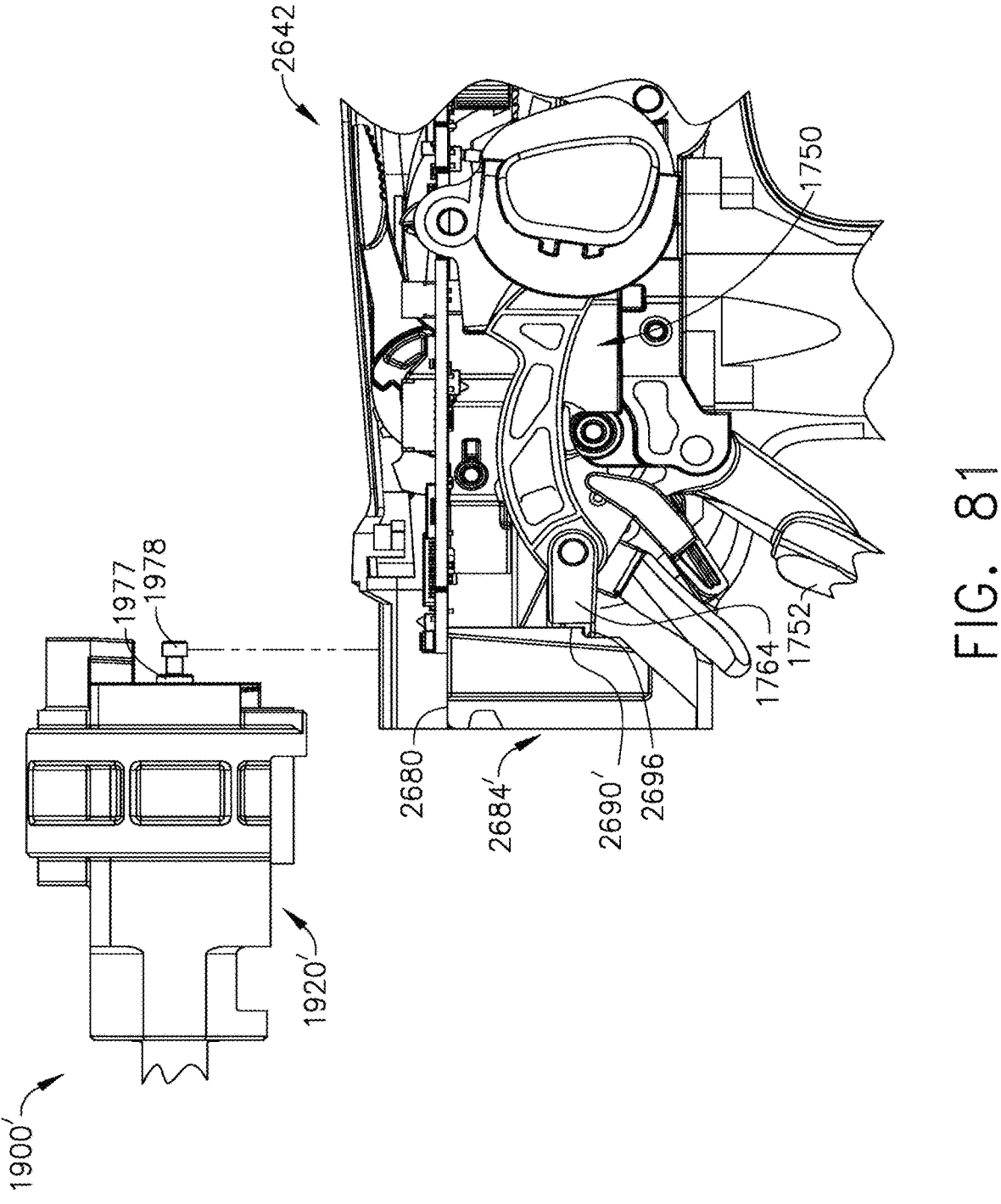
FIG. 81 is an exploded assembly view of an interchangeable shaft assembly and corresponding handle with some components thereof omitted for clarity and wherein the closure drive system is in a locked orientation.
Figures 82, 83:
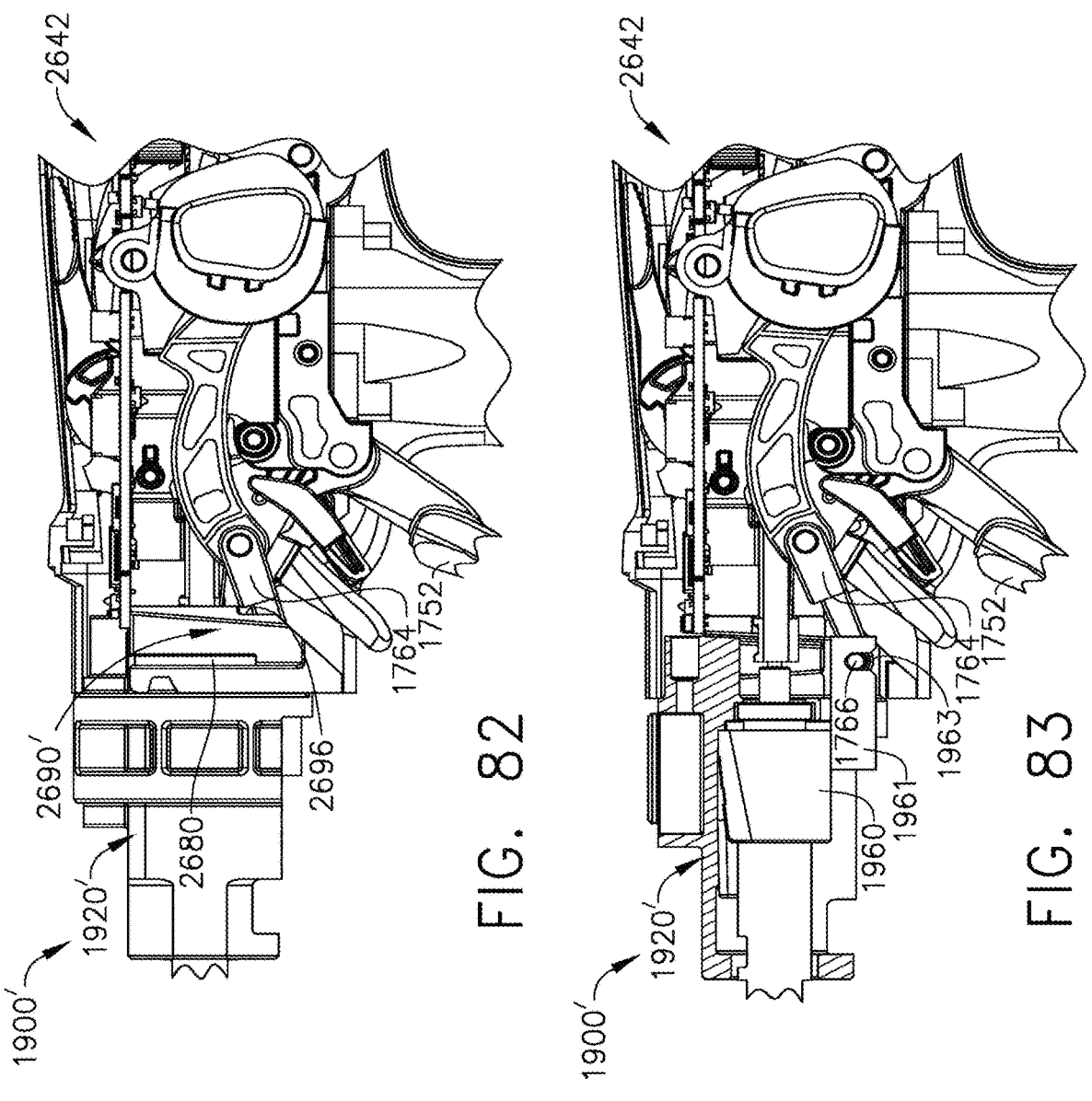
FIG. 82 is a side view of the end effector shaft assembly and handle of FIG. 81 coupled together with various components omitted for clarity and wherein the closure drive system is in an unlocked and unactuated position.
FIG. 83 is a side view of the end effector shaft assembly and handle of FIG. 82 with various components shown in cross-section for clarity.
Figures 84, 85:
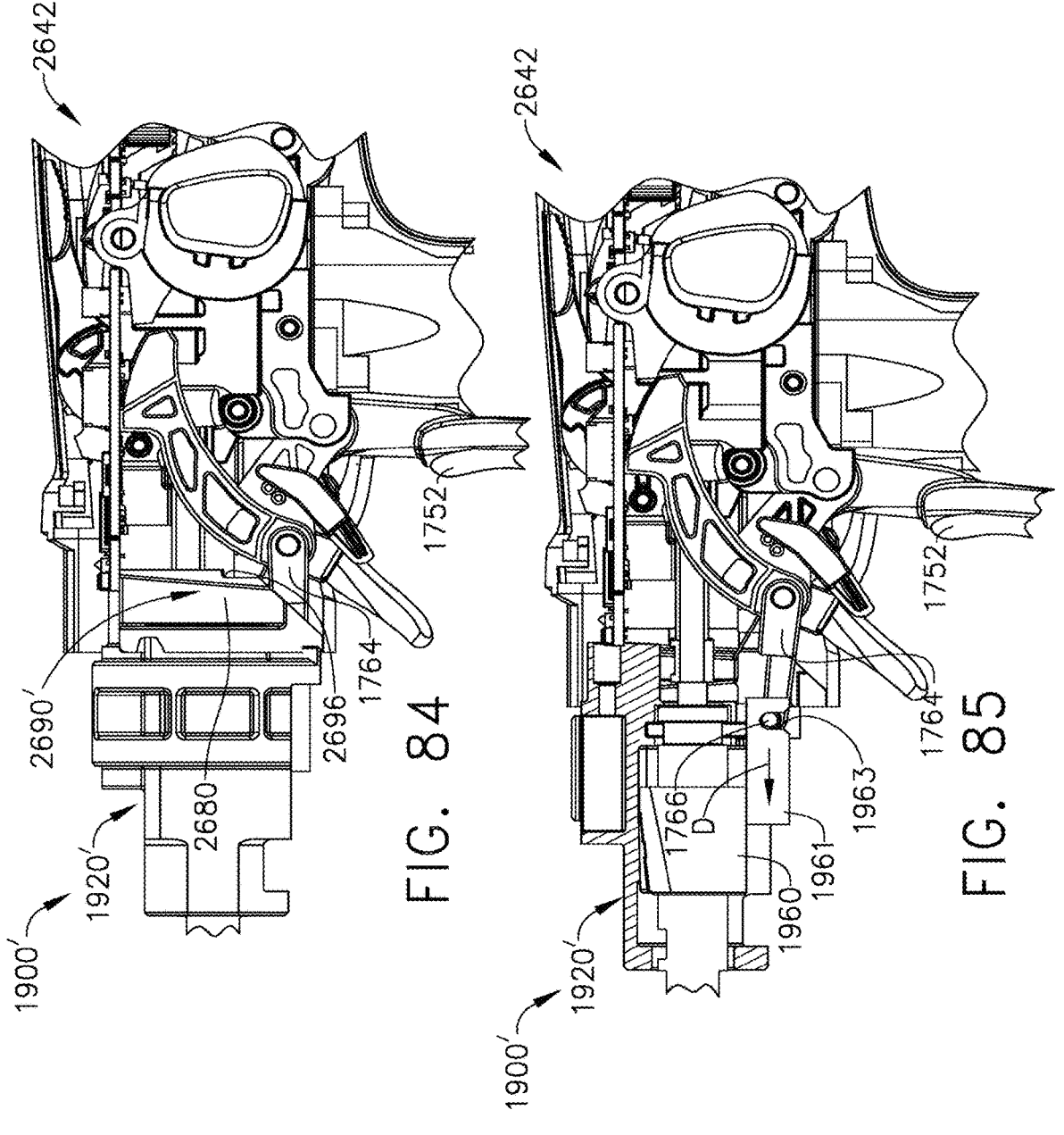
FIG. 84 is a side view of the end effector shaft assembly and handle of FIGS. 81-83 coupled together with various components omitted for clarity and wherein the closure drive system is in an actuated position.
FIG. 85 is a side view of the end effector shaft assembly and handle of FIG. 84 with various components shown in cross-section for clarity.
Figure 86:
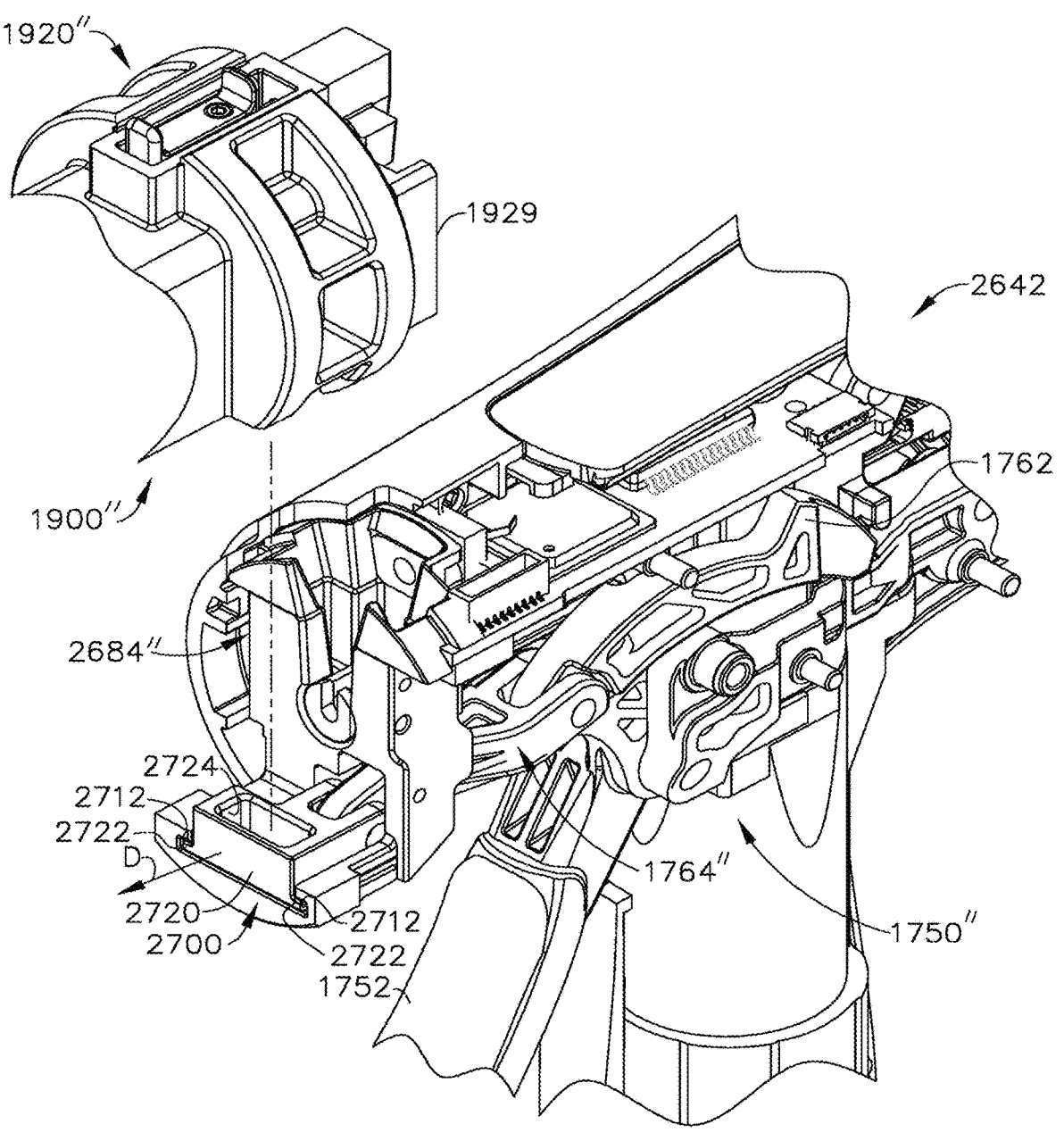
FIG. 86 is an exploded perspective assembly view of a portion of an interchangeable shaft assembly and a portion of a handle of a surgical instrument.
Figure 87:
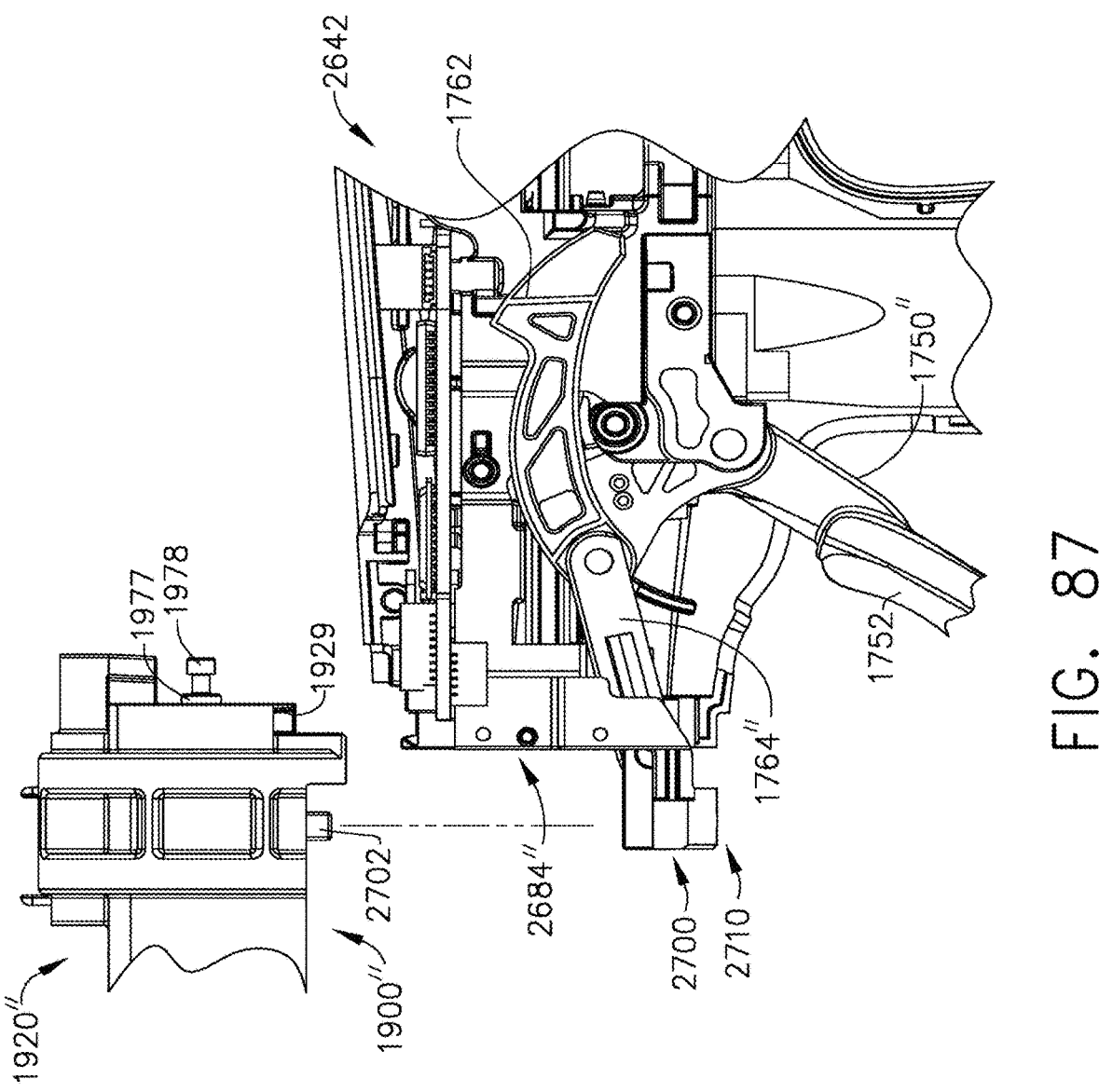
FIG. 87 is a side elevational view of the portions of the interchangeable shaft assembly and handle of FIG. 86.

Operation of the closure lockout assembly 2690 may be understood from reference to FIGS. 76-80. FIG. 76 illustrates the position of the closure attachment bar 1764 when the closure trigger 1752 is unactuated. As can be seen in that Figure, when in that position, the attachment lug 1766 is received within the proximal lockout slot segment 2692. Thus, if the clinician attempts to actuate the closure trigger 1752 when in that position (i.e., prior to operably attaching the interchangeable shaft assembly 1900' to the frame 2680 in operable engagement), the clinician will be unable to actuate the closure drive system 1750. After the clinician has attached the interchangeable shaft assembly 1900' to the frame 2684 such that it is fully seated and completely attached in operable engagement, the distal lockout slot segment 2694 in the shaft attachment module 1920" will open into the proximal lockout slot segment 2692 as shown in FIGS. 77 and 78. As the shaft attachment module 1920' is inserted into operable engagement with the frame attachment module 2684, the yoke arm 1961 protruding proximally from the closure tube attachment yoke 1960 will capture the attachment lug 1766 in the downwardly opening slot 1963 and drive it to the bottom of the proximal lockout slot 2692 as shown in FIG. 79. Thereafter, when the clinician desires to actuate the closure drive system 1750 by actuating the closure trigger 1752, the closure linkage assembly 1760 will be driven in the distal direction "D". As the closure attachment bar 1764 is advanced distally, the attachment lug 1766 is permitted to advance distally into the distal lockout slot 2694 for the distance necessary, for example, to result in the closure of the anvil or application of a corresponding actuation motion to the end effector operably coupled to the end effector shaft assembly 1900'. FIG. 80 illustrates the position of the closure attachment bar 1764 when the closure drive system 1750 has been fully actuated, for example, when the closure trigger 1752 has been fully depressed.

FIGS. 81-85 illustrate another lockout assembly 2690' for preventing the inadvertent actuation of the closure drive system 1750 until the interchangeable shaft assembly 1900' has been coupled in operable engagement with the frame 2680. In at least one form, a lockout shoulder 2696 is formed on the frame attachment module or frame attachment portion 2684' such that when the interchangeable shaft assembly 1900' has not been coupled in operable engagement with the frame 2680, the closure attachment bar 1764 is prevented from moving in the distal direction "D" by the shoulder 2696. See FIG. 81. As the shaft attachment module 1920' is inserted into operable engagement with the frame attachment module 2684', the yoke arm 1961 protruding proximally from the closure tube attachment yoke 1960 will capture the attachment lug 1766 on the closure attachment bar 1764 a move the closure attachment bar 1764 to the "unlocked" position shown in FIGS. 82 and 83. As can be particularly seen in FIG. 82, when in the unlocked position, the closure attachment bar 1764 is located below the shoulder 2696 on the frame attachment module 2684'. When the closure attachment bar is in the unlocked position, it may be advanced distally when the closure drive system 1750 is actuated by depressing the actuation trigger 1752.

Figure 88:
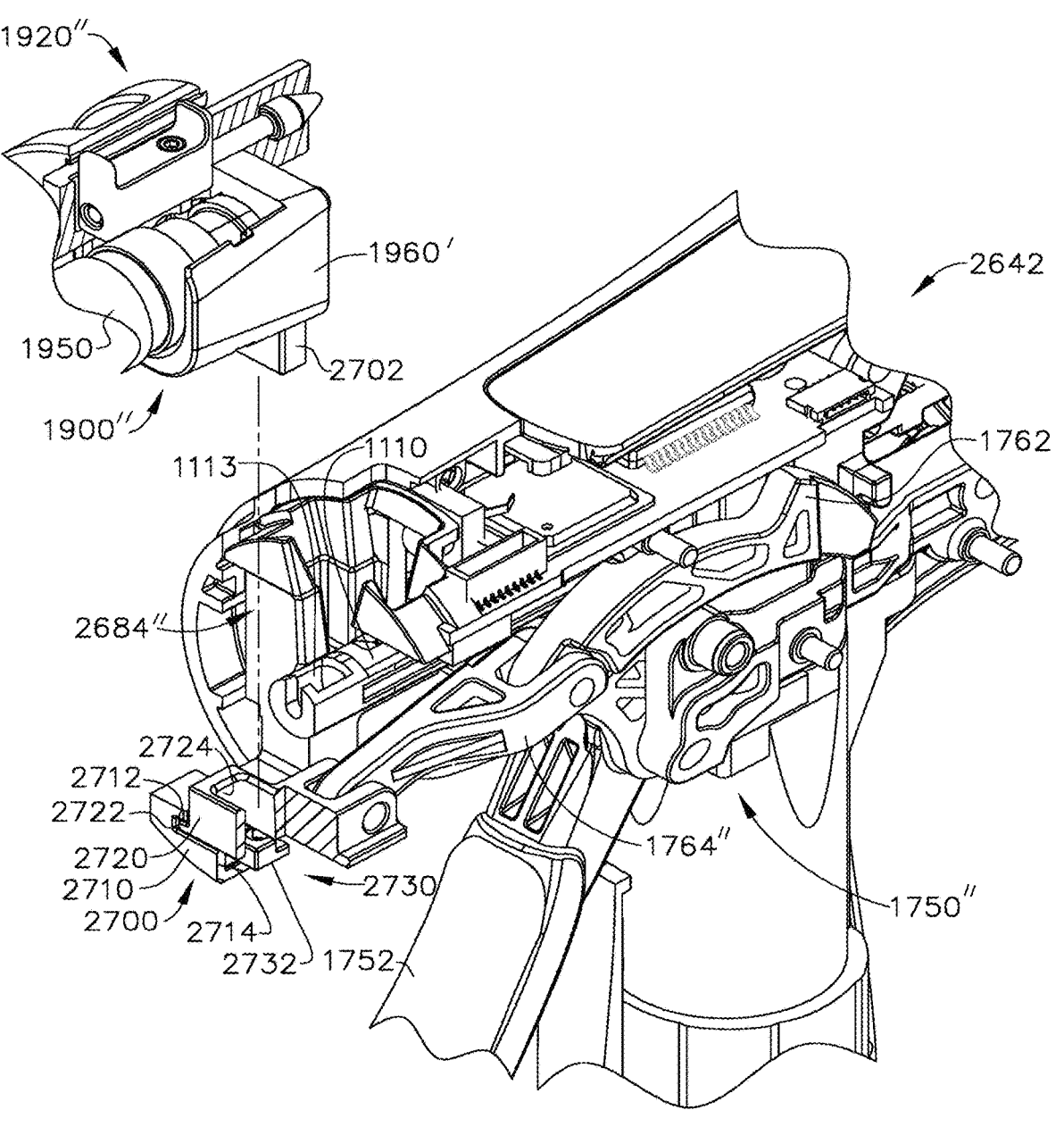
FIG. 88 is another exploded perspective assembly view of portions of the interchangeable shaft assembly and handle of FIGS. 86 and 87 with portions of the interchangeable shaft assembly shown in cross-section for clarity.
Figure 89:
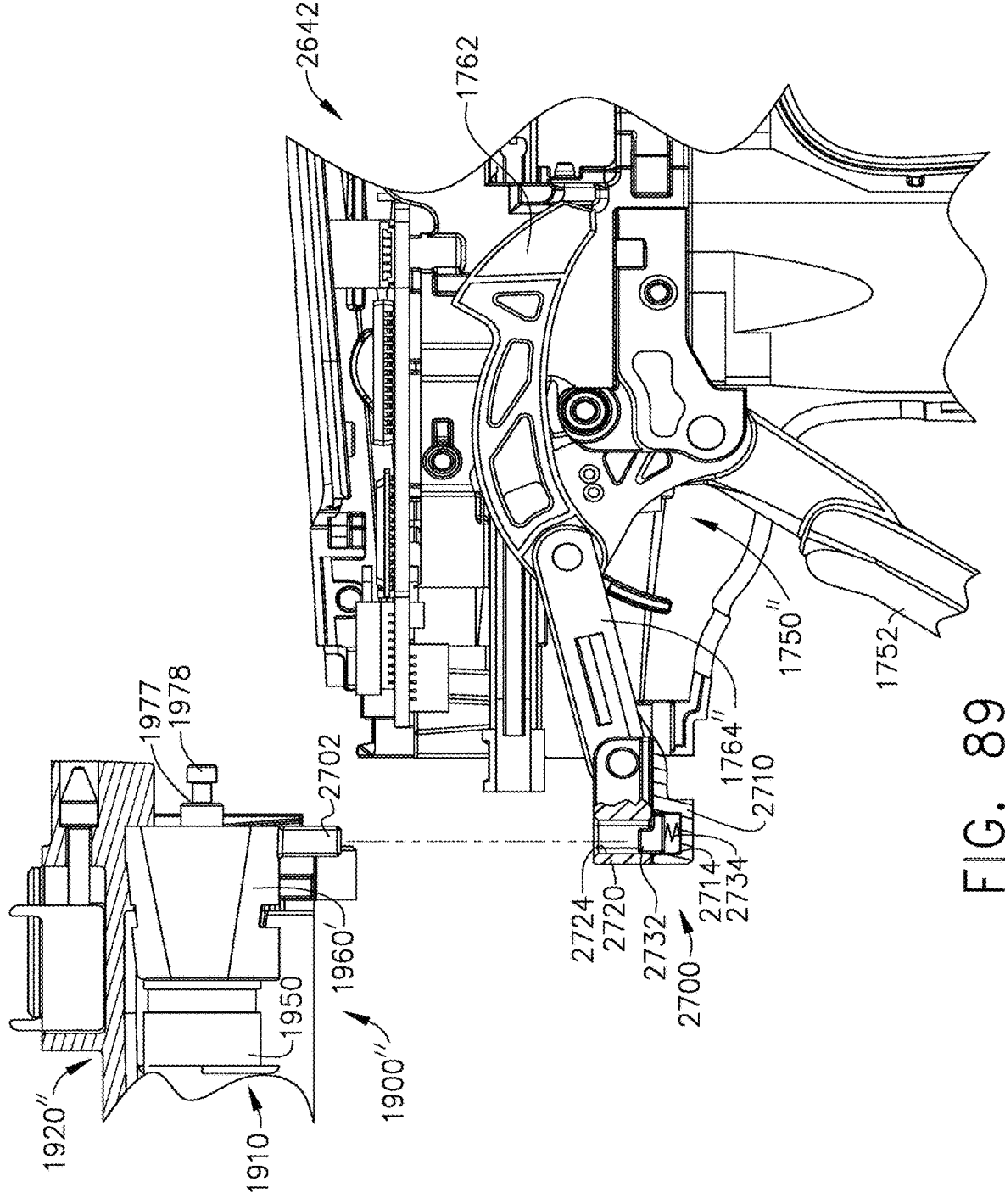
FIG. 89 is another side elevational view of portions of the interchangeable shaft assembly and handle of FIGS. 86-88 with portions thereof shown in cross-section for clarity.

FIGS. 86-91 illustrate another interchangeable shaft assembly 1900" and handle 2642 that employs a lockout assembly 2700 for preventing the inadvertent actuation of the closure drive system 1750". As can be seen in FIGS. 88 and 89, one form of lockout assembly 2700 includes an actuator slide member 2720 that is slidably journaled in a distally extending lock foot 2710 formed on the frame attachment module or frame attachment portion 2684". In particular, in at least one form, the actuator slide member 2720 has two laterally protruding slide tabs 2722 that are received in corresponding slots 2712 formed in the lock foot 2710. See FIG. 86. The actuator slide member 2720 is pivotally coupled to the closure attachment bar 1764" of the closure drive system 1750" and has an actuator pocket 2724 formed therein that is adapted to receive a downwardly-protruding actuator tab 2702 on the closure tube attachment yoke 1960'. As with the closure tube attachment yoke 1960 described above, the closure tube attachment closure yoke 1960' is rotatably affixed to the outer sleeve 1950 in the various manners described herein and which is axially movable within the shaft attachment module 1920'.

As can be seen in FIGS. 88-89, the lockout assembly 2700 may further include a movable lock member 2730 that is received in a cavity 2714 formed in the lock foot 2710. The lock member 2730 has a lock portion 2732 that is sized to extend into the actuator pocket 2724 such that when in that "locked" position, the lock member 2730 prevents the distal movement of the actuator slide member 2720 relative to the lock foot 2710. As can be most particularly seen in FIG. 89, a lock spring 2734 is provided in the cavity 2714 to bias the lock member 2730 into the locked position.

Figure 90:
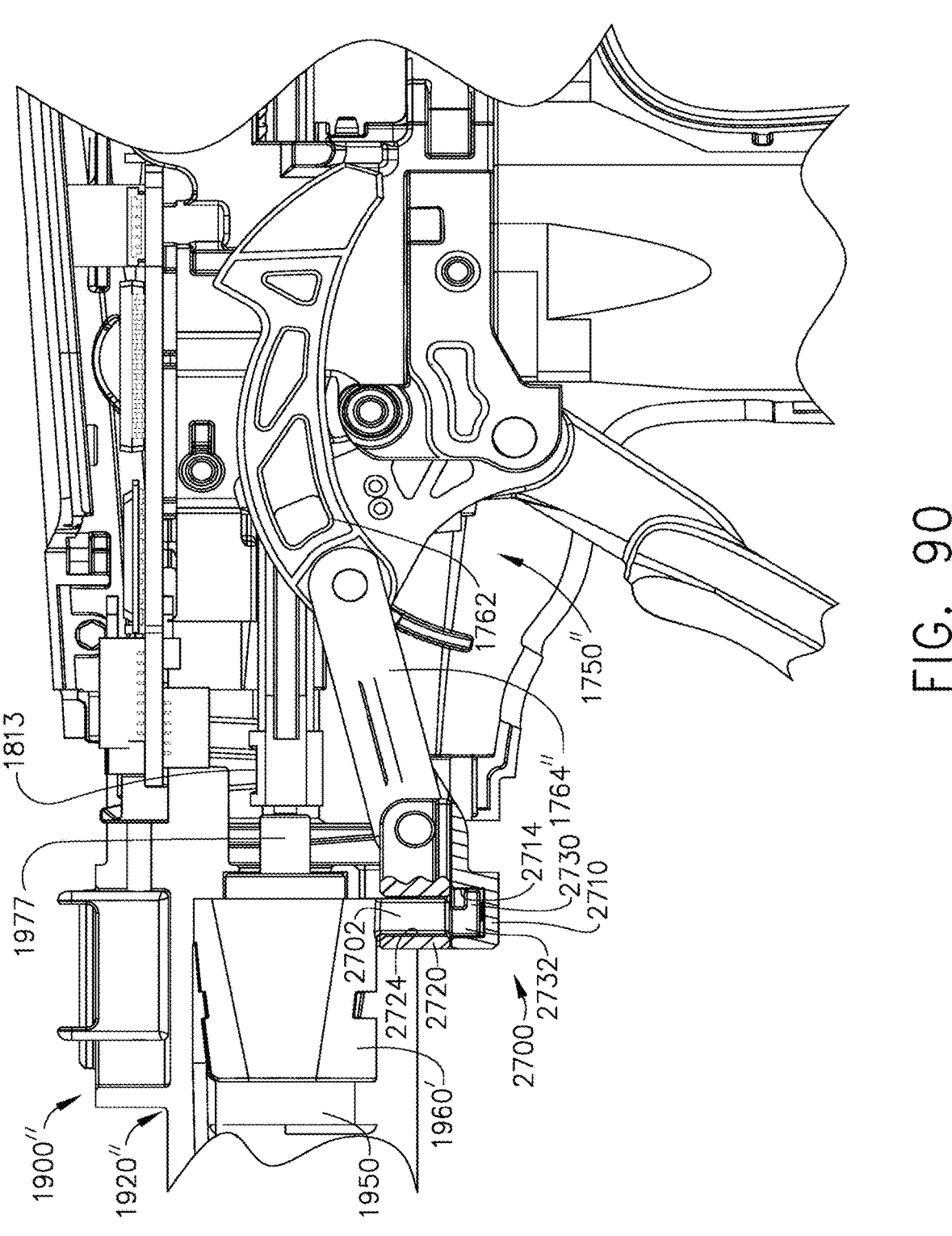
FIG. 90 is a side elevational view of the portions of the interchangeable shaft assembly and handle of FIGS. 86-89 after the interchangeable shaft assembly has been operably coupled to the handle and with portions of thereof shown in cross-section for clarity.
Figure 91:
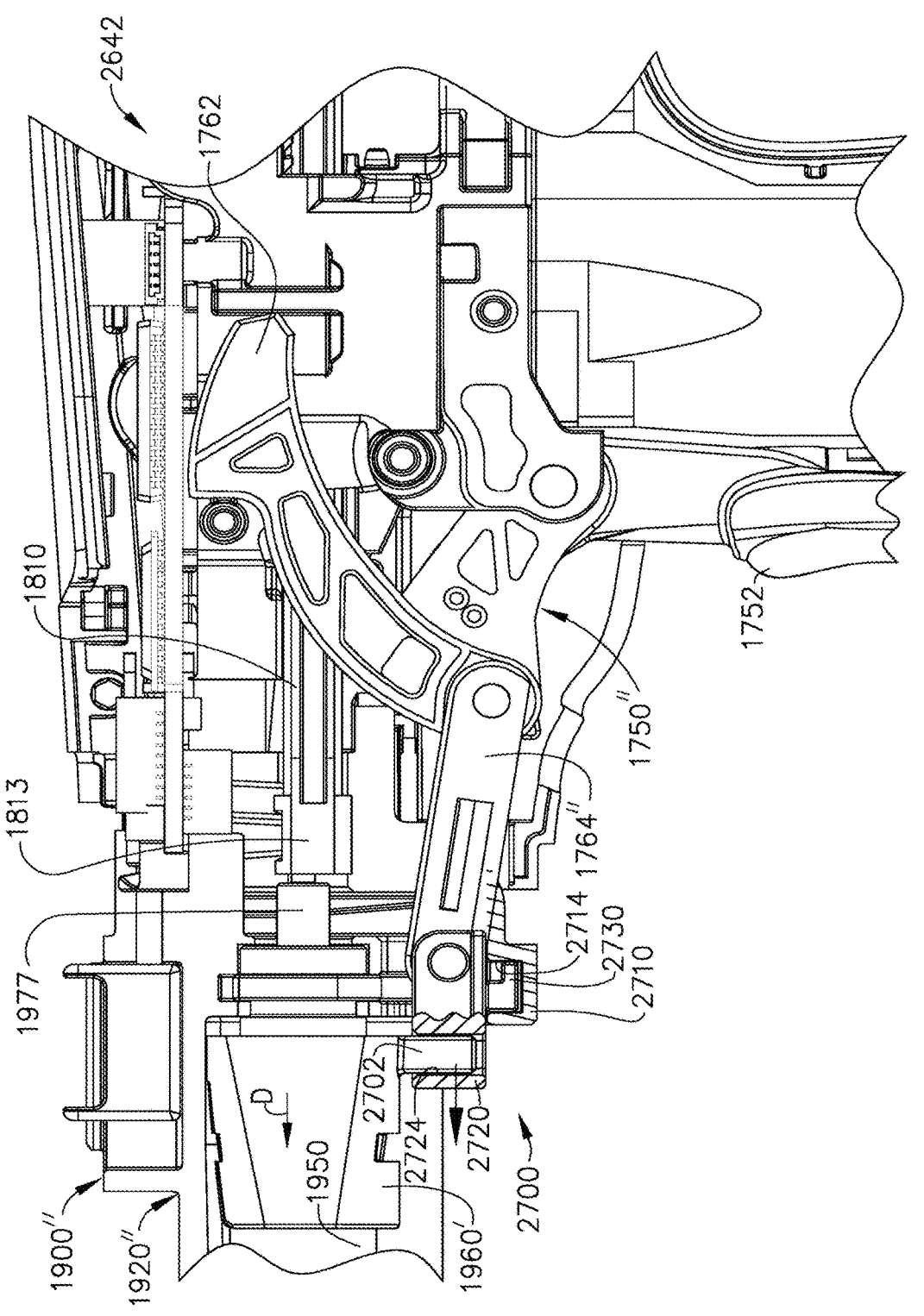
FIG. 91 is another side elevational view of portions of the interchangeable shaft assembly and handle coupled thereto with the closure drive system in a fully-actuated position.
Figure 92:
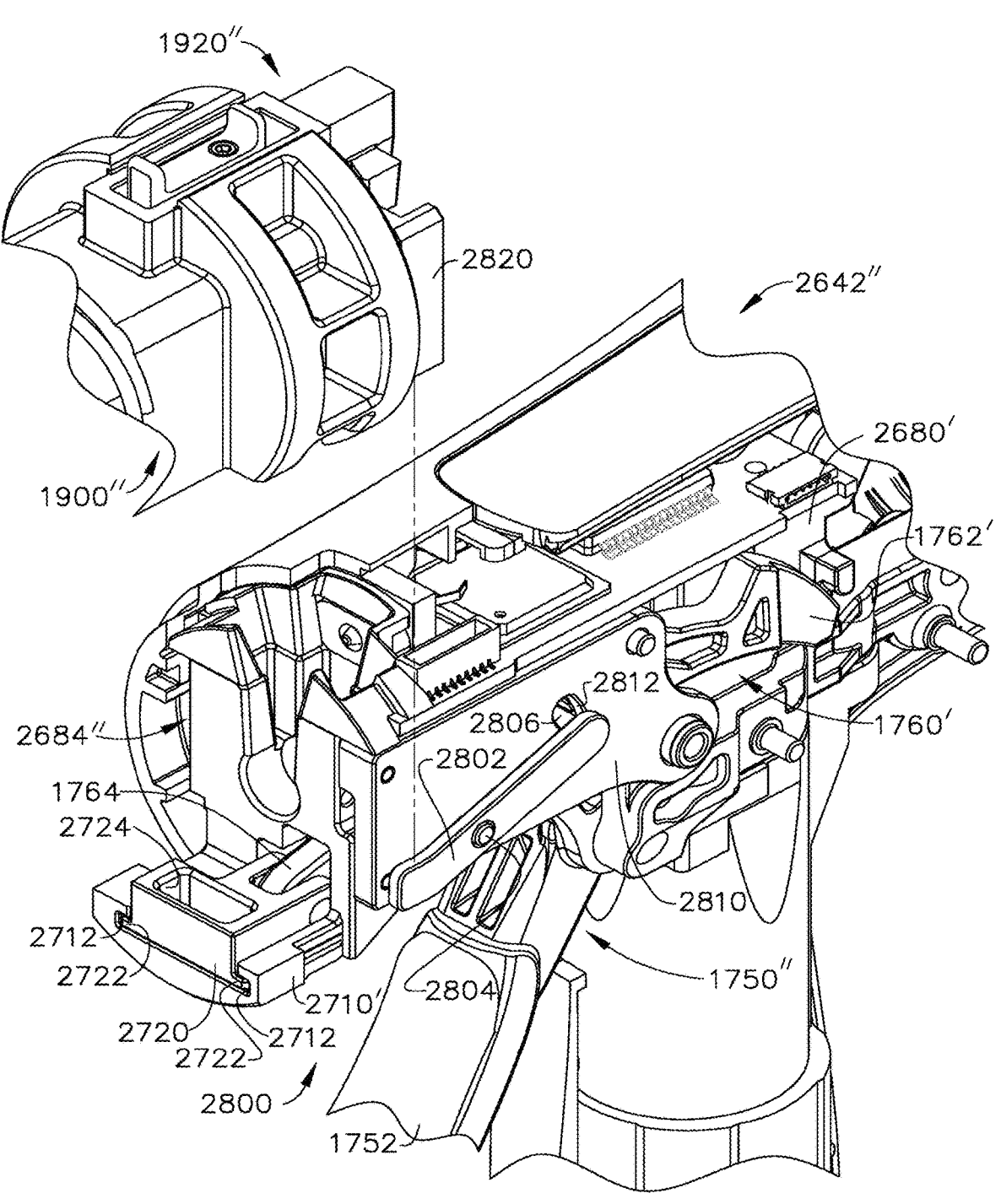
FIG. 92 is an exploded perspective assembly view of a portion of another interchangeable shaft assembly and a portion of a handle of another surgical instrument.
Figure 93:
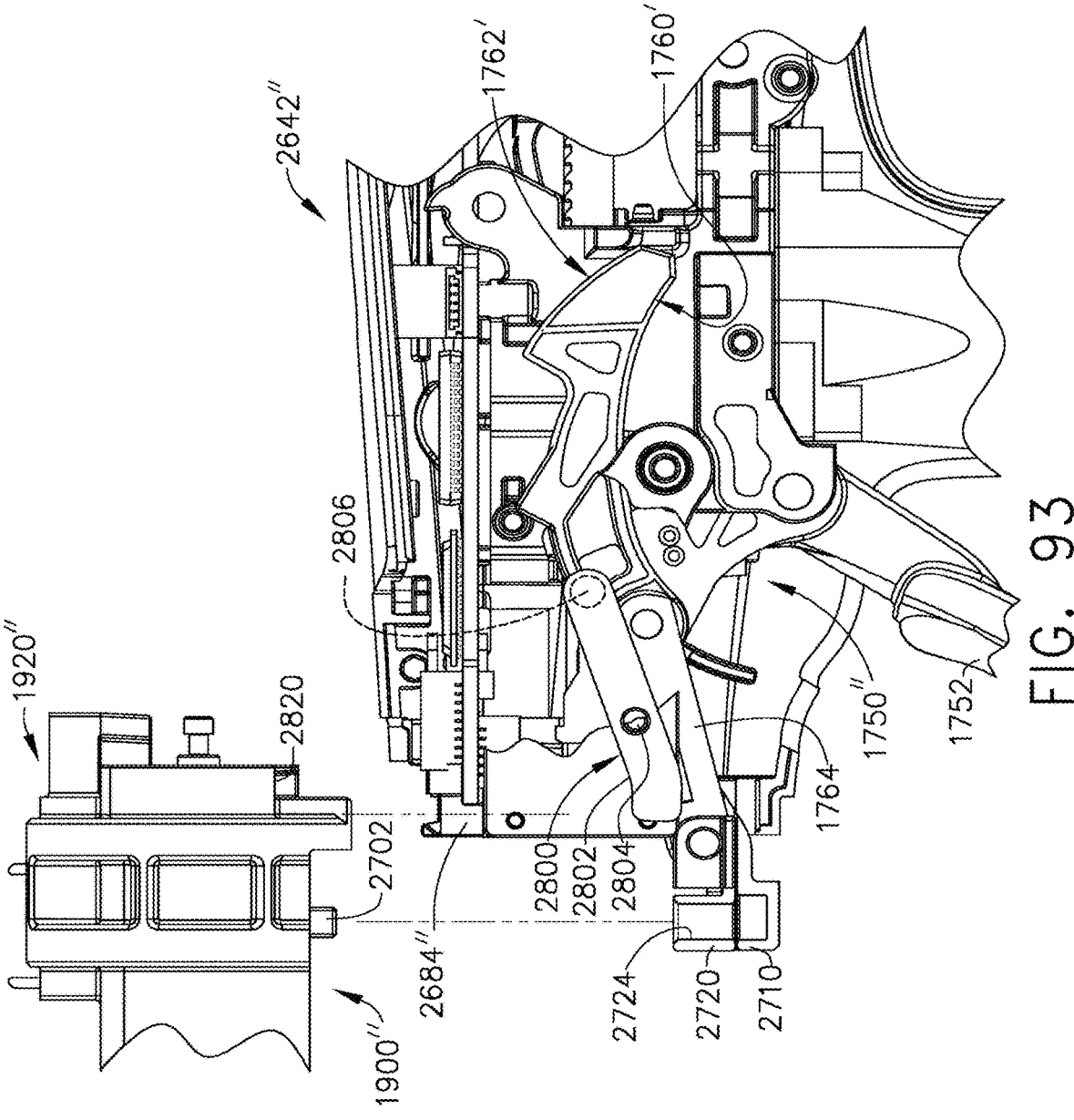
FIG. 93 is a side elevational view of portions of the interchangeable shaft assembly and handle of FIG. 92 in alignment prior to being coupled together.
Figure 94:
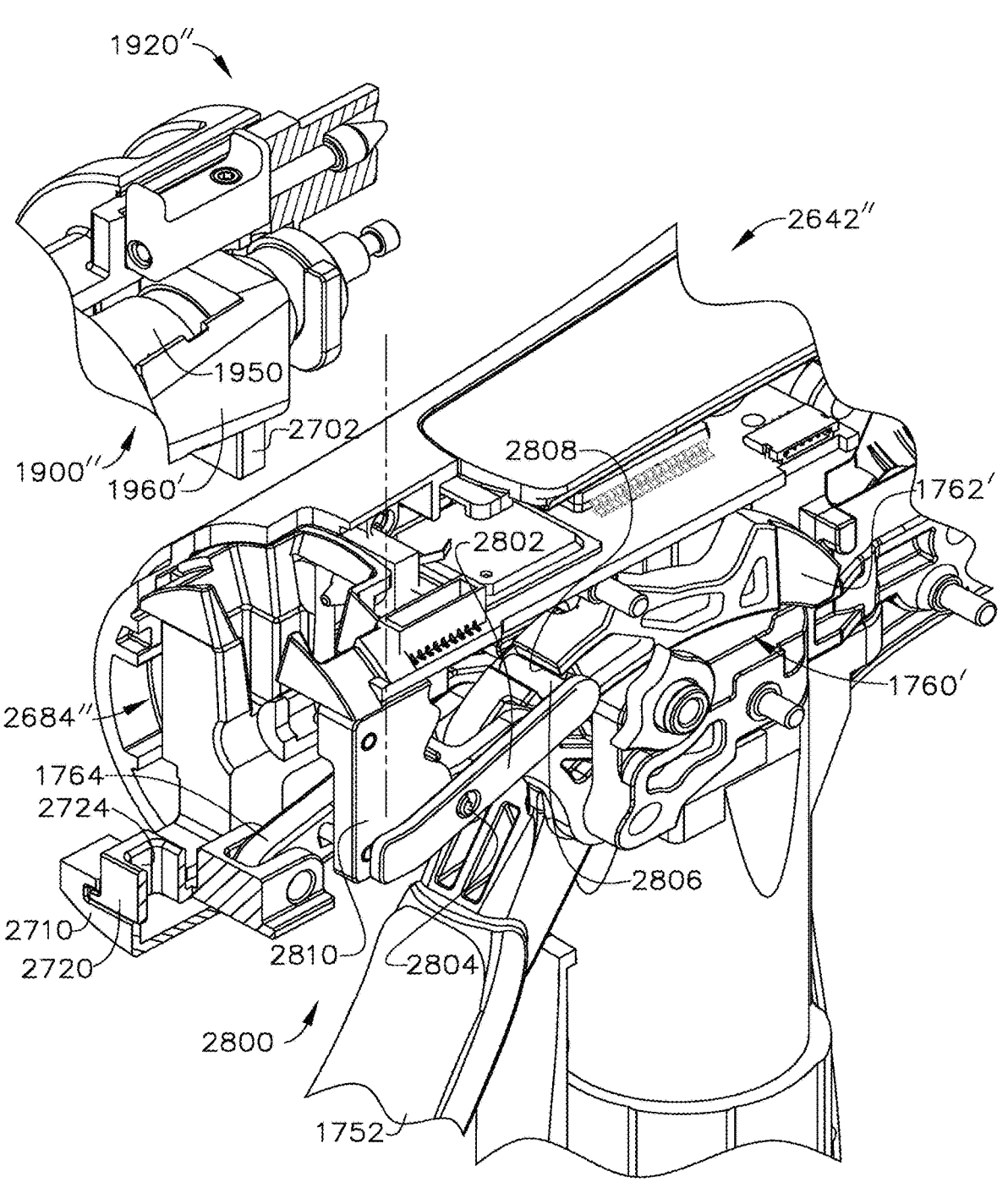
FIG. 94 is another exploded perspective view of the interchangeable shaft assembly and handle of FIGS. 92 and 93 with some portions thereof shown in cross-section.
Figure 95:
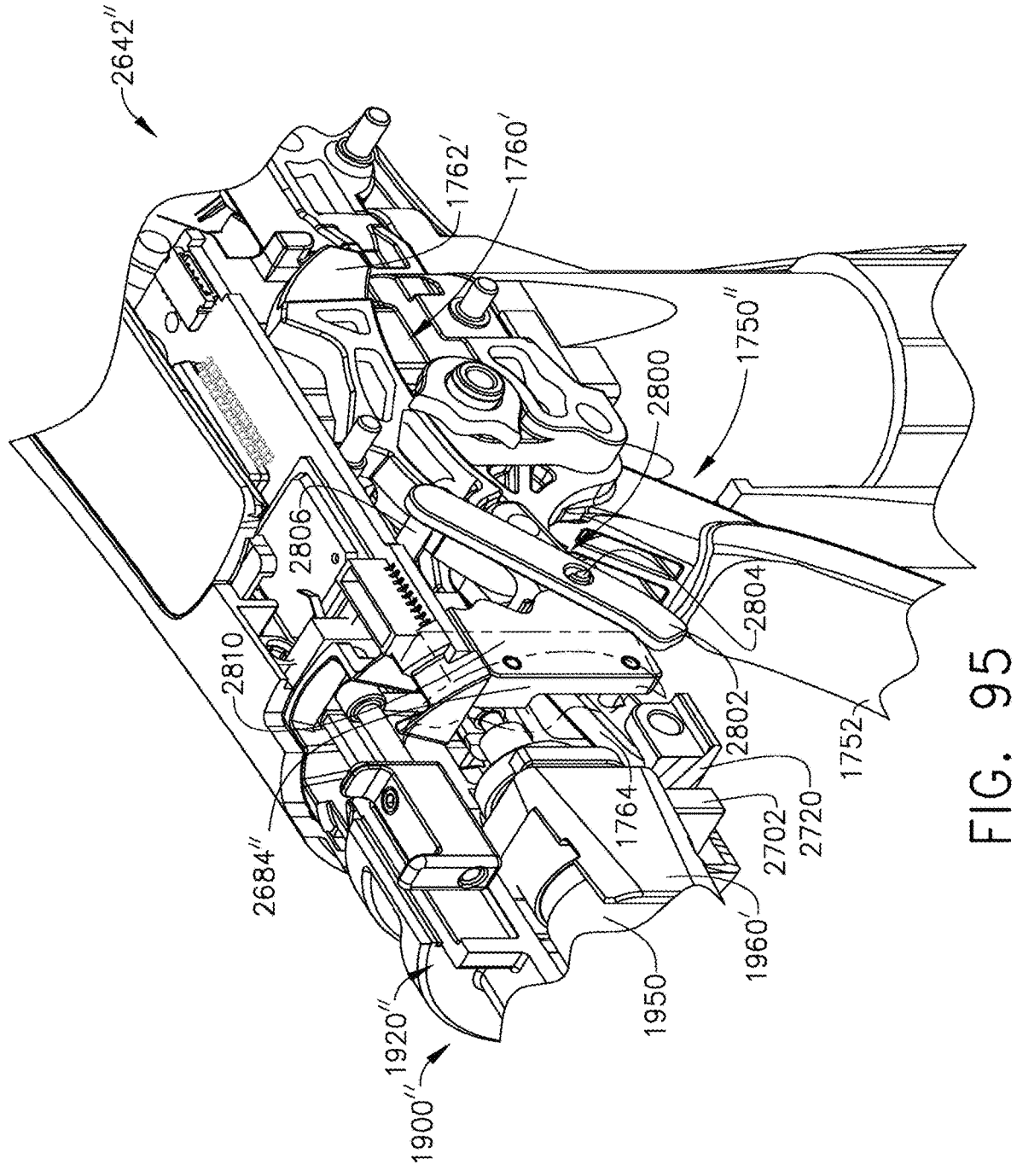
FIG. 95 is another perspective view of the interchangeable shaft assembly and handle of FIGS. 92-94 coupled together in operable engagement.
Figure 96:
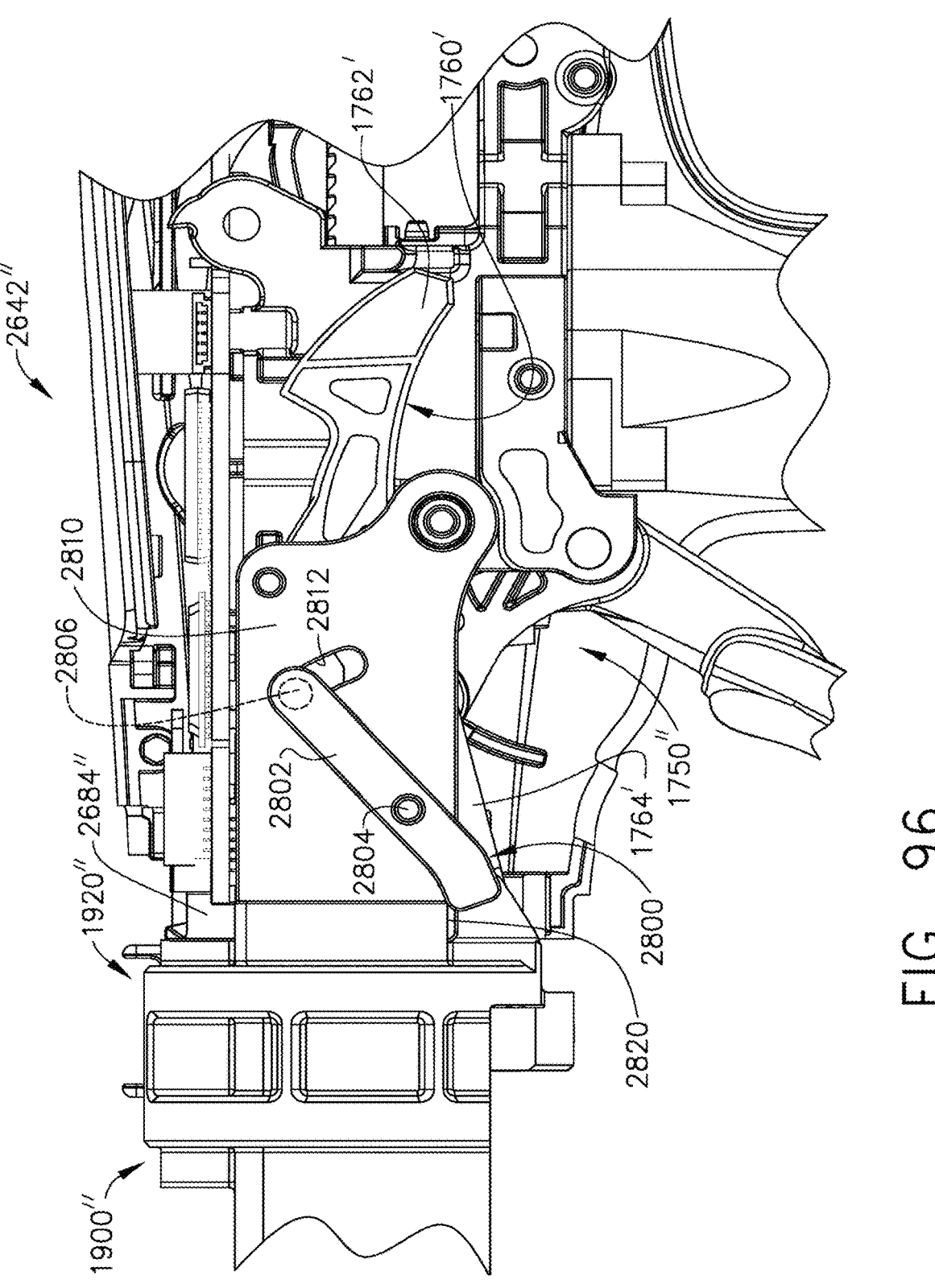
FIG. 96 is a side elevational view of the interchangeable shaft assembly and handle of FIG. 95.
Figure 97:
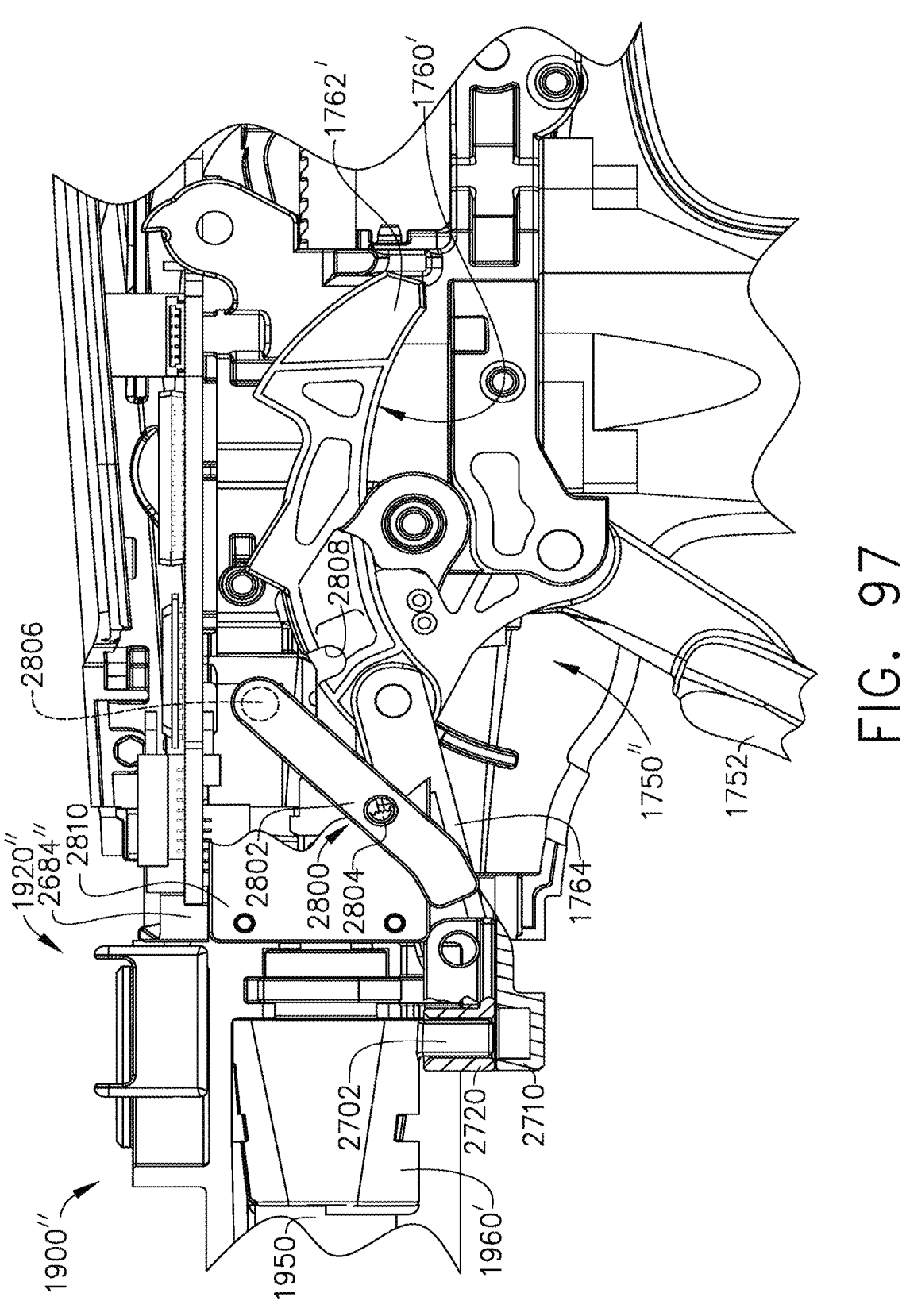
FIG. 97 is another side elevational view of the interchangeable shaft assembly and handle of FIG. 96 with some components thereof shown in cross-section.

FIG. 89 illustrates the lockout assembly 2700 in the locked position. When in that position, the lock portion 2732 is located in the actuator pocket 2724 and thereby prevents the distal movement of the actuator slide member 2720. Thus, if the clinician attempts to actuate the closure drive system 1750" by depressing the closure trigger 1752, the lock portion 2732 will prevent the advancement of the slide member 2720. FIG. 90 illustrates the position of the lock member 2730 after the actuator tab 2702 on the closure tube yoke 1960' has been inserted into the actuator pocket 2724 and has biased the lock member 2370 into an "unlocked" position in the bottom of the cavity 2714 wherein the actuator slide member 2720 may be advanced distally. FIG. 91 illustrates the position of the actuator slide 2720 after the closure trigger 1752 has been completely depressed to thereby axially advance the closure tube attachment yoke 1960' and the outer sleeve 1950 attached thereto.

FIGS. 92-98 illustrate another interchangeable shaft assembly 1900" and handle 2642" that employs a lockout assembly 2800 for preventing the inadvertent actuation of the closure drive system 1750". The closure drive system 1750" may be similar to the closure drive systems 1050 and 1750 described above and include a closure trigger 1752 and a closure linkage assembly 1760'. The closure linkage assembly 1760' may include a closure link 1762' that is pivotally coupled to the closure attachment bar 1764. In addition, an actuator slide member 2720 may be pivotally attached to the closure attachment bar 1764 and also be slidably journaled in a distally extending lock foot 2710' formed on the frame attachment module 2684". In particular, in at least one form, the actuator slide member 2720 has two laterally protruding slide tabs 2722 that are received in corresponding slots 2712 formed in the lock foot 2710. See FIG. 92. The actuator slide member 2720 is pivotally coupled to the closure attachment bar 1764 of the closure drive system 1750" and has an actuator pocket 2724 formed therein that is adapted to receive a downwardly-protruding actuator tab 2702 on the closure tube attachment yoke 1960'. As with the closure tube attachment yoke 1960 described above, the closure tube attachment closure yoke 1960' is rotatably affixed to the outer sleeve 1950 in the various manners described herein and which is axially movable within the shaft attachment module 1920".

In various forms, the lockout assembly 2800 may further include a movable lock bar or lock member 2802 that is pivotally attached to the frame attachment module 2684". For example, the lock bar 2802 may be pivotally mounted to a laterally protruding pin 2804 on the frame attachment module 2684". The lock bar 2802 may further have a lock pin 2806 protruding from a proximal portion thereof that is configured to extend into a lock slot 2808 provided in the closure link 1762' when the closure drive system 1750" in unactuated. See FIG. 94. Lock pin 2806 may extend through a lock slot 2812 that is provided in a side plate 2810 that is attached to the frame 2680'. The lock slot 2812 may serve to guide the lock pin 2806 between locked (FIGS. 92-94) and unlocked positions (FIGS. 95-98).

When the lockout assembly is in the locked position, the lock pin 2806 is received in the lock slot in 2808 in the closure link 1762'. When in that position, the lock pin prevents movement closure linkage assembly 1760'. Thus, if the clinician attempts to actuate the closure drive system 1750" by depressing the closure trigger 1752, the lock pin 2806 will prevent movement of the closure link 1762 and ultimately prevent the advancement of the slide member

Figure 98:
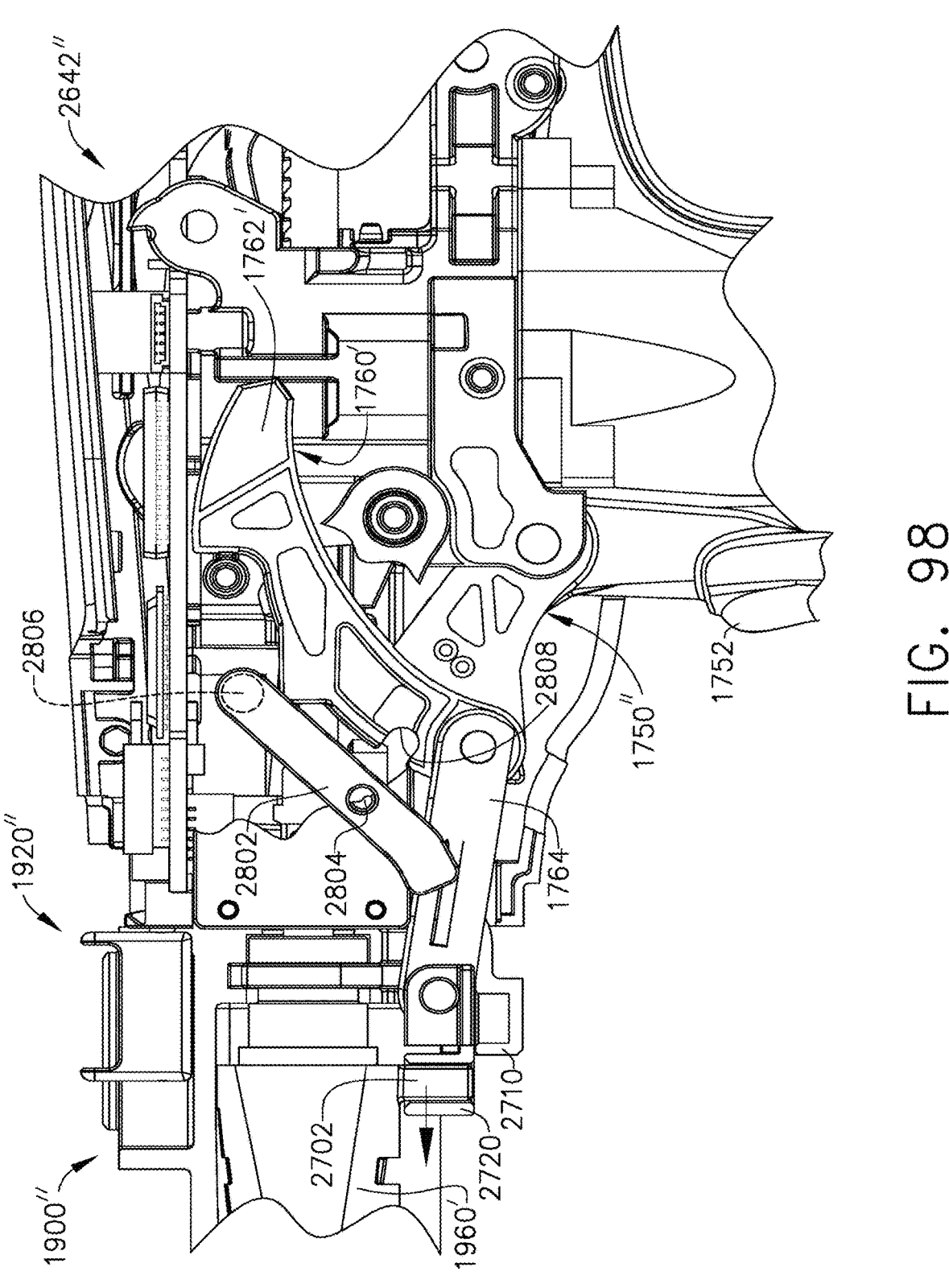
FIG. 98 is another side elevational view of the interchangeable shaft assembly and handle of FIGS. 92-96 with the closure trigger in a fully actuated position.

2720. FIGS. 95-98 illustrate the position of the lock bar 2602 after the shaft attachment module 1920" has been coupled in operable engagement with the frame attachment module 2684". When in that position, a lock release portion 2820 on the frame attachment module 2684" contacts the lock bar 2802 and causes it to pivot to thereby move the lock pin 2806 out of the lock slot 2808 in the closure link 1762'. As can also be seen in FIGS. 97 and 98, when the shaft attachment module 1920" has been coupled in operable engagement with the frame attachment module 2684", the actuator tab 2702 on the closure tube yoke 1960' is seated in the actuator pocket 2724 in the actuator slide member 2720. FIG. 98 illustrates the position of the actuator slide member 2720 after the closure trigger 1752 has been completely depressed to thereby axially advance the closure tube attachment yoke 1960' and the outer sleeve 1950 attached thereto in the distal direction "D".

Figure 99:
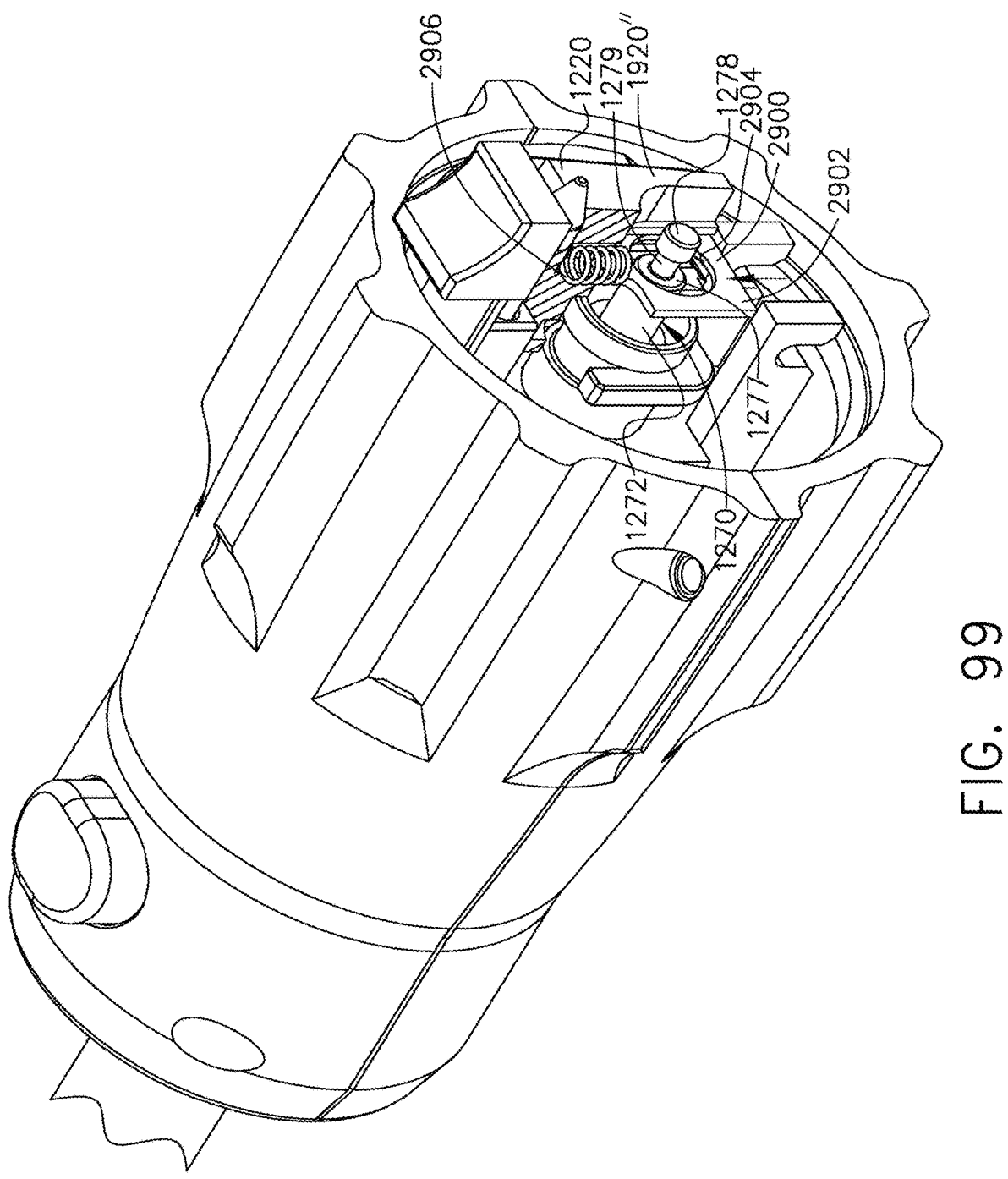
FIG. 99 is a perspective view of a portion of another interchangeable shaft assembly that includes a shaft locking assembly arrangement.
Figure 100:
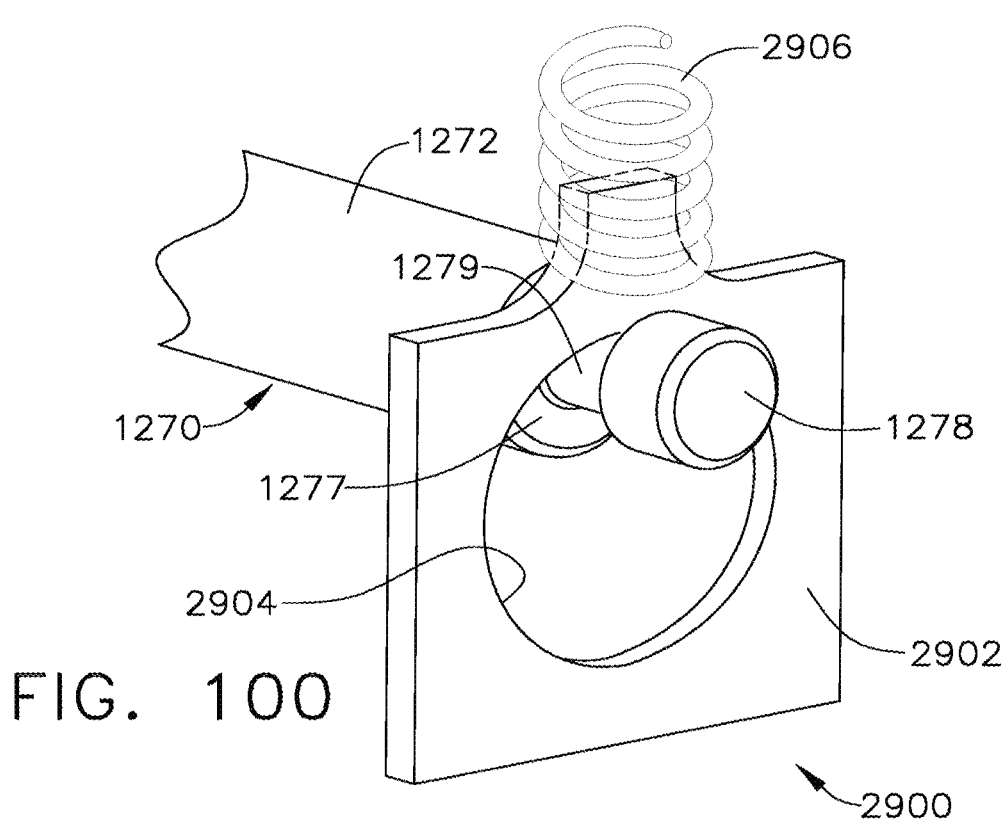
FIG. 100 is a perspective view of the shaft locking assembly arrangement depicted in FIG. 99 in a locked position with the intermediate firing shaft portion of the firing member of an interchangeable shaft assembly.
Figure 101:
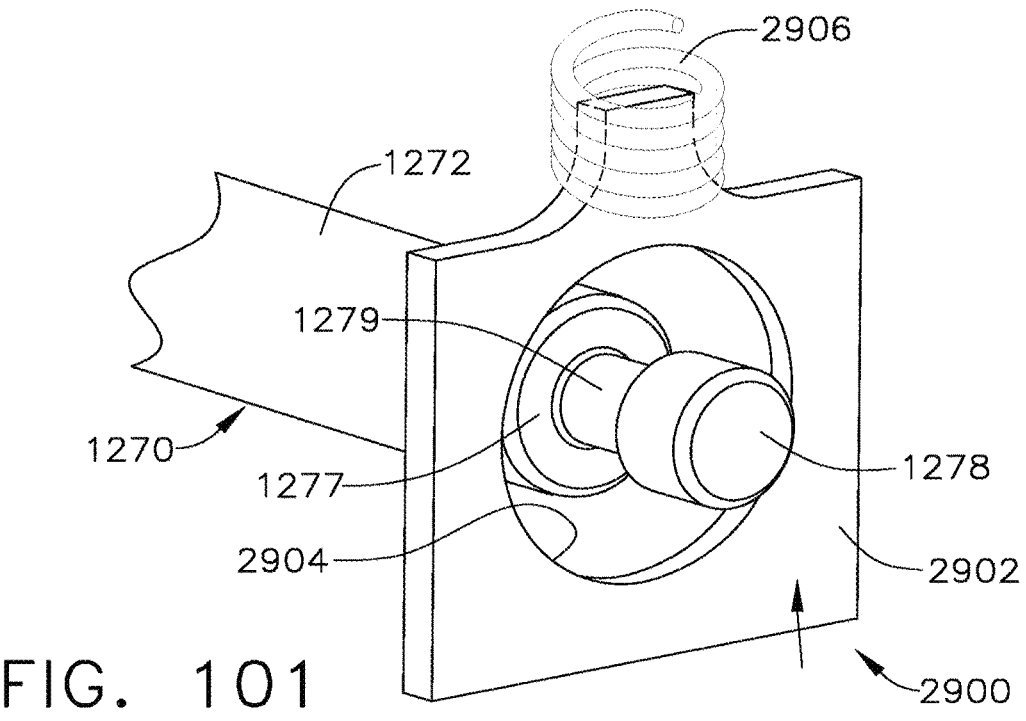
FIG. 101 is another perspective view of the shaft locking assembly and intermediate firing member portion with the shaft locking assembly in an unlocked position.

Referring now to FIGS. 99-101, there is shown a shaft locking assembly 2900 that is configured to prevent axial movement of the firing member 1270 unless the interchangeable shaft assembly has been coupled in operable engagement with the surgical instrument. More particularly, the shaft locking assembly 2900 may prevent axial movement of the firing member 1270 unless the firing member has been coupled in operable engagement with the longitudinally movable drive member 1110 (the longitudinally movable drive member 1110 may be seen in FIG. 88). In at least one form, the shaft locking assembly 2900 may comprise a shaft locking member or locking plate 2902 that has a shaft clearance hole 2904 therethrough and is supported by a portion of the shaft attachment frame or module 1920" for slidable travel in directions "LD" that are substantially transverse to the shaft axis SA-SA. See FIG. 99. The shaft locking plate 2902 may, for example, move between a locked position shown in FIG. 100 wherein the shaft locking plate 2902 extends into the recessed area 1279 between the attachment lug 1278 and the proximal end 1277 of the intermediate firing shaft portion 1272. When in that locked position, the shaft locking plate 2902 prevents any axial movement of the intermediate firing shaft portion 1272. The shaft locking plate 2902 may be biased into the locked position by a lock spring 2906 or other biasing arrangement. Note that FIG. 99 illustrates the locking plate 2902 in an unlocked configuration for clarity purposes. When the interchangeable shaft assembly is not attached to a surgical instrument, the locking plate 2902 will be biased into the locked position as shown in FIG. 100. It will be appreciated that such arrangement prevents any inadvertent axial movement of the firing member 1270 when the interchangeable shaft assembly has not been attached in operable engagement with a surgical instrument (e.g., hand-held instrument, robotic system, etc.).

As was discussed in detail above, during the coupling of the interchangeable shaft assembly to the surgical instrument, the attachment lug 1278 on the end of the intermediate firing shaft portion 1272 enters a cradle 1113 in the distal end of the longitudinally movable drive member 1110. See FIG. 88. As the attachment lug 1278 enters the cradle 1113, the distal end of the longitudinally movable drive member 1110 contacts the shaft locking plate 2902 and moves it to an unlocked position (FIG. 101) wherein the distal end of the longitudinally movable drive member 1110 and the proximal end 1277 of the intermediate firing shaft portion 1272 may axially move within the shaft clearance hole 2904 in response to actuation motions applied to the longitudinally movable drive member 1110.

Figure 102:
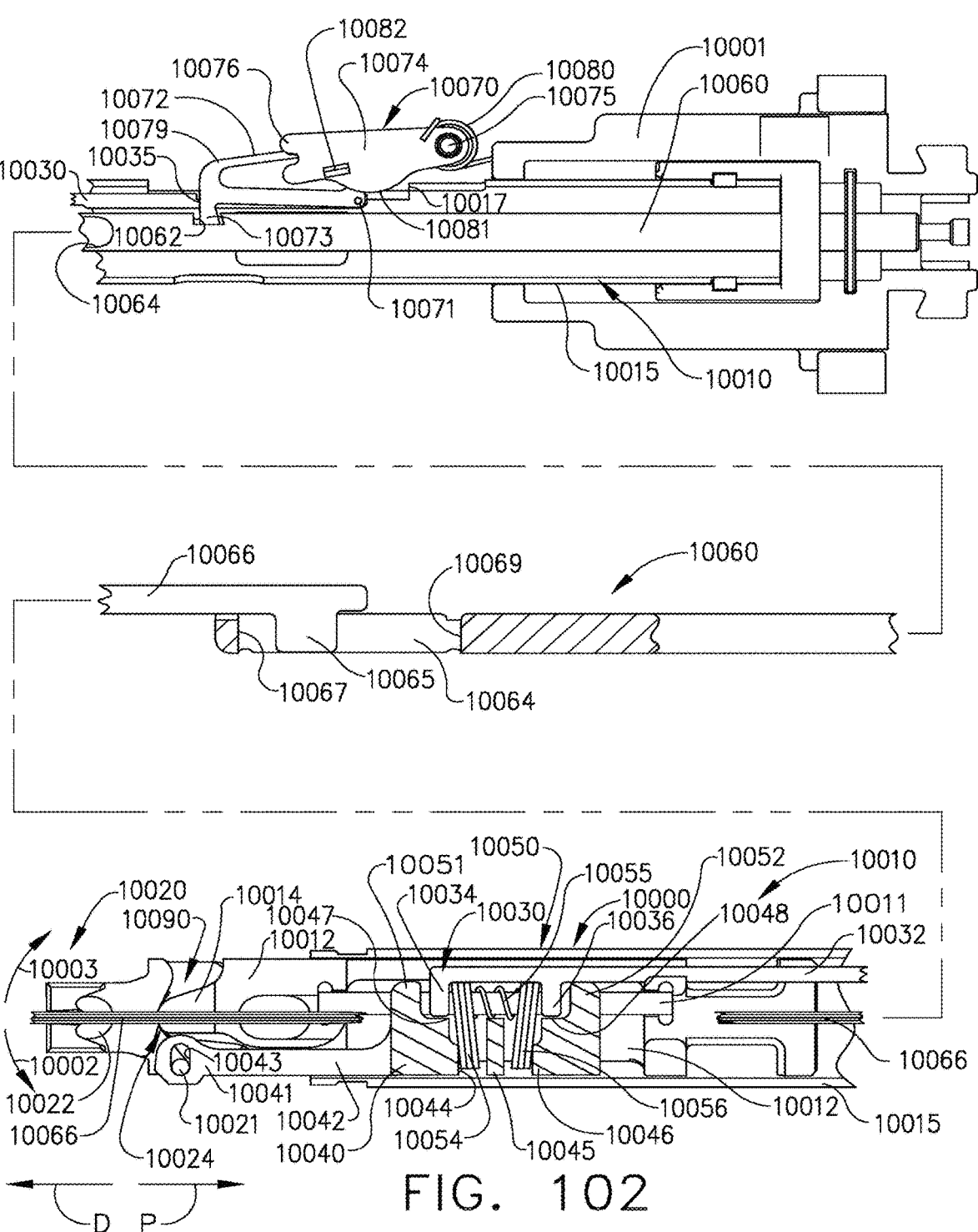
Figure 103:
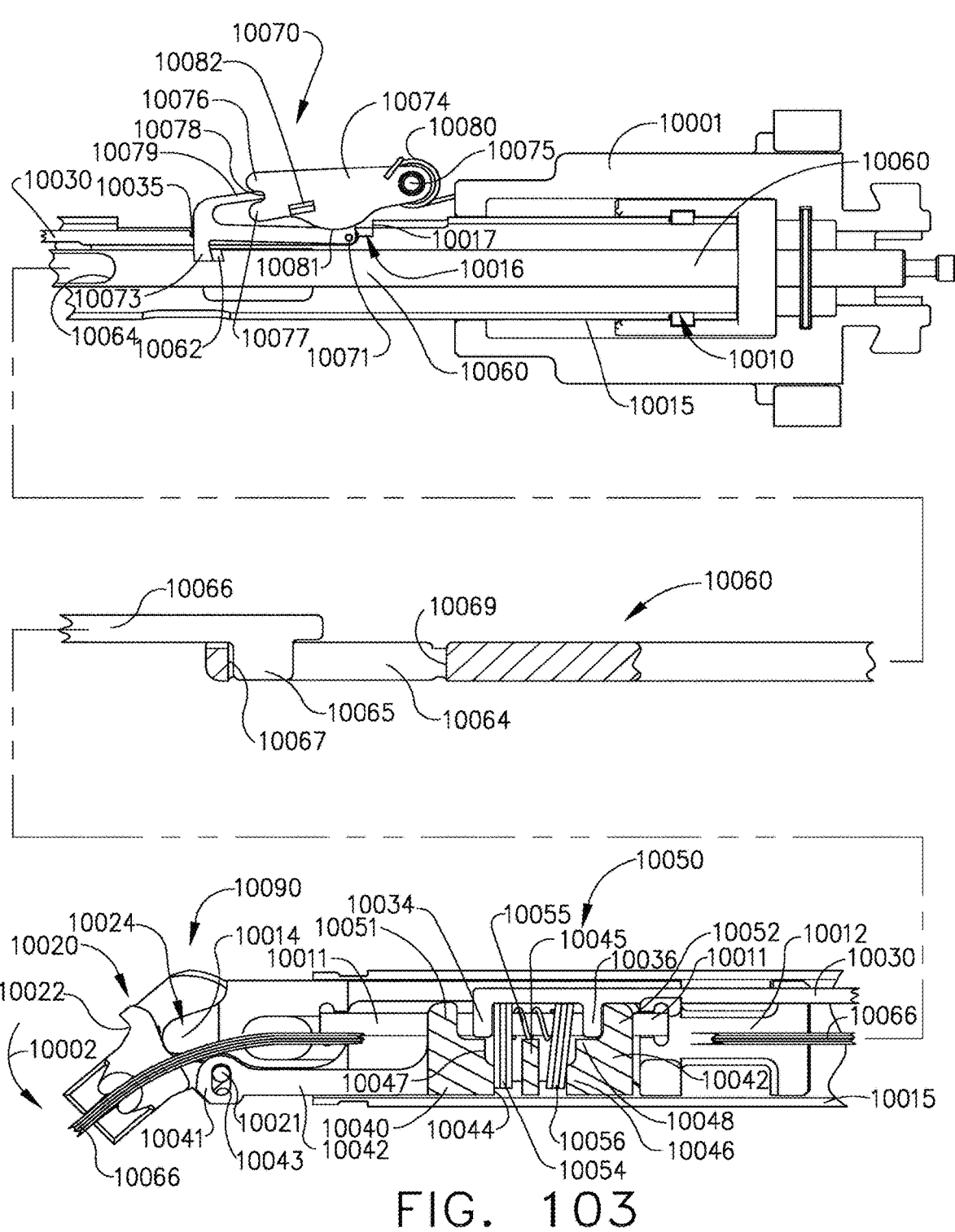
FIG. 103 is a schematic illustrating the clutch assembly of FIG. 102 in its engaged position and the articulation lock of FIG. 102 in a first unlocked condition which permits the articulation of the end effector of FIG. 102 in a first direction.
Figure 104:
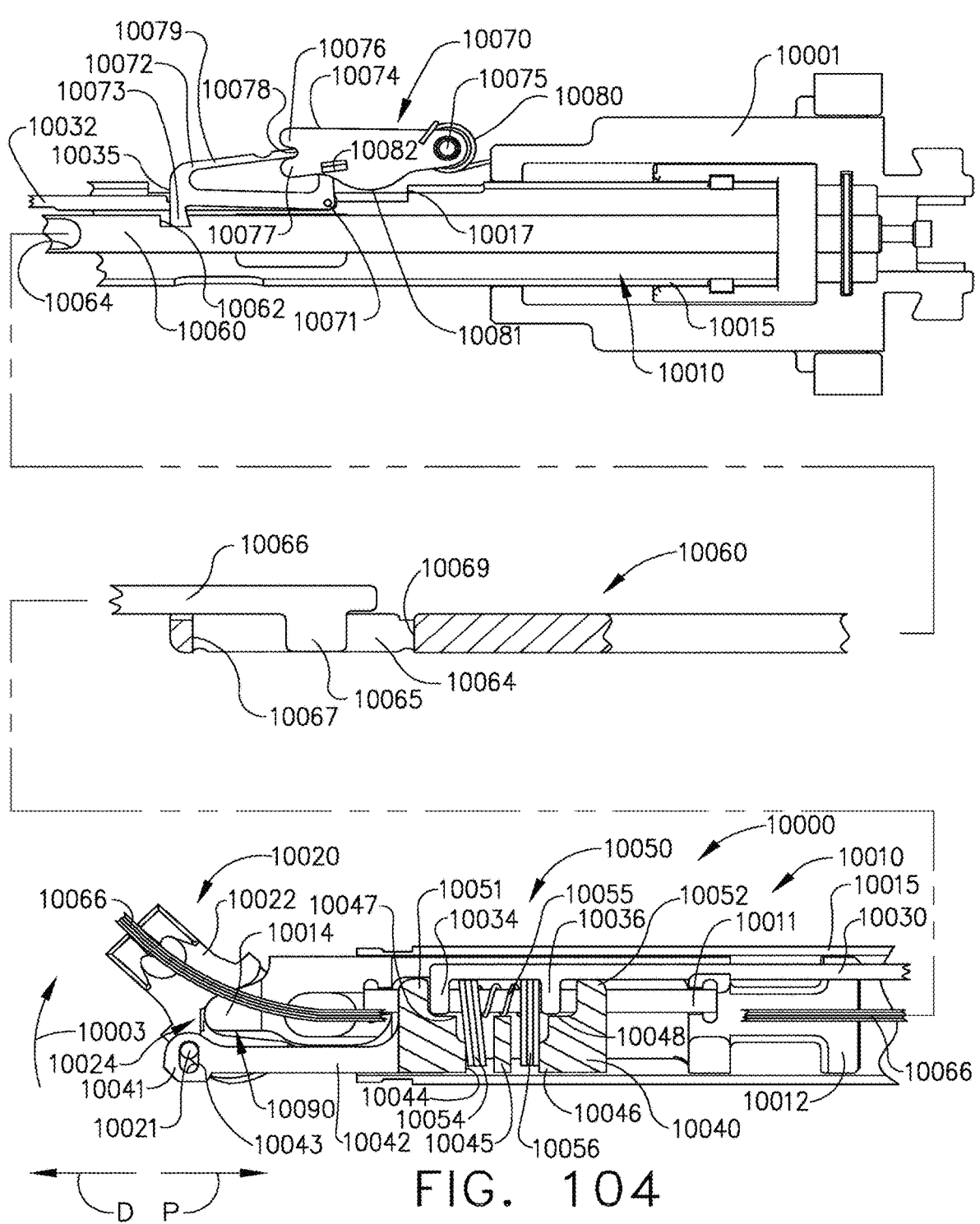
FIG. 104 is a schematic illustrating the clutch assembly of FIG. 102 in its engaged position and the articulation lock of FIG. 102 in a second unlocked condition which permits the articulation of the end effector of FIG. 102 in a second direction.

Turning now to FIGS. 102-112, a surgical instrument, such as surgical instrument 10000, and/or any other surgical instrument, such as surgical instrument system 1000, for example, can comprise a shaft 10010 and an end effector 10020, wherein the end effector 10020 can be articulated relative to the shaft 10010. Further to the above, the surgical instrument 10000 can comprise a shaft assembly comprising the shaft 10010 and the end effector 10020 wherein the shaft assembly can be removably attached to a handle of the surgical instrument 10000. Referring primarily to FIGS. 102-104, the shaft 10010 can comprise a shaft frame 10012 and the end effector 10020 can comprise an end effector frame 10022 wherein the end effector frame 10022 can be rotatably coupled to the shaft frame 10012 about an articulation joint 10090. With regard to the articulation joint 10090, in at least one example, the shaft frame 10012 can comprise a pivot pin 10014 which can be received within a pivot aperture 10024 defined in the end effector frame 10022. The end effector frame 10022 can further comprise a drive pin 10021 extending therefrom which can be operably engaged with an articulation driver. The drive pin 10021 can be configured to receive a force applied thereto and, depending on the direction in which the force is applied to the drive pin 10021, rotate the end effector 10020 in a first direction or a second, opposite, direction. More particularly, when a force is applied to the drive pin 10021 in the distal direction by the articulation driver, the articulation driver can push the drive pin 10021 around the pivot pin 10014 and, similarly, when a force is applied to the drive pin 10021 in the proximal direction by the articulation driver, the articulation driver can pull the drive pin 10021 around the pivot pin 10014 in the opposite direction, for example. To the extent that the drive pin 10021 were to be placed on the opposite side of the articulation joint 10090, for example, the distal and proximal movements of the articulation driver would produce an opposite effect on the end effector 10020.

Further to the above, referring again to FIGS. 102-104, the surgical instrument 10000 can comprise an articulation driver system including a proximal articulation driver 10030 and a distal articulation driver 10040. When a drive force is transmitted to the proximal articulation driver 10030, whether it be in the proximal direction or the distal direction, the drive force can be transmitted to the distal articulation driver 10040 through an articulation lock 10050, as described in greater detail further below. In various circumstances, further to the above, a firing member 10060 of the surgical instrument 10000 can be utilized to impart such a drive force to the proximal articulation driver 10040. For instance, referring primarily to FIGS. 102-112, the surgical instrument 10000 can comprise a clutch system 10070 which can be configured to selectively connect the proximal articulation driver 10030 to the firing member 10060 such that the movement of the firing member 10060 can be imparted to the proximal articulation driver 10030. In use, the clutch system 10070 can be movable between an engaged state (FIGS. 102-108 and 111) in which the proximal articulation driver 10030 is operably engaged with the firing member 10060 and a disengaged state (FIGS. 109, 110, and 112) in which the proximal articulation driver 10030 is not operably engaged with the firing member 10060. In various circumstances, the clutch system 10070 can comprise an engagement member 10072 which can be configured to directly connect the proximal articulation driver 10030 to the firing member 10060. The engagement member 10072 can comprise at least one drive tooth 10073 which can be received within a drive recess 10062 defined in the firing member 10060 when the clutch system 10070 is in its engaged state. In certain circumstances, referring primarily to FIGS. 28 and 31, the engagement member 10072 can comprise a first drive tooth 10073 that extends to one side of the proximal articulation driver 10030 and a second drive tooth 10073 that extends to the other side of the proximal articulation driver 10030 in order to engage the drive recess 10062 defined in the firing member 10060.

Further to the above, referring again to FIGS. 102-112, the clutch system 10070 can further comprise an actuator member 10074 which can be configured to rotate or pivot the engagement member 10072 about a pivot pin 10071 mounted to a proximal end 10039 (FIG. 104A) of the proximal articulation driver 10030. The actuator member 10074 can comprise a first, or outer, projection 10076 and a second, or inner, projection 10077 between which can be defined a recess 10078 configured to receive a control arm 10079 defined in the engagement member 10072. When the actuator member 10074 is rotated away from the firing member 10060, i.e., away from a longitudinal axis of the shaft 10010, the inner projection 10077 can contact the control arm 10079 of the engagement member 10072 and rotate the engagement member 10072 away from the firing member 10060 to move the drive teeth 10073 out of the drive notch 10062 and, as a result, disengage the engagement member 10072 from firing member 10060. Concurrently, the engagement member 10072 can also be disengaged from the proximal articulation driver 10030. In at least one circumstance, the proximal articulation driver 10030 can comprise a drive notch 10035 defined therein which can also be configured to receive a portion of the drive teeth 10073 when the engagement member 10072 is in an engaged position wherein, similar to the above, the drive teeth 10073 can be removed from the drive notch 10035 when the engagement member 10072 is moved into its disengaged position. In certain other circumstances, referring primarily to FIG. 108, the drive teeth 10073 can define a recess 10083 therebetween which can be received in the drive notch 10035. In either event, in a way, the engagement member 10072 can be configured to, one, simultaneously engage the drive notch 10035 in the proximal articulation driver 10030 and the drive notch 10062 in the firing member 10060 when the engagement member 10072 is in its engaged position and, two, be simultaneously disengaged from the drive notch 10035 and the drive notch 10062 when the engagement member 10072 is moved into its disengaged position. With continuing reference to FIGS. 102-104, the actuator member 10074 can be rotatably or pivotably mounted to a housing at least partially surrounding the shaft 10010 via a pivot pin 10075. In some circumstances, the pivot pin 10075 can be mounted to a handle frame 10001 and/or a handle housing surrounding the handle frame 10001, such as a handle housing including portions 11002 and 11003 as illustrated in FIG. 131, for example. The surgical instrument 10000 can further comprise a torsion spring 10080 at least partially surrounding said pivot pin 10075 which can be configured to impart a rotational bias to the actuator member 10074 in order to bias the actuator 10074, and the engagement member 10072, toward the firing member 10060 and to bias the engagement member 10072 into its engaged position. To this end, the outer projection 10076 of the actuator member 10074 can contact the control arm 10079 of the engagement member 10072 and pivot the engagement member 10072 inwardly about the pivot pin 10071.

Figure 108:
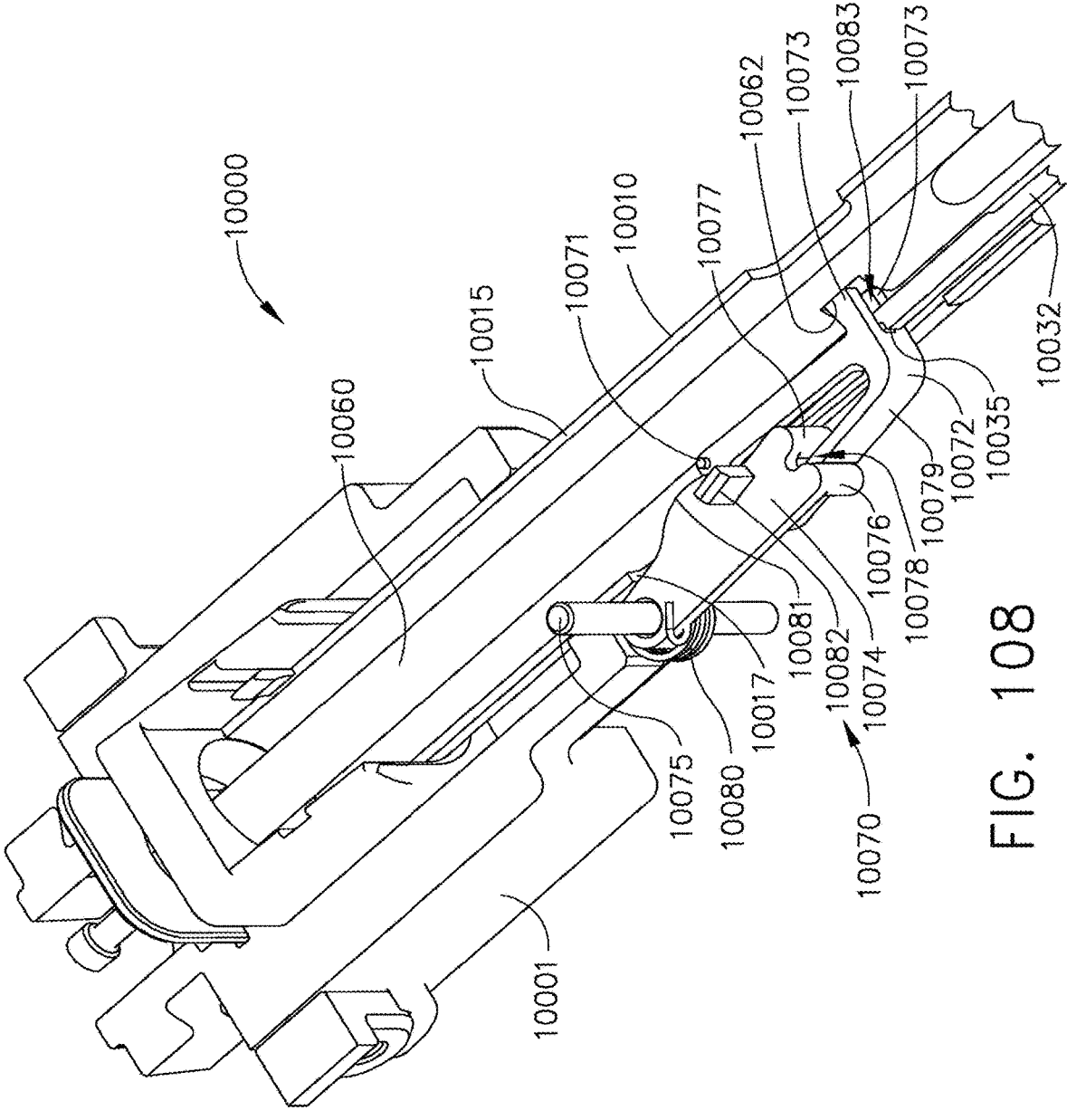
FIG. 108 is a partial perspective view of the shaft assembly of FIG. 105 illustrating the clutch assembly of FIG. 102 in its engaged position with additional portions removed for the purposes of illustration.
Figure 109:
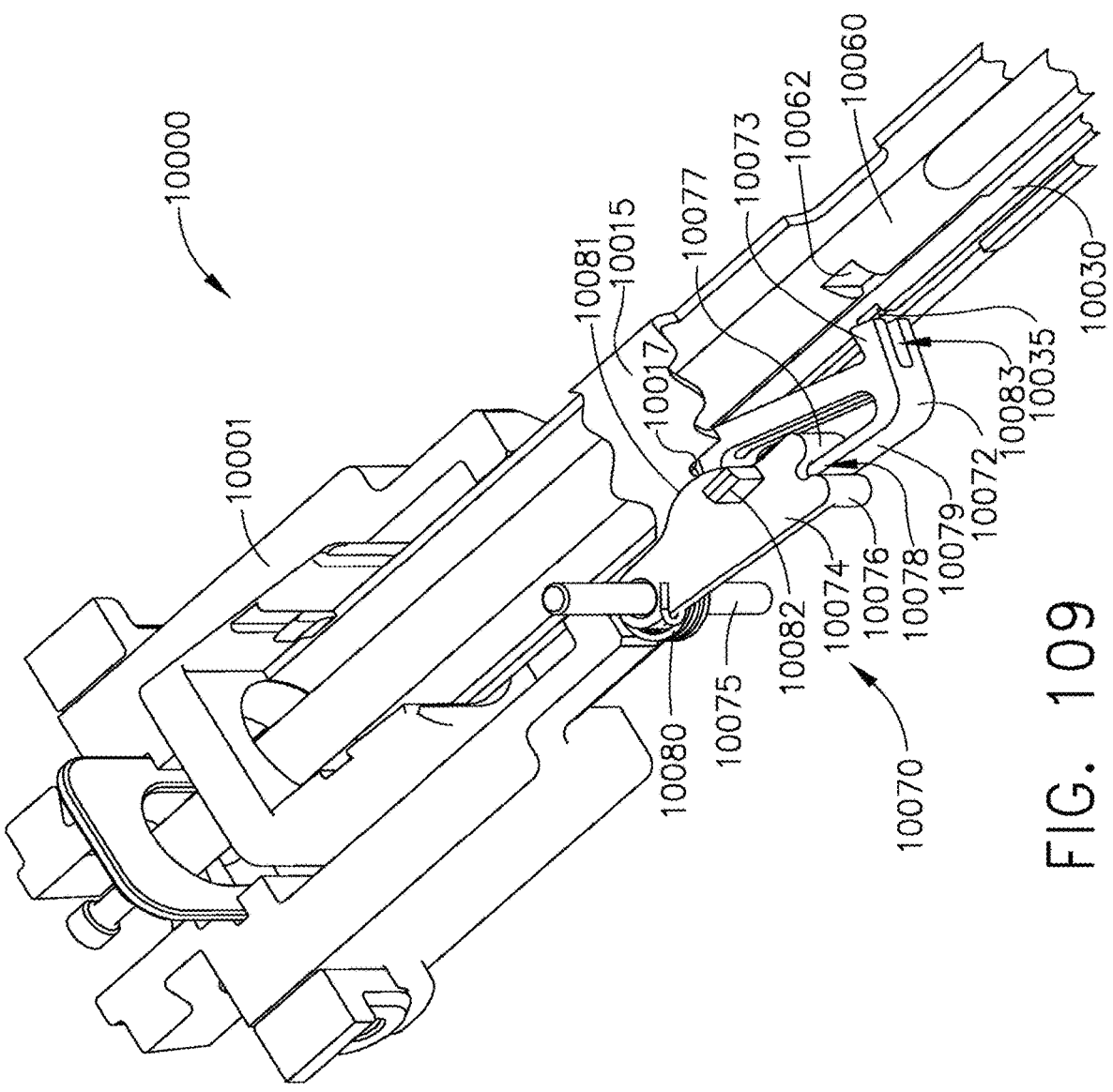
FIG. 109 is a partial perspective view of the shaft assembly of FIG. 105 illustrating the clutch assembly of FIG. 102 in a disengaged position with additional portions removed for the purposes of illustration.
Figure 110:
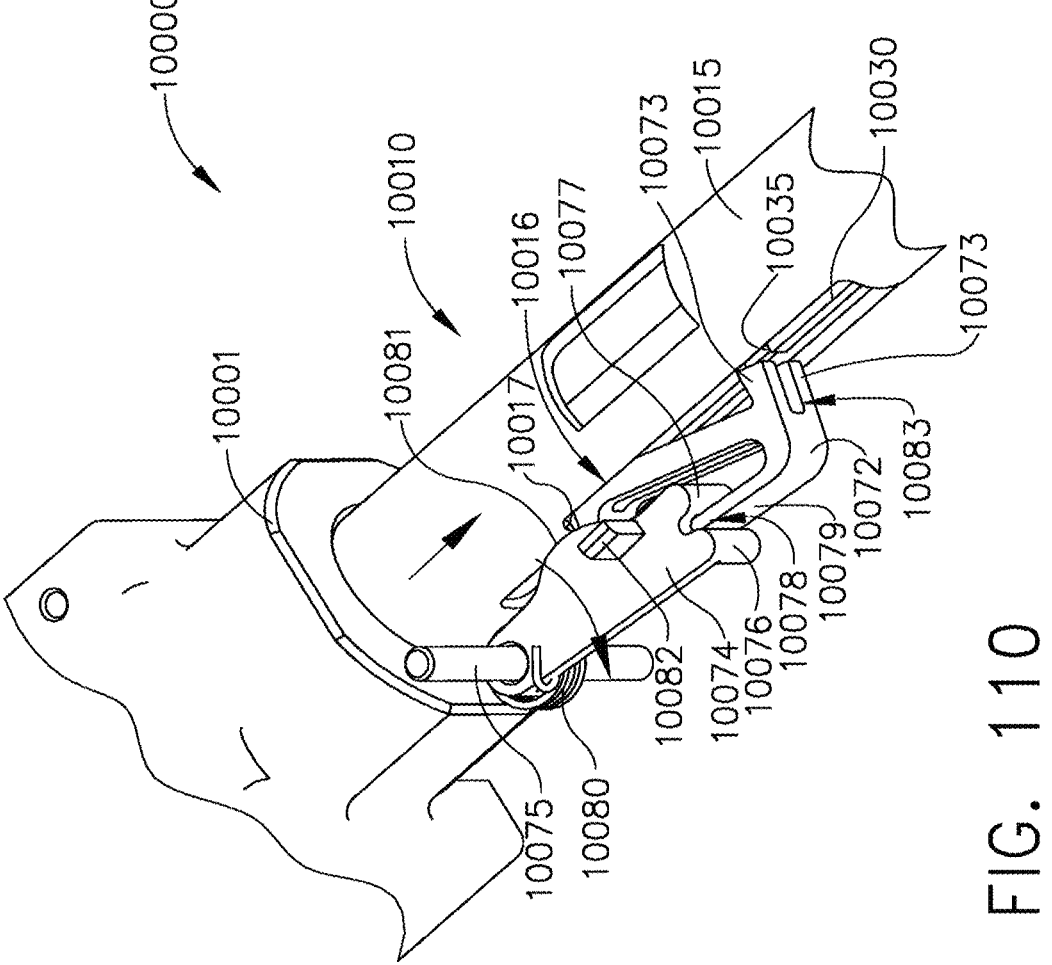
FIG. 110 is a partial perspective view of the shaft assembly of FIG. 105 illustrating the clutch assembly of FIG. 102 moved into a disengaged position by a closure drive of the shaft assembly.
Figures 111, 112:
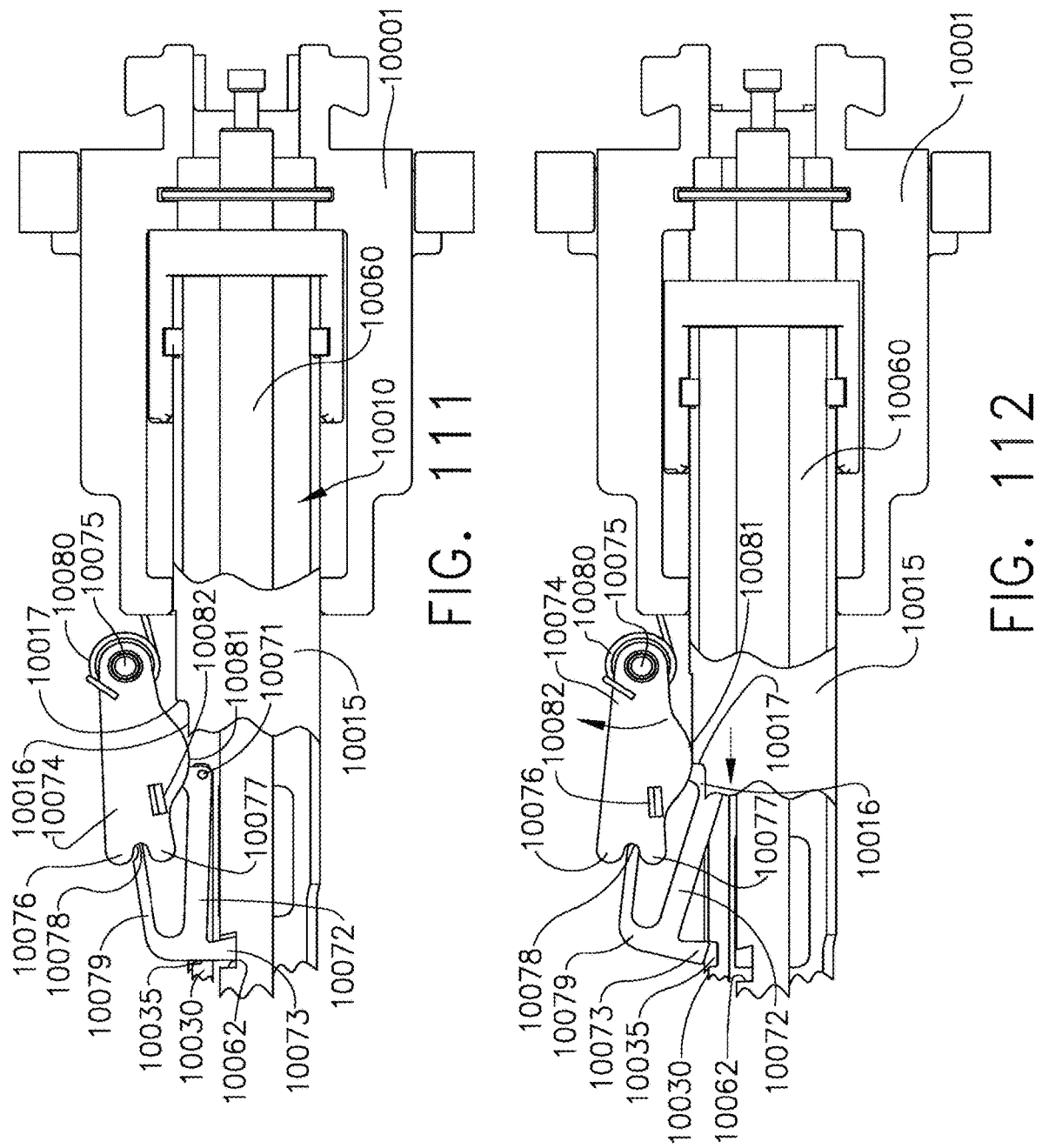
FIG. 111 is a partial plan view of the shaft assembly of FIG. 105 illustrating the clutch assembly of FIG. 102 in its engaged position with additional portions removed for the purposes of illustration.
FIG. 112 is a partial plan view of the shaft assembly of FIG. 105 illustrating the clutch assembly of FIG. 102 in a disengaged position with additional portions removed for the purposes of illustration.

Upon comparing FIGS. 108 and 109, further to the above, the reader will note that the clutch system 10070 has been moved between its engaged state (FIG. 108) and its disengaged state (FIG. 109). A similar comparison can be drawn between FIGS. 111 and 112 wherein the reader will appreciate that a closure tube 10015 of the shaft 10010 has been advanced from a proximal position (FIG. 111) to a distal position (FIG. 112) to move clutch system 10070 between its engaged state (FIG. 111) and its disengaged state (FIG. 112). More particularly, the actuator member 10074 can include a cam follower portion 10081 which can be contacted by the closure tube 10015 and displaced into its disengaged position when the closure tube 10015 is advanced distally to close an anvil, for example, of the end effector 10020. The interaction of a closure tube and an anvil is discussed elsewhere in the present application and is not repeated herein for the sake of brevity. In various circumstances, referring primarily to FIG. 107, the cam follower portion 10081 of the actuator member 10074 can be positioned within a window 10016 defined in the closure tube 10015. When the clutch system 10070 is in its engaged state, the edge or sidewall 10017 of the window 10016 can contact the cam follower portion 10081 and pivot the actuator member 10074 about the pivot pin 10075. In effect, the sidewall 10017 of the window 10016 can act as a cam as the closure tube 10015 is moved into its distal, or closed, position. In at least one circumstance, the actuator member 10074 can comprise a stop extending therefrom which can be configured to engage a housing of the handle, for example, and limit the travel of the actuator member 10074. In certain circumstances, the shaft assembly can include a spring positioned intermediate the housing of the shaft assembly and a ledge 10082 extending from the actuator member 10074 which can be configured to bias the actuator member 10074 into its engaged position. In the distal, closed, position of the closure tube 10015, discussed above, the closure tube 10015 can remain positioned underneath the cam follower portion 10081 to hold the clutch system 10070 in its disengaged state. In such a disengaged state, the movement of the firing member 10060 is not transferred to the proximal articulation driver 10030, and/or any other portion of the articulation driver system. When the closure tube 10015 is retracted back into its proximal, or open, position, the closure tube 10015 can be removed from underneath the cam follower portion 10081 of the actuator member 10074 such that the spring 10080 can bias the actuator member 10074 back into the window 10016 and allow the clutch system 10070 to re-enter into its engaged state.

When the proximal articulation driver 10030 is operatively engaged with the firing member 10060 via the clutch system 10070, further to the above, the firing member 10060 can move the proximal articulation driver 10030 proximally and/or distally. For instance, proximal movement of the firing member 10060 can move the proximal articulation driver 10030 proximally and, similarly, distal movement of the firing member 10060 can move the proximal articulation driver 10030 distally. Referring primarily to FIGS. 102-104, movement of the proximal articulation driver 10030, whether it be proximal or distal, can unlock the articulation lock 10050, as described in greater detail further below. With principal reference to FIG. 102, the articulation lock 10050 can comprise a frame which is co-extensive with a frame 10042 of the distal articulation driver 10040. Collectively, the frame of the articulation lock 10050 and the frame 10042 can be collectively referred to hereinafter as frame 10042. The frame 10042 can comprise a first, or distal, lock cavity 10044 and a second, or proximal, lock cavity 10046 defined therein, wherein the first lock cavity 10044 and the second lock cavity 10046 can be separated by an intermediate frame member 10045. The articulation lock 10050 can further include at least one first lock element 10054 at least partially positioned within the first lock cavity 10044 which can be configured to inhibit or prevent the proximal movement of the distal articulation driver 10040. With regard to the particular embodiment illustrated in FIGS. 102-104, there are three first lock elements 10054 positioned within the first lock cavity 10044 which can all act in a similar, parallel manner and can co-operatively act as a single lock element. Other embodiments are envisioned which can utilize more than three or less than three first lock elements 10054. Similarly, the articulation lock 10050 can further include at least one second lock element 10056 at least partially positioned within the second lock cavity 10046 which can be configured to inhibit or prevent the distal movement of the distal articulation driver 10040. With regard to the particular embodiment illustrated in FIGS. 102-104, there are three second lock elements 10056 positioned within the second lock cavity 10046 which can all act in a similar, parallel manner and can co-operatively act as a single lock element. Other embodiments are envisioned which can utilize more than three or less than three second lock elements 10056.

Figure 104A:
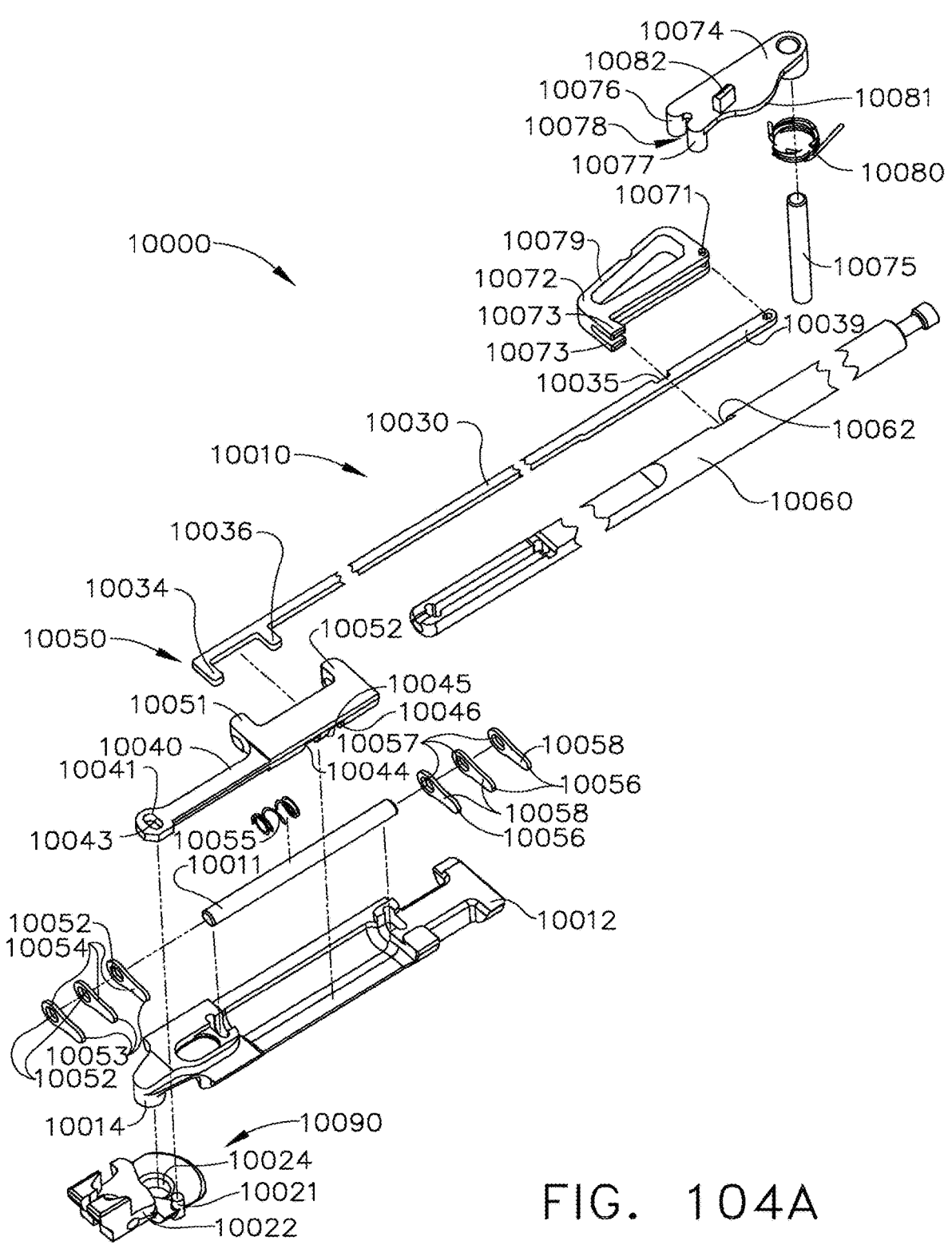
FIG. 104A is an exploded view of the clutch assembly and the articulation lock of FIG. 102.
Figure 105:
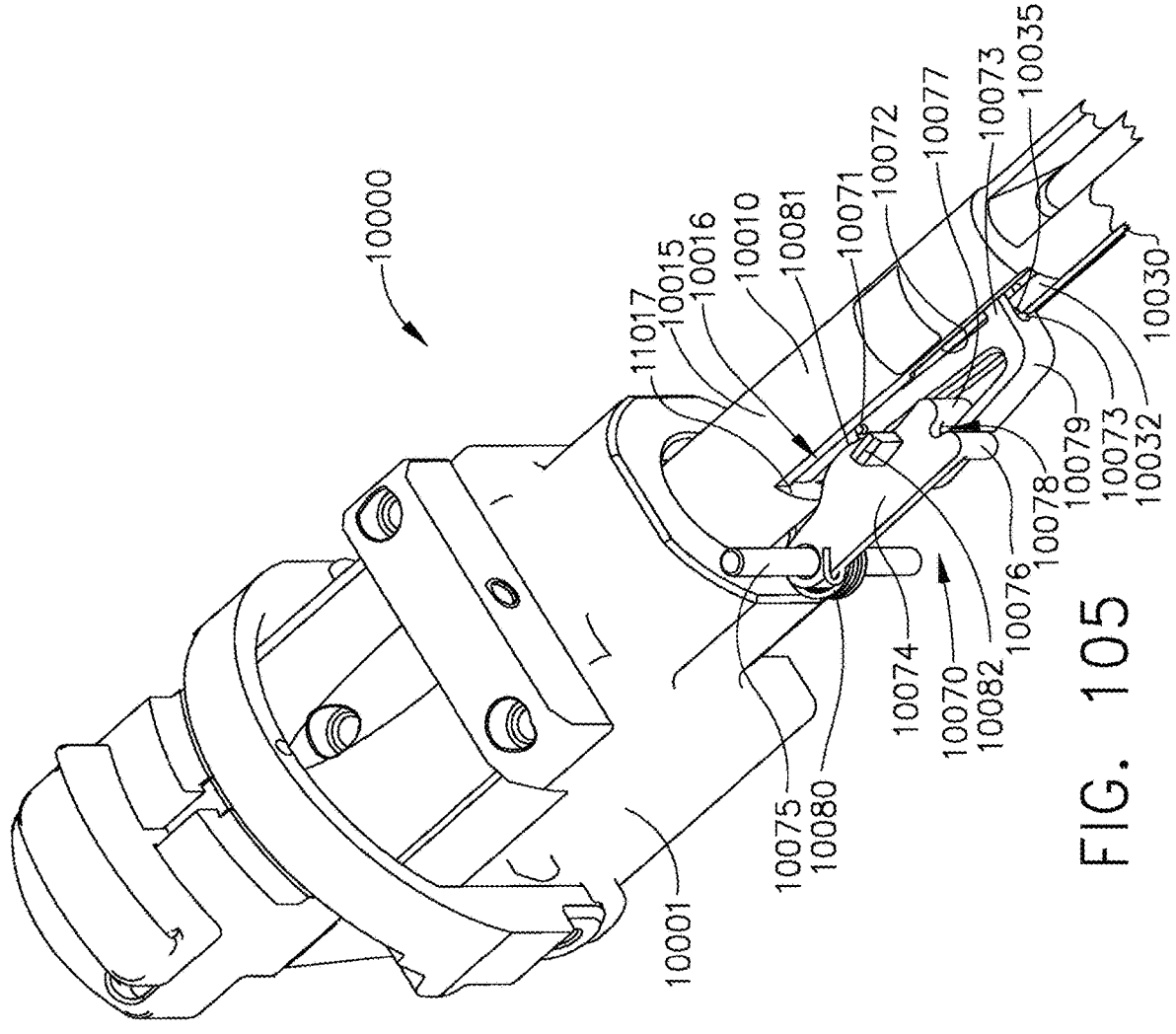
FIG. 105 is a partial perspective view of a shaft assembly including the clutch assembly of FIG. 102 in its engaged position with portions of the shaft assembly removed for the purposes of illustration.
Figures 106, 107:
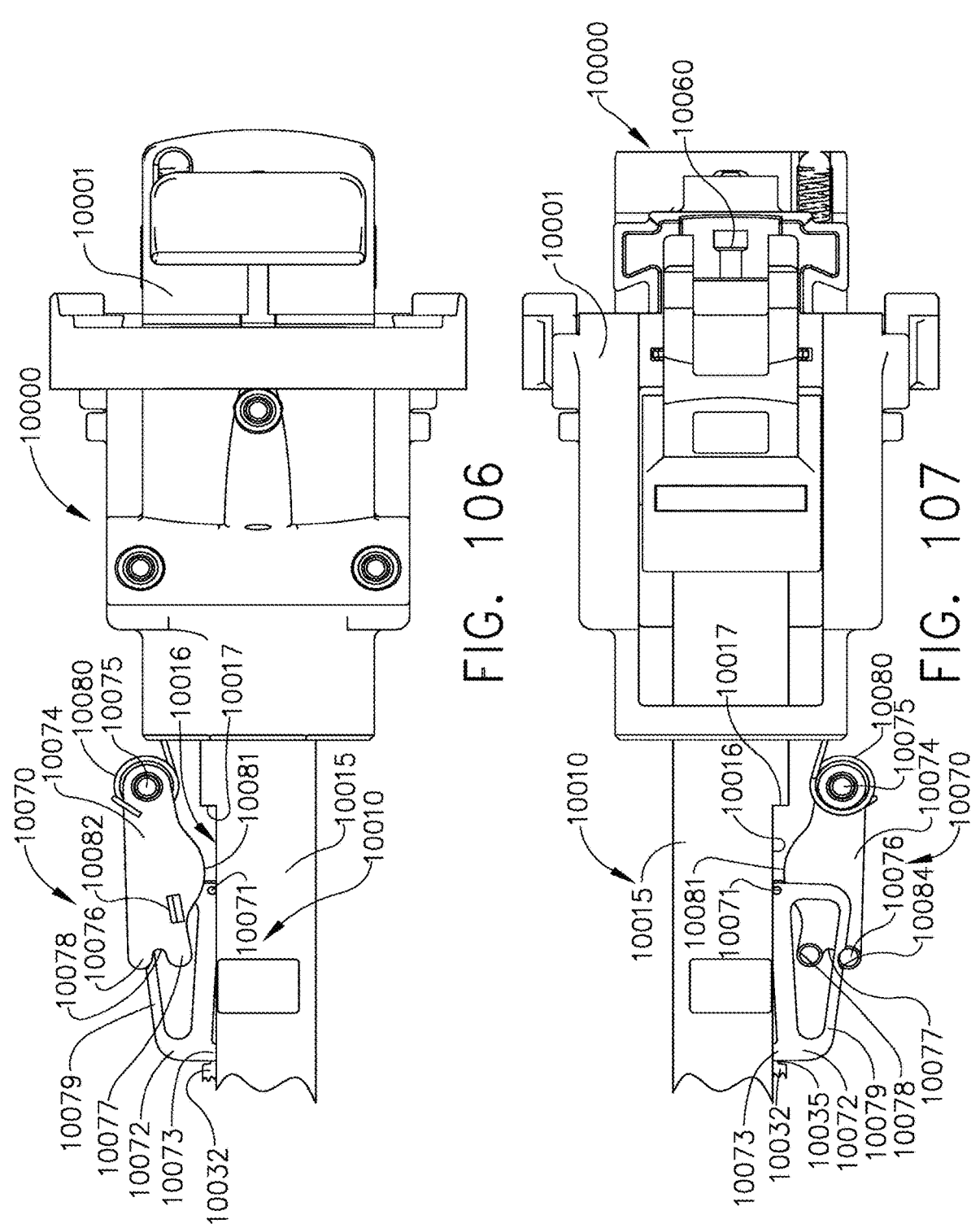
FIG. 106 is a partial top plan view of the shaft assembly of FIG. 105 illustrating the clutch assembly of FIG. 102 in its engaged position.
FIG. 107 is a partial bottom plan view of the shaft assembly of FIG. 105 illustrating the clutch assembly of FIG. 102 in its engaged position.

Further to the above, referring primarily to FIG. 104A, each first lock element 10054 can comprise a lock aperture 10052 and a lock tang 10053. The lock tang 10053 can be disposed within the first lock cavity 10044 and the lock aperture 10052 can be slidably engaged with a frame rail 10011 mounted to the shaft frame 10012. Referring again to FIG. 102, the frame rail 10011 extends through the apertures 10052 in the first lock elements 10054. As the reader will note, with further reference to FIG. 102, the first lock elements 10054 are not oriented in a perpendicular arrangement with the frame rail 10011; rather, the first lock elements 10054 are arranged and aligned at a non-perpendicular angle with respect to the frame rail 10011 such that the edges or sidewalls of the lock apertures 10052 are engaged with the frame rail 10011. Moreover, the interaction between the sidewalls of the lock apertures 10052 and the frame rail 10011 can create a resistive or friction force therebetween which can inhibit relative movement between the first lock elements 10054 and the frame rail 10011 and, as a result, resist a proximal pushing force P applied to the distal articulation driver 10040. Stated another way, the first lock elements 10054 can prevent or at least inhibit the end effector 10020 from rotating in a direction indicated by arrow 10002. If a torque is applied to the end effector 10020 in the direction of arrow 10002, a proximal pushing force P will be transmitted from the drive pin 10021 extending from the frame 10022 of the end effector 10024 to the frame 10042 of the distal articulation driver 10040. In various circumstances, the drive pin 10021 can be closely received within a pin slot 10043 defined in the distal end 10041 of the distal articulation driver 10040 such that the drive pin 10021 can bear against a proximal sidewall of the pin slot 10043 and transmit the proximal pushing force P to the distal articulation driver 10040. Further to the above, however, the proximal pushing force P will only serve to bolster the locking engagement between the first lock elements 10054 and the frame rail 10011. More particularly, the proximal pushing force P can be transmitted to the tangs 10053 of the first lock elements 10054 which can cause the first lock elements 10054 to rotate and decrease the angle defined between first lock elements 10054 and the frame rail 10011 and, as a result, increase the bite between the sidewalls of the lock apertures 10052 and the frame rail 10011. Ultimately, then, the first lock elements 10054 can lock the movement of the distal articulation driver 10040 in one direction.

In order to release the first lock elements 10054 and permit the end effector 10020 to be rotated in the direction indicated by arrow 10002, referring now to FIG. 103, the proximal articulation driver 10030 can be pulled proximally to straighten, or at least substantially straighten, the first lock elements 10054 into a perpendicular, or at least substantially perpendicular, position. In such a position, the bite, or resistive force, between the sidewalls of the lock apertures 10052 and the frame rail 10011 can be sufficiently reduced, or eliminated, such that the distal articulation driver 10040 can be moved proximally. In order to straighten the first lock elements 10054 into the position illustrated in FIG. 103, the proximal articulation driver 10030 can be pulled proximally such that a distal arm 10034 of the proximal articulation driver 10030 contacts the first lock elements 10054 to pull and rotate the first lock elements 10054 into their straightened position. In various circumstances, the proximal articulation driver 10030 can continue to be pulled proximally until a proximal arm 10036 extending therefrom contacts, or abuts, a proximal drive wall 10052 of the frame 10042 and pulls the frame 10042 proximally to articulate the end effector 10002. In essence, a proximal pulling force can be applied from the proximal articulation driver 10030 to the distal articulation driver 10040 through the interaction between the proximal arm 10036 and the proximal drive wall 10052 wherein such a pulling force can be transmitted through the frame 10042 to the drive pin 10021 to articulate the end effector 10020 in the direction indicated by arrow 10002. After the end effector 10020 has been suitably articulated in the direction of arrow 10002, the proximal articulation driver 10040 can be released, in various circumstances, to permit the articulation lock 10050 to re-lock the distal articulation member 10040, and the end effector 10020, in position. In various circumstances, the articulation lock 10050 can comprise a spring 10055 positioned intermediate the group of first lock elements 10054 and the group of second lock elements 10056 which can be compressed when the first lock elements 10054 are straightened to unlock the proximal movement of the distal articulation driver 10040, as discussed above. When the proximal articulation driver 10030 is released, the spring 10055 can resiliently re-expand to push the first lock elements 10054 into their angled positions illustrated in FIG. 102.

Concurrent to the above, referring again to FIGS. 102 and 103, the second lock elements 10056 can remain in an angled position while the first lock elements 10054 are locked and unlocked as described above. The reader will appreciate that, although the second lock elements 10056 are arranged and aligned in an angled position with respect to the shaft rail 10011, the second lock elements 10056 are not configured to impede, or at least substantially impede, the proximal motion of the distal articulation driver 10040. When the distal articulation driver 10040 and articulation lock 10050 are slid proximally, as described above, the second lock elements 10056 can slide distally along the frame rail 10011 without, in various circumstances, changing, or at least substantially changing, their angled alignment with respect to the frame rail 10011. While the second lock elements 10056 are permissive of the proximal movement of the distal articulation driver 10040 and the articulation lock 10050, the second lock elements 10056 can be configured to selectively prevent, or at least inhibit, the distal movement of the distal articulation driver 10040, as discussed in greater detail further below.

Similar to the above, referring primarily to FIG. 104A, each second lock element 10056 can comprise a lock aperture 10057 and a lock tang 10058. The lock tang 10058 can be disposed within the second lock cavity 10046 and the lock aperture 10057 can be slidably engaged with the frame rail 10011 mounted to the shaft frame 10012. Referring again to FIG. 102, the frame rail 10011 extends through the apertures 10057 in the second lock elements 10056. As the reader will note, with further reference to FIG. 102, the second lock elements 10056 are not oriented in a perpendicular arrangement with the frame rail 10011; rather, the second lock elements 10056 are arranged and aligned at a non-perpendicular angle with respect to the frame rail 10011 such that the edges or sidewalls of the lock apertures 10057 are engaged with the frame rail 10011. Moreover, the interaction between the sidewalls of the lock apertures 10057 and the frame rail 10011 can create a resistive or friction force therebetween which can inhibit relative movement between the second lock elements 10056 and the frame rail 10011 and, as a result, resist a distal force D applied to the distal articulation driver 10040. Stated another way, the second lock elements 10056 can prevent or at least inhibit the end effector 10020 from rotating in a direction indicated by arrow 10003. If a torque is applied to the end effector 10020 in the direction of arrow 10003, a distal pulling force D will be transmitted from the drive pin 10021 extending from the frame 10022 of the end effector 10024 to the frame 10042 of the distal articulation driver 10040. In various circumstances, the drive pin 10021 can be closely received within the pin slot 10043 defined in the distal end 10041 of the distal articulation driver 10040 such that the drive pin 10021 can bear against a distal sidewall of the pin slot 10043 and transmit the distal pulling force D to the distal articulation driver 10040. Further to the above, however, the distal pulling force D will only serve to bolster the locking engagement between the second lock elements 10056 and the frame rail 10011. More particularly, the distal pulling force D can be transmitted to the tangs 10058 of the second lock elements 10056 which can cause the second lock elements 10056 to rotate and decrease the angle defined between second lock elements 10056 and the frame rail 10011 and, as a result, increase the bite between the sidewalls of the lock apertures 10057 and the frame rail 10011. Ultimately, then, the second lock elements 10056 can lock the movement of the distal articulation driver 10040 in one direction.

In order to release the second lock elements 10056 and permit the end effector 10020 to be rotated in the direction indicated by arrow 10003, referring now to FIG. 104, the proximal articulation driver 10030 can be pushed distally to straighten, or at least substantially straighten, the second lock elements 10056 into a perpendicular, or at least substantially perpendicular, position. In such a position, the bite, or resistive force, between the sidewalls of the lock apertures 10057 and the frame rail 10011 can be sufficiently reduced, or eliminated, such that the distal articulation driver 10040 can be moved distally. In order to straighten the second lock elements 10056 into the position illustrated in FIG. 104, the proximal articulation driver 10030 can be pushed distally such that the proximal arm 10036 of the proximal articulation driver 10030 contacts the second lock elements 10056 to push and rotate the second lock elements 10056 into their straightened position. In various circumstances, the proximal articulation driver 10030 can continue to be pushed distally until the distal arm 10034 extending therefrom contacts, or abuts, a distal drive wall 10051 of the frame 10042 and pushes the frame 10042 distally to articulate the end effector 10020. In essence, a distal pushing force can be applied from the proximal articulation driver 10030 to the distal articulation driver 10040 through the interaction between the distal arm 10034 and the distal drive wall 10051 wherein such a pushing force can be transmitted through the frame 10042 to the drive pin 10021 to articulate the end effector 10020 in the direction indicated by arrow 10003. After the end effector 10020 has been suitably articulated in the direction of arrow 10003, the proximal articulation driver 10040 can be released, in various circumstances, to permit the articulation lock 10050 to re-lock the distal articulation member 10040, and the end effector 10020, in position. In various circumstances, similar to the above, the spring 10055 positioned intermediate the group of first lock elements 10054 and the group of second lock elements 10056 can be compressed when the second lock elements 10056 are straightened to unlock the distal movement of the distal articulation driver 10040, as discussed above. When the proximal articulation driver 10040 is released, the spring 10055 can resiliently re-expand to push the second lock elements 10056 into their angled positions illustrated in FIG. 102.

Concurrent to the above, referring again to FIGS. 102 and 104, the first lock elements 10054 can remain in an angled position while the second lock elements 10056 are locked and unlocked as described above. The reader will appreciate that, although the first lock elements 10054 are arranged and aligned in an angled position with respect to the shaft rail 10011, the first lock elements 10054 are not configured to impede, or at least substantially impede, the distal motion of the distal articulation driver 10040. When the distal articulation driver 10040 and articulation lock 10050 are slid distally, as described above, the first lock elements 10054 can slide distally along the frame rail 10011 without, in various circumstances, changing, or at least substantially changing, their angled alignment with respect to the frame rail 10011. While the first lock elements 10054 are permissive of the distal movement of the distal articulation driver 10040 and the articulation lock 10050, the first lock elements 10054 are configured to selectively prevent, or at least inhibit, the proximal movement of the distal articulation driver 10040, as discussed above.

In view of the above, the articulation lock 10050, in a locked condition, can be configured to resist the proximal and distal movements of the distal articulation driver 10040. In terms of resistance, the articulation lock 10050 can be configured to prevent, or at least substantially prevent, the proximal and distal movements of the distal articulation driver 10040. Collectively, the proximal motion of the distal articulation driver 10040 is resisted by the first lock elements 10054 when the first lock elements 10054 are in their locked orientation and the distal motion of the distal articulation driver 10040 is resisted by the second lock elements 10056 when the second lock elements 10056 are in their locked orientation, as described above. Stated another way, the first lock elements 10054 comprise a first one-way lock and the second lock elements 10056 comprise a second one-way lock which locks in an opposite direction.

When the first lock elements 10054 are in a locked configuration, referring again to FIG. 102 and as discussed above, an attempt to move the distal articulation driver 10040 proximally may only serve to further decrease the angle between the first lock elements 10054 and the frame rail 10011. In various circumstances, the first lock elements 10054 may flex while, in at least some circumstances, the first lock elements 10054 may abut a distal shoulder 10047 defined in the first lock cavity 10044. More precisely, the outer-most first lock element 10054 may abut the distal shoulder 10047 while the other first lock elements 10054 may abut an adjacent first lock element 10054. In some circumstances, the distal shoulder 10047 can arrest the movement of the first lock elements 10054. In certain circumstances, the distal shoulder 10047 can provide strain relief. For instance, once the distal shoulder 10047 is in contact with the first lock elements 10054, the distal shoulder 10047 can support the first lock elements 10054 at a location which is adjacent to, or at least substantially adjacent to, the lock rail 10011 such that only a small lever arm, or torque arm, separates opposing forces transmitted through the first lock elements 10054 at different locations thereof. In such circumstances, in effect, the force transmitted through the tangs 10053 of the first lock elements 10054 may be reduced or eliminated.

Similar to the above, when the second lock elements 10056 are in a locked configuration, referring again to FIG. 102 and as discussed above, an attempt to move the distal articulation driver 10040 distally may only serve to further decrease the angle between the second lock elements 10056 and the frame rail 10011. In various circumstances, the second lock elements 10056 may flex while, in at least some circumstances, the second lock elements 10056 may abut a proximal shoulder 10048 defined in the second lock cavity 10046. More precisely, the outer-most second lock element 10056 may abut the proximal shoulder 10048 while the other second lock elements 10056 may abut an adjacent second lock element 10056. In some circumstances, the proximal shoulder 10048 can arrest the movement of the second lock elements 10056. In certain circumstances, the proximal shoulder 10048 can provide strain relief. For instance, once the proximal shoulder 10048 is in contact with the second lock elements 10056, the proximal shoulder 10048 can support the second lock elements 10056 at a location which is adjacent to, or at least substantially adjacent to, the lock rail 10011 such that only a small lever arm, or torque arm, separates opposing forces transmitted through the second lock elements 10056 at different locations thereof. In such circumstances, in effect, the force transmitted through the tangs 10058 of the second lock elements 10056 may be reduced or eliminated.

Discussed in connection with the illustrative embodiment illustrated in FIGS. 102-112, an initial proximal movement of the proximal articulation driver 10030 can unlock the proximal movement of the distal articulation driver 10040 and the articulation lock 10050 while a further proximal movement of the proximal articulation driver 10030 can drive the distal articulation driver 10040 and the articulation lock 10050 proximally. Similarly, an initial distal movement of the proximal articulation driver 10030 can unlock the distal movement of the distal articulation driver 10040 and the articulation lock 10050 while a further distal movement of the proximal articulation driver 10030 can drive the distal articulation driver 10040 and the articulation lock 10050 distally. Such a general concept is discussed in connection with several additional illustrative embodiments disclosed below. To the extent that such discussion is duplicative, or generally cumulative, with the discussion provided in connection with the illustrative embodiment disclosed in FIGS. 102-112, such discussion is not reproduced for the sake of brevity.

Figures 113, 114:
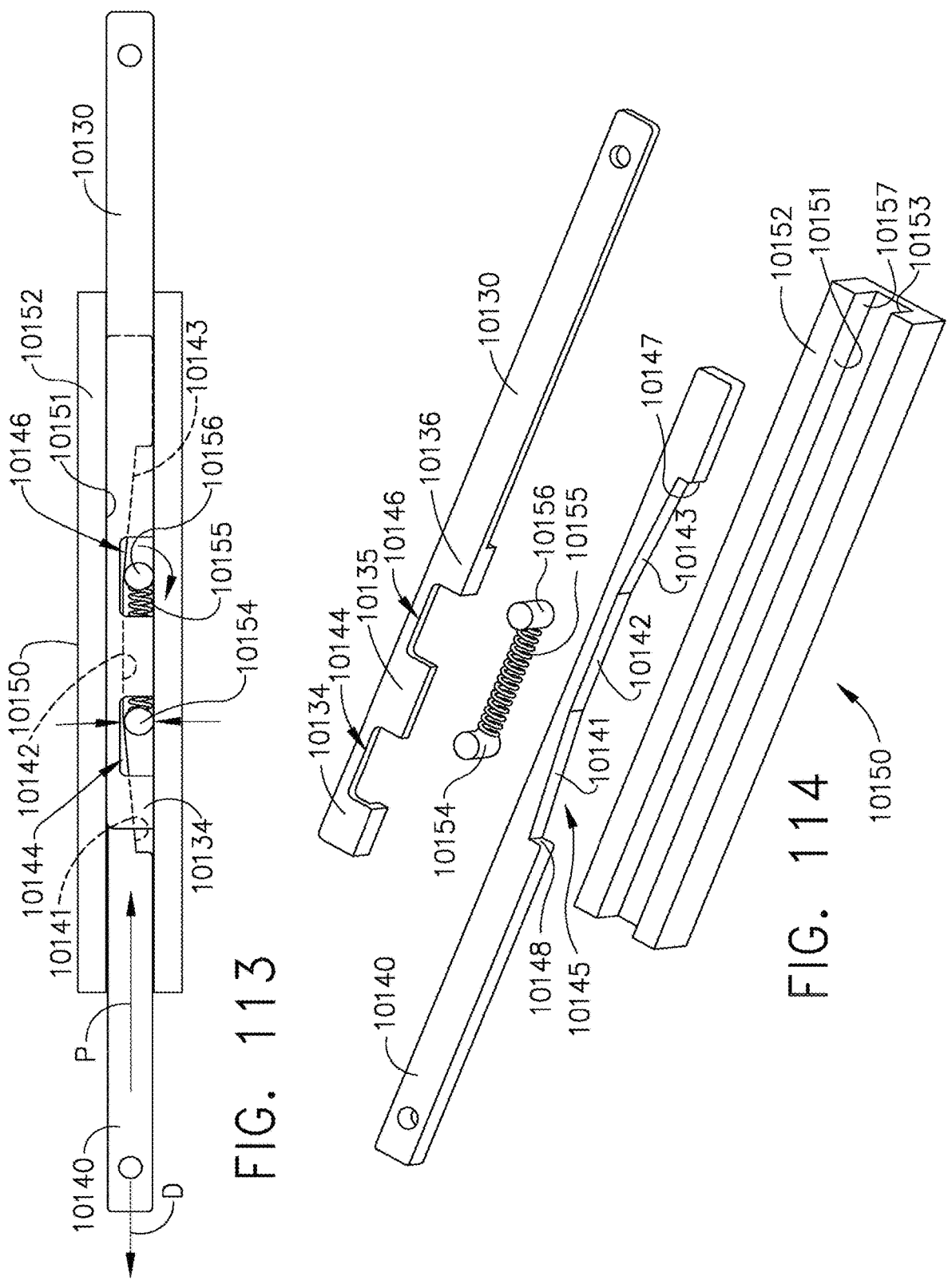
FIG. 113 is a plan view of an alternative embodiment of an articulation lock illustrated in a locked condition.
FIG. 114 is an exploded view of the articulation lock of FIG. 113.

Turning now to FIGS. 113 and 114, a surgical instrument, such as surgical instrument 10000, and/or any other surgical instrument system, for example, can comprise a proximal articulation driver 10130, a distal articulation driver 10140, and an articulation lock 10150. The articulation lock 10150 can comprise a frame 10152 which can include a slot, or lock channel, 10151 defined therein configured to receive at least a portion of the proximal articulation driver 10130 and at least a portion of the distal articulation driver 10140. The articulation lock 10150 can further comprise a first lock element 10154 positioned within a first, or distal, lock cavity 10144 and a second lock element 10155 positioned within a second, or proximal, lock cavity 10146. Similar to the above, the first lock element 10154 can be configured to resist a proximal pushing force P transmitted through the distal articulation driver 10140. To this end, the distal articulation driver 10140 can include a lock recess 10145 defined therein which can include one or more lock surfaces configured to engage the first lock element 10154 and prevent the movement of the distal articulation driver 10140 relative to the lock frame 10152. More specifically, a sidewall of the lock recess 10145 can comprise a first, or distal, lock surface 10141 which can be configured to wedge the first lock element 10154 against a sidewall, or lock wall, 10153 of the lock channel 10151 and, owing to this wedged relationship, the distal articulation driver 10140 may not be able to pass between the first lock element 10154 and the opposing sidewall 10157 of the lock channel 10151. The reader will appreciate that the lock recess 10145 is contoured such that it gradually decreases in depth toward the distal end of the lock recess 10145 wherein, correspondingly, the distal articulation driver 10140 gradually increases in thickness toward the distal end of the lock recess 10145. As a result, a proximal pushing force P applied to the distal articulation driver 10140 may only serve to further increase the resistance, or wedging force, holding the distal articulation driver 10140 in position.

In order to pull the distal articulation driver 10140 proximally, the proximal articulation driver 10130 can be configured to, one, displace the distal lock element 10154 proximally to unlock the articulation lock 10150 in the proximal direction and, two, directly engage the distal articulation driver 10140 and apply a proximal pulling force thereto. More specifically, further to the above, the proximal articulation driver 10130 can comprise a distal arm 10134 configured to initially engage the first lock element 10154 and a proximal arm 10136 which can be configured to then engage a proximal drive wall 10147 defined at the proximal end of the lock recess 10145 and pull the distal articulation driver 10140 proximally. Similar to the above, the proximal movement of the distal articulation driver 10140 can be configured to articulate the end effector of the surgical instrument. Once the end effector has been suitably articulated, the proximal articulation driver 10130 can be released, in various circumstances, to permit a spring 10155 positioned intermediate the first lock element 10154 and the second lock element 10156 to expand and sufficiently reposition the first lock element 10154 relative to the first lock surface 10141 and re-lock the distal articulation driver 10140 and the end effector in position.

Concurrent to the above, the second lock element 10156 may not resist, or at least substantially resist, the proximal movement of the distal articulation driver 10140. When the articulation lock 10150 is in a locked condition, the second lock element 10156 may be positioned between a second, or proximal, lock surface 10143 of the lock recess 10145 and the lock wall 10153 of the lock channel 10151. As the distal articulation driver 10140 is pulled proximally by the proximal articulation driver 10130, further to the above, a dwell portion 10142 of the lock recess 10145 may move over the second lock element 10156. In various circumstances, the dwell portion 10142 of the lock recess 10145 may comprise the widest portion of the recess 10145 which may, as a result, permit relative sliding movement between the distal articulation driver 10140 and the second lock element 10156 as the distal articulation driver 10140 is pulled proximally. In some circumstances, the second lock element 10156 can be configured to roll within the dwell portion 10142 thereby reducing the resistance force between the distal articulation driver 10140 and the second lock element 10156. As the reader will appreciate, the second lock element 10156 may be permissive to the proximal movement of the distal articulation driver 10140 but can be configured to selectively resist the distal movement of the distal articulation driver 10140 as discussed in greater detail further below.

Similar to the above, the second lock element 10156 can be configured to resist a distal pulling force D transmitted through the distal articulation member 10140. To this end, the second lock surface 10143 of the lock recess 10145 can be configured to wedge the second lock element 10156 against the lock wall 10153 of the lock channel 10151 and, owing to this wedged relationship, the distal articulation driver 10140 may not be able to pass between the second lock element 10156 and the opposing sidewall 10157 of the lock channel 10151. The reader will appreciate that the lock recess 10145 is contoured such that it gradually decreases in depth toward the proximal end of the lock recess 10145 wherein, correspondingly, the distal articulation driver 10140 gradually increases in thickness toward the proximal end of the lock recess 10145. As a result, a distal pulling force D applied to the distal articulation driver 10140 may only serve to further increase the resistance, or wedging force, holding the distal articulation driver 10140 in position.

In order to push the distal articulation driver 10140 distally, the proximal articulation driver 10130 can be configured to, one, displace the second lock element 10156 distally to unlock the articulation lock 10150 in the distal direction and, two, directly engage the distal articulation driver 10140 and apply a distal pushing force thereto. More specifically, further to the above, the proximal arm 10136 of the proximal articulation driver 10130 can be configured to initially engage the second lock element 10156 wherein the distal arm 10134 can then engage a distal drive wall 10148 defined at the distal end of the lock recess 10145 and push the distal articulation driver 10140 distally. Similar to the above, the distal movement of the distal articulation driver 10140 can be configured to articulate the end effector of the surgical instrument. Once the end effector has been suitably articulated, the proximal articulation driver 10130 can be released, in various circumstances, to permit the spring 10155 to expand and sufficiently re-position the second lock element 10156 relative to the second lock surface 10143 in order to re-lock the distal articulation driver 10140 and the end effector in position.

Concurrent to the above, the first lock element 10154 may not resist, or at least substantially resist, the distal movement of the distal articulation driver 10140. When the articulation lock 10150 is in a locked condition, the first lock element 10154 may be positioned between the first lock surface 10141 of the lock recess 10145 and the lock wall 10153 of the lock channel 10151, as discussed above. As the distal articulation driver 10140 is pushed distally by the proximal articulation driver 10130, further to the above, the dwell portion 10142 of the lock recess 10145 may move over the first lock element 10154. In various circumstances, the dwell portion 10142 may permit relative sliding movement between the distal articulation driver 10140 and the first lock element 10154 as the distal articulation driver 10140 is pushed distally. In some circumstances, the first lock element 10154 can be configured to roll within the dwell portion 10142 thereby reducing the resistance force between the distal articulation driver 10140 and the first lock element 10154. As the reader will appreciate, the first lock element 10154 may be permissive to the distal movement of the distal articulation driver 10140 but can selectively resist the proximal movement of the distal articulation driver 10140, as discussed above.

Further to the above, the first lock surface 10141, the dwell 10142, and the second lock surface 10143 of the lock recess 10145 can define a suitable contour. Such a contour can be defined by first, second, and third flat surfaces which comprise the first lock surface 10141, the dwell 10142, and the second lock surface 10143, respectively. In such circumstances, definitive breaks between the first lock surface 10141, the dwell 10142, and the second lock surface 10143 can be identified. In various circumstances, the first lock surface 10141, the dwell 10142, and the second lock surface 10143 can comprise a continuous surface, such as an arcuate surface, for example, wherein definitive breaks between the first lock surface 10141, the dwell 10142, and the second lock surface 10143 may not be present.

Figures 115, 116:
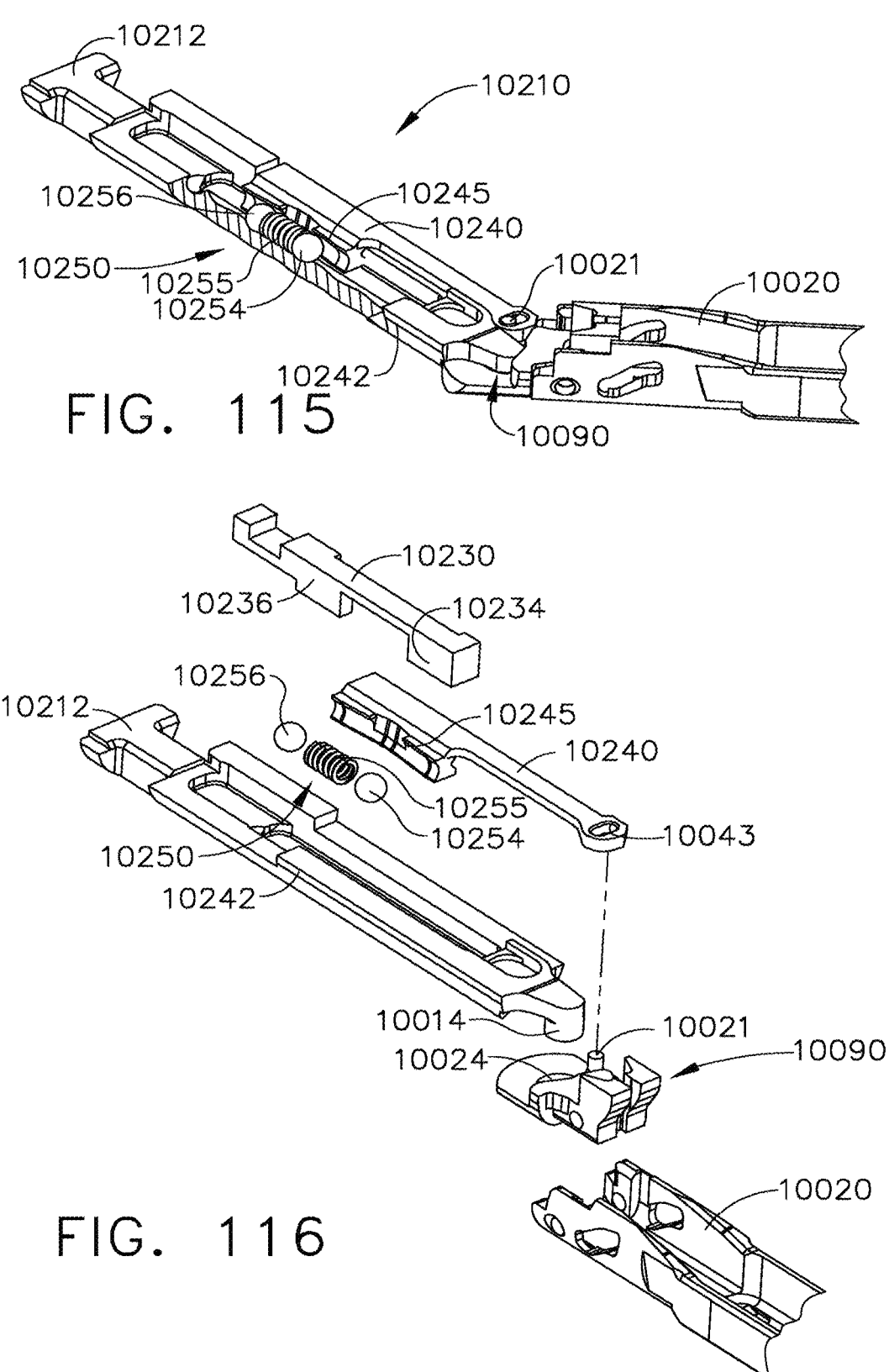
FIG. 115 is a cross-sectional view of another alternative embodiment of an articulation lock illustrated in a locked condition.
Figures 117, 118:
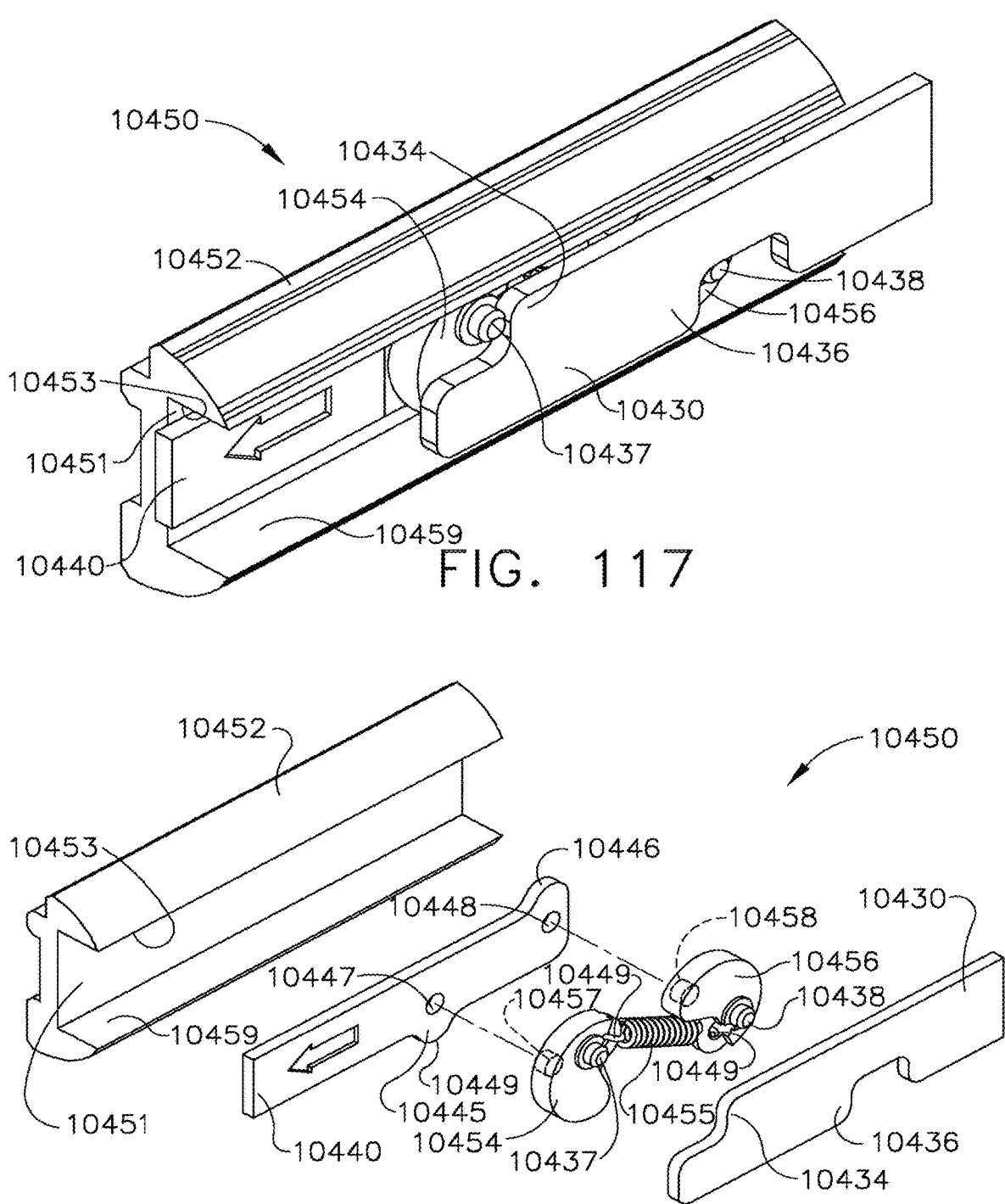

Turning now to FIGS. 115 and 116, a surgical instrument, such as surgical instrument 10000, and/or any other surgical instrument system, for example, can comprise a shaft 10210, an articulation driver system comprising a proximal articulation driver 10230 and a distal articulation driver 10240, and an articulation lock 10250 configured to releasably hold the distal articulation driver 10240 in position. The general operation of the articulation driver system is the same as, or at least substantially similar to, the articulation driver system discussed in connection with the embodiment disclosed in FIGS. 113 and 114 and, as a result, such discussion is not repeated herein for the sake of brevity. As the reader will appreciate, referring to FIGS. 115 and 116, the articulation lock 10250 can comprise a first lock element 10254 which can provide a one-way lock configured to releasably inhibit the proximal movement of the distal articulation driver 10240 and a second lock element 10256 which can provide a second one-way lock configured to releasably inhibit the distal movement of the distal articulation driver 10240. Similar to the above, the first lock element 10254 and the second lock element 10256 can be positioned within a lock recess 10245 defined in the distal articulation driver 10240 and can be biased into a locked condition by a biasing member, or spring, 10255, for example. In order to unlock the first lock element 10254, similar to the above, the proximal articulation driver 10230 can be pulled proximally such that a distal hook 10234 contacts the first lock element 10254 and pulls the first lock element 10254 proximally. Thereafter, the proximal articulation driver 10230 can be pulled further proximally until the distal hook 10234 contacts the distal articulation driver frame 10242 and pulls the distal articulation driver 10240 proximally and articulates the end effector 10020, similar to the embodiments described above. In order to unlock the second lock element 10256, similar to the above, the proximal articulation driver 10230 can be pushed distally such that a proximal hook 10236 contacts the second lock element 10256 and pushes the second lock element 10256 distally. Thereafter, the proximal articulation driver 10230 can be pushed further distally until the proximal hook 10236 contacts the distal articulation driver frame 10242 and pushes the distal articulation driver 10240 distally and articulate the end effector 10020 in an opposite direction, similar to the embodiments described above. In various circumstances, the first lock element 10254 and the second lock element 10256 can each comprise a rotatable spherical element, or bearing, for example, which can be configured to reduce the sliding friction between the lock elements 10254, 10256, the shaft frame 10212, the proximal articulation driver 10230, and/or the distal articulation driver 10240.

Turning now to FIGS. 125-130, a surgical instrument, such as surgical instrument 10000, and/or any other surgical instrument system, for example, can comprise an articulation driver system comprising a proximal articulation driver 10330 and a distal articulation driver 10340, and an articulation lock 10350 configured to releasably hold the distal articulation driver 10340 in position. In many aspects, the general operation of the articulation driver system is the same as, or at least substantially similar to, the articulation driver system discussed in connection with the embodiments disclosed above and, as a result, such aspects are not repeated herein for the sake of brevity. As the reader will appreciate, primarily referring to FIGS. 125 and 126, the articulation lock 10350 can comprise a first lock element 10354 which can provide a one-way lock configured to releasably inhibit the proximal movement of the distal articulation driver 10340 and a second lock element 10356 which can provide a second one-way lock configured to releasably inhibit the distal movement of the distal articulation driver 10340. Similar to the above, the first lock element 10354 can be positioned within a first, or distal, lock recess 10344 and the second lock element 10356 can be positioned within a second, or proximal, lock recess 10346 defined in the distal articulation driver 10340 and can be biased into a locked condition by a biasing member, or spring, 10355, for example. In order to unlock the first lock element 10354, referring generally to FIG. 129, the proximal articulation driver 10330 can be pulled proximally such that a distal hook 10334 contacts the first lock element 10354 and pulls the first lock element 10354 proximally. Thereafter, as illustrated in FIG. 129, the proximal articulation driver 10330 can be pulled further proximally until the first lock element 10354 contacts an intermediate shoulder 10345 extending from a frame 10342 of the articulation driver frame 10340 and pulls the distal articulation driver 10340 proximally to articulate the end effector, similar to the embodiments described above. Once the end effector has been sufficiently articulated, the proximal articulation driver 10330 can be released which can permit the biasing spring 10355 to displace the lock elements 10354 and 10356 away from each other and seat the lock elements 10354 and 10356 in a locked condition, as illustrated in FIG. 130. In order to unlock the second lock element 10356, referring generally to FIG. 127, the proximal articulation driver 10330 can be pushed distally such that a proximal hook 10336 contacts the second lock element 10356 and pushes the second lock element 10356 distally. Thereafter, the proximal articulation driver 10330 can be pushed further distally until the second lock element 10356 contacts the intermediate shoulder 10345 of the distal articulation driver frame 10342 and pushes the distal articulation driver 10340 distally to articulate the end effector in an opposite direction, similar to the embodiments described above. Once the end effector has been sufficiently articulated, similar to the above, the proximal articulation driver 10330 can be released which can permit the biasing spring 10355 to displace the lock elements 10354 and 10356 away from each other and seat the lock elements 10354 and 10356 in a locked condition, as illustrated in FIG. 128.

In various circumstances, further to the above, the first lock element 10354 and the second lock element 10356 can each comprise a wedge, for example, which can be configured to lock the distal articulation driver 10340 in position. Referring primarily again to FIGS. 125 and 126, the articulation lock 10350 can comprise a frame 10352 including a lock channel 10351 defined therein which can be configured to receive at least a portion of the proximal articulation driver 10330 and at least a portion of the distal articulation driver 10340. The first lock cavity 10344, further to the above, can be defined between the distal articulation driver 10340 and a lock wall 10353 of the lock channel 10351. When a proximal load P is transmitted to the distal articulation driver 10340 from the end effector, the distal articulation driver 10340 can engage a wedge portion 10358 of the first lock element 10354 and bias the first lock element 10354 against the lock wall 10353. In such circumstances, the proximal load P may only increase the wedging force holding the first lock element 10354 in position. In effect, the first lock element 10354 can comprise a one-way lock which can inhibit the proximal movement of the distal articulation driver 10340 until the first lock element 10354 is unlocked, as described above. When the first lock element 10354 is unlocked and the distal articulation driver 10340 is being moved proximally, the second lock element 10356 may not resist, or at least substantially resist, the proximal movement of the distal articulation driver 10340. Similar to the above, the second lock cavity 10346, further to the above, can be defined between the distal articulation driver 10340 and the lock wall 10353. When a distal load D is transmitted to the distal articulation driver 10340 from the end effector, the distal articulation driver 10340 can engage a wedge portion 10359 of the second lock element 10356 and bias the second lock element 10356 against the lock wall 10353. In such circumstances, the distal load D may only increase the wedging force holding the second lock element 10356 in position. In effect, the second lock element 10356 can comprise a one-way lock which can inhibit the distal movement of the distal articulation driver 10340 until the second lock element 10356 is unlocked, as described above. When the second lock element 10356 is unlocked and the distal articulation driver 10340 is being moved distally, the first lock element 10354 may not resist, or at least substantially resist, the distal movement of the distal articulation driver 10340.

Figures 119, 120, 121:
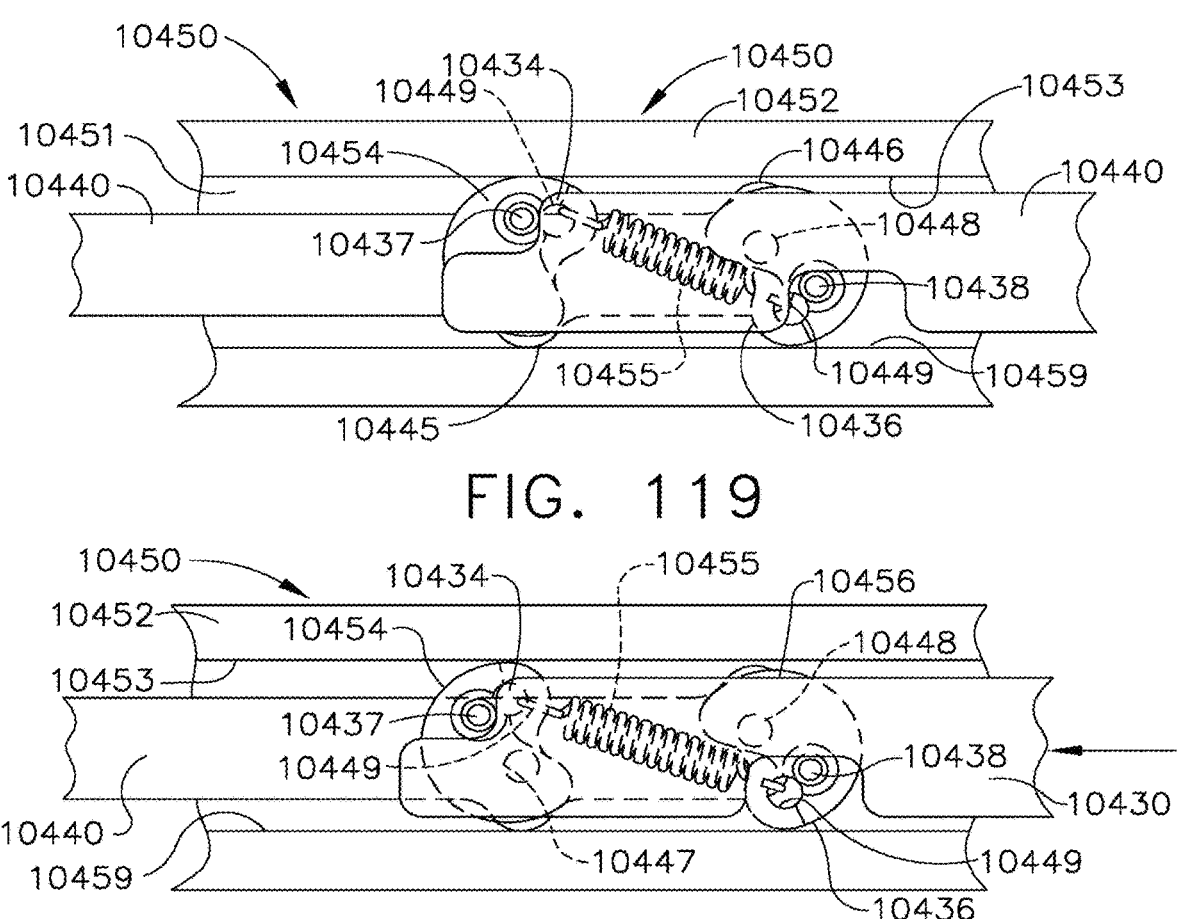
Figure 122:
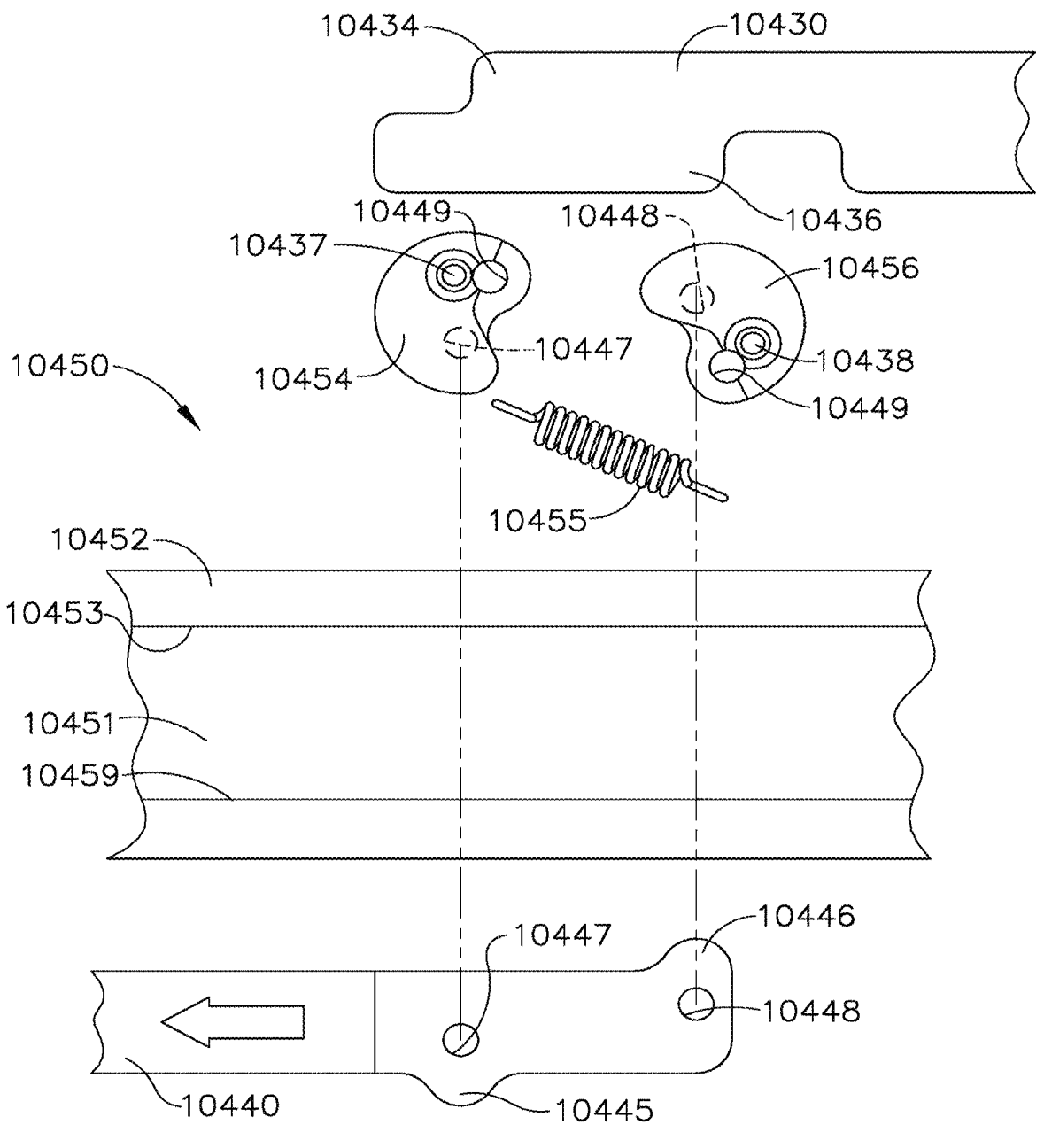
Figure 123:
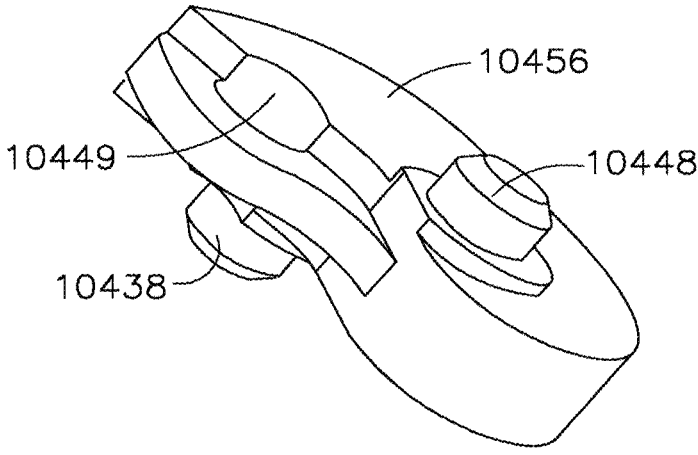
Figure 124:
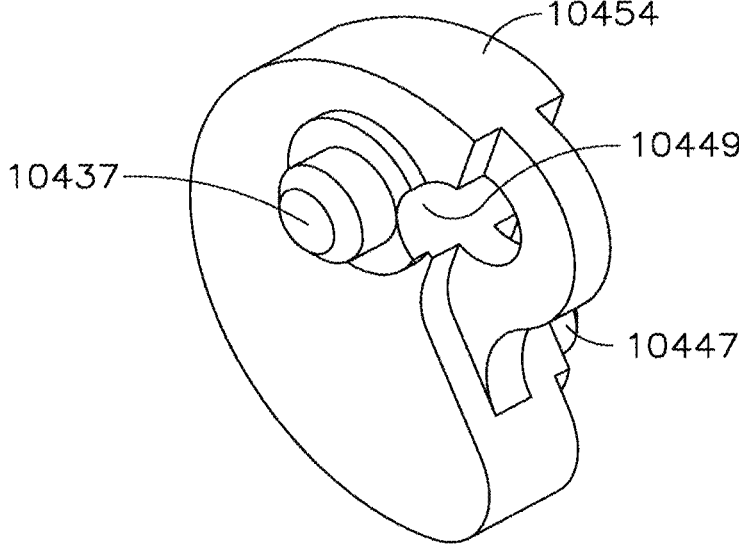

Turning now to FIGS. 117-124, a surgical instrument, such as surgical instrument 10000, and/or any other surgical instrument system, for example, can comprise an articulation driver system comprising a proximal articulation driver 10430 and a distal articulation driver 10440, and an articulation lock 10450 configured to releasably hold the distal articulation driver 10440 in position. As the reader will appreciate, primarily referring to FIGS. 117 and 118, the articulation lock 10450 can comprise a first lock cam 10454 which can provide a one-way lock configured to releasably inhibit the distal movement of the distal articulation driver 10440 and a second lock cam 10456 which can provide a second one-way lock configured to releasably inhibit the proximal movement of the distal articulation driver 10440. The first lock cam 10454 can be rotatably mounted to the distal articulation driver 10440 and can include a projection 10457 rotatably positioned within a pivot aperture 10447 defined in the distal articulation driver 10440. Similarly, the second lock cam 10456 can be rotatably mounted to the distal articulation driver 10440 and can include a projection 10458 rotatably positioned within a pivot aperture 10448 which is also defined in the distal articulation driver 10440. The articulation lock 10450 can further comprise a frame 10452 having a lock channel 10451 defined therein which can be configured to receive at least a portion of the proximal articulation driver 10430, at least a portion of the distal articulation driver 10440, the first lock cam 10454, and the second lock cam 10456. The lock channel 10451 can comprise a first lock wall 10453 and a second lock wall 10459 wherein, when the articulation lock 10450 is in a locked state, the first lock cam 10454 can be biased into engagement with the first lock wall 10453 and the second lock cam 10456 can be biased into engagement with the second lock wall 10459. The first lock cam 10454 can be configured to bias a first bearing point 10445 of the distal articulation driver 10440 against the second lock wall 10459 when the first lock cam 10454 is in its locked position. Similarly, the second lock cam 10456 can be configured to bias a second bearing point 10446 of the distal articulation driver 10440 against the first lock wall 10453 when the second lock cam 10454 is in its locked position. Such a locked state is illustrated in FIG. 119. As also illustrated in FIG. 119, the articulation lock 10450 can be biased into a locked state by a spring 10455. The spring 10455 can be configured to rotate the first lock cam 10454 about its projection 10457 such that a lobe of the first lock cam 10454 engages the first lock wall 10453 and, similarly, to rotate the second lock cam 10456 about its projection 10458 such that a lobe of the second lock cam 10456 engages the second lock wall 10459. In various circumstances, the first lock cam 10454 and the second lock cam 10456 can each comprise a spring aperture 10449 defined therein which can be configured to receive an end of the spring 10455 such that the spring 10455 can apply the biasing forces discussed above.

In order to unlock the first lock cam 10454, referring generally to FIG. 120, the proximal articulation driver 10430 can be pushed distally such that a distal drive shoulder 10434 of the proximal articulation driver 10430 contacts the first lock cam 10454 and pushes the first lock cam 10454 distally. In various circumstances, the first lock cam 10454 can comprise a drive pin 10437 extending therefrom which can be contacted by the distal drive shoulder 10434 such that, as the proximal articulation driver 10430 is pushed distally, the first lock cam 10454 and the distal articulation driver 10440 can be slid distally relative to the first lock surface 10451. In some circumstances, the first lock cam 10454 may rotate about its projection 10447 in order to accommodate such movement. In any event, similar to the above, the distal movement of the distal articulation driver 10440 can articulate the end effector. Once the end effector has been sufficiently articulated, the proximal articulation driver 10430 can be released which can permit the biasing spring 10455 to displace the lock cams 10454 and 10456 into engagement with the lock surfaces 10453 and 10459, respectively, and place the articulation lock 10450 in its locked condition, as illustrated in FIG. 119. In order to unlock the second lock cam 10456, referring generally to FIG. 121, the proximal articulation driver 10430 can be pulled proximally such that a proximal drive shoulder 10436 contacts the second lock cam 10456 and pulls the second lock cam 10456 proximally. In various circumstances, the second lock cam 10456 can comprise a drive pin 10438 extending therefrom which can be contacted by the proximal drive shoulder 10436 such that, as the proximal articulation driver 10430 is pulled proximally, the second lock cam 10456 and the distal articulation driver 10440 can be slid proximally relative to the second lock surface 10459. In some circumstances, the second lock cam 10456 may rotate about its projection 10458 in order to accommodate such movement. In any event, similar to the above, the proximal movement of the distal articulation driver 10440 can articulate the end effector in an opposite direction. Similar to the above, once the end effector has been sufficiently articulated, the proximal articulation driver 10430 can be released which can permit the biasing spring 10455 to displace the lock cams 10454 and 10456 into engagement with lock surfaces 10453 and 10459, respectively, and place the articulation lock 10450 in its locked condition, as illustrated in FIG. 119.

Further to the above, when a proximal load P is transmitted to the distal articulation driver 10440 from the end effector when the articulation lock 10450 is in its locked condition, the second lock cam 10456 will be further biased into engagement with the lock wall 10459. In such circumstances, the proximal load P may only increase the wedging force holding the second lock cam 10456 in position. In effect, the second lock cam 10456 can comprise a one-way lock which can inhibit the proximal movement of the distal articulation driver 10440 until the second lock cam 10456 is unlocked, as described above. When the second lock cam 10456 is unlocked and the distal articulation driver 10440 is being moved proximally, the first lock cam 10454 may not resist, or at least substantially resist, the proximal movement of the distal articulation driver 10440. When a distal load D is transmitted to the distal articulation driver 10440 from the end effector when the articulation lock 10450 is in its locked condition, the first lock cam 10454 will be further biased into engagement with the lock wall 10453. In such circumstances, the distal load D may only increase the wedging force holding the first lock cam 10454 in position. In effect, the first lock cam 10454 can comprise a one-way lock which can inhibit the distal movement of the distal articulation driver 10440 until the first lock cam 10454 is unlocked, as described above. When the first lock cam 10454 is unlocked and the distal articulation driver 10440 is being moved distally, the second lock cam 10454 may not resist, or at least substantially resist, the distal movement of the distal articulation driver 10440.

As discussed above, a surgical instrument can comprise a firing drive for treating tissue captured within an end effector of the surgical instrument, an articulation drive for articulating the end effector about an articulation joint, and a clutch assembly which can be utilized to selectively engage the articulation drive with the firing drive. An illustrative clutch assembly 10070 was discussed above while another illustrative clutch assembly, i.e., clutch assembly 11070, is discussed below. In various circumstances, the surgical instruments disclosed herein can utilize either clutch assembly.

Turning now to FIGS. 131-149, a surgical instrument can utilize a shaft assembly 11010 which can include an end effector 10020, an articulation joint 10090, and an articulation lock 10050 which can be configured to releasably hold the end effector 10020 in position. The reader will appreciate that portions of the end effector 10020 have been removed in FIGS. 131-133 for the purposes of illustration; however, the end effector 10020 can include a staple cartridge positioned therein and/or an anvil rotatably coupled to a channel supporting the staple cartridge. The operation of the end effector 10020, the articulation joint 10090, and the articulation lock 10050 was discussed above and is not repeated herein for sake of brevity. The shaft assembly 11010 can further include a proximal housing comprised of housing portions 11002 and 11003, for example, which can connect the shaft assembly 11010 to a handle of a surgical instrument. The shaft assembly 11010 can further include a closure tube 11015 which can be utilized to close and/or open the anvil of the end effector 10020. Primarily referring now to FIGS. 132-134, the shaft assembly 11010 can include a spine 11004 which can be configured to fixably support the shaft frame portion 10012, which is discussed above in connection with articulation lock 10050. The spine 11004 can be configured to, one, slidably support a firing member 11060 therein and, two, slidably support the closure tube 11015 which extends around the spine 11004. The spine 11004 can also be configured to slidably support a proximal articulation driver 11030. In various circumstances, the spine 11004 can comprise a proximal end 11009 which is supported by a frame portion 11001 that can be configured to permit the spine 11004 to be rotated about its longitudinal axis.

Further to the above, the shaft assembly 11010 can include a clutch assembly 11070 which can be configured to selectively and releasably couple the proximal articulation driver 11030 to the firing member 11060. The clutch assembly 11070 can comprise a lock collar, or sleeve, 11072 positioned around the firing member 11060 wherein the lock sleeve 11072 can be rotated between an engaged position in which the lock sleeve 11072 couples the proximal articulation driver 11030 to the firing member 11060 and a disengaged position in which the proximal articulation driver 11030 is not operably coupled to the firing member 11060. When lock sleeve 11072 is in its engaged position (FIGS. 135, 136, 138, 139, 141, and 145-149), further to the above, distal movement of the firing member 11060 can move the proximal articulation driver 11030 distally and, correspondingly, proximal movement of the firing member 11060 can move the proximal articulation driver 11030 proximally. When lock sleeve 11072 is in its disengaged position (FIGS. 142-144), movement of the firing member 11060 is not transmitted to the proximal articulation driver 11030 and, as a result, the firing member 11060 can move independently of the proximal articulation driver 11030. In various circumstances, the proximal articulation driver 11030 can be held in position by the articulation lock 11050 when the proximal articulation driver 11030 is not being moved in the proximal or distal directions by the firing member 11060.

Referring primarily to FIG. 134, the lock sleeve 11072 can comprise a cylindrical, or an at least substantially cylindrical, body including a longitudinal aperture defined therein configured to receive the firing member 11060. The lock sleeve 11072 can comprise a first, inwardly-facing lock member 11073 and a second, outwardly-facing lock member 11078. The first lock member 11073 can be configured to be selectively engaged with the firing member 11060. More particularly, when the lock sleeve 11072 is in its engaged position, the first lock member 11073 can be positioned within a drive notch 11062 defined in the firing member 11060 such that a distal pushing force and/or a proximal pulling force can be transmitted from the firing member 11060 to the lock sleeve 11072. When the lock sleeve 11072 is in its engaged position, the second lock member 11078 can be positioned within a drive notch 11035 defined in the proximal articulation driver 11035 such that the distal pushing force and/or the proximal pulling force applied to the lock sleeve 11072 can be transmitted to the proximal articulation driver 11030. In effect, the firing member 11060, the lock sleeve 11072, and the proximal articulation driver 11030 will move together when the lock sleeve 11072 is in its engaged position. On the other hand, when the lock sleeve 11072 is in its disengaged position, the first lock member 11073 may not be positioned within the drive notch 11062 of the firing member 11060 and, as a result, a distal pushing force and/or a proximal pulling force may not be transmitted from the firing member 11060 to the lock sleeve 11072. Correspondingly, the distal pushing force and/or the proximal pulling force may not be transmitted to the proximal articulation driver 11030. In such circumstances, the firing member 11060 can be slid proximally and/or distally relative to the lock sleeve 11072 and the proximal articulation driver 11030. In order to accommodate such relative movement, in such circumstances, the firing member 11060 can include a longitudinal slot or groove 11061 defined therein which can be configured to receive the first lock member 11073 of the lock sleeve 11072 when the lock sleeve 11072 is in its disengaged position and, furthermore, accommodate the longitudinal movement of the firing member 11060 relative to the lock sleeve 11072. In various circumstances, the second lock member 11078 can remain engaged with the drive notch 11035 in the proximal articulation driver 11030 regardless of whether the lock sleeve 11072 is in its engaged position or its disengaged position.

Further to the above, the clutch assembly 11070 can further comprise a rotatable lock actuator 11074 which can be configured to rotate the lock sleeve 11072 between its engaged position and its disengaged position. In various circumstances, the lock actuator 11074 can comprise a collar which can surround the lock sleeve 11072, a longitudinal aperture extending through the collar, and referring primarily to FIG. 135, an inwardly-extending drive element 11077 engaged with the lock sleeve 11072. Referring again to FIG. 134, the lock sleeve 11072 can comprise a longitudinal slot 11079 defined therein within which the drive element 11077 of the lock actuator 11074 can be received. Similar to the above, the lock actuator 11074 can be moved between an engaged position in which the lock actuator 11074 can position the lock sleeve 11072 in its engaged position and a disengaged position in which the lock actuator 11074 can position the lock sleeve 11072 in its disengaged position. In order to move the lock sleeve 11072 between its engaged position and its disengaged position, the lock actuator 11074 can be rotated about its longitudinal axis such that the drive element 11077 extending therefrom engages a sidewall of the slot 11079 to impart a rotational force to the lock sleeve 11072. In various circumstances, the lock actuator 11074 can be constrained such that it does not move longitudinally with the lock sleeve 11072. In such circumstances, the lock actuator 11074 may rotate within an at least partially circumferential window 11089 defined in the shaft spine 11004. In order to accommodate the longitudinal movement of the lock sleeve 11072 when the lock sleeve 11072 is in its engaged position, the lock sleeve 11072 can further include a longitudinal opening 11079 within which the drive element 11077 can travel. In various circumstances, the longitudinal opening 11079 can include a center notch 11076 which can correspond with the unarticulated position of the end effector 10020. In such circumstances, the center notch 11076 can serve as a detent configured to releasably hold or indicate the centered orientation of the end effector 10020, for example.

Further to the above, referring primarily to FIG. 134, the lock actuator 11074 can further comprise a cam follower 11081 extending outwardly therefrom which can be configured to receive a force applied thereto in order to rotate the lock sleeve 11072 as described above. In various circumstances, the shaft assembly 11010 can further comprise a switch drum 11075 which can be configured to apply a rotational force to the cam follower 11081. The switch drum 11075 can extend around the lock actuator 11074 and include a longitudinal slot 11083 defined therein within which the cam follower 11081 can be disposed. When the switch drum 11075 is rotated, a sidewall of the slot 11083 can contact the cam follower 11081 and rotate the lock actuator 11074, as outlined above. The switch drum 11075 can further comprise at least partially circumferential openings 11085 defined therein which, referring to FIG. 137, can be configured to receive circumferential mounts 11007 extending from the shaft housing comprising housing halves 11002 and 11003 and permit relative rotation, but not translation, between the switch drum 11075 and the shaft housing. Referring again to FIG. 134, the switch drum 11075 can be utilized to rotate the lock actuator 11074 and the lock sleeve 11072 between their engaged and disengage positions. In various circumstances, the shaft assembly 11010 can further comprise a biasing member, such as spring 11080, for example, which can be configured to bias the switch drum 11075 in a direction which biases the lock actuator 11074 and the lock sleeve 11072 into their engaged positions. Thus, in essence, the spring 11080 and the switch drum 11075 can be configured to bias the articulation drive system into operative engagement with the firing drive system. As also illustrated in FIG. 134, the switch drum 11075 can comprise portions of a slip ring assembly 11005 which can be configured to conduct electrical power to and/or from the end effector 10020 and/or communicate signals to and/or from the end effector 10020. The slip ring assembly 11005 can comprise a plurality of concentric, or at least substantially concentric, conductors 11008 on opposing sides thereof which can be configured to permit relative rotation between the halves of the slip ring assembly 11005 while still maintaining electrically conductive pathways therebetween. U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, is incorporated by reference in its entirety. U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481, is incorporated by reference in its entirety.

In various circumstances, further to the above, the closure mechanism of the shaft assembly 11010 can be configured to bias the clutch assembly 11070 into its disengaged state. For instance, referring primarily to FIGS. 134 and 144-147, the closure tube 11015 can be advanced distally to close the anvil of the end effector 10020, as discussed above and, in doing so, cam the lock actuator 11074 and, correspondingly, the lock sleeve 11072, into their disengaged positions. To this end, the closure tube 11015 can comprise a cam window 11016, through which the cam follower 11081 extending from the lock actuator 11074 can extend. The cam window 11016 can include an angled sidewall, or cam edge, 11017 which can be configured to engage the cam follower 11081 as the closure tube 11015 is moved distally between an open, or unclosed, position (FIGS. 145-149) to a closed position (FIGS. 142-144) and rotate the lock actuator 11074 from its engaged position (FIGS. 145-149) to its disengaged position (FIGS. 142-144). Upon comparing FIGS. 144 and 149, the reader will appreciate that, when the cam follower 11081 and the lock actuator 11074 are cammed into their disengaged position, the cam follower 11081 can rotate the switch drum 11075 and compress the spring 11080 between the switch drum 11075 and the shaft housing. As long as the closure tube 11015 remains in its advanced, closed position, the articulation drive will be disconnected from the firing drive. In order to re-engage the articulation drive with the firing drive, the closure tube 11015 can be retracted into its unactuated position, which can also open the end effector 10020, and can, as a result, pull the cam edge 11017 proximally and permit the spring 11080 to re-bias the lock actuator 11074 and the lock sleeve 11072 into their engaged positions.

As described elsewhere in greater detail, the surgical instrument 1010 may include several operable systems that extend, at least partially, through the shaft 1210 and are in operable engagement with the end effector 1300. For example, the surgical instrument 1010 may include a closure assembly that may transition the end effector 1300 between an open configuration and a closed configuration, an articulation assembly that may articulate the end effector 1300 relative to the shaft 1210, and/or a firing assembly that may fasten and/or cut tissue captured by the end effector 1300. In addition, the surgical instrument 1010 may include a housing such as, for example, the handle 1042 which may be separably couplable to the shaft 1210 and may include complimenting closure, articulation, and/or firing drive systems that can be operably coupled to the closure, articulation, and firing assemblies, respectively, of the shaft 1210 when the handle 1042 is coupled to the shaft 1210.

In use, an operator of the surgical instrument 1010 may desire to reset the surgical instrument 1010 and return one or more of the assemblies of the surgical instrument 1010 to a default position. For example, the operator may insert the end effector 1300 into a surgical site within a patient through an access port and may then articulate and/or close the end effector 1300 to capture tissue within the cavity. The operator may then choose to undo some or all of the previous actions and may choose to remove the surgical instrument 1010 from the cavity. The surgical instrument 1010 may include one more systems configured to facilitate a reliable return of one or more of the assemblies described above to a home state with minimal input from the operator thereby allowing the operator to remove the surgical instrument from the cavity.

Referring to FIG. 150, the surgical instrument 1010 may include an articulation control system 3000. A surgical operator may utilize the articulation control system 3000 to articulate the end effector 1300 relative to the shaft 1210 between an articulation home state position and an articulated position. In addition, the surgical operator may utilize the articulation control system 3000 to reset or return the articulated end effector 1300 to the articulation home state position. The articulation control system 3000 can be positioned, at least partially, in the handle 1042. In addition, as illustrated in the illustrative schematic block diagram in FIG. 151, the articulation control system 3000 may comprise a controller such as, for example, controller 3002 which can be configured to receive an input signal and, in response, activate a motor such as, for example, motor 1102 to cause the end effector 1300 to articulate in accordance with such an input signal. Examples of suitable controllers are described elsewhere in this document and include but are not limited to microcontroller 7004 (See FIG. 185).

Further to the above, the end effector 1300 can be positioned in sufficient alignment with the shaft 1210 in the articulation home state position, also referred to herein as an unarticulated position such that the end effector 1300 and at least a portion of shaft 1210 can be inserted into or retracted from a patient's internal cavity through an access port such as, for example, a trocar positioned in a wall of the internal cavity without damaging the axis port. In certain embodiments, the end effector 1300 can be aligned, or at least substantially aligned, with a longitudinal axis "LL" passing through the shaft 1210 when the end effector 1300 is in the articulation home state position, as illustrated in FIG. 150. In at least one embodiment, the articulation home state position can be at any angle up to and including 5°, for example, with the longitudinal axis on either side of the longitudinal axis. In another embodiment, the articulation home state position can be at any angle up to and including 3°, for example, with the longitudinal axis on either side of the longitudinal axis.

In yet another embodiment, the articulation home state position can be at any angle up to and including 7°, for example, with the longitudinal axis on either side of the longitudinal axis.

The articulation control system 3000 can be operated to articulate the end effector 1300 relative to the shaft 1210 in a plane intersecting the longitudinal axis in a first direction such as, for example, a clockwise direction and/or a second direction opposite the first direction such as, for example, a counterclockwise direction. In at least one instance, the articulation control system 3000 can be operated to articulate the end effector 1300 in the clockwise direction form the articulation home state position to an articulated position at a 10° angle with the longitudinal axis on the right to the longitudinal axis, for example. In another example, the articulation control system 3000 can be operated to articulate the end effector 1300 in the counterclockwise direction form the articulated position at the 10° angle with the longitudinal axis to the articulation home state position. In yet another example, the articulation control system 3000 can be operated to articulate the end effector 1300 relative to the shaft 1210 in the counterclockwise direction from the articulation home state position to an articulated position at a 10° angle with the longitudinal axis on the left of the longitudinal axis. The reader will appreciate that the end effector can be articulated to different angles in the clockwise direction and/or the counterclockwise direction in response to the operator's commands.

Referring to FIG. 150, the handle 1042 of the surgical instrument 1010 may comprise an interface 3001 which may include a plurality of inputs that can be utilized by the operator, in part, to articulate the end effector 1300 relative to the shaft 1210, as described above. In certain embodiments, the interface 3001 may comprise a plurality of switches which can be coupled to the controller 3002 via electrical circuits, for example. In the embodiment illustrated in FIG. 151, the interface 3001 comprises three switches 3004A-C, wherein each of the switches 3004A-C is coupled to the controller 3002 via one of three electrical circuits 3006A-C, respectively. The reader will appreciate that other combinations of switches and circuits can be utilized with the interface 3001.

Further to the above, the controller 3002 may comprise a processor 3008 and/or one or more memory units 3010. By executing instruction code stored in the memory 3010, the processor 3008 may control various components of the surgical instrument 1, such as the motor 1102 and/or a user display. The controller 3002 may be implemented using integrated and/or discrete hardware elements, software elements, and/or a combination of both. Examples of integrated hardware elements may include processors, microprocessors, microcontrollers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, microcontroller, system-on-chip (SoC), and/or system-in-package (SIP). Examples of discrete hardware elements may include circuits and/or circuit elements (e.g., logic gates, field effect transistors, bipolar transistors, resistors, capacitors, inductors, relay and so forth). In other embodiments, the controller 3002 may include a hybrid circuit comprising discrete and integrated circuit elements or components on one or more substrates, for example.

Referring again to FIG. 151, the surgical instrument 1010 may include a motor controller 3005 in operable communication with the controller 3002. The motor controller 3005 can be configured to control a direction of rotation of the motor 1102. For example, the motor 1102 can be powered by a battery such as, for example, the battery 1104 and the motor controller 3002 may be configured to determine the voltage polarity applied to the motor 1102 by the battery 1104 and, in turn, the direction of rotation of the motor 1102 based on input from the controller 3002. For example, the motor 1102 may reverse the direction of its rotation from a clockwise direction to a counterclockwise direction when the voltage polarity applied to the motor 1102 by the battery 1104 is reversed by the motor controller 3005 based on input from the controller 3002. Examples of suitable motor controllers are described elsewhere in this document and include but are not limited to the driver 7010 (FIG. 185).

In addition, as described elsewhere in this document in greater detail, the motor 1102 can be operably coupled to an articulation drive such as, for example, the proximal articulation drive 10030 (FIG. 37). In use, the motor 1102 can drive the proximal articulation drive 10030 distally or proximally depending on the direction in which the motor 1102 rotates. Furthermore, the proximal articulation drive 10030 can be operably coupled to the end effector 1300 such that, for example, the axial translation of the proximal articulation drive 10030 proximally may cause the end effector 1300 to be articulated in the counterclockwise direction, for example, and/or the axial translation of the proximal articulation drive 10030 distally may cause the end effector 1300 to be articulated in the clockwise direction, for example.

Further to the above, referring again to FIG. 151, the interface 3001 can be configured such that the switch 3004A can be dedicated to clockwise articulation of the end effector 1300 and the switch 3004B can be dedicated to counterclockwise articulation of the end effector 1300. For example, the operator may articulate the end effector 1300 in the clockwise direction by closing the switch 3004A which may signal the controller 3002 to cause the motor 1102 to rotate in the clockwise direction thereby, as a result, causing the proximal articulation drive 10030 to be advanced distally and causing the end effector 1300 to be articulated in the clockwise direction. In another example, the operator may articulate the end effector 1300 in the counterclockwise direction by closing the switch 3004B which may signal the controller 3002 to cause the motor 1102 to rotate in the counterclockwise direction, for example, and retracting the proximal articulation drive 10030 proximally to articulate the end effector 1300 to in the counterclockwise direction.

Further to the above, the switches 3004A-C can comprise open-biased dome switches, as illustrated in FIG. 154. Other types of switches can also be employed such as, for example, capacitive switches. In the embodiment illustrated in FIG. 154, the dome switches 3004A and 3004B are controlled by a rocker 3012. Other means for controlling the switches 3004A and 3004B are also contemplated within the scope of the present disclosure. In the neutral position, illustrated in FIG. 154, both of the switches 3004A and 3004B are biased in the open position. The operator, for example, may articulate the end effector 1300 in the clockwise direction by tilting the rocker forward thereby depressing the dome switch 3004A, as illustrated in FIG. 155. In result, the circuit 3006A (FIG. 151) may be closed signaling the controller 3002 to activate the motor 1102 to articulate the end effector 1300 in the clockwise direction, as described above. The motor 1102 may continue to articulate the end effector 1300 until the operator releases the rocker 3012 thereby allowing the dome switch 3004A to return to the open position and the rocker 3012 to the neutral position. In some circumstances, the controller 3002 may be able to identify when the end effector 1300 has reached a predetermined maximum degree of articulation and, at such point, interrupt power to the motor 1102 regardless of whether the dome switch 3004A is being depressed. In a way, the controller 3002 can be configured to override the operator's input and stop the motor 1102 when a maximum degree of safe articulation is reached. Alternatively, the operator may articulate the end effector 1300 in the counterclockwise direction by tilting the rocker back thereby depressing the dome switch 3004B, for example. In result, the circuit 3006B may be closed signaling the controller 3002 to activate the motor 1102 to articulate the end effector 1300 in the counterclockwise direction, as described above. The motor 1102 may continue to articulate the end effector 1300 until the operator releases the rocker 3012 thereby allowing the dome switch 3004B to return to the open position and the rocker 3012 to the neutral position. In some circumstances, the controller 3002 may be able to identify when the end effector 1300 has reached a predetermined maximum degree of articulation and, at such point, interrupt power to the motor 1102 regardless of whether the dome switch 3004B is being depressed. In a way, the controller 3002 can be configured to override the operator's input and stop the motor 1102 when a maximum degree of safe articulation is reached.

In certain embodiments, the articulation control system 3000 may include a virtual detent that may alert the operator when the end effector reaches the articulation home state position. For example, the operator may tilt the rocker 3012 to articulate the end effector 1300 from an articulated position to the articulation home state position. Upon reach the articulation home state position, the controller 3002 may stop the articulation of the end effector 1300. In order to continue past the articulation home state position, the operator may release the rocker 3012 and then tilt it again to restart the articulation. Alternatively, a mechanical detent can also be used to provide haptic feedback for the operator that the end effect reached the articulation home state position. Other forms of feedback may be utilized such as audio feedback, for example.

Further to the above, the articulation control system 3000 may include a reset input which may reset or return the end effector 1300 to the articulation home state position if the end effector 1300 is in an articulated position. For example, as illustrated in FIG. 160, upon receiving a reset input signal, the controller 3002 may determine the articulation position of the end effector 1300 and, if the end effector 1300 is in the articulation home state position, the controller 3002 may take no action. However, if the end effector 1300 is in an articulated position when it receives a reset input signal, the controller may activate the motor 1102 to return the end effector 1300 to the articulation home state position. As illustrated in FIG. 156, the operator may depress the rocker 3012 downward to close the dome switches 3004A and 3004B simultaneously, or at least within a short time period from each other, which may transmit the reset input signal to the controller 3002 to reset or return the end effector 1300 to the articulation home state position. The operator may then release the rocker 3012 thereby allowing the rocker 3012 to return to the neutral position and the switches 3004A and 3004B to the open positions. Alternatively, the interface 3001 of articulation control system 3000 may include a separate reset switch such as, for example, another dome switch which can be independently closed by the operator to transmit the reset input signal to the controller 3002.

Referring to FIGS. 157-159, in certain embodiments, the interface 3001 of the surgical instrument 1010 may include an interface rocker 3012A which may include a contact member 3013 which can be configured to assist the rocker 3012A into its neutral position, as illustrated in FIG. 157. The contact member 3013 can comprise an arcuate surface 3017 which can be biased against the interface housing 3011 by a biasing member and/or by biasing forces applied thereto by the dome switches 3004A and 3004B. The contact member 3013 may be configured to rock, or rotate, when the operator tilts the rocker 3012A forward, as illustrated in FIG. 158, or back in order to articulate the end effector 1300 in the clockwise direction or the counterclockwise direction, respectively. When the rocker 3012A is released, the arcuate surface of the rocker 3012A can be rotated back into its neutral position against the interface housing 3011 by the biasing forces applied thereto. In various circumstances, the contact member 3013 may be displaced away from the interface housing 3011 when the operator depresses the rocker 3012A downwardly, as illustrated in FIG. 159, to depress the dome switches 3004A and 3004B simultaneously, or at least within a short time period from each other, which may transmit the reset input signal to the controller 3002 to reset or return the end effector 1300 to the articulation home state position, as discussed above.

As described above, the controller 3002 can be configured to determine the articulation position of the end effector 1300. Knowledge of the articulation position of the end effector 1300 may allow the controller 3002 to determine whether the motor 1102 needs to be activated to return the end effector 1300 to the articulation home state position and, if so, to determine the direction of rotation, and the amount of the rotation, of the motor 1102 required to return the end effector 1300 to the articulation home state position. In certain embodiments, the controller 3002 may track the articulation of the end effector 1300 and store the articulation position of the end effector 1300, for example, in the memory 3010. For example, the controller 3002 may track the direction of rotation, speed of rotation, and the time of rotation of the motor 1102 when the motor 1102 is used to articulate the end effector 1300. In some circumstances, the controller 3002 can be configured to evaluate the displacement of the firing system when the firing system is used to drive the articulation system. More specifically, when the articulation drive is coupled to the firing drive, the controller 3002 can monitor the firing drive in order to determine the displacement of the articulation drive. The processor 3008 may calculate the articulation position of the end effector 1300 based on these parameters and store the displaced position of the articulation drive in the memory 3010, for example. The reader will appreciate that other parameters can be tracked and other algorithms can be utilized by the processor 3010 to calculate the articulation position of the end effector 1300, all of which are contemplated by the present disclosure. The stored articulation position of the end effector 1300 can be continuously updated as the end effector 1300 is articulated. Alternatively, the stored articulation position can be updated at discrete points, for example, when the operator releases the dome switch 3004A or the switch 3004B after depressing the same to articulate the end effector 1300.

In any event, upon receiving the reset input signal, the processor 3008 may access the memory 3010 to recover the last stored articulation position of the end effector 1300. If the last stored articulation position is not the articulation home state position, the processor 3008 may calculate the direction and time of rotation of the motor 1102 required to return the end effector 1300 to the articulation home state position based on the last stored articulation position. In some circumstances, the processor 3008 may calculate the distance and direction in which the firing drive needs to be displaced in order to place the articulation drive in its home state position. In either event, the controller 3002 may activate the motor 1102 to rotate accordingly to return the end effector 1300 to the articulation home state position. Furthermore, the processor 3008 may also update the stored articulation position to indicate articulation home state position. However, if the last stored articulation position is the articulation home state position, the controller 3002 may take no action. In some circumstances, the controller 3002 may alert the user through some form of feedback that the end effector and the articulation system is in its home state position. For example, the controller 3002 can be configured to activate a sound and/or a light signal to alert the operator that the end effector 1300 is in the articulation home state position.

In certain embodiments, the surgical instrument 1010 may include a sensor configured to detect the articulation position of the end effector 1300 and communicate the same to the controller 3002. Similar to the above, the detected articulation position of the end effector 1300 can be stored in the memory 3010 and can be continuously updated as the end effector 1300 is articulated or can be updated when the operator releases the dome switch 3004A or after depressing the same to articulate the end effector 1300, for example.

In certain embodiments, it may be desirable to include a warning step prior to resetting or returning the end effector 1300 to the articulation home state position to allow an operator a chance to remedy an erroneous activation of the reset switch. For example, the controller 3002 can be configured to react to a first transmission of the reset input signal to the controller 3002 by activating a light and/or a sound signal alerting the operator that the rocker 3012 has been depressed. In addition, the controller 3002 can also be configured to react to a second transmission of the reset input signal to the controller 3002 within a predetermined time period from the first transmission by activating the motor 1102 to return the end effector 1300 to the articulation home state position. Said another way, a first downward depression of the rocker 3012 may yield a warning to the operator and a second downward depression of the rocker 3012 within a predetermined time period from the first downward depression may cause the controller 3002 to activate the motor 1102 to return the end effector 1300 to the articulation home state position.

Further to the above, the interface 3001 may include a display which can be used by the controller 3002 to communicate a warning message to the operator in response to the first downward depression of the rocker 3012. For example, in response to the first downward depression of the rocker 3012, the controller 3002 may prompt the operator through the display to confirm that the operator wishes to return the end effector 1300 to the articulation home state position. If the operator responds by depressing the rocker 3012 a second time within the predetermined period of time, the controller 3012 may react by activating the motor 1102 to return the end effector 1300 to the articulation home state position.

As described elsewhere in greater detail, the end effector 1300 of the surgical instrument 1010 may include a first jaw comprising an anvil such as, for example, the anvil 1310 and a second jaw comprising a channel configured to receive a staple cartridge such as, for example, the staple cartridge 1304 which may include a plurality of staples. In addition, the end effector 1300 can be transitioned between an open configuration and a closed configuration. Furthermore, the surgical instrument 1010 may include a closure lock and the handle 1042 may include a release member for the closure lock such as, for example, the release member 1072 which can be depressed by the operator to release the closure lock thereby returning the end effector 1300 to the open configuration. In addition, the controller 3002 can be coupled to a sensor 3014 configured to detect the release of the closure lock by the release member 1272. Furthermore, the surgical instrument 1010 may include a firing drive such as, for example, the firing drive 1110 which can be operably coupled to a firing member such as, for example, the firing member 10060. The controller 3002 can be coupled to a sensor 3015 configured to detect the position of the firing drive 1110. The firing drive 1110 can be moved axially to advance the firing member 10060 from a firing home state position to a fired position to deploy the staples from the staple cartridge 1304 and/or cut tissue captured between the anvil 1310 and the staple cartridge 1304 when the end effector 1300 is in the closed configuration.

Also, as described elsewhere in greater detail, the proximal articulation drive 10030 of the surgical instrument 1010 can be selectively coupled with the firing drive 1110 such that, when the firing drive 1110 is motivated by the motor 1102, the proximal articulation drive 10030 can be driven by the firing drive 1110 and the proximal articulation drive 10030 can, in turn, articulate the end effector 1300 relative to the shaft 1210, as described above. Furthermore, the firing drive 1110 can be decoupled from the proximal articulation drive 10030 when the end effector 1300 is in the closed configuration. This arrangement permits the motor 1102 to motivate the firing drive 1110 to move the firing member 10060 between the firing home state position and the fired position independent of the proximal articulation drive 10030.

Further to the above, as described else wherein in greater detail, the surgical instrument 1010 can include a clutch system 10070 (See FIG. 37) which can be engaged when the end effector 1300 is transitioned from the open configuration to the closed configuration and disengaged when the end effector 1300 is transitioned from the closed configuration to the open configuration. When engaged, the clutch system 10070 may operably couple the firing drive 1110 to the proximal drive member 10030 and when the clutch member is disengaged, the firing drive 1110 may be decoupled from the proximal articulation drive. Since the firing drive 1110 can be decoupled and moved independently from the proximal articulation drive 10030, the controller 3002 may be configured to guide the firing drive 1110 to locate the proximal articulation drive 10030 and re-couple the proximal articulation drive 10030 to the firing drive 1110 once again. The controller 3002 may track the direction of rotation, speed of rotation and the time of rotation of the motor 1102 when the firing drive 1110 is coupled to the proximal articulation drive 10030 to determine and store the location of the proximal articulation drive 10030, for example, in memory 3010. The controller 3002 may, as described elsewhere herein, monitor the displacement of the firing system used to drive the articulation system. Other parameters and algorithms can be utilized to determine the location of the proximal articulation drive 10030. In certain embodiments, the firing drive 1110 may include a sensor configured to detect when the firing drive 1110 is coupled to the proximal articulation drive 10030 and communicate the same to the controller 3002 to confirm the coupling engagement between the firing drive 1110 and the proximal articulation drive 10030. In certain embodiments, when the controller 3002 is not configured to store and access the articulation position of the end effector 1300, the controller may activate the motor 1102 to motivate the firing drive 1110 to travel along its full range of motion until the firing drive 1110 comes into coupling arrangement with the proximal articulation drive 10030.

Further to the above, in certain embodiments, the firing home state position of the firing member 10060 can be located at a proximal portion of the end effector 1300. Alternatively, the firing home state position of the firing member 10060 can be located at a distal portion of the end effector 1300. In certain embodiments, the firing home state position may be defined at a position where the firing member 10060 is sufficiently retracted relative to the end effector 1300 such that the end effector 1300 can be freely moved between the open configuration and the closed configuration. In other circumstances, the firing home state position of the firing member 10060 can be identified as the position of the firing member which positions the articulation drive system and the end effector in its articulated home state position.

Referring again to FIG. 151, the interface 3001 of the surgical instrument 1010 may include a home state input. The operator may utilize the home state input to transmit a home state input signal to the controller 3002 to return the surgical instrument 1010 to home state which may include returning the end effector 1300 to the articulation home state position and/or the firing member 10060 to the firing home state position. As illustrated in FIG. 154, the home state input may include a switch such as, for example, the switch 3004C which can be coupled to the controller 3002 via an electrical circuit 3006C. As illustrated in FIGS. 152 and 153, the home state input may include a cap or a cover such as, for example, cover 3014 which can be depressed by the operator to close the switch 3004C and transmit the home state input signal through the circuit 3006C to the controller 3002.

Referring again to FIG. 161, the controller 3002, upon receiving the home state input signal, may check the position of the firing drive 1110 through the sensor 3015 and may check the memory 3010 for the last updated articulation position. If the controller 3002 determines that the end effector 1300 is in the articulation home state position and the firing drive 1110 is positioned such that it is coupled to the proximal articulation drive 10030, the controller 3002 may take no action. Alternatively, the controller 3002 may provide feedback to the operator that the surgical instrument 1010 is at home state. For example, the controller 3002 can be configured to activate a sound and/or a light signal or transmit a message through the display to alert the operator that the surgical instrument 1010 is at home state. However, if the controller 3002 determines that the end effector 1300 is not in the articulation home state position and the firing drive 1110 is positioned such that it is coupled to the proximal articulation drive 10030, the controller 3002 may activate the motor 1102 to motivate the firing drive 1110 to move the proximal articulation drive 10030 which can, in turn, articulate the end effector 1300 relative to the shaft 1210 back to the articulation home state position. Alternatively, if the controller 3002 determines that the end effector 1300 is in the articulation home state position but the firing drive 1110 is not positioned such that it is coupled to the proximal articulation drive 10030, the controller 3002 may activate the motor 1102 to move the firing drive 1110 to a position wherein the firing drive 1110 is coupled to the articulation drive 10030. In doing so, the motor 1102 may retract the firing member 10060 to the firing home state position.

In certain embodiments, referring to FIG. 162, the controller 3002, upon receiving the home state input signal, may check whether the end effector 1300 is in the open configuration through the sensor 3016. Other means for determining whether the end effector 1300 is in the open configuration can be employed. If the controller 3002 determines that the end effector 1300 is in the open configuration, the controller 3002 may proceed as described above. However, if the controller 3002, upon receiving the home state input signal, determines that the end effector 1300 is in the closed configuration, the controller 3002 may prompt the operator to confirm that the operator wishes to return the surgical instrument 1010 to home state. This step can be a precautionary step to prevent the operator from accidentally opening the end effector 1300 during a surgical procedure, for example. In certain embodiments, the controller 3002 may prompt the operator by displaying a message on a display coupled to the controller 3002, for example, requesting the operator to return the end effector 1300 to the open configuration by depressing the release member 1072. If the operator does not release the end effector 1300 to the open configuration, the controller 3002 may take no action. In other embodiments, the controller 3002 may alert the operator by displaying an error message or activating a sound or a light. However, if the operator releases the end effector 1300 to the open configuration, the controller 3002 may reset the surgical instrument as described above.

Referring to FIG. 163, the firing member 10060 may comprise a separate firing reset input which may include a switch and an electrical circuit coupling the switch to controller 3002, wherein the switch can be configured to close the circuit and transmit a firing reset input signal to the controller 3002. The controller 3002, upon receiving the firing reset input signal may check whether the firing member 10060 is in the firing home state position. As described elsewhere in greater detail, the firing member 10060 may be operably coupled to the firing drive 1110 which may comprise a sensor such as, for example, sensor 3015 (See FIG. 151) that may transmit the location of the firing drive 1110 to the controller 3002. Accordingly, the controller 3002 can determine the location of the firing member 10060 by monitoring the location of the firing drive 1110. In any event, if the controller 3002 determines that the firing member 10060 is in the firing home state position, the controller may take no action or may alert the operator that the firing member 10060 is already in the firing home state position by activating a sound and/or a light. On the hand, if the controller 3002 determines that the firing member 10060 is not in the firing home state position, the controller 3002 may activate the motor 1102 to motivate the firing drive 1110 to return the firing member 10060 to the firing home state position.

As described elsewhere in greater detail, the surgical instrument 1010 may include several assemblies that extend, at least partially, through the shaft 1210 and may be in operable engagement with the end effector 1300. For example, the surgical instrument 1010 may include a closure assembly that may transition the end effector 1300 between an open configuration and a closed configuration, an articulation assembly that may articulate the end effector 1300 relative to the shaft 1210, and/or a firing assembly that may fasten and/or cut tissue captured by the end effector 1300. In addition, the surgical instrument 1010 may include a housing such as, for example, the handle 1042 which may be separably coupable to the shaft 1210 and may include complimenting closure, articulation, and/or firing drive systems that can be operably coupled to the closure, articulation, and/or firing assemblies, respectively, of the shaft 1210 when the handle 1042 is coupled to the shaft 1210.

In use, the assemblies described above and their corresponding drive systems may be operably connected. Attempting to separate the handle 1042 from the shaft 1210 during operation of the surgical instrument 1010 may sever the connections between the assemblies and their corresponding drive systems in a manner that may cause one or more of these assemblies and their corresponding drive systems to be out of alignment. On the other hand, preventing the user from separating the handle 1042 from the shaft 1210 during operation, without more, may lead to confusion, frustration, and/or an erroneous assumption that the surgical instrument is not operating properly.

The surgical instrument 1010 may include a safe release system 3080 that may be configured to return one or more of the assemblies and/or corresponding drive systems of the surgical instrument 1010 to a home state thereby allowing the operator to safely separate the handle 1042 from the shaft 1210. The term home state as used herein may refer to a default state wherein one or more of the assemblies and/or corresponding drive systems of the surgical instrument 1010 may reside or may be returned to their default position such as, for example, their position prior to coupling the handle 1042 with the shaft 1210.

Referring to FIG. 150, the safe release system 3080 of the surgical instrument 1010 may include a locking member such as, for example, locking member 3082 which can be moved between a locked configuration and an unlocked configuration. As illustrated in FIG. 164 and as described elsewhere in greater detail, the shaft 1210 may be aligned and coupled with the handle 1042 of the surgical instrument 1010. In addition, the locking member 3082 may be moved from the unlocked configuration to the locked configuration to lock the handle in coupling engagement with the shaft 1210. The locking member 3082 can be positioned at a proximal portion of the shaft 1210, as illustrated in FIG. 166 and may include a latch member 3083 that can be advanced into a receiving slot 3085 positioned in the handle 1042 when the locking member 3082 is moved to the locked configuration and the handle 1042 is coupled to the shaft 1210. In addition, the latch member 3083 can be retracted out of the receiving slot 3085 when the locking member 3082 is moved to the unlocked configuration thereby allowing the handle 1042 to be separated from the shaft 1210, as illustrated in FIG. 167.

Referring to FIG. 151, the safe release system 3080 may further include an interlock switch 3084 which can be coupled to the controller 3002 via an electric circuit 3086 which can be configured to transmit a home state input signal to the controller 3002. In addition, the interlock switch 3084 may be operably coupled to the locking member 3082. For example, the switch 3086 can be moved to close the circuit 3086 when the locking member is moved to the unlocked configuration, as illustrated in FIG. 167 and can be moved to open the circuit 3086 when the locking member 3082 is moved to the locked configuration, as illustrated in FIG. 166. In this example, the controller 3002 can be configured to recognize the closing of the circuit 3086 as a transmission of the home state input signal. Alternatively, in another example, the switch 3086 can be moved to open the circuit 3086 when the locking member is moved to the unlocked configuration and can be moved to close the circuit 3086 when the locking member 3082 is moved to the locked configuration. In this example, the controller 3002 can be configured to recognize the opening of the circuit 3086 as a transmission of the home state input signal.

Referring again to FIG. 166 and FIG. 167, the locking member 3082 may include a first surface 3090 and a second surface 3092 which can be separated by a ramp 3094, wherein the locking member 3082 can be positioned relative to the switch 3084 such that the first surface 3090 and the second 3092 may be slidably movable relative to the switch 3084 when the handle 1042 is coupled to the shaft 1210. Furthermore, as illustrated in FIG. 166, the first surface 3090 may extend in a first plane and the second surface 3092 may extend in a second plane, wherein the switch 3084 can be closer to the first plane that the second plane. Furthermore, as illustrated in FIG. 166, the switch 3084 may be depressed by the first surface 3090 when the locking member 3082 is in the locked configuration and the latch member 3083 is received within the receiving slot 3085, thereby closing the circuit 3086 (FIG. 151) and transmitting the home state input signal to the controller 3002. However, as the locking member 3082 is moved to the unlocked configuration and the latch member 3083 is retracted from the receiving slot 3085, the switch 3084 may slide along the ramp 3094 to face the second surface 3092 which may provide the biased switch 3084 with sufficient room to return to the open position, as illustrated in FIG. 166.

In certain embodiments, as illustrated in FIGS. 151 and 165, a first end 3084*a* of the switch 3084 can be positioned in the handle 1042, for example, at a distal portion thereof and a second end 3084*b* of the switch 3084 can be positioned in the shaft 1210, for example, at a proximal portion thereof and can be operably coupled with the locking member 3082. In these embodiments, the switch 3084 may not close the circuit 3086 until the handle 1042 is coupled to the shaft 1210 to permit the locking member 3082 to bring the second end 3084*b* of the switch 3084 into contact with the first end 3084*a* thereby closing the circuit 3086 and transmitting the home state input signal to the controller 3002. In other embodiments, the locking member 3082, the first end 3084*a*, and the second end 3084*b* of the switch 3084 can be placed in the handle 1042 to permit closure of the circuit 3086 and transmission of the home state input signal to the controller 3002 prior to coupling the handle 1042, for example, to return the firing drive system to its default position to ensure proper alignment with the firing assembly when the shaft 1210 is coupled to the handle 1042.

As described elsewhere in greater detail, the end effector 1300 of the surgical instrument 1010 may include a first jaw comprising an anvil such as, for example, the anvil 1310 and a second jaw comprising a channel configured to receive a staple cartridge such as, for example, the staple cartridge 1304 which may include a plurality of staples. In addition, the end effector 1300 can be transitioned between an open configuration and a closed configuration. For example, the surgical instrument 1010 may include a closure lock for locking the end effector 1300 in a closed configuration and the handle 1042 may include a release member for the closure lock such as, for example, the release member 1072 which can be depressed by the operator to release the closure lock thereby returning the end effector 1300 to the open configuration. In addition, the controller 3002 can be coupled to a sensor 3014 configured to detect the release of the closure lock by the release member 1072. Furthermore, the surgical instrument 1010 may include a firing drive such as, for example, the firing drive 1110 which can be operably coupled to a firing member such as, for example, the firing member 10060. The controller 3002 can be coupled to a sensor 3015 configured to detect the position of the firing drive 1110. In addition, the firing drive 1110 can be advanced axially, as illustrated in FIG. 167A, to advance the firing member 10060 between an unfired position and a fired position to deploy the staples of the staple cartridge 1304 and/or cut tissue captured between the anvil 1310 and the staple cartridge 1304 when the end effector 1300 is in the closed configuration. Furthermore, the firing drive can be retracted by the motor 1102 from the advanced position, for example, the position illustrated in FIG. 167A to a default or retracted position as illustrated in FIG. 167B when the locking member 3082 is moved from the closed configuration to the open configuration.

Further to the above, as described elsewhere in greater detail, the proximal articulation drive 10030 of the surgical instrument 1010 can be selectively coupled with the firing drive 1110 such that, when the firing drive 1110 is motivated by the motor 5, the proximal articulation drive 10030 can be driven by the firing drive 1110 and the proximal articulation drive 10030 can, in turn, articulate the end effector 1300 relative to the shaft 1210 between the articulation home state position and the articulate position, as described above. Furthermore, the firing drive 1110 can be decoupled from the proximal articulation drive 10030, for example, when the end effector 1300 is in the closed configuration. This arrangement permits the motor 1102 to motivate the firing drive 1110 to move the firing member 10060 between the unfired position and the fired position independent of the proximal articulation drive 10030. Since the firing drive 1110 can be decoupled from and moved independently from the proximal articulation drive 10030, the controller 3002 may be configured to guide the firing drive 1110 to locate and reconnect with the proximal articulation drive 10030. In a way, the controller 3002 can remember where it left the proximal articulation drive 10030. More particularly, the controller 3002 can, one, evaluate the position of the firing drive 1110 when the proximal articulation drive 10030 is decoupled from the firing drive 1110 and, two, remember where the proximal articulation drive 10030 is when the controller 3002 is instructed to reconnect the firing drive 1110 with the proximal articulation drive 10030. In such circumstances, the controller 3002 can move the firing drive 1110 into a position in which the clutch assembly 10070, for example, can reconnect the proximal articulation drive 10030 to the firing drive 1110. The controller 3002 may track the direction of rotation, speed of rotation and the time of rotation of the motor 1102 when the firing drive 1110 is coupled to the proximal articulation drive 10030 to determine and store the location of the proximal articulation drive 10030, for example, in the memory 3010. Other parameters and algorithms can be utilized to determine the location of the proximal articulation drive 10030. In certain embodiments, the firing drive 1110 may include a sensor configured to detect when the firing drive 1110 is coupled to the proximal articulation drive 10030 and communicate the same to the controller 3002 to confirm the coupling engagement between the firing drive 1110 and the proximal articulation drive 10030. In certain embodiments, when the controller 3002 is not configured to store and access the proximal articulation drive 10030, the controller may activate the motor 1102 to motivate the firing drive 1110 to travel along its full range of motion until the firing drive 1110 comes into coupling arrangement with the proximal articulation drive 10030.

Referring now to FIGS. 151 and 165, the safe release system 3080 may react to an operator's attempt to separate the handle 1042 from the shaft 1210 by resetting the surgical instrument 1010 to the home state, for example, as soon as the operator moves the locking member 3082 from the locked configuration to the unlocked configuration. As described above, the switch 3084 can be operably coupled to the locking member 3082 such that when the locking member 3082 is moved from the locked configuration to the unlocked configuration, the switch 3084 may be moved to open the circuit 3086 thereby transmitting the home state input signal to the controller 3002. Alternatively, movement of the switch 3084 from its locked configuration to its unlocked configuration may allow the circuit 3086 to close thereby transmitting the home state input signal to the controller 3002.

Referring again to FIG. 168, the controller 3002, upon receiving the home state input signal, may check the position of the firing drive 1110 through the sensor 3015 and may check the memory 3010 for the last updated articulation position of the end effector and, correspondingly, the last position of the proximal articulation drive 10030. If the controller 3002 determines that the end effector 1300 is in the articulation home state position and the firing drive 1110 is positioned such that it is coupled to the proximal articulation drive 10030, the controller 3002 may take no action and the user may remove the shaft assembly from the handle. Alternatively, the controller 3002 may provide feedback to the operator that the surgical instrument 1010 is at home state and/or it is safe to separate the handle 1042 from the shaft 1210. For example, the controller 3002 can be configured to activate a sound and/or a light signal and/or transmit a message through a display (not shown) coupled to the controller 3002 to alert the operator that the surgical instrument 1010 is at home state and/or it is safe to separate the handle 1042 from the shaft 1210. However, if the controller 3002 determines that the end effector 1300 is not in the articulation home state position and the firing drive 1110 is positioned such that it is coupled to the proximal articulation drive 10030, the controller 3002 may activate the motor 1102 to motivate the firing drive 1110 to move the proximal articulation drive 10030 which can, in turn, articulate the end effector 1300 relative to the shaft 1210 back to the articulation home state position. Alternatively, if the controller 3002 determines that the end effector 1300 is in the articulation home state position but the firing drive 1110 is not positioned such that it is coupled to the proximal articulation drive 10030, the controller 3002 may activate the motor 1102 to move the firing drive 1110 to a position wherein the firing drive 1110 is couplable to the articulation drive 9. In doing so, the firing member 9 may retract the firing member 10060 to the firing home state position. As described above, the controller 3002 may optionally provide the feedback to the operator that the surgical instrument 1010 is at home state and that it is safe to separate the handle 1042 from the shaft 1210.

In certain embodiments, referring to FIG. 169, the controller 3002, upon receiving the home state input signal, may check whether the end effector 1300 is in the open configuration through the sensor 3016. Other means for determining that the end effector 1300 is in the open configuration can be employed. If the controller 3002 determines that the end effector 1300 is in the open configuration, the controller 3002 may proceed to reset the surgical instrument 1010 to home state, as described above. However, if the controller 3002, upon receiving the home state input signal, determines that the end effector 1300 is in the closed configuration, the controller 3002 may prompt the operator to confirm that the operator wishes to separate the handle 1042 from the shaft 1210. This step can be a precautionary step to prevent resetting the surgical instrument 1010 if the operator accidentally moved the locking member 3082 thereby erroneously transmitting a home state input signal to the controller

3002 while the end effector 1300 is in use and clamping tissue, for example. In certain embodiments, the controller 3002 may prompt the operator by displaying a message on the display coupled to the controller 3002, for example, requesting the operator to return the end effector 1300 to the open configuration by depressing the release member 1072. In addition to the mechanical locking member 3082, the safe release system 3080 may also include an electronic lock (not shown) which may be controlled by the controller 3002. The electronic lock can be configured to prevent the operator from separating the handle 1042 and the shaft 1210 until the operator depresses the release member 1072. If the operator does not release the end effector 1300 to the open configuration, the controller 3002 may take no action. In other embodiments, the controller 3002 may alert the operator by displaying an error message or activating a sound and/or a light signal. On the other hand, if the operator releases the end effector 1300 to the open configuration, the controller 3002 may reset the surgical instrument 1010 as described above. If an electronic lock is used, the controller 3002 may then release the electronic lock to permit the operator to separate the handle 1042 from the shaft 1210. In addition, the controller 3002 may then alert the operator that it is now safe to remove the handle 1042 from the shaft 1210, as described above. The above process may be further configured in accordance with the teachings of U.S. Pat. No. 12,193,671, incorporated by reference above.

Referring now to FIG. 170, an electric motor 5002 for a surgical instrument (illustrated elsewhere) can comprise a motor housing 5004 and a shaft 5006 extending from the motor housing 5004. While electric motor 5002 is described herein as one example, other electric motors, such as motor 1102, for example, can incorporate the teachings disclosed herein. The shaft 5006 can be fixed to a rotor (not illustrated) positioned within the motor housing 5004, and the shaft 5006 can rotate as the rotor rotates. The shaft 5006 can rotate in one direction during a first operating state, for example, and can rotate in a second direction during the second operating state, for example. Furthermore, the rotation of the electric motor 5002 in one direction can implement a first surgical function, and the rotation of the electric motor 5002 in another direction can implement a second surgical function. In various embodiments, the electric motor 5002 and/or the shaft 5006 thereof can be operably coupled to a firing element (illustrated elsewhere), and can drive the firing element during a firing sequence. For example, clockwise rotation of the electric motor 5002 can drive the firing element distally, and counterclockwise rotation of the electric motor 5002 can drive the firing element proximally. Alternatively, counterclockwise rotation of the electric motor 5002 can drive the firing element distally, and clockwise rotation of the electric motor 5002 can drive the firing element proximally. In other words, the electric motor can advance the firing element during the first operating state and can retract the firing element during the second operating state, or vice versa. In other embodiments, the electric motor 5002 can be operably coupled to an articulation mechanism (illustrated elsewhere), and can articulate an end effector relative to a handle of the surgical instrument. For example, clockwise rotation of the electric motor 5002 can articulate the end effector in a first direction, and counterclockwise rotation of the electric motor 5002 can articulate the end effector in a second direction.

In various embodiments, a resonator or amplifier 5020 can be mounted on the shaft 5006 of the electric motor 5002. A washer 5008 can secure the resonator 5020 relative to the shaft 5006, for example. Furthermore, the resonator 5020 can be fixedly secured to the shaft 5006 such that the resonator 5020 rotates and/or moves with the shaft 5006. In various embodiments, the resonator 5020 and/or various portions thereof can be fastened to the shaft 5006 and/or can be integrally formed therewith, for example.

Referring now to FIGS. 170-172, the resonator 5020 can comprise a body 5022 comprising a mounting bore 5040 (FIGS. 171 and 172) for receiving the shaft 5006 (FIG. 170). For example, the shaft 5006 can extend through the mounting bore 5040 when the resonator 5020 is secured to the shaft 5006. The mounting bore 5040 and the shaft 5006 can be coaxial, for example. In various embodiments, the body 5022 of the resonator 5020 can be balanced and/or symmetrical relative to the mounting bore 5040, and the center of mass of the body 5022 can be positioned along the central axis of the mounting bore 5040, for example. In such embodiments, the center of mass of the body 5022 can be positioned along the axis of rotation of the shaft 5006, and the body 5022 can be balanced relative to the shaft 5006, for example.

In various circumstances, the resonator 5020 can further comprise a pendulum 5030 extending from the body 5022. For example, the pendulum 5030 can comprise a spring or bar 5032 extending from the body 5022 and a weight 5034 extending from the spring 5032. In certain circumstances, the resonator 5020 and/or the pendulum 5030 thereof can be designed to have an optimized natural frequency. As described herein, an optimized natural frequency can amplify the haptic feedback generated when the electric motor 5002 oscillates between clockwise and counterclockwise rotations, e.g., during the third operating state. In various circumstances, the resonator 5020 can further comprise a counterweight 5024 extending from the body 5022. Referring primarily to FIG. 172, the pendulum 5030 can extend from the body 5022 in a first direction X, and the counterweight 5024 can extend from the body 5022 in a second direction Y. The second direction Y can be different than and/or opposite to the first direction X, for example. In various embodiments, the counterweight 5024 can be designed to balance the mass of the pendulum 5030 relative to the mounting bore 5040 (FIGS. 171 and 172) through the body 5022. For example, the geometry and material of the counterweight 5024 can be selected such that the center of mass 5028 (FIG. 172) of the entire resonator 5020 is positioned along the central axis of the mounting bore 5040 of the body 5022, and thus, along the axis of rotation of the resonator 5020 and the shaft 5006 (FIG. 170).

The center of mass 5028 of the resonator 5020 (CM$_R$) can be determined from the following relationship:

$$CM_R = \frac{1}{m_R}(CM_B \cdot m_B + CM_C \cdot m_C + CM_S \cdot m_S + CM_W \cdot m_W),$$

where m$_R$ is the total mass of the resonator 5020, CM$_B$ is the center of mass of the body 5022, CM$_C$ is the center of mass of the counterweight 5024, CM$_S$ is the center of mass of the spring 5032, CM$_W$ is the center of mass of the weight 5034, m$_B$ is the mass of the body 5022, m$_C$ is the mass of the counterweight 5024, m$_S$ is the mass of the spring 5032, and m$_W$ is the mass of the weight 5034. Where the center of mass of the body 5022 is positioned along the central axis of the mounting bore 5040 and the resonator 5020 comprises a uniform thickness and uniform density, the resonator 5020 can be balanced relative to the central axis of the mounting bore 5040 according to the following simplified relationship:

$$A_C \cdot CM_C = A_S \cdot CM_S + A_W \cdot CM_W,$$

wherein A$_C$ is the area of the counterweight 5024, A$_S$ is the area of the spring 5032, and A$_W$ is the area of the weight 5034.

In various circumstances, when the center of mass 5028 of the resonator 5020 is centered along the central axis of the mounting hole 5040, and thus, along the axis of rotation of the shaft 5006 (FIG. 170), the resonator 5020 can be balanced relative to its axis of rotation thereof. In such embodiments, because the resonator 5020 is balanced, the background haptic feedback can be minimized during the first and second operating states. In various circumstances, the resonator 5020 can include additional or fewer components. The various components of the resonator 5020 can be balanced such that the center of mass 5028 of the entire resonator 5020 is balanced relative to the axis of rotation of the resonator 5020. Additionally, in some embodiments, the material and/or density of various components of the resonator 5020 can differ from various other components of the resonator 5020. The material and/or density of the various components can be selected to balance the mass of the resonator 5020 relative to the axis of rotation and/or to optimize the natural frequency of the resonator 5020 and/or the pendulum 5030 thereof, as described herein.

Referring still to FIGS. 170-172, the spring 5032 of the pendulum 5030 can be deflectable and/or deformable. For example, rotation of the resonator 5020 can cause the spring 5032 of the pendulum 5030 to deflect. The spring 5032 can deflect upon initial rotation of the resonator 5020, and can remain deflected as the resonator 5020 continues to rotate in the same direction and at the same rotational speed. Because the deflection of the spring 5032 remains at least substantially constant during continued substantially constant rotation of the resonator 5020 in one direction, the background haptic feedback can remain minimized during the first and second operating states. When the rotational direction of the resonator 5020 changes, the spring 5032 can deflect in a different direction. For example, the spring 5032 can deflect in a first direction when the resonator 5020 rotates clockwise and can deflect in a second direction when the resonator 5020 rotates counterclockwise. The second direction can be opposite to the first direction, for example. In other words, as the electric motor 5020 oscillates between clockwise rotation and counterclockwise rotation, the spring 5032 can repeatedly deflect in different directions in response to the changes in the direction of rotation. Repeated deflections of the spring 5032 in opposite directions, i.e., deflective oscillations, can generate the amplified haptic feedback. For example, the haptic feedback generated by the oscillating resonator 5020, which is driven by the oscillating motor 5002 (FIG. 170), can be sufficiently amplified such that it provides a signal to the operator indicative of a particular condition of the surgical instrument. The amplified haptic feedback generated by the oscillating resonator 5020 and motor 5002 can be substantially greater than the background haptic feedback generated during the sustained rotation of the resonator 5020 and motor 5002 in the same direction.

In use, the rotation of the pendulum 5030 can generate a centrifugal force on the weight 5034, and the spring 5032 of the pendulum 5030 can elongate in response to the centrifugal force. In various embodiments, the resonator 5020 and/or the motor 5002 can comprise a retainer for limiting radial elongation of the spring 5032. Such a retainer can retain the pendulum 5030 within a predefined radial boundary 5050 (FIG. 170). In various circumstances, the centrifugal force exerted on the weight 5034 during the third operating state may be insufficient to elongate the pendulum 5030 beyond the redefined radial boundary 5050.

In various circumstances, the resonator 5020 can be designed to amplify the haptic feedback generated by the electric motor 5002 (FIG. 170) during the third operating state. In other words, the resonator 5020 can be designed such that the natural frequency of the resonator 5020 is optimized, and the electric motor 5002 can oscillate at a frequency that drives the resonator 5020 to oscillate at its optimized natural frequency. In various embodiments, the optimized natural frequency of the resonator 5020 can be related to the frequency of oscillations of the electric motor 5002. The optimized natural frequency of the resonator 5020 can coincide with and/or correspond to the oscillation frequency of the electric motor 5002, for example. In certain embodiments, the optimized natural frequency of the resonator 5020 can be offset from the oscillation frequency of the electric motor 5002, for example.

In certain embodiments, the natural frequency of the resonator 5020 can be approximated by the natural frequency of the pendulum 5030. For example, substantially non-oscillating components can be ignored in the natural frequency approximation. In certain embodiments, the body 5022 and the counterweight 5024 can be assumed to be substantially non-oscillating components of the resonator 5020, and thus, assumed to have a negligible or inconsequential effect on the natural frequency of the resonator 5020. Accordingly, the oscillating component of the resonator 5020, e.g., the pendulum 5030, can be designed to amplify the haptic feedback generated by the electric motor 5002 (FIG. 170) during the third operating state. Where the mass of the spring 5032 is substantially less than the mass of the weight 5034, the natural frequency of the pendulum 5030 ($f_p$) can be approximated by the following relationship:

$$f_P \cong \frac{1}{2\pi} \sqrt{\frac{k_S}{m_W}},$$

wherein $k_S$ is the spring constant of the spring 5032 and $m_W$ is the mass of the weight 5034. The spring constant of the spring 5032 ($k_S$) can be determined from the following relationship:

$$k_S = \frac{3E_S I_S}{L_S^3},$$

where $E_S$ is the modulus of elasticity of the spring 5032, $I_S$ is the second moment of inertia of the spring 5032, and $L_S$ is the length of the spring 5032. In various embodiments, the spring constant ($k_S$) of the spring 5032 and/or the mass of the weight 5034 ($m_W$) can be selected such that the natural frequency of the pendulum 5030 ($f_p$) relates to the oscillation frequency of the electric motor 5002 during the third operating state. For example, the natural frequency of the pendulum 5030 can be optimized by varying the spring constant of the spring 5032 and/or the mass of the weight 5034.

Referring still to FIGS. 170-172, the natural frequency of the resonator 5020 and/or the pendulum 5030 thereof can be optimized to a frequency that provides the optimal haptic feedback to the operator. For example, the natural frequency of the resonator 5020 can be optimized to between approximately 50 Hz and approximately 300 Hz in order to enhance the feedback experienced by the operator. In some embodiments, the natural frequency of the resonator 5020 can be optimized to a frequency less than approximately 50 Hz, for example, and, in other embodiments, the resonator 5020 can be optimized for a frequency greater than approximately 300 Hz, for example. Furthermore, the electric motor 5002 (FIG. 170) can oscillate at a frequency that drives the resonator 5020 to oscillate at or near the natural frequency thereof. In certain embodiments, the electric motor 5002 can drive the resonator 5020 to oscillate within a range of amplifying frequencies inclusive of the natural frequency of the resonator 5020.

In various embodiments, the oscillation frequency of the electric motor 5002 can coincide with and/or correspond to the natural frequency of the resonator 5020 in order to drive the resonator 5020 at or near its natural frequency. In certain embodiments, the oscillation frequency of the electric motor 5002 can be near or at the natural frequency of the resonator 5020 and, in other embodiments, the oscillation frequency of the electric motor 5002 can be offset from the natural frequency of the resonator 5020. In various embodiments, the oscillation frequency of the electric motor 5002 can be optimized to coincide with the natural frequency of the resonator 5020. Furthermore, in certain embodiments, the oscillation frequency of the electric motor 5002 and the natural frequency of the resonator 5020 can be cooperatively selected, designed and/or optimized to amplify the haptic feedback generated by the electric motor 5002 during the third operating state.

Referring primarily to FIG. 170, the electric motor 5002 can generate the amplified haptic feedback when the electric motor 5002 oscillates between the clockwise direction and the counterclockwise direction during the third operating state. Additionally, the rotation of the electric motor 5002 during the first and second operating states can drive the firing member (illustrated elsewhere) during a firing stroke. For example, clockwise rotation of the electric motor 5002 can advance the firing element distally and counterclockwise rotation of the electric motor 5002 can retract the firing element proximally. Accordingly, when the electric motor 5002 oscillates between the clockwise direction and the counterclockwise direction, the distal end of the firing element may move between a slightly more distal position and a slightly more proximal position. However, the electric motor 5002 can be significantly geared down such that oscillations of the electric motor 5002 during the third operating state move the distal end of the firing element an insignificant and/or imperceptible distance. In various embodiments, the gear ratio can be approximately 200:1 to approximately 800:1, for example. In certain embodiments, the firing element can remain stationary during the third operating state. For example, slack between the motor 5002 and distal end of the firing element can absorb the oscillations of the electric motor 5002. For instance, referring to FIGS. 102-104, such slack is present between the firing member 10060 and the knife bar 10066. In various circumstances, the knife bar 10066 can comprise a drive tab 10065 which extends into a drive slot 10064 defined in the firing member 10060 wherein the length of the drive slot 10064 between a distal end 10067 and a proximal end 10069 thereof can be longer than the drive tab 10065. In use, sufficient travel of the firing member 10060 must occur before the distal end 10067 or the proximal end 10069 come into contact with the drive tab 10065.

Referring now to FIGS. 173-176, the electric motor 5002 (FIGS. 173 and 174) can be positioned within a handle 5101 (FIG. 173) of a surgical instrument 5100 (FIG. 173). In various embodiments, a resonator or amplifier 5120 can be mounted on the shaft 5006 of the electric motor 5002. The shaft 5006 can be fixed to the rotor (not illustrated) positioned within the motor housing 5004, and the shaft 5006 can rotate as the rotor rotates. The washer 5008 can secure the resonator 5120 relative to the shaft 5006, for example. Furthermore, the resonator 5120 can be secured to the shaft 5006 such that the resonator 5120 rotates and/or moves with the shaft 5006. In some circumstances, a key can be utilized to transmit the rotational movement of the shaft 5006 to the resonator 5120, for example. In various circumstances, the resonator 5120 and/or various portions thereof can be fastened to the shaft 5006 and/or can be integrally formed therewith, for example.

Referring primarily to FIGS. 175 and 176, similar to the resonator 5020, the resonator 5120 can comprise a body 5122 comprising a mounting bore 5140 for receiving the shaft 5006 (FIGS. 173 and 174) of the electric motor 5002 (FIGS. 173 and 174). For example, the shaft 5006 can extend through the mounting bore 5140 when the resonator 5120 is secured to the shaft 5006. In various embodiments, the body 5122 of the resonator 5120 can be balanced and symmetrical relative to the mounting bore 5140, and the center of mass of the body 5122 can be positioned along the central axis of the mounting bore 5140, for example. Further, the center of mass of the body 5122 can be positioned along the axis of rotation of the resonator 5120 and the shaft 5006 such that the body 5122 is balanced relative to the shaft 5006, for example.

In various embodiments, the resonator 5120 can further comprise a pendulum 5130 extending from the body 5122. For example, the pendulum 5130 can comprise a spring or bar 5132 extending from the body 5122 and a weight 5134 extending from the spring 5132. In certain embodiments, the spring 5132 can extend along an axis that defines at least one contour between the body 5122 and the weight 5134. The spring 5132 can wind, bend, twist, turn, crisscross, and/or zigzag, for example. The geometry of the spring 5132 can affect the spring constant thereof, for example. In at least one embodiment, the spring 5132 can form a first loop 5137 on a first lateral side of the resonator 5120 and a second loop 5138 on a second lateral side of the resonator 5120. An intermediate portion 5139 of the spring 5132 can traverse between the first and second loops 5137, 5138, for example. Similar to the spring 5032, the spring 5132 can be deflectable, and can deflect in response to rotations and/or oscillations of the resonator 5120. Furthermore, in certain embodiments, the weight 5134 can include a pin 5136, which can provide additional mass to the weight 5134, for example. As described herein, the mass of the weight 5134 and the geometry and properties of the spring 5132 can be selected to optimize the natural frequency of the pendulum 5130, and thus, the natural frequency of the entire resonator 5120, for example.

Referring still to FIGS. 175 and 176, the resonator 5120 can further comprise a counterweight 5124 extending from the body 5122. In certain embodiments, a pin 5126 can extend from the counterweight 5124, and can provide additional mass to the counterweight 5124, for example. The pendulum 5130 can extend from the body 5122 in a first direction X, and the counterweight 5124 can extend from the body 5122 in a second direction Y. The second direction Y can be different than and/or opposite to the first direction X, for example. In various embodiments, the counterweight

5124 can be designed to balance the mass of the pendulum 5130 relative to the mounting bore 5140 through the body 5120. For example, the geometry and material of the counterweight 5124 can be selected such that the center of mass 5128 of the resonator 5120 is positioned along the central axis of the mounting bore 5140 of the body 5122, and thus, along the axis of rotation A (FIG. 173) of the resonator 5120.

Similar to the resonator 5020, the resonator 5120 can be designed to amplify the haptic feedback generated by the electric motor 5002 (FIGS. 173 and 174) during the third operating state. In other words, the resonator 5120 can be designed such that the natural frequency of the resonator 5120 is optimized, and the electric motor 5002 can oscillate at a frequency that drives the resonator 5120 to oscillate at or near its optimized natural frequency. For example, the electric motor 5002 can drive the resonator 5120 to oscillate within a range of amplifying frequencies inclusive of the natural frequency of the resonator 5120. In certain embodiments, the natural frequency of the resonator 5120 can be approximated by the natural frequency of the pendulum 5130. In such embodiments, the pendulum 5130 can be designed to amplify the haptic feedback generated by the electric motor 5002 during the third operating state. For example, the pendulum 5130 can be designed to have an optimized natural frequency, and the electric motor 5002 can drive the resonator 5120 to oscillate at or near the optimized natural frequency of the pendulum 5130 in order to amplify the haptic feedback generated during the third operating state.

Referring now to FIGS. 177-180, the electric motor 5002 (FIGS. 177 and 178) can be positioned within the handle 5101 (FIG. 177) of the surgical instrument 5100 (FIG. 177). In various embodiments, a resonator or amplifier 5220 can be mounted on the shaft 5006 (FIG. 170) of the electric motor 5002. The shaft 5006 can be fixed to the rotor (not illustrated) positioned within the housing 5004, and the shaft 5006 can rotate as the rotor rotates. The washer 5008 (FIG. 170) can secure the resonator 5220 relative to the shaft 5006, for example. Furthermore, the resonator 5220 can be secured to the shaft 5006 such that the resonator 5220 rotates and/or moves with the shaft 5006. In various embodiments, the resonator 5220 and/or various portions thereof can be fastened to the shaft 5006 and/or can be integrally formed therewith, for example.

Referring primarily to FIGS. 179 and 180, similar to the resonators 5020, 5120, the resonator 5220 can comprise a body 5222 comprising a mounting bore 5240 for receiving the shaft 5006 (FIGS. 176 and 177) of the electric motor 5002 (FIGS. 176 and 177). For example, the shaft 5006 can extend through the mounting bore 5240 when the resonator 5220 is secured to the shaft 5006. In various embodiments, the body 5222 of the resonator 5220 can be balanced and symmetrical relative to the mounting bore 5240, and the center of mass of the body 5222 can be positioned along the central axis of the mounting bore 5240, for example. Further, the center of mass of the body 5222 can be positioned along the axis of rotation of the shaft 5006 such that the body 5222 is balanced relative to the shaft 5006, for example.

In various embodiments, the resonator 5220 can further comprise a pendulum 5230 extending from the body 5222. For example, the pendulum 5230 can comprise a spring or bar 5232 extending from the body 5222 and a weight 5234 extending from the spring 5232. In various embodiments, the spring 5232 can curve, wind, bend, twist, turn, crisscross, and/or zigzag between the body 5222 and the weight 5234. Furthermore, in certain embodiments, the weight 5234 can include a pin 5236, which can provide additional mass to the weight 5234, for example. As described herein, the mass of the weight 5234 and the geometry and properties of the spring 5232 can be selected to optimize the natural frequency of the pendulum 5230, and thus, the natural frequency of the entire resonator 5220, for example.

In various embodiments, a retainer can limit or constrain radial elongation of the spring 5232 and/or the pendulum 5230 during rotation and/or oscillation. For example, a retainer can comprise a barrier or retaining wall around at least a portion of the pendulum 5230. During the first and second operating states, for example, the spring 5232 may deform and extend the weight 5234 toward the barrier, which can prevent further elongation of the spring 5232. For example, referring primarily to FIGS. 179 and 180, the resonator 5220 can comprise a retainer 5244. The retainer 5244 can comprise a first leg 5246, which can be secured to the body 5222 and/or to a counterweight 5224 of the resonator 5220. The first leg 5246 can be fixed to the resonator 5220, and can be formed as an integral piece therewith and/or fastened thereto, for example. The retainer 5244 can further comprise a second leg or barrier leg 5248, which can extend past the weight 5234 of the pendulum 5230 when the spring 5232 is undeformed. The barrier leg 5248 can define the radial boundary 5050 beyond which the pendulum 5230 cannot extend. In other words, the barrier leg 5248 can block radial extension of the pendulum 5230. For example, the barrier leg 5248 can be out of contact with the pendulum 5230 when the spring 5232 is undeformed because the pendulum 5230 can be positioned within the radial boundary 5050. In other words, a gap 5249 (FIG. 180) can be defined between the weight 5234 and the barrier leg 5248 when the spring 5234 is undeformed. Further, the barrier leg 5248 can remain out of contact with the pendulum 5230 when the resonator 5220 oscillates during the third operating state. For example, the centrifugal force on the oscillating pendulum 5230 during the third operating state may be insufficient to extend the weight 5234 of the pendulum 5230 beyond the predefined radial boundary 5050 of the motor 5002. Though the gap 5249 may be reduced during the third operating state, the weight 5234 can remain out of contact with the barrier leg 5248, for example. In such embodiments, the natural frequency of the pendulum 5230 can be substantially unaffected by the retainer 5244 during the third operating state.

In various embodiments, when the resonator 5220 rotates during the first and second operating states, the spring 5232 of the pendulum 5230 can be substantially deformed and/or elongated. For example, the rotation of the resonator 5220 can generate a centrifugal force on the spring 5232, and the spring 5232 may elongate in response to the centrifugal force. In certain embodiments, the weight 5234 of the pendulum 5230 can move toward and into abutting contact with the barrier leg 5248 of the retainer 5244. In such embodiments, the barrier 5248 can limit or constrain further radial elongation of the spring 5232 during the first and second operating states.

In various embodiments, the retainer 5244 can be substantially rigid such that the retainer 5244 resists deformation and/or elongation. In certain embodiments, the retainer 5244 can be integrally formed with the resonator 5220 and/or secured relative thereto. In some embodiments, the retainer 5244 can be secured to the motor 5002 (FIGS. 177 and 1781). For example, the retainer 5244 can be fixed relative to the rotor and/or the shaft 5006 (FIGS. 177 and 178) of the motor 5002 and can rotate and/or move therewith. In such embodiments, the retainer 5244 can rotate with the resonator 5220, for example. In various embodiments, the retainer 5244 can be fastened to the motor 5002 and/or can be integrally formed therewith, for example. In certain embodiments, the retainer 5244 can remain stationary relative to the rotating shaft 5008 and/or resonator 5220, for example.

Referring still to FIGS. 179 and 180, the resonator 5220 can further comprise the counterweight 5224 extending from the body 5222. In certain embodiments, a pin 5226 can extend from the counterweight 5224, and can provide additional mass to the counterweight 5224, for example. The pendulum 5230 can extend from the body 5222 in a first direction, and the counterweight 5224 can extend from the body 5222 in a second direction. The second direction can be different than and/or opposite to the first direction of the pendulum 5230, for example. In various embodiments, the counterweight 5224 can be designed to balance the mass of the pendulum 5230 and the retainer 5244 relative to the mounting bore 5240 through the body 5220 of the resonator 5220. For example, the geometry and material of the counterweight 5224 can be selected such that the center of mass 5228 of the resonator 5220 is positioned along the central axis of the mounting bore 5240 of the body 5222, and thus, along the axis of rotation A (FIG. 177) of the shaft 5008 (FIGS. 177 and 178) and the resonator 5220.

Similar to the resonators 5020, 5120, the resonator 5220 can be designed to amplify the haptic feedback generated by the electric motor 5002 during the third operating state. In other words, the resonator 5220 can be designed such that the natural frequency of the resonator 5220 is optimized, and the electric motor 5002 can oscillate at a frequency that drives the resonator 5220 to oscillate at or near its optimized natural frequency. For example, the electric motor 5002 can drive the resonator 5220 to oscillate within a range of amplifying frequencies inclusive of the natural frequency of the resonator 5220. In certain embodiments, the natural frequency of the resonator 5220 can be approximated by the natural frequency of the pendulum 5230. In such embodiments, the pendulum 5230 can be designed to amplify the haptic feedback generated by the electric motor 5002 during the third operating state. For example, the pendulum 5230 can be designed to have an optimized natural frequency, and the electric motor 5002 can drive the resonator 5220 to oscillate at or near the optimized natural frequency of the pendulum 5230 to amplify the haptic feedback generated during the third operating state.

Referring now to FIG. 181, the electric motor 5002 can be positioned within the handle 5101 of the surgical instrument 5100. In various embodiments, a resonator or amplifier 5320, similar to resonator 5220, for example, can be mounted on the shaft 5006 (FIG. 170) of the electric motor 5002. The resonator 5320 can comprise a body 5322 comprising a mounting bore 5340, for example, a pendulum 5330 comprising a spring 5332, a weight 5334, and a pin 5336, for example, and a counterweight 5324 comprising a pin 5326, for example. In various embodiments, the center of mass of the resonator 5320 can lie along the axis of rotation A, and the geometry and material of the resonator 5230 can be selected to optimize the natural frequency thereof.

In various embodiments, a retaining ring 5344, similar to retainer 5244, can limit or constrain radial elongation of the spring 5332 and/or the pendulum 5230 during rotation and/or oscillation. In various embodiments, the retaining ring 5344 can comprise a barrier or retaining wall around at least a portion of the pendulum 5330. In certain embodiments, the retaining ring 5344 can comprise a ring encircling the resonator 5320, for example. In various embodiments, the retaining ring 5344 can be attached to the electric motor 5002, such as the motor housing 5004, for example. In other embodiments, the retaining ring 5344 can be attached to the handle 5101 of the surgical instrument 5100, for example. In still other embodiments, the retaining ring 5344 can be attached to the rotor and/or the shaft 5006 (FIG. 170) of the electric motor 5002 such that the retaining ring 5344 rotates with the shaft 5006 and/or the resonator 5320, for example. In various embodiments, the retaining ring 5344 can be substantially rigid such that it resists deformation and/or elongation.

The retaining ring 5344 can define the radial boundary beyond which the pendulum 5330 cannot extend. For example, the pendulum 5330 can be out of contact with the retaining ring 5344 when the spring 5332 is undeformed. In other words, a gap can be defined between the weight 5334 of the pendulum 5330 and the retaining ring 5344 when the spring 5334 is undeformed. Further, the pendulum 5330 can remain out of contact with the retaining ring 5344 when the resonator 5320 oscillates during the third operating state. For example, the centrifugal force on the oscillating pendulum 5330 during the third operating state may be insufficient to extend the weight 5334 of the pendulum 5330 beyond the predefined radial boundary. Though the gap defined between the weight 5334 and the retaining ring 5344 may be reduced during the third operating state, the weight 5334 can remain out of contact with the retaining ring 5344, for example. In such embodiments, the natural frequency of the pendulum 5330 can be substantially unaffected by the retaining ring 5344 during the third operating state.

In various embodiments, when the resonator 5320 rotates during the first and second operating states, the spring 5332 of the pendulum 5330 can be substantially deformed and/or elongated. For example, the rotation of the resonator 5320 can generate a centrifugal force on the spring 5332, and the spring 5332 may elongate in response to the centrifugal force. In certain embodiments, the weight 5334 of the pendulum 5330 can move toward and into abutting contact with the retaining ring 5344. In such embodiments, the retaining ring 5344 can limit or constrain further radial elongation of the spring 5332 during the first and second operating states.

In various embodiments, the surgical instrument 5100 (FIG. 177) can comprise a control system (not shown), which can control the electric motor 5002. In various embodiments, the control system can comprise one or more computers, processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, and/or chip sets, for example. The control system can initiate, pause, resume, and/or terminate various operating states of the electric motor 5002. For example, the electric motor 5002 can perform a first function, e.g., advancing the firing element distally, during the first operating state, and can subsequently switch to the second operating state to perform a second function, e.g., retracting the firing element proximally. The firing element can be advanced distally to transect a predefined length of tissue, and/or to eject and/or form a predefined number of staples (illustrated elsewhere), for example. In various embodiments, when the predefined length of tissue has been transected and/or the predefined number of staples have been ejected and/or formed, the control system can control the electric motor 5002 to switch to the second operating state.

The firing element can be retracted proximally during the second operating state to prepare for a subsequent firing stroke, for example. In certain embodiments, the electric motor 5002 can switch to the third operating state before the firing element completes the predefined transection length, and/or ejection and/or formation of the predefined number of staples. For example, the electric motor 5002 can prematurely switch from the first operating state to the third operating state to communicate a signal indicative of a condition of the surgical instrument to the operator. In various embodiments, the electric motor 5002 can switch to the third operating state to communicate a potential overload warning signal to the operator. In other embodiments, the amplified haptic feedback can communicate a status update to the operator such as, for example, a signal that the firing element has reached a distal-most position and/or successfully completed a firing stroke.

In various embodiments, the surgical instrument 5100 may be designed to overcome a maximum threshold force in order to transect tissue. When the force applied to the firing element exceeds the maximum threshold force, the surgical instrument 5100 may not perform as intended. For example, when the firing element attempts to transect thicker and/or tougher tissue, the thicker and/or tougher tissue may exert a force on the firing element that exceeds the maximum threshold force. Accordingly, the firing element may be unable to transect the thicker and/or tougher tissue. In such embodiments, the electric motor 5002 can switch to the third operating state in order to warn the operator that overload and/or failure of the surgical instrument 5100 is possible. In various embodiments, the surgical instrument 5100 can comprise a sensor (not shown). The sensor can be positioned in the end effector (illustrated elsewhere), for example, and can be configured to detect the force applied to the firing element during the firing sequence. In certain embodiments, the sensor and the control system can be in signal communication. In such embodiments, when the force detected by the sensor exceeds the maximum threshold force, the control system can switch the electric motor 5002 to the third operating state. In the third operating state, as described herein, advancement of the firing element can be paused and the electric motor can generate amplified haptic feedback to communicate the potential overload warning to the operator.

In response to the amplified haptic feedback, the operator can decide whether to resume the first operating state or to initiate the second operating state. For example, the operator can decide to resume advancement of the firing element distally, i.e., operate the surgical instrument in a warned operating state, or to heed the potential overload warning and retract the firing element proximally, i.e., operate the surgical instrument in a modified operating state. If the operator decides to operate the surgical instrument in the warned operating state, the surgical instrument 5100 may be at risk of failure. In various embodiments, the surgical instrument 5100 can comprise an input key (not shown), such as a plurality of lever(s) and/or button(s), for example. In various embodiments, the input key can be in signal communication with the control system. The operator can control the surgical instrument by entering input via the input key. For example, the operator can select a first button of the input key to resume advancement of the firing element, i.e., enter the warned operating state, or can select a second button of the input key to retract the firing element, i.e., enter the modified operating state. In various embodiments, the operator can select an additional button and/or lever to select yet a different operating state.

Though the surgical instrument 5100 may fail when operated in the warned operating state, the operator of the surgical instrument 5100 may decide that the failure risk is outweighed by the necessity and/or urgency of the surgical function. For example, when time is essential, the operator may decide that the risk of instrument failure is outweighed by a critical need to expeditiously complete (or attempt to complete) a surgical transection and/or stapling. Furthermore, by allowing the operator to determine the course of action, the holistic knowledge of the operator can be applied to the surgical procedure, and the operator is less likely to become confused and/or frustrated with the surgical instrument 5100.

In various embodiments, a different motor can generate feedback to communicate with the operator. For example, a first motor can drive the firing member during a firing sequence, and a second motor can generate feedback. In various embodiments, the second motor can generate sensory feedback such as, for example, a noise, a light, and/or a tactile signal to communicate with the operator. Furthermore, in certain embodiments, the control system can control the multiple motors of the surgical instrument.

Referring primarily to FIG. 180, a method of operating a surgical system or surgical instrument can include a plurality of operating states of the surgical instrument. For example, the surgical instrument can first operate in an initial operating state 5402, and can subsequently operate in one of the secondary operating states 5412 or 5414. The secondary operating state can be a warned operating state 5412, for example, or a modified operating state 5414, for example. When the surgical instrument operates in the initial operating state 5402, an initial surgical function can be initiated at step 5404. The initial surgical function can be one or more of various functions of the surgical instrument, such as, clamping tissue between jaws of an end effector, articulating the end effector, advancing the firing member, retracting the firing member, opening the end effector jaws, and/or repeating and/or combining various function(s), for example. After initiation of the initial surgical function, the surgical instrument can detect a condition of the surgical instrument at step 5406. For example, where the initial surgical function is advancing the firing member, a sensor can detect a clinically-important condition, such as a force on the advancing firing member that exceeds a threshold force, for example.

Referring still to FIG. 180, in response to the detected condition, the surgical instrument can pause the initial surgical function at step 5408. Further, at step 5410 the surgical instrument can provide feedback to the operator of the surgical instrument. The feedback can be a sensory feedback, such as a noise, a light, and/or a tactile signal, for example. In certain embodiments, a first motor can pause the initial surgical function and a second motor can generate the sensory feedback. Alternatively, as described herein, a multi-function electric motor, such as the electric motor 5002, for example, can switch from the first operating state, or advancing state, to the third operating state, or feedback state, in which the electric motor oscillates to generate the amplified haptic feedback. When the multi-function electric motor oscillates to generate the amplified haptic feedback, advancement and/or retraction of the firing element can be paused and/or reduced to an insignificant and/or imperceptible amount due to the high gear ratio between the electric motor and the firing member. In such embodiments, where the multi-function motor switches from the first operating state to the third operating state, pausing of the initial surgical function at step 5408 and providing feedback to the operator at step 5410 can occur simultaneously or nearly simultaneously, for example.

In certain embodiments, after the surgical instrument has communicated feedback indicative of a particular condition to the operator, the operator can determine how to proceed. For example, the operator can decide between a plurality of possible operating states. In various embodiments, the operator can decide to enter a warned operating state 5412, or a modified operating state 5414. For example, referring still to FIG. 180, the operator can select the initial surgical function at step 5416, or can select a modified surgical function at step 5418. In various embodiments, the operator can interface with a key, button, and/or lever, for example, to select one of the secondary operating states. If the operator selects the initial surgical function at step 5416, the surgical instrument can resume the initial surgical function at step 5418. If the operator selects the modified surgical function at step 5420, the surgical instrument can initiate the modified surgical function at step 5422.

FIGS. 183-192 illustrate various embodiments of an apparatus, system, and method for absolute position sensing on rotary or linear drive endocutter. Microcontroller controlled endocutters require position and velocity values to be able to properly control articulation, firing, and other surgical functions. This has been accomplished in the past via use of rotary encoders attached to the drive motors, which enable the microcontroller to infer the position by counting the number of steps backwards and forwards the motor has taken. It is preferable, in various circumstances, to replace this system with a compact arrangement which provides a unique position signal to the microcontroller for each possible location of the drive bar or knife. Various illustrative implementations of such absolute position sensor arrangements for rotary or linear drive endocutter are now described with particularity in connection with FIGS. 183-192.

FIG. 183 is an exploded perspective view of a surgical instrument handle 1042 of FIG. 34 showing a portion of a sensor arrangement 7002 for an absolute positioning system 7000, according to one embodiment. The surgical instrument handle 1042 of FIG. 34 has been described in detail in connection with FIG. 34. Accordingly, for conciseness and clarity of disclosure, other than describing the elements associated with the sensor arrangement 7002 for an absolute positioning system 7000, such detailed description of the surgical instrument handle 1042 of FIG. 34 will not be repeated here. Accordingly, as shown in FIG. 183, the surgical instrument handle 1042 of the housing 1040 operably supports a firing drive system 1100 that is configured to apply firing motions to corresponding portions of the interchangeable shaft assembly. The firing drive system 1100 may employ an electric motor 1102. In various forms, the motor 1102 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. A battery 1104 (or "power source" or "power pack"), such as a Li ion battery, for example, may be coupled to the handle 1042 to supply power to a control circuit board assembly 1106 and ultimately to the motor 1102. The battery pack housing 1104 may be configured to be releasably mounted to the handle 1042 for supplying control power to the surgical instrument 1010 (FIG. 33). A number of battery cells connected in series may be used as the power source to power the motor. In addition, the power source may be replaceable and/or rechargeable.

As outlined above with respect to other various forms, the electric motor 1102 can include a rotatable shaft (not shown) that operably interfaces with a gear reducer assembly 1108 that is mounted in meshing engagement with a with a set, or rack, of drive teeth 1112 on a longitudinally-movable drive member 1110. In use, a voltage polarity provided by the battery can operate the electric motor 1102 in a clockwise direction wherein the voltage polarity applied to the electric motor by the battery can be reversed in order to operate the electric motor 1102 in a counter-clockwise direction. When the electric motor 1102 is rotated in one direction, the drive member 1110 will be axially driven in the distal direction "D". When the motor 1102 is driven in the opposite rotary direction, the drive member 1110 will be axially driven in a proximal direction "P". The handle 1042 can include a switch which can be configured to reverse the polarity applied to the electric motor 1102 by the battery. As with the other forms described herein, the handle 1042 can also include a sensor that is configured to detect the position of the drive member 1110 and/or the direction in which the drive member 1110 is being moved.

FIG. 184 is a side elevational view of the handle of FIG. 183 with a portion of the handle housing removed showing a portion of a sensor arrangement 7002 for an absolute positioning system 7000, according to one embodiment. The housing 1040 of the handle 1042 supports the control circuit board assembly 1106, which comprises the necessary logic and other circuit components necessary to implement the absolute positioning system 7000.

FIG. 185 is a schematic diagram of an absolute positioning system 7000 comprising a microcontroller 7004 controlled motor drive circuit arrangement comprising a sensor arrangement 7002, according to one embodiment. The electrical and electronic circuit elements associated with the absolute positioning system 7000 and/or the sensor arrangement 7002 are supported by the control circuit board assembly 1106. The microcontroller 7004 generally comprises a memory 7006 and a microprocessor 7008 ("processor") operationally coupled. The processor 7008 controls a motor driver 7010 circuit to control the position and velocity of the motor 1102. The motor 1102 is operatively coupled to a sensor arrangement 7002 and an absolute position sensor 7012 arrangement to provide a unique position signal to the microcontroller 7004 for each possible location of a drive bar or knife of the surgical instrument 1010 (FIG. 33). The unique position signal is provided to the microcontroller 7004 over feedback element 7024. It will be appreciated that the unique position signal may be an analog signal or digital value based on the interface between the position sensor 7012 and the microcontroller 7004. In one embodiment described hereinbelow, the interface between the position sensor 7012 and the microcontroller 7004 is standard serial peripheral interface (SPI) and the unique position signal is a digital value representing the position of a sensor element 7026 over one revolution. The value representative of the absolute position of the sensor element 7026 over one revolution can be stored in the memory 7006. The absolute position feedback value of the sensor element 7026 corresponds to the position of the articulation and knife elements. Therefore, the absolute position feedback value of the sensor element 7026 provides position feedback control of the articulation and knife elements.

The battery 1104, or other energy source, provides power for the absolute positioning system 7000. In addition, other sensor(s) 7018 may be provided to measure other parameters associated with the absolute positioning system 7000. One or more display indicators 7020, which may include an audible component, also may provided.

As shown in FIG. 185, a sensor arrangement 7002 provides a unique position signal corresponding to the location of the longitudinally-movable drive member 1110. The electric motor 1102 can include a rotatable shaft 7016 that operably interfaces with a gear assembly 7014 that is mounted in meshing engagement with a with a set, or rack, of drive teeth 1112 (FIG. 183) on the longitudinally-movable drive member 1110. The sensor element 7026 may be operably coupled to the gear assembly 7104 such that a single revolution of the sensor element 7026 corresponds to some linear longitudinal translation of the longitudinally-movable drive member 1110, as described in more detail hereinbelow. In one embodiment, an arrangement of gearing and sensors can be connected to the linear actuator via a rack and pinion arrangement, or a rotary actuator via a spur gear or other connection. For embodiments comprising a rotary screw-drive configuration where a larger number of turns would be required, a high reduction gearing arrangement between the drive member and the sensor, like a worm and wheel, may be employed.

In accordance one embodiment of the present disclosure, the sensor arrangement 7002 for the absolute positioning system 7000 provides a more robust position sensor 7012 for use with surgical devices. By providing a unique position signal or value for each possible actuator position, such arrangement eliminates the need for a zeroing or calibration step and reduces the possibility of negative design impact in the cases where noise or power brown-out conditions may create position sense errors as in conventional rotary encoder configurations.

In one embodiment, the sensor arrangement 7002 for the absolute positioning system 7000 replaces conventional rotary encoders typically attached to the motor rotor and replaces it with a position sensor 7012 which generates a unique position signal for each rotational position in a single revolution of a sensor element associated with the position sensor 7012. Thus, a single revolution of a sensor element associated with the position sensor 7012 is equivalent to a longitudinal linear displacement d1 of the of the longitudinally-movable drive member 1110. In other words, d1 is the longitudinal linear distance that the longitudinally-movable drive member 1110 moves from point a to point b after a single revolution of a sensor element coupled to the longitudinally-movable drive member 1110. The sensor arrangement 7002 may be connected via a gear reduction that results in the position sensor 7012 completing only a single turn for the full stroke of the longitudinally-movable drive member 1110. With a suitable gear ratio, the full stroke of the longitudinally-movable drive member 1110 can be represented in one revolution of the position sensor 7012.

A series of switches $7022a$ to $7022n$, where n is an integer greater than one, may be employed alone or in combination with gear reduction to provide a unique position signal for more than one revolution of the position sensor 7012. The state of the switches $7022a$-$7022n$ are fed back to the microcontroller 7004 which applies logic to determine a unique position signal corresponding to the longitudinal linear displacement d1+d2+ . . . dn of the longitudinally-movable drive member 1110.

Accordingly, the absolute positioning system 7000 provides an absolute position of the longitudinally-movable drive member 1110 upon power up of the instrument without retracting or advancing the longitudinally-movable drive member 1110 to a reset (zero or home) position as may be required with conventional rotary encoders that merely count the number of steps forwards or backwards that motor has taken to infer the position of a device actuator, drive bar, knife, and the like.

In various embodiments, the position sensor 7012 of the sensor arrangement 7002 may comprise one or more magnetic sensor, analog rotary sensor like a potentiometer, array of analog Hall-effect elements, which output a unique combination of position signals or values, among others, for example.

In various embodiments, the microcontroller 7004 may be programmed to perform various functions such as precise control over the speed and position of the knife and articulation systems. Using the known physical properties, the microcontroller 7004 can be designed to simulate the response of the actual system in the software of the controller 7004. The simulated response is compared to (noisy and discrete) measured response of the actual system to obtain an "observed" response, which is used for actual feedback decisions. The observed response is a favorable, tuned, value that balances the smooth, continuous nature of the simulated response with the measured response, which can detect outside influences on the system.

In various embodiments, the absolute positioning system 7000 may further comprise and/or be programmed to implement the following functionalities. A feedback controller, which can be one of any feedback controllers, including, but not limited to: PID, state feedback and adaptive. A power source converts the signal from the feedback controller into a physical input to the system, in this case voltage. Other examples include, but are not limited to pulse width modulated (PWMed) voltage, current and force. The motor 1102 may be a brushed DC motor with a gearbox and mechanical links to an articulation or knife system. Other sensor(s) 7018 may be provided to measure physical parameters of the physical system in addition to position measured by the position sensor 7012. Since it is a digital signal (or connected to a digital data acquisition system) its output will have finite resolution and sampling frequency. A compare and combine circuit may be provided to combine the simulated response with the measured response using algorithms such as, without limitation, weighted average and theoretical control loop that drives the simulated response towards the measured response. Simulation of the physical system takes in account of properties like mass, inertial, viscous friction, inductance resistance, etc. to predict what the states and outputs of the physical system will be by knowing the input.

In one embodiment, the microcontroller 7004 may be an LM 4F230H5QR, available from Texas Instruments, for example. In one embodiment, the Texas Instruments LM4F230H5QR is an ARM Cortex-M4F Processor Core comprising on-chip memory 7006 of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare software, 2 KB electrically erasable programmable read-only memory (EEPROM), two pulse width modulation (PWM) modules, with a total of 16 advanced PWM outputs for motion and energy applications, two quadrature encoder inputs (QEI) analog, two 12-bit Analog-to-Digital Converters (ADC) with 12 analog input channels, among other features that are readily available for the product datasheet. Other microcontrollers may be readily substituted for use in the absolute positioning system 7000. Accordingly, the present disclosure should not be limited in this context.

In one embodiment, the driver 7010 may be a A3941 available from Allegro Microsystems, Inc. The A3941 driver

7010 is a full-bridge controller for use with external N-channel power metal oxide semiconductor field effect transistors (MOSFETs) specifically designed for inductive loads, such as brush DC motors. The driver 7010 comprises a unique charge pump regulator provides full (>10 V) gate drive for battery voltages down to 7 V and allows the A3941 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted for use in the absolute positioning system 7000. Accordingly, the present disclosure should not be limited in this context.

Having described a general architecture for implementing various embodiments of an absolute positioning system 7000 for a sensor arrangement 7002, the disclosure now turns to FIGS. 186-192 for a description of one embodiment of a sensor arrangement for the absolute positioning system 7000. In the embodiment illustrated in FIG. 186, the sensor arrangement 7002 comprises a magnetic position sensor 7100, a bipolar magnet 7102 sensor element, a magnet holder 7104 that turns once every full stroke of the longitudinally-movable drive member 1110 (FIGS. 183-185), and a gear assembly 7106 to provide a gear reduction. A structural element such as bracket 7116 is provided to support the gear assembly 7106, the magnet holder 7104, and the magnet 7102. The magnetic position sensor 7100 comprises one or more than one magnetic sensing elements such as Hall elements and is placed in proximity to the magnet 7102. Accordingly, as the magnet 7102 rotates, the magnetic sensing elements of the magnetic position sensor 7100 determine the absolute angular position of the magnetic 7102 over one revolution.

In various embodiments, any number of magnetic sensing elements may be employed on the absolute positioning system 7000, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In the illustrated embodiment, the gear assembly 7106 comprises a first gear 7108 and a second gear 7110 in meshing engagement to provide a 3:1 gear ratio connection. A third gear 7112 rotates about shaft 7114. The third gear is in meshing engagement with the longitudinally-movable drive member 1110 and rotates in a first direction as the longitudinally-movable drive member 1110 advances in a distal direction D (FIG. 183) and rotates in a second direction as the longitudinally-movable drive member 1110 retracts in a proximal direction P (FIG. 183). The second gear 7110 rotates about the same shaft 7114 and therefore, rotation of the second gear 7110 about the shaft 7114 corresponds to the longitudinal translation of the longitudinally-movable drive member 1110. Thus, one full stroke of the longitudinally-movable drive member 1110 in either the distal or proximal directions D, P corresponds to three rotations of the second gear 7110 and a single rotation of the first gear 7108. Since the magnet holder 7104 is coupled to the first gear 7108, the magnet holder 7104 makes one full rotation with each full stroke of the longitudinally-movable drive member 1110.

FIG. 187 is an exploded perspective view of the sensor arrangement 7002 for the absolute positioning system 7000 showing a control circuit board assembly 1106 and the relative alignment of the elements of the sensor arrangement 7002, according to one embodiment. The position sensor 7100 (not shown in this view) is supported by a position sensor holder 7118 defining an aperture 7120 suitable to contain the position sensor 7100 is precise alignment with a rotating magnet 7102 below. The fixture 7120 is coupled to the bracket 7116 and to the control circuit board assembly 1106 and remains stationary while the magnet 7102 rotates with the magnet holder 7104. A hub 7122 is provided to mate with the first gear 7108/magnet holder 7104 assembly.

FIGS. 188-190 provide additional views of the sensor arrangement 7002, according to one embodiment. In particular, FIG. 188 shows the entire sensor arrangement 7002 positioned in operational mode. The position sensor holder 7118 is located below the control circuit board assembly 1106 and encapsulates the magnet holder 7104 and magnet 7102. FIG. 189 shows the magnet 7102 located below the aperture 7120 defined in the position sensor holder 7118. The position sensor 7100 and the control circuit board assembly 1106 are not shown for clarity. FIG. 190 shows the sensor arrangement 7002 with the control circuit board assembly 1106, the position sensor holder 7118, the position sensor 7100, and the magnet 7102 removed to show the aperture 7124 that receives the magnet 7102.

FIG. 191 is a top view of the sensor arrangement 7002 shown with the control circuit board 1106 removed but the electronic components still visible to show the relative position between the position sensor 7100 and the circuit components 7126, according to one embodiment. In the embodiment illustrated in connection with FIGS. 186-191, the gear assembly 7106 composed of first gear 7108 and second gear 7110 have a 3:1 gear ratio such that three rotations of the second gear 7110 provides a single rotation of the first gear 7108 and thus the magnet holder 7104. As previously discussed, the position sensor 7100 remains stationary while the magnet holder 7104/magnet 7102 assembly rotates.

As discussed above, a gear assembly can be utilized to drive the magnet holder 7104 and the magnet 7102. A gear assembly can be useful in various circumstances as the relative rotation between one gear in the gear assembly and another gear in the gear assembly can be reliably predicted. In various other circumstances, any suitable drive means can be utilized to drive the holder 7104 and the magnet 7102 so long as the relationship between the output of the motor and the rotation of the magnet 7102 can be reliably predicted. Such means can include, for example, a wheel assembly including at least two contacting wheels, such as plastic wheels and/or elastomeric wheels, for example, which can transmit motion therebetween. Such means can also include, for example, a wheel and belt assembly.

FIG. 192 is a schematic diagram of one embodiment of a position sensor 7100 sensor for an absolute positioning system 7000 comprising a magnetic rotary absolute positioning system, according to one embodiment. In one embodiment, the position sensor 7100 may be implemented as an AS5055EQFT single-chip magnetic rotary position sensor available from austriamicrosystems, AG. The position sensor 7100 is interfaced with the microcontroller 7004 to provide an absolute positioning system 7000. The position sensor 7100 is a low voltage and low power component and includes four integrated Hall-effect elements 7128A, 7128B, 7128C, 7128D in an area 7130 of the position sensor 7100 that is located above the magnet 7104 (FIGS. 186, 187). A high resolution ADC 7132 and a smart power management controller 7138 are also provided on the chip. A CORDIC processor 7136 (for COordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits and magnetic field information are transmitted over a standard SPI interface 7134 to the host processor, microcontroller 7004. The position sensor 7100 provides 12 or 14 bits of resolution. In the embodiment illustrated in FIG. 191, the position sensor 7100 is an AS5055 chip provided in a small QFN 16-pin 4×4×0.85 mm package.

The Hall-effect elements 7128A, 7128B, 7128C, 7128D are located directly above the rotating magnet. The Hall-effect is a well known effect and will not be described in detail herein for the sake of conciseness and clarity of disclosure. Generally, the Hall-effect is the production of a voltage difference (the Hall voltage) across an electrical conductor, transverse to an electric current in the conductor and a magnetic field perpendicular to the current. It was discovered by Edwin Hall in 1879. The Hall coefficient is defined as the ratio of the induced electric field to the product of the current density and the applied magnetic field. It is a characteristic of the material from which the conductor is made, since its value depends on the type, number, and properties of the charge carriers that constitute the current. In the AS5055 position sensor 7100, the Hall-effect elements 7128A, 7128B, 7128C, 7128D are capable producing a voltage signal that is indicative of the absolute position of the magnet 7104 (FIGS. 186, 187) in terms of the angle over a single revolution of the magnet 7104. This value of the angle, which is unique position signal, is calculated by the CORDIC processor 7136 is stored onboard the AS5055 position sensor 7100 in a register or memory. The value of the angle that is indicative of the position of the magnet 7104 over one revolution is provided to the host processor 7004 in a variety of techniques, e.g., upon power up or upon request by the host processor 7004.

The AS5055 position sensor 7100 requires only a few external components to operate when connected to the host microcontroller 7004. Six wires are needed for a simple application using a single power supply: two wires for power and four wires 7140 for the SPI serial communication interface 7134 with the host microcontroller 7004. A seventh connection can be added in order to send an interrupt to the host microcontroller 7004 to inform that a new valid angle can be read.

Upon power-up, the AS5055 position sensor 7100 performs a full power-up sequence including one angle measurement. The completion of this cycle is indicated as an INT request at output pin 7142 and the angle value is stored in an internal register. Once this output is set, the AS5055 position sensor 7100 suspends to sleep mode. The external microcontroller 7004 can respond to the INT request at 7142 by reading the angle value from the AS5055 position sensor 7100 over the SPI interface 7134. Once the angle value is read by the microcontroller 7004, the INT output 7142 is cleared again. Sending a "read angle" command by the SPI interface 7134 by the microcontroller 7004 to the position sensor 7100 also automatically powers up the chip and starts another angle measurement. As soon ad the microcontroller 7004 has completed reading of the angle value, the INT output 7142 is cleared and a new result is stored in the angle register. The completion of the angle measurement is again indicated by setting the INT output 7142 and a corresponding flag in the status register.

Due to the measurement principle of the AS5055 position sensor 7100, only a single angle measurement is performed in very short time (~600 µs) after each power-up sequence. As soon as the measurement of one angle is completed, the AS5055 position sensor 7100 suspends to power-down state. An on-chip filtering of the angle value by digital averaging is not implemented, as this would require more than one angle measurement and consequently, a longer power-up time which is not desired in low power applications. The angle jitter can be reduced by averaging of several angle samples in the external microcontroller 7004. For example, an averaging of 4 samples reduces the jitter by 6 dB (50%).

As discussed above, the motor 1102 positioned within the handle 1042 of surgical instrument system 1000 can be utilized to advance and/or retract the firing system of the shaft assembly 1200, including firing members 1272 and 1280, for example, relative to the end effector 1300 of the shaft assembly 1200 in order to staple and/or incise tissue captured within the end effector 1300. In various circumstances, it may be desirable to advance the firing members 1272 and 1280 at a desired speed, or within a range of desired speeds. Likewise, it may be desirable to retract the firing members 1272 and 1280 at a desired speed, or within a range of desired speeds. In various circumstances, the microcontroller 7004 of the handle 1042, for example, and/or any other suitable controller, can be configured to control the speed of the firing members 1272 and 1280. In some circumstances, the controller can be configured to predict the speed of the firing members 1272 and 1280 based on various parameters of the power supplied to the motor 1102, such as voltage and/or current, for example, and/or other operating parameters of the motor 1102. The controller can also be configured to predict the current speed of the firing members 1272 and 1280 based on the previous values of the current and/or voltage supplied to the motor 1102, and/or previous states of the system like velocity, acceleration, and/or position. Furthermore, the controller can also be configured to sense the speed of the firing members 1272 and 1280 utilizing the absolute positioning sensor system described above, for example. In various circumstances, the controller can be configured to compare the predicted speed of the firing members 1272 and 1280 and the sensed speed of the firing members 1272 and 1280 to determine whether the power to the motor 1102 should be increased in order to increase the speed of the firing members 1272 and 1280 and/or decreased in order to decrease the speed of the firing members 1272 and 1280. U.S. patent application Ser. No. 12/235,782, entitled MOTOR-DRIVEN SURGICAL CUTTING INSTRUMENT, now U.S. Pat. No. 8,210,411, is incorporated by reference in its entirety. U.S. patent application Ser. No. 11/343,803, entitled SURGICAL INSTRUMENT HAVING RECORDING CAPABILITIES, now U.S. Pat. No. 7,845,537, is incorporated by reference in its entirety.

Using the physical properties of the instruments disclosed herein, turning now to FIGS. 198 and 199, a controller, such as microcontroller 7004, for example, can be designed to simulate the response of the actual system of the instrument in the software of the controller. The simulated response is compared to a (noisy and discrete) measured response of the actual system to obtain an "observed" response, which is used for actual feedback decisions. The observed response is a favorable, tuned, value that balances the smooth, continuous nature of the simulated response with the measured response, which can detect outside influences on the system. With regard to FIGS. 198 and 199, a firing element, or cutting element, in the end effector 1300 of the shaft assembly 1200 can be moved at or near a target velocity, or speed. The systems disclosed in FIGS. 198 and 199 can be utilized to move the cutting element at a target velocity. The systems can include a feedback controller 4200, which can be one of any feedback controllers, including, but not limited to a PID, a State Feedback, LQR, and/or an Adaptive controller, for example. The systems can further include a power source. The power source can convert the signal from the feedback controller 4200 into a physical input to the system, in this case voltage, for example. Other examples include, but are not limited to, pulse width modulated (PWM) voltage, frequency modulated voltage, current, torque, and/or force, for example.

With continued reference to FIGS. 198 and 199, the physical system referred to therein is the actual drive system of the instrument configured to drive the firing member, or cutting member. One example is a brushed DC motor with gearbox and mechanical links to an articulation and/or knife system. Another example is the motor 1102 disclosed herein that operates the firing member 10060 and the articulation driver 10030, for example, of an interchangeable shaft assembly. The outside influence 4201 referred to in FIGS. 198 and 199 is the unmeasured, unpredictable influence of things like tissue, surrounding bodies and friction on the physical system, for example. Such outside influence can be referred to as drag and can be represented by a motor 4202 which acts in opposition to the motor 1102, for example. In various circumstances, outside influence, such as drag, is the primary cause for deviation of the simulation of the physical system from the actual physical system. The systems depicted in FIGS. 198 and 199 and further discussed below can address the differences between the predicted behavior of the firing member, or cutting member, and the actual behavior of the firing member, or cutting member.

With continued reference to FIGS. 198 and 199, the discrete sensor referred to therein measures physical parameters of the actual physical system. One embodiment of such a discrete sensor can include the absolute positioning sensor 7102 and system described herein. As the output of such a discrete sensor can be a digital signal (or connected to a digital data acquisition system) its output may have finite resolution and sampling frequency. The output of the discrete sensor can be supplied to a microcontroller, such as microcontroller 7004, for example. In various circumstances, the microcontroller can combine the simulated, or estimated, response with the measured response. In certain circumstances, it may be useful to use enough measured response to ensure that the outside influence is accounted for without making the observed response unusably noisy. Examples for algorithms that do so include a weighted average and/or a theoretical control loop that drives the simulated response towards the measured response, for example. Ultimately, further to the above, the simulation of the physical system takes in account of properties like mass, inertial, viscous friction, and/or inductance resistance, for example, to predict what the states and outputs of the physical system will be by knowing the input. FIG. 199 shows an addition of evaluating and measuring the current supplied to operate the actual system, which is yet another parameter that can be evaluated for controlling the speed of the cutting member, or firing member, of the shaft assembly 1200, for example. By measuring current in addition to or in lieu of measuring the voltage, in certain circumstances, the physical system can be made more accurate. Nonetheless, the ideas disclosed herein can be extended to the measurement of other state parameters of other physical systems.

Having described various embodiments of an absolute positioning system 7000 to determine an absolute position signal/value of a sensor element corresponding to a unique absolute position of elements associated with articulation and firing, the disclosure now turns to a description of several techniques for employing the absolute position/value in a position feedback system to control the position of the articulation and knife to compensate for knife band splay in a powered articulated surgical instrument 1010 (FIG. 33). The absolute positioning system 7000 provides a unique position signal/value to the microcontroller for each possible location of the drive bar or knife along the length of the staple cartridge.

The operation of the articulation joint 1350 has been described in connection with FIG. 37 and will not be repeated in detail in this section for conciseness and clarity of disclosure. The operation of the articulation joint 10090 has been described in connection with FIG. 102 and will not be repeated in detail in this section for conciseness and clarity of disclosure. FIG. 193 illustrates an articulation joint 8000 in a straight position, i.e., at a zero angle $\theta_0$ relative to the longitudinal direction depicted as longitudinal axis L-A, according to one embodiment. FIG. 195 illustrates the articulation joint 8000 of FIG. 193 articulated in one direction at a first angle $\theta_1$ defined between the longitudinal axis L-A and the articulation axis A-A, according to one embodiment. FIG. 195 illustrates the articulation joint 8000 of FIG. 194 articulated in another direction at a second angle $\theta_2$ defined between the longitudinal axis L-A and the articulation axis A'-A, according to one embodiment.

The surgical instrument according to the present disclosure utilizes multiple flexible knife bands 8002 to transfer compressive force to a translating a knife element in the cartridge (not shown) of the end effector 1300 (FIG. 37). The flexible knife bands 8002 enable the end-effector 1300 (FIG. 33) to articulate through a variety of angles $\theta$. The act of articulating, however, causes the flexible knife bands 8002 to splay. Splay of the flexible knife bands 8002 changes the effective transection length $T_1$ in the longitudinal direction. Thus, it is difficult to determine the exact position of the knife past the articulation joint 8000 when the flexible knife bands 8002 are articulated past an angle of $\theta$=0. As previously discussed, the position of the articulation and knife element can be determined directly using the absolute position feedback signal/value from the absolute positioning system 7000 when the articulation angle is zero $\theta_0$ as shown in FIG. 194. However, when the flexible knife bands 8002 deviate from a zero angle $\theta_0$ from the longitudinal axis L-A, the absolute position of the knife within the cartridge cannot be precisely determined based on the absolute position signal/value provided by the absolute positioning system 7000 to the microcontroller 7004, without knowing the articulation angle $\theta$.

In one embodiment, the articulation angle $\theta$ can be determined fairly accurately based on the firing drive of the surgical instrument. As outlined above, the movement of the firing member 10060 can be tracked by the absolute positioning system 7000 wherein, when the articulation drive is operably coupled to the firing member 10060 by the clutch system 10070, for example, the absolute positioning system 7000 can, in effect, track the movement of the articulation system via the firing member 10060. As a result of tracking the movement of the articulation system, the controller of the surgical instrument can track the articulation angle $\theta$ of the end effector, such as end effector 10020, for example. In various circumstances, as a result, the articulation angle $\theta$ can be determined as a function of longitudinal displacement DL of the flexible knife bands 8002. Since the longitudinal displacement DL of the flexible knife bands 8002 can be precisely determined based on the absolute position signal/value provided by the absolute positioning system 7000, an algorithm may be employed to compensate for the error in displacement of the knife following the articulation joint 8000.

In another embodiment, the articulation angle $\theta$ can be determined by locating sensors on the flexible knife bands 8002 distal D to the articulation joint 8000. The sensors can be configured to sense the amount of tension or compression in the articulated flexible knife bands 8002. The measured tension or compression results are provided to the microcontroller 7004 to calculate the articulation angle $\theta$ based on the amount of tension or compression measured in the knife bands 8002. Suitable sensors such as microelectronic mechanical systems (MEMS) devices and strain gauges may be readily adapted to make such measurements. Other techniques include locating a tilt sensor, inclinometer, accelerometer, or any suitable device for measuring angles, in the articulation joint 8000 to measure the articulation angle $\theta$.

In various embodiments, several techniques for compensating for splay of the flexible knife bands 8002 in a powered articulatable surgical instrument 1010 (FIG. 33) are described hereinbelow in the context of a powered surgical instrument 1010 comprising an absolute positioning system 7000 and a microcontroller 7004 with data storage capability such as memory 7006.

FIG. 196 illustrates one embodiment of a logic diagram 8100 for a method of compensating for the effect of splay in flexible knife bands 8002 on transection length $T_1$. The method will be described in connection with FIGS. 185 and 192-196. Accordingly, in one embodiment of a method 8100 of compensating for the effect of splay in flexible knife bands 8002 on transection length $T_1$, the relationship between articulation angle $\theta$ of the end effector 1300 (FIG. 37), or end effector 10020 (FIG. 102), for example, and effective transection length $T_1$ distal of the articulation joint 8000 is initially characterized and the characterization data is stored in the memory 7006 of the surgical instrument 1010 (FIG. 33). In one embodiment, the memory 7006 is a nonvolatile memory such as flash memory, EEPROM, and the like. The processor 7008 portion of the microcontroller 7004 accesses 8102 the characterization data stored in the memory 7006. The processor 7008 tracks 8104 the articulation angle of the end effector 1300 during use of the surgical instrument 1010. The processor 7008 adjusts 8106 the target transection length $T_1$ by the surgical instrument 1010 based on the known articulation angle $\theta_M$ and the stored characterization data representative of the relationship between the articulation angle $\theta_S$ and the transection length $T_1$.

In various embodiments, the characterization data representative of the relationship between the articulation angle $\theta$ of the end effector 1300 (FIG. 37) and the effective transection length $T_1$ may be completed for the shaft of the surgical instrument 1010 (FIG. 33) during manufacturing. In one embodiment, the output of the characterization 8102 process is a lookup table implemented in the memory 7006. Accordingly, in one embodiment, the processor 7008 accesses the characterization data from the lookup table implemented in the memory 7006. In one aspect, the lookup table comprises an array that replaces runtime computation with a simpler array indexing operation. The savings in terms of processing time can be significant, since retrieving a value from the memory 7006 by the processor 7008 is generally faster than undergoing an "expensive" computation or input/output operation. The lookup table may be precalculated and stored in static program storage, calculated (or "pre-fetched") as part of a program's initialization phase (memoization), or even stored in hardware in application-specific platforms. In the instant application, the lookup table stores the output values of the characterization of the relationship between articulation angle of the end effector 1300 (FIG. 37) and effective transection length. The lookup table stores these output values in an array and, in some programming languages, may include pointer functions (or offsets to labels) to process the matching input. Thus, for each unique value of linear displacement $D_L$ there is a corresponding articulation angle $\theta$. The articulation angle $\theta$ is used to calculate a corresponding transection length $T_1$ displacement distal the articulation joint 8000, the articulation joint 1350, or the articulation joint 10090, for example. The corresponding transection length $T_1$ displacement is stored in the lookup table and is used by the microcontroller 7004 to determine the position of the knife past the articulation joint. Other lookup table techniques are contemplated within the scope of the present disclosure.

In one embodiment, the output of the characterization 8102 process is a best curve fit formula, linear or nonlinear. Accordingly, in one embodiment, the processor 7008 is operative to execute computer readable instructions to implement a best curve fit formula based on the characterization data. Curve fitting is the process of constructing a curve, or mathematical function that has the best fit to a series of data points, possibly subject to constraints. Curve fitting can involve either interpolation, where an exact fit to the data is required. In the instant disclosure, the curve represents the transection length $T_1$ displacement of the flexible knife bands 8002 distal D of the articulated articulation joint 8000 (FIG. 37) based on the articulation angle $\theta$, which depends on the linear displacement $D_L$ of the flexible knife bands 8002 proximal P to the articulation joint 1350. The data points such as linear displacement $D_L$ of the flexible knife bands 8002 proximal to the articulation joint 1350, displacement $T_1$ of the flexible knife bands 8002 distal the articulated articulation joint 1350, and articulation angle $\theta$ can be measured and used to generate a best fit curve in the form of an $n^{th}$ order polynomial (usually a $3^{rd}$ order polynomial would provide a suitable curve fit to the measured data). The microcontroller 7004 can be programmed to implement the $n^{th}$ order polynomial. In use, input the $n^{th}$ order polynomial is the linear displacement of the flexible knife bands 8002 derived from the unique absolute position signal/value provided by the absolute positioning system 7000.

In one embodiment, the characterization 8102 process accounts for articulation angle $\theta$ and compressive force on the knife bands 8002.

In one embodiment, the effective transection length is a distance between the distal most surface of the knife blade in relationship to a predetermined reference in the handle of the surgical instruments 1010.

In various embodiments, the memory 7006 for storing the characterization may be a nonvolatile memory located on the on the shaft, the handle, or both, of the surgical instrument 1010 (FIG. 33).

In various embodiments, the articulation angle $\theta$ can be tracked by a sensor located on the shaft of the surgical instrument 1010 (FIG. 33). In other embodiments, the articulation angle $\theta$ can be tracked by a sensor on the handle of the surgical instrument 1010 or articulation angle $\theta$ can be tracked by variables within the control software for the surgical instrument 1010.

In one embodiment, the characterization is utilized by control software of the microcontroller 7004 communicating with the non-volatile memory 7006 to gain access to the characterization.

A control system, such as the control system illustrated in FIG. 200 and/or FIG. 203, for example, can be utilized to control any of the surgical instruments disclosed herein. In various circumstances, the control system can comprise a microcontroller, such as microcontroller 7004, for example, which can be configured to operate the various systems of a surgical instrument. Further to the above, the control system can comprise assembly detection means for detecting whether a shaft assembly, such as shaft assembly 1200, for example, has been assembled, or at least partially assembled, to the handle 1042. Such assembly detection means can comprise the Hall effect sensor 4002 described above, for example, and means for maintaining the handle 1042 in a powered-down condition if the shaft assembly is not assembled to the handle 1042, and means for maintaining the handle 1042 in a powered-up condition if the shaft assembly is assembled to the handle 1042, further to the above. As outlined above, the microcontroller 7004, for example, can include such means. The control system can further comprise power communication means for communicating electrical power to and/or from the shaft assembly and/or signal communication means for communicating communication signals to and/or from the shaft assembly. Such power communication means and signal communication means can comprise the electrical connector 4000, a corresponding electrical connector on the shaft assembly, and/or the microcontroller 7004, for example.

With further reference to FIGS. 200 and 203, the control system can further comprise at least one closure trigger switch and at least one closure trigger circuit which can be configured to communicate to the microcontroller 7004, and/or be interpreted by the microcontroller 7004, that the closure trigger 1052, discussed above, has been closed. Various switches can include a potentiometer and/or a Hall effect sensor, for example. The control system can further comprise unclosed operating means for operating the surgical instrument in an unclosed operating condition when the closure trigger 1052 is in an unclosed position and closed operating means for operating the surgical instrument in a closed operating condition when the closure trigger 1052 is in a closed position. The control system can comprise a power supply, such as battery 1104, for example, and means for distributing power from the power supply throughout the control system. The control system can comprise a motor, such as motor 1102, for example, a motor power switch, such as firing trigger 1120, for example, and motor operating means for operating the motor 1102 in a desired way, as described elsewhere herein. Such motor operating means, in certain circumstances, can be configured to control the motor 1102 utilizing pulse width modulated (PWM) voltage control, for example. Moreover, PWM voltage control can be utilized to control the speed of the firing members 1272 and 1280, for example. In the unclosed operating condition of the surgical instrument, in some circumstances, the battery 1104 may be disconnected from the motor 1102 while, in certain circumstances, a motor controller can be configured to prevent the operation of the motor 1102 even though electrical power may be supplied to the motor 1102 until the microcontroller 7004 detects the closure of the closure trigger 1052. In such circumstances, the microcontroller 7004 can then operate the surgical instrument in its closed operating state. In the closed operating state, power can be supplied to the motor 1102 and the motor controller can be configured to operate the motor 1102 in response to the operation of the firing trigger 1120. FIGS. 204-206 illustrate various operations for operating the motor 1102 and the firing members 1272 and 1280, for example.

With further reference to FIGS. 200 and 203, the control system can comprise a 12-bit magnetic rotary encoder, for example, and can be configured to monitor the position of the firing members 1272 and 1280. In various circumstances, the control system can include the absolute positioning sensor 7102 and the sensing system described above to monitor the position of the firing members 1272 and 1280. The control system can also comprise manual drive means for manually moving the firing members 1272 and 1280 and/or means for operating another system of the surgical instrument in light of the operation of the manual drive means. For instance, the manual drive means may comprise a manually-actuatable bailout assembly 1130, for example, which is described above. Also, for instance, the operation of the manual drive means may electrically deactivate the motor 1102. In some circumstances, the operation of the manual drive means can disconnect the battery 1104 from the motor 1102. In certain circumstances, the operation of the manual drive means can be detected by a motor controller which can be configured to prevent the operation of the motor 1102 even though electrical power may be supplied to the motor 1102. In various circumstances, the motor controller can comprise the microcontroller 7004, for example.

With further reference to FIGS. 200 and 203, the control system can further comprise communication means for communicating with the operator of the instrument. In various circumstances, the communication means can comprise one or more light emitting diode (LED) lights, for example, on the handle 1042, for example, which can be configured to communicate to the operator of the surgical instrument that the surgical instrument is in a particular operating condition, for example. In at least one circumstance, the handle 1042 can include a green LED light, for example, which, when lit, can indicate that the surgical instrument is in an assembled, closed, and powered-up condition, for example. In such circumstances, the lit green LED light can indicate that the surgical instrument is ready for use. The handle 1042 can include a red LED light, for example, which, when lit, can indicate that the surgical instrument is in either an unassembled, unclosed, and/or powered-down condition. In such circumstances, the lit red LED light can indicate that the surgical instrument is not ready for use. Further to the above, the LED lights can be in electrical communication with output channels of the microcontroller 7004 wherein the microcontroller 7004 can be configured to determine and/or set the operating condition of the surgical instrument and communicate that condition through the LED lights, for example. In some circumstances, the communication means can include a display screen on the handle 1042, for example, which can be configured to communicate information to the operator of the surgical instrument. Further to the above, the microcontroller 7004 can be in electrical communication with the display screen to communicate the operating condition of the surgical instrument, for example.

With further reference to FIGS. 200 and 203, and with additional reference to FIGS. 201 and 202, the control system can comprise a plurality of switches in electrical communication with the microcontroller 7004, for example. The switches can include the switches discussed above and/or in connection with any system and/or subsystem of the surgical instrument described herein. The switches can comprise a switch array which can be included in a switch circuit in electrical communication with the microcontroller 7004, for example. In certain circumstances, the switch circuit can include a 16-bit I/O encoder, for example, which can communicate with the microcontroller 7004. Moreover, the switch circuit can comprise a bus which is in electrical communication with the microcontroller 7004 and one or more contacts in the electrical connector 4000. Ultimately, then, the switch circuit and the switch array can span the handle 1042 and the shaft assembly 1200, for example. In various circumstances, the microcontroller 7004 can be configured to identify the shaft assembly attached to the handle 1042 and adjust the length of the firing stroke applied to the firing members 1272 and 1280, for example.

Various embodiments described herein are described in the context of staples removably stored within staple cartridges for use with surgical stapling instruments. In some circumstances, staples can include wires which are deformed when they contact an anvil of the surgical stapler. Such wires can be comprised of metal, such as stainless steel, for example, and/or any other suitable material. Such embodiments, and the teachings thereof, can be applied to embodiments which include fasteners removably stored with fastener cartridges for use with any suitable fastening instrument.

Various embodiments described herein are described in the context of linear end effectors and/or linear fastener cartridges. Such embodiments, and the teachings thereof, can be applied to non-linear end effectors and/or non-linear fastener cartridges, such as, for example, circular and/or contoured end effectors. For example, various end effectors, including non-linear end effectors, are disclosed in U.S. patent application Ser. No. 13/036,647, filed Feb. 28, 2011, entitled SURGICAL STAPLING INSTRUMENT, now U.S. Pat. No. 8,561,870, which is hereby incorporated by reference in its entirety. Additionally, U.S. patent application Ser. No. 12/893,461, filed Sep. 29, 2012, entitled STAPLE CARTRIDGE, now U.S. Pat. No. 8,733,613, is hereby incorporated by reference in its entirety. U.S. patent application Ser. No. 12/031,873, filed Feb. 15, 2008, entitled END EFFECTORS FOR A SURGICAL CUTTING AND STAPLING INSTRUMENT, now U.S. Pat. No. 7,980,443, is also hereby incorporated by reference in its entirety. U.S. Pat. No. 8,393,514, entitled SELECTIVELY ORIENTABLE IMPLANTABLE FASTENER CARTRIDGE, which issued on Mar. 12, 2013, is also hereby incorporated by reference in its entirety.

While various details have been set forth in the foregoing description, the various embodiments may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing discussion, it is appreciated that, throughout the foregoing description, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely illustrative, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to,"

"conformable/conformed to," etc. Those skilled in the art will recognize that "configured to" can generally encompass active-state components and/or inactive-state components and/or standby-state components, unless context requires otherwise.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

The disclosure of U.S. Patent Application Publication No. 2010/0264194, entitled SURGICAL STAPLING INSTRUMENT WITH AN ARTICULATABLE END EFFECTOR, filed on Apr. 22, 2010, now U.S. Pat. No. 8,308,040, is incorporated herein by reference in its entirety. The disclosure of U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358, is incorporated herein by reference in its entirety.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

What is claimed is:

1. A surgical instrument, comprising:
(a) a proximal housing, the proximal housing comprising:
(i) a motor, and
(ii) a firing drive, wherein the motor is configured to actuate the firing drive between a default position and an advanced position;
(b) an interchangeable assembly configured to selectively couple with the proximal housing, wherein the interchangeable assembly comprises:
(i) an elongated shaft,
(ii) an articulation joint coupled with the elongated shaft,
(iii) an end effector coupled to the articulation joint, and
(iv) an articulation driver configured to actuate relative to the elongated shaft to articulate the end effector between an articulation home state position and an articulated position, wherein the articulation driver is configured to operatively couple with the firing drive when the interchangeable assembly is coupled with the proximal housing, wherein the firing drive and the articulation driver, while operatively coupled with each other, are configured to cooperatively articulate the end effector relative to the elongated shaft in response to the firing drive actuating between the default position and the advanced position; and
(c) a safe release comprising:
(i) a lock configured to transition between a locked configuration and an unlocked configuration, wherein the lock, while in the locked configuration, is configured to inhibit decoupling of the interchangeable assembly and the proximal housing, wherein the lock, while in the unlocked configuration, is configured to allow decoupling of the interchangeable assembly and the proximal housing, and

(ii) a switch, wherein the switch is configured to generate a home state input signal in response to the lock transitioning into the unlocked configuration, wherein the firing drive is configured to automatically actuate to the default position in response to the switch generating the home state input signal.

2. The surgical instrument of claim 1, wherein the firing drive and the articulation driver, while operatively coupled with each other, are configured to cooperatively articulate the end effector into the articulation home state position in response to the switch generating the home state input signal.

3. The surgical instrument of claim 1, wherein the end effector further comprises a knife.

4. The surgical instrument of claim 3, wherein the interchangeable assembly further comprises a knife bar configured to actuate relative to the elongated shaft to thereby fire the knife of the end effector.

5. The surgical instrument of claim 4, wherein the firing drive is configured to operatively couple with the knife bar in order to actuate the knife bar relative to the elongated shaft.

6. The surgical instrument of claim 5, further comprising a clutch configured to operatively couple the firing drive between the knife bar and the articulation driver.

7. The surgical instrument of claim 5, wherein the firing drive is configured to actuate the knife bar to a home position in response to receiving the home input signal.

8. The surgical instrument of claim 1, wherein the lock of the safe release is slidably coupled to the interchangeable assembly.

9. The surgical instrument of claim 8, wherein the switch is attached to the proximal housing.

10. The surgical instrument of claim 9, further comprising a controller, wherein the switch is in communication with the controller.

11. The surgical instrument of claim 10, wherein the controller is configured to receive the home state input signal and thereby instruct the firing drive to return to the home state position via the motor.

12. The surgical instrument of claim 11, wherein the controller is configured to generate an operator prompt in response to receiving the home state input signal.

13. The surgical instrument of claim 12, wherein the lock comprises a latch.

14. The surgical instrument of claim 13, wherein the latch is configured to be housed within a receiving slot defined by the proximal housing in the locked configuration.

15. The surgical instrument of claim 1, wherein the end effector further comprises a pair of jaws.

16. The surgical instrument of claim 15, wherein the end effector further comprises a staple cartridge.

17. The surgical instrument of claim 1, wherein eh end effector is configured to grasp, sever, and staple tissue.

18. A surgical instrument, comprising:
(a) a proximal housing, the proximal housing comprising:
    (i) a motor,
    (ii) a controller configured to activate the motor, and
    (iii) a firing drive, wherein the motor is configured to actuate the firing drive between a default position and an advanced position;
(b) an interchangeable assembly configured to selectively couple with the proximal housing, wherein the interchangeable assembly comprises:

114

(i) an elongated shaft,
(ii) an articulation joint coupled with the elongated shaft,
(iii) an end effector coupled to the articulation joint, and
(iv) an articulation driver configured to articulate the end effector between an articulation home state position and an articulated position, wherein the articulation driver is configured to operatively couple with the firing drive when the interchangeable assembly is coupled with the proximal housing, wherein the firing drive is configured to actuate the articulation driver in response to the firing drive actuating between the default position and the advanced position; and
(c) a safe release configured to transition between a locked configuration and an unlocked configuration, wherein the safe release, while in the locked configuration, is configured to inhibit decoupling of the interchangeable assembly and the proximal housing, wherein the safe release, while in the unlocked configuration, is configured to allow decoupling of the interchangeable assembly and the proximal housing, wherein the safe release is configured to generate a home state input signal in response to transitioning into the unlocked configuration, wherein the firing drive is configured to automatically actuate to the default position in response to the safe release generating the home state input signal.

19. The surgical instrument of claim 18, wherein the interchangeable assembly comprises a knife bar, wherein the firing drive is configured to selectively coupled with either the knife bar or the articulation driver.

20. A surgical instrument, comprising:
(a) a proximal housing, the proximal housing comprising:
    (i) a motor,
    (ii) a controller configured to activate the motor, and
    (iii) a firing drive, wherein the motor is configured to actuate the firing drive between a default position and an advanced position;
(b) an interchangeable assembly configured to selectively couple with the proximal housing, wherein the interchangeable assembly comprises:
    (i) an elongated shaft, and
    (ii) an end effector coupled to the elongated shaft, wherein the firing drive, while the interchangeable assembly is coupled to the proximal housing, is configured to manipulate the end effector in response to the firing drive actuating between the default position and an advanced position; and
(c) a safe release configured to transition between a locked configuration and an unlocked configuration, wherein the safe release, while in the locked configuration, is configured to inhibit decoupling of the interchangeable assembly and the proximal housing, wherein the safe release, while in the unlocked configuration, is configured to allow decoupling of the interchangeable assembly and the proximal housing, wherein the safe release is configured to generate a home state input signal in response to transitioning into the unlocked configuration, wherein the firing drive is configured to automatically actuate to the default position in response to the safe release generating the home state input signal.

* * * * *